US012630603B2

(12) United States Patent
Bot et al.

(10) Patent No.: US 12,630,603 B2
(45) Date of Patent: May 19, 2026

(54) CHIMERIC ANTIGEN RECEPTOR T CELL THERAPY

(71) Applicant: KITE PHARMA, INC., Santa Monica, CA (US)

(72) Inventors: Adrian Bot, Beverly Hills, CA (US); John Rossi, Newbury Park, CA (US); Vicki Plaks, Santa Monica, CA (US); Szu-Ting Chou, Los Angeles, CA (US); William Go, Thousand Oaks, CA (US); Jenny Jiyun Kim, Thousand Oaks, CA (US)

(73) Assignee: KITE PHARMA, INC., Santa Monica, CA (US)

( * ) Notice: Subject to any disclaimer, the term of this patent is extended or adjusted under 35 U.S.C. 154(b) by 368 days.

(21) Appl. No.: 17/180,753

(22) Filed: Feb. 20, 2021

(65) Prior Publication Data

US 2022/0169694 A1 Jun. 2, 2022

Related U.S. Application Data

(60) Provisional application No. 63/121,428, filed on Dec. 4, 2020, provisional application No. 63/092,195, filed
(Continued)

(51) Int. Cl.
*C07K 14/725* (2006.01)
*A61K 38/00* (2006.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
CPC ...................... C07K 14/7051; C07K 2319/00; A61K 35/17; A61K 45/06; A61K 38/00; A61P 35/00; C12N 5/0636
See application file for complete search history.

(56) References Cited

U.S. PATENT DOCUMENTS

2011/0245107 A1 10/2011 Kuchroo et al.
2017/0224798 A1 8/2017 Cooper et al.
(Continued)

FOREIGN PATENT DOCUMENTS

WO 2020028647 A1 2/2020
WO 2021085398 6/2021

OTHER PUBLICATIONS

Kueberuwa, G., et al (2017) CCR7+ selected gene-modified T cells maintain a central memory phenotype and display enhanced persistence in peripheral blood in vivo Journal for ImmunoTherapy of Cancer 5(14) 1-14 (Year: 2017).*
(Continued)

*Primary Examiner* — Joanne Hama
*Assistant Examiner* — Audrey L Buttice
(74) *Attorney, Agent, or Firm* — Carla Mouta-Bellum

(57) ABSTRACT
The disclosure provides methods of treating a malignancy comprising administering an effective dose of a chimeric antigen receptor genetically modified T cell immunotherapy and methods for manufacturing such immunotherapy. Some aspects of the disclosure relate to methods of determining objective response of a patient to a T cell immunotherapy based on the levels of attributes prior to and after administration of the immunotherapy to the patient.

14 Claims, 213 Drawing Sheets

Related U.S. Application Data on Oct. 15, 2020, provisional application No. 63/060,819, filed on Aug. 4, 2020, provisional application No. 63/044,676, filed on Jun. 26, 2020, provisional application No. 63/031,224, filed on May 28, 2020, provisional application No. 63/010,240, filed on Apr. 15, 2020, provisional application No. 62/979,001, filed on Feb. 20, 2020.

(51) Int. Cl.

| | |
|---|---|
| *A61K 40/11* | (2025.01) |
| *A61K 40/31* | (2025.01) |
| *A61K 40/42* | (2025.01) |
| *A61K 45/06* | (2006.01) |
| *A61P 35/00* | (2006.01) |
| *C12N 5/0783* | (2010.01) |

(52) U.S. Cl.
CPC ...... *A61K 40/4211* (2025.01); *A61K 40/4219* (2025.01); *A61K 40/4224* (2025.01); *A61K 45/06* (2013.01); *A61P 35/00* (2018.01); *C12N 5/0636* (2013.01); *A61K 38/00* (2013.01); *A61K 2239/31* (2023.05); *A61K 2239/38* (2023.05); *A61K 2239/48* (2023.05); *C07K 2319/00* (2013.01)

(56) References Cited

U.S. PATENT DOCUMENTS

| | | | | |
|---|---|---|---|---|
| 2018/0133296 | A1* | 5/2018 | Barrett | C07K 16/2803 |
| 2018/0243411 | A1 | 8/2018 | June et al. | |
| 2018/0305452 | A1 | 10/2018 | Orentas et al. | |
| 2019/0314410 | A1 | 10/2019 | Rossi et al. | |

OTHER PUBLICATIONS

Xu, Y., (2014) Closely related T-memory stem cells correlate with in vivo expansion of CAR.CD19-T cells and are preserved by IL-7 and IL-15 Blood 123(24); 3750-3759 (Year: 2014).*

Vairy, S., et al.(2018) CTL019 (tisagenlecleucel): CAR-T therapy for relapsed and refractory B-cell acute lymphoblastic leukemia Drug, Design, Development and Therapy 12; 3885-3898 (Year: 2018).*

Xu, Y., (2014) Closely related T-memory stem cells correlate with in vivo expansion of CAR.CD19-T cells and are preserved by IL-7 and IL-15 Blood 123(24); 3750-3759—Supplemental Materials (Year: 2014).*

Chow, V.A., et al (2018) Translating anti-CD19 CAR-T cell therapy into clinical practice for relapsed/refractory diffuse large B-cell lymphoma Blood 132(8); 777-781; pdf pp. 1-9 (Year: 2018).*

NCT02614066 (Sponsor: Kite, A Gilead Company) Posted Jan. 22, 2019 (Year: 2019).*

Friedman, K.M, et al (2018) Effective targeting of Multiple B-cell Maturation Antigen-expressing hematological malignancies by Anti-B-Cell Maturation Antigen Chimeric Antigen Receptor T cells Human Gene Therapy 29(5); 585-601 (Year: 2018).*

NCT02614066 (Sponsor: Kite, A Gilead Company) Posted Mar. 22, 2023 (Year: 2023).*

Clinical Trial NCT03105336 v26 (Sponsor: Kite, A Gilead Company) update posted Feb. 15, 2019 (Year: 2019).*

Foon, K.A., et al (2012) Novel therapies for aggressive B-Cell lymphoma Advances in Hematology 302570; 1-22 (Year: 2012).*

Yang, Y., et al (2017) TCR engagement negatively affects CD8 but not CD4 CAR T cell expansion and leukemic clearance Sci Transl Med 9(417); 1-23 (Year: 2017).*

Lewandowska, A.M., et al (2017) Environmental risk factors for cancer—review paper Ann. Agric. Environ. Med. 26(1); 1-7 (Year: 2017).*

Cuzick, J. (2017) Preventive therapy for cancer Lancet Oncol 18; e472-e482 (Year: 2017).*

DeCensi, A., et al (2015) Barriers to preventative therapy for breast and other major cancers and strategies to improve uptake ecancer 9(595); 1-12 (Year: 2015).*

Xu, X., et al (2019) Mechanisms of Relapse after CD19 CAR T-cell therapy for acute lymphoblastic leukemia and its prevention and treatment strategies Frontiers in Immunology 10(2664); 1-15 (Year: 2019).*

Neelapu, S.S. (2017) Axicabtagene Ciloleucel CAR T-cell Therapy in Refractory Large B-Cell Lymphoma N. Engl. J. Med. 377(26); 2531-2544 and supplemental materials (Year: 2017).*

Sommermeyer, D., et al (2016) Chimeric antigen receptor-modified T cells derived from defined CD8+ and CD4+ subsets confer superior antitumor reactivity in vivo Leukemia 30(2); 492-500 (Year: 2016).*

Chong et al., "PD-1 blockade modulates chimeric antigen receptor (CAR)-modified T cells: refueling the CAR", Blood, Feb. 23, 2017, Vo. 129, No. 8, pp. 1039-1041.

Frey et al. "Cytokine Release Syndrome with Chimeric Antigen Receptor T Cell Therapy", Biol. Blood Marrow Transplant, 25, 2019; e123-e127.

"KYMRIAH Prescribing information", Novartis, May 31, 2018, p. 1-25.

Locke et al., "Tumor burden, inflammation, and product attributes determine outcomes of axicabtagene ciloleucel in large B-cell lymphoma", Blood, Oct. 13, 2020, vol. 4, No. 19, pp. 4898-4911.

Park et al., "Long-Term Follow-up of CD19 CAR Therapy in Acute Lymphoblastic Leukemia", N. Engl. J. Med, Feb. 1, 2018, 378:5; pp. 449-459.

Tsujikawa et al., "Quantitative Multiplex Immunohistochemistry Reveals Myeloid-Inflamed Tumor-Immune Complexity Associated with Poor Prognosis", Cell Reports, 2017, 19, pp. 203-217.

International Search Report and Written Opinion in International Application No. PCT/US2021/018936, dated May 5, 2021.

Office Action issued on Oct. 14, 2024 in foreign counterpart TW Application No. 110106008 with English translation. (16 Pages).

Park J. et al. "Long-Term Follow-up of CD19 CAR Therapy in Acute Lymphoblastic Leukemia" New Engl J. of Medicine 378 (449-459), Feb. 2018.

Chong E.A. et al. "PD-1 blockade modulates chimeric antigen receptor (CAR)-modified T cells: refueling the CAR" Blood 129(8): 1039-1041 Epub Dec. 28, 2016.

Novartis KYMRIAH prescribing information May 31, 2018.

Locke F.L. et al. "Tumor burden, inflammation, and product attributes determine outcomes of axicabtagene ciloleucel in large B-cell lymphoma" Blood Adv (2020) 4 (19): 4898-4911.

Frey N. et al. "Cytokine Release Syndrome with Chimeric Antigen Receptor T Cell Therapy" Biol Blood Marrow Transpl e123-e127.

Tsujikawa T. et al. "Quantitative Multiplex Immunohistochemistry Reveals Myeloid-Inflamed Tumor-Immune Complexity Associated with Poor Prognosis" Cell Reports 203-217 Apr. 4, 2017.

Chono H. et al. Engineering of CD19 CAR T Cells from Non-Hodgkin Lymphoma Patients in a Closed System in Combination with Retronectin/OKT3 Stimulation vol. 124.21 (3 pages).

Jesuraj N. et al. "A Novel Phase-Change Hydrogel Substrate for T Cell Activation Promotes Increased Expansion of CD8+ Cells Expressing Central Memory and Naive Phenotype Markers" vol. 128, Issue 22, Dec. 2, 2016, p. 3368-3370.

Stock S. et al. "Influence of Retronectin-Mediated T-cell Activation on Exapansion and Phenotype of CD19-Specific Chimeric Antigen Receptor T Cells" Human Gene Therapy, vol. 29: 1167-1182.

Stock S. "Idelalsib for Optimized CD19-spefic chimeric antigen receptor T cells in chronic lymphocytic leukemia patients" nternational Journal of Cancer, 145: 1312-1324 (2019).

Tomida A. et al. "Combination Therapy of GD2-Specific CAR-T Cells with Tyrosine Kinase Inhibitors for Neuroblastoma" Mol Ther, vol. 28, p. 146.

Schubert M-L et al. "Third Generation CAR T Cells within the Heidelberg Car Trial 1 (HD-CAR-1) Display an Excellent Safety Profile and Might Improve Persistence of Car T Cells" Bone Marrow Transplant, 46th Annual Meeting of the European Society for Blood and Marrow, pp. 46-47.

(56) References Cited

OTHER PUBLICATIONS

Sauter, C.S. et al. "CD19 CAR T cells following autologous transplantation in poor-risk relapsed and refractory B-cell non-Hodgkin lymphoma" Blood vol. 134: 626-635.
Filosto, S. et al. "Product Attributes of CAR T-Cell Therapy Differentially Associate with Efficacy and Toxicity in Second-Line Large B-cell Lymphoma (ZUMA-7)" Blood Cancer Discovery, Jan. 2024, 22-33.
European Search Report issued on Dec. 2, 2024 in counterpart EP Application 21 756 616.5 (11 pages).
Article 94(3) Communication issued on Dec. 11, 2025 in Foreign Counterpart EP Application No. 21 756 616.5 (6 pages).
Notice of Rejection issued Dec. 29, 2025 in Foreign Counterpart TW Application No. 110106008 with English translation. (8 pages).

\* cited by examiner

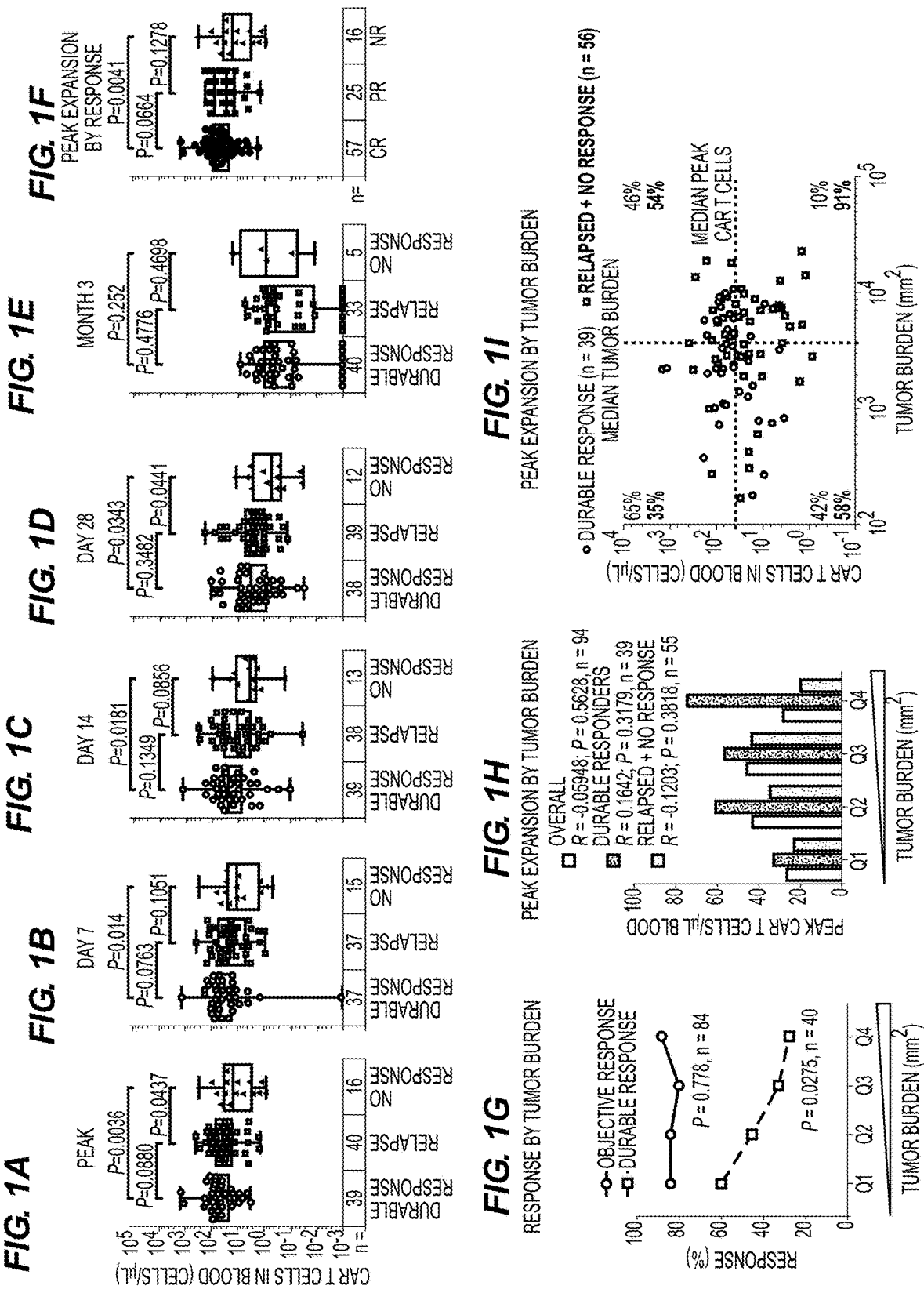

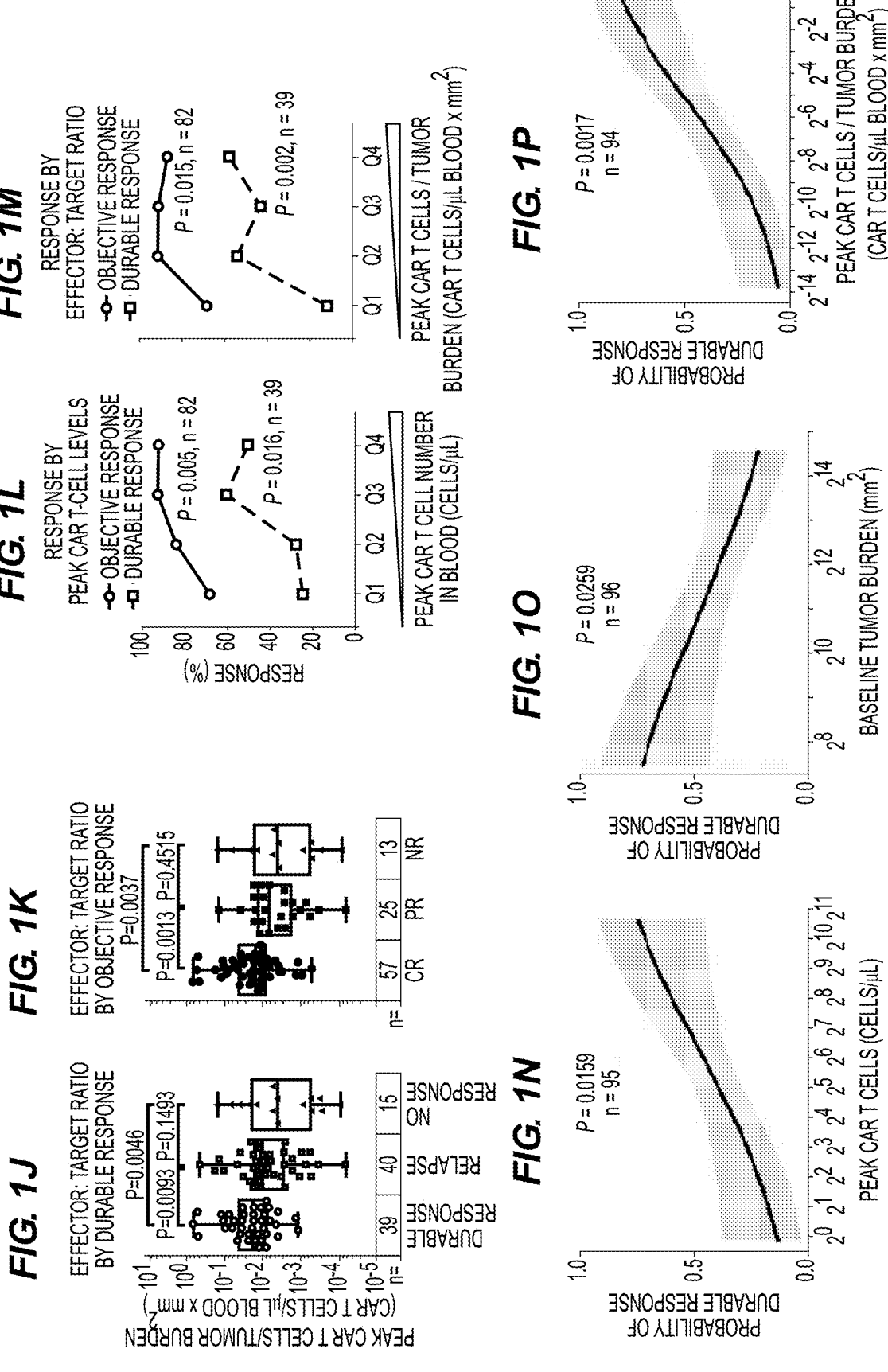

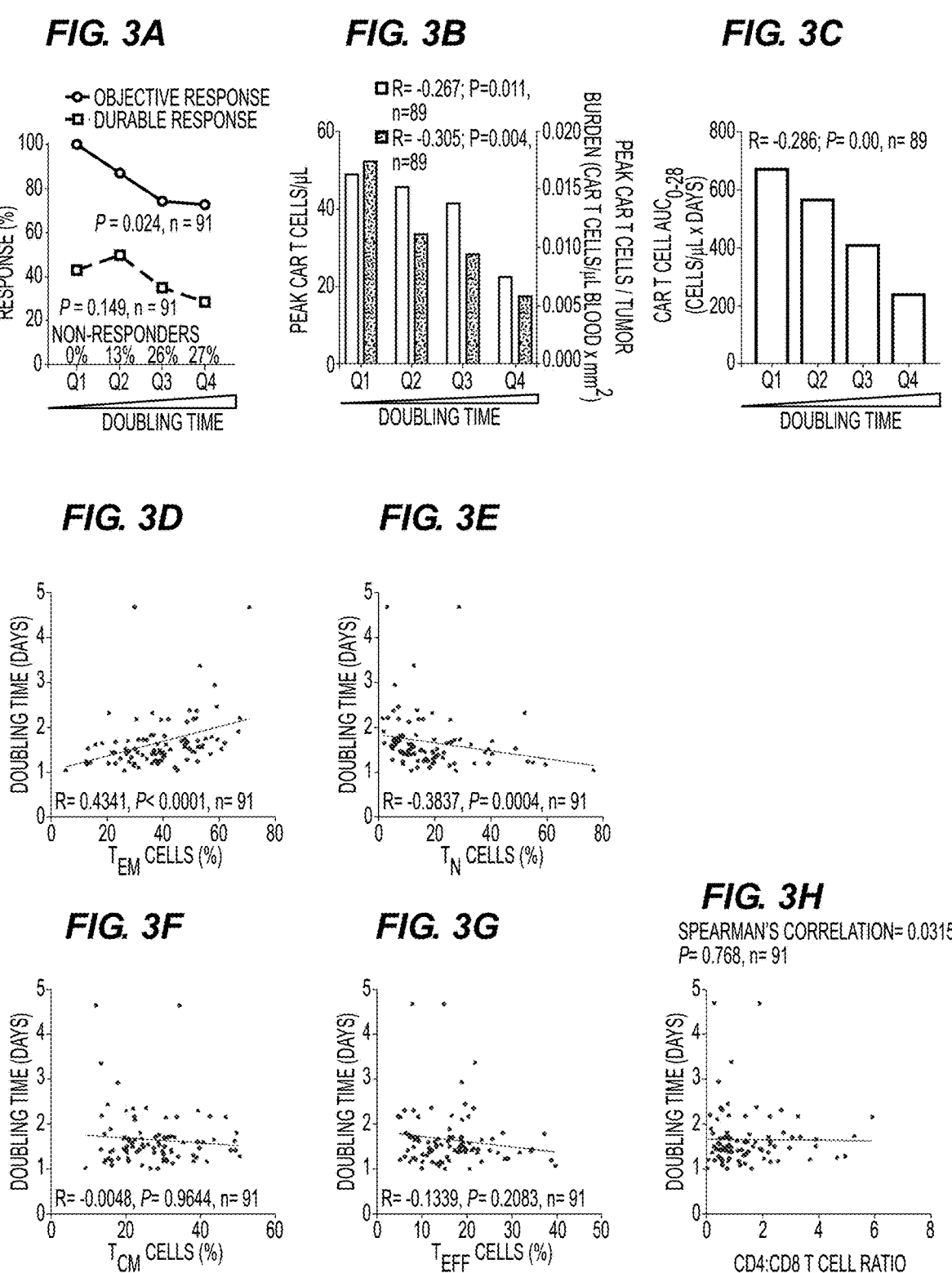

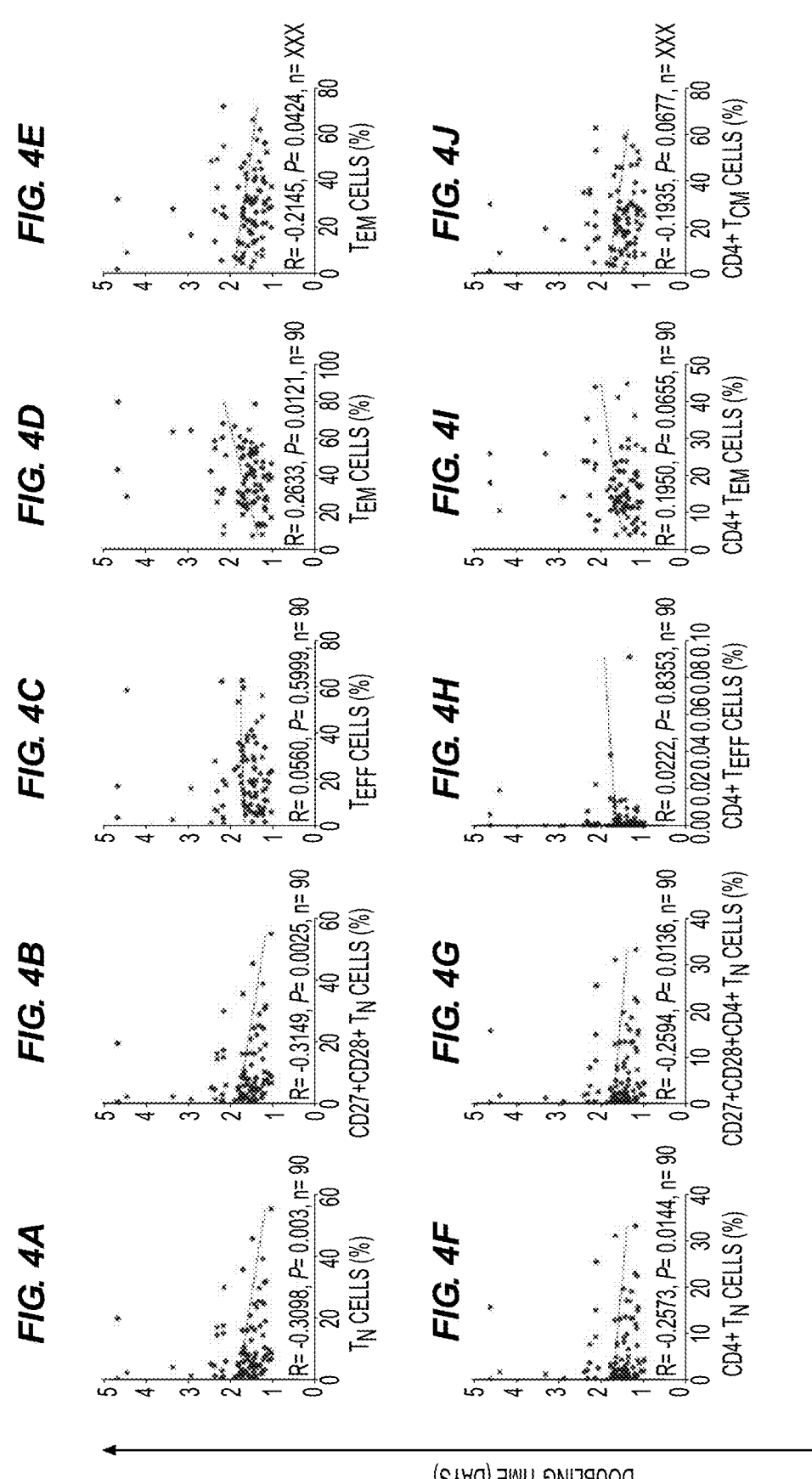

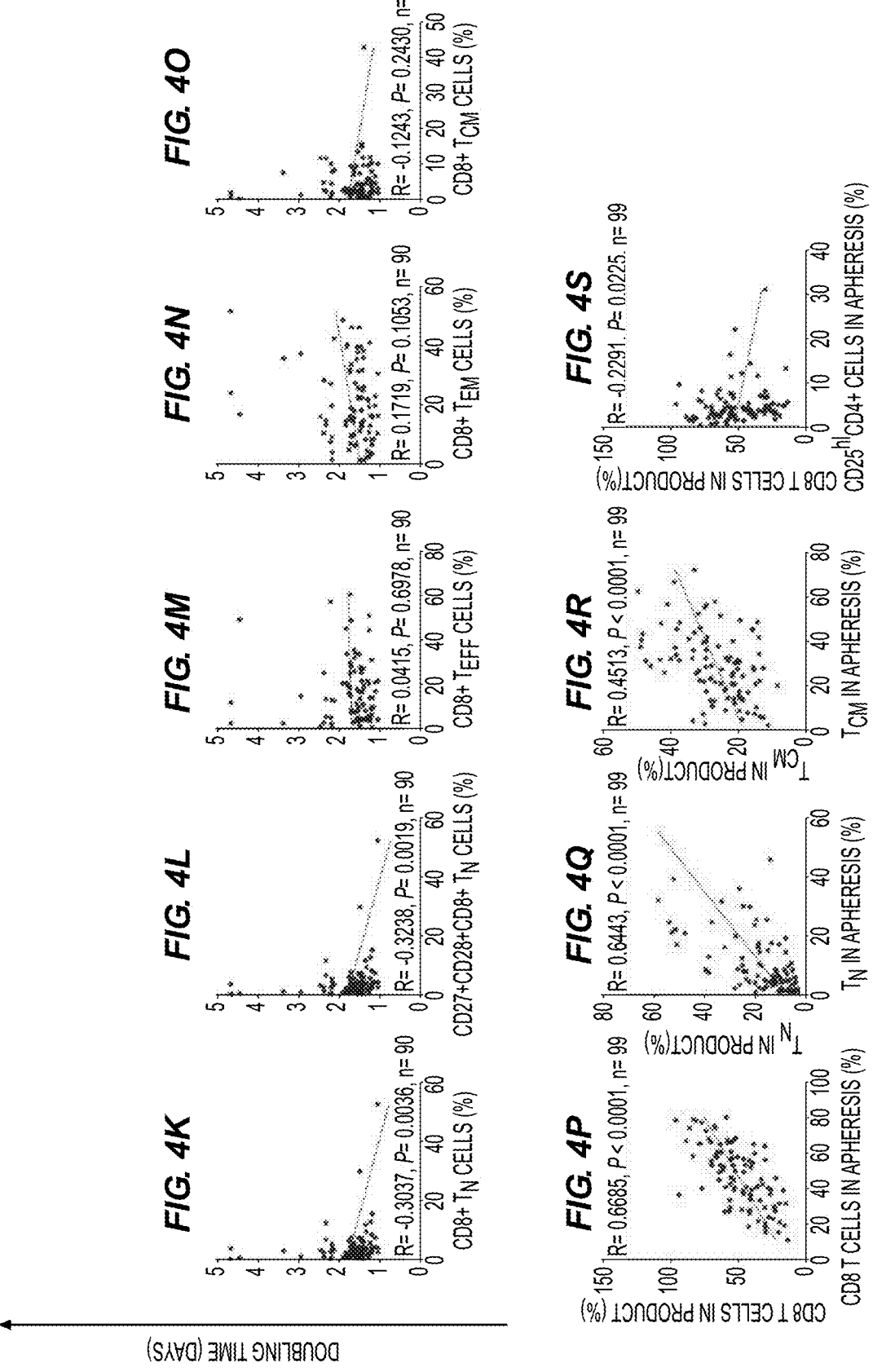

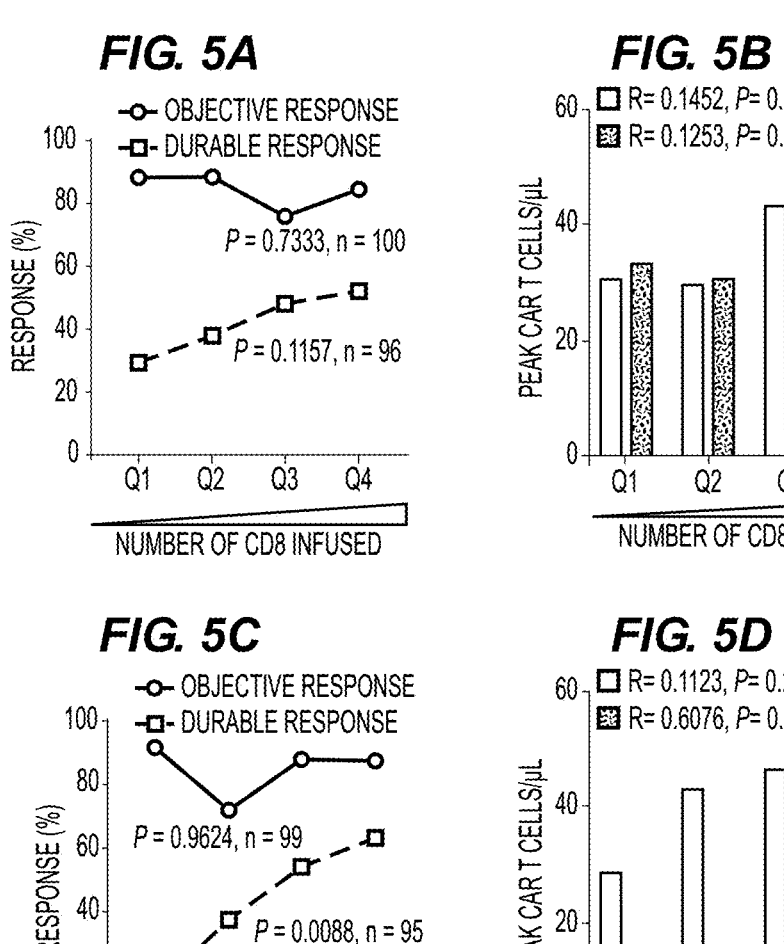
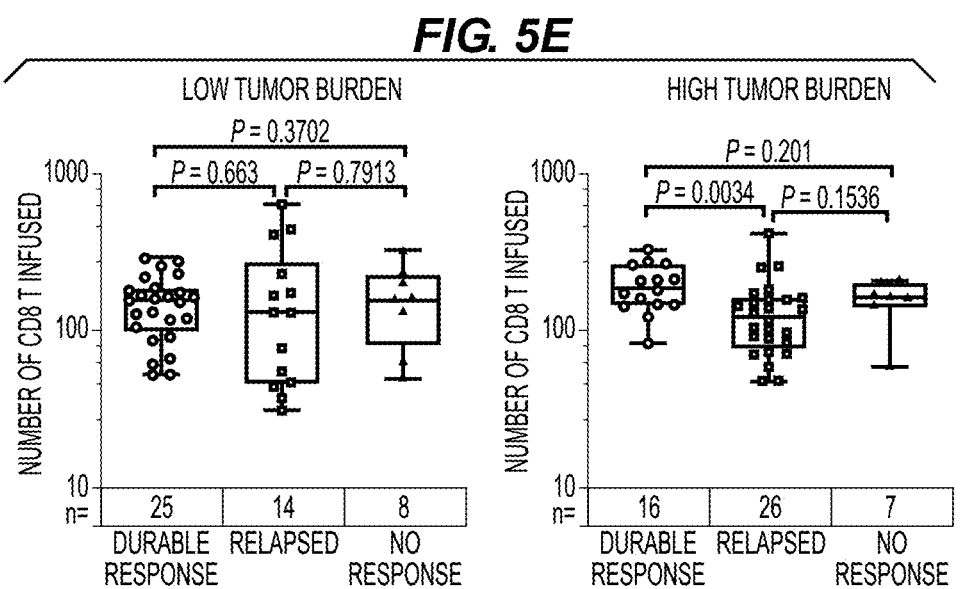

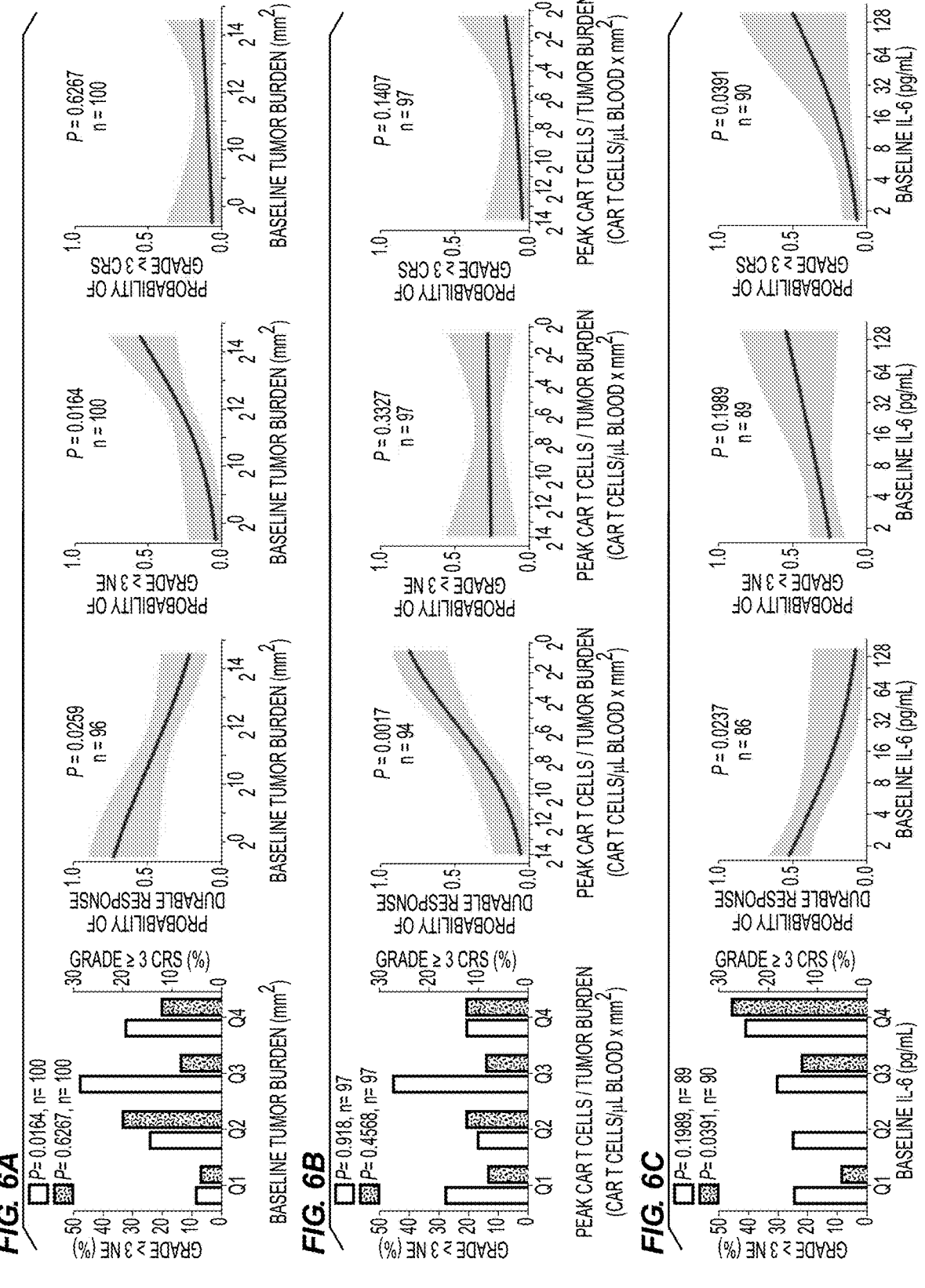

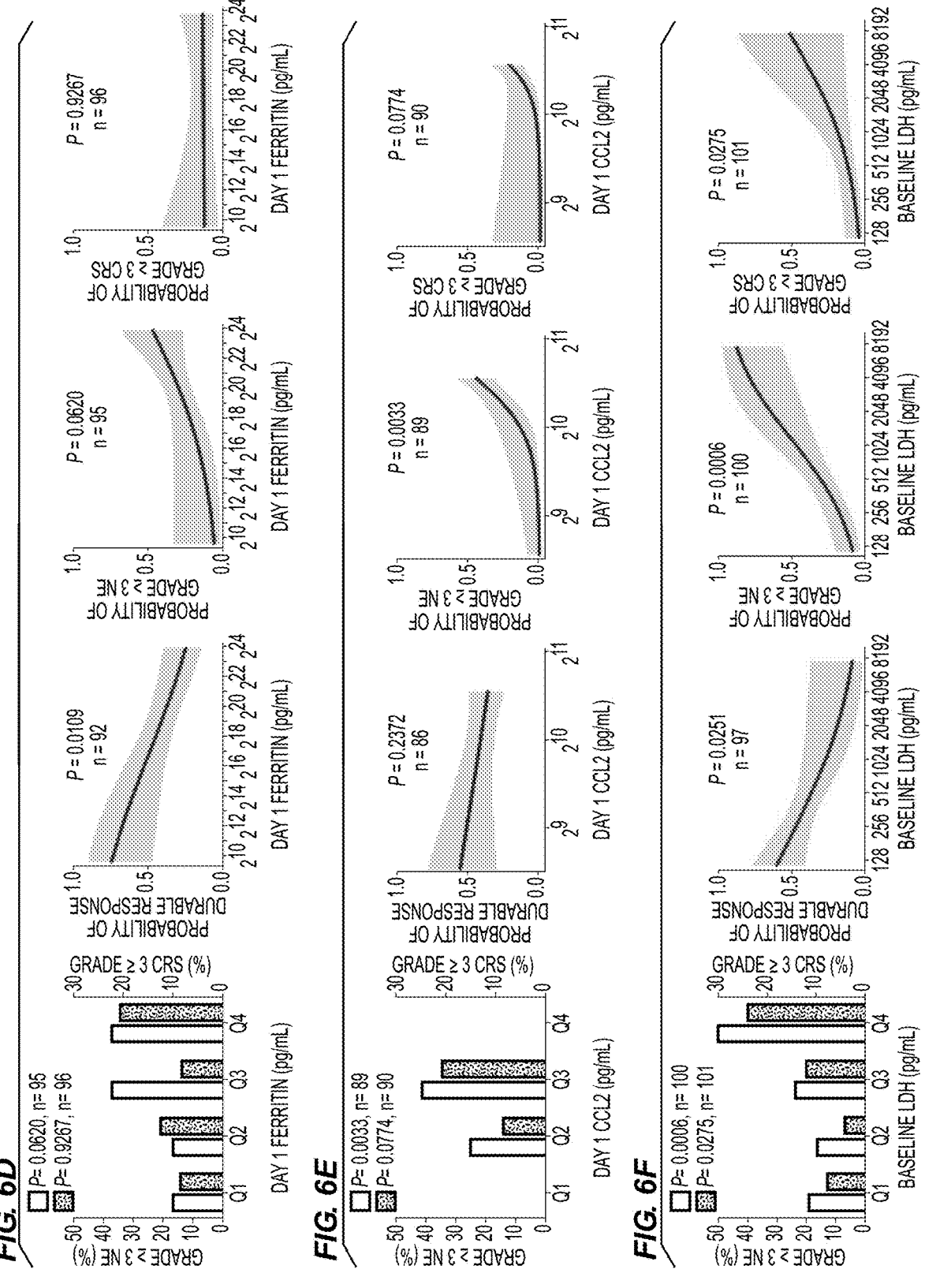

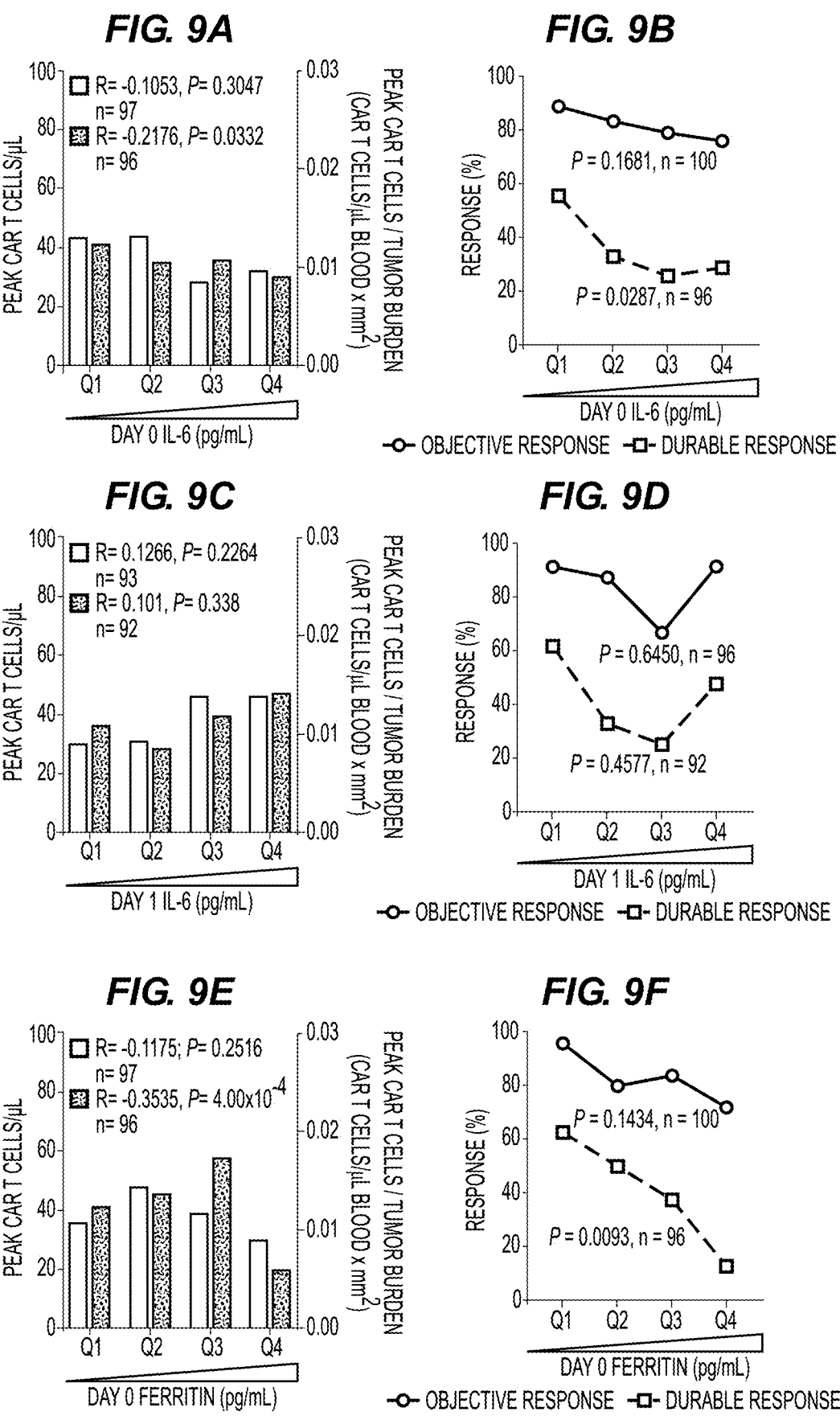

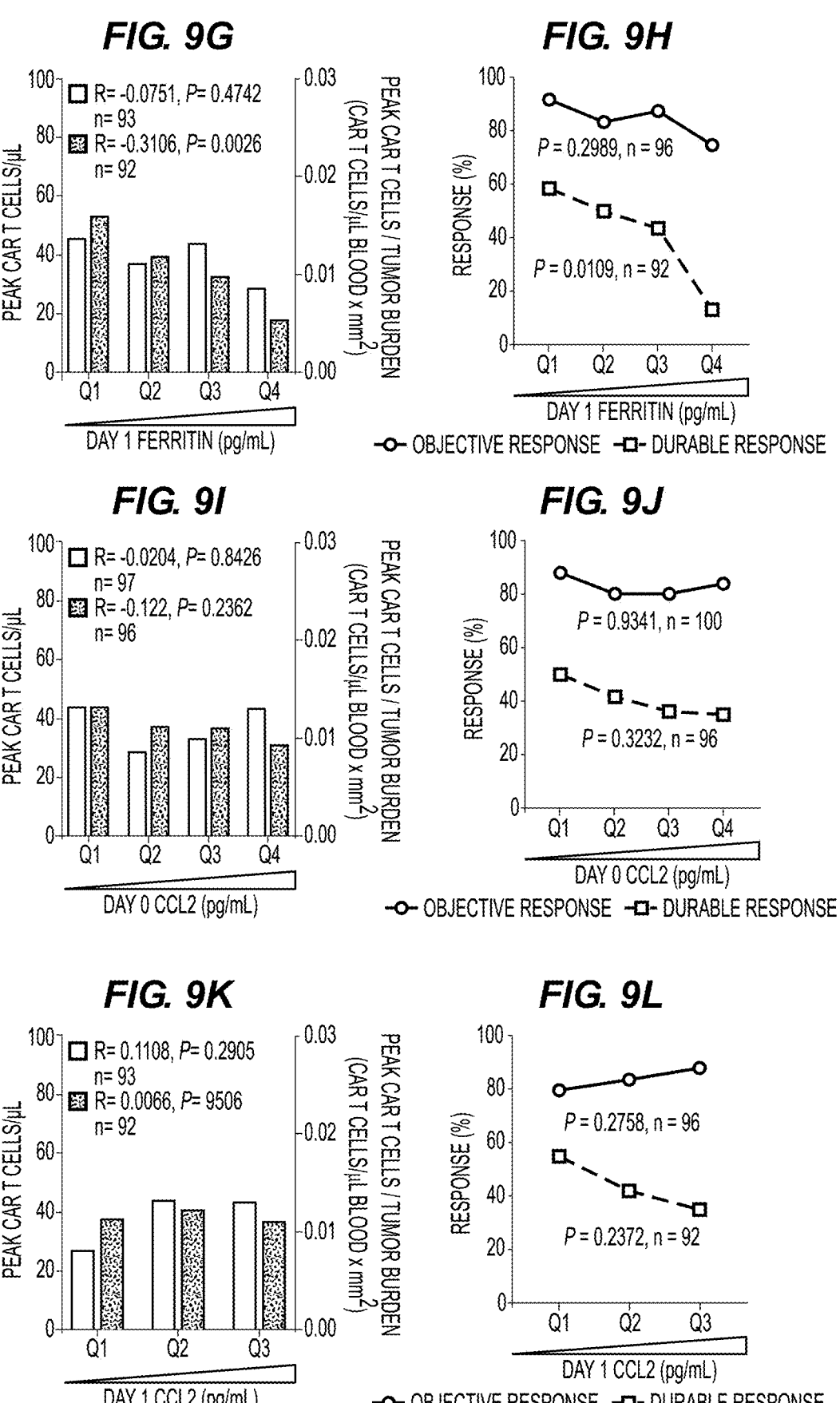

| STATISTICAL TEST | COMPARISON | BASELINE | DAY 0 | DAY 1 | DAY 3 | DAY 5 | DAY 7 | DAY 14 | DAY 28 | PEAK | AUC$_{0-28}$ |
|---|---|---|---|---|---|---|---|---|---|---|---|
| | *P* VALUE FROM SPECIFIED FERRITIN MEASUREMENT | | | | | | | | | | |
| DUNN'S TEST | DURABLE VS RELAPSED | 0.136 | 0.004 | 0.004 | 0.036 | 0.053 | 0.009 | 0.107 | 0.001 | 0.01 | 0.016 |
| | DURABLE VS NO RESPONSE | 0.046 | 0.005 | 0.015 | 0.054 | 0.339 | 0.286 | 0.471 | 0.148 | 0.228 | 0.227 |
| | RELAPSED VS NO RESPONSE | 0.197 | 0.313 | 0.417 | 0.444 | 0.24 | 0.143 | 0.266 | 0.164 | 0.18 | 0.223 |
| KW TEST | OVERALL | 0.094 | 0.002 | 0.005 | 0.04 | 0.108 | 0.022 | 0.196 | 0.002 | 0.025 | 0.037 |

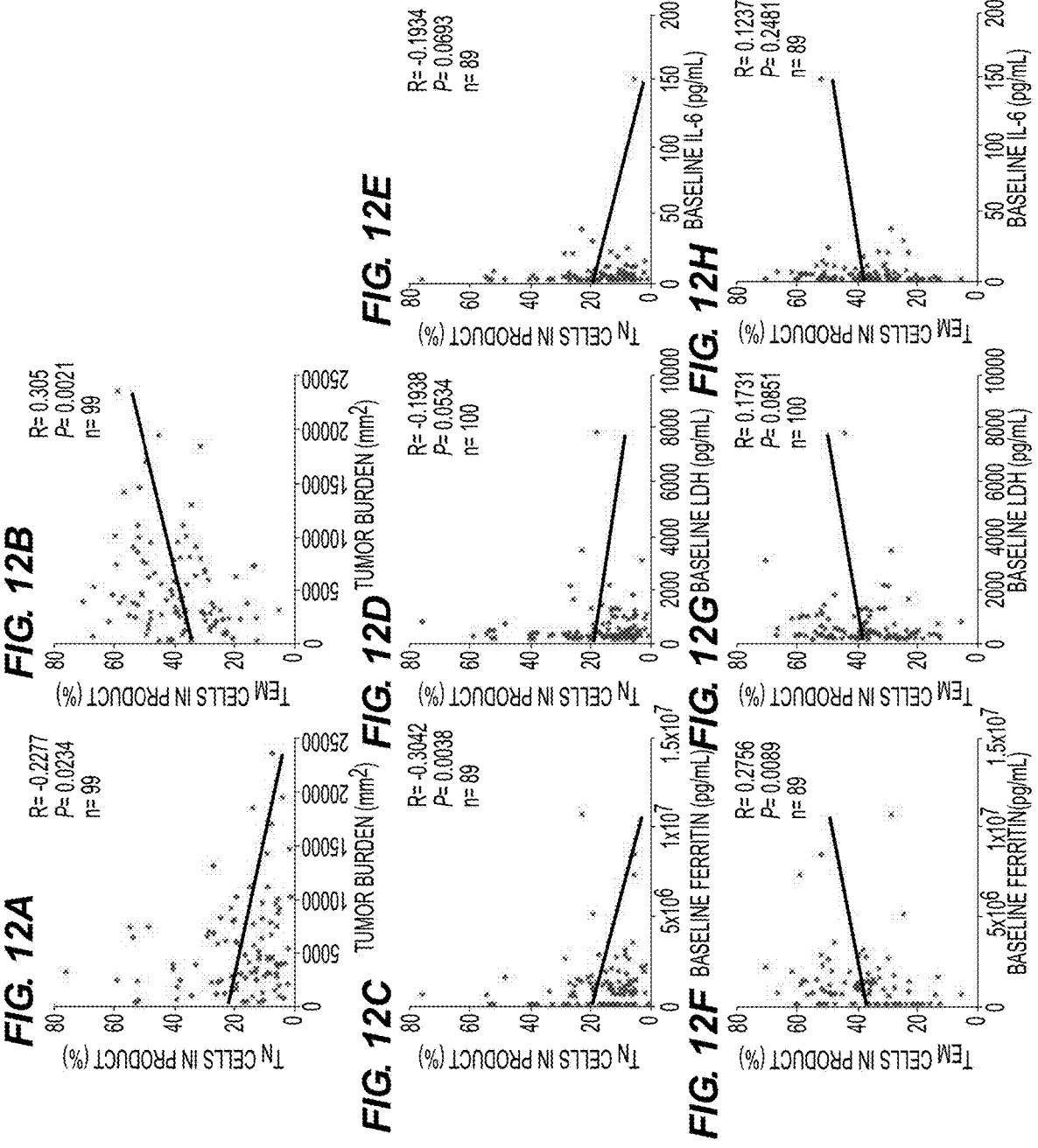

FIG. 13A          FIG. 13B
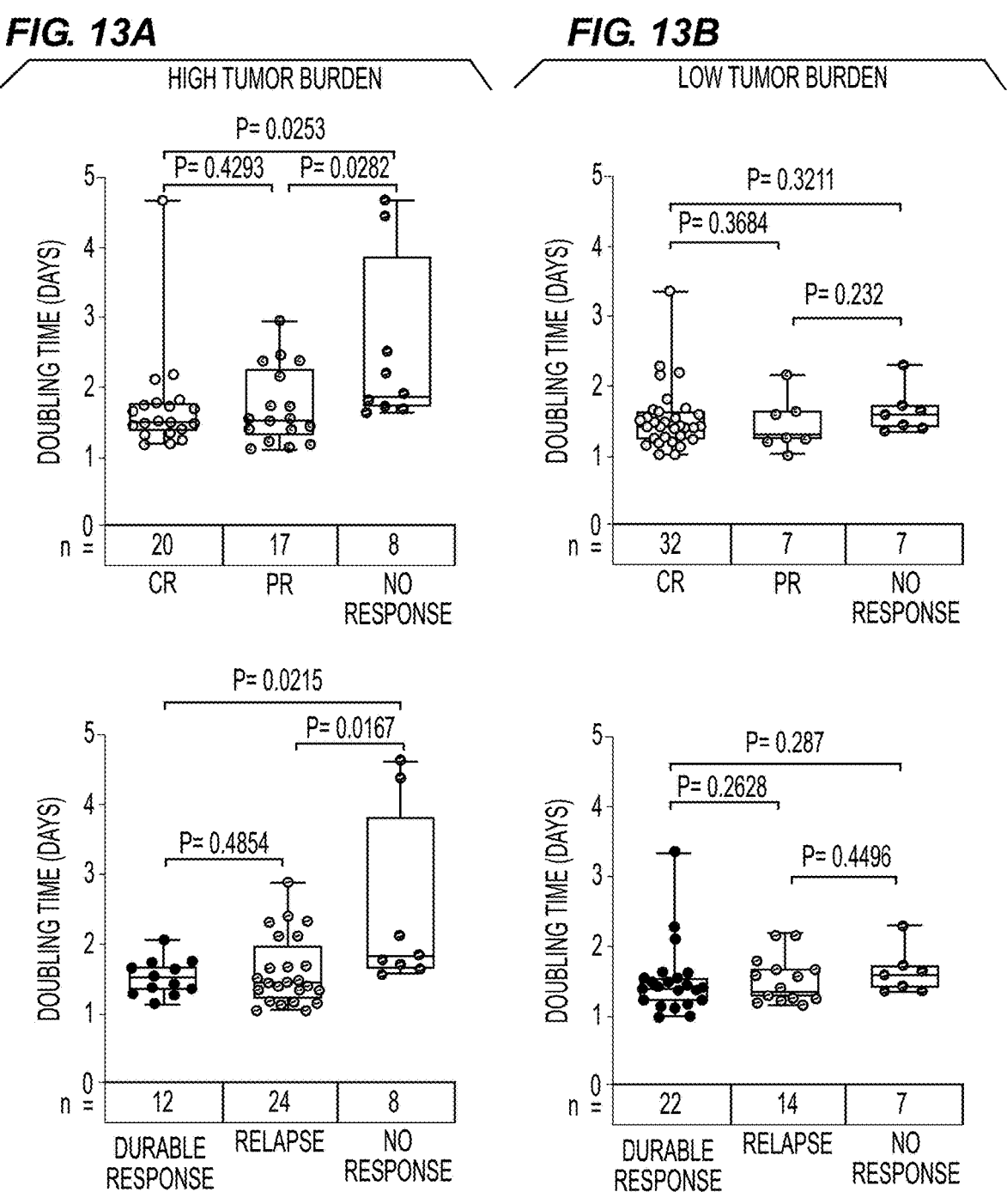

*P* = 0.9660, n = 100

*P* = 0.9296, n = 96

—O— OBJECTIVE RESPONSE  —□— DURABLE RESPONSE

□ R= -0.1155; *P*= 0.2572
 n= 98
▧ R= -0.0322; *P*= 0.7543
 n= 97

*P* = 0.8519, n = 99

*P* = 0.0586, n = 95

—O— OBJECTIVE RESPONSE  —□— DURABLE RESPONSE

□ R= 0.0206; *P*= 0.8414
 n= 97
▧ R= 0.5509; *P*≤ 0.0001
 n= 97

*P* = 0.8366, n = 100

*P* = 0.6540, n = 96

—O— OBJECTIVE RESPONSE  —□— DURABLE RESPONSE

□ R= 0.0787, *P*= 0.4412
 n= 98
▧ R= 0.1428, *P*= 0.163
 n= 97

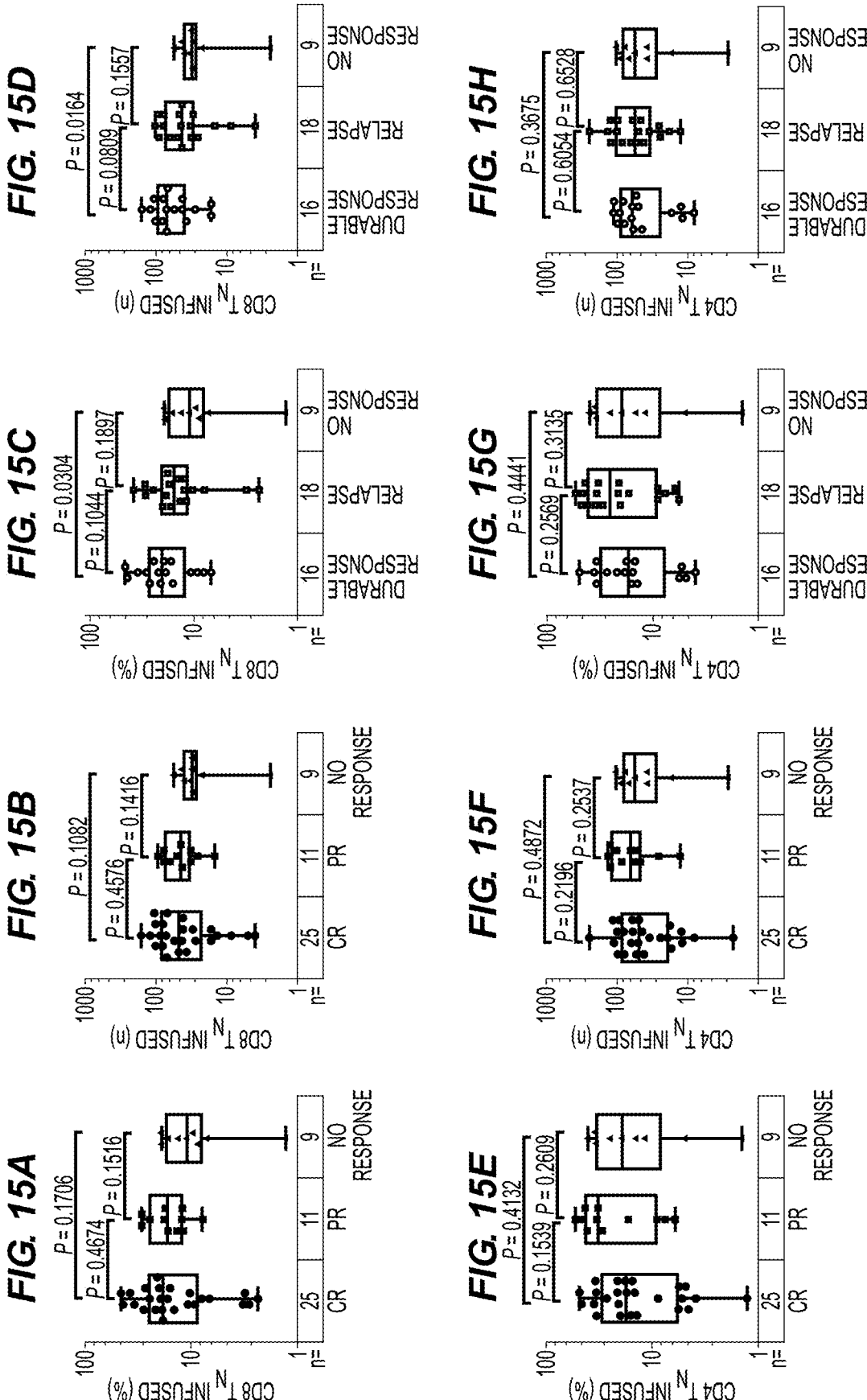

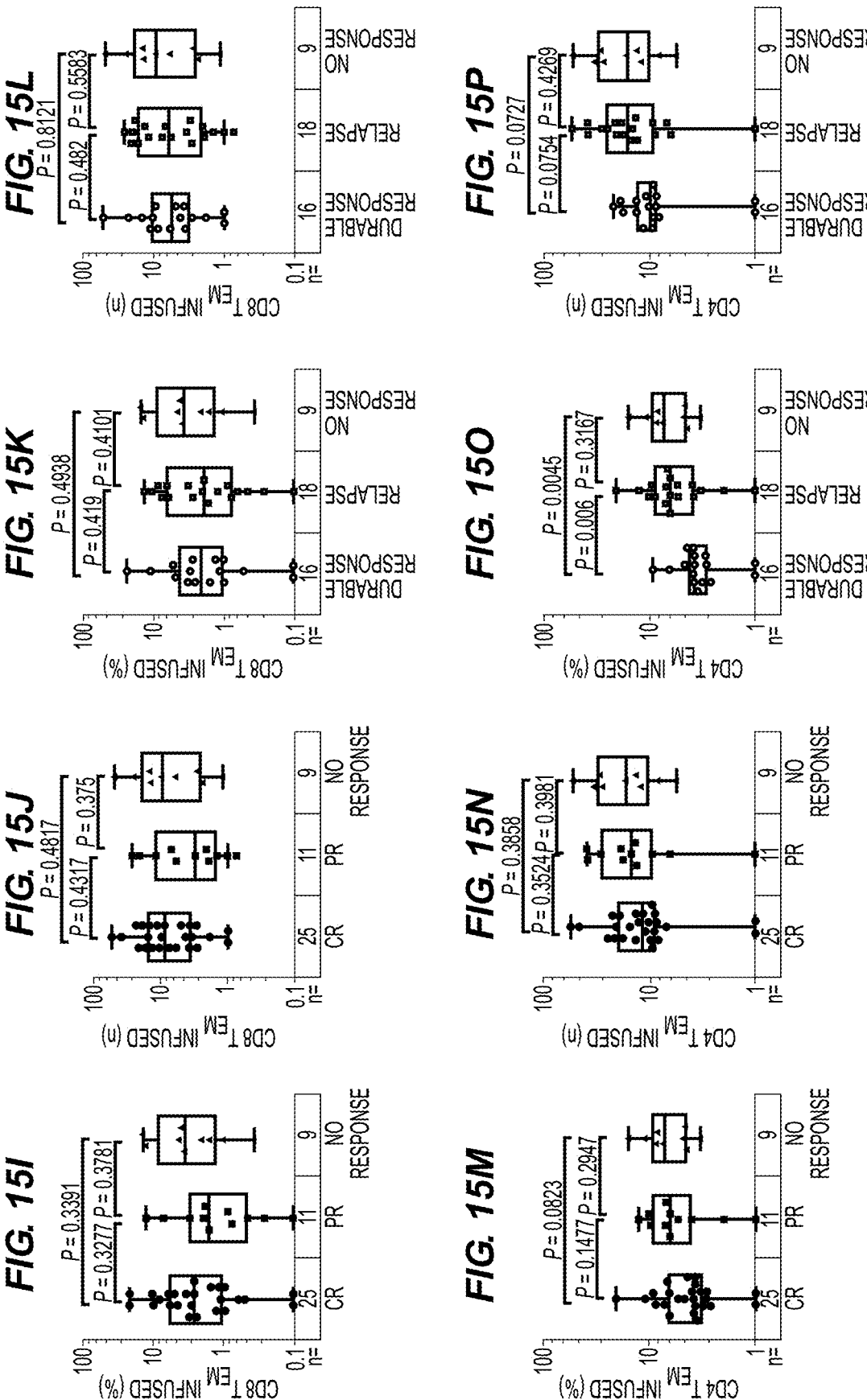

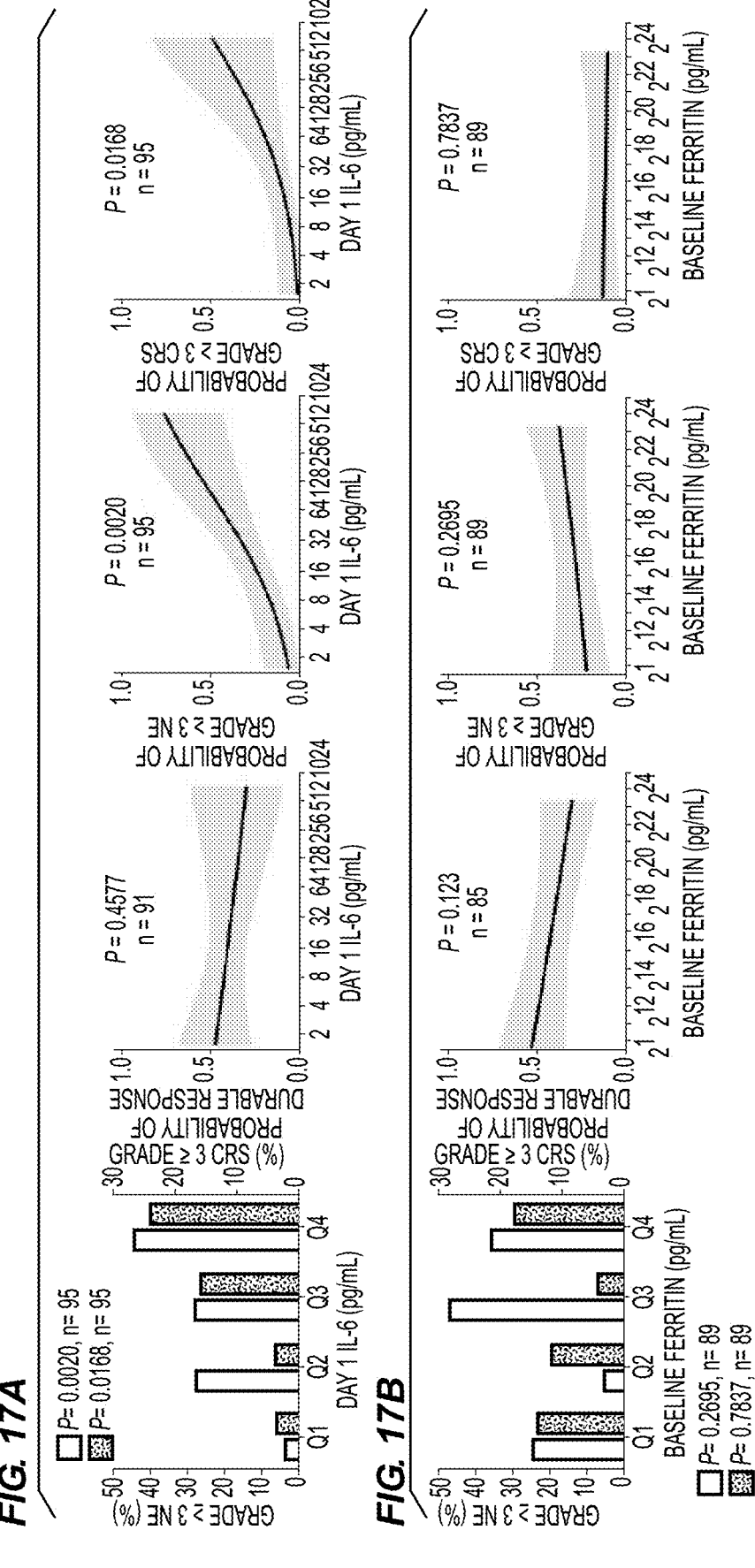

FIG. 20A
PEAK CAR T CELLS/TUMOR BURDEN    EFFICACY(DURABLE RESPONSE VS OTHER)
FIG. 20B
PEAK CAR T CELLS/TUMOR BURDEN    SAFETY (NE ≥ 3)
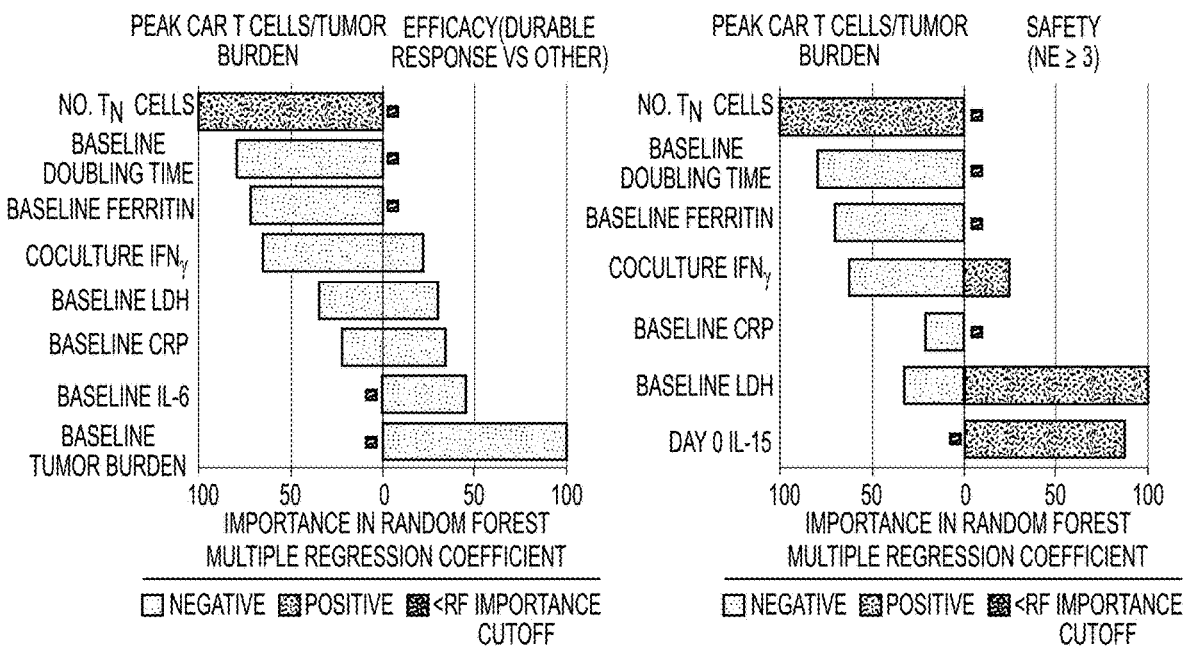
FIG. 20C
PEAK CAR T CELLS/TUMOR BURDEN    SAFETY (CRS ≥ 3)
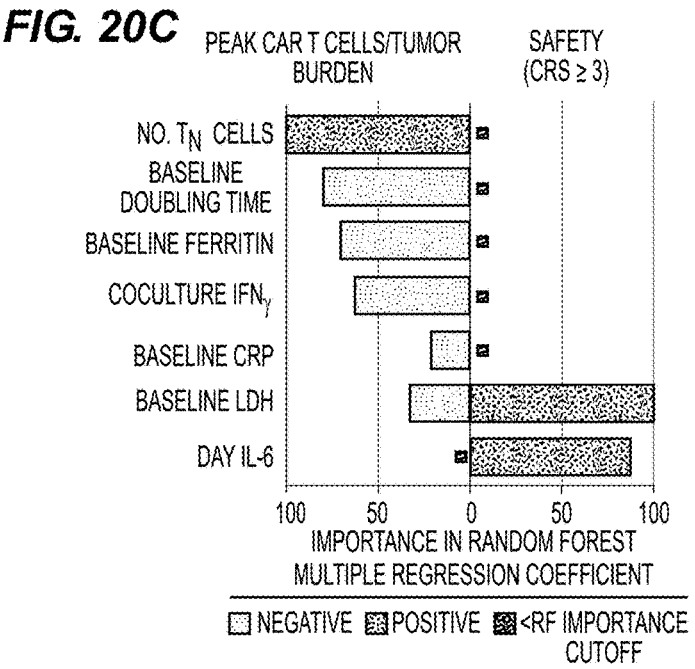

FIG. 21A

CAR T-CELL EXPANSION
PEAK CAR T CELLS

|  | QUARTILE 1 (n = 25) | QUARTILE 2 (n = 24) | QUARTILE 3 (n = 25) | QUARTILE 4 (n = 24) |
|---|---|---|---|---|
| MEDIAN PEAK CAR T CELLS, RANGE, CELLS/μL BLOOD | 4.47 (0.84, 14.68) | 26.25 (16.89, 35.27) | 58.63 (41.23, 82.96) | 127.83 (84.92, 1513.69) |

PEAK CAR T CELLS/TUMOR BURDEN

|  | QUARTILE 1 (n = 25) | QUARTILE 2 (n = 24) | QUARTILE 3 (n = 24) | QUARTILE 4 (n = 24) |
|---|---|---|---|---|
| MEDIAN PEAK CAR T CELLS/TUMOR BURDEN (RANGE), CELLS/μL BLOOD X mm$^2$ | 0.001 (1e-04, 0.004) | 0.01 (0.0041, 0.01) | 0.02 (0.01, 0.03) | 0.07 (0.03, 0.69) |

PEAK CAR T CELLS/BODY WEIGHT

|  | QUARTILE 1 (n = 25) | QUARTILE 2 (n = 24) | QUARTILE 3 (n = 25) | QUARTILE 4 (n = 24) |
|---|---|---|---|---|
| MEDIAN PEAK CAR T CELLS/BODY WEIGHT (RANGE), CELLS/μL BLOOD X kg | 0.07 (0.01, 0.16) | 0.33 (0.17, 0.49) | 0.71 (0.52, 1) | 1.75 (1.01, 23.81) |

*FIG. 21B*

BASELINE CHARACTERISTICS

TUMOR BURDEN

| | QUARTILE 1 (n = 25) | QUARTILE 2 (n = 25) | QUARTILE 3 (n = 25) | QUARTILE 4 (n = 25) |
|---|---|---|---|---|
| MEDIAN TUMOR BURDEN, (RANGE), mm³ | 1008 (171, 2158) | 2847 (2200, 3719) | 5167 (3723, 7138) | 9371 (7141, 23297) |

*FIG. 21C*

FERRITIN

| MEDIAN FERRITIN (RANGE), pg/mL, BASELINE | QUARTILE 1 (n = 28) | QUARTILE 2 (n = 17) | QUARTILE 3 (n = 23) | QUARTILE 4 (n = 22) |
|---|---|---|---|---|
| MEDIAN (MIN, MAX) | 800 (780, 800 ) | 586400 (442400, 776800) | 1103300 (795080, 1393170) | 2517655 (1464050, 10576100) |

| MEDIAN FERRITIN (RANGE), pg/mL, DAY0 | QUARTILE 1 (n = 25) | QUARTILE 2 (n = 25) | QUARTILE 3 (n = 25) | QUARTILE 4 (n = 25) |
|---|---|---|---|---|
| MEDIAN (MIN, MAX) | 800 (780, 576200) | 760500 (578700, 1012400) | 1526800 (1030450, 2016210) | 2897500 (2087000, 14038250) |

FIG. 21C (CONTINUED)

LDH

|  | QUARTILE 1 (n = 26) | QUARTILE 2 (n = 25) | QUARTILE 3 (n = 25) | QUARTILE 4 (n = 25) |
|---|---|---|---|---|
| MEDIAN LDH (RANGE), pg/mL, BASELINE | | | | |
| MEDIAN (MIN, MAX) | 183.5 (116, 219) | 258 222, 356 | 457 (357, 743) | 1196 (765, 7802) |

IL6

|  | QUARTILE 1 | QUARTILE 2 | QUARTILE 3 | QUARTILE 4 |
|---|---|---|---|---|
| MEDIAN IL6 (RANGE), pg/mL, BASELINE | (n = 41) | (n = 4) | (n = 23) | (n = 22) |
| MEDIAN (MIN, MAX) | 1.6 (1.6, 1.6) | 3.44 (3.35, 3.6) | 4.9 (3.8, 6.8) | 12.67 (7.1, 150.3) |
| MEDIAN IL6 (RANGE), pg/mL, DAY0 | (n = 45) | (n = 6) | (n = 24) | (n = 25) |
| MEDIAN (MIN, MAX) | 1.6 (1.6, 1.6) | 3.36 (3.23, 3.4) | 4.13 (3.48, 6.5) | 12.22 (6.73, 123.1) |
| MEDIAN IL6 (RANGE), pg/mL DAY 1 | (n = 24) | (n = 24) | (n = 24) | (n = 24) |
| MEDIAN (MIN, MAX) | 3.29 (1.6, 6.14) | 10.88 (6.5, 14.1) | 21.55 (14.85, 34.05) | 84.4 (34.46, 693.5) |

FIG. 21C (CONTINUED)

CCL2

| MEDIAN CCL2 (RANGE), pg/mL, BASELINE | QUARTILE 1 (n = 23) | QUARTILE 2 (n = 22) | QUARTILE 3 (n = 23) | QUARTILE 4 (n = 22) |
|---|---|---|---|---|
| MEDIAN (MIN, MAX) | 229 ( 95.82, 278.5 ) | 305.94 ( 281.6, 332.48 ) | 372.2 ( 342.1, 430) | 528.5 ( 431.7, 887.73) |
| MEDIAN CCL2 (RANGE), pg/mL, DAY 0 | QUARTILE 1 (n = 25) | QUARTILE 2 (n = 25) | QUARTILE 3 (n = 25) | QUARTILE 4 (n = 25) |
| MEDIAN (MIN, MAX) | 469.3 ( 264.06, 591.14) | 734.3 ( 597.6, 852.1) | 1057.3 ( 860.42, 1294.2 ) | 1500 (1307.61, 1500) |
| MEDIAN CCL2 (RANGE), pg/mL, DAY 1 | QUARTILE 1 (n = 24) | QUARTILE 2 (n = 24) | QUARTILE 3 (n = 48) | |
| MEDIAN (MIN, MAX) | 518.6 ( 373.21, 742.59) | 1151.74 ( 759.07, 1366.2 ) | 1500 ( 1384.5, 1500 ) | |

DAY 1 CXCL10

| MEDIAN DAY 1 CXCL10 (RANGE), pg/mL | QUARTILE 1 (n = 24) | QUARTILE 2 (n = 24) | QUARTILE 3 (n = 24) | QUARTILE 4 (n = 24) |
|---|---|---|---|---|
| MEDIAN (MIN, MAX) | 416.48 (151.8, 531.7) | 743.6 (556.5, 952.7) | 1189.7 (963.8, 1463.2) | 1827 (1545.7, 2000) |

DAY 1/DAY 0 IFN$\gamma$

| MEDIAN DAY 1/DAY 0 IFN$\gamma$ (RANGE) | QUARTILE 1 (n = 24) | QUARTILE 2 (n = 24) | QUARTILE 3 (n = 24) | QUARTILE 4 (n = 23) |
|---|---|---|---|---|
| MEDIAN (MIN, MAX) | 1.8 | 7.62 | 16.09 | 39.19 |
| | (0.98, 3.29) | (3.49, 10.57) | (10.61, 25.42) | (25.71, 250.13) |

FIG. 21D

INFUSED NAIVE-LIKE T CELLS

|  | QUARTILE 1 (n = 25) | QUARTILE 2 (n = 25) | QUARTILE 3 (n = 25) | QUARTILE 4 (n = 25) |
|---|---|---|---|---|
| MEDIAN INFUSED $T_N$ CELLS (RANGE), CELLS | 14.64 (2.09, 23.15) | 29.61 (23.54, 39.79) | 54.84 (39.97, 77.84) | 105.24 (80.19, 214.95) |

INFUSED NAIVE-LIKE T CELLS/TUMOR BURDEN

|  | QUARTILE 1 (n = 25) | QUARTILE 2 (n = 25) | QUARTILE 3 (n = 25) | QUARTILE 4 (n = 24) |
|---|---|---|---|---|
| MEDIAN INFUSED $T_N$ CELLS/TUMOR BURDEN (RANGE), CELLS/mm$^2$ | 0.0025 (2e-04, 0.01) | 0.01 (0.01, 0.01) | 0.02 (0.01, 0.03) | 0.07 (0.03, 0.49) |

INFUSED CD8 T CELLS

|  | QUARTILE 1 (n = 25) | QUARTILE 2 (n = 25) | QUARTILE 3 (n = 25) | QUARTILE 4 (n = 25) |
|---|---|---|---|---|
| MEDIAN INFUSED CD8 T CELLS (RANGE), CELLS | 61.86 (31.99, 93.07) | 132.83 (93.21, 151.89) | 166.23 (152.27, 201.42) | 261.42 (202.82, 642.49) |

INFUSED CD8 T CELLS/TUMOR BURDEN

|  | QUARTILE 1 (n = 25) | QUARTILE 2 (n = 25) | QUARTILE 3 (n = 25) | QUARTILE 4 (n = 24) |
|---|---|---|---|---|
| MEDIAN INFUSED CD8 T | 0.01 | 0.03 | 0.05 | 0.15 |

FIG. 21D (CONTINUED)

| CELLS/TUMOR BURDEN (RANGE), CELLS/mm$^2$ | (0.0047, 0.02) | (0.02, 0.03) | (0.04, 0.08) | (0.08, 1.52) |
|---|---|---|---|---|

INFUSED NAIVE-LIKE CD8 T CELLS/TUMOR BURDEN

| | QUARTILE 1 (n = 12) | QUARTILE 2 (n = 11) | QUARTILE 3 (n = 11) | QUARTILE 4 (n = 11) |
|---|---|---|---|---|
| MEDIAN INFUSED CD8 T$_N$ CELLS/TUMOR BURDEN (RANGE), CELLS/mm$^2$ | 0.0026 (3e-04, 0.0049) | 0.01 (0.01, 0.01) | 0.01 (0.01, 0.02) | 0.03 (0.02, 0.43) |

INFUSED CD4 T CELLS

| | QUARTILE 1 (n = 25) | QUARTILE 2 (n = 25) | QUARTILE 3 (n = 25) | QUARTILE 4 (n = 25) |
|---|---|---|---|---|
| MEDIAN INFUSED CD4 T CELLS (RANGE), CELLS | 64.48 (7.64, 99.15) | 120.13 (102.5, 148.32) | 174.55 (156.15, 189.94) | 216.35 (190.85, 374.05) |

INFUSED CD4 T CELLS/TUMOR BURDEN

| | QUARTILE 1 (n = 25) | QUARTILE 2 (n = 25) | QUARTILE 3 (n = 25) | QUARTILE 4 (n = 24) |
|---|---|---|---|---|
| MEDIAN INFUSED CD4 T CELLS/TUMOR BURDEN (RANGE), CELLS/mm$^2$ | 0.01 (0.0025, 0.02) | 0.03 (0.02, 0.04) | 0.05 (0.04, 0.09) | 0.14 (0.09, 1.37) |

INFUSED CD3 T CELLS

| | QUARTILE 1 (n = 25) | QUARTILE 2 (n = 25) | QUARTILE 3 (n = 25) | QUARTILE 4 (n = 25) |
|---|---|---|---|---|

FIG. 21D (CONTINUED)

| MEDIAN INFUSED CD3 T CELLS (RANGE), CELLS | 212.61 (147.43, 241) | 272.4 (243.45, 289.64) | 320.85 (289.67, 353.86) | 446.92 (356.21, 717.87) |
|---|---|---|---|---|

INFUSED CD3 T CELLS/TUMOR BURDEN

| | QUARTILE 1 (n = 25) | QUARTILE 2 (n = 25) | QUARTILE 3 (n = 25) | QUARTILE 4 (n = 24) |
|---|---|---|---|---|
| MEDIAN INFUSED CD3 T CELLS/TUMOR BURDEN (RANGE), CELLS/mm$^2$ | 0.03 (0.01, 0.04) | 0.06 (0.05, 0.08) | 0.1 (0.08, 0.16) | 0.3 (0.17, 2.15) |

FIG. 21E

DOUBLING TIME

| | QUARTILE 1 (n = 23) | QUARTILE 2 (n = 23) | QUARTILE 3 (n = 23) | QUARTILE 4 (n = 22) |
|---|---|---|---|---|
| MEDIAN DOUBLING TIME (RANGE), DAYS | 1.2 (1.04, 1.33) | 1.44 (1.35, 1.52) | 1.65 (1.53, 1.75) | 2.21 (1.79, 4.67) |

IFNγ IN COCULTURE

| | QUARTILE 1 (n = 26) | QUARTILE 2 (n = 25) | QUARTILE 3 (n = 25) | QUARTILE 4 (n = 25) |
|---|---|---|---|---|
| IFNγ IN COCULTURE(RANGE), pg/mL | 2641 (381, 3481) | 4675 (3519, 5844) | 6846 (6006, 8280) | 10914 (8372, 17791) |

*FIG. 22*

| OUTCOME | DURABLE RESPONSE | | GRADE ≥ 3 NE | | GRADE ≥ 3 CRS | | PEAK CAR T CELLS | | PEAK CAR T CELLS/TUMOR BURDEN | |
|---|---|---|---|---|---|---|---|---|---|---|
| SAMPLE SIZE | 97 | | 101 | | 101 | | 98 | | 97 | |
| OVERALL AUC | 0.5591 | | 0.5667 | | 0.4751 | | 2.0168 | | 2.5096 | |
| NUMBER OF COVARIATES | 5 | | 3 | | 2 | | 4 | | 6 | |
| HIGHEST AUC | 0.6636 | | 0.567 | | 0.4751 | | 2.001 | | 2.4743 | |
| HIGHEST AUC ACHIEVED AT TOP X | 3 | | 2 | | 2 | | 2 | | 4 | |
| RANK | ATTRIBUTE | REGRESSION COEFFICIENT | ATTRIBUTE | REGRESSION COEFFICIENT | ATTRIBUTE | REGRESSION COEFFICIENT | ATTRIBUTE | REGRESSION COEFFICIENT | ATTRIBUTE | REGRESSION COEFFICIENT |
| 1 | BASELINE TUMOR BURDEN | − | BASELINE LDH | + | BASELINE LDH | + | NUMBER OF $T_N$ CELLS IN PRODUCT | + | NUMBER OF $T_N$ CELLS IN PRODUCT | + |
| 2 | BASELINE IL-6 | − | DAY 0 IL-15 | + | BASELINE IL-6 | + | BASELINE DOUBLING TIME | − | BASELINE DOUBLING TIME | − |
| 3 | BASELINE CRP | − | COCULTURE IFN-γ | + | COCULTURE IFN-γ | | BASELINE FERRITIN | + | BASELINE FERRITIN | − |
| 4 | BASELINE LDH | − | BASELINE TUMOR BURDEN | − | DAY 0 IL-15 | | COCULTURE IFN-γ | − | COCULTURE IFN-γ | − |
| 5 | COCULTURE IFN-γ | − | NUMBER OF CD4 T CELLS IN PRODUCT | | NUMBER OF CD8 T CELLS IN PRODUCT | | TOTAL T CELLS IN PRODUCT | | BASELINE LDH | − |

FIG. 22 (CONTINUED)

| # | | | | | |
|---|---|---|---|---|---|
| 6 | BASELINE FERRITIN | NUMBER OF $T_N$ CELLS IN PRODUCT | BASELINE DOUBLING TIME | NUMBER OF CD8 T CELLS IN PRODUCT | — |
| 7 | NUMBER OF $T_N$ CELLS IN PRODUCT | BASELINE DOUBLING TIME | BASELINE WEIGHT | BASELINE IL-6 | BASELINE CRP |
| 8 | TRANSDUCTION EFFICIENCY | NUMBER OF CD8 T CELLS IN PRODUCT | DAY 0 IFN-γ | DISEASE STAGE | TRANSDUCTION EFFICIENCY |
| 9 | DISEASE STAGE | BASELINE IL-6 | TRANSDUCTION EFFICIENCY | TRANSDUCTION EFFICIENCY | BASELINE IL-6 |
| 10 | BASELINE DOUBLING TIME | BASELINE WEIGHT | NUMBER OF $T_N$ CELLS IN PRODUCT | NUMBER OF CD4 T CELLS IN PRODUCT | NUMBER OF CD4 T CELLS IN PRODUCT |
| 11 | TOTAL T CELLS IN PRODUCT | TRANSDUCTION EFFICIENCY | BASELINE TUMOR BURDEN | BASELINE TUMOR BURDEN | DISEASE STAGE |
| 12 | NUMBER OF CD8 T CELLS IN PRODUCT | DAY 0 IFN-γ | BASELINE CRP | BASELINE CRP | DAY 0 IFN-γ |
| 13 | DAY 0 IL-15 | TOTAL T CELLS IN PRODUCT | DISEASE STAGE | DAY 0 IFN-γ | TOTAL T CELLS IN PRODUCT |
| 14 | DAY 0 IFN-γ | DISEASE STAGE | BASELINE FERRITIN | BASELINE LDH | NUMBER OF CD8 T CELLS IN PRODUCT |
| 15 | BASELINE WEIGHT | BASELINE FERRITIN | NUMBER OF CD4 T CELLS IN PRODUCT | BASELINE WEIGHT | DAY 0 IL-15 |
| 16 | NUMBER OF CD4 T CELLS IN PRODUCT | BASELINE CRP | TOTAL T CELLS IN PRODUCT | DAY 0 IL-15 | BASELINE WEIGHT |

ABBREVIATIONS: CAR, CHIMERIC ANTIGEN RECEPTOR; CRP, C-REACTIVE PROTEIN; CRS, CYTOKINE RELEASE SYNDROME; IFN, INTERFERON; IL, INTERLEUKIN; LDH, LACTATE DEHYDROGENASE; NE, NEUROLOGIC EVENTS; $T_N$, NAIVE-LIKE T CELLS (CD45RA+CCR7+).

EVOLUTION OF TME GENE SIGNATURES POST-AXI-CEL INFUSION ASSOCIATED WITH CLINICAL OUTCOMES

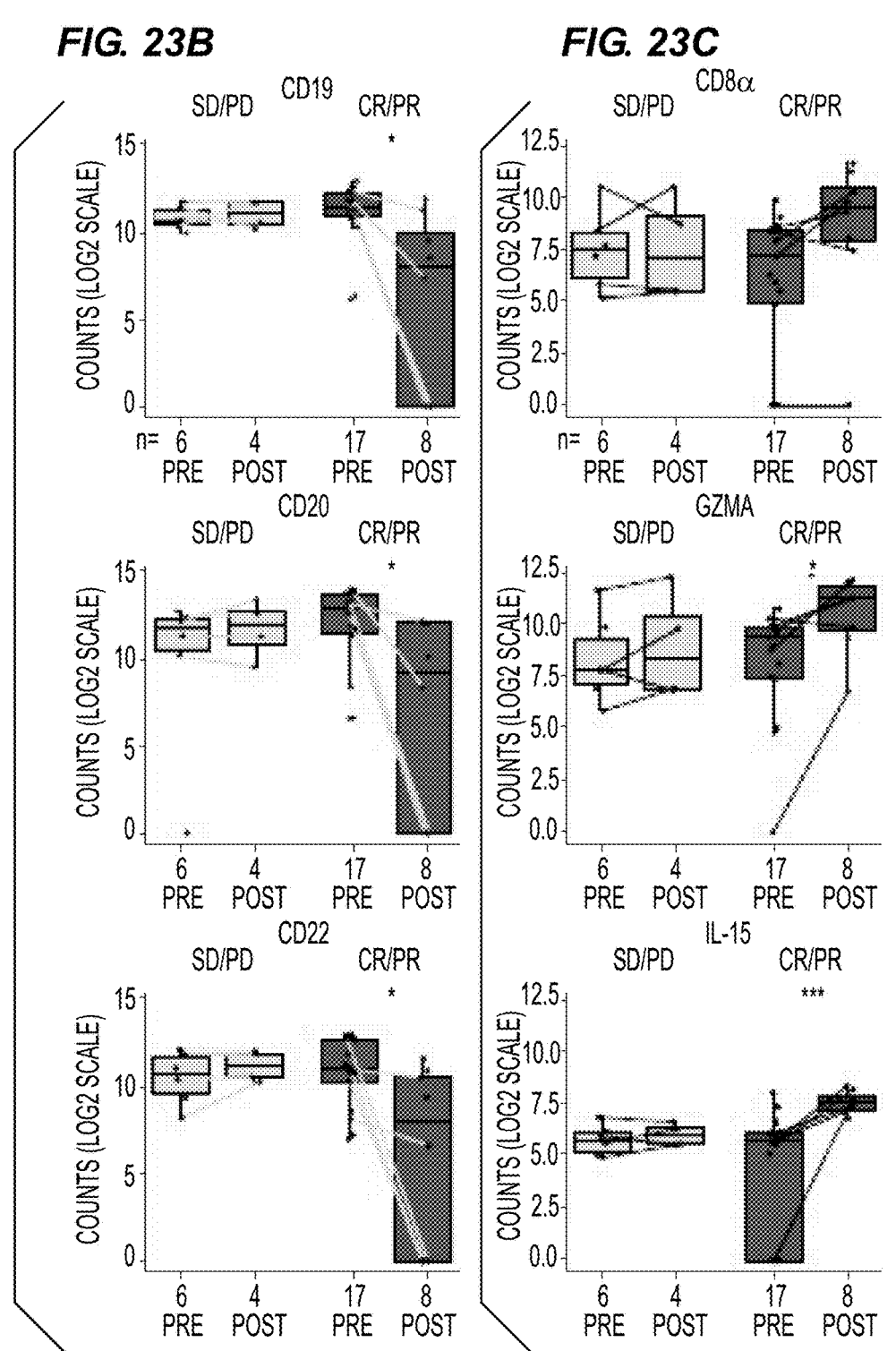
EVOLUTION OF TME GENE SIGNATURES POST-AXI-CEL INFUSION ASSOCIATED WITH CLINICAL OUTCOMES

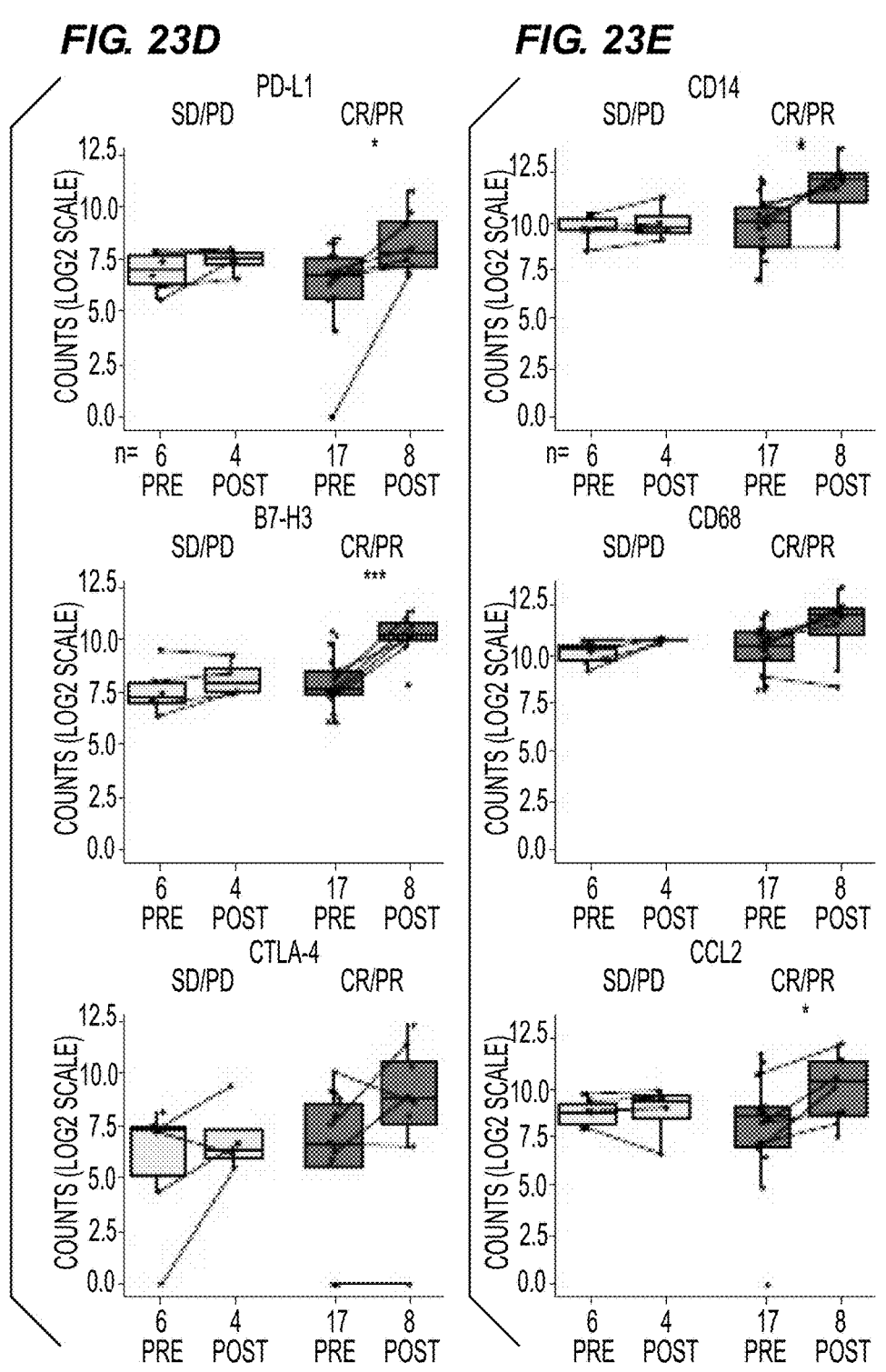
EVOLUTION OF TME GENE SIGNATURES POST-AXI-CEL INFUSION ASSOCIATED WITH CLINICAL OUTCOMES DYNAMIC CHANGES IN TME GENE SIGNATURES WERE EVIDENT POST-AXI-CEL AND CORRELATED WITH CLINICAL OUTCOMES

FIG. 24C

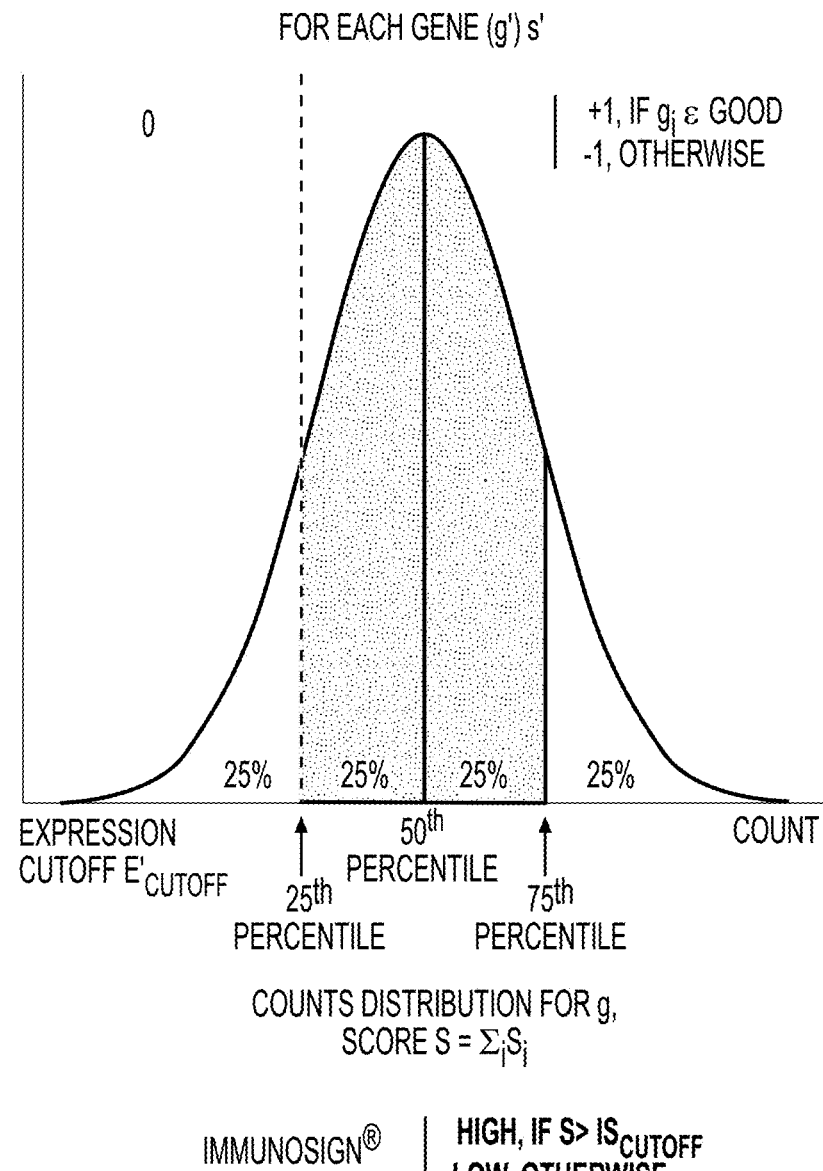

FOR EACH GENE (g') s'

0

+1, IF $g_i$ ε GOOD
-1, OTHERWISE

25%　25%　25%　25%

EXPRESSION
CUTOFF $E'_{CUTOFF}$

25th
PERCENTILE

50th
PERCENTILE

75th
PERCENTILE

COUNT

COUNTS DISTRIBUTION FOR $g_i$
SCORE $S = \Sigma_i S_i$

IMMUNOSIGN®

HIGH, IF S> $IS_{CUTOFF}$
LOW, OTHERWISE

WHERE $IS_{CUTOFF}$ IS ARBITRARILY THE
25TH PERCENTILE OF ALL S VALUES

DYNAMIC CHANGES IN TIME GENE SIGNATURES WERE EVIDENT
POST-AXI-CEL AND CORRELATED WITH CLINICAL OUTCOMES

DYNAMIC CHANGES IN TME GENE SIGNATURES WERE EVIDENT POST-AXI-CEL AND CORRELATED WITH CLINICAL OUTCOMES

*FIG. 25*

| PANEL NAME | ANALYSED GENES | SAMPLE TIMEPOINT | SAMPLE TYPE |
|---|---|---|---|
| IMMUNOSIGN EXPANDED 43 IMMUNE GENE PANEL | 44 ENDOGENOUS 8 HOUSEKEEPING 14 CONTROLS | BASELINE EARLY AFTER AXI-CEL INFUSION RELAPSE (PAIRED AND UNPAIRED SAMPLES) | FRESH FROZEN BIOPSIES |
| PANCANCER IMMUNE PROFILING + CAR T GENE PANEL | 770 ENDOGENOUS 2 CAR T 14 CONTROLS | BASELINE EARLY AFTER AXI-CEL INFUSION RELAPSE (UNPAIRED SAMPLES ONLY) | FRESH FROZEN BIOPSIES |
| PANCANCER IMMUNE + IMMUNOSIGN GENE PANEL | 770 ENDOGENOUS 6 IMMUNOSIGN 14 CONTROLS | BASELINE EARLY AFTER AXI-CEL INFUSION | FORMALIN-FIXED, PARAFFIN-EMBEDDED BLOCKS |

GENE-EXPRESSION PROFILING PANELS

FIG. 26

| PLATFORM | PANEL | GENES |
|---|---|---|
| NANOSTRING | IMMUNOSIGN EXPANDED 43 IMMUNE GENE PANEL | CTLA4, CD3G, CD3E, REN, GZMK, CCL5, ITGAE, PRF1, ICOS, STAT1, CCR2, GZMH, IRF1, GZMA, GZMB, CXCL11, STAT4, LAG3, CD3D, CXCL9, GZMM, IL17A, CD84A, CX3CL1, TNFRSF18, CD69, CD274, IL15, PF4, IFNG, CXCL13, PROM1, PDCD1, TNFRSF9, TSLP, CCL2, CD247, GNLY, LTK, TBX21, VEGFA, CXCR3 |
| | PANCANCER IMMUNE PROFILING+ CAR T GENE PANEL | ADAPTIVE IMMUNE RESPONSE:<br>• B CELLS: eg, BLK, CD19, CR2, MS4A1, TNFRSF17<br>• T CELLS: eg, CD2 CD2E, CD3G, CD6<br>INNATE IMMUNE RESPONSE:<br>• CYTOTOXIC CELLS: eg, CD8, BCL2<br>• MACROPHAGES: eg, APOE, CCL7<br>• DENDRITIC CELLS: eg, CCL12, CCL17<br>• GRANULOCYTES: eg, CMA1, CSF3R |
| IMMUNOSIGN | IMMUNOSIGN 15 | LAG3, IFNG, IL17A, CCL5, CXCL9, CXCL13, GZMH, GNLY, PF4, ITGAE, IHH PROM1, REN, TSLP, VEGFA |
| | IMMUNOSIGN 21 | CD3D, CD3E, CD3G, CD8A, CD69, IL15, CCL2, CCR2, IRF1, GZMA, GZMB, GZMK, GZMM, PRF1,CXCR3, CXCL10, CXCL 11, STAT1, STAT4, TBX21 |

GENES INTERROGATED BY NANOSTRING PANELS AND IMMUNOSIGN 15 AND 21

AT RELAPSE, THE TME EVOLVED TOWARDS AN IMMUNE-DETRIMENTAL CONTEXTURE WITH REDUCTION OF T CELL, CAR T CELL, AND MYELOID CELL GENES AND IMMUNOSIGN

FIG. 27A (CONT. 1)
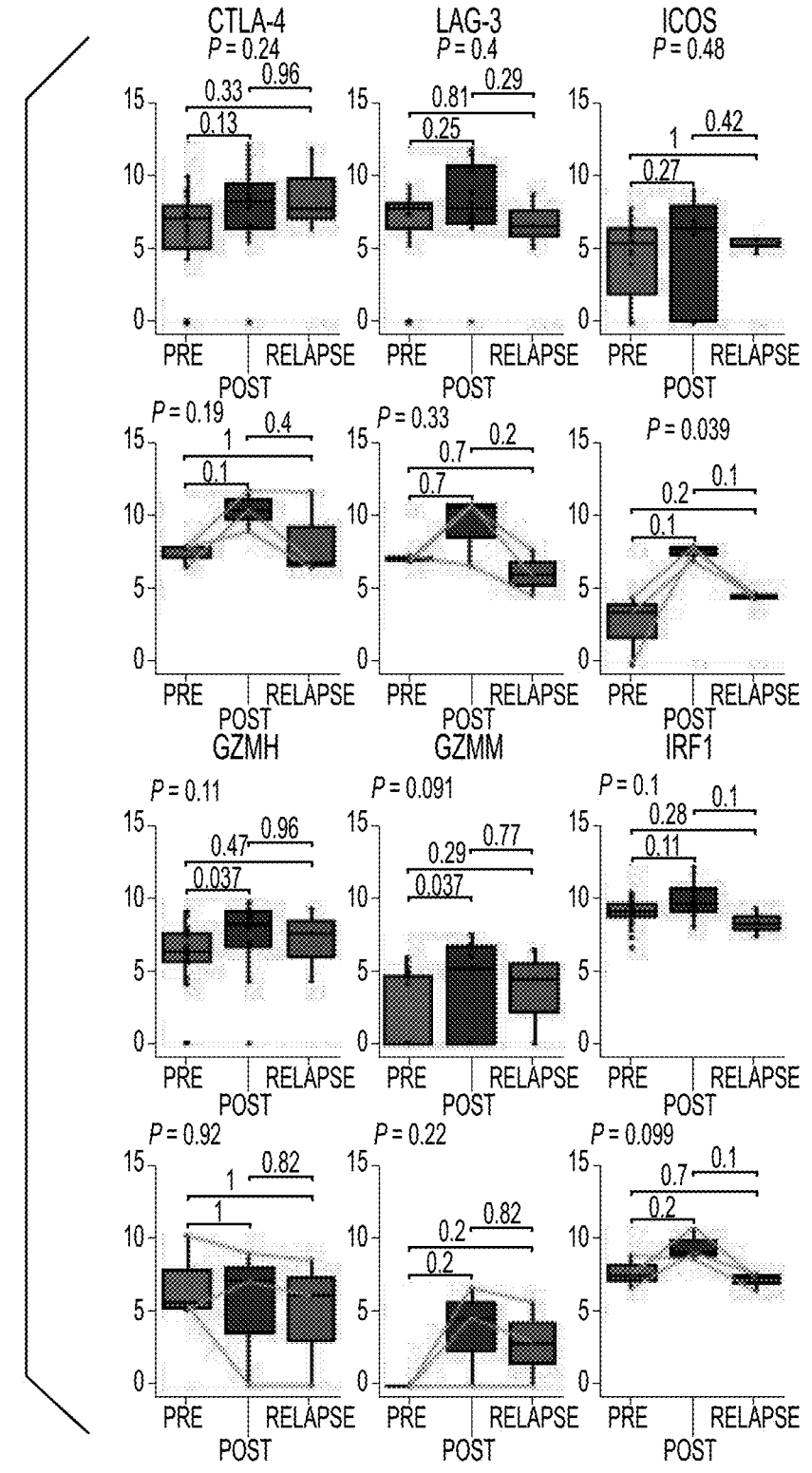
AT RELAPSE, THE TME EVOLVED TOWARDS AN IMMUNE-DETRIMENTAL CONTEXTURE WITH
REDUCTION OF T CELL, CAR T CELL, AND MYELOID CELL GENES AND IMMUNOSIGN

FIG. 27A (CONT. 2)
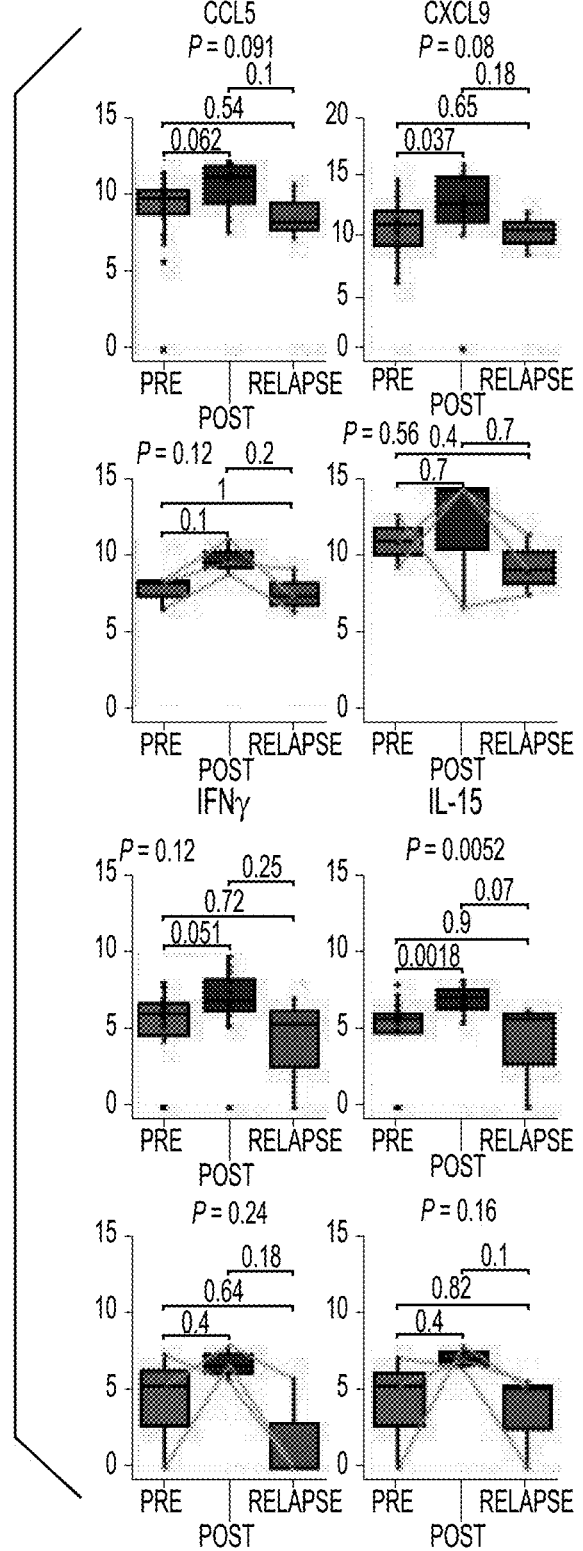
AT RELAPSE, THE TME EVOLVED TOWARDS AN IMMUNE-DETRIMENTAL CONTEXTURE WITH REDUCTION OF T CELL, CAR T CELL, AND MYELOID CELL GENES AND IMMUNOSIGN

CAR T AND MYELOID CELL GENES

AT RELAPSE, THE TME EVOLVED TOWARDS AN IMMUNE-DETRIMENTAL CONTEXTURE WITH REDUCTION OF T CELL, CAR T CELL, AND MYELOID CELL GENES AND IMMUNOSIGN

AT RELAPSE, THE TME EVOLVED TOWARDS AN IMMUNE-DETRIMENTAL CONTEXTURE WITH REDUCTION OF T CELL, CAR T CELL, AND MYELOID CELL GENES AND IMMUNOSIGN

AT RELAPSE, THE TME EVOLVED TOWARDS AN IMMUNE-DETRIMENTAL CONTEXTURE WITH UPREGULATION OF B CELL-, CTA-, AND TREG-RELATED GENES

FIG. 28A (CONT.-1)
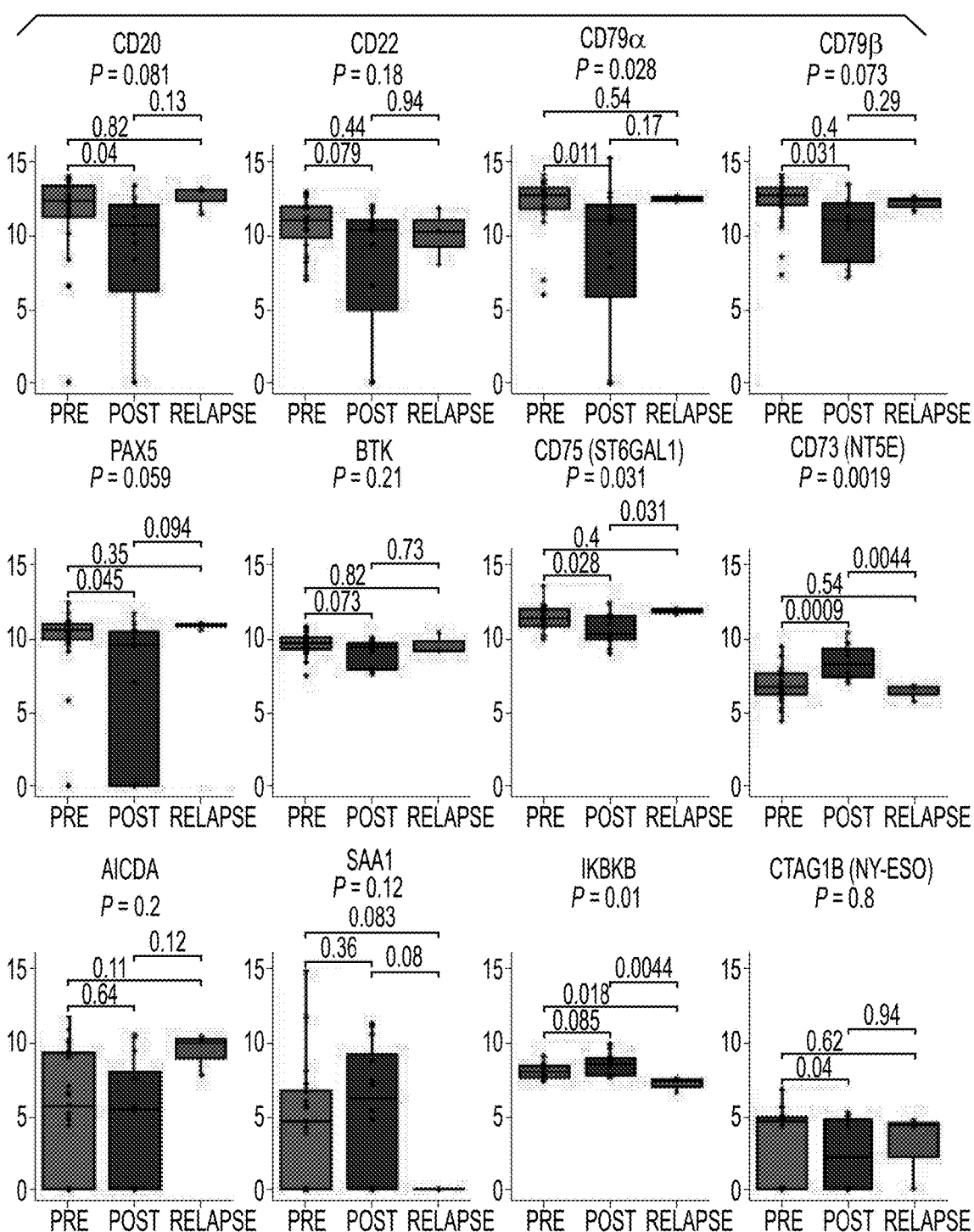
AT RELAPSE, THE TME EVOLVED TOWARDS AN IMMUNE-DETRIMENTAL CONTEXTURE WITH
UPREGULATION OF B CELL-, CTA-, AND TREG-RELATED GENES AT RELAPSE, THE TME EVOLVED TOWARDS AN IMMUNE-DETRIMENTAL CONTEXTURE WITH
UPREGULATION OF B CELL-, CTA-, AND TREG-RELATED GENES AN IMMUNOLOGICALLY INVOLVED, PRETREATMENT TME ASSOCIATED WITH AXI-CEL CLINICAL RESPONSE AN IMMUNOLOGICALLY INVOLVED, PRETREATMENT TME ASSOCIATED WITH AXI-CEL CLINICAL RESPONSE

IMMUNOSCORE TL

IMMUNOSIGN 21

AN IMMUNOLOGICALLY INVOLVED, PRETREATMENT TME ASSOCIATED WITH AXI-CEL CLINICAL RESPONSE

FIG. 30B          FIG. 30C

IMMUNISCORE TL CORRELATED WITH TUMOR-INFILTRATING IMMUNE CELL DENSITY
AND IMMUNOSIGN 15 AND 21 PRETREATMENT (PRELYMPHODEPLETION)

IMMUNISCORE TL CORRELATED WITH TUMOR-INFILTRATING IMMUNE CELL DENSITY AND IMMUNOSIGN 15 AND 21 PRETREATMENT (PRELYMPHODEPLETION)

REPRESENTATIVE EXPRESSION OF TUMOUR-INFILTRATING IMMUNE CELLS IN
PATIENTS WITH CR VERSYS PR/SD/PD AS ASSESSED USING IMMUNOSCORE TL, TCE, AND SC

REPRESENTATIVE EXPRESSION OF TUMOUR-INFILTRATING IMMUNE CELLS IN
PATIENTS WITH CR VERSYS PR/SD/PD AS ASSESSED USING IMMUNOSCORE TL, TCE, AND SC

PRETREATMENT TUMOR DENSITY OF TREG AND MYELOID
CELLS IN ASSOCIATION WITH AXI-CEL RESPONSE

FIG. 32B (CONT.-1)
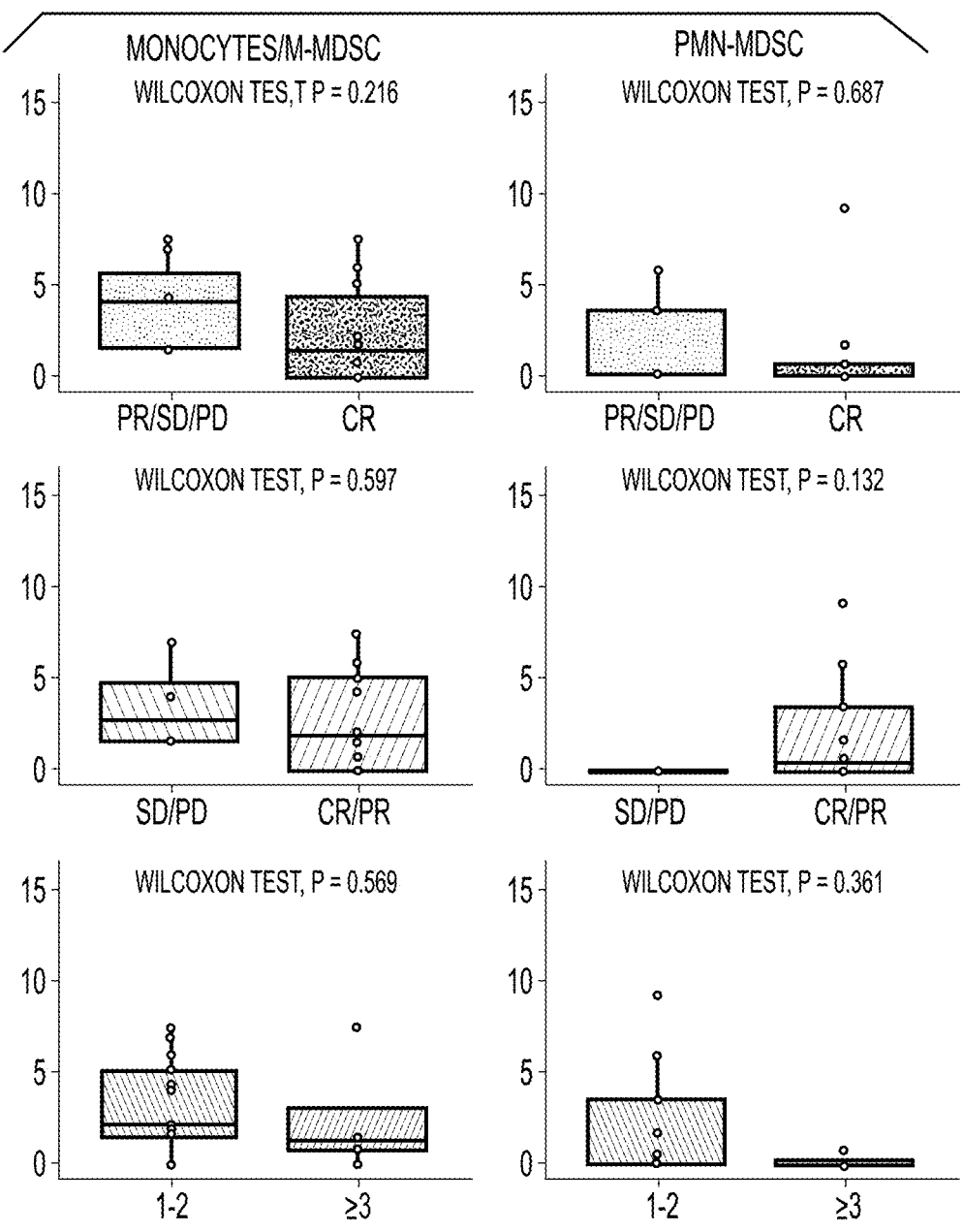
PRETREATMENT TUMOR DENSITY OF TREG AND MYELOID
CELLS IN ASSOCIATION WITH AXI-CEL RESPONSE DENSITY OF ACTIVATED TUMOR-INFILTRATING T CELLS WITHIN THE TME BEFORE
LYMPHODEPLETION ASSOCIATED WITH AXI-CEL CLINICAL OUTCOMES DENSITY OF ACTIVATED TUMOR-INFILTRATING T CELLS WITHIN THE TME BEFORE LYMPHODEPLETION ASSOCIATED WITH AXI-CEL CLINICAL OUTCOMES DENSITY OF ACTIVATED TUMOR-INFILTRATING T CELLS WITHIN THE TME BEFORE LYMPHODEPLETION ASSOCIATED WITH AXI-CEL CLINICAL OUTCOMES

FIG. 34A

PANELS

| PANEL NAME | ANALYSED MARKERS |
|---|---|
| TCE | CD3, CD8, FoxP3, PD-1, LAG-3, TIM-3 |
| SC | CD11b, CD14, CD15, CD68, S100A9, LOX-1 |

CELL TYPE MARKER SIGNATURES

| CELL TYPE | MARKER SIGNATURE |
|---|---|
| T CELLS | CD3+ |
| CD8+ T CELLS | CD3+ CD8+ |
| CD4+ T CELLS | CD3+ CD8- FoxP3- |
| Tregs | CD3+ CD8- FoxP3+ |
| CD8+ T CELLS WITH 0 CHECKPOINTS | CD3+ CD8+ PD-1- LAG-3- TIM-3- |
| CD8+ T CELLS WITH 1 CHECKPOINT | CD3+ CD8+ PD-1+ LAG-3- TIM-3- |
|  | CD3+ CD8+ PD-1- LAG-3+ TIM-3- |
|  | CD3+ CD8+ PD-1- LAG-3+ TIM-3+ |
| CD8+ T CELLS WITH 2 CHECKPOINTS | CD3+ CD8+ PD-1+ LAG-3- TIM-3+ |
|  | CD3+ CD8+ PD-1- LAG-3+ TIM-3+ |
| CD8+ T CELLS WITH 3 CHECKPOINTS | CD3+ CD8+ PD-1+ LAG-3+ TIM-3+ |
| CD4+ T CELLS WITH 0 CHECKPOINTS | CD3+ CD8- FoxP3- PD-1- LAG-3- TIM-3- |
| CD4+ T CELLS WITH 1 CHECKPOINT | CD3+ CD8- FoxP3- PD-1+ LAG-3- TIM-3- |
|  | CD3+ CD8- FoxP3- PD-1- LAG-3+ TIM-3- |

IMMUNOSCORE TCE AND SC PANELS, CELL TYPE MARKER SIGNATURES, AND ASSOCIATIONS
BETWEEN PRETREATMENT TME IMMUNE CELL DENSITY AND CLINICAL OUTCOMES

FIG. 34B

| | |
|---|---|
| CD4+ T CELLS WITH 2 CHECKPOINTS | CD3+ CD8- FoxP3- PD-1+ LAG-3+ TIM-3- |
| | CD3+ CD8- FoxP3- PD-1+ LAG-3- TIM-3+ |
| | CD3+ CD8- FoxP3- PD-1- LAG-3+ TIM-3+ |
| CD4+ T CELLS WITH 3 CHECKPOINTS | CD3+ CD8- FoxP3- PD-1+ LAG-3+ TIM-3+ |
| Tregs WITH 0 CHECKPOINTS | CD3+ CD8- FoxP3+ PD-1- LAG-3- TIM-3- |
| Tregs WITH 1 CHECKPOINT | CD3+ CD8- FoxP3+ PD-1+ LAG-3- TIM-3- |
| | CD3+ CD8- FoxP3+ PD-1- LAG-3+ TIM-3- |
| | CD3+ CD8- FoxP3+ PD-1+ LAG-3+ TIM-3- |
| Tregs WITH 2 CHECKPOINTS | CD3+ CD8- FoxP3+ PD-1+ LAG-3- TIM-3+ |
| | CD3+ CD8- FoxP3+ PD-1- LAG-3+ TIM-3+ |
| Tregs WITH 3 CHECKPOINTS | CD3+ CD8- FoxP3+ PD-1+ LAG-3+ TIM-3+ |
| GRANULOCYTES | CD11b+ CD15+ CD14- |
| NEUTROPHILS | CD11b+ CD15+ CD14- LOX-1- |
| PMN-MDSC | CD11b+ CD15+ CD14- LOX-1+ |
| MONONUCLEAR CELLS | CD11b+ CD15- CD14+ |
| MONOCYTES/M-MDSC | CD11b+ CD15- CD14+ S100A9+ CD68- |
| MACROPHAGES | CD68+ |

IMMUNOSCORE TCE AND SC PANELS, CELL TYPE MARKER SIGNATURES, AND ASSOCIATIONS BETWEEN PRETREATMENT TME IMMUNE CELL DENSITY AND CLINICAL OUTCOMES

FIG. 34C

ASSOCIATIONS BETWEEN PRETREATMENT TME IMMUNE CELL DENSITY AND CLINICAL OUTCOMES

| CELL TYPE | DENSITY (CELL COUNT/mm²), MEDIAN (RANGE) | DENSITY (CELL COUNT/mm²) IN PATIENTS WITH CR/PR, MEDIAN AND RANGE | DENSITY (CELL COUNT/mm²) IN PATIENTS WITH SD/PD, MEDIAN AND RANGE | T-TEST (CR/PR vs SD/PD) |
|---|---|---|---|---|
| CD8+ T CELL SUBSETS | | | | |
| CD3+ CD8+ PD-1- LAG-3- TIM-3- | 121 (6-1254) | 128 (12-1250) | 89 (6-254) | 0.382 |
| CD3+ CD8+ PD-1+ LAG-3- TIM-3- | 23 (2-978) | 36 (4-976) | 9 (2-21) | 0.0346 |
| CD3+ CD8+ PD-1+ LAG-3+ TIM-3- | 1 (0-130) | 2 (0-131) | 0.00 (0-0.5) | 0.0305 |
| CD3+ CD8+ PD-1+ LAG-3+ TIM-3+ | 11 (0-317) | 15 (0-317) | 3 (0-9) | 0.123 |
| CD3+ CD8+ PD-1- LAG-3+ TIM-3- | 1 (0-21) | 2 (0-21) | 1 (0-1) | 0.477 |
| CD3+ CD8+ PD-1- LAG-3+ TIM-3+ | 3 (0-66) | 3 (0-66) | 1.5 (0-8) | 0.482 |
| CD4+ T CELL SUBSETS | | | | |
| Thelper CELLS (CD3+ CD8- FoxP3-) | 172 (5-1295) | 172 (5-1300) | 191 (7-457) | 0.798 |
| Treg CELLS (CD3+ CD8- FoxP3+) | 20 (0-1170) | 19 (-01170) | 86 (1-440) | 0.798 |
| MYELOID CELLS SUBSETS | | | | |
| GRANULOCYTES (CD11b+ CD15+ CD14-) | 2 (0-900) | 3 (0-900) | 2 (0-7) | 0.23 |
| MONONUCLEAR CELLS (CD11b+ CD15- CD14+) | 1215 (170-3206) | 1343 (399-3376) | 839 (170-2224) | 0.37 |
| MACROPHAGES (CD68+) | 530 (85-1745) | 973 (126-1830) | 328 (85-1811) | 0.397 |

IMMUNOSCORE TCE AND SC PANELS, CELL TYPE MARKER SIGNATURES, AND ASSOCIATIONS BETWEEN PRETREATMENT TME IMMUNE CEL DENSITY AND CLINICAL OUTCOMES

FIG. 35A

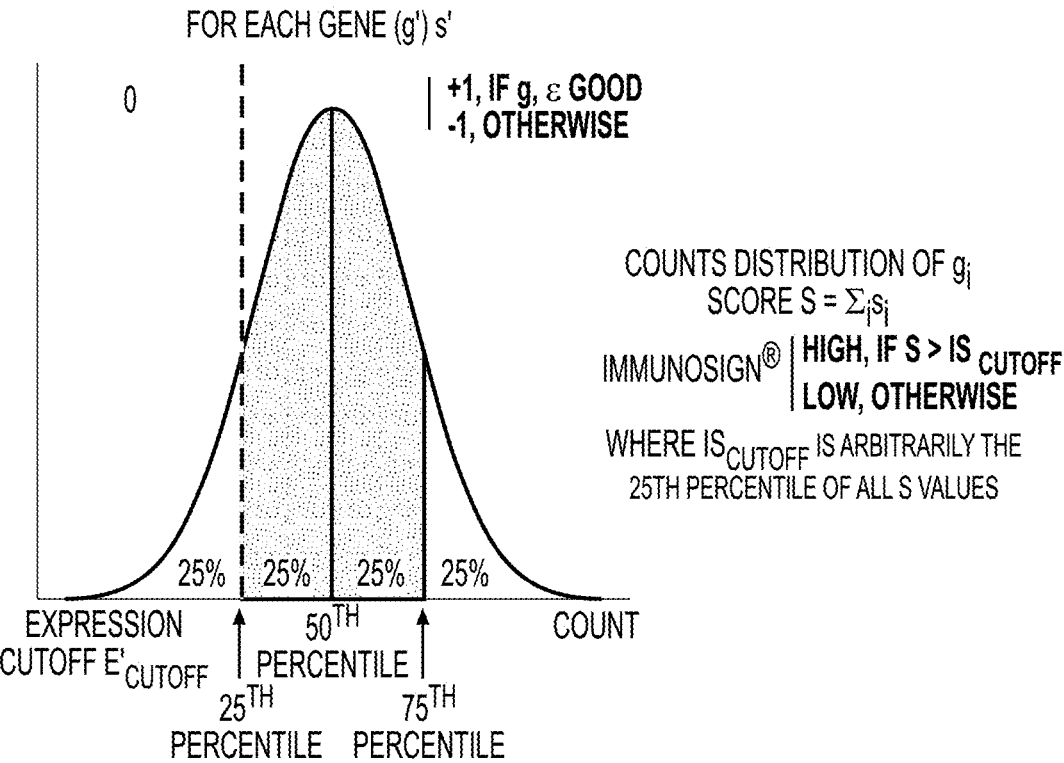

3 TYPES OF PARAMETERS TO OPTIMIZE

• E'$_{CUTOFF}$ EXPRESSION CUTOFF: 25$^{TH}$, 50$^{TH}$, OR 75$^{TH}$ PERCENTILE OF DISTIBUTION

• S$_i$ CONTRIBUTION OF THE GENE: -1/1 OR 0 (ZERO MEANS THE GENE IS REMOVED FROM THE SIGNATURE)

• IS$_{CUTOFF}$ (OPTIMIZED BY A ROC ANALYSIS)

NUMBER OF PARAMETER SETS:

$$N=(NE_{CUTOFF})^{44} \times (Nsi)^{44} = 3^{44} \times 2^{44} =$$

$$1.73 \times 10^{34} \text{ CONFIGURATIONS TO TEST}$$

OPTIMIZED IMMUNE INDEXES TAILORED TO AXI-CEL RESPONSE

*FIG. 35B*

| OPTIMIZED SIGNATURES | P VALUES | GEOMETRIC MEAN OF P VALUES | GENES |
|---|---|---|---|
| OBJECTIVE RESPONSE | 0.00161<br>0.03934<br>0.00328 | 0.00592 | CD3D, CD69, IRF1, CXCL9, CXCL10, STAT1, VEGFA, PDCD1, CD274 |
| BEST RESPONSE | 0.12793<br>0.00155<br>0.00722 | 0.01127 | GZMA, CD69, IRF1, CXCL9, CXCL10, STAT1, VEGFA |
| WORST GRADE OF NE | 0.00226<br>0.00323<br>0.03333 | 0.00624 | CD8A, PRF1, IRF1, CCL5, CXCL9, CCL2, STAT1, STAT4, VEGFA, CTLA4, PDCD1, CD274 |

OPTIMIZED IMMUNE INDEXES TAILORED TO AXI-CEL RESPONSE

*FIG. 36*

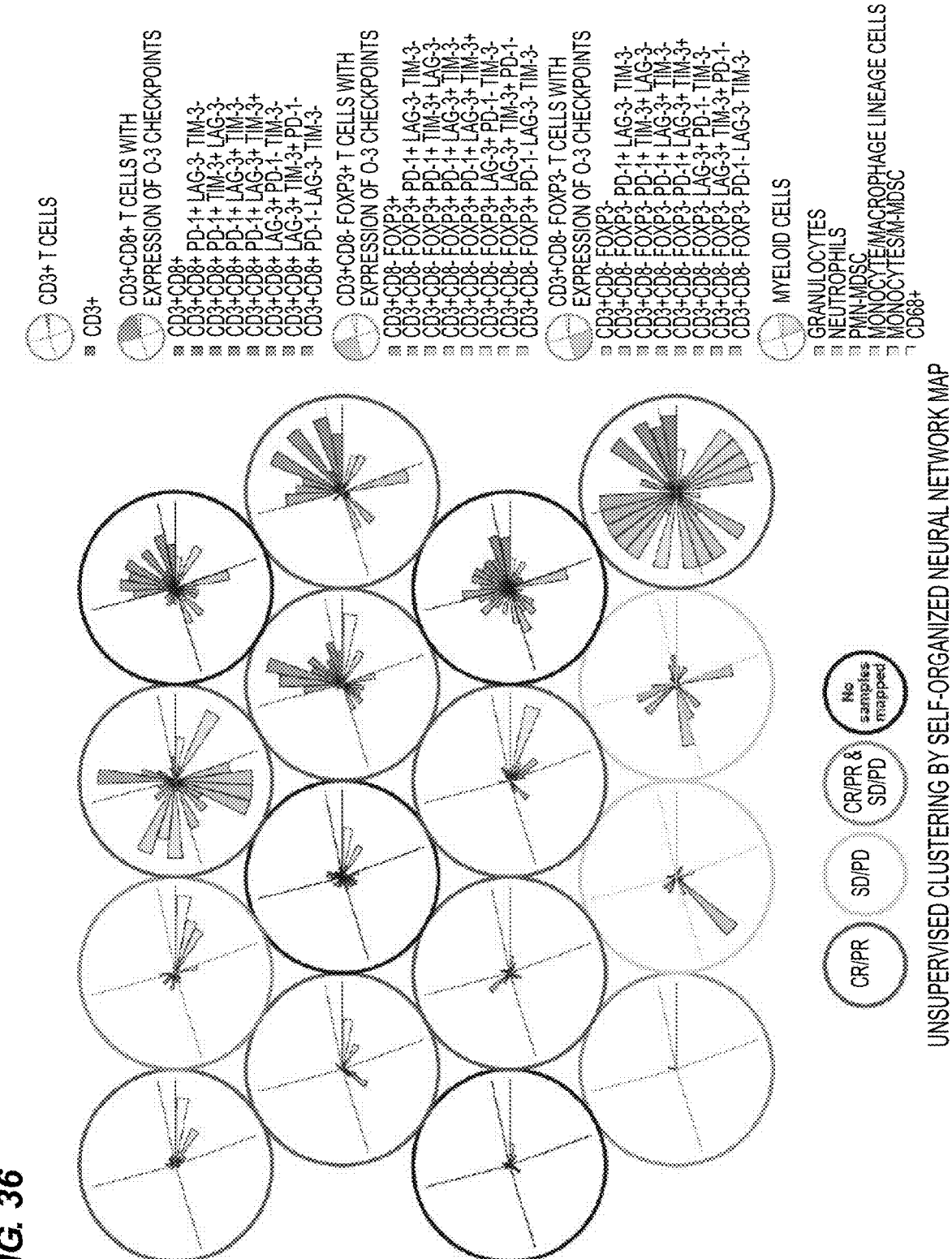

CD3+ T CELLS

CD3+

CD3+CD8+ T CELLS WITH
EXPRESSION OF 0-3 CHECKPOINTS

CD3+CD8+
CD3+CD8+ PD-1+ LAG-3- TIM-3-
CD3+CD8+ PD-1+ TIM-3+ LAG-3-
CD3+CD8+ PD-1+ LAG-3+ TIM-3-
CD3+CD8+ PD-1+ LAG-3+ TIM-3+
CD3+CD8+ LAG-3+ TIM-3-
CD3+CD8+ LAG-3+ PD-1- TIM-3-
CD3+CD8+ LAG-3+ TIM-3+ PD-1-
CD3+CD8+ PD-1- LAG-3- TIM-3-

CD3+CD8- FOXP3+ T CELLS WITH
EXPRESSION OF 0-3 CHECKPOINTS

CD3+CD8- FOXP3+
CD3+CD8- FOXP3+ PD-1+ LAG-3- TIM-3-
CD3+CD8- FOXP3+ PD-1+ TIM-3+ LAG-3-
CD3+CD8- FOXP3+ PD-1+ LAG-3+ TIM-3-
CD3+CD8- FOXP3+ PD-1+ LAG-3+ TIM-3+
CD3+CD8- FOXP3+ LAG-3+ TIM-3-
CD3+CD8- FOXP3+ LAG-3+ PD-1- TIM-3-
CD3+CD8- FOXP3+ LAG-3+ TIM-3+ PD-1-
CD3+CD8- FOXP3+ PD-1- LAG-3- TIM-3-

CD3+CD8- FOXP3- T CELLS WITH
EXPRESSION OF 0-3 CHECKPOINTS

CD3+CD8- FOXP3-
CD3+CD8- FOXP3- PD-1+ LAG-3- TIM-3-
CD3+CD8- FOXP3- PD-1+ TIM-3+ LAG-3-
CD3+CD8- FOXP3- PD-1+ LAG-3+ TIM-3-
CD3+CD8- FOXP3- PD-1+ LAG-3+ TIM-3+
CD3+CD8- FOXP3- LAG-3+ TIM-3-
CD3+CD8- FOXP3- LAG-3+ PD-1- TIM-3-
CD3+CD8- FOXP3- LAG-3+ TIM-3+ PD-1-
CD3+CD8- FOXP3- PD-1- LAG-3- TIM-3-

MYELOID CELLS

GRANULOCYTES
NEUTROPHILS
PMN-MDSC
MONOCYTE/MACROPHAGE LINEAGE CELLS
MONOCYTES/M-MDSC
CD68+

CR/PR     SD/PD     CR/PR & SD/PD     No samples mapped

UNSUPERVISED CLUSTERING BY SELF-ORGANIZED NEURAL NETWORK MAP

*FIG. 37A*

ADAPTIVE IMMUNITY

| GENES | LOG2 FOLD CHANGE | P VALUE |
|---|---|---|
| FOXJ1 | -3.1832 | 0.0006 |
| LY96 | 0.5567 | 0.0261 |
| TSLP | -2.7129 | 0.0332 |
| NFATC2 | 1.3314 | 0.0378 |
| CD3D | 3.1268 | 0.0465 |
| ITGB2 (CD18) | 1.1350 | 0.0470 |
| HLA-DQB1 | -4.1927 | 0.0477 |
| CD3E | 3.1062 | 0.0528 |
| HLA-DQA1 | -4.4489 | 0.0740 |
| CTLA4 | 3.1996 | 0.0755 |
| F2RL1 | -2.4653 | 0.0767 |
| NCR1 | -2.1561 | 0.0848 |
| MYD88 | 0.4438 | 0.1142 |
| TLR2 | 0.7081 | 0.1350 |
| CD79A | -0.6559 | 0.1351 |
| VCAM1 | 1.0141 | 0.1385 |
| CD1D | -2.1457 | 0.1683 |
| SYK | 0.6412 | 0.1702 |
| TREM1 | -2.3325 | 0.1780 |
| MICA | -1.6771 | 0.1793 |
| CD4 | 0.7218 | 0.1844 |
| PIK3CD | 0.7732 | 0.1949 |
| FYN | 0.7118 | 0.2151 |
| LCK | 0.6642 | 0.2403 |
| HLA-G | 0.6008 | 0.2407 |
| TLR4 | 0.6501 | 0.2408 |

| GENES | LOG2 FOLD CHANGE | P VALUE |
|---|---|---|
| HLA-B | 0.2024 | 0.5845 |
| KIR3DL1 | -0.6740 | 0.5954 |
| CD8A | 0.4272 | 0.6052 |
| CD40LG | 0.6766 | 0.6095 |
| SELL | -0.7827 | 0.6107 |
| BLK | -0.6860 | 0.6138 |
| REL | 0.2351 | 0.6174 |
| IFITM1 | 0.2005 | 0.6263 |
| HLA-DPB1 | 0.3019 | 0.6709 |
| CD3G | 0.6599 | 0.6897 |
| LILRB1 | -0.4000 | 0.6929 |
| HLA-A | 0.1538 | 0.7023 |
| CD81 | 0.1166 | 0.7175 |
| HLA-DRA | 0.2372 | 0.7249 |
| SLAMF7 | 0.3505 | 0.7417 |
| KLRC1 | 0.3674 | 0.7656 |
| TAP1 | 0.1290 | 0.7658 |
| NFKBIA | 0.1163 | 0.7792 |
| PSMB9 | 0.0995 | 0.7815 |
| KLRG1 | -0.4032 | 0.7852 |
| BTLA | 0.2458 | 0.7883 |
| CD74 | -0.1616 | 0.7888 |
| BLNK | -0.1116 | 0.7900 |
| CHUK | 0.0472 | 0.8032 |
| KLRF1 | 0.3485 | 0.8049 |
| CD207 | -0.3248 | 0.8069 |

GENE LIST BY PATHWAY FOR PATIENTS WHO SUBSEQUENTLY RESPONDED TO AXI-CEL

*FIG. 37B*

| Gene | | |
|---|---|---|
| CD8B | -1.4898 | 0.2756 |
| TNFRSF14 | -0.4607 | 0.2799 |
| HLA-DRB4 | 2.8808 | 0.2842 |
| KLRB1 | 1.8167 | 0.3033 |
| HLA-E | 0.4185 | 0.3282 |
| CD19 | 0.4461 | 0.3483 |
| KIR3DL2 | -1.4271 | 0.3515 |
| CD209 | 1.2370 | 0.3607 |
| PDCD1LG2 | 1.3966 | 0.3618 |
| FCGR2B | -0.7620 | 0.3930 |
| MICB | -0.2812 | 0.4213 |
| LAMP3 | 1.2391 | 0.4245 |
| FCGR1A | -1.0002 | 0.4375 |
| KLRD1 | -0.8974 | 0.4405 |
| CD28 | 1.1478 | 0.4507 |
| COL3A1 | -0.5732 | 0.4609 |
| LILRB3 | 1.0339 | 0.4627 |
| SOCS1 | -0.3963 | 0.4941 |
| TAP2 | -0.1663 | 0.5279 |
| ICOSLG | 0.3472 | 0.5280 |
| BTK | -0.2337 | 0.5339 |

| Gene | | |
|---|---|---|
| HLA-DMB | 0.2869 | 0.5548 |
| PDCD1 | 0.7778 | 0.5837 |

| Gene | | |
|---|---|---|
| CD274 | -0.2789 | 0.8300 |
| TRAF6 | -0.0514 | 0.8324 |
| ZAP70 | -0.2901 | 0.8375 |
| HLA-DRB3 | 0.1290 | 0.8380 |
| HLA-C | -0.0852 | 0.8400 |
| INPP5D | -0.0583 | 0.8572 |
| PVR | 0.2346 | 0.8572 |
| CD80 | 0.1894 | 0.8609 |
| SH2D1B | -0.2327 | 0.8662 |
| C3 | -0.2942 | 0.8697 |
| SLAMF6 | -0.2533 | 0.8736 |
| LAG3 | -0.2261 | 0.8890 |
| NFATC1 | -0.0740 | 0.8983 |
| SH2D1A | 0.2018 | 0.9034 |
| CD86 | 0.1261 | 0.9166 |
| NFKB1 | -0.0262 | 0.9241 |
| CD22 | -0.0834 | 0.9265 |
| TAPBP | -0.0181 | 0.9285 |
| PSMB8 | 0.0259 | 0.9305 |
| PSMB10 | 0.0107 | 0.9654 |
| HLA-DPA1 | -0.0308 | 0.9662 |

| Gene | | |
|---|---|---|
| RELA | 0.0039 | 0.9846 |

GENE LIST BY PATHWAY FOR PATIENTS WHO SUBSEQUENTLY RESPONDED TO AXI-CEL

FIG. 37C

ADHESION

| GENES | LOG2 FOLD CHANGE | P VALUE |
|---|---|---|
| FEZ1 | -3.6577 | 0.018232 |
| ITGA4 (VLA-4) | 2.0320 | 0.021871 |
| CD97 | 1.1099 | 0.025304 |
| AMICA1 | 1.3021 | 0.046227 |
| EPCAM | -2.3635 | 0.118228 |
| ICAM3 | 0.4368 | 0.299528 |
| ITGB3 | -1.3624 | 0.360703 |
| ITGAE (CD103) | 0.2446 | 0.410591 |
| CDH5 | 0.8414 | 0.417494 |
| CEACAM6 | -1.3563 | 0.446863 |
| CDH1 (Cadherin) | 1.2309 | 0.455318 |
| ICAM4 | -1.0237 | 0.494104 |
| ITGA5 | -0.5581 | 0.561377 |
| ICAM2 | -0.1150 | 0.619920 |
| ICAM1 | 0.2462 | 0.678177 |
| CEACAM8 | 0.3620 | 0.823503 |
| CD99 | 0.0771 | 0.835581 |
| ITGA6 | -0.2262 | 0.870876 |

ANTIGEN PRESENTATION

| GENES | LOG2 FOLD CHANGE | P VALUE |
|---|---|---|
| CLEC4A (CROSS PRIMING) | 0.8884 | 0.007050 |
| HLA-DQB1 | -4.1927 | 0.047749 |
| HLA-DQA1 | -4.4489 | 0.073989 |
| CD1D | -2.1457 | 0.168275 |
| HLA-G | 0.6008 | 0.240743 |
| HLA-DRB4 | 2.8808 | 0.284153 |
| HLA-E | 0.4185 | 0.328196 |
| CD2 | 1.5808 | 0.329804 |
| CD1B | 0.6191 | 0.423737 |
| LILRB3 | 1.0339 | 0.462669 |
| HLA-DMB | 0.2869 | 0.554796 |
| HLA-B | 0.2024 | 0.584497 |
| HLA-DPB1 | 0.3019 | 0.670942 |
| HLA-A | 0.1538 | 0.702289 |
| HLA-DRA | 0.2372 | 0.724866 |
| HLA-DRB3 | 0.1290 | 0.838039 |
| HLA-C | -0.0852 | 0.839977 |
| CD1E | 0.2377 | 0.869071 |
| CD1C | -0.2262 | 0.899272 |
| HLA-DPA1 | -0.0308 | 0.966216 |
| HLA-DMA | -0.0037 | 0.994478 |

GENE LIST BY PATHWAY FOR PATIENTS WHO SUBSEQUENTLY RESPONDED TO AXI-CEL

FIG. 37D

TRANSCRIPTION FACTORS

| GENES | LOG2 FOLD CHANGE | P VALUE |
|---|---|---|
| FOXJ1 | -3.1832 | 0.000602 |
| POU2AF1 | -1.0083 | 0.009996 |
| MAF | 2.0916 | 0.018206 |
| DDX43 | -1.5259 | 0.168084 |
| DDX58 | 1.1224 | 0.172451 |
| CREBBP | -1.4761 | 0.216824 |
| CTCFL | -1.1936 | 0.445552 |
| PAX5 | -0.2578 | 0.490773 |

CTA, TAA, AND CELLULAR MORPHOLOGY

| GENES | LOG2 FOLD CHANGE | P VALUE |
|---|---|---|
| MAGEB2 | -3.9143 | 0.02931 |
| PRAME | -3.3117 | 0.05676 |
| DMBT1 | -1.9332 | 0.06236 |
| MAGEA3 | -2.2497 | 0.14418 |
| MAGEA12 | -1.6265 | 0.23438 |
| LTK | -1.5382 | 0.29317 |
| MAGEA1 | -1.4835 | 0.32163 |
| CT45A1 | -1.8926 | 0.34643 |
| IGLL1 | -1.2756 | 0.40062 |
| MAGEC2 | 0.5984 | 0.41835 |
| GAGE1 | 0.5830 | 0.42506 |
| MAGEC1 | -1.1541 | 0.44242 |
| IFNGR1 | 0.1355 | 0.70416 |
| MAGEA4 | -0.3979 | 0.72827 |
| CTAGE1 | -0.0103 | 0.99358 |

GENE LIST BY PATHWAY FOR PATIENTS WHO SUBSEQUENTLY RESPONDED TO AXI-CEL

*FIG. 37E*

B CELL GENES

| GENES | LOG2 FOLD CHANGE | P VALUE |
|---|---|---|
| POU2AF1 | -1.0083 | 0.01 |
| CD79A | -0.6559 | 0.13507 |
| SYK | 0.6412 | 0.17021 |
| PIK3CD | 0.7732 | 0.19493 |
| FYN | 0.7118 | 0.21514 |
| MAPK3 | -0.2787 | 0.2316 |
| FOS | 1.3529 | 0.30073 |
| CD19 | 0.4461 | 0.34831 |
| FCGR2B | -0.7620 | 0.39302 |
| PAX5 | -0.2578 | 0.49077 |
| MS4A1 (CD20) | -1.1053 | 0.51196 |
| BTK | -0.2337 | 0.53391 |
| BLK | -0.6860 | 0.61376 |
| REL | 0.2351 | 0.61744 |
| IFITM1 | 0.2005 | 0.62633 |
| CD79B | 0.2118 | 0.64698 |
| CD81 | 0.1166 | 0.71747 |
| NFKBIA | 0.1163 | 0.77923 |
| PSMB9 | 0.0995 | 0.78154 |
| BLNK | -0.1116 | 0.78999 |
| CHUK | 0.0472 | 0.80323 |
| INPP5D | -0.0583 | 0.85716 |
| NFATC1 | -0.0740 | 0.89826 |
| NFKB1 | -0.0262 | 0.92411 |
| CD22 | -0.0834 | 0.92647 |
| PSMB8 | 0.0259 | 0.93047 |

APOPTOSIS AND CELL CYCLE REGULATION

| GENES | LOG2 FOLD CHANGE | P VALUE |
|---|---|---|
| TP53 | 1.6703 | 0.005914 |
| PLA2G6 (PHOSPHOLIPASE) | 0.6605 | 0.014285 |
| LY96 | 0.5567 | 0.026065 |
| MAP3K7 | -0.3830 | 0.058719 |
| TNFSF10 | 0.7661 | 0.064560 |
| PRF1 | 1.1380 | 0.137301 |
| BID | -1.7189 | 0.166447 |
| PIK3CD | 0.7732 | 0.194927 |
| MAPK3 | -0.2787 | 0.231596 |
| TLR4 | 0.6501 | 0.240769 |
| FOS | 1.3529 | 0.300730 |
| FADD | -0.9231 | 0.401037 |
| ATM | -1.0470 | 0.460481 |
| HMGB1 | 0.2192 | 0.513621 |
| CD14 | 0.3551 | 0.537115 |
| CASP3 | 0.1521 | 0.550382 |
| CASP8 | -0.1440 | 0.571440 |
| BCL2 | 0.4609 | 0.612849 |
| MAPK8 | -0.1100 | 0.633618 |
| BCL2L1 | 0.1540 | 0.741953 |
| G2MB | 0.4996 | 0.747951 |
| NFKBIA | 0.1163 | 0.779227 |
| PSMB9 | 0.0995 | 0.781535 |
| CHUK | 0.0472 | 0.803234 |
| TNF | 0.1872 | 0.881326 |
| NFKB1 | -0.0262 | 0.924107 |

GENE LIST BY PATHWAY FOR PATIENTS WHO SUBSEQUENTLY RESPONDED TO AXI-CEL

FIG. 37F

| PSMB8 | 0.0259 | 0.930474 |
|---|---|---|
| BAX | 0.0204 | 0.938744 |
| PSMB10 | 0.0107 | 0.965378 |
| RELA | 0.0039 | 0.984588 |
| FAS | -0.0017 | 0.999141 |

| PSMB10 | 0.0107 | 0.96538 |
|---|---|---|
| RELA | 0.0039 | 0.98459 |

IFN SIGNALING

| GENES | LOG2 FOLD CHANGE | P VALUE |
|---|---|---|
| IFIT2 | 2.0871 | 0.009030 |
| IFI27 | 1.0768 | 0.103323 |
| IL12A | -1.9400 | 0.153863 |
| IFI16 | 0.3286 | 0.256958 |
| IFNL1 | 0.6113 | 0.383894 |
| IFNAR2 | 0.1788 | 0.390312 |
| IFITM2 | -0.2977 | 0.456613 |
| IFNB1 | -0.7220 | 0.597622 |
| IFITM1 | 0.2005 | 0.626333 |
| IFNA1 | -0.5135 | 0.654399 |
| IFIH1 | -0.1614 | 0.671432 |
| IFNGR1 | 0.1355 | 0.704159 |
| IFNA17 | -0.5337 | 0.719128 |
| IFNL2 | -0.5288 | 0.743415 |
| IFI35 | 0.0935 | 0.785225 |
| IFNG | 0.3051 | 0.815850 |

GENE LIST BY PATHWAY FOR PATIENTS WHO SUBSEQUENTLY RESPONDED TO AXI-CEL

*FIG. 37G*

| | | |
|---|---|---|
| IFIT1 | 0.2774 | 0.868506 |
| IFNA8 | 0.1247 | 0.911898 |
| IFNA2 | -0.1340 | 0.914563 |
| IFNAR1 | -0.0182 | 0.940189 |
| IFNA7 | -0.1008 | 0.951013 |

CHEMOTAXIS

| GENES | LOG2 FOLD CHANGE | P VALUE |
|---|---|---|
| CCL20 | -3.6096 | 0.01255 |
| CXCL12 | 2.4523 | 0.02438 |
| STAT1 | 1.0713 | 0.04024 |
| CXCL9 | 2.3180 | 0.04476 |
| CXCL10 | 3.0609 | 0.05743 |
| CXCR1 | 1.7556 | 0.07535 |
| CCL4 | 0.9372 | 0.09252 |
| CXCL11 | 2.2305 | 0.09309 |
| CCL21 | 3.0379 | 0.10269 |
| CCL5 | 1.2900 | 0.10598 |
| CCL23 | 1.2538 | 0.16417 |
| CCL19 | 1.5536 | 0.18538 |
| CCL14 | 1.7563 | 0.19362 |
| PIK3CD | 0.7732 | 0.19493 |
| CCR5 | 1.9615 | 0.21 |
| MAPK3 | -0.2787 | 0.2316 |
| CXCL13 | 2.3402 | 0.23704 |
| CCL3L1 | 0.5824 | 0.3047 |
| CCR2 | 1.6306 | 0.32449 |

| GENES | LOG2 FOLD CHANGE | P VALUE |
|---|---|---|
| CCL15 | -0.6578 | 0.60929 |
| CCL2 | 0.5010 | 0.61813 |
| CCR3 | -0.6633 | 0.61855 |
| CCR4 | 0.7357 | 0.64026 |
| CXCL2 | 0.6590 | 0.67045 |
| CCR6 | -0.5512 | 0.71121 |
| CXCR3 | 0.4231 | 0.74076 |
| CCL22 | -0.4583 | 0.77235 |
| NFKBIA | 0.1163 | 0.77923 |
| CHUK | 0.0472 | 0.80323 |
| CXCL1 | 0.3131 | 0.8265 |
| CXCR5 | -0.2526 | 0.83416 |
| STAT3 | -0.1244 | 0.83602 |
| IL1RN | -0.1902 | 0.89213 |
| CCL18 | -0.1551 | 0.91192 |
| NFKB1 | -0.0262 | 0.92411 |
| IL5 | 0.0933 | 0.93051 |
| IL17F | -0.0994 | 0.93806 |
| CSF1 | 0.0976 | 0.94836 |

GENE LIST BY PATHWAY FOR PATIENTS WHO SUBSEQUENTLY RESPONDED TO AXI-CEL

*FIG. 37H*

| | | |
|---|---|---|
| CCR1 | -1.3447 | 0.33091 |
| CXCR4 | -0.5415 | 0.36741 |
| CCR7 | -1.3048 | 0.42576 |
| JAK3 | 0.4695 | 0.44846 |
| JAK2 | 0.3205 | 0.49331 |
| PF4 | -1.0427 | 0.50815 |
| FPR2 | 0.9224 | 0.54456 |
| STAT5B | 0.2151 | 0.54848 |
| CXCL16 | 0.7579 | 0.56119 |
| CXCL14 | 1.0435 | 0.57101 |
| CXCR6 | 0.8895 | 0.59087 |

| | | |
|---|---|---|
| CCL13 | 0.0789 | 0.9623 |
| IL2 | 0.0432 | 0.96624 |
| LCN2 | -0.0586 | 0.97106 |
| IL1A | -0.0311 | 0.97896 |
| LTBR | 0.0207 | 0.98039 |
| RELA | 0.0039 | 0.98459 |
| IL1B | 0.0299 | 0.98481 |
| CX3CL1 | 0.0192 | 0.98839 |
| BATF | -0.0156 | 0.98927 |
| FAS | -0.0017 | 0.99914 |

INNATE IMMUNITY

| GENES | LOG2 FOLD CHANGE | P VALUE |
|---|---|---|
| CD97 | 1.1099 | 0.025304 |
| LY96 | 0.5567 | 0.026065 |
| MIF | -0.5502 | 0.032185 |
| TSLP | -2.7129 | 0.033206 |
| NFATC2 | 1.3314 | 0.037792 |
| NOD2 | 2.2840 | 0.044841 |
| MRC1 (MANNOSE RC) | 2.6106 | 0.045737 |

| GENES | LOG2 FOLD CHANGE | P VALUE |
|---|---|---|
| CD4 | 0.7218 | 0.184401 |
| IRF1 | 0.5544 | 0.201850 |
| MASP1 | -1.2831 | 0.205758 |
| MAPK11 | -1.7621 | 0.211440 |
| FYN | 0.7118 | 0.215140 |
| MAPK3 | -0.2787 | 0.231596 |
| IRGM | -1.4631 | 0.233422 |

GENE LIST BY PATHWAY FOR PATIENTS WHO SUBSEQUENTLY RESPONDED TO AXI-CEL

FIG. 37I

| | LOG2 FOLD CHANGE | P VALUE |
|---|---|---|
| ITGB2 (CD18) | 1.1350 | 0.046960 |
| PECAM1 | 0.6749 | 0.063964 |
| F2RL1 | -2.4653 | 0.076711 |
| SLC11A1 | -2.9996 | 0.093065 |
| MYD88 | 0.4438 | 0.114176 |
| FCER1G | 0.8341 | 0.133193 |
| TLR2 | 0.7081 | 0.134993 |
| CD68 | 0.6823 | 0.137069 |
| SYK | 0.6412 | 0.170208 |
| DDX58 | 1.1224 | 0.172451 |
| TREM1 | -2.3325 | 0.178027 |
| SERPING1 | 0.8720 | 0.183261 |

INNATE IMMUNITY (CONTINUED)

| GENES | LOG2 FOLD CHANGE | P VALUE |
|---|---|---|
| CD209 | 1.2370 | 0.360681 |
| CFI | -1.3966 | 0.369630 |
| TLR3 | -1.2783 | 0.373480 |
| ITGAX | 0.6416 | 0.381319 |
| TBK1 | 0.1279 | 0.395740 |
| LY86 | -1.0527 | 0.400783 |
| FADD | -0.9231 | 0.401037 |
| LGALS3 | 0.4226 | 0.419422 |
| IDO1 | 1.0644 | 0.425662 |
| FCER1A | 0.6549 | 0.430121 |
| FCGR1A | -1.0002 | 0.437519 |
| KLRD1 | -0.8974 | 0.440469 |

| | LOG2 FOLD CHANGE | P VALUE |
|---|---|---|
| LCK | 0.6642 | 0.240264 |
| TLR4 | 0.6501 | 0.240769 |
| ARG1 | 1.4660 | 0.255157 |
| HLA-DRB4 | 2.8808 | 0.284153 |
| MUC1 | -1.6719 | 0.294129 |
| FOS | 1.3529 | 0.300730 |
| CRP | 0.8023 | 0.312939 |
| CCR2 | 1.6306 | 0.324495 |
| CLEC4C | 1.1661 | 0.325412 |
| C1QA | 0.6567 | 0.340275 |
| GNLY | 1.4477 | 0.349740 |
| CEACAM1 | 1.1428 | 0.351840 |

| GENES | LOG2 FOLD CHANGE | P VALUE |
|---|---|---|
| TLR5 | -0.5505 | 0.695429 |
| FCGR2A | 0.2172 | 0.698975 |
| CCR6 | -0.5512 | 0.711211 |
| S100A8 | 0.7233 | 0.712439 |
| CD81 | 0.1166 | 0.717473 |
| STAT6 | -0.0782 | 0.719154 |
| NLRP3 | -0.5064 | 0.733287 |
| IGF2R | 0.1053 | 0.734930 |
| BCL2L1 | 0.1540 | 0.741953 |
| CD55 | -0.4286 | 0.763898 |
| NFKBIA | 0.1163 | 0.779227 |
| PSMB9 | 0.0995 | 0.781535 |

GENE LIST BY PATHWAY FOR PATIENTS WHO SUBSEQUENTLY RESPONDED TO AXI-CEL

*FIG. 37J*

| | | | | | |
|---|---|---|---|---|---|
| DEFB1 (DEFENSIN) | 1.1419 | 0.443054 | S100B | 0.3789 | 0.791542 |
| CEACAM6 | -1.3563 | 0.446863 | CR1 | -0.3031 | 0.797142 |
| C1QB | 0.5945 | 0.453711 | CHUK | 0.0472 | 0.803234 |
| C9 | -0.9909 | 0.477640 | CD58 | 0.2367 | 0.814480 |
| C3AR1 | 0.8893 | 0.484308 | CD47 | -0.0601 | 0.814941 |
| SOCS1 | -0.3963 | 0.494084 | S100A12 | -0.4161 | 0.816364 |
| PLAUR | 0.8872 | 0.511184 | PSEN1 | 0.0373 | 0.817273 |
| HMGB1 | 0.2192 | 0.513621 | NFKB2 | 0.1194 | 0.822894 |
| CLEC6A | 0.9258 | 0.518917 | PLAU | 0.2218 | 0.826967 |
| TANK | -0.2444 | 0.520793 | TRAF6 | -0.0514 | 0.832429 |
| BTK | -0.2337 | 0.533914 | RELB | -0.0711 | 0.832735 |
| CD14 | 0.3551 | 0.537115 | HLA-C | -0.0852 | 0.839977 |
| NLRC5 | 0.2217 | 0.554535 | CD59 | 0.0547 | 0.868308 |
| PIN1 | -0.0947 | 0.556858 | C3 | -0.2942 | 0.869652 |
| C1S | 0.3841 | 0.567096 | TLR7 | -0.1945 | 0.892662 |
| MAPK14 | 0.1362 | 0.568067 | LTF | -0.2629 | 0.897184 |
| CASP8 | -0.1440 | 0.571440 | NFATC1 | -0.0740 | 0.898264 |
| HLA-B | 0.2024 | 0.584497 | ITGAM | 0.1403 | 0.909635 |
| NOD1 | -0.4307 | 0.588873 | NFKB1 | -0.0262 | 0.924107 |
| SELL | -0.7827 | 0.610710 | BST2 | 0.0323 | 0.928094 |
| BCL2 | 0.4609 | 0.612849 | PSMB8 | 0.0259 | 0.930474 |
| LAMP1 | 0.1624 | 0.619570 | SIGIRR | -0.0918 | 0.934984 |
| TLR9 | -0.4466 | 0.622362 | MAP4K2 | -0.0164 | 0.963186 |

GENE LIST BY PATHWAY FOR PATIENTS WHO SUBSEQUENTLY RESPONDED TO AXI-CEL

*FIG. 37K*

| MME | -0.6659 | 0.625523 |
|---|---|---|
| MAPK8 | -0.1100 | 0.633618 |
| IRF7 | 0.1647 | 0.660912 |
| TLR8 | 0.3576 | 0.675343 |
| CASP1 | 0.4957 | 0.684011 |
| CD3G | 0.6599 | 0.689718 |

| PSMB10 | 0.0107 | 0.965378 |
|---|---|---|
| CD44 | 0.0328 | 0.965971 |
| LCN2 | -0.0586 | 0.971065 |
| RELA | 0.0039 | 0.984588 |
| IL1B | 0.0299 | 0.984815 |
| C5 | 0.0153 | 0.991488 |

GENE LIST BY PATHWAY FOR PATIENTS WHO SUBSEQUENTLY RESPONDED TO AXI-CEL

FIG. 38A

| CYTOKINE GENE | T CELL GENE | PEARSON CORRELATION | PEARSON P VALUE | SPEARMAN CORRELATION | SPEARMAN P VALUE | SPEARMAN BH P VALUE | PEARSON BH P VALUE |
|---|---|---|---|---|---|---|---|
| STAT4 | CD3D | 0.7238 | 2.93E-05 | 0.8636 | 1.34E-08 | 1.39E-06 | 0.00102 |
| CCR5 | CD3D | 0.7271 | 2.58E-05 | 0.8012 | 8.76E-07 | 3.97E-05 | 0.00102 |
| CCL5 | CD3D | 0.7129 | 4.37E-05 | 0.7962 | 1.15E-06 | 3.97E-05 | 0.00114 |
| IL7R | CD3D | 0.6777 | 0.00014 | 0.7727 | 3.72E-06 | 9.68E-05 | 0.00297 |
| CXCL13 | CD3D | 0.2859 | 0.15676 | 0.7550 | 8.30E-06 | 0.00017 | 0.47951 |
| CCR2 | CD3D | 0.4984 | 0.00956 | 0.7487 | 1.09E-05 | 0.00019 | 0.05848 |
| CXCR6 | CD3D | 0.8154 | 3.88E-07 | 0.7220 | 3.13E-05 | 0.00046 | 4.04E-05 |
| IL7 | CD3D | 0.5151 | 0.00709 | 0.7132 | 4.32E-05 | 0.00056 | 0.04941 |
| CCL21 | CD3D | 0.5022 | 0.00893 | 0.6849 | 0.00011 | 0.00131 | 0.05807 |
| IL18 | CD3D | 0.5814 | 0.00184 | 0.6618 | 0.00023 | 0.00219 | 0.02393 |
| CSF1 | CD3D | 0.6507 | 0.00032 | 0.6150 | 0.00083 | 0.00702 | 0.00474 |
| CCR4 | CD3D | 0.5148 | 0.00713 | 0.6126 | 0.00088 | 0.00702 | 0.04941 |
| IL17RA | CD3D | 0.4296 | 0.02852 | 0.5973 | 0.00128 | 0.00947 | 0.14744 |
| IL1R1 | CD3D | 0.2373 | 0.24304 | 0.5904 | 0.0015 | 0.01039 | 0.61742 |
| STAT1 | CD3D | 0.5271 | 0.00566 | 0.5739 | 0.00217 | 0.01328 | 0.04941 |
| CCL4 | CD3D | 0.3263 | 0.10379 | 0.5369 | 0.00469 | 0.02707 | 0.39979 |
| IL1R2 | CD3D | 0.5244 | 0.00596 | 0.5305 | 0.0053 | 0.02903 | 0.04941 |
| IL21 | CD3D | 0.5610 | 0.00287 | 0.5249 | 0.0059 | 0.0307 | 0.03316 |

CORRELATIONS BETWEEN PRETREATMENT GENE EXPRESSION OF CYTOKINES, CYTOKINE-RESPONSIVE TRANSCRIPTION FACTORS, AND T CELL MARKERS

*FIG. 38B*

| | | | | | | |
|---|---|---|---|---|---|---|
| IL6ST | CD3D | 0.4613 | 0.0177 | 0.5170 | 0.00684 | 0.03389 | 0.10225 |
| IL10 | CD3D | 0.1798 | 0.37957 | 0.5125 | 0.00743 | 0.03512 | 0.80562 |
| CXCL9 | CD3D | 0.2372 | 0.24341 | 0.5074 | 0.00815 | 0.03686 | 0.61742 |
| CCL19 | CD3D | 0.5381 | 0.00458 | 0.4930 | 0.0105 | 0.04551 | 0.0476 |
| CCL22 | CD3D | 0.4266 | 0.02977 | 0.4670 | 0.01616 | 0.06464 | 0.14744 |
| LTB | CD3D | 0.3908 | 0.04839 | 0.4600 | 0.01805 | 0.06951 | 0.21879 |
| CXCL14 | CD3D | 0.2639 | 0.1926 | 0.4554 | 0.01939 | 0.07202 | 0.54137 |
| CXCL10 | CD3D | 0.1854 | 0.36457 | 0.4299 | 0.02836 | 0.10171 | 0.80562 |
| IL15 | CD3D | 0.1331 | 0.51674 | 0.4209 | 0.03224 | 0.10748 | 0.81412 |
| CCL5 | CD8A | 0.6867 | 0.00011 | 0.7942 | 3.31E-06 | 0.00034 | 0.01111 |
| CCL4 | CD8A | 0.4347 | 0.02647 | 0.7231 | 4.81E-05 | 0.00167 | 0.44394 |
| IL17RA | CD8A | 0.1924 | 0.34628 | 0.6786 | 0.0002 | 0.00499 | 0.89561 |
| CXCL9 | CD8A | 0.3111 | 0.12183 | 0.6725 | 0.00024 | 0.00499 | 0.88173 |
| CXCR3 | CD8A | 0.4968 | 0.00983 | 0.6278 | 0.0006 | 0.01033 | 0.20442 |
| IL18 | CD8A | 0.2893 | 0.15176 | 0.6321 | 0.0007 | 0.01038 | 0.88173 |

CORRELATIONS BETWEEN PRETREATMENT GENE EXPRESSION OF CYTOKINES,
CYTOKINE-RESPONSIVE TRANSCRIPTION FACTORS, AND T CELL MARKERS

*FIG. 38C*

| | | | | | | |
|---|---|---|---|---|---|---|
| IL15 | CD8A | 0.1056 | 0.60759 | 0.6205 | 0.00093 | 0.01203 | 0.89561 |
| IL10 | CD8A | 0.2991 | 0.13776 | 0.5938 | 0.00138 | 0.01597 | 0.88173 |
| CCR5 | CD8A | 0.6112 | 0.00091 | 0.5727 | 0.00223 | 0.0232 | 0.02368 |
| STAT1 | CD8A | 0.4263 | 0.02988 | 0.5644 | 0.00312 | 0.02953 | 0.44394 |
| CCL3L1 | CD8A | 0.3776 | 0.05721 | 0.5562 | 0.00367 | 0.03138 | 0.62582 |
| IL7R | CD8A | 0.2887 | 0.15261 | 0.5262 | 0.00575 | 0.04275 | 0.88173 |
| IL18 | CD4 | 0.7729 | 3.69E-06 | 0.7908 | 3.68E-06 | 0.00038 | 0.00019 |
| CCL5 | CD4 | 0.7195 | 3.43E-05 | 0.7579 | 1.28E-05 | 0.00044 | 0.00071 |
| CCR2 | CD4 | 0.6105 | 0.00093 | 0.7359 | 1.83E-05 | 0.00048 | 0.0107 |
| CCL19 | CD4 | 0.5505 | 0.00357 | 0.7149 | 6.40E-05 | 0.00133 | 0.02852 |
| STAT4 | CD4 | 0.6748 | 0.00016 | 0.6806 | 0.00013 | 0.00209 | 0.00232 |
| IL6ST | CD4 | 0.5034 | 0.00875 | 0.6896 | 0.00014 | 0.00209 | 0.06068 |
| IL17RA | CD4 | 0.4468 | 0.02211 | 0.6862 | 0.00016 | 0.00209 | 0.12376 |
| IL7R | CD4 | 0.7819 | 2.40E-06 | 0.6507 | 0.00032 | 0.00331 | 0.00019 |
| CSF1 | CD4 | 0.7365 | 1.79E-05 | 0.6397 | 0.00043 | 0.00409 | 0.00062 |
| IL1R2 | CD4 | 0.5393 | 0.00447 | 0.6281 | 0.00059 | 0.00513 | 0.03318 |
| CCL21 | CD4 | 0.3045 | 0.13038 | 0.6086 | 0.00097 | 0.00777 | 0.40588 |

CORRELATIONS BETWEEN PRETREATMENT GENE EXPRESSION OF CYTOKINES, CYTOKINE-RESPONSIVE TRANSCRIPTION FACTORS, AND T CELL MARKERS

CORRELATION STUDIES BETWEEN PRETREATMENT TME GENE EXPRESSION
OF CYTOKINES AND IMMUNE GENES OR IMMUNE CELL DENSITY

CORRELATION STUDIES BETWEEN PRETREATMENT TME GENE EXPRESSION
OF CYTOKINES AND IMMUNE GENES OR IMMUNE CELL DENSITY

CORRELATION STUDIES BETWEEN PRETREATMENT TME GENE EXPRESSION
OF CYTOKINES AND IMMUNE GENES OR IMMUNE CELL DENSITY

CORRELATION STUDIES BETWEEN PRETREATMENT TME GENE EXPRESSION
OF CYTOKINES AND IMMUNE GENES OR IMMUNE CELL DENSITY

CORRELATION STUDIES BETWEEN PRETREATMENT TME GENE EXPRESSION
OF CYTOKINES AND IMMUNE GENES OR IMMUNE CELL DENSITY

CORRELATION BETWEEN PRETREATMENT TME T CELL DENSITY AND
TUMOUR BURDEN IN RELATION TO AXI-CEL CLINICAL OUTCOMES

CORRELATION BETWEEN PRETREATMENT TME T CELL DENSITY AND
TUMOUR BURDEN IN RELATION TO AXI-CEL CLINICAL OUTCOMES

*FIG. 42*

| | n (%) |
|---|---|
| TOTAL NUMBER OF BIOPSIES WITH KNOWN ANATOMIC LOCATION | 31 (100) |
| LOCATION OF BIOPSY | |
| LYMPH NODE | 10 (32) |
| SKIN | 4 (13) |
| ABDOMEN | 3 (10) |
| LOWER QUADRANT | 2 (6) |
| AXILLARY MASS | 1 (3) |
| GASTRIC | 1 (3) |
| LIVER | 1 (3) |
| LUNG | 1 (3) |
| MEDIASTINAL | 1 (3) |
| MESENTERIC | 1 (3) |
| MUSCLE | 1 (3) |
| NECK | 1 (3) |
| PELVIC MASS | 1 (3) |
| RETROPERITONEAL | 1 (3) |
| RIGHT CALF | 1 (3) |
| TESTICLE | 1 (3) |

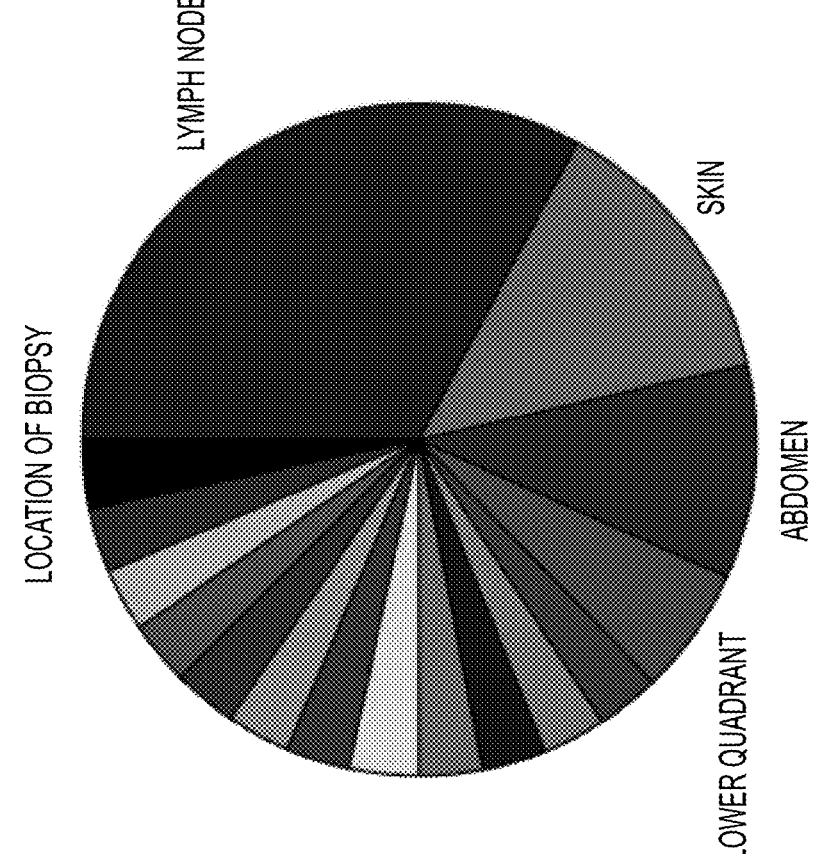

LOCATION OF BIOPSY

LYMPH NODE

SKIN

ABDOMEN

LOWER QUADRANT

ORIGIN OF ZUMA-1 TUMOURAL BIOPSIES ANALYSED IN THIS STUDY WITH KNOWN ANATOMIC LOCATION

PROPOSED MODEL LINKING PRETREATMENT TUMOUR IMMUNE CONTEXTURE AND AN IMMUNOLOGICALLY INVOLVED TME WITH RESPONSE TO AXI-CEL sVCAM-1

ZUMA-2 COHORT 1, N=68, NE GRAD 4 VS. NON-NE, VCAM1, MEDIAN+(Q1, Q3) LINE PLOT OVER TIME

FIG. 57 (CONT. -1)
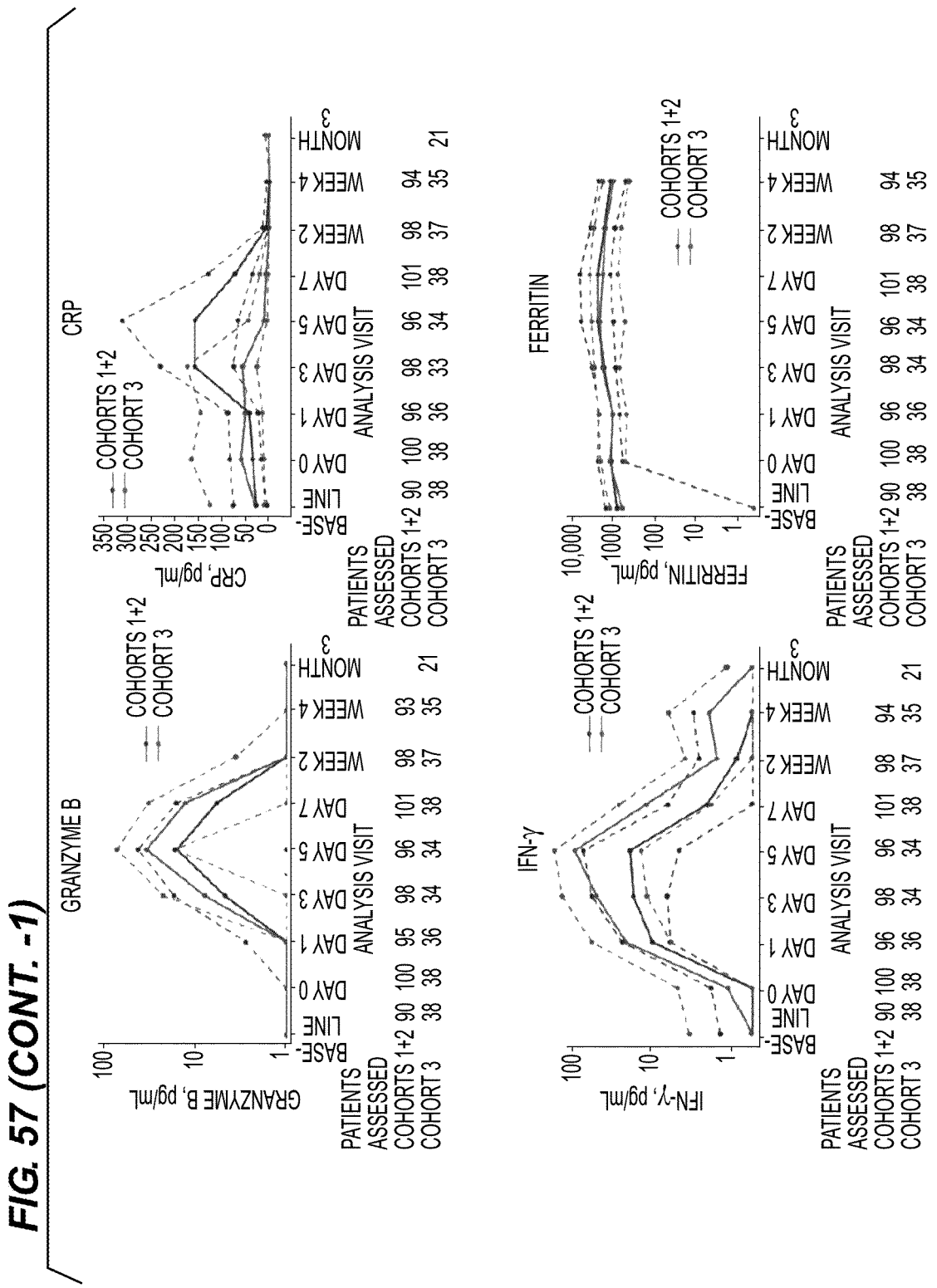

PATIENT HISTORY

HISTORY: 21-YEAR OLD MAN WITH REFRACTORY, STAGE IVB PMBCL WHO RECEIVED 2 PRIOR THERAPIES AND PALLIATIVE EXTERNAL BEAM RADIATION; BEST RESPONSE TO LAST THERAPY WAS PD

AT BASELINE: MRSA IMPETIGO, IPI SCORE OF 2, NO CNS DISEASE INVOLVEMENT ON MRI, NEW-ONSET B SYPMTOMS AND RAPID DISEASE PROGRESSION AT ENROLLMENT; PATIENT RECEIVED NARCOTICS AND STEROIDS DUE TO PAIN; ECOG PERFORMANCE STATUS IMPROVED FROM 2 TO 1.

TREATMENT MANAGEMENT

BEFORE LEUKAPHERESIS PATIENT HAD NEW AND WORSENING LESIONS AND PATIENT WAS CONSIDERED TO HAVE NEW-ONSET B SYMPTOMS. BEFORE CONDITIONING CHEMOTHERAPY,, PATIENT HAD INCREASED LDH AND WORSENING LIVER FUNCTION. BEFORE AXI-CELL INFUSION, CHEST X-RAY AND THORACENTESIS SHOWED NEW MALIGNANT PLEURAL EFFUSION; INFECTIOUS WORKUP REVEALED NEGATIVE NASOPHARYNGEAL VIRAL SWAB, URINALYSIS, AND BLOOD CULTURES BUT CMV REACTIVATION. DAY 0: FEVER (40°C) AND TACHYCARDIA; AXI-CEL DOSE OF $2.0 \times 10^6$ CAR T CELLS/kg DAY 2: FEVER (40°C) AND TACHYCARDIA; TOCILIZUMAB (8 mg/kg IV) ADMINISTERED PER PROTOCOL DAY 3: GRADE 2 CRS DAY 6: GRADE 2 CONFUSION, SOMNOLANCE: LEVETIRACETAM (1000 mg TWICE DAILY) ADMINISTERED DAY 7: GRADE 3 CARDIOMYOPATHY TREATED WITH NOREPINEPHRINE (10ug/MIN TITRATED TO 20ug/MIN WITH EPINEPHRINE (10ug/kg); GRADE 4 OBTUNDATION: URGENT NONCONTRAST HEAD CT SCAN SHOWED EVIDENCE OF LEUKOENCEPHALOPATHY, PATIENT WAS INTUBATED AND DAILY SOLUMEDROL WAS INITIATED. PATIENT HAD BILATTERAL DILATED AND NONREACTIVE PUPILS, AND STAT NONCONTRAST HEAD CT SHOWED DIFFUSE CEREBRAL EDEMA ONSET SINCE CT 3 HOURS PRIOR. VENTILATOR RATE WAS INCREASED, HEAD OF BED RAISED, AND PATIENT ADMINISTERED 23% HYPERTONIC SALINE AND MANNITOL (1 g/kg) DAY 9: GRADE 5 CEREBRAL EDEMA

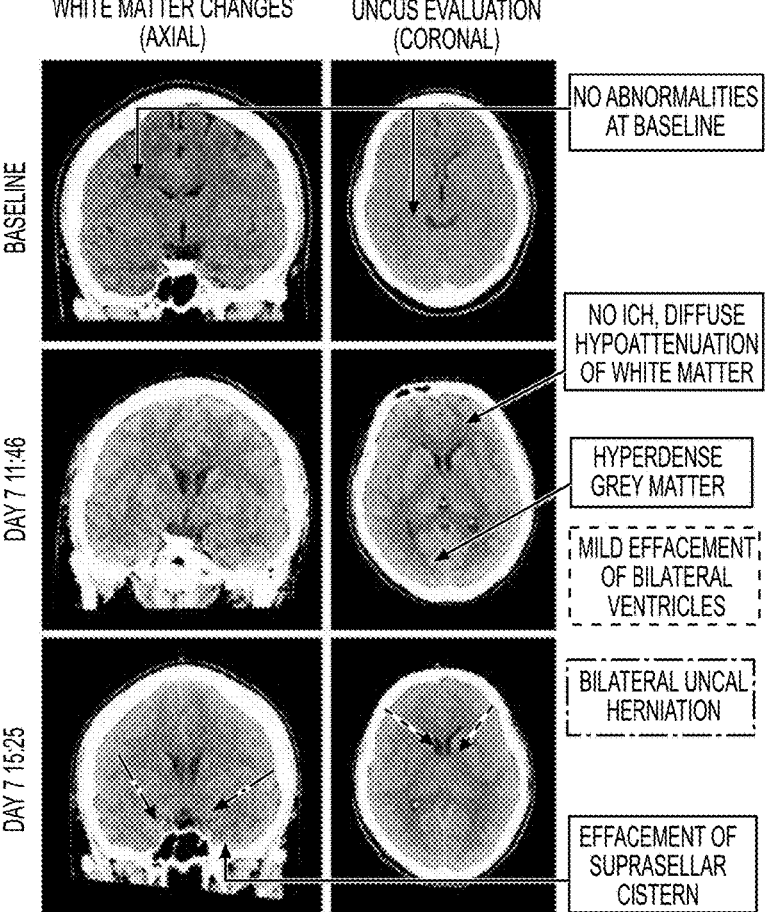

WHITE MATTER CHANGES (AXIAL)     UNCUS EVALUATION (CORONAL)

BASELINE     DAY 7 11:46     DAY 7 15:25

NO ABNORMALITIES AT BASELINE

NO ICH, DIFFUSE HYPOATTENUATION OF WHITE MATTER

HYPERDENSE GREY MATTER

MILD EFFACEMENT OF BILATERAL VENTRICLES

BILATERAL UNCAL HERNIATION

EFFACEMENT OF SUPRASELLAR CISTERN

POST-HOC TRANSLATIONAL FINDINGS

PRETREATMENT SERUM SHOWED LEVELS OF PROINLAMMATORY, CELL ADHESION/VASCULAR DAMAGE MARKERS AND CHEMOKINES THAT WERE CONSISTENT WITH THE PRESENCE OF ACTIVATED MYELOID AND LYMPHOID CELLS, SUGGESTING A PRE-EXISTING INFLAMMATORY OR INFECTIOUS PROCESS. CSF ANALYSIS FROM DAY 0 DEMONSTRATED VALUES FOR CRP, VCAM-1, ICAM-1, IL-2Rα, AND IP-10 THAT WERE THE HIGHEST REPORTED IN THE STUDY TO DATE. THE HIGHLY ELEVATED LEVELS OF VCAM-1 AND ICAM-1 SUGGESTED A FAVORABLE ENVIRONMENT FOR TRAFFICKING OF IMMUNE CELLS. CAR T CELL LEVEL IN BLOOD AT DAY 7 WAS SIMILAR TO THE MEDIAN IN COHORTS 1 AND 2 ANALYSIS OF A CSF SAMPLE FROM DAY 9 WAS CONSISTENT WITH RECRUITMENT OF LYPHOCYTES (CAR+ AND CAR-) AND MYELOID CELLS

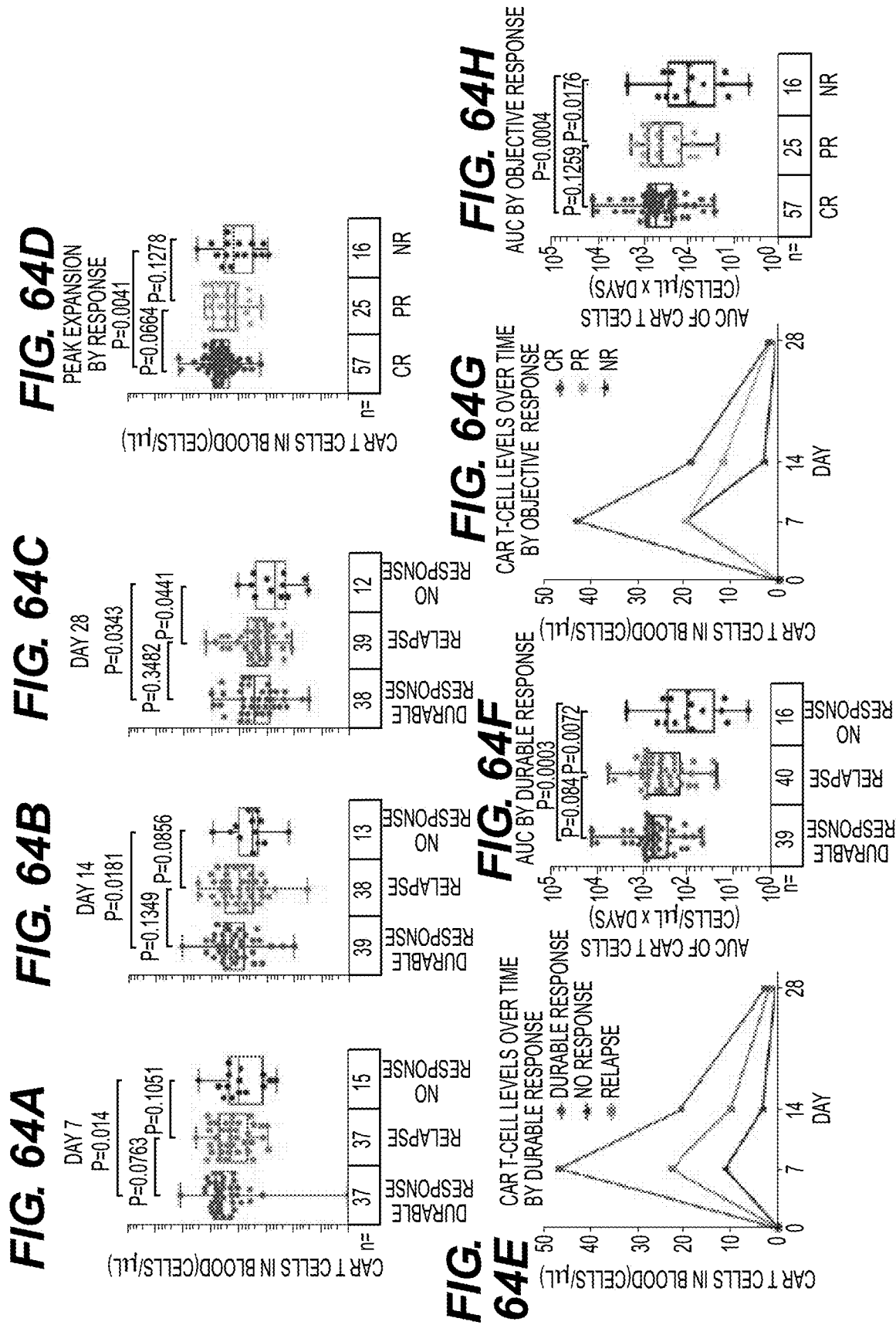

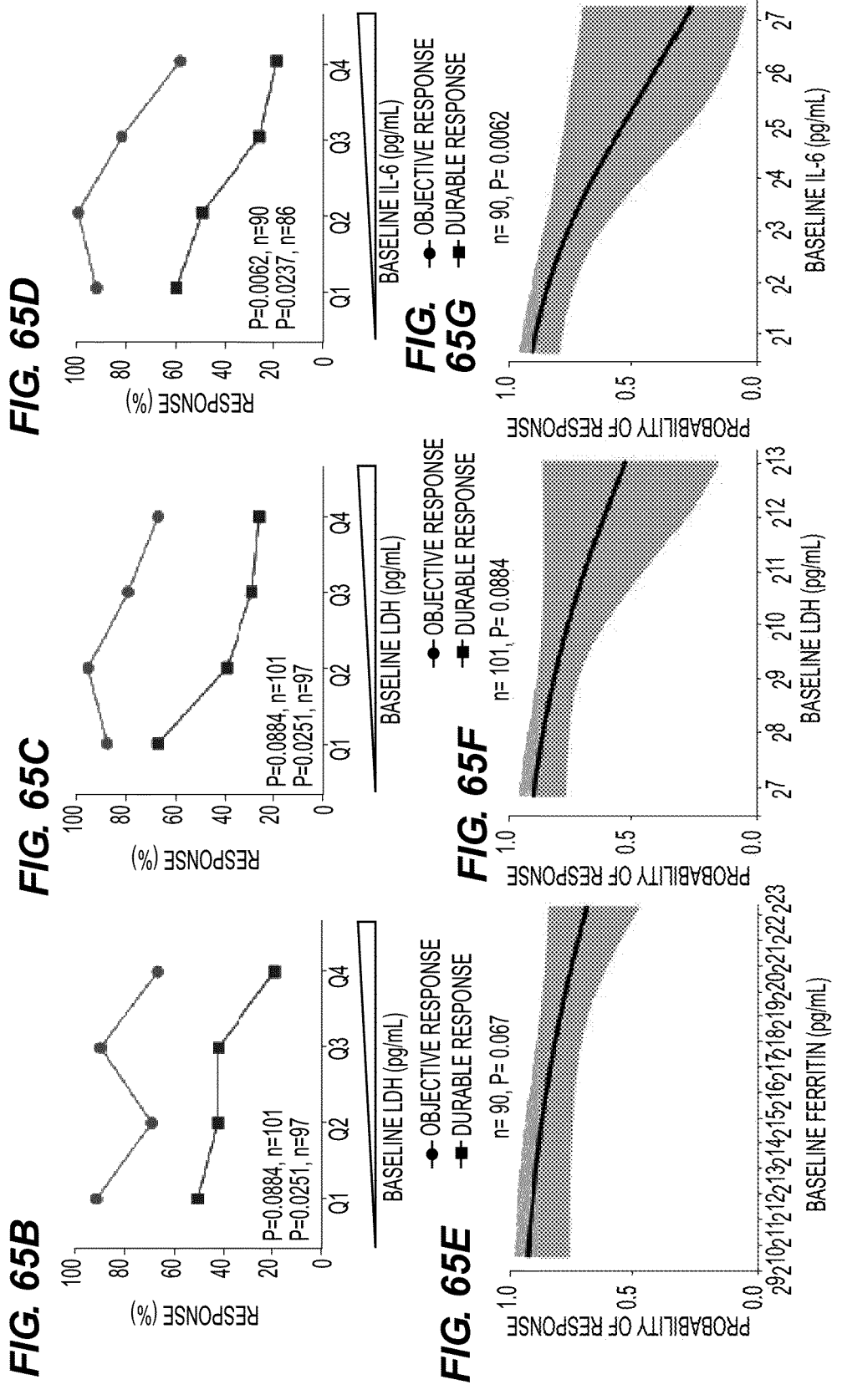

| STATISTICAL TEST | COMPARISON | | P VALUE FROM SPECIFIED FERRITIN MEASUREMENT | | | | | | | | |
|---|---|---|---|---|---|---|---|---|---|---|---|
| | | BASELINE | DAY 0 | DAY 1 | DAY 3 | DAY 5 | DAY 7 | DAY 14 | DAY 28 | PEAK | AUC$_{0-28}$ |
| DUNN'S TEST | DURABLE VS RELAPSED | 0.136 | 0.004 | 0.0004 | 0.036 | 0.053 | 0.009 | 0.107 | 0.001 | 0.01 | 0.016 |
| | DURABLE VS NO RESPONSE | 0.046 | 0.005 | 0.015 | 0.054 | 0.339 | 0.286 | 0.471 | 0.148 | 0.228 | 0.227 |
| | RELAPSED VS NO RESPONSE | 0.197 | 0.313 | 0.417 | 0.444 | 0.24 | 0.143 | 0.266 | 0.164 | 0.18 | 0.223 |
| KW TEST | OVERALL | 0.094 | 0.002 | 0.005 | 0.04 | 0.108 | 0.022 | 0.196 | 0.002 | 0.025 | 0.037 |

FIG. 70 SUPPLEMENTAL TABLE 4

| CHARACTERISTICS | NON-RESPONDER, n | RESPONDER, n | RESPONDER, MEDIAN | NON-RESPONDER, MEDIAN | RATIO OF RESPONDER: NON-RESPONDER | P VALUE | ODDS RATIO |
|---|---|---|---|---|---|---|---|
| DOUBLING TIME IN DAYS | 76 | 15 | 1.490 | 1.730 | 1.161 | 0.025 | 0.582 |
| LOG2(TOTAL # OF CCR7+CD45RA+ T CELLS [1x10$^6$]) | 84 | 16 | 5.421 | 4.820 | 0.889 | 0.033 | 1.790 |
| CCR7+CD45RA+ T CELLS (%) | 84 | 16 | 15.450 | 9.500 | 0.615 | 0.093 | 2.021 |
| CCR7-CD45RA- T CELLS (%) | 84 | 16 | 37.500 | 39.550 | 1.055 | 0.109 | 0.631 |
| TOTAL CCR7+CD45RA+ T CELLS (n) | 84 | 16 | 42.868 | 28.817 | 0.672 | 0.119 | 1.832 |
| VIABILITY (%) | 84 | 17 | 94.500 | 93.600 | 0.990 | 0.166 | 1.383 |
| LOG2(TOTAL # OF CCR7-CD45RA- T CELLS [1x10$^6$]) | 84 | 16 | 6.784 | 7.012 | 1.034 | 0.169 | 0.651 |
| CCR7+ T CELLS/CCR7- CELLS | 84 | 16 | 0.733 | 0.691 | 0.943 | 0.186 | 1.795 |
| CCR7- T CELLS, (%) | 84 | 16 | 57.800 | 59.200 | 1.024 | 0.204 | 0.686 |
| CCR7+ T CELLS, (%) | 84 | 16 | 42.350 | 40.900 | 0.966 | 0.263 | 1.388 |
| LOG2(NUMBER OF CCR7- T CELLS [1x10$^6$]) | 84 | 16 | 7.270 | 7.567 | 1.041 | 0.289 | 0.732 |
| INTERFERON-γ BY COCULTURE (pg/mL) | 84 | 17 | 5834.500 | 7801.000 | 1.337 | 0.308 | 0.773 |
| LOG2(NUMBER OF CCR7+CD45RA- T CELLS [1x10$^6$]) | 84 | 16 | 6.175 | 6.347 | 1.028 | 0.359 | 0.772 |
| CD3- CELLS (%) | 84 | 16 | 2.250 | 2.700 | 1.200 | 0.367 | 0.795 |
| T CELLS (%) | 84 | 16 | 97.750 | 97.300 | 0.995 | 0.367 | 1.258 |
| CCR7+CD45A- T CELLS (1x10$^6$), n | 84 | 16 | 72.241 | 81.496 | 1.128 | 0.371 | 0.793 |
| CCR7-CD45RA- T CELLS, n | 84 | 16 | 110.217 | 129.143 | 1.172 | 0.380 | 0.806 |
| NO. CCR7+CD45A+ T CELLS (1x10$^6$)/TUMOR BURDEN AT BASELINE | 84 | 15 | 0.010 | 0.007 | 0.704 | 0.390 | 1.655 |
| CCR7+CD45A- T CELLS, (%) | 84 | 16 | 24.950 | 30.800 | 1.234 | 0.425 | 0.808 |
| LOG2(NO. CD8 T CELLS IN PRODUCT/ (DOUBLING TIME x TUMOR BURDEN AT BASELINE (LOCAL)) | 76 | 14 | -5.439 | -5.899 | 1.085 | 0.433 | 1.280 |
| NO. CD4 T CELLS INFUSED /TUMOR BURDEN AT BASELINE | 84 | 15 | 0.038 | 0.045 | 1.190 | 0.456 | 1.573 |
| INTERFERON-γ NORMALIZE BY TRANSDUCTION EFFICIANCY (pg/mL) | 84 | 17 | 10126.823 | 12313.290 | 1.216 | 0.467 | 0.831 |
| LOG2(NO. CD8 T CELLS INFUSED/DOUBLING TIME AT BASELINE) | 76 | 14 | 6.547 | 6.532 | 0.998 | 0.471 | 1.231 |

FIG. 70 (CONT. -1)

| CHARACTERISTICS | RESPONDER, n | NON-RESPONDER, n | RESPONDER, MEDIAN | NON-RESPONDER, MEDIAN | RATIO OF RESPONDER:NON-RESPONDER | P VALUE | ODDS RATIO |
|---|---|---|---|---|---|---|---|
| LOG2(NUMBER OF CD3- T CELLS [1x10^6]) | 84 | 16 | 2.738 | 3.255 | 1.189 | 0.485 | 0.824 |
| LOG2(NO. CCR7+ T CELLS [1x10^6]) | 84 | 16 | 7.029 | 6.847 | 0.974 | 0.485 | 1.206 |
| NUMBER OF CD8 T CELLS INFUSED/DOUBLING TIME AT BASELINE | 76 | 14 | 93.512 | 92.519 | 0.989 | 0.501 | 1.249 |
| NUMBER OF CD3- T CELLS (1x10^6) | 84 | 16 | 6.674 | 9.603 | 1.439 | 0.510 | 1.848 |
| NO. CCR7+ T CELLS (10^6)/TUMOR BURDEN AT BASELINE | 84 | 15 | 0.033 | 0.037 | 1.136 | 0.532 | 1.282 |
| CCR7+ T CELLS (1x10^6), n | 84 | 16 | 130.601 | 115.147 | 0.882 | 0.543 | 1.193 |
| CCR7- T CELLS (1x10^6), n | 84 | 16 | 154.312 | 189.827 | 1.230 | 0.585 | 0.870 |
| TOTAL CAR + T CELLS IN PRODUCT BAG (1x10^6) | 84 | 17 | 160.000 | 170.000 | 1.063 | 0.596 | 0.864 |
| CCR7- CD45RA+ T CELLS (1x10^6), n | 84 | 16 | 43.152 | 55.506 | 1.286 | 0.713 | 1.111 |
| LOG2(TOTAL T CELLS [1x10^6]) | 84 | 17 | 8.217 | 8.405 | 1.023 | 0.732 | 0.913 |
| LOG2(NUMBER OF CD8 T CELLS [1x10^6]) | 84 | 16 | 7.219 | 7.351 | 1.018 | 0.733 | 0.910 |
| LOG2(TOTAL CAR+ T CELLS IN PRODUCT BAG [1x10^6]) | 84 | 17 | 7.322 | 7.409 | 1.012 | 0.755 | 0.918 |
| CD4 T CELLS (%) | 84 | 16 | 49.500 | 44.550 | 0.900 | 0.777 | 1.080 |
| CD8 T CELLS (%) | 84 | 16 | 50.550 | 55.500 | 1.098 | 0.778 | 0.926 |
| CCR7- CD45RA+ T CELLS (%) | 84 | 16 | 15.250 | 15.900 | 1.043 | 0.792 | 1.077 |
| CD4/CD8 RATIO | 84 | 16 | 0.985 | 0.803 | 0.815 | 0.803 | 1.074 |
| LOG2(NO. T CELLS (1e6) | 84 | 16 | 8.175 | 8.321 | 1.018 | 0.837 | 0.945 |
| LOG2(NO. CD4 T CELLS INFUSED / TUMOR BURDEN AT BASELINE) | 84 | 15 | -4.711 | -4.459 | 0.947 | 0.852 | 1.054 |
| LOG2(INTERFERON-Y BY COCULTURE (pg/mL)) | 84 | 17 | 12.510 | 12.929 | 1.033 | 0.853 | 0.951 |
| TRANSDUCTION EFFICIENCY OF TRANSDUCTION RATE (%) | 84 | 17 | 53.750 | 52.100 | 0.969 | 0.874 | 1.043 |
| NO. CCR7-CD45RA- T CELLS (1x10^6)/ TUMOR BURDEN AT BASELINE | 84 | 15 | 0.028 | 0.035 | 1.264 | 0.881 | 1.046 |
| NO. CD4 T CELLS (1x10^6) | 84 | 16 | 162.309 | 143.657 | 0.885 | 0.914 | 0.971 |
| TOTAL T CELLS (1x10^6) | 84 | 17 | 297.482 | 338.983 | 1.140 | 0.919 | 0.974 |
| LOG2(NO CCR7- CD45RA+ T CELLS [1x10^6]) | 84 | 16 | 5.431 | 5.795 | 1.067 | 0.924 | 1.027 |
| NO. CCR7- CD45RA+ T CELLS (1x10^6) / TUMOR BURDEN AT BASELINE | 84 | 15 | 0.011 | 0.010 | 0.910 | 0.930 | 1.026 |

FIG. 70 (CONT. -2)

| CHARACTERISTICS | RESPONDER, n | NON-RESPONDER, n | RESPONDER, MEDIAN | NON-RESPONDER, MEDIAN | RATIO OF RESPONDER: NON-RESPONDER | p VALUE | ODDS RATIO |
|---|---|---|---|---|---|---|---|
| NUMBER OF CD8 T CELLS (1 x 10⁶) | 84 | 16 | 148.958 | 163.281 | 1.096 | 0.943 | 1.020 |
| NUMBER OF CD8 T CELLS IN PRODUCT / (DOUBLING TIME x TUMOR BURDEN AT BASELINE [LOCAL]) | 76 | 14 | 0.023 | 0.017 | 0.727 | 0.957 | 1.016 |
| LOG2(NUMBER OF CD8 T CELLS INFUSED / TUMOR BURDEN AT BASELINE] | 84 | 15 | -4.820 | -4.974 | 1.032 | 0.964 | 1.013 |
| LOG2(NUMBER OF CD4 T CELLS [1x10⁶]) | 84 | 16 | 7.343 | 7.166 | 0.976 | 0.966 | 0.988 |
| NUMBER OF CD8 T CELLS INFUSED /TUMOR BURDEN AT BASELINE | 84 | 15 | 0.035 | 0.032 | 0.899 | 0.991 | 0.997 |
| NUMBER OF T CELLS (1 x 10⁶) | 84 | 16 | 289.029 | 319.723 | 1.106 | 0.993 | 0.998 |
| VECTOR COPY NUMBER | 82 | 15 | 0.200 | 0.210 | 1.050 | 0.995 | 0.998 |

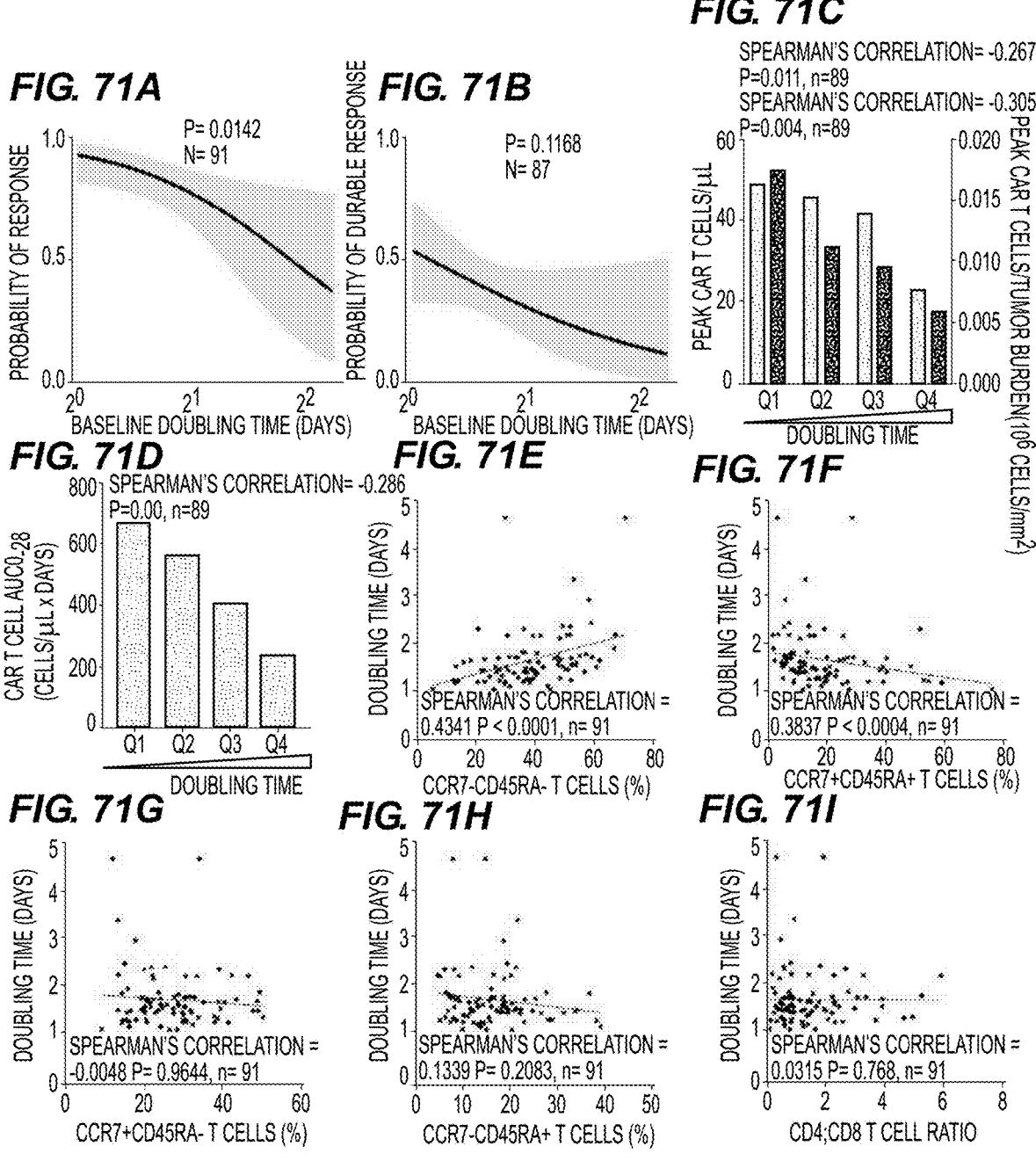

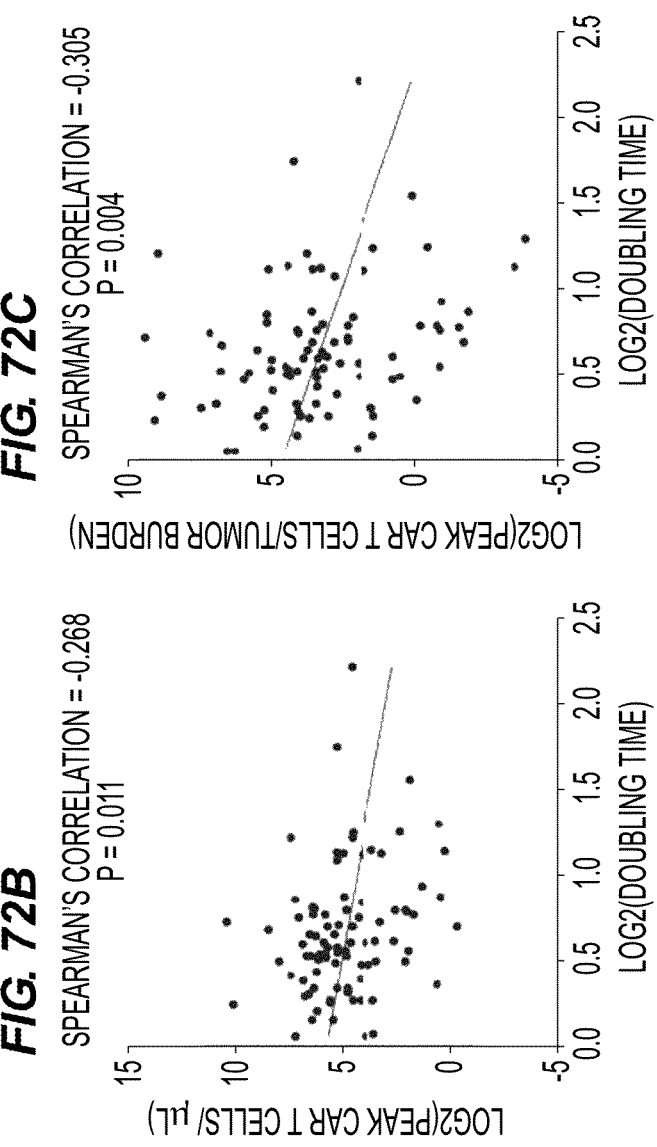
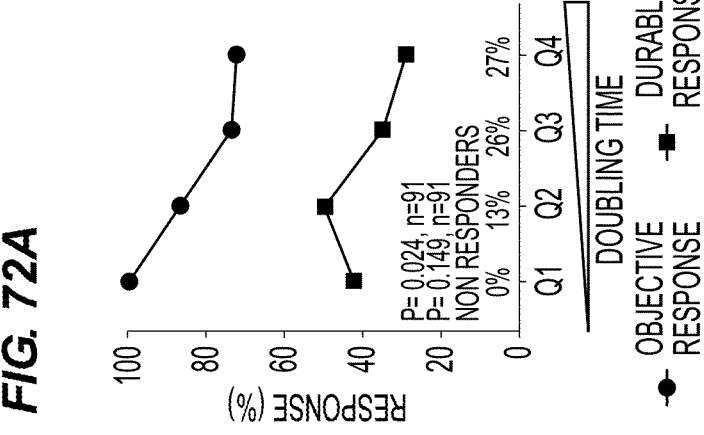

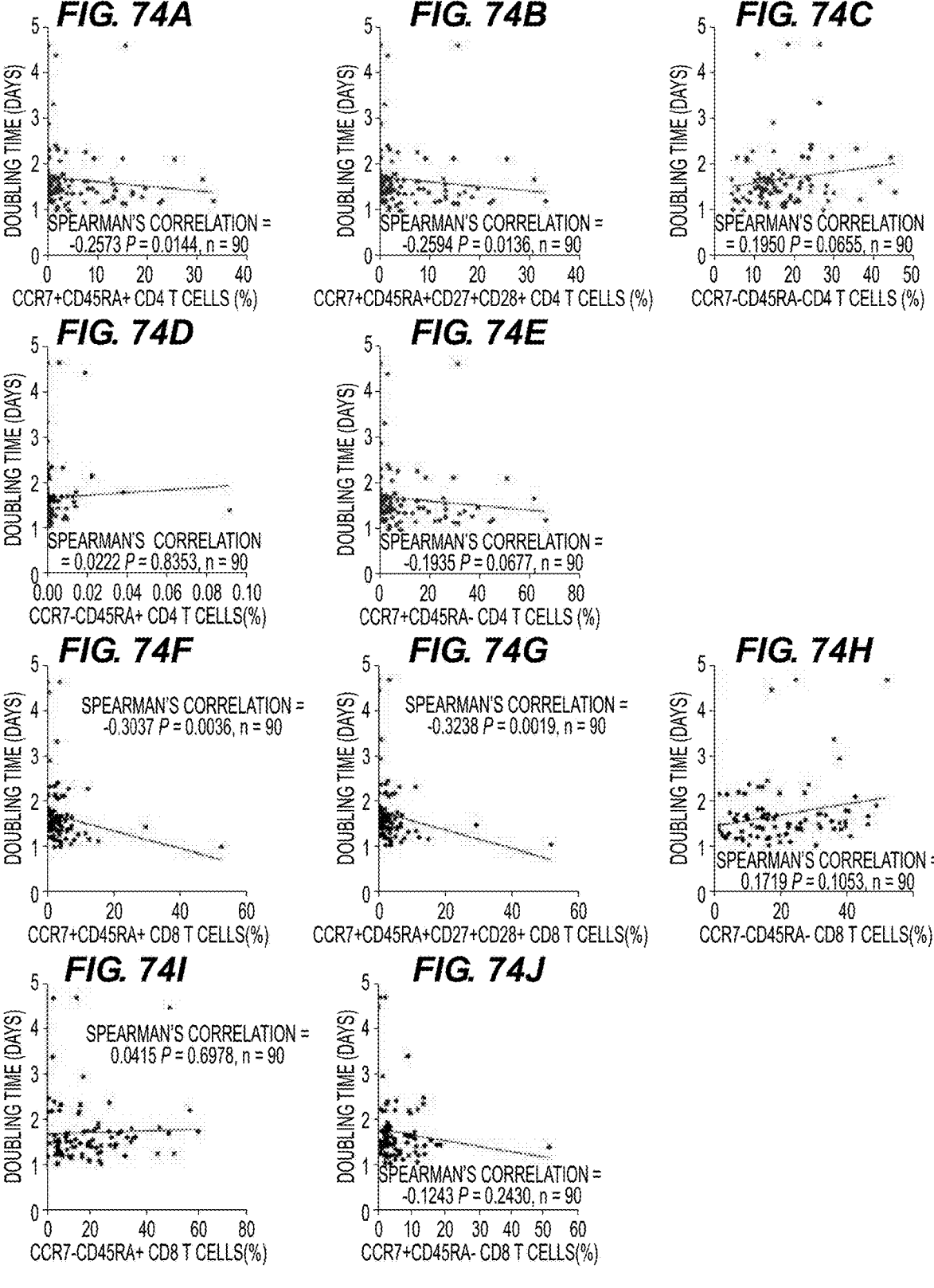

FIG. 74A
DOUBLING TIME (DAYS)
SPEARMAN'S CORRELATION = -0.2573 P = 0.0144, n = 90
CCR7+CD45RA+ CD4 T CELLS (%)

FIG. 74B
DOUBLING TIME (DAYS)
SPEARMAN'S CORRELATION = -0.2594 P = 0.0136, n = 90
CCR7+CD45RA+CD27+CD28+ CD4 T CELLS (%)

FIG. 74C
DOUBLING TIME (DAYS)
SPEARMAN'S CORRELATION = 0.1950 P = 0.0655, n = 90
CCR7-CD45RA-CD4 T CELLS (%)

FIG. 74D
DOUBLING TIME (DAYS)
SPEARMAN'S CORRELATION = 0.0222 P = 0.8353, n = 90
CCR7-CD45RA+ CD4 T CELLS(%)

FIG. 74E
DOUBLING TIME (DAYS)
SPEARMAN'S CORRELATION = -0.1935 P = 0.0677, n = 90
CCR7+CD45RA- CD4 T CELLS (%)

FIG. 74F
DOUBLING TIME (DAYS)
SPEARMAN'S CORRELATION = -0.3037 P = 0.0036, n = 90
CCR7+CD45RA+ CD8 T CELLS(%)

FIG. 74G
DOUBLING TIME (DAYS)
SPEARMAN'S CORRELATION = -0.3238 P = 0.0019, n = 90
CCR7+CD45RA+CD27+CD28+ CD8 T CELLS(%)

FIG. 74H
DOUBLING TIME (DAYS)
SPEARMAN'S CORRELATION = 0.1719 P = 0.1053, n = 90
CCR7-CD45RA- CD8 T CELLS(%)

FIG. 74I
DOUBLING TIME (DAYS)
SPEARMAN'S CORRELATION = 0.0415 P = 0.6978, n = 90
CCR7-CD45RA+ CD8 T CELLS(%)

FIG. 74J
DOUBLING TIME (DAYS)
SPEARMAN'S CORRELATION = -0.1243 P = 0.2430, n = 90
CCR7+CD45RA- CD8 T CELLS(%)

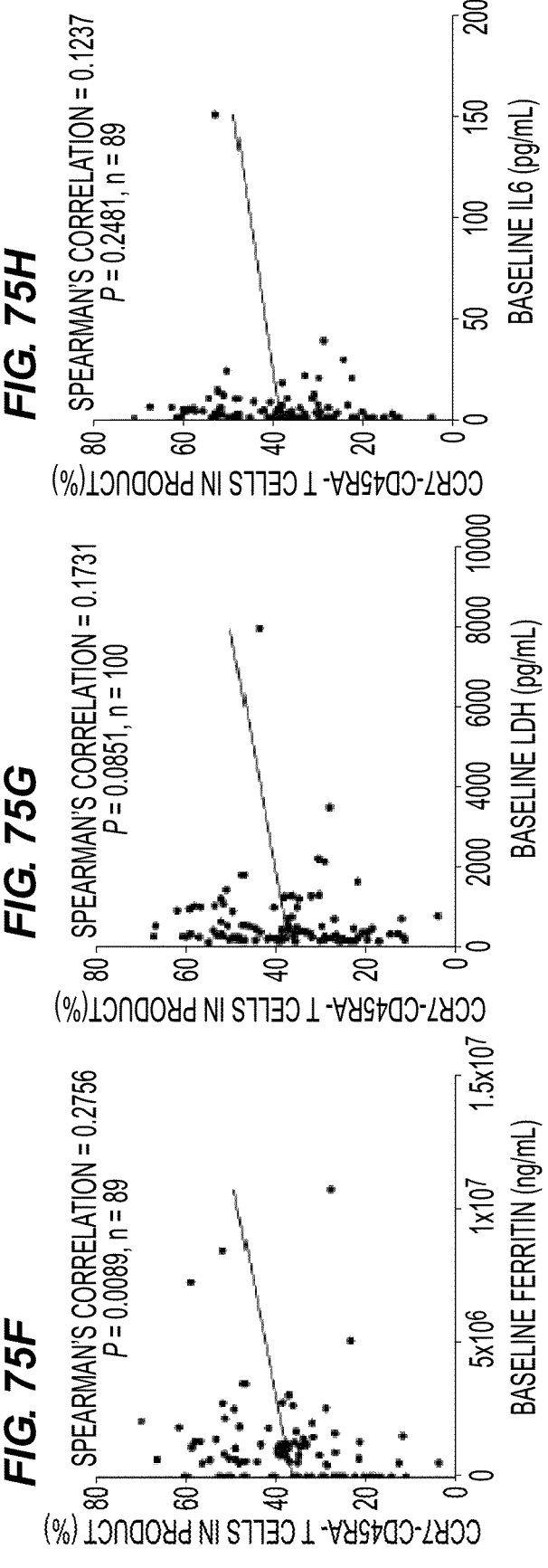

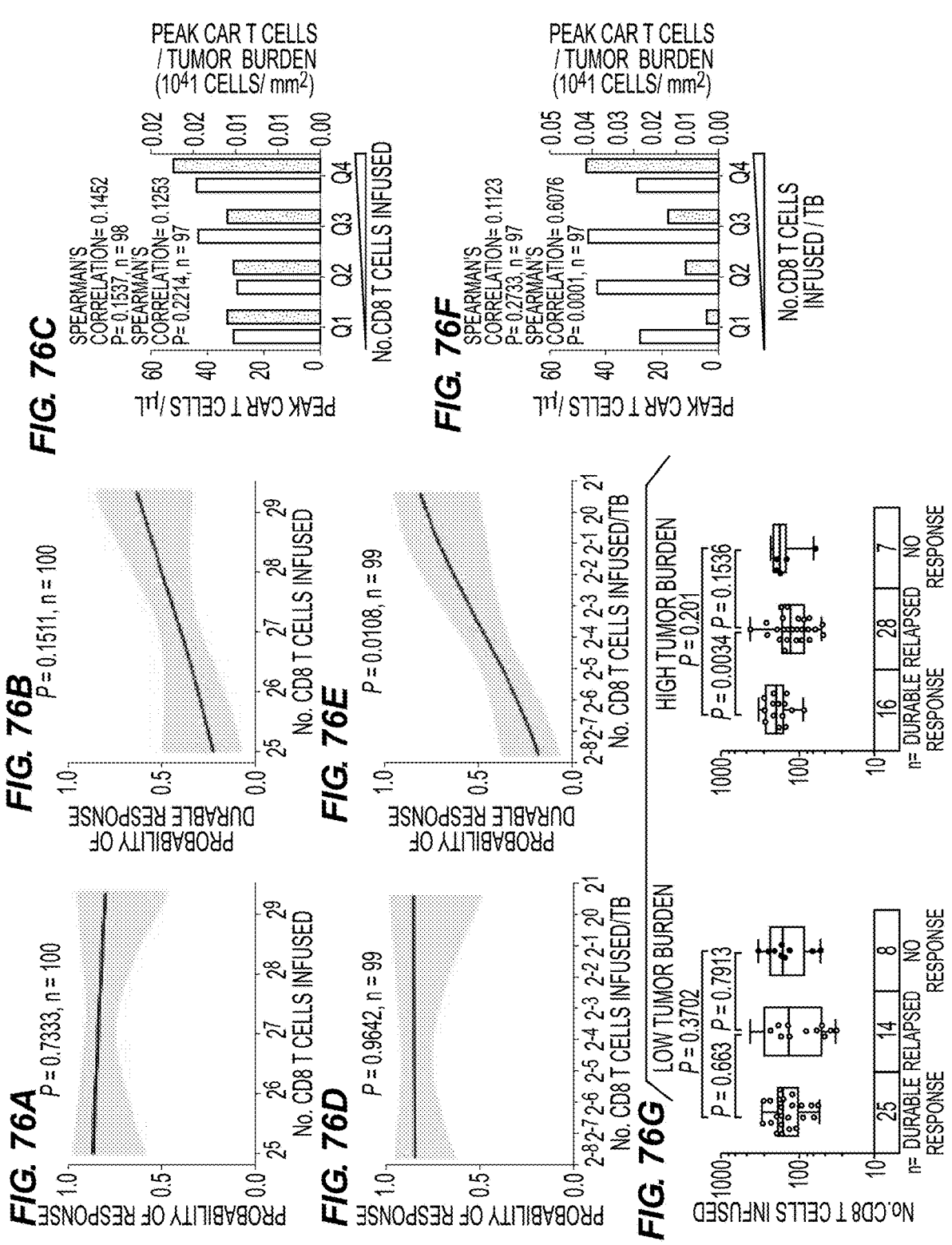

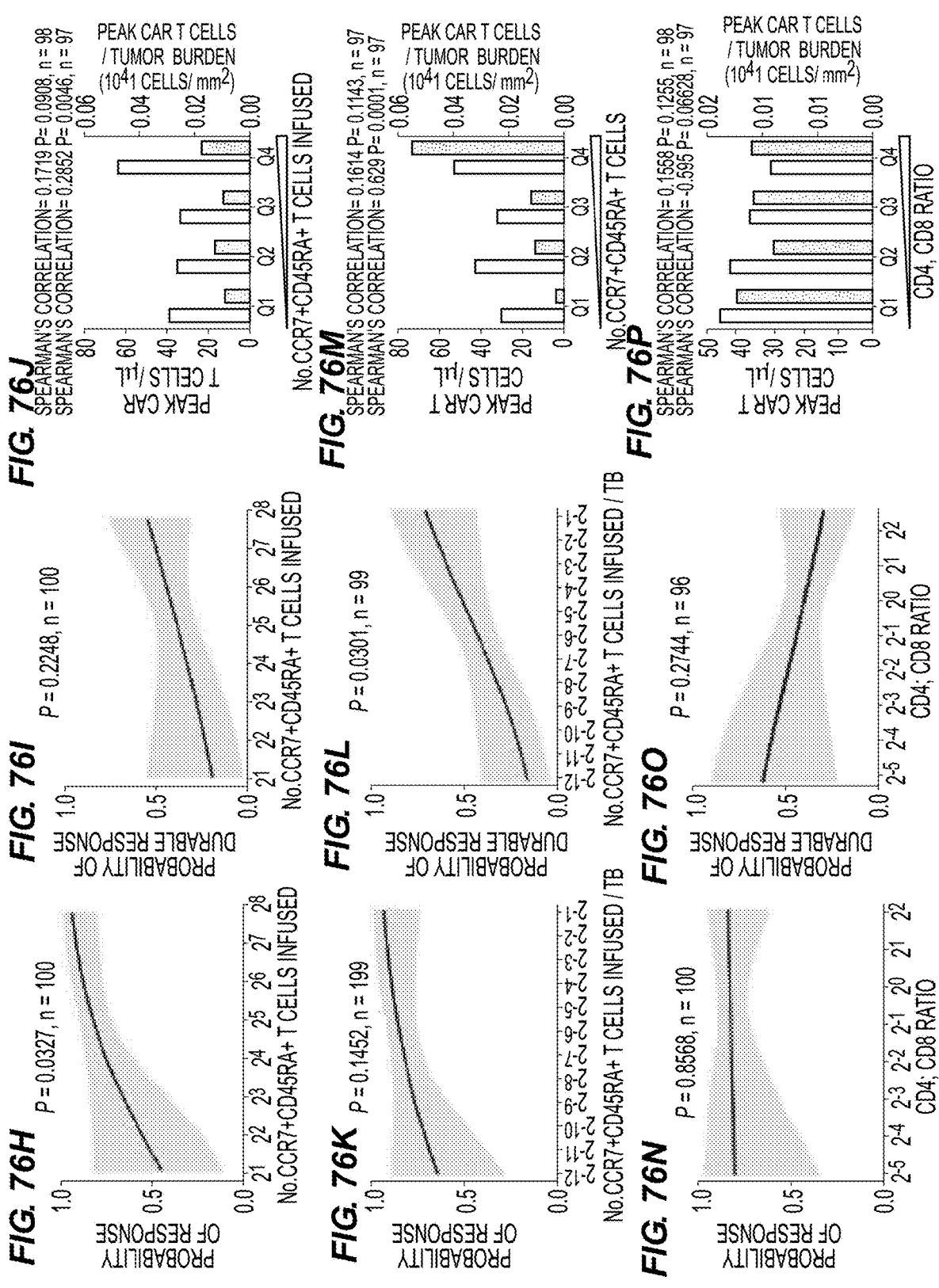

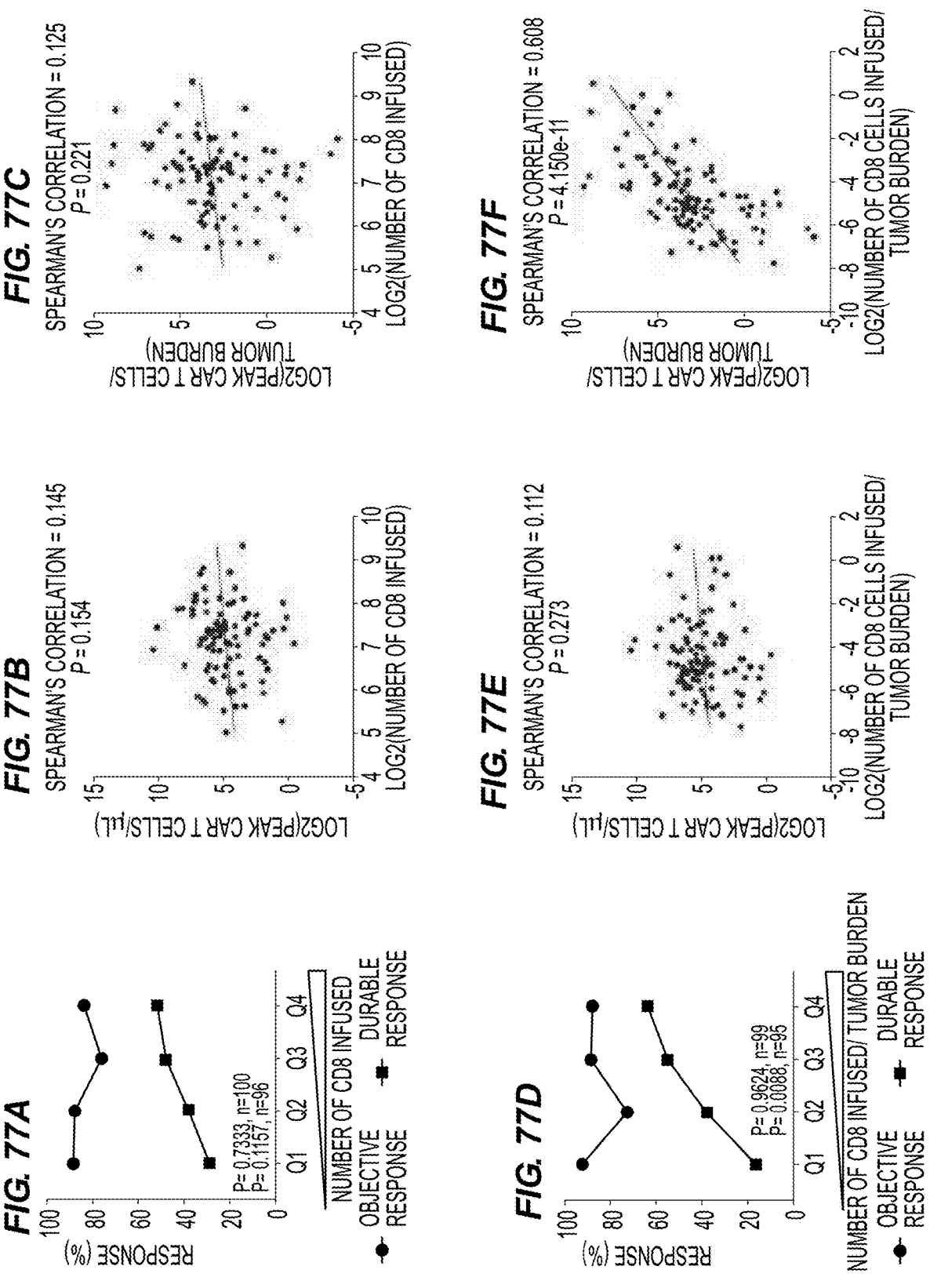

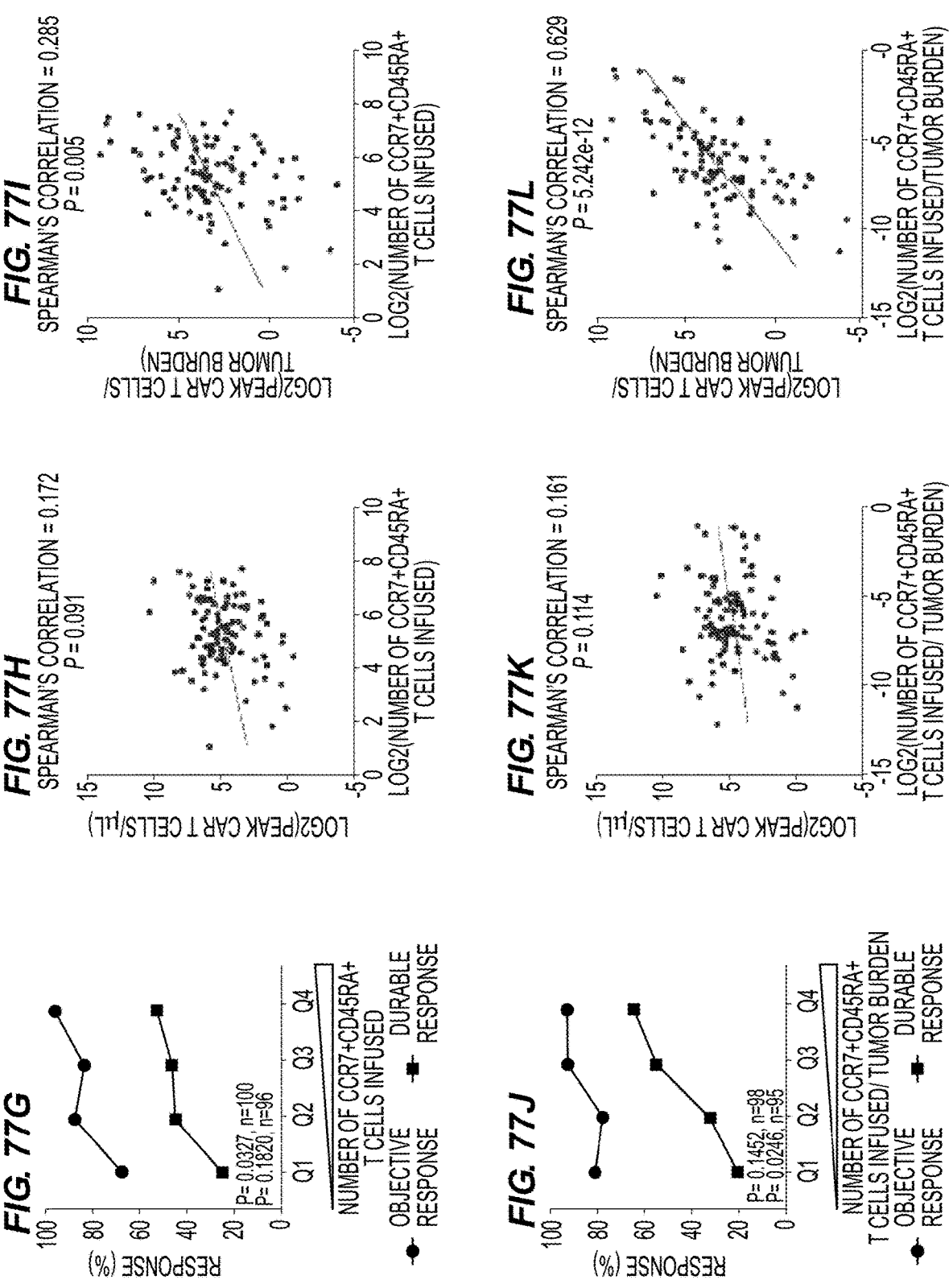

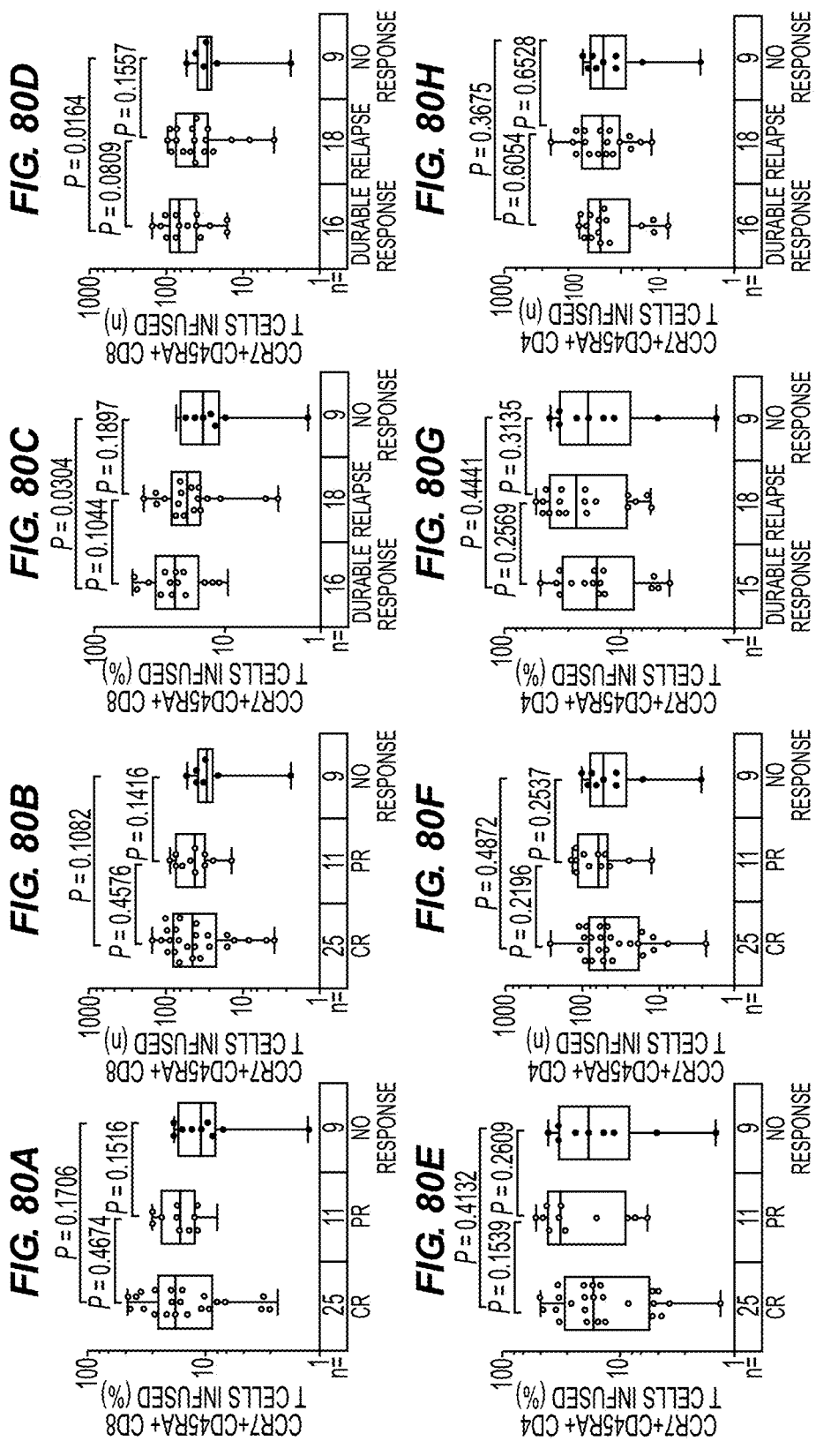

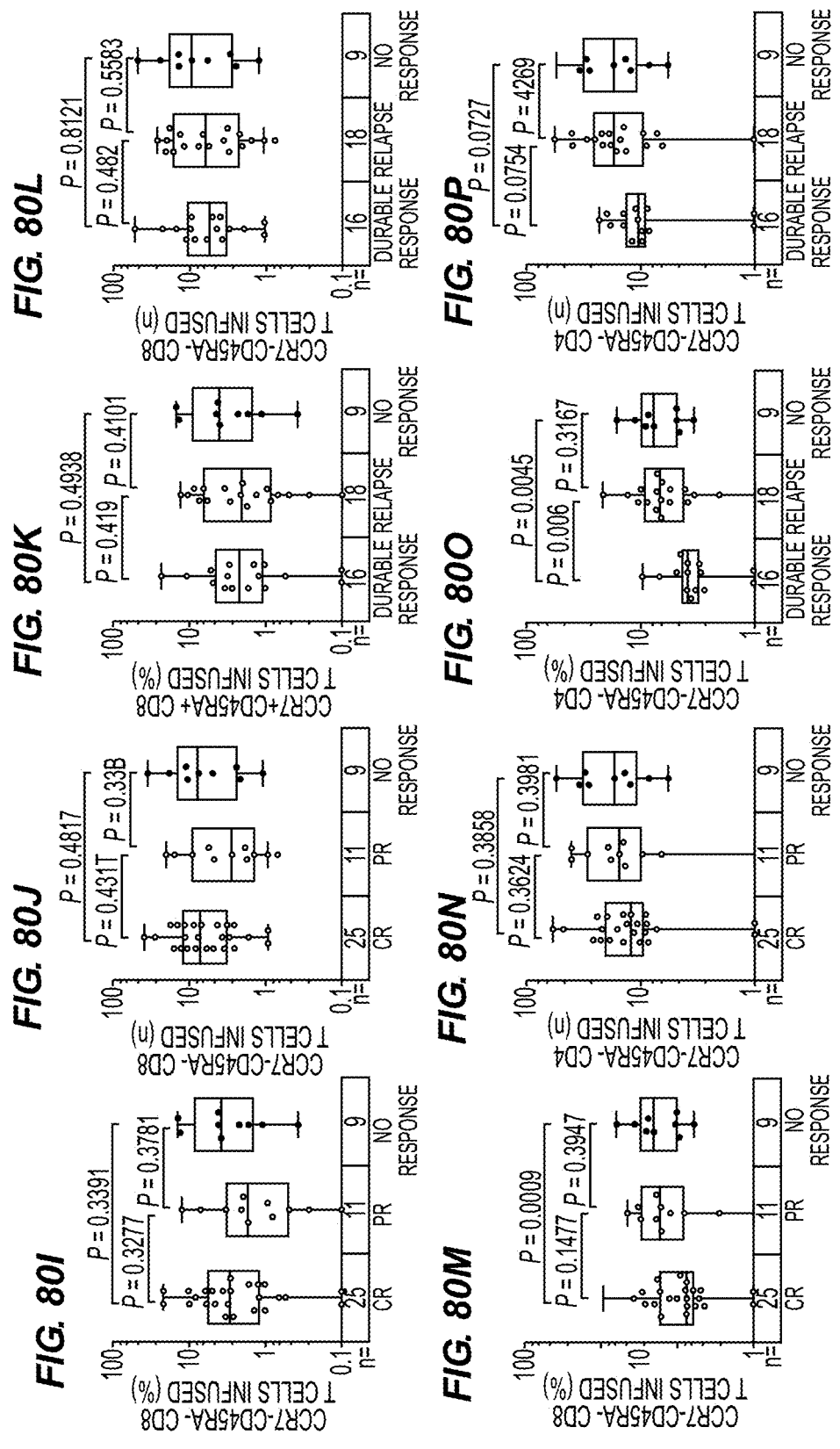

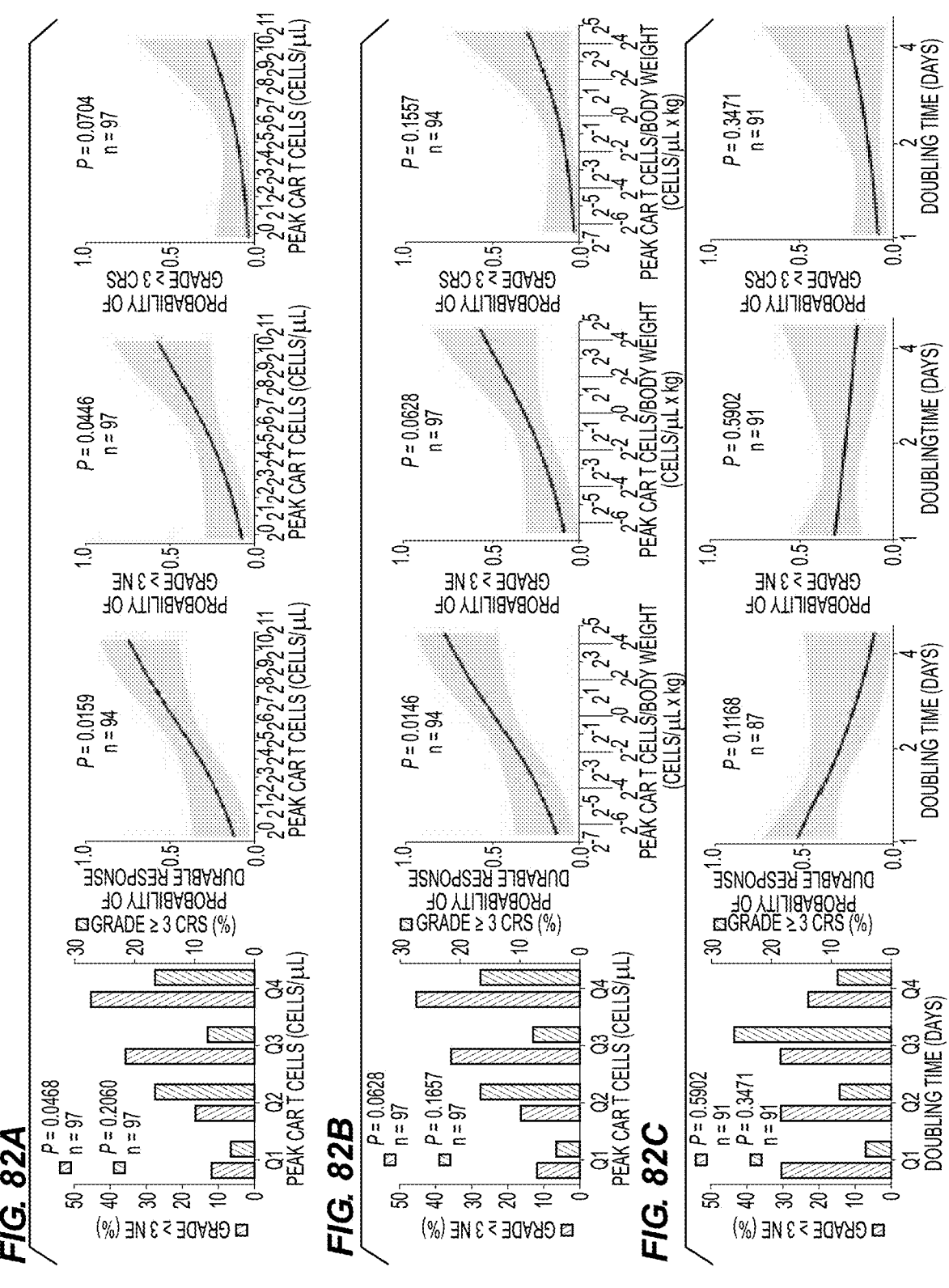

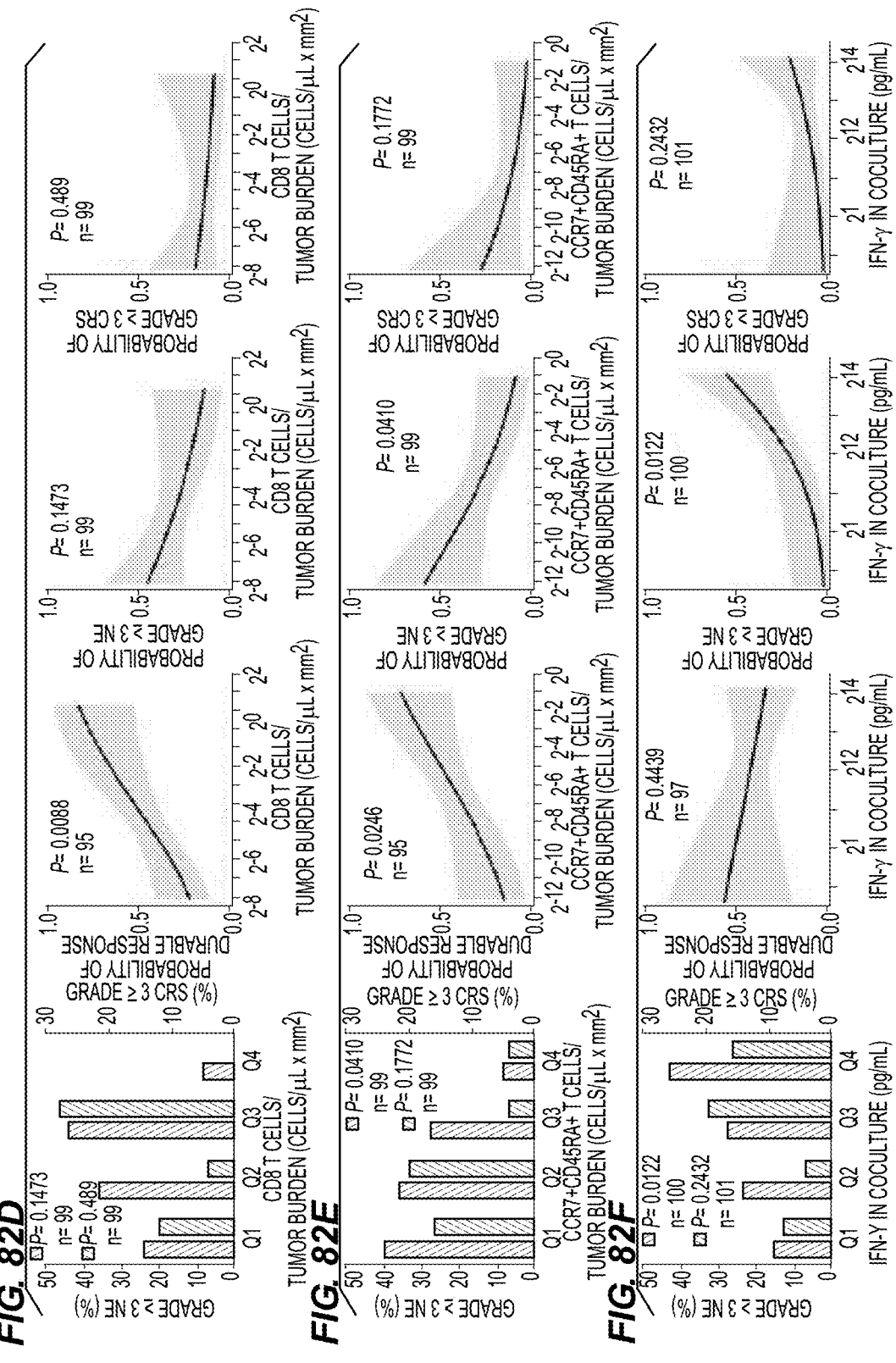

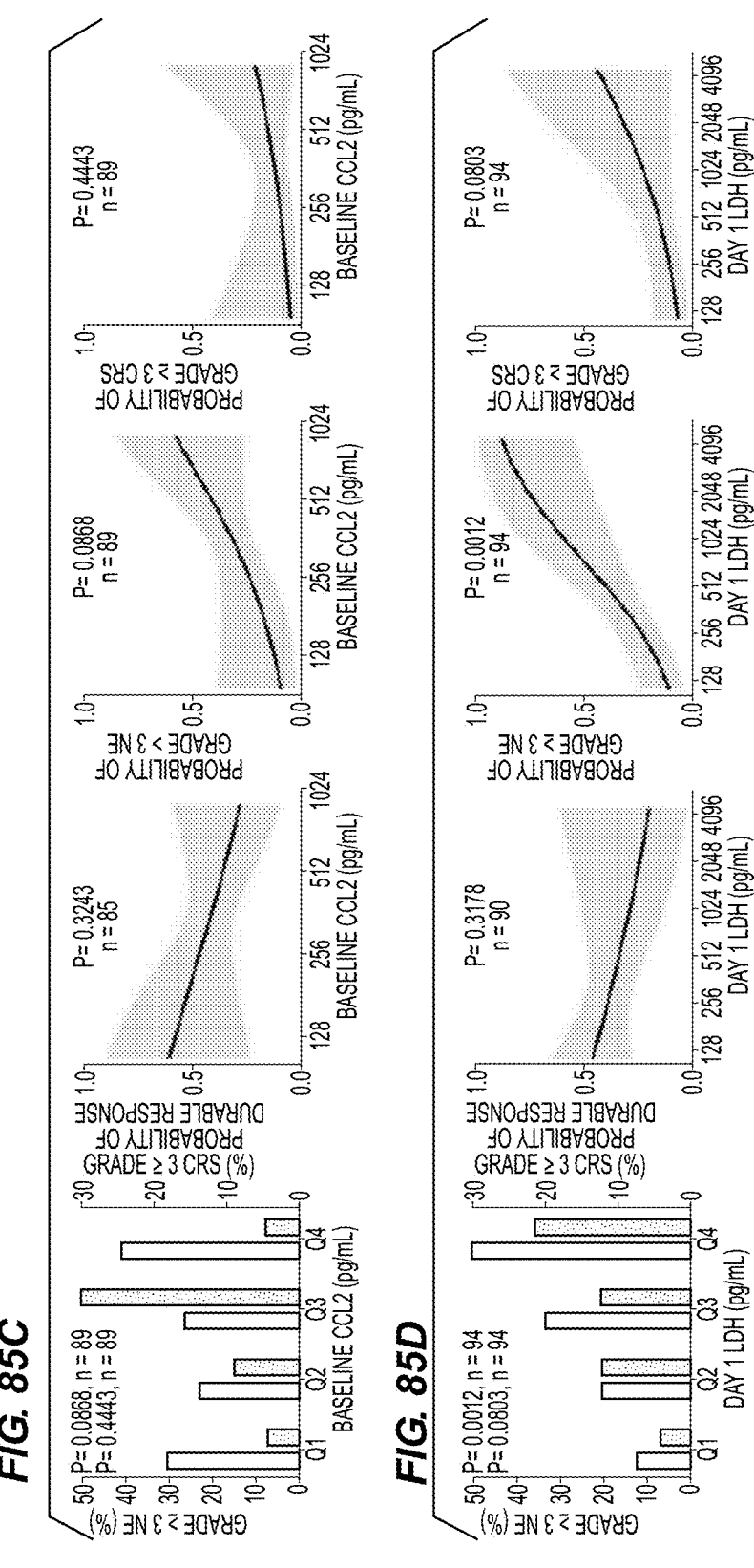

| SUMMARY OF COVARIATES WITH SIGNIFICANT ASSOCIATION IN THE MULTIVARIATE ANALYSIS WITH OUTCOMES AND DIRECTION OF ASSOCIATION | | | |
|---|---|---|---|
| COVARIATE | DURABLE RESPONSE | GRADE ≥3 NE | GRADE ≥3 CRS |
| BASELINE TUMOR BURDEN ⇩ | | | |
| BASELINE IL-6 | ⇩ | | |
| BASELINE CRP | ⇩ | | ⇧ |
| COCULTURE IFN-γ | ⇩ | ⇧ | |
| BASELINE LDH | ⇩ | ⇧ | ⇧ |
| DAY 0 IL-15 | | ⇧ | |

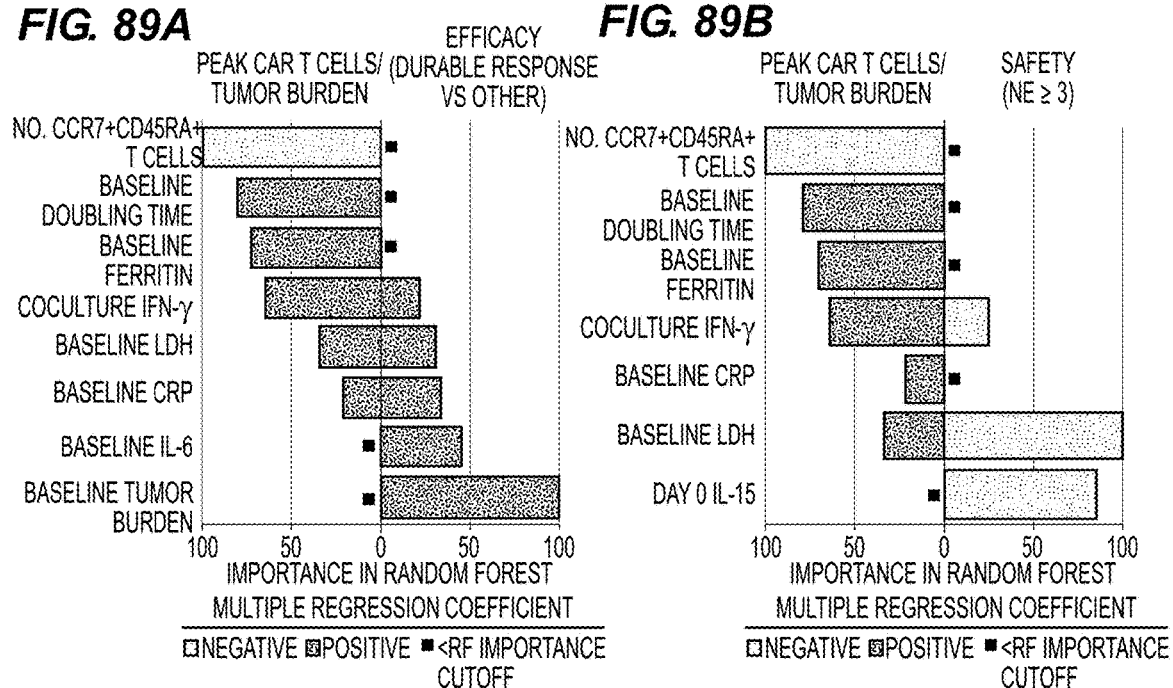
*FIG. 89A*
*FIG. 89B*
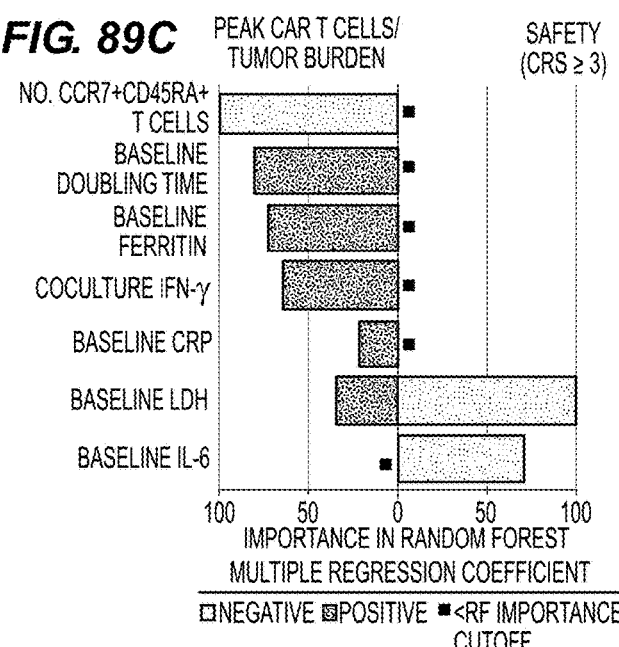
*FIG. 89C*

FIG. 90A

NUMBER OF COVARIATES

| OUTCOME | DURABLE RESPONSE | | GRADE ≥ 3 NE | | GRADE ≥ 3 CRS | | PEAK CAR T CELLS | | PEAK CAR T CELLS/TUMOR BURDEN | |
|---|---|---|---|---|---|---|---|---|---|---|
| SAMPLE SIZE | 97 | | 101 | | 101 | | 98 | | 97 | |
| OVERALL AUC | 0.5591 | | 0.5667 | | 0.4751 | | 2.0168 | | 2.5096 | |
| HIGHEST AUC | 0.6636 / 5 | | 0.567 / 3 | | 0.4751 / 2 | | 2.001 / 4 | | 2.4743 / 6 | |
| HIGHEST AUC ACHIEVED AT TOP X | 3 | | 2 | | 2 | | 2 | | 4 | |
| RANK | ATTRIBUTE | REGRESSION COEFFICIENT | ATTRIBUTE | REGRESSION COEFFICIENT | ATTRIBUTE | REGRESSION COEFFICIENT | ATTRIBUTE | REGRESSION COEFFICIENT | ATTRIBUTE | REGRESSION COEFFICIENT |
| 1 | BASELINE TUMOR BURDEN | − | BASELINE LDH | + | BASELINE LDH | + | NUMBER OF CCR7+ CD45RA+ T CELLS IN PRODUCT | + | NUMBER OF CCR7+ CD45RA+ T CELLS IN PRODUCT | + |
| 2 | BASELINE IL-6 | − | DAY 0 IL-15 | + | BASELINE IL-6 | + | BASELINE DOUBLING TIME | − | BASELINE DOUBLING TIME | − |
| 3 | BASELINE CRP | − | COCULTURE IFN-γ | + | COCULTURE IFN-g | | BASELINE FERRITIN | + | BASELINE FERRITIN | − |
| 4 | BASELINE LDH | − | BASELINE TUMOR BURDEN | | DAY 0 IL-15 | | COCULTURE IFN-γ | − | COCULTURE IFN-γ | − |
| 5 | COCULTURE IFN-γ | − | NUMBER OF CD4 T CELLS IN PRODUCT | | NUMBER OF CD8 T CELLS IN PRODUCT | | TOTAL T CELLS IN PRODUCT | | BASELINE LDH | − |
| 6 | BASELINE FERRITIN | | NUMBER OF CCR7+ CD45RA+ T CELLS IN PRODUCT | | BASELINE DOUBLING TIME | | NUMBER OF CD8 T CELLS IN PRODUCT | | BASELINE CRP | − |
| 7 | NUMBER OF CCR7+ CD45RA+ T CELLS IN PRODUCT | | BASELINE DOUBLING TIME | | BASELINE WEIGHT | | BASELINE IL-6 | | TRANSDUCTION EFFICIENCY | |
| 8 | TRANSDUCTION EFFICIENCY | | NUMBER OF CD8 T CELLS IN PRODUCT | | DAY 0 IFN-γ | | DISEASE STAGE | | BASELINE IL-6 | |
| 9 | DISEASE STAGE | | BASELINE IL-6 | | TRANSDUCTION EFFICIENCY | | TRANSDUCTION EFFICIENCY | | NUMBER OF CD4 T CELLS IN PRODUCT | |
| 10 | BASELINE DOUBLING TIME | | BASELINE WEIGHT | | NUMBER OF CCR7+ CD45RA+ T CELLS IN PRODUCT | | NUMBER OF CD4 T CELLS IN PRODUCT | | DISEASE STAGE | |
| 11 | TOTAL T CELLS IN PRODUCT | | TRANSDUCTION EFFICIENCY | | BASELINE TUMOR BURDEN | | BASELINE TUMOR BURDEN | | DAY 0 IFN-γ | |

FIG. 90B

| | | | | |
|---|---|---|---|---|
| 12 | NUMBER OF CD8 T CELLS IN PRODUCT | DAY 0 IFN-γ | BASELINE CRP | TOTAL T CELLS IN PRODUCT |
| 13 | DAY 0 IL-15 | TOTAL T CELLS IN PRODUCT | DAY 0 IFN-γ | NUMBER OF CD8 T CELLS IN PRODUCT |
| 14 | DAY 0 IFN-γ | DISEASE STAGE | BASELINE LDH | DAY 0 IL-15 |
| 15 | BASELINE WEIGHT | BASELINE FERRITIN | BASELINE WEIGHT | BASELINE WEIGHT |
| 16 | NUMBER OF CD4 T CELLS IN PRODUCT | BASELINE CRP | NUMBER OF CD4 T CELLS IN PRODUCT | |
| | | TOTAL T CELLS IN PRODUCT | DAY 0 IL-15 | |

ABBREVIATIONS: CAR, CHIMERIC ANTIGEN RECEPTOR; CRP, C-REACTIVE PROTEIN; CRS, CYTOKINE RELEASE SYNDROME; IFN, INTERFERON; IL INTERLEUKIN; LDH, LACTATE DEHYDROGENASE; NE, NEUROLOGIC EVENTS.

FIG. 92

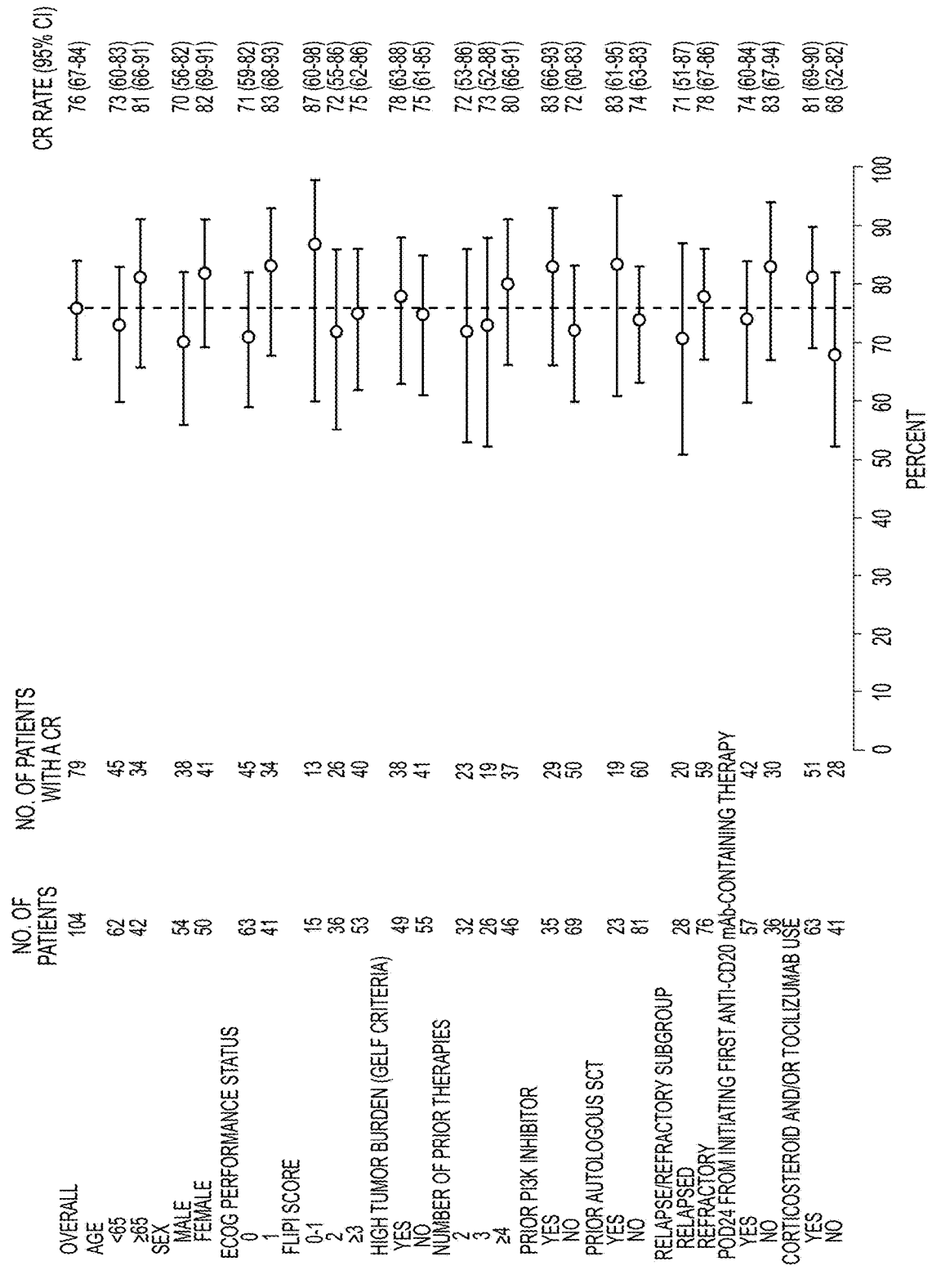

| | NO. OF PATIENTS | NO. OF PATIENTS WITH A CR | | CR RATE (95% CI) |
|---|---|---|---|---|
| OVERALL | 104 | 79 | | 76 (67-84) |
| AGE | | | | |
| <65 | 62 | 45 | | 73 (60-83) |
| ≥65 | 42 | 34 | | 81 (66-91) |
| SEX | | | | |
| MALE | 54 | 38 | | 70 (56-82) |
| FEMALE | 50 | 41 | | 82 (69-91) |
| ECOG PERFORMANCE STATUS | | | | |
| 0 | 63 | 45 | | 71 (59-82) |
| 1 | 41 | 34 | | 83 (68-93) |
| FLIPI SCORE | | | | |
| 0-1 | 15 | 13 | | 87 (60-98) |
| 2 | 36 | 26 | | 72 (55-86) |
| ≥3 | 53 | 40 | | 75 (62-86) |
| HIGH TUMOR BURDEN (GELF CRITERIA) | | | | |
| YES | 49 | 38 | | 78 (63-88) |
| NO | 55 | 41 | | 75 (61-85) |
| NUMBER OF PRIOR THERAPIES | | | | |
| 2 | 32 | 23 | | 72 (53-86) |
| 3 | 26 | 19 | | 73 (52-88) |
| ≥4 | 46 | 37 | | 80 (66-91) |
| PRIOR PI3K INHIBITOR | | | | |
| YES | 35 | 29 | | 83 (66-93) |
| NO | 69 | 50 | | 72 (60-83) |
| PRIOR AUTOLOGOUS SCT | | | | |
| YES | 23 | 19 | | 83 (61-95) |
| NO | 81 | 60 | | 74 (63-83) |
| RELAPSE/REFRACTORY SUBGROUP | | | | |
| RELAPSED | 28 | 20 | | 71 (51-87) |
| REFRACTORY | 76 | 59 | | 78 (67-86) |
| POD24 FROM INITIATING FIRST ANTI-CD20 mAb-CONTAINING THERAPY | | | | |
| YES | 57 | 42 | | 74 (60-84) |
| NO | 36 | 30 | | 83 (67-94) |
| CORTICOSTEROID AND/OR TOCILIZUMAB USE | | | | |
| YES | 63 | 51 | | 81 (69-90) |
| NO | 41 | 28 | | 68 (52-82) |

PERCENT

PATIENTS IN ONGOING RESPONSE AT 12 MONTHS

PATIENTS RELAPSED AT 12 MONTHS

FIG. 99A

| BIOMARKER, MEDIAN (RANGE) | FOLLICULAR LYMPHOMA (n=124) | | | MARGINAL ZONE LYMPHOMA (n=22) | | | ALL PATIENTS (N=146) | | |
|---|---|---|---|---|---|---|---|---|---|
| | BASELINE* | PEAK | $AUC_{0-28}$ | BASELINE | PEAK | $AUC_{0-28}$ | BASELINE | PEAK | $AUC_{0-28}$ |
| SAA, pg/mL | $6.6 \times 10^6$ ($6.2 \times 10^5$ - $7.7 \times 10^8$) | $1.4 \times 10^8$ ($1.4 \times 10^6$ - $1.4 \times 10^9$‡) | $1.2 \times 10^9$ ($1.5 \times 10^7$ - $1.6 \times 10^{10}$) | $6.1 \times 10^6$ ($1.3 \times 10^6$ - $1.4 \times 10^9$‡) | $4.3 \times 10^8$ ($1.5 \times 10^7$ - $1.4 \times 10^9$‡) | $2.8 \times 10^9$ ($1.4 \times 10^8$ - $1.7 \times 10^{10}$) | $6.7 \times 10^6$ ($6.2 \times 10^5$ - $1.4 \times 10^9$‡) | $1.9 \times 10^8$ ($1.4 \times 10^6$ - $1.4 \times 10^9$‡) | $1.5 \times 10^9$ ($1.5 \times 10^7$ - $1.7 \times 10^{10}$) |
| CRP, mg/L | 7.1 ($2.8 \times 10^{-5}$ - 249.3) | 67.0 (2.9 - 496.0‡) | 611.3 (13.3 - 5828.9) | 8.0 (0.5 - 106.9) | 112.5 (12.6 - 439.3) | 778.7 (129.2 - 4871.0) | 7.2 ($2.8 \times 10^{-5}$ - 249.3) | 73.1 (2.9 - 496.0‡) | 675.0 (13.3 - 5828.9) |
| FERRITIN, ng/mL | 190.0 (0.02 - 2354.0) | 663.6 (86.4 - 5237.9) | $1.4 \times 10^4$ (498.8 - $1.1 \times 10^5$) | 131.8 (13.3 - 1107.3) | 571.1 (235.8 - $2.5 \times 10^4$) | $1.2 \times 10^4$ (3450.0 - $1.7 \times 10^5$) | 183.6 (0.02 - 2354.0) | 653.3 (86.4 - $2.5 \times 10^4$) | $1.4 \times 10^4$ (498.8 - $1.7 \times 10^5$) |
| CCL17 (TARC), pg/mL | 1170.2 (45.9 - 4480.0‡) | 1215.9 (73.2 - 4480.0‡) | $1.9 \times 10^4$ (1995.7 - $1.4 \times 10^5$) | 507.1 (112.5 - 4480.0‡) | 981.8 (167.9 - 4480.0‡) | $1.6 \times 10^4$ (1966.1 - $8.4 \times 10^4$) | 1037.2 (45.9 - 4480.0‡) | 1171.2 (73.2 - 4480.0‡) | $1.8 \times 10^4$ (1966.1 - $1.4 \times 10^5$) |
| CXCL10 (IP-10), pg/mL | 343.8 (74.3 - 2000.0‡) | 1077.3 (165.9 - 2000.0‡) | $1.7 \times 10^4$ (2805.9 - $6.1 \times 10^4$) | 400.1 (215.6 - 2000.0‡) | 2000.00 (598.4 - 2000.0‡) | $2.9 \times 10^4$ (6962.3 - $5.9 \times 10^4$) | 347.2 (74.3 - 2000.0‡) | 1303.8 (165.9 - 2000.0‡) | $1.8 \times 10^4$ (2805.9 - $6.1 \times 10^4$) |
| CCL26 (EOTAXIN-3), pg/mL | 10.2+ (10.2+ - 259.6) | 10.2+ (10.2+ - 283.4) | 336.6 (81.6 - 2322.1) | 10.2+ (10.2+ - 10.2+) | 10.2+ (10.2+ - 155.7) | 336.6 (122.4 - 2046.6) | 10.2+ (10.2+ - 259.6) | 10.2+ (10.2+ - 283.4) | 336.6 (81.6 - 2322.1) |
| IL-8, pg/mL | 9.1 (1.1+ - 131.4) | 38.4 (4.8 - 750.0‡) | 594.3 (127.1 - 5695.5) | 12.8 (2.8 - 42.5) | 48.7 (6.5 - 750.0‡) | 679.7 (145.7 - 6886.5) | 9.6 (1.1+ - 131.4) | 41.1 (4.8 - 750.0‡) | 606.9 (127.1 - 6886.5) |
| CCL2 (MCP-1), pg/mL | 324.4 (139.6 - 1076.2) | 790.1 (249.3 - 1500.0‡) | $1.3 \times 10^4$ (4200.4 - $2.5 \times 10^4$) | 305.3 (128.0 - 808.5) | 785.3 (306.6 - 1500.0‡) | $1.2 \times 10^4$ (4726.7 - $3.2 \times 10^4$) | 322.3 (128.0 - 1076.2) | 785.3 (249.3 - 1500.0‡) | $1.3 \times 10^4$ (4200.4 - $3.2 \times 10^4$) |
| CCL22 (MDC), pg/mL | 1819.6 (88.3+ - $3.0 \times 10^4$‡) | 1088.4 (88.3+ - $3.0 \times 10^4$‡) | $2.6 \times 10^4$ (3783.9 - $7.3 \times 10^5$) | 2859.2 (851.7 - $3.0 \times 10^4$‡) | 1211.6 (480.9 - 5747.9) | $2.7 \times 10^4$ (9111.9 - $1.4 \times 10^5$) | 1830.2 (88.3+ - $3.0 \times 10^4$‡) | 1104.3 (88.3+ - $3.0 \times 10^4$‡) | $2.6 \times 10^4$ (3783.9 - $7.3 \times 10^5$) |
| CCL3 (MIP-1α), pg/mL | 13.8+ (13.8+ - 888.8) | 13.8+ (13.8 - 466.6) | 455.4 (262.2 - 8966.6) | 13.8+ (13.8 - 507.1) | 13.8+ (13.8 - 129.8) | 455.4 (165.6 - 2058.6) | 13.8+ (13.8 - 888.8) | 13.8+ (13.8 - 466.6) | 455.4 (165.6 - 8966.6) |
| CCL4 (MIP-1β), pg/mL | 127.5 (27.8 - 679.5) | 183.5 (54.4 - 630.3) | 3652.5 (1471.3 - 9516.2) | 112.0 (46.8 - 395.7) | 226.7 (116.6 - 1063.9) | 3845.6 (1638.7 - $1.0 \times 10^4$) | 127.0 (27.8 - 679.5) | 185.0 (54.4 - 1063.9) | 3652.5 (1471.3 - $1.0 \times 10^4$) |

*FIG. 99B*

| | | | | | | | | | |
|---|---|---|---|---|---|---|---|---|---|
| GRANZYME B, pg/mL | 1.0+ (1.0+-92.1) | 8.2* (1.0+-1062.7) | 94.7* (19.0-5872.4) | 1.0+ (1.0+-3304.1) | 33.4 (1.0+-1816.8) | 299.7 (33.0-2.7x10⁴) | 1.0+ (1.0+3304.1) | 9.7 (1.0+-1816.8) | 127.6 (19.0-2.7x10⁴) |
| IFN-γ, pg/mL | 7.5+ (7.5+-57.9) | 95.5 (7.5+-1876.0‡) | 855.3 (142.5-1.3x10⁴) | 7.5+ (7.5+-452.8) | 714.1 (27.4-1876.0‡) | 3584.9 (428.2-2.4x10⁴) | 7.5+ (7.5+-452.8) | 115.0 (7.5+-1876.0‡) | 1007.0 (142.5-2.4x10⁴) |
| GM-CSF, pg/mL | 1.9+ (1.9+-48.6) | 1.9+ (1.9+-48.6) | 62.7 (15.2-319.6) | 1.9+ (1.9+-1.9+) | 3.2 (1.9+-132.4) | 62.7 (35.6-519.5) | 1.9+ (1.9+-1.9+) | 1.9+ (1.9+-132.4) | 62.7 (15.2-519.5) |
| IL-10, pg/mL | 0.7+ (0.7+-24.1) | 9.5 (0.7+-331.5) | 97.1 (23.1-1883.5) | 1.6 (0.7+-23.0) | 19.7 (3.3-226.0) | 182.0 (56.1-549.6) | 0.7 (0.7+-24.1) | 10.7 (0.7+-331.5) | 101.0 (23.1-1883.5) |
| IL-12-P70, pg/mL | 1.2+ (1.2+, 1.2+) | 1.2+ (1.2+, 9.0) | 39.6 (9.6, 66.9) | 1.2+ (1.2+, 2.7) | 1.2+ (1.2+, 10.0) | 39.6 (17.2, 105.0) | 1.2+ (1.2+, 2.7) | 1.2+ (1.2+, 10.0) | 39.6 (9.6, 105.0) |
| IL-16, pg/mL | 320.8 (95.6-2541.4) | 289.5 (87.3-2257.7) | 6122.5 (1822.0-2.0x10⁴) | 280.2 (140.1-2096.0) | 344.9 (138.6-3740.0‡) | 7172.5 (2624.2-3.3x10⁴) | 310.6 (95.6-2541.4) | 291.3 (87.3-3740.0‡) | 6511.2 (1822.0-3.3x10⁴) |
| IL-17, pg/mL | 9.3+ (9.3+-37.6) | 9.3+ (9.3+-418.1) | 306.9 (74.4-1737.7) | 9.3+ (9.3+-25.8) | 9.3+ (9.3+-90.3) | 306.9 (111.6-590.4) | 9.3+ (9.3+-37.6) | 9.3+ (9.3+-418.1) | 306.9 (74.4-1737.7) |
| IL-1RA, pg/mL | 491.7 (140.3-3011.0) | 1169.5 (221.0-9000.0‡) | 1.9x10⁴ (2464.7-1.8x10⁵) | 469.0 (221.3-1727.0) | 2371.7 (409.0-9000.0‡) | 3.1x10⁴ (6722.2-1.5x10⁵) | 482.9 (140.3-3011.0) | 1293.8 (221.0-9000.0‡) | 1.9x10⁴ (2464.7-1.8x10⁵) |
| IL-2Rα, ng/mL | 3.8 (3.3x10⁻³-84.9) | 12.1 (1.4-100.0‡) | 186.3 (30.7-1837.4) | 3.7 (1.1-40.7) | 14.1 (3.7-100.0‡) | 209.7 (91.4-1123.1) | 3.8 (3.3x10⁻³-84.9) | 12.4 (1.4-100.0‡) | 195.7 (30.7-1837.4) |
| IL-4, pg/mL | 0.5+ (0.5+-0.5+) | 0.5+ (0.5+-5.4) | 16.5 (4.0-86.2) | 0.5+ (0.5+-0.5+) | 0.5+ (0.5+-4.7) | 16.5 (9.4-31.2) | 0.5+ (0.5+-0.5+) | 0.5+ (0.5+-5.4) | 16.5 (4.0-86.2) |
| IL-5, pg/mL | 6.3+ (6.3+-6.3+) | 6.3+ (6.3+-919.1) | 207.9 (50.4-5365.9) | 6.3+ (6.3+-6.3+) | 6.3+ (6.3+-242.3) | 207.9 (119.7-1859.9) | 6.3+ (6.3+-6.3+) | 6.3+ (6.3+-919.1) | 207.9 (50.4-5365.9) |
| IL-6, pg/mL | 1.6+ (1.6+-23.5) | 15.3 (1.6+-976.0‡) | 188.2 (12.8-2.3x10⁴) | 1.6+ (1.6+-23.2) | 233.1 (6.9-976.0‡) | 1371.3 (94.1-6903.1) | 1.6+ (1.6+-23.5) | 18.8 (1.6+-976.0‡) | 257.4 (12.8-2.3x10⁴) |
| TNF-α, pg/mL | 3.95 (0.7+-50.1) | 4.6 (0.7+-62.7) | 88.2 (23.1-716.8) | 4.6 (1.7-31.9) | 6.2 (3.0-23.8) | 115.6 (40.5-282.7) | 4.1 (0.7+-50.1) | 4.9 (0.7+-62.7) | 93.0 (23.1-716.8) |
| IL-15, pg/mL | 2.1 (1.4+-29.2) | 33.8 (9.3-104.3) | 466.4 (72.4-1451.5) | 2.9 (1.4+-6.0) | 47.8 (20.6-203.4) | 660.8 (343.3-1424.1) | 2.9 (1.4+-29.2) | 34.8 (9.3-203.4) | 483.8 (72.4-1451.5) |
| IL-2, pg/mL | 0.9+ (0.9+-90.6) | 3.1 (0.9+-90.6) | 38.0 (17.1-343.7) | 0.9+ (0.9+-2.4) | 7.2 (0.9+-181.6) | 66.1 (21.0-662.2) | 0.9+ (0.9+-5.1) | 4.0 (0.9+-181.6) | 41.1 (17.1-662.2) |
| IL-7, pg/mL | 14.9 (1.4+-46.6) | 31.7 (9.1-82.9) | 730.5 (142.7-1808.2) | 13.9 (6.7-29.1) | 30.0 (15.1-84.7) | 691.0 (235.6-1776.8) | 14.8 (1.4+-46.6) | 31.5 (9.1-84.7) | 716.9 (142.7-1808.2) |

FIG. 101

| | BIOMARKER MEDIAN LEVELS (RANGE) | ONGOING RESPONSE (n=53) | RELAPSE (n=19) | P VALUE |
|---|---|---|---|---|
| INFLAMMATORY | SAA, pg/mL | | | |
| | BASELINE | $6.6 \times 10^6$ ($7.4 \times 10^5$ - $5.8 \times 10^8$) | $4.6 \times 10^6$ ($6.2 \times 10^5$ - $3.7 \times 10^8$) | 0.7110 |
| | PEAK | $1.9 \times 10^8$ ($1.5 \times 10^6$ - $1.4 \times 10^9$†) | $3.2 \times 10^7$ ($1.4 \times 10^6$ - $8.3 \times 10^8$) | 0.0007 |
| | $AUC_{0-28}$ | $1.5 \times 10^9$ ($3.8 \times 10^7$ - $1.3 \times 10^{10}$) | $3.8 \times 10^8$ ($1.5 \times 10^7$ - $5.4 \times 10^9$) | 0.0021 |
| | CRP, mg/L | | | |
| | BASELINE | 7.5 (0.4 - 136.3) | 7.1 (0.9 - 169.5) | 0.8181 |
| | PEAK | 71.5 (2.9 - 496.0†) | 32.1 (8.1 - 224.1) | 0.0056 |
| | $AUC_{0-28}$ | 541.5 (59.8 - 3477.9) | 348.9 (73.7 - 1746.0) | 0.0157 |
| | FERRITIN, ng/mL | | | |
| | BASELINE | 183.9 (10.8 - 1987.8) | 394.6 (23.7 - 1303.3) | 0.0329 |
| | PEAK | 631.9 (91.3 - 4570.7) | 773.4 (215.2 - 3734.1) | 0.4510 |
| | $AUC_{0-28}$ | $1.4 \times 10^4$ (1516.6 - $1.0 \times 10^5$) | $2.0 \times 10^4$ (4143.0 - $9.0 \times 10^4$) | 0.1969 |
| | GM-CSF, pg/mL | | | |
| | BASELINE | 1.9* (1.9* - 1.9*) | 1.9* (1.9* - 1.9*) | 1.0000 |
| | PEAK | 1.9* (1.9* - 48.6) | 1.9* (1.9* - 13.5) | 0.1764 |
| | $AUC_{0-28}$ | 62.7 (36.1 - 319.6) | 62.7 (62.7 - 103.3) | 0.0948 |
| | TNF-α, pg/mL | | | |
| | BASELINE | 3.8 (0.7* - 32.8) | 9.7 (1.4 - 50.1) | 0.0190 |
| | PEAK | 4.5 (2.0 - 62.7) | 5.4 (1.7 - 15.0) | 0.2223 |
| | $AUC_{0-28}$ | 89.3 (30.2 - 716.8) | 115.5 (39.8 - 331.4) | 0.1191 |
| CHEMOKINE | CCL17 (TARC), pg/mL | | | |
| | BASELINE | 796.4 (83.2 - 4480.0†) | 4480.0+ (45.9 - 4480.0†) | 0.0059 |
| | PEAK | 991.2 (113.0 - 4480.0†) | 1605.4 (94.2 - 4480.0†) | 0.0875 |
| | $AUC_{0-28}$ | $1.6 \times 10^4$ (2248.9 - $8.1 \times 10^4$) | $2.9 \times 10^4$ (1995.7 - $1.4 \times 10^5$) | 0.0586 |
| | CXCL10 (IP-10), pg/mL | | | |
| | BASELINE | 414.9 (74.3 - 2000.0†) | 347.9 (145.9 - 799.7) | 0.5313 |
| | PEAK | 1353.2 (264.4 - 2000.0†) | 845.9 (286.0 - 2000.0†) | 0.0307 |
| | $AUC_{0-28}$ | $1.8 \times 10^4$ (3362.2 - $6.1 \times 10^4$) | $1.5 \times 10^4$ (6964.9 - $2.9 \times 10^4$) | 0.1047 |
| | CCL26 (EOTAXIN-3), pg/mL | | | |
| | BASELINE | 10.2* (10.2* - 89.7) | 10.2 (10.2* - 72.8) | 0.2050 |
| | PEAK | 10.2* (10.2* - 283.4) | 10.2* (10.2* - 123.9) | 0.4373 |
| | $AUC_{0-28}$ | 336.6 (193.8 - 1868.9) | 336.6 (336.6 - 2322.1) | 0.2647 |

FIG. 101 (CONT. -1)

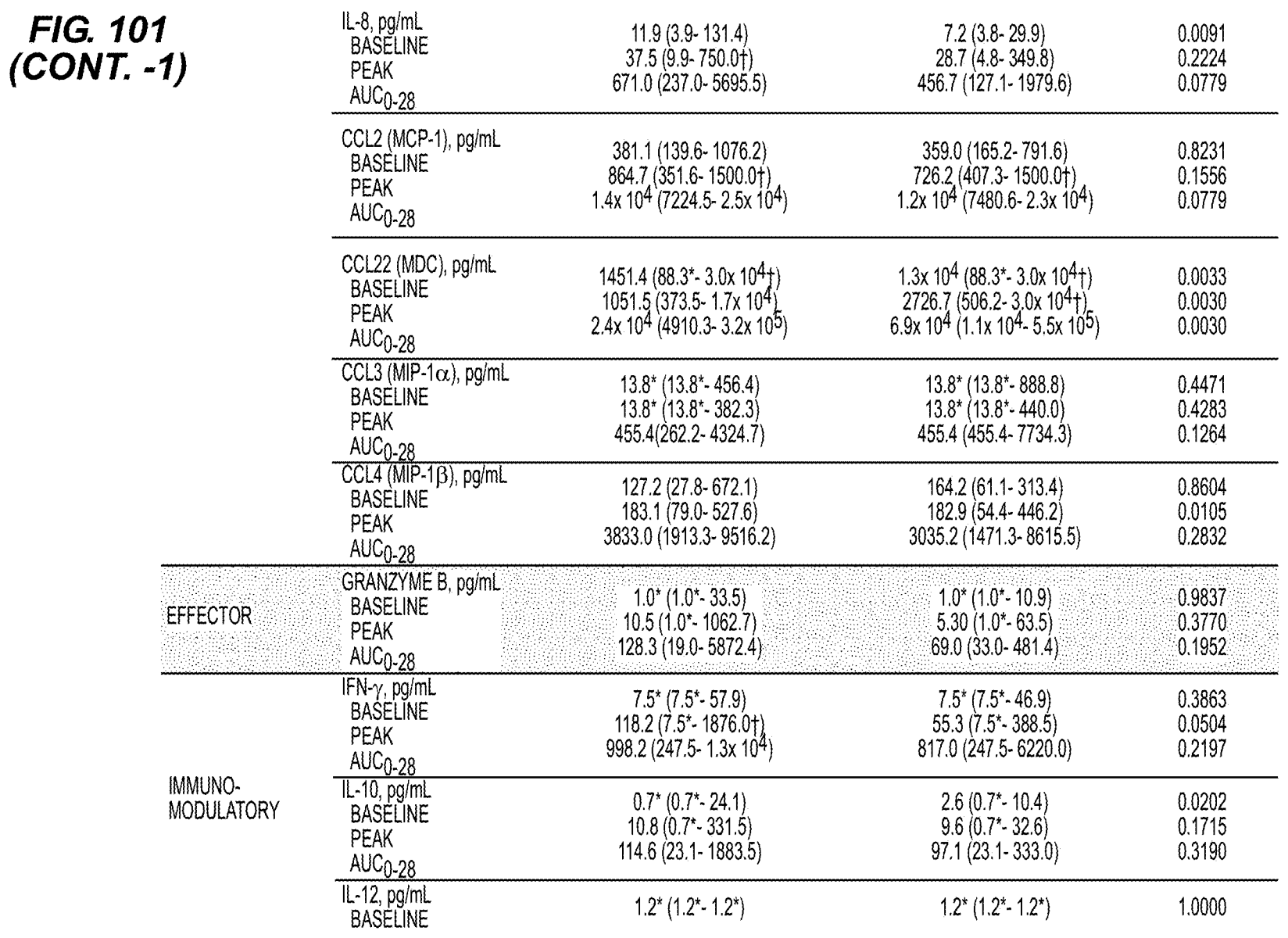

| | | | p-value |
|---|---|---|---|
| IL-8, pg/mL | | | |
| BASELINE | 11.9 (3.9-131.4) | 7.2 (3.8-29.9) | 0.0091 |
| PEAK | 37.5 (9.9-750.0†) | 28.7 (4.8-349.8) | 0.2224 |
| AUC$_{0-28}$ | 671.0 (237.0-5695.5) | 456.7 (127.1-1979.6) | 0.0779 |
| CCL2 (MCP-1), pg/mL | | | |
| BASELINE | 381.1 (139.6-1076.2) | 359.0 (165.2-791.6) | 0.8231 |
| PEAK | 864.7 (351.6-1500.0†) | 726.2 (407.3-1500.0†) | 0.1556 |
| AUC$_{0-28}$ | $1.4\times10^4$ (7224.5-$2.5\times10^4$) | $1.2\times10^4$ (7480.6-$2.3\times10^4$) | 0.0779 |
| CCL22 (MDC), pg/mL | | | |
| BASELINE | 1451.4 (88.3*-$3.0\times10^4$†) | $1.3\times10^4$ (88.3*-$3.0\times10^4$†) | 0.0033 |
| PEAK | 1051.5 (373.5-$1.7\times10^4$) | 2726.7 (506.2-$3.0\times10^4$†) | 0.0030 |
| AUC$_{0-28}$ | $2.4\times10^4$ (4910.3-$3.2\times10^5$) | $6.9\times10^4$ ($1.1\times10^4$-$5.5\times10^5$) | 0.0030 |
| CCL3 (MIP-1α), pg/mL | | | |
| BASELINE | 13.8* (13.8*-456.4) | 13.8* (13.8*-888.8) | 0.4471 |
| PEAK | 13.8* (13.8*-382.3) | 13.8* (13.8*-440.0) | 0.4283 |
| AUC$_{0-28}$ | 455.4 (262.2-4324.7) | 455.4 (455.4-7734.3) | 0.1264 |
| CCL4 (MIP-1β), pg/mL | | | |
| BASELINE | 127.2 (27.8-672.1) | 164.2 (61.1-313.4) | 0.8604 |
| PEAK | 183.1 (79.0-527.6) | 182.9 (54.4-446.2) | 0.0105 |
| AUC$_{0-28}$ | 3833.0 (1913.3-9516.2) | 3035.2 (1471.3-8615.5) | 0.2832 |
| EFFECTOR — GRANZYME B, pg/mL | | | |
| BASELINE | 1.0* (1.0*-33.5) | 1.0* (1.0*-10.9) | 0.9837 |
| PEAK | 10.5 (1.0*-1062.7) | 5.30 (1.0*-63.5) | 0.3770 |
| AUC$_{0-28}$ | 128.3 (19.0-5872.4) | 69.0 (33.0-481.4) | 0.1952 |
| IFN-γ, pg/mL | | | |
| BASELINE | 7.5* (7.5*-57.9) | 7.5* (7.5*-46.9) | 0.3863 |
| PEAK | 118.2 (7.5*-1876.0†) | 55.3 (7.5*-388.5) | 0.0504 |
| AUC$_{0-28}$ | 998.2 (247.5-$1.3\times10^4$) | 817.0 (247.5-6220.0) | 0.2197 |
| IMMUNO-MODULATORY — IL-10, pg/mL | | | |
| BASELINE | 0.7* (0.7*-24.1) | 2.6 (0.7*-10.4) | 0.0202 |
| PEAK | 10.8 (0.7*-331.5) | 9.6 (0.7*-32.6) | 0.1715 |
| AUC$_{0-28}$ | 114.6 (23.1-1883.5) | 97.1 (23.1-333.0) | 0.3190 |
| IL-12, pg/mL | | | |
| BASELINE | 1.2* (1.2*-1.2*) | 1.2* (1.2*-1.2*) | 1.0000 |

FIG. 101 (CONT. -2)

| | | | |
|---|---|---|---|
| PEAK | 1.2* (1.2- 3.3) | 1.2* (1.2*- 1.2*) | 0.4064 |
| AUC$_{0-28}$ | 39.6 (22.8- 51.2) | 39.6 (39.6- 39.6) | 0.0580 |
| IL-16, pg/mL BASELINE | 316.9 (97.7- 2541.4) | 548.5 (161.6- 1303.0) | 0.0024 |
| PEAK | 266.7 (87.3- 2257.7) | 490.9 (200.2- 1322.7) | 0.0021 |
| AUC$_{0-28}$ | 6036.6 (2550.0- 2.0x10$^4$) | 8223.4 (5447.3- 1.9x10$^4$) | 0.0095 |
| IL-17, pg/mL BASELINE | 9.3* (9.3*- 37.6) | 9.3* (9.3*- 9.3*) | 0.5706 |
| PEAK | 9.3* (9.3*- 117.6) | 9.3* (9.3*- 115.2) | 0.7058 |
| AUC$_{0-28}$ | 306.9 (306.9- 1114.1) | 306.9 (306.9- 677.6) | 0.7314 |
| IL-1RA, pg/mL BASELINE | 516.3 (176.8- 1850.0) | 489.0 (239.1- 1033.5) | 0.3920 |
| PEAK | 1233.2 (239.0- 9000.0†) | 1144.0 (285.8- 4463.8) | 0.4743 |
| AUC$_{0-28}$ | 2.0x10$^4$ (6705.3- 1.0x10$^5$) | 1.8x10$^4$ (6192.5- 7.6x10$^4$) | 0.5313 |
| IL-2Rα, pg/mL BASELINE | 3.6 (1.2- 84.9) | 11.6 (1.1- 21.2) | 0.0545 |
| PEAK | 13.8 (1.4- 100.0†) | 15.9 (2.2- 51.0) | 0.5827 |
| AUC$_{0-28}$ | 232.3 (38.8- 1837.4) | 284.3 (52.3- 758.2) | 0.3643 |
| IL-4, pg/mL BASELINE | 0.5* (0.5*- 0.5*) | 0.5* (0.5*- 0.5*) | 1.0000 |
| PEAK | 0.5* (0.5*- 3.7) | 0.5* (0.5*- 0.5*) | 0.3015 |
| AUC$_{0-28}$ | 16.5 (9.5- 34.1) | 16.5 (16.5- 16.5) | 0.5516 |
| IL-5, pg/mL BASELINE | 6.3* (6.3*- 6.3*) | 6.3* (6.3*- 6.3*) | 1.0000 |
| PEAK | 6.3* (6.3*- 919.1) | 6.3* (6.3*- 104.1) | 0.2328 |
| AUC$_{0-28}$ | 207.9 (158.2- 5365.9) | 207.9 (207.9- 633.8) | 0.3399 |
| IL-6, pg/mL BASELINE | 1.6* (1.6*- 8.7) | 1.6* (1.6*- 7.1) | 0.0837 |
| PEAK | 24.7 (1.6*- 976.0†) | 3.6* (1.6*- 976.0†) | 0.0002 |
| AUC$_{0-28}$ | 361.8 (52.8- 7163.1) | 68.3 (52.8- 1.0x10$^4$) | 0.0003 |
| IL-15, pg/mL BASELINE (HOMEOSTATIC) | 3.0 (1.4*- 29.2) | 3.1 (1.4*- 5.4) | 0.5709 |
| PEAK | 37.9 (15.4- 82.0) | 31.2 (14.3- 93.3) | 0.3955 |
| AUC$_{0-28}$ | 513.9 (233.8- 845.9) | 442.1 (173.0- 1451.5) | 0.2059 |
| IL-2, pg/mL BASELINE | 0.9* (0.9*- 5.1) | 0.9* (0.9*- 3.0) | 0.0279 |

FIG. 101 (CONT. -3)

| | | | |
|---|---|---|---|
| PEAK | 4.1 (0.9*-48.7) | 0.9* (0.9*-23.0) | 0.0605 |
| AUC$_{0-28}$ | 41.3 (29.7-184.4) | 32.2 (29.7-112.0) | 0.1693 |
| IL-7, pg/mL | | | |
| BASELINE | 15.5 (1.4*-36.9) | 13.8 (7.1-46.6) | 0.7640 |
| PEAK | 31.8 (16.2-61.2) | 29.8 (14.3-45.9) | 0.2832 |
| AUC$_{0-28}$ | 689.3 (247.0-1748.5) | 714.4 (368.5-1154.7) | 0.5147 |

*ASSIGNED BELOW THE LIMIT OF QUANTIFICATION VALUE FOR CYTOKINE ANALYSIS IN SERUM.
†ASSIGNED UPPER LIMIT OF QUANTIFICATION VALUE FOR CYTOKINE ANALYSIS IN SERUM.
P-VALUES WERE CALCULATED USING WILCOXON TWO-SAMPLE TEST. BASELINE VALUES WERE ASSESSED AT LEUKAPHERESIS.
CCL, C-C MOTIF CHEMOKINE LIGAND; CRP, C-REACTIVE PROTEIN; CXCL, C-X-C MOTIF CHEMOKINE LIGAND; GM-CSF, GRANULOCYTE-MACROPHAGE COLONY-STIMULATING FACTOR; IFN, INTERFERON; IL, INTERLEUKIN; IP, INTER γ-INDUCED PROTEIN; MCP, MONOCYTE ATTRACTANT PROTEIN; MDC, MACROPHAGE-DERIVED CHEMOKINE; MIP, MACROPHAGE INFLAMMATORY PROTEIN; Rα, RECEPTOR ALPHA; RA, RECEPTOR AGONIST; SAA, SERUM AMYLOID A; TARC, THYMUS AND ACTIVATION REGULATED CHEMOKINE; TNF, TUMOR NECROSIS FACTOR.

*FIG. 103*

| FUNCTION | BIOMARKER MEDIAN LEVELS (RANGE) | CYTOKINE RELEASE SYNDROME | | | NEUROLOGIC EVENTS | | |
|---|---|---|---|---|---|---|---|
| | | GRADE ≥3 (n=8) | GRADE 0-2 (n=116)* | P VALUE | GRADE ≥3 (n=19) | GRADE 0-2 (n=105)† | P VALUE |
| | SAA, pg/mL | | | | | | |
| | BASELINE | $5.6 \times 10^6$ ($7.8 \times 10^5$-$9.9 \times 10^7$) | $6.7 \times 10^6$ ($6.2 \times 10^5$-$7.7 \times 10^8$) | 0.3765 | $4.5 \times 10^6$ ($7.8 \times 10^5$-$2.5 \times 10^8$) | $8.1 \times 10^6$ ($6.2 \times 10^5$-$7.7 \times 10^8$) | 0.4801 |
| | PEAK | $5.6 \times 10^8$ ($7.9 \times 10^6$-$1.4 \times 10^9$§) | $1.4 \times 10^8$ ($1.4E \times 10^6$-$1.4 \times 10^9$§) | 0.5966 | $4.9 \times 10^8$ ($7.0 \times 10^7$-$1.4 \times 10^9$§) | $1.2 \times 10^8$ ($1.4 \times 10^6$-$1.4 \times 10^9$§) | 0.0050 |
| | $AUC_{0-28}$ | $9.2 \times 10^8$ ($2.0 \times 10^7$-$7.4 \times 10^9$) | $1.2 \times 10^9$ ($1.5 \times 10^7$-$1.6 \times 10^{10}$) | 0.8828 | $2.9 \times 10^9$ ($3.7 \times 10^8$-$7.4 \times 10^9$) | $1.0 \times 10^9$ ($1.5 \times 10^7$-$1.6 \times 10^{10}$) | 0.0149 |
| | CRP, mg/L | | | | | | |
| | BASELINE | 4.9 (0.6-39.3) | 7.2 ($2.8 \times 10^{-5}$‡249.3) | 0.2203 | 4.9 (0.7-58.1) | 7.4 ($2.8 \times 10^{-5}$‡249.3) | 0.0824 |
| | PEAK | 44.8 (3.9-152.3) | 68.3 (2.9-496.0§) | 0.5794 | 89.8 (22.1-496.0§) | 64.1 (2.9-496.0§) | 0.3079 |
| INFLAMMATORY | $AUC_{0-28}$ | 372.1 (13.3-1092.8) | 628.1 (59.8-5828.9) | 0.2568 | 599.7 (181.5-3477.9) | 617.6 (13.3-5828.9) | 0.8951 |
| | FERRITIN, ng/mL | | | | | | |
| | BASELINE | 220.5 (23.3‡838.0) | 187.1 (0.0‡2354.0) | 0.9135 | 111.0 (10.8-838.0) | 205.4 (0.0‡2354.0) | 0.0330 |
| | PEAK | 1381.6 (86.4-3734.1) | 646.7 (91.3-5237.9) | 0.0904 | 573.3 (137.7-4570.7) | 667.1 (86.4-5237.9) | 0.8897 |
| | $AUC_{0-28}$ | $2.5 \times 10^4$ ($498.8$-$9.0 \times 10^4$) | $1.4 \times 10^4$ ($1516.6$-$1.1 \times 10^5$) | 0.1284 | $1.4 \times 10^4$ ($2727.9$-$9.0 \times 10^4$) | $1.4 \times 10^4$ ($498.8$-$1.1 \times 10^5$) | 0.9613 |
| | TNF-α, pg/mL | | | | | | |
| | BASELINE | 8.6 (1.6-32.8) | 3.8 (0.7‡50.1) | 0.1336 | 4.6 (0.7‡27.8) | 3.9 (0.7‡50.1) | 0.7453 |
| | PEAK | 7.9 (6.4-26.2) | 4.5 (0.7‡62.7) | 0.0005 | 6.6 (2.4-26.2) | 4.4 (0.7-62.7) | 0.0062 |

*FIG. 115*

ZUMA-1 STUDY DESIGN

| ORIGINAL AE MANAGEMENT | | REVISED AE MANAGEMENT |
|---|---|---|
| PHASE 2 (n=101) | | PHASE 2 |
| COHORT 1 REFRACTORY DLBCL (n=77) | COHORT 2 REFRACTORY PMBCL/TFL (n=24) | COHORT 6 R/R LBCL[a] (n=40) |

KEY ELIGIBILITY CRITERIA
- COHORTS 1+2; NO RESPONSE TO LAST CHEMOTHERAPY OR RELAPSE ≤12 MONTHS POST-ASCT
- COHORT 6: R/R LBCL AFTER ≥2 LINES OF THERAPY

OPTIONAL BRIDGING THERAPY ALLOWED IN COHORT 6 ONLY
- DEXAMETHASONE,[b] HIGH-DOSE METHYLPREDNISOLONE + RITUXIMAB[c], OR BENDAMUSTINE + RITUXIMAB[d]

CONDITIONING REGIMEN (ALL COHORTS)
- CYCLOPHOPHAMIDE 500 mg/m$^2$ + FLUDARABINE 30 mg/m$^2$ FOR 3 DAYS

AXI-CEL (ALL COHORTS)
- 2x10$^6$ CAR+ T CELLS/kg[e]

COHORT 6 PRIMARY ENDPOINT
- INCIDENCE AND SEVERITY OF CRS AND NEs

*FIG. 116*

AE MANAGEMENT IN ZUMA-1

| | | AE GRADE | | | |
|---|---|---|---|---|---|
| | | 1 | 2 | 3 | 4 |
| COHORT 1+2 AE MGMT | CRS | TOCILIZUMAB: NO CORTICOSTEROID: NO | TOCILIZUMAB: YES[a] CORTICOSTEROID: YES[a] | TOCILIZUMAB: YES CORTICOSTEROID: YES | TOCILIZUMAB: YES CORTICOSTEROID: YES |
| | NE | TOCILIZUMAB: NO CORTICOSTEROID: NO | TOCILIZUMAB: YES CORTICOSTEROID: NO | TOCILIZUMAB: YES CORTICOSTEROID: YES[b] | TOCILIZUMAB: YES CORTICOSTEROID: YES |
| COHORT 6 AE MGMT | CRS | TOCILIZUMAB: YES[c] CORTICOSTEROID: YES[d] | TOCILIZUMAB: YES CORTICOSTEROID: YES | TOCILIZUMAB: YES CORTICOSTEROID: YES | TOCILIZUMAB: YES CORTICOSTEROID: YES, HD |
| | NE | TOCILIZUMAB: NO CORTICOSTEROID: YES | TOCILIZUMAB: YES[e] CORTICOSTEROID: YES | TOCILIZUMAB: YES[e] CORTICOSTEROID: YES, HD | TOCILIZUMAB: YES[e] CORTICOSTEROID: YES, HD |

- PATIENTS IN COHORT 6 RECEIVED ONCE-DAILY ORAL DEXAMETHASONE 10 mg ON DAYS 0 (BEFORE AXI-CEL INFUSION), 1, AND 2
- CORTICOSTEROIDS AND TOCILIZUMAB WERE STARTED EARLIER IN COHORT 6 THAN IN COHORT 1+2[1,2]

CHIMERIC ANTIGEN RECEPTOR T CELL THERAPY

CROSS-REFERENCE TO RELATED APPLICATIONS

This application claims benefit of priority from provisional applications numbers 63/121,428 filed Dec. 4, 2020, 63/092,195 filed Oct. 15, 2020, 63/060,819 filed Aug. 4, 2020, 63/044,676 filed Jun. 26, 2020, 63/031,224 filed May 28, 2020, 63/010,240 filed Apr. 15, 2020 and 62/979,001 filed Feb. 20, 2020, all of which are incorporated by reference herein in their entireties.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) which comprise binding domains capable of interacting with a particular tumor antigen, allow T cells to target and kill cancer cells that express the particular tumor antigen.

There is a need to understand how attributes of CAR-positive T cells and patients' immunological status correlate with clinical outcomes.

SUMMARY

Provided herein are methods and uses of cells (e.g., engineered T cells) and/or compositions thereof, for the treatment of subjects having a disease or condition, which generally is or includes a cancer or a tumor, such as a leukemia or a lymphoma. In some aspects, the methods and uses provide for or achieve improved response and/or more durable responses or efficacy and/or a reduced risk of toxicity or other side effects, in subjects treated with some methods, as compared to certain alternative methods. In some embodiments, the methods comprise the administration of specified numbers or relative numbers of the engineered cells, the administration of defined ratios of particular types of the cells, treatment of particular patient populations, such as those having a particular risk profile, staging, and/or prior treatment history, administration of additional therapeutic agents and/or combinations thereof.

Also provided are methods that involve assessing particular parameters, e.g., expression of specific biomarkers or analytes, that can be correlated with an outcome, such as a therapeutic outcome, including a response, such as a complete response (CR) or a partial response (PR); or a safety outcome, such as a development of a toxicity, for example, neurotoxicity or CRS, after administration of a cell therapy. Also provided are methods to assess the likelihood of response and/or likelihood of risk of toxicity, based on assessment of the parameters, such as expression of biomarkers or analytes.

In one aspect, the disclosure provides methods of increasing the efficacy of T cell therapy without exacerbating toxicity. In one aspect, increasing the efficacy of T cell therapy without exacerbating toxicity may be achieved by systematic evaluation of bridging therapy agents to curb pre-treatment tumor burden and inflammation prior to CAR T-cell infusion. In one aspect, increasing the efficacy of T cell therapy without exacerbating toxicity may be achieved by testing of agents that modulate effects on myeloid cells or low dose corticosteroid administered immediately pre- or post-CAR T-cell infusion. In one aspect, increasing the efficacy of T cell therapy without exacerbating toxicity may be achieved by optimizing the CAR configuration to eliminate excess production of myeloid and type-1 molecules by the CAR-T cells in the product. In one aspect, increasing the efficacy of T cell therapy without exacerbating toxicity may be achieved through dosing and/or process optimizations to increase both the percentage and number of product CCR7+ CD45RA+ and/or CD8+ T cells. In one aspect, the latter may be used in the context of bulky disease. In one aspect, increasing the efficacy of T cell therapy without exacerbating toxicity may be achieved by improving T-cell fitness through optimization of product T-cell metabolism. In one aspect, this may be further combined with immune checkpoint modulators.

In one aspect, the disclosure provides that in vivo CAR T-cell expansion commensurate with pretreatment tumor burden and influenced by intrinsic product T-cell fitness, dose of specialized T-cell subsets, and host systemic inflammation, may be determining factors for durable response to T cell therapy. Accordingly, the disclosure provides a method of improving the response to CAR T-cell therapy by manipulating CAR T-cell expansion commensurate with pretreatment tumor burden, intrinsic product T-cell fitness, dose of specialized T-cell subsets in the product, and the level of systemic inflammation in the subject to be treated. In on embodiment, the number of CAR T cells in peripheral blood within 2 weeks after infusion of the T cell product associates positively and can be predictive of clinical efficacy.

In one aspect, the disclosure provides that suboptimal product T-cell fitness is related to primary treatment resistance. Accordingly, in one embodiment, the method provides a method of improving the efficacy of a T-cell product for T-cell therapy by improving the product's T-cell fitness.

In one aspect, the disclosure provides that the majority of CCR7+CD45RA+ T cells in the axicabtagene ciloleucel product infusion bag are stem-like memory cells, not canonical naïve T cells. In one embodiment, these cells may be characterized as reported in Arihara Y. et al. *Journal for ImmunoTherapy of Cancer* (2019); 7(1):P210.

In one aspect, the disclosure provides that limited numbers of CCR7+CD45RA+ or CD8+ T cells in proportion to tumor burden were associated with a failure to achieve durable response to CAR T-cell treatment. Accordingly, in one embodiment, the disclosure provides a method for improving the effectiveness of a T-cell product for T-cell therapy by increasing the percentage and/or number of CCR7+CD45RA+ and/or CD8+ T cell in the product, particularly normalized to tumor burden.

In one embodiment, the numbers of specialized CD4+ T cells correlated with clinical response. Accordingly, in one embodiment, the disclosure provides a method for improving the effectiveness of a T-cell product for T-cell therapy by increasing the percentage and/or number of specialized CD4+ T cells in the product.

In one embodiment, high tumor burden, pronounced inflammatory status (reflected by myeloid activation markers pre- and post-CAR T-cell infusion), and excess type-1 cytokines associated negatively with durable efficacy and positively with severe toxicities and thus are targetable parameters for improving T cell therapy.

In on embodiment, peak CAR T-cell levels in blood normalized to pre-treatment tumor burden associated with durable response. This index was positively associated with durable response rate and separated subsets of patients with high (~60%) versus low (~10%) probability of achieving a durable response. Accordingly, manipulation of peak CAR T-cell levels in blood normalized to pre-treatment tumor burden is a means for improving durable response to T cell therapy.

In one embodiment, the disclosure provides a method of treating cancer in a subject in need thereof comprising improving activation and expansion within 2 weeks, 3 weeks, or 4 weeks of administration of a therapeutically effective amount of CAR T-cells administered to the subject.

In one aspect, the disclosure provides a method of manufacturing an effective dose of engineered T cells for CAR T-cell therapy comprising: (a) preparing a population of engineered T cells comprising a chimeric antigen receptor (CAR); (b) measuring the T cell expansion capability of the population; and (c) preparing an effective dose of engineered T cells for CAR T-cell therapy for treating a malignancy in a patient in need thereof based on the T cell expansion capability of the population. In some embodiments, the T cell expansion capability relates to in vivo expansion. In some embodiments, the T cell expansion capability relates to in vitro expansion. In some embodiments, the T cell expansion capability is measured during the manufacturing process. In some embodiments, the T cell expansion capability is determined by measuring doubling time. In some embodiments, the doubling time is between about 1-4.7 days, about 1.8-4.7 days, about 1-1.5 days, or less than about 1.5 days. In some embodiments, the doubling time is about 1.3 days, about 1.5 days, or about 1.8 days. In some embodiments, the doubling time is about 1.6 days. In some embodiments, a doubling time of about 1.6 days associates with response to the CAR T cell therapy. In some embodiments, the doubling time is about 2.1 days. In some embodiments, a doubling time of about 2.1 days associates with nonresponse to the CAR T cell therapy. In some embodiments, the doubling time is <2 days. In some embodiments, in patients with high tumor burden, patients with objective response or a durable response have in vitro doubling times <2 days. In some embodiments, an in vitro doubling time >2 days is associated with relapse or non-response.

In another aspect, the disclosure provides a method of manufacturing engineered T cells for CAR T-cell therapy comprising: (a) non-specifically stimulating the engineered T cells in the presence of anti-CD3 antibodies and expanding the engineered T cells in the presence of IL-2, wherein the engineered T cells comprise a chimeric antigen receptor (CAR); (b) measuring the doubling time of the population during the expansion process; (c) harvesting the engineered T cells after expansion; and (d) preparing an effective dose of engineered T cells for CAR T-cell therapy (CAR T-Cells) based on the doubling time of the engineered T cells. In some embodiments, the engineered T cells are expanded for about 2-7 days in the presence of IL-2. In some embodiments, the doubling time is measured by determining the number of total viable cells at the start of expansion and at the time of harvesting the engineered T cells (CAR T-cells).

In another aspect, the disclosure provides a method of treating a malignancy in a patient comprising: (a) measuring levels of one or more attributes in the apheresis starting material or in a population of engineered T cells comprising a chimeric antigen receptor (CAR); (b) determining a patient's response to the treatment with the engineered T cells based on the measured levels of one or more attributes compared to a reference level; and (c) administering a therapeutically effective dose of the engineered T cells to the patient based on the levels of one or more of the attributes. In some embodiments, the one or more attributes is doubling time or CAR T cell phenotype. In some embodiments, the CAR T cell phenotype is determined by percentage of CCR7 and CD45RA double positive cells (e.g., T cells of naïve-like phenotype). In some embodiments, the doubling time is about 1.6 days. In some embodiments, the doubling time is about 2.1 days. In some embodiments, the doubling time is <2 days. In some embodiments, the attribute is intrinsic CAR T cell fitness, the levels of specialized CAR T-cell subsets in the CAR T-cell population (e.g., the numbers of CD8 and naïve-like CD8 cells in the infusion product), the number of CD28+CD27+ $T_N$ cells in the apheresis starting material, and/or the proportion of T cells with CD25$^{hi}$ CD4 expression (possibly representing regulatory T cells) in the apheresis material.

In still another aspect, the disclosure provides a method of manufacturing or determining quality of a population of engineered T cells comprising: (a) preparing a population of engineered T cells comprising a chimeric antigen receptor (CAR); (b) measuring the levels of one or more attributes of the population; and (c) determining whether the population is suitable for treating malignancy in a patient in need thereof based on the measured levels of one or more attributes compared to a reference level. In another aspect, the disclosure provides a method of manufacturing an effective dose of engineered T cells comprising: (a) preparing a population of engineered T cells comprising a chimeric antigen receptor (CAR); (b) measuring the levels of one or more attributes of the population; and (c) preparing an effective dose of engineered T cells for treating malignancy in a patient in need thereof based on the measured levels of one or more attributes compared to a reference level. In yet another aspect, the disclosure provides a method of manufacturing an effective dose of engineered T cells comprising: (a) measuring the amount of one or more phenotype markers in a population of cells; and (b) preparing an effective dose of engineered T cells for treating a cancer in a patient in need thereof based on the measured amount of the one or more phenotype markers. In some embodiments, one phenotype marker is CCR7 or CD45RA. In some embodiments, the disclosure provides a method of improving the effectiveness of a CAR T-cell product by increasing the percentage and/or number of product CCR7+CD45RA+ and/or CD8+ T cells in the product. In some embodiments, this is achieved through optimization of the process for producing the T-cell product. In some embodiments, the percentage and/or number of CCR7+CD45RA+ and/or CD8+ T cells in the product is adjusted based on the pre-treatment tumor burden of the subject receiving the treatment.

In another aspect, the disclosure provides a method of determining whether a patient will respond to CAR T cell therapy comprising: (a) measuring in vivo CAR T-cell expansion after administration of CAR T-cells relative to pretreatment tumor burden to obtain a value and (b) determining if the patient will achieve durable response based on the value.

In another aspect, the disclosure provides a method of determining whether a patient will respond to CAR T cell therapy comprising: (a) measuring the intrinsic cell fitness of the CAR T-cell population to be administered (e.g., infusion product) to obtain a value and (b) determining if the patient will achieve durable response based on the value. In some embodiments, the method further comprises administering an effective dose of CAR T-cells to the patient, wherein the effective dose is determined using the value. In some embodiments, the intrinsic cell fitness is assessed based on the capacity of the CAR T cells to expand during nonspecific stimulation in vitro (e.g., shorter doubling time), the differentiation state of the CAR T cells (favorable juvenile phenotype), the levels of specialized CAR T-cell subsets in the CAR T-cell population (e.g., the numbers of CD8 and naïve-like CD8 cells (e.g., CD8+ CCR7+CD45RA+ T Cells) in the infusion product), and the in vivo CAR T cell expansion rate.

In another aspect, the disclosure provides a method of determining whether a patient will respond to CAR T cell therapy comprising: (a) measuring the levels of specialized T-cell subsets in the T-cell population to be administered (e.g., infusion product) to obtain a value and (b) determining if the patient will achieve durable response based on the value. In some embodiments, the method further comprises administering an effective dose of CAR T-cells to the patient, wherein the effective dose is determined using the value.

In another aspect, the disclosure provides a method of determining whether a patient will respond to CAR T cell therapy comprising: (a) measuring the levels of one or more inflammatory cytokines in a blood sample from the patient pre-therapy and post-therapy to obtain a value per cytokine and (b) determining if the patient will achieve durable response based on the value(s). In one embodiment, the value(s) for myeloid activation marker(s) (e.g., IL6, ferritin, CCL2) pre- and post-CAR T-cell treatment associate negatively with durable efficacy/response and positively with severe toxicities. In one embodiment, the higher the values for treatment-related type-1 cytokines the lower the durable efficacy and the higher the severe toxicities after infusion-product administration. In some embodiments, the higher the pretreatment serum levels of LDH and pro-inflammatory markers such as IL6, CRP, and ferritin, the lower the clinical efficacy of the CAR T-cell treatment. In some embodiments, the method further comprises administering an effective dose of CAR T-cells to the patient, wherein the effective dose is determined using one or more of said value(s).

In some embodiments, the higher the pre-treatment levels of circulating pro-inflammatory cytokines the higher the toxicity (e.g., cytokine release syndrome and/or neurotoxicity) of the CAR T cell treatment. In some embodiments, the disclosure provides a method of assessing or predicting toxicity of CAR T-cell treatment in a patient comprising (a) measuring pretreatment tumor burden, tissue hypoxia, LDH, serum ferritin, and/or postconditioning serum IL15 levels at day 0 (day of infusion product administration) and (b) determining that the patient will experience toxicity of grade ≥3 neurologic events (NE) based on those measurements. In some embodiments, the method further comprises administering an effective dose of CAR T cells to the patient, wherein the effective dose is determined on the basis of the predicted toxicity. In some embodiments, the disclosure provides a method of assessing toxicity of CAR T-cell treatment in a patient comprising (a) measuring pretreatment IL6 levels (b) determining that the patient will experience toxicity of grade ≥3 cytokine release syndrome (CRS) based on the measurement. In some embodiments, the method further comprises administering an effective dose of CAR T cells to the patient, wherein the effective dose is determined on the basis of the predicted toxicity. In some embodiments, the method further comprises administering one or more agents that reduce the treatment-associated toxicity as preventative measures and/or to reduce CRS and/or NE (neurologic events) symptoms.

In another aspect, the disclosure provides a method of determining whether a patient will respond to CAR T cell therapy comprising: (a) measuring the peak CAR T-cell levels in the blood post CAR T-administration to obtain a value (b) normalizing the value to pretreatment tumor burden; and (c) determining if the patient will achieve durable response based on the normalized value. In some embodiments, the value is positively associated with durable response and separates subsets of patients with higher (~60%) vs. lower (~10%) probability of achieving a durable response. In some embodiments, the CAR T-cell levels are calculated by enumerating the number of CAR T-cells per unit of blood volume.

In another aspect, the disclosure provides a method to assess or predict primary treatment resistance comprising (a) measuring the doubling time of the population of T-cells in the infusion product to obtain a value and (b) assessing or predicting primary treatment resistance based on the value. In some embodiments, the method further comprises administering an effective dose of CAR T-cells to the patient, wherein the effective dose is determined using the value. In some embodiments, the higher doubling time is associated with primary treatment resistance. In some embodiments, a product doubling time >1.6 days is associated with nonresponse. In some embodiments, in patients with high tumor burden, patients with objective response or a durable response have doubling times <2 days. In some embodiments, a doubling time >2 days is associated with relapse or non-response. In some embodiments, the higher the number of CD28+CD27+ $T_N$ cells in the apheresis starting material the better (shorter) the infusion product doubling time.

In another aspect, the disclosure provides a method of increasing the reduction in tumor volume after CAR T cell treatment with an infusion product, comprising increasing the numbers of CD8 and naïve-like CD8 CAR T cells in the infusion product relative to a reference standard. In another aspect, the disclosure provides a method of improving durable efficacy of CAR T-cell treatment in a patient, comprising increasing the total number of infused T cells of naïve-like phenotype (CCR7+CD45RA+) relative to a reference standard. In some embodiments, the method further comprises administering an effective dose of CAR T-cells to the patient, wherein the effective dose is determined using the number of CD28+CD27+ $T_N$ cells in the apheresis starting material and/or the total number of infused CAR T cells of naïve-like phenotype (CCR7+CD45RA+). In one embodiment (e.g., axicabtagene ciloleucel), the CCR7+ CD45RA+ cells are actually stem-like memory cells and not canonical naïve T cells.

In another aspect, the disclosure provides a method of increasing efficacy of CAR T-cell treatment, preferably without increasing toxicity, comprising administering immediately pre- or post-CAR T-cell infusion one or more agents known to modulate effects on myeloid cells and/or low dose corticosteroids. In another aspect, the disclosure provides a method of increasing efficacy of CAR T-cell treatment, preferably without increasing toxicity, comprising systematic evaluation of bridging therapy agents (e.g., agents administered between conditioning and CAR T cell treatment) to curb tumor burden and/or inflammation pre-CAR T-cell infusion. In another aspect, the disclosure provides a method of increasing efficacy of CAR T-cell treatment, preferably without increasing toxicity, comprising reducing excess production of myeloid and type-1 cytokines by the infusion product cells. In another aspect, the disclosure provides a method of increasing efficacy of CAR T-cell treatment, preferably without increasing toxicity, comprising dosing or process optimizations to increase both the percentage and number of product $T_N$ and CD8+ T cells, especially in context of bulky disease, relative to a reference standard. In another aspect, the disclosure provides a method of increasing efficacy of CAR T-cell treatment, preferably without increasing toxicity, comprising improving T-cell fitness through optimizing infusion product T-cell metabolism or combining with immune checkpoint modulators. In one embodiment (e.g., axicabtagene ciloleucel), the TN cells are that are identified as CCR7+CD45RA+ cells are actually stem-like memory cells and not canonical naïve T cells.

In some embodiments, the population of T cells is obtained from apheresis material. In some embodiments, the method further comprises engineering the population of T cells to express a CAR. In some embodiments, the CAR T cells are engineered to express a chimeric antigen receptor that targets a tumor antigen. In some embodiments, the chimeric antigen receptor targets a tumor antigen selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

In some embodiments, the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T-cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma)), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

In some embodiments, the therapeutically effective dose is between $75\text{-}200\times10^6$ engineered T cells. In some embodiments, the therapeutically effective dose is $2\times10^6$ CAR T cells per kilogram of body weight. In some embodiments, the engineered T cells are autologous or allogeneic T cells. In some embodiments, the response is measured within about 1 month, about 3 months, about 6 months, about 9 months, or about 12 months after administration of the engineered T cells.

The following embodiments are exemplary, but not limited, embodiments of the disclosure.

1. A method of manufacturing an immunotherapy product with improved clinical efficacy and/or decreased toxicity comprising:
   (i) Preparing a T cell product from a population of lymphocytes comprising T cells with various baseline T cell phenotypes, wherein no specific T cell phenotype has been enriched during the preparation of the product;
   (ii) Increasing or maximizing the percentage of T cells with naïve phenotype (CD45RA+ CCR7+) in the product;
   (iii) Increasing or maximizing the percentage of CD8+ T cells with naïve phenotype (CD45RA+ CCR7+) in the product;
   (iv) Decreasing or minimizing the percentage and number of T cells with differentiated phenotype (CCR7−) in the product;
   (v) Decreasing or minimizing the percentage and number of IFN gamma producing cells in the product;
   (vi) Including at least $20\times10^6$ T cells with naïve phenotype in the product;
   (vii) Including at least $100\times10^6$ CD8 T cells in the product; and/or

(viii) Including at least 15×10^6 CD8 T cells of naïve
phenotype in the product;
    wherein the product is an immunotherapy infusion
product and the various baseline T cell phenotypes
comprise T$_{CM}$, central memory T cells (CD45RA–
CCR7+); T$_{EFF}$, effector T cells (CD45RA+
CCR7–); T$_{EM}$, effector memory T cells
(CD45RA–CCR7–); and/or T$_N$, naïve-like T cells
(CD45RA+CCR7+);
    preferably, wherein the term T cells with naïve
phenotype means T cells that are CD45RA+
CCR7+ and comprises stem-like memory cells.
2. The method of claim 1, wherein:
(i) increasing or maximizing the percentage of T cells
with naïve phenotype (CD45RA+ CCR7+) in the
product increases product efficacy without increas-
ing toxicity;
(ii) increasing or maximizing the percentage of CD8+
T cells with naïve phenotype (CD45RA+ CCR7+) in
the product increases product efficacy without
increasing toxicity;
(iii) decreasing or minimizing the percentage and num-
ber of T cells with differentiated phenotype (CCR7–)
in the product improves safety profile;
(iv) decreasing or minimizing the percentage and num-
ber of IFN gamma producing cells in the product
improves safety profile;
(v) including at least 20×10^6 T cells with naïve phe-
notype in the product improves efficacy without
increasing toxicity;
(vi) including at least 100×10^6 CD8 T cells in the
product improves efficacy; and/or
(vii) including at least 15×10^6 CD8 T cells of naïve
phenotype in the product improves efficacy without
increasing toxicity;
    wherein the product is an infusion bag for immuno-
therapy.
3. A method of preparing a personalized immunotherapy
product for infusion to a subject in need thereof com-
prising:
(i) Preparing a population of lymphocytes comprising
CD8+ T cells and naïve T cells;
(ii) Determining the subject's tumor burden; and
(iii) Increasing the cumulative cell dose to be infused to
the subject based on the measured tumor burden to
increase the ratio of infused CD8+ T cells/tumor
burden; and/or
(iv) Increasing the cumulative cell dose to be infused
based on the measured tumor burden to increase the
ratio of infused naïve T cells/tumor burden;
    Wherein the method enhances the efficacy of the
immunotherapy product; preferably, wherein the
term naïve T cells means T cells that are
CD45RA+CCR7+ and comprises stem-like
memory cells.
4. The method of any one of claims 1 through 3, wherein
the population of lymphocytes from which the T cell
product is prepared is the product of leukapheresis of
Peripheral Blood Mononuclear Cells (PBMCs).
5. The method of any one of claims 1 through 4, wherein
the population of lymphocytes from which the T cell
product is prepared is a population of lymphocytes
prepared by in vitro differentiation of stem cells.
6. The method of any one of claims 1 through 5, wherein
the T cells are genetically modified.

7. The method of any one of claims 1 through 6, wherein
the cells are autologous, allogeneic, or differentiated in
vitro from a universal perpetually renewable cell popu-
lation.
8. The method of claim 7, wherein the universal perpetu-
ally renewable cell population is a population of stem
cells.
9. A method of manufacturing an effective dose of engi-
neered lymphocytes comprising:
(i) preparing a population of engineered lymphocytes,
optionally comprising a chimeric antigen receptor
(CAR), and optionally starting with an apheresis
product;
(ii) measuring the expansion capability of the popula-
tion of engineered lymphocytes during manufactur-
ing of an infusion product, or in the final infusion
product, comprising the engineered lymphocytes;
and
(iii) preparing an effective dose of engineered lympho-
cytes in an infusion product for treating a cancer in
a subject in need thereof based on the expansion
capability of the engineered lymphocyte population.
10. The method of claim 9, wherein the engineered
lymphocyte population expansion capability is deter-
mined by measuring doubling time.
11. The method of claim 10, wherein the doubling time is
about 1.0, 1.1, about 1.2, about 1.3, about 1.4 days,
about 1.5 days, about 1.6, about 1.7 days, about 1.8,
about 1.9, or about 2 days.
12. The method of claim 10, wherein the doubling time is
about 2.1 days.
13. The method of claim 10, wherein the doubling time is
about 1.6 or >1.6 days.
14. The method of claim 10, wherein the doubling time is
<2 days.
15. The method of claim 10, wherein the doubling time is
>2 days.
16. The method of claim 10, wherein the doubling time is
greater than about 2 days.
17. The method of claim 10, wherein the doubling time is
less than about 2 days.
18. The method of any one of claims 10 through 17,
wherein the doubling time of the population of engi-
neered lymphocytes (e.g., CAR T cells) is measured
during preparation of the infusion product.
19. The method of any one of claims 1 through 18, further
comprising manipulating the population of engineered
lymphocytes during manufacturing of the infusion
product to produce an infusion product with a prede-
termined engineered lymphocyte population doubling
time.
20. The method of claim 19, wherein the predetermined
doubling time is about 1.6 or >1.6 days, about 2 days,
or greater than about 2 days.
21. The method of claim 19, wherein the predetermined
doubling time is about <1.6 days, about 2 days, or
smaller than about 2 days.
22. The method of anyone of claims 9 through 21,
wherein the engineered lymphocytes are T lympho-
cytes engineered to comprise a CAR or an exogenous
TCR.
23. The method of anyone of claims 9 through 22,
wherein manipulating the population of engineered
lymphocytes comprises manipulating the composition
of the final infusion product in terms of numbers of
T$_{CM}$, central memory T cells (CD45RA–CCR7+);
T$_{EFF}$, effector T cells (CD45RA+CCR7–); T$_{EM}$, effector memory T cells (CD45RA–CCR7–); and/or $T_N$, naïve-like T cells (CD45RA+CCR7+), preferably, wherein the term $T_N$ naïve-like T cells means T cells that are CD45RA+CCR7+ and comprises stem-like memory cells.

24. The method of claim 23, wherein the greater the percentage of $T_{EM}$ cells in the infusion product the higher the doubling time.

25. The method of claim 23, wherein the higher the percentage of $T_N$ cells in the infusion product, the lower the doubling time.

26. The method of anyone of claims 9 through 25, wherein the lower the doubling time of the population of engineered lymphocytes in the final infusion product, the greater the in vivo engineered lymphocyte (e.g., CAR T cells) levels after administration to the subject in need thereof.

27. The method of anyone of claims 9 through 26, wherein the lower the doubling time of the population of engineered lymphocytes in the final infusion product, the greater the efficacy of the final infusion product.

28. The method of anyone of claims 9 through 27, further comprising measuring the proportion of T cells with a juvenile phenotype in the apheresis product from which the population of engineered lymphocytes is prepared, wherein the higher the proportion of cells with a juvenile phenotype (e.g., CD28+CD27+ $T_N$ cells, CD45RA+CCR7+ cells) the lower the doubling time of the infusion product.

29. The method of anyone of claims 1 through 28, comprising expanding the lymphocytes to produce the infusion product in the presence of IL-2.

30. The method of anyone of claims 9 through 29, wherein the engineered lymphocytes are expanded for about 2-7 days in the presence of IL-2.

31. The method of anyone of claims 9 through 30, wherein the doubling time is measured by determining the number of total viable cells at the start of expansion and at the time of harvesting the engineered lymphocytes.

32. A T cell immunotherapy product produced according to any one of the methods of claims 1 through 31.

33. The T cell immunotherapy product of claim 32, wherein the product is an infusion product.

34. The T cell immunotherapy product of any one of claims 32 and 33, wherein the T cells are CAR T-cells.

35. A method of selecting a donor for allogeneic T cell immunotherapy comprising:
(i) Collecting a sample of T lymphocytes from a subject;
(ii) Selecting the subject to be a donor for allogeneic T cell immunotherapy based on one or more of the following:
  a. the percentage of T cells with naïve phenotype (CD45RA+ CCR7+) in the sample;
  b. the percentage of CD8+ T cells with naïve phenotype (CD45RA+ CCR7+) in the sample;
  c. the percentage and number of T cells with differentiated phenotype (CCR7–) in the sample; and
  d. the percentage and number of IFNgamma producing cells in the sample; and, optionally,
(iii) preparing an allogeneic T cell product from the selected subject;
(iv) administering the product to a subject in need thereof, preferably, wherein the term T cells with naïve phenotype means T cells that are CD45RA+CCR7+ and comprises stem-like memory cells.

36. The method of claim 35, wherein the sample of T lymphocytes is prepared by leukapheresis of PBMCs from the subject.

37. The method of claim 36, wherein the leukapheresis sample is further subject to T lymphocyte enrichment through positive selection for CD4+ and/or CD8+ cells.

38. A method of increasing the efficacy and/or reducing the toxicity of CAR-T cell immunotherapy in a subject in need thereof comprising:
(i) Decreasing the subject's tumor burden prior to CAR T-cell immunotherapy;
(ii) Decreasing the subject's systemic inflammatory state prior to CAR T-cell immunotherapy;
(iii) Reducing myeloid cell activity in the subject prior to CAR T-cell immunotherapy;
(iv) Reducing the MCP-1 and/or IL-6 activity prior to, or early after CAR T-cell administration;
(v) Reducing the activity of activated T cells in the subject/T-cell product prior to CAR T-cell immunotherapy;
(vi) Increasing the dosage of the CAR T cell immunotherapy in a manner commensurate with the subject's pre-treatment tumor burden; and/or
(vii) Re-dosing subjects with high tumor burden; whereby the efficacy of CAR T cell immunotherapy is increased and/or toxicity is decreased.

39. The method of claim 38, wherein the decrease of the subject's tumor burden comprises administration of bridging therapy and/or the reducing the activity of activated T cells in the subject/T-cell product prior to CAR T-cell therapy is accomplished by a) separation/removal of differentiated cells (effector memory and/or effector cells; b) enriching the product for juvenile T cells (CCR7+); c) removing or diminishing the percentage and number of differentiated T cells in the T cell product infusion bag through separation techniques; and/or d) treating the product T cells during or after manufacturing process with pharmacological agents or biological response modifiers that would reduce excessive T cell activity (e.g., JAK/STAT inhibitors).

40. The method of claim 39, wherein the bridging therapy comprises one or more of CHOP, R-CHOP (rituximab, cyclophosphamide, doxorubicin, vincristine, and prednisolone), G-CHOP (obinutuzumab, cyclophosphamide, doxorubicin, vincristine, and prednisolone), corticosteroids, bendamustine, platinum compounds, anthracyclines, venetoclax, zanubrutinib, phosphoinositide 3-kinase (PI3K) inhibitors, and inhibitors of the PI3K/Akt/mTOR pathway.

41. The method of claim 40, wherein the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032).

42. The method of claim 39, wherein the bridging therapy comprises one or more of acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denileukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin difti-tox, pembrolizumab, plerixafor, polatuzumab vedotin-piiq, mogamulizumab-kpc, corticosteroids, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

43. The method of any one of claims 38 through 42, further comprising administering anti-inflammatory treatment to the subject prior to CAR T-cell immuno-therapy.

44. The method of any one of claims 38 through 43, wherein reducing myeloid cell activity, MCP-1, and/or IL-6 activity comprises administering to the subject a monoclonal antibody against MCP-1, CRP, IL-6, IL-1, CSF1R, GM-CSF and/or a small molecule.

45. The method of claim 44, wherein the small molecule is a JAK/STAT inhibitor.

46. The method of claim 45, wherein the JAK/STAT inhibitor is selected from tofacitinib, ruxolitinib, filgo-tinib, baricitinib, peficitinib, oclacitinib, upadicitinib, solcitinib, decernotinib, SHR0302, AC430, PF-06263276, BMS-986165, lestaurtinib, PF-06651600, PF-04965841, abrocitinib, sttatic, pep-tidomimetics, and combinations thereof.

47. A method of increasing the efficacy and/or reducing the toxicity of CAR-T cell immunotherapy in a subject in need thereof comprising:
    (i) Identifying a subject positive for marker(s) of tox-icity in response to CAR T-cell immunotherapy and taking measures to reduce those markers; and/or
    (ii) Reducing IL-15 elevation post-conditioning and pre-CAR T cell immunotherapy in the subject.

48. The method of claim 47, wherein the positive marker of toxicity is high tumor burden and/or increased pre-treatment levels of inflammatory markers.

49. The method of claim 48, wherein the inflammatory markers are selected from IL6, CRP, and ferritin.

50. The method of anyone of claims 47 through 49, wherein reduction of IL-15 elevation post-conditioning and pre-CAR T cell immunotherapy is accomplished by selection of a pre-conditioning protocol.

51. The method of claim 50, wherein the pre-conditioning protocol comprises cyclophosphamide, fludarabine, bendamustine, Anti-Human Thymocyte Globulin, car-mustine, radiation, etoposide, cytarabine, melphalan, rituximab, or combinations thereof 52. A method of predicting toxicity in response to CAR T-cell therapy in a subject in need thereof comprising:
    (i) measuring one or more subject's attributes selected from:
        a. pre-treatment tumor burden;
        b. pre-treatment blood levels of LDH, ferritin, and/or IL-6;
        c. blood levels of IL-15 post-conditioning therapy and pre-CAR T cell treatment;
        d. blood levels of MCP-1, CRP, IL-6, IFNgamma, and/or CXCL10 one day post CAR T cell treat-ment; and/or
        e. changes in one or more of (a) through (d) between pre and post-conditioning; day 1 and day 0; day 0 and baseline, and/or day 1 and baseline;
    (ii) predicting toxicity in response to CAR T cell therapy based on one or more of those measure-ments; and, optionally, (iii) administering to the subject one or more agents to prevent or minimize toxicity.

53. A method of predicting Grade ≥3 NE in response to CAR T cell treatment in a subject in need thereof comprising:
    (i) measuring baseline serum LDH and/or day 0 serum IL-15 to obtain a value;
    (ii) predicting Grade ≥3 NE in response to CAR T cell treatment based on the value; and, optionally,
    (iii) administering to the subject one or more agents to prevent or minimize toxicity.

54. The method of claim 53, wherein baseline LDH and/or day 0 IL-15 associate positively with Grade ≥3 NE in response to CAR T cell treatment.

55. A method of predicting Grade ≥3 CRS in response to CAR T cell treatment in a subject in need thereof comprising:
    (i) measuring baseline serum LDH and/or baseline serum IL-6 to obtain a value;
    (ii) predicting Grade ≥3 CRS in response to CAR T cell treatment based on the value; and, optionally,
    (iii) administering to the subject one or more agents to prevent or minimize toxicity.

56. The method of claim 55, wherein baseline LDH and/or baseline IL-6 associate positively with Grade ≥3 CRS in response to CAR T cell treatment.

57. A method of predicting Grade 3+ neurotoxicity in response to CAR T cell treatment in a subject in need thereof comprising:
    (i) measuring day 1/day 0 serum IFNgamma fold change to obtain a value;
    (ii) predicting Grade 3+ neurotoxicity in response to CAR T cell treatment based on the value; and, optionally,
    (iii) administering to the subject one or more agents to prevent or minimize toxicity.

58. The method of claim 57, wherein day 1/day 0 serum IFNgamma fold change greater than about 25 results in grade 3+ neurotoxicity.

59. The method of claim 57, wherein day 1/day 0 serum IFNgamma fold change greater than about 30, about 35, about 40, about 45, or about 50 results in grade 3+ neurotoxicity.

60. A method of predicting neurologic toxicity in response to CAR T cell treatment in a subject in need thereof comprising:
    (i) measuring pretreatment product T-cell IFNgamma production to obtain a value;
    (ii) predicting severe neurotoxicity and decreased effi-cacy in response to CAR T cell treatment based on the value; and, optionally,
    (iii) administering to the subject one or more agents to prevent or minimize toxicity.

61. The method of claim 60, further comprising modu-lating the pretreatment product T-cell IFNgamma pro-duction level to improve the effectiveness and/or decrease the toxicity of the CAR T cell treatment.

62. A method of predicting toxicity in response to CAR T cell treatment in a subject in need thereof comprising:
    (i) measuring the tumor burden, inflammatory status reflected by myeloid activation markers pre- and post-treatment, and/or treatment-related type-1 cyto-kines in the subject to obtain a level for each,
    (ii) predicting toxicity based on those levels; and, optionally,
    (iii) administering to the subject one or more agents to prevent or minimize toxicity.

63. The method of claim 62, wherein high tumor burden, pronounced inflammatory status reflected by myeloid activation markers pre- and post-engineered lymphocyte (CAR T cells) infusion, and excess treatment-related type-1 cytokines associate positively with severe toxicity.

64. A method of predicting toxicity in response to CAR T cell treatment in a subject in need thereof comprising:
(i) measuring the peak CAR T cell level after treatment,
(ii) predicting toxicity based on those levels; and, optionally,
(iii) administering to the subject one or more agents to prevent or minimize toxicity.

65. The method of claim 64, wherein the peak CAR T cell level associates positively with severe neurotoxicity.

66. The method of any one of claims 35 through 65, further comprising administering to the subject one or more agents capable of reducing the adverse effects, optionally selected from agents that have a direct relation to or a direct effect on the measured attributes.

67. The method of claim 66, wherein the agent(s) is administered prior to T cell treatment.

68. The method of claim 66, wherein the agent(s) is administered concurrently with or after administration of the CAR T cell treatment.

69. The method of anyone of claims 66 through 68, wherein the agent(s) is selected from tocilizumab (or another anti-IL6/IL6R agent/antagonist), a corticosteroid therapy, or an anti-seizure medicine for toxicity prophylaxis based on the measured levels of the one or more attributes, or combinations thereof.

70. The method of anyone of claims 66 through 68, wherein the agent(s) is selected from inhibitors of GM-CSF, CSF1, GM-CSFR, or CSF1R, anti-thymocyte globulin, lenzilumab, mavrilimumab, cytokines, and/or anti-inflammatory agents.

71. The method of any one of claims 52 through 70, wherein "based on the value" or "based on the measured level" or "based on those measurements" of one or more attributes means by comparison to a known reference value for each attribute.

72. The method of any one of claims 52 through 71, wherein "based on the value" or "based on the measured level" or "based on those measurements" of one or more attributes means by determining in which known reference quartile does the value or measured level fit.

73. The method of claim 73, wherein the known reference quartiles are those shown in the FIGS.

74. A method of predicting efficacy in response to CAR T cell therapy in a subject in need thereof comprising:
(i) Measuring one or more subject and T cell product attributes selected from:
a. Tumor burden;
b. Dose of CD8+ T cells administered or to be administered to the subject (e.g., the number of infused CD8 T cells);
c. Dose of naïve T cells (CCR7+CD45RA+) administered or to be administered to the subject;
d. Peak CAR levels in the blood after CAR T cell therapy; and/or
e. Level of inflammatory markers;
(ii) Predicting treatment efficacy based on one or more of those measurements, preferably wherein the term naïve T cells means CCR7+CD45RA+ T cells and comprises stem-like memory cells.

75. The method of claim 74, wherein "based on those measurements" of one or more attributes means by comparison to a known reference value for each attribute.

76. The method of claim 74, wherein "based on those measurements" of one or more attributes means by determining in which known reference quartile does the value or measure level fit.

77. The method of claim 76, wherein the known reference quartiles are those shown in the FIGS.

78. A method of predicting response to CAR T cell treatment in a subject in need thereof comprising:
(i) measuring the rate of in vivo CAR T cell expansion relatively to pretreatment tumor burden, the intrinsic T-cell fitness of the product, the dose of specialized T cell subsets, and/or host systemic inflammation (e.g., levels of inflammatory markers) of the subject to obtain a value;
(ii) predicting response to CAR T cell treatment based on the value.

79. The method of claim 78, wherein the rate of in vivo CART cell expansion relatively to pretreatment tumor burden, intrinsic product T-cell fitness (optionally relatively to pretreatment tumor burden) and the dose of specialized T cell subsets associate positively with durable response.

80. The method of claim 78, wherein pre-treatment and post-treatment subject systemic inflammation associates negatively with durable response.

81. The method of anyone of claims 78 through 80, wherein suboptimal product T-cell fitness is associated with primary treatment resistance, and limited numbers of naïve-like or CD8+ T cells in proportion to tumor burden are associated with a failure to achieve durable response.

82. The method of any one of claims 78 through 81, wherein the doubling time of the cells in the product is a measure of the intrinsic product T-cell fitness.

83. The method of claim 82, wherein there is an approximately 100% rate of objective response in subjects in which the doubling time of the cells in the infusion product the subject receives falls within quartile Q1 of FIG. 3.

84. The method of claim 82, wherein approximately 100 out of every one hundred subjects that receive an infusion product where the doubling time of the cells falls in quartile Q1 of FIG. 3 have an objective response.

85. The method of claim 82, wherein if the subject receives an infusion product where the doubling time of the cells falls in quartile Q1 of FIG. 3, the subject has approximately 100% chance of having an objective response.

86. The method of claim 82, wherein approximately 80% of all nonresponders received infusion products in Q3 and Q4 of FIG. 3 of the doubling time.

87. The method of claim 82, wherein there is an approximately 27% durable response rate in subjects in the highest doubling time quartile of FIG. 3.

88. The method of claim 82, wherein approximately 27 out of every one hundred subjects that receive an infusion product where the doubling time of the cells falls in the highest quartile of FIG. 3 have a durable response.

89. The method of claim 82, wherein if the subject receives an infusion product where the doubling time of the cells falls in the highest quartile of FIG. 3, the subject has approximately 27% chance of have a durable response.

90. The method of anyone of claims 75 through 89, wherein there is an approximately 16% response rate in subjects having number of infused CD8 T cells/pretreatment tumor burden falling within the lowest quartile of FIG. 5 whereas there is an approximately 58% response rate in subjects having number of infused CD8 T cells/pretreatment tumor burden falling within the top quartile of FIG. 5.

91. The method of anyone of claims 75 through 89, wherein approximately 16 out of every one hundred subjects that receive an infusion product wherein the number of infused CD8 T cells/pretreatment tumor burden falls within the lowest quartile of FIG. 5 have a response.

92. The method of anyone of claims 75 through 89, wherein if the subject receives an infusion product wherein the number of infused CD8 T cells/pretreatment tumor burden falls within the lowest quartile of FIG. 5, the subject has approximately 16% chance of having a response.

93. The method of anyone of claims 75 through 89, wherein approximately 58 out of every one hundred subjects that receive an infusion product wherein the number of infused CD8 T cells/pretreatment tumor burden falls within the top quartile of FIG. 5 have a response.

94. The method of anyone of claims 75 through 89, wherein if the subject receives an infusion product wherein the number of infused CD8 T cells/pretreatment tumor burden falls within top quartile of FIG. 5, the subject has approximately 58% chance of having a response.

95. The method of anyone of claims 75 through 89, wherein subjects in the top quartile of inflammatory markers have durable response rates of approximately 19-26% (2.6-3.2 fold) lower than those in the first quartile of FIG. 9.

96. The method of anyone of claims 75 through 89, wherein there is between approximately 19% and approximately 26% durable response rate in subjects having a level of proinflammatory markers in the top quartile of FIG. 9, wherein the proinflammatory markers are baseline ferritin, baseline LDH, and baseline IL-6.

97. The method of anyone of claims 75 through 89, wherein approximately 19 to 26 out of every one hundred subjects that having a baseline level of proinflammatory markers in the top quartile quartile of FIG. Shave a durable response.

98. The method of anyone of claims 75 through 89, wherein if the subject has a baseline level of proinflammatory markers in the top quartile of FIG. 9, the subject has approximately 19% to 26% chance of having a durable response.

99. The method of anyone of claims 83 through 98, wherein the quartiles are those shown in the FIGS. and Tables.

100. A method of predicting response to engineered lymphocytes (e.g., CAR T cell) treatment comprising:
(i) measuring the peak engineered lymphocyte (e.g., CAR T-cell) levels in the blood post treatment with an engineered lymphocyte (e.g., CAR T-cell) infusion product and normalize them to pretreatment tumor burden to obtain a value;

(ii) predicting response to the engineered lymphocyte cell (e.g., CAR T-cell) treatment based on the value.

101. The method of claim 100, wherein the peak engineered lymphocyte (e.g., CAR T cells) levels in the blood post treatment normalized to pretreatment tumor burden associate positively with durable response.

102. The method of anyone of claims 100 through 101, wherein in the highest tumor burden quartile, subjects who achieved a durable response have a greater than 3-fold higher peak CAR T-cell expansion compared with subjects who relapse or have no response.

103. The method of anyone of claims 100 through 101, wherein there is a lower durable response rate (approximately 12%) in in subjects within the lowest quartile of peak CAR T-cell/tumor burden ratio than in the top quartiles (>50%).

104. The method of anyone of claims 100 through 101, wherein in the highest tumor burden quartile, subjects who achieved a durable response had a greater than 3-fold higher peak CAR T-cell expansion compared with subjects who relapsed or had no response (median, 74.4 vs 20.2 CAR T cells/$\mu$L blood).

105. The method of anyone of claims 100 through 101, wherein in the highest tumor burden quartile, subjects who achieved a durable response have a greater than 3-fold higher peak CAR T-cell expansion compared with subjects who relapse or have no response.

106. The method of anyone of claims 100 through 101, wherein there is a lower durable response rate (approximately 12%) in in subjects within the lowest quartile of peak CAR T-cell/tumor burden ratio than in the top quartiles (>50%).

107. The method of anyone of claims 100 through 101, wherein in the highest tumor burden quartile, subjects who achieved a durable response had a greater than 3-fold higher peak CAR T-cell expansion compared with subjects who relapsed or had no response (median, 74.4 vs 20.2 CAR T cells/$\mu$L blood).

108. The method of anyone of claims 100 through 106, wherein the quartiles are those shown in the FIG.

109. A method of predicting peak engineered lymphocyte levels in the blood after administration of an engineered lymphocyte infusion product to a subject comprising:
(i) measuring the number of TN cells in the infusion product, the baseline doubling time of the engineered lymphocytes in the infusion product, coculture IFN-$\gamma$, baseline LDH, baseline CRP, and/or the baseline ferritin level in the blood of the subject to obtain a value;
(ii) predicting peak engineered lymphocyte levels in the blood based on the value; and/or
(iii) preparing an effective dose of engineered lymphocytes based on the value; and/or;
(iv) administering an effective dose of engineered lymphocytes based on the value; wherein the peak engineered lymphocyte levels in the blood associate positively with response.

110. The method of claim 109, wherein the number of $T_N$ cells in the infusion product and the level of baseline ferritin level associate positively with the peak engineered lymphocyte (e.g., CAR T cells) levels.

111. The method of anyone of claims 109 through 110, wherein the baseline doubling time of the engineered lymphocytes in the infusion product associates negatively with the peak engineered lymphocytes levels.

112. The method of anyone of claims 109 through 111, wherein the number of $T_N$ cells in the infusion product associates positively with the peak engineered lymphocytes/tumor burden.

113. The method of claim anyone of claims 109 through 112, wherein the baseline doubling time, baseline ferritin, coculture IFN-γ, baseline LDH, and baseline CRP associate negatively with peak engineered lymphocytes/tumor burden.

114. A method of predicting response to engineered lymphocyte (e.g., CAR T cell) treatment comprising:
(i) measuring the level of IFN-γ (e.g., coculture IFN-γ) of a population of engineered lymphocytes (e.g., CAR T cells) in an infusion product to obtain a value;
(ii) predicting response to the engineered lymphocyte (e.g., CAR T cells) treatment based on the value.

115. The method of claim 114, wherein the level of coculture IFN-γ associates negatively with the peak engineered lymphocytes levels, and the peak engineered lymphocyte levels associates positively with response.

116. A method of predicting response to CAR T cell treatment in subject comprising:
(i) measuring the levels of type-1 cytokines in the blood of the subject post-treatment to obtain a value;
(ii) predicting response to CAR T cell treatment based on the value.

117. The method of claim 116, wherein the level of type-1 cytokines in the blood post treatment associates negatively with durable efficacy.

118. A method of predicting response to CAR T cell treatment in subject comprising:
(i) measuring baseline tumor burden, baseline IL6, baseline CRP, baseline LDH, and coculture IFN-γ to obtain a value;
(ii) predicting response to CAR T cell treatment based on the value.

119. The method of claim 118, wherein the baseline tumor burden, baseline IL6, baseline CRP, baseline LDH, and coculture IFN-γ associate negatively with durable response.

120. The method of anyone of claims 118 through 119, wherein the higher the tumor burden, the lower the response rate.

121. The method of anyone of claims 118 through 120, wherein the higher the tumor burden, the lower the probability of durable response.

122. The method of anyone of claims 118 through 121, there is between approximately 20% and approximately 40% durable response rate in subjects having a tumor burden falling in quartiles Q3 and Q4.

123. The method of anyone of claims 118 through 121, wherein between 20 and 40 subjects out of every one hundred subjects having a tumor burden falling in quartiles Q3 and Q4 have a durable response.

124. The method of anyone of claims 118 through 121, wherein if the subject's tumor burden falls in quartiles Q3 or Q4, the subject has between 20% and 40% chance of having a durable response.

125. The method of anyone of claims 118 through 121, wherein there is between approximately 40% and approximately 60% durable response rate in subjects having a tumor burden falling in quartiles Q1 and Q2.

126. The method of anyone of claims 118 through 121, wherein between 40 and 60 subjects out of every one hundred subjects having a tumor burden falling in quartiles Q1 and Q2 have a durable response.

127. The method of anyone of claims 118 through 121, wherein if the subject's tumor burden falls in quartiles Q1 or Q2, the subject has between 40% and 60% chance of having a durable response.

128. The method of anyone of claims 122 through 128, wherein the quartiles are those shown in the FIGS.

129. A method of treating a cancer in a subject in need thereof with an infusion product comprising engineered lymphocytes comprising:
(i) measuring levels of one or more attributes in a population of lymphocytes from an apheresis product; and/or
(ii) measuring levels of one or more attributes in a population of engineered lymphocytes (e.g., CAR T cells) during manufacturing of the final infusion product and/or in the final infusion product; and
(iii) determining or predicting a subject's response to treatment with the engineered lymphocytes based on the measured levels of one or more attributes compared to a reference level; and, optionally,
(iv) administering a therapeutically effective dose of the engineered lymphocytes to the subject, wherein the therapeutically effective dose is determined based on the levels of one or more attributes of the population of engineered lymphocytes in the infusion product and/or of the T cells in the apheresis product.

130. The method of claim 129, wherein the engineered lymphocytes are CAR-T lymphocytes.

131. The method of anyone of claims 129 through 130, wherein the T cell composition of the final infusion product is manipulated during its manufacturing to achieve pre-determined levels of engineered lymphocytes with select attributes in the infusion product.

132. The method of anyone of claims 129 through 131, wherein the one or more attributes is T cell fitness, including doubling time and T cell phenotype (e.g., the levels of specialized CAR T-cell subsets in the CAR T-cell population).

133. The method of anyone of claims 129 through 132, wherein the T cell phenotype that is measured is that of the population of engineered lymphocytes in the final infusion product.

134. The method of anyone of claims 129 through 132, wherein the T cell phenotype that is measured is that of the population of engineered lymphocytes during manufacturing of the final infusion product, and the T cell phenotype of the final infusion product.

135. The method of anyone of claims 129 through 135, wherein the population of engineered lymphocytes (e.g., CAR T cells) is to be infused into the subject and the phenotype is determined by measuring the percentage of CD3 positive cells infused, the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/tumor burden; the percentage of CD4 positive cells infused, the number of CD4 positive cells infused, the number of CD4 positive cells infused/tumor burden; and/or the CD4:CD8 ratio in the cells infused, preferably wherein the term $T_N$ cells means T cells that are CD45RA+CCR7+ and comprises stem-like memory cells.

136. The method of anyone of claims 129 through 135, wherein the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/tumor burden; and the number of CD4 positive cells infused/tumor burden associate positively with or are predictive of durable response to treatment 137. The method of anyone of claims 129 through 136, wherein the percentage of CD3 cells infused, the percentage of CD4 cells infused, and the number of CD4 cells infused associate negatively with, or are predictive of, no durable response.

138. The method of anyone of claims 129 through 137, wherein the frequency and proportion of $T_N$ (CD45RA+CCR7+) and TEM CD8+ or CD4+ T cells (CD45RA−CCR7−) in the CAR T-cell infusion product associate with clinical efficacy, positively and negatively, respectively.

139. The method of anyone of claims 129 through 138, wherein the frequency and proportion of $T_N$ (CD45RA+CCR7+) and TEM CD8+ or CD4+ T cells (CD45RA−CCR7−) in the engineered lymphocyte (CAR T cells) infusion product are manipulated during manufacturing of the infusion product to improve clinical efficacy.

140. The method of anyone of claims 129 through 139, wherein the % of CD3 cells infused, the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/tumor burden; and the number of CD4 positive cells infused/tumor burden associate positively with or are predictive of peak engineered lymphocyte (e.g., peak engineered lymphocyte (CAR T cells)) levels in the blood past administration of the infusion product.

141. The method of anyone of claims 129 through 140, wherein the percentage of CD4 cells infused and the number of CD4 cells infused associate negatively with, or are predictive of lower, peak engineered lymphocyte (e.g., peak engineered lymphocyte (CAR T cells)) levels past administration of the infusion product.

142. The method of anyone of claims 129 through 141, wherein the number and percentage of naïve-like CD8 positive T cells (e.g., CD8+ CCR7+ CD45RA+ T Cells) in the infusion product associates positively, or is predictive of, durable response whereas the number of effector memory CD4 positive T cells associates negatively with durable response to CAR T cell therapy.

143. The method of anyone of claims 129 through 142, wherein the attributes that are measured are attributes of the population of T cells in the apheresis product.

144. The method of claim 143, wherein the attributes of the apheresis product are the proportion of effector memory T cells within total CD3+ T cells or CD4 and CD8 subsets, the number of CD27+CD28+ $T_N$ cells, and/or the proportion of T cells with CD25hi CD4 expression, preferably wherein the term $T_N$ cells means CD45RA+CCR7+ T cells.

145. The method of anyone of claims 143 through 144, wherein the more juvenile the phenotype of the T cells (e.g., the higher the number of CD28+CD27+ TN cells)

in the apheresis starting material the better (shorter) the doubling time of the engineered lymphocytes in the infusion product.

146. The method of anyone of claims 129 through 145, wherein the measured attribute is the doubling time of the population of engineered lymphocytes in the infusion product.

147. The method of claim 146, wherein the doubling time is about 1.0, 1.1, about 1.2, about 1.3, about 1.4 days, about 1.5 days, about 1.6, about 1.7 days, about 1.8, about 1.9, and about 2.

148. The method of claim 146, wherein the doubling time is about 2.1 days.

149. The method of claim 146, wherein the doubling time is about 1.6 or >1.6 days.

150. The method of claim 146, wherein the doubling time is <2 days.

151. The method of claim 146, wherein the doubling time is >2 days.

152. The method of claim 146, wherein the doubling time is greater than about 2 days.

153. The method of claim 146, wherein the doubling time is less than about 2 days.

154. The method of claim 146, wherein a doubling time <2 days associates positively with or is predictive of objective response (complete response, partial response, or non-response) or durable response in subjects with high tumor burden.

155. The method of claim 146, wherein a doubling time of about 2.1 days associates with nonresponse to the CAR T cell therapy.

156. The method of claim 146, wherein a doubling time >2 days associates with relapse or non-response.

157. The method of claim 146, wherein relapse is measured within 1 year post treatment.

158. The method of claim 146, wherein a doubling time of about 2.1 associates with non-response.

159. The method of claim 146, wherein a doubling time of about 1.6 or >1.6 days associates with non-response.

160. The method of claim 146, wherein there is an approximately 100% rate of objective response in subjects in which the doubling time of the cells in the infusion product the subject receives falls within quartile Q1.

161. The method of claim 146, wherein approximately 100 out of every one hundred subjects that receive an infusion product where the doubling time of the cells falls in quartile Q1 have an objective response.

162. The method of claim 146, wherein if the subject receives an infusion product where the doubling time of the cells falls in quartile Q1, the subject has approximately 100% chance of having an objective response.

163. The method of claim 146, wherein approximately 80% of all nonresponders received infusion products in Q3 and Q4 of the doubling time.

164. The method of claim 146, wherein there is an approximately 27% durable response rate in subjects in the highest doubling time quartile.

165. The method of claim 146, wherein approximately 27 out of every one hundred subjects that receive an infusion product where the doubling time of the cells falls in the highest quartile have a durable response.

166. The method of claim 146, wherein if the subject receives an infusion product where the doubling time of the cells falls in the highest quartile, the subject has approximately 27% chance of have a durable response.

167. The method of anyone of claims 160 through 166, wherein the quartiles are those shown in the FIGS.

168. The method of claim 129, wherein the CD4:CD8 ratio positively associates with durable response.

169. The method of anyone of claims 129 through 168, wherein the therapeutically effective dose is calculated and/or manipulated by calculating or manipulating the doubling time, phenotype, and other attributes of the cells in the infusion product used to prepare the therapeutically effective dose.

170. The method of claim 169, wherein the attributes of the population of engineered lymphocyte (e.g., CAR T cells) in the product that are manipulated during manufacturing to improve subject response and/or reduce therapeutic dose are selected from the following attributes: the doubling time, the percentage of CD3 positive cells infused, the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/tumor burden; the percentage of CD4 positive cells infused, the number of CD4 positive cells infused, the number of CD4 positive cells infused/tumor burden; CD4:CD8 ratio in the cells infused, the frequency and proportion of $T_N$ and $T_{EM}$ CD8+ or CD4+ T cells, and/or the number of percentage of naïve-like T cells.

171. A method of treating a cancer with engineered lymphocytes (e.g., CAR T cells) in a subject in need thereof comprising:
   (i) measuring levels of one or more pretreatment attributes of the subject,
   (ii) determining or predicting a subject's response to treatment with engineered lymphocytes based on the measured levels of one or more attributes compared to a reference level; and, optionally,
   (iii) administering a therapeutically effective dose of the engineered lymphocytes to the subject, wherein the therapeutically effective dose is determined based on the level of one or more pre-treatment attributes of the subject.

172. The method of claim 171, wherein the pretreatment attributes are reflective of or are markers of the subject's systemic inflammation.

173. The method of claim 171, wherein the pretreatment attributes show pronounced inflammatory status reflected by the levels of myeloid activation markers (e.g., IL6, ferritin, CCL2) in the serum of the subject.

174. The method of claim 171, wherein the pretreatment attributes are selected from baseline tumor burden, baseline IL-6, baseline CRP, baseline LDH, baseline ferritin, disease stage, Day 0 IL-15, Day 0 IFN-γ, baseline weight, baseline CCL2, wherein Day 0 is the day of administration of the engineered lymphocytes.

175. The method of claim 174, wherein baseline levels are the last values measured prior to conditioning therapy.

176. The method of anyone of claims 100 through 175 and 197 through 208, wherein the engineered lymphocytes (e.g., CAR T cells) target a tumor antigen.

177. The method of claim 176, wherein the tumor antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

178. The method of claim 177, wherein the target antigen is CD19.

179. The method of claim 178, wherein the cancer is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CIVIL), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

180. The method of claim 179, wherein the cancer is (relapsed or refractory) diffuse large B-cell lymphoma (DLBCL) not otherwise specified, primary mediastinal large B-cell lymphoma, high grade B-cell lymphoma, DLBCL arising from follicular lymphoma, or mantle cell lymphoma.

181. The method of anyone of claims 100 through 180, wherein the therapeutically effective amount or effective dose of the engineered lymphocytes (e.g., CAR T cells) may be at least about $10^4$ cells, at least about $10^5$ cells, at least about $10^6$ cells, at least about $10^7$ cells, at least about $10^8$ cells, at least about $10^9$, or at least about $10^{10}$ cells.

182. The method of anyone of claims 100 through 180, wherein the therapeutically effective amount or effective dose of the engineered lymphocytes (e.g., CAR T cells) is about $10^4$ cells, about $10^5$ cells, about $10^6$ cells, about $10^7$ cells, or about $10^8$ cells.

183. The method of anyone of claims 100 through 180 wherein the therapeutically effective amount or effective dose of the engineered lymphocytes (e.g., CAR T cells) may be about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

184. The method of anyone of claims 100 through 180, wherein the therapeutically effective amount or effective dose of the engineered lymphocytes (e.g., CAR T cells) may be between about $1\times10^6$ and about $2\times10^6$ engineered viable lymphocytes (e.g., CAR T cells) per kg body weight up to a maximum dose of about $1\times10^8$ engineered viable lymphocytes (e.g., CAR T cells).

185. The method anyone of claims 100 through 180, wherein the therapeutically effective dose is between 75 and $200\times10^6$ engineered lymphocytes.

186. A method of predicting efficacy in response to CAR T cell therapy in a subject having a tumor in need thereof comprising measuring the baseline (preconditioning) levels of CD3D, CD69, IRF1, CXCL9, CXCL10, STAT1, VEGFA, PDCD1, and/or CD274 genes in a sample of the subject's tumor, predicting the tumor's response based on one or more of those measurements; and, optionally, administering a therapeutically effective amount of CAR T cells to the subject based on the measurements.

187. The method of claim 186, wherein the expression levels of the CD3D, CD69, IRF1, CXCL9, CXCL10, STAT1 genes correlates positively with objective response (CR/PR) and the expression levels of the VEGFA, PDCD1, and/or CD274 genes correlates negatively with objective response (CR/PR); and, optionally, administering a therapeutically effective amount of CAR T cells to the subject based on the measurements.

188. A method of predicting efficacy in response to CAR T cell therapy in a subject having a tumor in need thereof comprising measuring the baseline (preconditioning) levels of GZMA, CD69, IRF1, CXCL9, CXCL10, STAT1, and/or VEGFA genes in a sample of the subject's tumor and predicting the tumor's best response based on one or more of those measurements; and, optionally, administering a therapeutically effective amount of CAR T cells to the subject based on the measurements.

189. The method of claim 188, wherein the expression levels of the GZMA, CD69, IRF1, CXCL9, CXCL10, STAT1, genes correlates positively with best response and the expression levels of the VEGFA gene correlates negatively with best response; and, optionally, administering a therapeutically effective amount of CAR T cells to the subject based on the measurements.

190. A method of predicting adverse events in response to CAR T cell therapy in a subject in need thereof comprising measuring the baseline (preconditioning) levels of CD8A, PRF1, IRF1, CCL5, CXCL9, CCL2, STAT1, STAT4, VEGFA, CTLA4, PDCD1, and/or CD274 in a sample of the subject's tumor and predicting the grade of neurologic events based on one or more of those measurements; and, optionally, administering a therapeutically effective amount of CAR T cells to the subject based on the measurements.

191. The method of claim 190, wherein the lower the expression levels of at least one of those genes, the worse the grade of neurologic events.

192. A method of predicting efficacy in response to CAR T cell therapy in a subject having a tumor in need thereof comprising measuring the baseline (preconditioning) profile of pretreatment tumor immune infiltrates in a sample of the subject's tumor and predicting the subject's response to the treatment based on one or more of those measurements; and, optionally, administering a therapeutically effective amount of CAR T cells to the subject based on the measurements.

193. The method of claim 192, wherein if the subject's tumor measurements fall within cluster A defined by pre-treatment infiltration with immune cells comprising activated CD8 T cells the subject will fall within those having a complete response whereas if the measurements fall within cluster B, the subject will fall among those having progressive disease.

194. A method of predicting neurotoxicity in response to CAR T cell therapy in a subject in need thereof comprising measuring the baseline (preconditioning) density of Treg cells and polymorphonuclear myeloid-derived suppressor cells (PMN-MDSCs) in a sample of the subject's tumor and predicting the treatment's neurotoxicity based on one or more of those measurements; and, optionally, administering a therapeutically effective amount of CAR T cells and anti-neurotoxicity agents to the subject based on the measurements.

195. The method of claim 194, wherein the lower the density of Treg and PMN-MDSC cells, the worse the neurotoxicity (Grade 3).

196. A method of predicting efficacy in response to CAR T cell treatment in a subject having a tumor in need thereof comprising measuring pretreatment density of Treg (CD3+CD8−FoxP3+) in a sample of the subject's tumor, wherein said pretreatment density correlates positively with tumor microenvironment features that are desirable for efficacy, including CD8+PD-1+ T cell density; and, optionally, administering a therapeutically effective amount of CAR T cells to the subject based on the measurements.

197. A method of predicting efficacy in response to CAR T cell therapy in a subject having a tumor in need thereof comprising measuring the baseline (preconditioning) density of CD3+, CD8+, and activated CD8+ T cells in a sample of the subject's tumor and predicting the treatment efficacy based on that measurements; and, optionally, administering a therapeutically effective amount of CAR T cells to the subject based on the measurements.

198. The method of claim 197, wherein the levels of CD3+, CD8+, and activated CD8+ T cells associate positively with response to treatment.

199. The method of claim 198, wherein activated CD8+ T cells have expression of one checkpoint gene selected from PD-1 and LAG-3.

200. A method of predicting efficacy in response to CAR T cell therapy in a subject having a tumor in need thereof comprising measuring the baseline (preconditioning) tumor burden and/or tumor-infiltrating T cell density in a sample of the subject's tumor and predicting the treatment efficacy based on those measurements; and, optionally, administering a therapeutically effective amount of CAR T cells to the subject based on the measurements.

201. The method of claim 200, wherein low tumor burden and high tumor-infiltrating T cell density correlate positively with complete response.

202. A method of predicting T cell gene expression and density as a surrogate for T cell involvement, which correlates positively with response in CAR T cell treatment of a tumor in a subject in need thereof, comprising measuring the baseline (preconditioning) levels of IL-7/IL-7R, IL-18, CCL5, CCR5, IL-15 and IL-21 and predicting T cell gene expression and density based on those measurements, wherein pretreatment expression in a sample of the subject's tumor of IL-7/IL-7R, IL-18, and CCL5 correlate with CD3δ, CD8α, CD4; CCR5 and IL-15 correlate with CD3δ, CD8α; and IL-21 correlates with CD3δ; and, optionally, administering a therapeutically effective amount of CAR T cells to the subject based on the measurements.

203. A method of predicting T cell gene expression and density as a surrogate for T cell involvement in CAR T cell treatment of a tumor in a subject in need thereof, comprising measuring tumor of CCL5 and CCR5 in a sample of the subject's tumor and predicting T cell gene expression and density based on the measurement, wherein pretreatment expression in a sample of the subject's tumor of CCL5 and CCR5 correlates positively with density of CD8+ and CD4+ T cells by IHC; and, optionally, administering a therapeutically effective amount of CAR T cells to the subject based on the measurements.

204. A method of predicting myeloid cell density in a tumor in a subject in need of CAR T cell treatment, comprising measuring tumor CCR5, IL-1R, STAT1, FPR2, and CXCL9 levels in a sample of the subject's tumor and predicting myeloid cell density based on the measurement, wherein pretreatment expression in a sample of the subject's tumor of CCR5, IL-1R, STAT1, FPR2, and CXCL9 correlates positively with myeloid cell density (CD11b+ and CD14+); and, optionally, administering a therapeutically effective amount of CAR T cells to the subject based on the measurements.

205. A method of predicting peak CAR T cell levels normalized to tumor burden after CAR T cell administration to a subject having a tumor in need thereof, comprising measuring pretreatment CD8+PD1+ T cell density in a sample of the subject's tumor and predicting CAR T cell levels normalized to tumor burden, wherein pretreatment CD8+PD-1+ T cell density associates positively with CAR T cell levels; and, optionally, administering a therapeutically effective amount of CAR T cells to the subject based on the measurements.

206. A method of predicting efficacy in response to CAR T cell treatment in a subject having a tumor in need thereof comprising measuring pretreatment density of activated CD8+PD-1+LAG-3+/–TIM-3– T cells in a sample of the subject's tumor and predicting efficacy based on that measurement, wherein said pretreatment density correlates positively with clinical efficacy; and, optionally, administering a therapeutically effective amount of CAR T cells to the subject based on the measurements.

207. A method of predicting neurotoxicity in response to CAR T cell treatment in a subject having a tumor in need thereof comprising measuring pretreatment density of CD3+CD8–FoxP3+ (Treg) cells and/or CCL22 gene expression in a sample of the subject's tumor and predicting neurotoxicity based on that measurement, wherein density and gene expression levels associate positively with low-grade neurotoxicity and high activated T cell density; and, optionally, administering a therapeutically effective amount of CAR T cells and an anti-neurotoxicity treatment/agent to the subject based on the measurements.

208. A method of predicting CART cell efficacy in treating a tumor in a subject in need thereof, comprising measuring, early post treatment (within 1-2 weeks), the increase of T cell related genes (e.g., CD8α, immune effector molecules (granzyme A), key T cell growth factors and chemokines (IL-15), interferon (IFN)☐-regulated immune checkpoints (PD-L1, B7-H3, CTLA-4), and myeloid-related genes and corresponding chemokines (CD14, CCL2)) in conjunction with the decrease of B cell related genes (e.g., including CD19, CD20, CD22, and CD75 (ST6GAL1), B cell transcriptional master switch PAX5, and transcriptional coactivator POU2AF1), in a sample of the subject's tumor and predicting CAR T cell efficacy based on the measurement; wherein a decrease in B cell related genes correlates positively with tumor response and an increase in T cell related genes correlates positively with tumor response; and, optionally, administering a therapeutically effective amount of CAR T cells to the subject based on the measurements.

209. A method of decreasing primary resistance to CART cell treatment in a subject having a tumor in need thereof, comprising administering to the subject a therapeutically effective amount of one or more of the following:

(i) an agent that modulates the methylation state of the subject's tumor, preferably DNA demethylating inhibitors (DDMTi) 5-aza-2'-deoxycytidine (decitabine) and 5-azacytidine or other cytosine analogs;

(ii) an agent that modulates the acetylation state of the subject's tumor, preferably HDAC inhibitors;

(iii) a checkpoint blocking agent, preferably one or more agents that block immune checkpoint receptors on the surface of T cells, such as cytotoxic T lymphocyte antigen 4 (CTLA-4), lymphocyte activation gene-3 (LAG-3), T-cell immunoglobulin mucin domain 3 (TIM-3), B- and T-lymphocyte attenuator (BTLA), T-cell immunoglobulin and T-cell immu- noreceptor tyrosine-based inhibitory motif (ITIM) domain, and programmed cell death 1 (PD-1); and/or (iv) an agonist of 41BB, OX40, and/or TLR.

and, optionally, administering a therapeutically effec- tive amount of CAR T cells to the subject.

210. The method of claim 209, wherein the administration of any one of (i) through (iv) is done prior to, during, and/or after administration of the CAR T cell treatment.

211. The method of claim 210, wherein the administration is done prior to conditioning treatment.

212. The method of any one of claims 209 through 211, wherein the administration is intravenously or intratumoral.

213. A method of preparing a CAR T cell product that decreases or overcomes primary resistance to CAR T cell treatment comprising improving the CAR T cells by co-expressing gamma chain receptor cytokines under constitutive or inducible promoters in the CAR T cells; reprogramming CAR T cells to overcome detrimental tumor microenvironments (e.g., engineering to express gamma chain receptor cytokines) optimizing T cell manufacturing to help CAR T cells overcome detrimental tumor microenvironments (growing T cells in the presence of gamma chain cytokines (e.g., IL-2, IL-4, IL-7, IL-9, IL-15, and IL-21).

214. A method of increasing the efficacy CAR-T cell immunotherapy in a subject in need thereof comprising:

(i) Modulating the subject's tumor microenvironment prior to CAR T cell treatment by one or more of:

(a) optimization of bridging therapy to modulate the tumor microenvironment to a more favorable immune permissive state, preferably by administering bridging therapy with IMIDs (e.g., lenoalidomide) and/or local radiation;

(b) optimization of bridging therapy to diminish tumor burden prior to CAR T cell treatment administration, preferably by administering bridging therapy with R-CHOP, bendamustine, alkylating agents, and/or platinum based agents;

(c) optimization of conditioning treatment to modulate the tumor microenvironment to a more favorable immune permissive state, preferably addition of local irradiation to cyclophosphamide/fludarabine conditioning and/or using platinum-based agents as conditioning agents; and/or (ii) Co-administering biological response modifiers together or post-CAR T cell administration to enable CAR T cell activity, preferably gamma chain cytokines (e.g., IL-15 and/or checkpoint blocking agents (e.g. anti-CTLA-4);

and, optionally, administering a therapeutically effective amount of CAR T cells to the subject based on the measurements.

215. The method of any one of claims 47 through 70, 194, 195, and 207, wherein toxicity is managed or reduced by administration of a steroid and/or an anti-IL6R antibody.

216. The method of claim 215, wherein toxicity is managed by one of the two protocols of FIG. 46.

217. The method of claim 215, wherein toxicity is managed according to one or more dosage regimens in Table 12.

218. The method of any one of claims 215 through 217, wherein levetiracetam is administered for prophylaxis and at the onset of grade ≥2 neurologic toxicities, if neurologic events occur after the discontinuation of prophylactic levetiracetam and/or levetiracetam is tapered and discontinued if the patient does not experience any grade ≥2 neurologic toxicities.

219. The method of claim 218, wherein levetiracetam is administered at 750 mg orally or intravenous twice daily, starting on day 0 of the treatment with engineered lymphocytes and/or at the onset of grade ≥2 neurologic toxicities.

220. The method of claim 215, wherein toxicity/adverse events is managed or reduced by a method as described in FIG. 56.

221. The method of claim 220, wherein patients receive levetiracetam (750 mg oral or intravenous twice daily) starting on day 0 of administration of T cell therapy; at the onset of grade ≥2 neurologic events, levetiracetam dose is increased to 1000 mg twice daily; if a patient did not experience any grade ≥2 neurologic event, levetiracetam is tapered and discontinued as clinically indicated; patients also receive tocilizumab (8 mg/kg IV over 1 hour [not to exceed 800 mg]) on day 2; further tocilizumab (±corticosteroids) may be recommended at the onset of grade 2 CRS in patients with comorbidities or older age, or otherwise in case of grade ≥3 CRS; for patients experiencing grade ≥2 neurologic events, tocilizumab is initiated, and corticosteroids are added for patients with comorbidities or older age, or if there is any occurrence of a grade ≥3 neurologic event with worsening symptoms despite tocilizumab use.

222. The method of claim 215, wherein toxicity/adverse events is/are managed or reduced by a method wherein patients receive dexamethasone 10 mg PO on Days 0 (prior to T cell therapy infusion), 1, and 2; steroids are also administered starting at Grade 1 NE, and for Grade 1 CRS when no improvement is observed after 3 days of supportive care; tocilizumab is also administered for Grade ≥1 CRS if no improvement is observed after 24 hours of supportive care.

223. The method of claim 215, wherein toxicity/adverse events is/are managed by administration of an antibody that depletes and/or neutralizes GM-CSF, preferably wherein the antibody is lenzilumab.

224. A method of treating relapsed/refractory indolent Non-Hodgkin Lymphoma (R/R NHL) in a subject in need thereof comprising administering to the subject a therapeutically effective amount of CAR T cells as a retreatment, wherein the subject has previously received a first treatment with CAR T cells.

225. The method of claim 224, wherein the first treatment with CAR T cells was administered as a first line therapy or a second line therapy, optionally wherein the lymphoma is R/R follicular lymphoma (FL) or marginal zone lymphoma (MZL) and optionally wherein the previous prior lines of therapy included anti-CD20 monoclonal antibody combined with an alkylating agent.

226. The method of claim 224, wherein the key retreatment eligibility criteria include response of a CR or PR at the month 3 disease assessment with subsequent progression; no evidence of CD19 loss in progression biopsy by local review; and/or no Grade 4 CRS or neurologic events, or life-threatening toxicities with the first treatment with CAR T cells.

227. A method of treating NHL (e.g., large B cell lymphoma (LBCL)) in a subject in need thereof comprising administering to the subject a therapeutically effective amount of CAR T cells, wherein the CAR T cells are administered as a first line therapy.

228. The method of claim 227, wherein the LBCL is high risk/high grade LBCL with MYC and BCL2 and/or BCL6 translocations or DLBCL with IPI score ≥3 any time before enrollment.

229. The method of claim 227, wherein the first line therapy comprises both CAR T cell therapy in combination with an anti-CD20 monoclonal antibody and anthracycline-containing regimen.

230. The method of claim 227, wherein the method further comprises bridging therapy administered after leukapheresis and completed prior to initiating conditioning chemotherapy.

231. A method of predicting NE in response to the treatment of any one of claims 227-230 comprising measuring the peak serum level of IL-6, IL-5, IFN-γ, IL-8, GM-CSF, CCL26, Ferritin, IL-17, IL-10, CCL3, TNF-α, and/or Granzyme B, wherein the higher the peak serum level of one or more of these cytokines the higher the probability of Grade ≥3 NEs.

232. A method of predicting CRS in response to the treatment of any one of claims 227-230 comprising measuring peak serum levels of IL-6, IL-8, VCAM-1, GM-CSF, IL-17, ICAM-1, IL-4, IL-2, IL-12 P70, CCL17, CCL26, and/or IL-5, wherein the higher the peak serum level of one or more of these cytokines the higher the probability of Grade ≥3 CRS.

233. A method of reducing NE and/or CRS in response to the treatment of any one of claims 227-230, comprising administering to the subject an agent that decreases the serum level and/or activity of any one or more of the cytokines in claims 231 and 232, after CAR T cell treatment and/or prophylactically.

234. The method of any one of claims 186 through 233, wherein the CAR tumor antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

235. The method of claim 234, wherein the target antigen is CD19.

236. The method of any one of claims 186 through 223, wherein the cancer is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

237. The method of claim 235, wherein the cancer is (relapsed or refractory) diffuse large B-cell lymphoma (DLBCL) not otherwise specified, primary mediastinal large B-cell lymphoma, high grade B-cell lymphoma, DLBCL arising from follicular lymphoma, or mantle cell lymphoma.

238. The method of anyone of claims 186 through 236, wherein the therapeutically effective amount or effective dose of the engineered lymphocytes (e.g., CAR T cells) may be at least about $10^4$ cells, at least about $10^5$ cells, at least about $10^6$ cells, at least about $10^7$ cells, at least about $10^8$ cells, at least about $10^9$, or at least about $10^{10}$ cells.

239. The method of anyone of claims 186 through 236, wherein the therapeutically effective amount or effective dose of the engineered lymphocytes (e.g., CAR T cells) is about $10^4$ cells, about $10^5$ cells, about $10^6$ cells, about $10^7$ cells, or about $10^8$ cells.

240. The method of anyone of claims 186 through 236 wherein the therapeutically effective amount or effective dose of the engineered lymphocytes (e.g., CAR T cells) may be about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

241. The method of anyone of claims 186 through 236, wherein the therapeutically effective amount or effective dose of the engineered lymphocytes (e.g., CAR T cells) may be between about $1\times10^6$ and about $2\times10^6$ engineered viable lymphocytes (e.g., CAR T cells) per kg body weight up to a maximum dose of about $1\times10^8$ engineered viable lymphocytes (e.g., CAR T cells).

242. The method anyone of claims 186 through 236, wherein the therapeutically effective dose of CART cells is between 75 and $200\times10^6$ engineered lymphocytes.

The following embodiments are also exemplary, but not limiting, embodiments of the disclosure.

1. A method of manufacturing an immunotherapy product with improved clinical efficacy and/or decreased toxicity comprising:
   (i) Preparing a T cell product from a population of lymphocytes comprising T cells with various baseline T cell phenotypes, wherein no specific T cell phenotype has been enriched during the preparation of the product;
   (ii) Increasing or maximizing the percentage of T cells with naïve phenotype (CD45RA+CCR7+) in the product;
   (iii) Increasing or maximizing the percentage of CD8+ T cells with naïve phenotype (CD45RA+ CCR7+) in the product;
   (iv) Decreasing or minimizing the percentage and number of T cells with differentiated phenotype (CCR7–) in the product;
   (v) Decreasing or minimizing the percentage and number of IFN gamma producing cells in the product or during manufacturing (e.g., using cell sorting);
   (vi) Including at least $20\times10^6$ T cells with naïve phenotype in the product;
   (vii) Including at least $100\times10^6$ CD8 T cells in the product; and/or
   (viii) Including at least $15\times10^6$ CD8 T cells of naïve phenotype in the product;
   wherein the product is an immunotherapy infusion product and the various baseline T cell phenotypes comprise $T_{CM}$, central memory T cells (CD45RA– CCR7+); $T_{EFF}$, effector T cells (CD45RA+CCR7–); $T_{EM}$, effector memory T cells (CD45RA–CCR7–); and/or $T_N$, naïve-like T cells (CD45RA+CCR7+);
   preferably, wherein the term T cells with naïve phenotype means T cells that are CD45RA+CCR7+ and comprises stem-like memory cells: wherein the improvement and/or decreased toxicity are measured against a method of manufacturing an immunotherapy product as in (i) that does not include the recited step(s) (ii) through (viii).

2. The method of claim 1, wherein:
   (i) increasing or maximizing the percentage of T cells with naïve phenotype (CD45RA+CCR7+) in the product increases product efficacy without increasing toxicity;
   (ii) increasing or maximizing the percentage of CD8+ T cells with naïve phenotype (CD45RA+ CCR7+) in the product increases product efficacy without increasing toxicity;
   (iii) decreasing or minimizing the percentage and number of T cells with differentiated phenotype (CCR7–) in the product improves safety profile;
   (iv) decreasing or minimizing the percentage and number of IFN gamma producing cells in the product improves safety profile;
   (v) including at least $20\times10^6$ T cells with naïve phenotype in the product improves efficacy without increasing toxicity;
   (vi) including at least $100\times10^6$ CD8 T cells in the product improves efficacy; and/or
   (vii) including at least $15\times10^6$ CD8 T cells of naïve phenotype in the product improves efficacy without increasing toxicity;
   wherein the product is an infusion bag for immunotherapy.

3. A method of treating a cancer in a subject in need thereof with an infusion product comprising engineered lymphocytes comprising:
   (i) measuring levels of one or more attributes in a population of lymphocytes from an apheresis product; and/or
   (ii) measuring levels of one or more attributes in a population of engineered lymphocytes (e.g., CAR T cells) during manufacturing of the final infusion product and/or in the final infusion product; and
   (iii) determining or predicting a subject's response to treatment with the engineered lymphocytes based on the measured levels of one or more attributes compared to a reference level; and, optionally,
   (iv) administering a therapeutically effective dose of the engineered lymphocytes to the subject, wherein the therapeutically effective dose is determined based on the levels of one or more attributes of the population of engineered lymphocytes in the infusion product and/or of the T cells in the apheresis product; optionally wherein one or more of the following apply to the method:
   (v) wherein the engineered lymphocytes are CAR-T lymphocytes;
   (vi) the T cell composition of the final infusion product is manipulated during its manufacturing to achieve pre-determined levels of engineered lymphocytes with select attributes in the infusion product;
   (vii) the one or more attributes is T cell fitness, including doubling time and T cell phenotype (e.g., the levels of specialized CAR T-cell subsets in the CAR T-cell population);
   (viii) wherein the T cell phenotype that is measured is that of the population of engineered lymphocytes in the final infusion product;
   (ix) the T cell phenotype that is measured is that of the population of engineered lymphocytes during manufacturing of the final infusion product, and the T cell phenotype of the final infusion product
   (x) the population of engineered lymphocytes (e.g., CART cells) is to be infused into the subject and the phenotype is determined by measuring the percentage of CD3 positive cells infused, the number of CD3 cells infused, the number of CD3 cells infused/ tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/ tumor burden; the percentage of CD4 positive cells infused, the number of CD4 positive cells infused, the number of CD4 positive cells infused/tumor burden; and/or the CD4:CD8 ratio in the cells infused, preferably wherein the term $T_N$ cells means T cells that are CD45RA+CCR7+ and comprises stem-like memory cells;

(xi) the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/tumor burden; and the number of CD4 positive cells infused/tumor burden associate positively with or are predictive of durable response to treatment;

(xii) the percentage of CD3 cells infused, the percentage of CD4 cells infused, and the number of CD4 cells infused associate negatively with, or are predictive of, no durable response;

(xiii) the frequency and proportion of $T_N$ (CD45RA+ CCR7+) and TEM CD8+ or CD4+ T cells (CD45RA−CCR7−) in the CAR T-cell infusion product associate with clinical efficacy, positively and negatively, respectively;

(xiv) the frequency and proportion of $T_N$ (CD45RA+ CCR7+) and TEM CD8+ or CD4+ T cells (CD45RA−CCR7−) in the engineered lymphocyte (CAR T cells) infusion product are manipulated during manufacturing of the infusion product to improve clinical efficacy;

(xv) the % of CD3 cells infused, the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/ tumor burden; and the number of CD4 positive cells infused/tumor burden associate positively with or are predictive of peak engineered lymphocyte (e.g., peak engineered lymphocyte (CAR T cells)) levels in the blood past administration of the infusion product;

(xvi) the percentage of CD4 cells infused and the number of CD4 cells infused associate negatively with, or are predictive of lower, peak engineered lymphocyte (e.g., peak engineered lymphocyte (CAR T cells)) levels past administration of the infusion product;

(xvii) the number and percentage of naïve-like CD8 positive T cells (e.g., CD8+CCR7+CD45RA+ T Cells) in the infusion product associates positively, or is predictive of, durable response whereas the number of effector memory CD4 positive T cells associates negatively with durable response to CAR T cell therapy;

(xviii) the attributes that are measured are attributes of the population of T cells in the apheresis product;

(xix) the attributes of the apheresis product are the proportion of effector memory T cells within total CD3+ T cells or CD4 and CD8 subsets, the number of CD27+CD28+ TN cells, and/or the proportion of T cells with CD25hi CD4 expression, preferably wherein the term $T_N$ cells means CD45RA+CCR7+ T cell;

(xx) the more juvenile the phenotype of the T cells (e.g., the higher the number of CD28+CD27+ $T_N$ cells) in the apheresis starting material the better (shorter) the doubling time of the engineered lymphocytes in the infusion product; and/or (xxi) the measured attribute is the doubling time of the population of engineered lymphocytes in the infusion product.

4. The method of claim 3, wherein the therapeutically effective dose is calculated and/or manipulated by calculating or manipulating the doubling time, phenotype, and other attributes of the cells in the infusion product used to prepare the therapeutically effective dose.

5. The method of any one of claims 3 and 4, wherein the attributes of the population of engineered lymphocyte (e.g., CAR T cells) in the product that are manipulated during manufacturing to improve subject response and/ or reduce therapeutic dose are selected from the following attributes: the doubling time, the percentage of CD3 positive cells infused, the number of CD3 cells infused, the number of CD3 cells infused/tumor burden; the percentage of $T_N$ cells infused, the number of $T_N$ cells infused, the number of $T_N$ cells infused/tumor burden; the percentage of CD8 positive cells infused, the number of CD8 positive cells infused, the number of CD8 positive cells infused/tumor burden; the percentage of CD4 positive cells infused, the number of CD4 positive cells infused, the number of CD4 positive cells infused/tumor burden; CD4:CD8 ratio in the cells infused, the frequency and proportion of $T_N$ and $T_{EM}$ CD8+ or CD4+ T cells, and/or the number of percentage of naïve-like T cells.

6. A method of increasing the efficacy and/or reducing the toxicity of CAR-T or TCR-T cell immunotherapy in a subject in need thereof comprising:

(i) Reducing myeloid cell activity in the subject prior to CAR T-cell or TCR-T cell immunotherapy;

(ii) Reducing the MCP-1 and/or IL-6 activity prior to, or early after CAR T-cell or TCR-T cell administration;

(iii) Decreasing the subject's tumor burden prior to CAR T-cell or TCR-T cell immunotherapy;

(iv) Decreasing the subject's systemic inflammatory state prior to CAR T-cell or TCR-T cell immunotherapy;

(v) Reducing the activity of activated T cells in the subject/T-cell product prior to CAR T-cell or TCR-T cell immunotherapy;

(vi) Increasing the dosage of the CAR T cell immunotherapy in a manner commensurate with the subject's pre-treatment tumor burden; and/or (vii) Re-dosing subjects with high tumor burden; whereby the efficacy of CAR T-cell or TCR-T cell immunotherapy is increased and/or toxicity is decreased.

7. The method of claim 6, wherein the decrease of the subject's tumor burden comprises administration of bridging therapy and/or the reducing the activity of activated T cells in the subject/T-cell product prior to CAR T-cell or TCR-T cell therapy is accomplished by a) separation/removal of differentiated cells (effector memory and/or effector cells in the T cell product infusion bag; b) enriching the product for juvenile T cells (CCR7+); c) removing or diminishing the percentage and number of differentiated T cells in the T cell product infusion bag through separation techniques; and/or d) treating the product T cells during or after manufacturing process with pharmacological agents or biological response modifiers that would reduce excessive T cell activity (e.g., JAK/STAT inhibitors); optionally, wherein the bridging therapy comprises one or more of CHOP, R-CHOP (rituximab, cyclophosphamide, doxorubicin, vincristine, and prednisolone), G-CHOP (obinutuzumab, cyclophosphamide, doxorubicin, vincristine, and prednisolone), corticosteroids, bendamustine, platinum compounds, anthracyclines, venetoclax, zanubrutinib, phosphoinositide 3-kinase (PI3K) inhibitors, and inhibitors of the PI3K/Akt/mTOR pathway 8. The method of claim 7, wherein the bridging therapy comprises one or more of acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denileukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin diftitox, pembrolizumab, plerixafor, polatuzumab vedotin-piiq, mogamulizumab-kpc, corticosteroids, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

9. The method of any one of claims 3 through 7, further comprising administering anti-inflammatory treatment to the subject prior to CAR T-cell immunotherapy.

10. The method of any one of claims 6 through 9, wherein reducing myeloid cell activity, MCP-1, and/or IL-6 activity comprises administering to the subject a monoclonal antibody against MCP-1, CRP, IL-6, IL-1, CSF1R, GM-CSF and/or a small molecule.

11. A method of preparing a personalized immunotherapy product for infusion to a subject in need thereof comprising:
(i) Preparing a population of lymphocytes comprising CD8+ T cells and naïve T cells, optionally wherein the population of lymphocytes from which the T cell product is prepared is the product of leukapheresis of Peripheral Blood Mononuclear Cells (PBMCs);
(ii) Determining the subject's tumor burden; and
(iii) Increasing the cumulative cell dose to be infused to the subject based on the measured tumor burden to increase the ratio of infused CD8+ T cells/tumor burden; and/or
(iv) Increasing the cumulative cell dose to be infused based on the measured tumor burden to increase the ratio of infused naïve T cells/tumor burden;
Wherein the method enhances the efficacy of the immunotherapy product;
preferably, wherein the term naïve T cells means T cells that are CD45RA+CCR7+ and comprises stem-like memory cells; wherein the increase and the enhancement are measured against the cumulative cell dose that would have been administered without the adjustment to tumor burden.

12. A T cell immunotherapy product produced according to any one of the methods of claims 1, 2, and 11.

13. A method of selecting a donor for allogeneic T cell immunotherapy comprising:
(i) Collecting a sample of T lymphocytes from a subject; optionally wherein the sample of T lymphocytes is prepared by leukapheresis of PBMCs from the subject;
(ii) Selecting the subject to be a donor for allogeneic T cell immunotherapy based on one or more of the following:
a. the percentage of T cells with naïve phenotype (CD45RA+ CCR7+) in the sample;
b. the percentage of CD8+ T cells with naïve phenotype (CD45RA+ CCR7+) in the sample;
c. the percentage and number of T cells with differentiated phenotype (CCR7−) in the sample; and
d. the percentage and number of IFNgamma producing cells in the sample; and, optionally,
(iii) preparing an allogeneic T cell product from the selected subject;
(iv) administering the product to a subject in need thereof, preferably, wherein the term T cells with naïve phenotype means T cells that are CD45RA+ CCR7+ and comprises stem-like memory cells.

14. A method of increasing the efficacy and/or reducing the toxicity of CAR-T cell immunotherapy in a subject in need thereof comprising:
(i) Identifying a subject positive for marker(s) of toxicity in response to CAR T-cell immunotherapy and taking measures to reduce those markers; and/or
(ii) Reducing IL-15 elevation post-conditioning and pre-CAR T cell immunotherapy in the subject; and, optionally, administering immunotherapy to the subject.

15. The method of claim 14, wherein the positive marker of toxicity is high tumor burden and/or increased pre-treatment levels of inflammatory markers.

16. The method of claim 15, wherein the inflammatory markers are selected from IL6, CRP, and ferritin.

17. A method of predicting toxicity in response to CAR T-cell therapy in a subject in need thereof comprising:
(i) measuring one or more subject's attributes selected from:
a. pre-treatment tumor burden;
b. pre-treatment blood levels of LDH, ferritin, and/or IL-6;
c. blood levels of IL-15 post-conditioning therapy and pre-CAR T cell treatment;
d. blood levels of MCP-1, CRP, IL-6, IFNgamma, and/or CXCL10 one day post CAR T cell treatment; and/or
e. changes in one or more of (a) through (d) between pre and post-conditioning; day 1 and day 0; day 0 and baseline, and/or day 1 and baseline;
(ii) predicting toxicity in response to CAR T cell therapy based on one or more of those measurements; and, optionally,
(iii) administering to the subject one or more agents to prevent or minimize toxicity;
wherein (i)(a) through 1(e) associate positively with toxicity; and, optionally, administering immunotherapy to the subject.

18. A method of predicting Grade ≥3 NE in response to CAR T cell treatment in a subject in need thereof comprising:
    (i) measuring baseline serum LDH and/or day 0 serum IL-15 to obtain a value;
    (ii) predicting Grade ≥3 NE in response to CAR T cell treatment based on the value; and, optionally,
    (iii) administering to the subject one or more agents to prevent or minimize toxicity; wherein baseline LDH and/or day 0 IL-15 associate positively with Grade ≥3 NE in response to CAR T cell treatment; and, optionally, administering immunotherapy to the subject.

19. A method of predicting Grade ≥3 CRS in response to CAR T cell treatment in a subject in need thereof comprising:
    (i) measuring baseline serum LDH and/or baseline serum IL-6 to obtain a value;
    (ii) predicting Grade ≥3 CRS in response to CAR T cell treatment based on the value; and, optionally,
    (iii) administering to the subject one or more agents to prevent or minimize toxicity; wherein baseline LDH and/or baseline IL-6 associate positively with Grade ≥3 CRS in response to CAR T cell treatment.

20. A method of predicting Grade 3+ neurotoxicity in response to CAR T cell treatment in a subject in need thereof comprising:
    (i) measuring day 1/day 0 serum IFNgamma fold change to obtain a value;
    (ii) predicting Grade 3+ neurotoxicity in response to CAR T cell treatment based on the value; and, optionally,
    (iii) administering to the subject one or more agents to prevent or minimize toxicity; optionally, wherein day 1/day 0 serum IFNgamma fold change greater than about 25 results in grade 3+ neurotoxicity; and, optionally, administering immunotherapy to the subject.

21. The method of claim 20, wherein day 1/day 0 serum IFNgamma fold change greater than about 30, about 35, about 40, about 45, or about 50 results in grade 3+ neurotoxicity.

22. A method of predicting neurologic toxicity in response to CAR T cell treatment in a subject in need thereof comprising:
    (i) measuring pretreatment product T-cell IFNgamma production to obtain a value;
    (ii) predicting severe neurotoxicity and decreased efficacy in response to CAR T cell treatment based on the value; and, optionally,
    (iii) administering to the subject one or more agents to prevent or minimize toxicity; optionally, further comprising modulating the pretreatment product T-cell IFNgamma production level to improve the effectiveness and/or decrease the toxicity of the CAR T cell treatment; and, optionally, administering immunotherapy to the subject.

23. A method of predicting toxicity in response to CAR T cell treatment in a subject in need thereof comprising:
    (i) measuring the tumor burden, inflammatory status reflected by myeloid activation markers pre- and post-treatment, and/or treatment-related type-1 cytokines in the subject to obtain a level for each,
    (ii) predicting toxicity based on those levels; and, optionally,
    (iii) administering to the subject one or more agents to prevent or minimize toxicity; wherein high tumor burden, pronounced inflammatory status reflected by myeloid activation markers pre- and post-engineered lymphocyte (CAR T cells) infusion, and excess treatment-related type-1 cytokines associate positively with severe toxicity; and, optionally, administering immunotherapy to the subject.

24. A method of predicting toxicity in response to CAR T cell treatment in a subject in need thereof comprising:
    (i) measuring the peak CAR T cell level after treatment,
    (ii) predicting toxicity based on those levels; and, optionally,
    (iii) administering to the subject one or more agents to prevent or minimize toxicity, wherein the peak CAR T cell level associates positively with severe neurotoxicity; and, optionally, administering immunotherapy to the subject.

25. The method of any one of claims 14 through 24, further comprising administering to the subject one or more agents capable of reducing the adverse effects, optionally selected from agents that have a direct relation to or a direct effect on the measured attributes.

26. The method of anyone of claims 17 through 25, wherein the agent(s) is selected from tocilizumab (or another anti-IL6/IL6R agent/antagonist), a corticosteroid therapy, or an anti-seizure medicine for toxicity prophylaxis based on the measured levels of the one or more attributes, or combinations thereof; or
    from inhibitors of GM-CSF, CSF1, GM-CSFR, or CSF1R, anti-thymocyte globulin, lenzilumab, mavrilimumab, cytokines, and/or anti-inflammatory agents 27. The method of any one of claims 17 through 26, wherein "based on the value" or "based on the measured level" or "based on those measurements" of one or more attributes means by comparison to a known reference value for each attribute.

28. The method of any one of claims 17 through 27, wherein "based on the value" or "based on the measured level" or "based on those measurements" of one or more attributes means by determining in which known reference quartile does the value or measured level fit.

29. The method of claim 27 or 28, wherein the known reference quartiles are those shown in the respective figures selected from FIGS. 1 through 6; 9, 10, 12-19, 21, 22, 24-47, 50-53, 57-60, and 64-114.

30. A method of predicting efficacy in response to CAR T cell therapy in a subject in need thereof comprising:
    (i) Measuring one or more subject and T cell product attributes selected from:
        a. Tumor burden, which associates negatively with efficacy;
        b. Dose of CD8+ T cells administered or to be administered to the subject (e.g., the number of infused CD8 T cells), which associates positively with efficacy;
        c. Dose of naïve T cells (CCR7+ CD45RA+) administered or to be administered to the subject, which associates positively with efficacy;
        d. Peak CAR levels in the blood after CAR T cell therapy, which associates positively with efficacy; and/or
        e. Level of inflammatory markers produced in co-culture or at peak during infusion;
    (ii) Predicting treatment efficacy based on one or more of those measurements, preferably wherein the term naïve T cells means CCR7+CD45RA+ T cells and comprises stem-like memory cells; and, optionally, administering immunotherapy to the subject.

31. The method of claim 30, wherein "based on those measurements" of one or more attributes means by comparison to a known reference value for each attribute.

32. The method of claim 30, wherein "based on those measurements" of one or more attributes means by determining in which known reference quartile does the value or measure level fit.

33. The method of claim 3-32, wherein the known reference values and quartiles are those shown in the respective figures selected from FIGS. 1 through 6; 9, 10, 12-19, 21, 22, 24-47, 50-53, 57-60, and 64-114.

34. A method of predicting response to CAR T cell treatment in a subject in need thereof comprising:
   (i) measuring the rate of in vivo CAR T cell expansion relatively to pretreatment tumor burden, the intrinsic T-cell fitness of the product, the dose of specialized T cell subsets, and/or host systemic inflammation (e.g., levels of inflammatory markers) of the subject to obtain a value;
   (ii) predicting response to CAR T cell treatment based on the value; wherein the rate of in vivo CAR T cell expansion relatively to pretreatment tumor burden, intrinsic product T-cell fitness (optionally relatively to pretreatment tumor burden) and the dose of specialized T cell subsets associate positively with durable response; and/or; wherein pre-treatment and post-treatment subject systemic inflammation associates negatively with durable response; and/or wherein suboptimal product T-cell fitness is associated with primary treatment resistance, and limited numbers of naïve-like or CD8+ T cells in proportion to tumor burden are associated with a failure to achieve durable response; and, optionally, administering immunotherapy to the subject.

35. A method of predicting response to engineered lymphocytes (e.g., CAR T cell) treatment comprising:
   (i) measuring the peak engineered lymphocyte (e.g., CAR T-cell) levels in the blood post treatment with an engineered lymphocyte (e.g., CAR T-cell) infusion product and normalize them to pretreatment tumor burden to obtain a value;
   (ii) predicting response to the engineered lymphocyte cell (e.g., CAR T-cell) treatment based on the value, wherein the peak engineered lymphocyte (e.g., CAR T cells) levels in the blood post treatment normalized to pretreatment tumor burden associate positively with durable response; and, optionally, administering immunotherapy to the subject.

36. A method of predicting peak engineered lymphocyte levels in the blood after administration of an engineered lymphocyte infusion product to a subject comprising:
   (i) measuring the number of TN cells in the infusion product, the baseline doubling time of the engineered lymphocytes in the infusion product, coculture IFN-γ, baseline LDH, baseline CRP, and/or the baseline ferritin level in the blood of the subject to obtain a value;
   (ii) predicting peak engineered lymphocyte levels in the blood based on the value; and/or
   (iii) preparing an effective dose of engineered lymphocytes based on the value; and/or;
   (iv) administering an effective dose of engineered lymphocytes based on the value; wherein the peak engineered lymphocyte levels in the blood associate positively with response; wherein the number of $T_N$ cells in the infusion product and the level of baseline ferritin level associate positively with the peak engineered lymphocyte (e.g., CAR T cells) levels; wherein the baseline doubling time of the engineered lymphocytes in the infusion product associates negatively with the peak engineered lymphocytes levels; wherein the number of $T_N$ cells in the infusion product associates positively with the peak engineered lymphocytes/tumor burden and/or wherein the baseline doubling time, baseline ferritin, coculture IFN-γ, baseline LDH, and baseline CRP associate negatively with peak engineered lymphocytes/tumor burden; and, optionally, administering immunotherapy to the subject.

37. A method of predicting response to engineered lymphocyte (e.g., CAR T cell) treatment comprising:
   (i) measuring the level of IFN-γ (e.g., coculture IFN-γ) of a population of engineered lymphocytes (e.g., CAR T cells) in an infusion product to obtain a value;
   (ii) predicting response to the engineered lymphocyte (e.g., CAR T cells) treatment based on the value;
   (iii) wherein the level of coculture IFN-γ associates negatively with the peak engineered lymphocytes levels, and the peak engineered lymphocyte levels associates positively with response; and, optionally, administering immunotherapy to the subject.

38. A method of predicting response to CAR T cell treatment in subject comprising:
   (i) measuring the levels of type-1 cytokines in the blood of the subject post-treatment to obtain a value;
   (ii) predicting response to CAR T cell treatment based on the value;
   (iii) wherein the level of type-1 cytokines in the blood post treatment associates negatively with durable efficacy; and, optionally, administering immunotherapy to the subject.

39. A method of predicting response to CAR T cell treatment in subject comprising:
   (i) measuring baseline tumor burden, baseline IL6, baseline CRP, baseline LDH, and coculture IFN-γ to obtain a value;
   (ii) predicting response to CAR T cell treatment based on the value;
   (iii) wherein the baseline tumor burden, baseline IL6, baseline CRP, baseline LDH, and coculture IFN-γ associate negatively with durable response;
   (iv) wherein the higher the tumor burden, the lower the response rate;
   (v) wherein the higher the tumor burden, the lower the probability of durable response; and, optionally, administering immunotherapy to the subject.

40. A method of treating a cancer with engineered lymphocytes (e.g., CAR T cells) in a subject in need thereof comprising:
   (i) measuring levels of one or more pretreatment attributes of the subject,
   (ii) determining or predicting a subject's response to treatment with engineered lymphocytes based on the measured levels of one or more attributes compared to a reference level; and, optionally,
   (iii) administering a therapeutically effective dose of the engineered lymphocytes to the subject, wherein the therapeutically effective dose is determined based on the level of one or more pre-treatment attributes of the subject; optionally, wherein one or
more of the following applies:
(iv) the pretreatment attributes are reflective of or are
markers of the subject's systemic inflammation;
(v) the pretreatment attributes show pronounced
inflammatory status reflected by the levels of
myeloid activation markers (e.g., IL6, ferritin,
CCL2) in the serum of the subject;
(vi) the pretreatment attributes are selected from base-
line tumor burden, baseline IL-6, baseline CRP,
baseline LDH, baseline ferritin, disease stage, Day 0
IL-15, Day 0 IFN-γ, baseline weight, baseline CCL2,
wherein Day 0 is the day of administration of the
engineered lymphocytes; and/or
(vii) wherein baseline levels are the last values mea-
sured prior to conditioning therapy.
41. A method of predicting efficacy in response to CART
cell therapy in a subject having a tumor in need thereof
comprising measuring the baseline (preconditioning)
levels of CD3D, CD69, IRF1, CXCL9, CXCL10,
STAT1, VEGFA, PDCD1, and/or CD274 genes in a
sample of the subject's tumor, predicting the tumor's
response based on one or more of those measurements;
and, optionally, administering a therapeutically effec-
tive amount of CAR T cells to the subject based on the
measurements; wherein the expression levels of the
CD3D, CD69, IRF1, CXCL9, CXCL10, STAT1 genes
correlates positively with objective response (CR/PR)
and the expression levels of the VEGFA, PDCD1,
and/or CD274 genes correlates negatively with objec-
tive response (CR/PR); and, optionally, administering a
therapeutically effective amount of CAR T cells to the
subject based on the measurements.
42. A method of predicting efficacy in response to CAR T
cell therapy in a subject having a tumor in need thereof
comprising measuring the baseline (preconditioning)
levels of GZMA, CD69, IRF1, CXCL9, CXCL10,
STAT1, and/or VEGFA genes in a sample of the sub-
ject's tumor and predicting the tumor's best response
based on one or more of those measurements; and,
optionally, administering a therapeutically effective
amount of CAR T cells to the subject based on the
measurements; wherein the expression levels of the
GZMA, CD69, IRF1, CXCL9, CXCL10, STAT1,
genes correlates positively with best response and the
expression levels of the VEGFA gene correlates nega-
tively with best response; and, optionally, administer-
ing a therapeutically effective amount of CAR T cells
to the subject based on the measurements.
43. A method of predicting adverse events in response to
CAR T cell therapy in a subject in need thereof
comprising measuring the baseline (preconditioning)
levels of CD8A, PRF1, IRF1, CCL5, CXCL9, CCL2,
STAT1, STAT4, VEGFA, CTLA4, PDCD1, and/or
CD274 in a sample of the subject's tumor and predict-
ing the grade of neurologic events based on one or more
of those measurements; and, optionally, administering
a therapeutically effective amount of CAR T cells to the
subject based on the measurements; wherein the lower
the expression levels of at least one of those genes, the
worse the grade of neurologic events; and, optionally,
administering a therapeutically effective amount of
CAR T cells to the subject based on the measurements.
44. A method of predicting efficacy in response to CAR T
cell therapy in a subject having a tumor in need thereof
comprising measuring the baseline (preconditioning)
profile of pretreatment tumor immune infiltrates in a sample of the subject's tumor and predicting the sub-
ject's response to the treatment based on one or more
of those measurements; and, optionally, administering
a therapeutically effective amount of CAR T cells to the
subject based on the measurements wherein if the
subject's tumor measurements fall within cluster A
defined by pre-treatment infiltration with immune cells
comprising activated CD8 T cells the subject will fall
within those having a complete response whereas if the
measurements fall within cluster B, the subject will fall
among those having progressive disease.
45. A method of predicting neurotoxicity in response to
CAR T cell therapy in a subject in need thereof
comprising measuring the baseline (preconditioning)
density of Treg cells and polymorphonuclear myeloid-
derived suppressor cells (PMN-MDSCs) in a sample of
the subject's tumor and predicting the treatment's neu-
rotoxicity based on one or more of those measure-
ments; and, optionally, administering a therapeutically
effective amount of CAR T cells and anti-neurotoxicity
agents to the subject based on the measurements;
wherein the lower the density of Treg and PMN-MDSC
cells, the worse the neurotoxicity (Grade ≥3).
46. A method of predicting efficacy in response to CAR T
cell treatment in a subject having a tumor in need
thereof comprising:
(i) measuring pretreatment density of Treg (CD3+
CD8−FoxP3+) in a sample of the subject's tumor,
wherein said pretreatment density correlates posi-
tively with tumor microenvironment features that are
desirable for efficacy, including CD8+PD-1+ T cell
density; and, optionally, administering a therapeuti-
cally effective amount of CAR T cells to the subject
based on the measurements;
(ii) measuring the baseline (preconditioning) density of
CD3+, CD8+, and activated CD8+ T cells in a
sample of the subject's tumor and predicting the
treatment efficacy based on that measurements; and,
optionally, administering a therapeutically effective
amount of CAR T cells to the subject based on the
measurements, wherein the levels of CD3+, CD8+,
and activated CD8+ T cells associate positively with
response to treatment, preferably wherein activated
CD8+ T cells have expression of one checkpoint
gene selected from PD-1 and LAG-3;
(iii) measuring the baseline (preconditioning) tumor
burden and/or tumor-infiltrating T cell density in a
sample of the subject's tumor and predicting the
treatment efficacy based on those measurements;
and, optionally, administering a therapeutically
effective amount of CAR T cells to the subject based
on the measurements; wherein low tumor burden and
high tumor-infiltrating T cell density alone and com-
bined correlate positively with complete response:
(iv) measuring pretreatment density of activated CD8+
PD-1+LAG-3+/−TIM-3− T cells in a sample of the
subject's tumor and predicting efficacy based on that
measurement, wherein said pretreatment density cor-
relates positively with clinical efficacy; and, option-
ally, administering a therapeutically effective amount
of CAR T cells to the subject based on the measure-
ments;
(v) measuring tumor burden and/or peak CAR T levels,
wherein the higher the level(s), the lower the prob-
ability of durable response; and/or
(vi) measuring, early post treatment (within 1-2 weeks),
the increase of T cell related genes (e.g., CD8α, immune effector molecules (granzyme A), key T cell growth factors and chemokines (IL-15), interferon (IFN)□-regulated immune checkpoints (PD-L1, B7-H3, CTLA-4), and myeloid-related genes and corresponding chemokines (CD14, CCL2)) in conjunction with the decrease of B cell related genes (e.g., including CD19, CD20, CD22, and CD75 (ST6GAL1), B cell transcriptional master switch PAX5, and transcriptional coactivator POU2AF1), in a sample of the subject's tumor and predicting CAR T cell efficacy based on the measurement; wherein a decrease in B cell related genes correlates positively with tumor response and an increase in T cell related genes correlates positively with tumor response; and, optionally, administering a therapeutically effective amount of CAR T cells to the subject based on the measurements 47. A method of predicting T cell gene expression and density as a surrogate for T cell involvement in CAR T cell treatment of a tumor in a subject in need thereof, which correlates positively with response in CAR T cell treatment of a tumor in a subject in need thereof, comprising:
   (i) measuring the baseline (preconditioning) levels of IL-7/IL-7R, IL-18, CCL5, CCR5, IL-15 and IL-21 and predicting T cell gene expression and density based on those measurements, wherein pretreatment expression in a sample of the subject's tumor of IL-7/IL-7R, IL-18, and CCL5 correlate with CD3δ, CD8□, CD4; CCR5 and IL-15 correlate with CD3δ, CD8□□ and IL-21 correlates with CD3δ; and, optionally, administering a therapeutically effective amount of CAR T cells to the subject based on the measurements;
   (ii) measuring tumor of CCL5 and CCR5 in a sample of the subject's tumor and predicting T cell gene expression and density based on the measurement, wherein pretreatment expression in a sample of the subject's tumor of CCL5 and CCR5 correlates positively with density of CD8+ and CD4+ T cells by IHC;
   (iii) and, optionally, administering a therapeutically effective amount of CAR T cells to the subject based on the measurements.

48. A method of predicting myeloid cell density in a tumor in a subject in need of CAR T cell treatment, comprising measuring tumor CCR5, IL-1R, STAT1, FPR2, and CXCL9 levels in a sample of the subject's tumor and predicting myeloid cell density based on the measurement, wherein pretreatment expression in a sample of the subject's tumor of CCR5, IL-1R, STAT1, FPR2, and CXCL9 correlates positively with myeloid cell density (CD11b+ and CD14+); and, optionally, administering a therapeutically effective amount of CAR T cells to the subject based on the measurements.

49. A method of predicting peak CAR T cell levels normalized to tumor burden after CAR T cell administration to a subject having a tumor in need thereof, comprising measuring pretreatment CD8+PD1+ T cell density in a sample of the subject's tumor and predicting CAR T cell levels normalized to tumor burden, wherein pretreatment CD8+PD-1+ T cell density associates positively with CAR T cell levels; and, optionally, administering a therapeutically effective amount of CAR T cells to the subject based on the measurements.

50. A method of predicting neurotoxicity in response to CAR T cell treatment in a subject having a tumor in need thereof comprising measuring pretreatment density of CD3+CD8−FoxP3+ (Treg) cells and/or CCL22 gene expression in a sample of the subject's tumor and predicting neurotoxicity based on that measurement, wherein density and gene expression levels associate positively with low-grade neurotoxicity and high activated T cell density; and, optionally, administering a therapeutically effective amount of CAR T cells and an anti-neurotoxicity treatment/agent to the subject based on the measurements.

51. A method of decreasing primary resistance to CAR T cell treatment in a subject having a tumor in need thereof, comprising administering to the subject a therapeutically effective amount of one or more of the following:
   (i) an agent that modulates the methylation state of the subject's tumor, preferably DNA demethylating inhibitors (DDMTi) 5-aza-2'-deoxycytidine (decitabine) and 5-azacytidine or other cytosine analogs;
   (ii) an agent that modulates the acetylation state of the subject's tumor, preferably HDAC inhibitors;
   (iii) a checkpoint blocking agent, preferably one or more agents that block immune checkpoint receptors on the surface of T cells, such as cytotoxic T lymphocyte antigen 4 (CTLA-4), lymphocyte activation gene-3 (LAG-3), T-cell immunoglobulin mucin domain 3 (TIM-3), B- and T-lymphocyte attenuator (BTLA), T-cell immunoglobulin and T-cell immunoreceptor tyrosine-based inhibitory motif (ITIM) domain, and programmed cell death 1 (PD-1); and/or
   (iv) an agonist of 41BB, OX40, and/or TLR.
   and, optionally, administering a therapeutically effective amount of CAR T cells to the subject.

52. A method of preparing a CAR T cell product that decreases or overcomes primary resistance to CAR T cell treatment comprising improving the CAR T cells by co-expressing gamma chain receptor cytokines under constitutive or inducible promoters in the CAR T cells; reprogramming CAR T cells to overcome detrimental tumor microenvironments (e.g., engineering to express gamma chain receptor cytokines) optimizing T cell manufacturing to help CAR T cells overcome detrimental tumor microenvironments (growing T cells in the presence of gamma chain cytokines (e.g., IL-2, IL-4, IL-7, IL-9, IL-15, and IL-21).

53. A method of increasing the efficacy CAR-T cell immunotherapy in a subject in need thereof comprising:
   (i) Modulating the subject's tumor microenvironment prior to CAR T cell treatment by one or more of:
      (d) optimization of bridging therapy to modulate the tumor microenvironment to a more favorable immune permissive state, preferably by administering bridging therapy with IMIDs (e.g., lenoalidomide) and/or local radiation;
      (e) optimization of bridging therapy to diminish tumor burden prior to CAR T cell treatment administration, preferably by administering bridging therapy with R-CHOP, bendamustine, alkylating agents, and/or platinum based agents;
      (f) optimization of conditioning treatment to modulate the tumor microenvironment to a more favorable immune permissive state, preferably addition of local irradiation to cyclophosphamide/fludarabine conditioning and/or using platinum-based agents as conditioning agents; and/or (ii) Co-administering biological response modifiers together or post-CAR T cell administration to enable CAR T cell activity, preferably gamma chain cytokines (e.g., IL-15 and/or checkpoint blocking agents (e.g. anti-CTLA-4);

and, optionally, administering a therapeutically effective amount of CAR T cells to the subject based on the measurements.

54. A method of treating relapsed/refractory indolent Non-Hodgkin Lymphoma (R/R NHL) in a subject in need thereof comprising administering to the subject a therapeutically effective amount of CAR T cells as a retreatment, wherein the subject has previously received a first treatment with CAR T cells.

55. The method of claim 54, wherein the first treatment with CART cells was administered as a first line therapy or a second line therapy, optionally wherein the lymphoma is R/R follicular lymphoma (FL) or marginal zone lymphoma (MZL) and optionally wherein the previous prior lines of therapy included anti-CD20 monoclonal antibody combined with an alkylating agent.

56. The method of claim 54, wherein the key retreatment eligibility criteria include response of a CR or PR at the month 3 disease assessment with subsequent progression; no evidence of CD19 loss in progression biopsy by local review; and/or no Grade 4 CRS or neurologic events, or life-threatening toxicities with the first treatment with CAR T cells.

57. A method of treating NHL (e.g., large B cell lymphoma (LBCL)) in a subject in need thereof comprising administering to the subject a therapeutically effective amount of CAR T cells, wherein the CAR T cells are administered as a first line therapy.

58. The method of claim 57, wherein one of more of the following applies:

(i) the LBCL is high risk/high grade LBCL with MYC and BCL2 and/or BCL6 translocations or DLBCL with IPI score ≥3 any time before enrollment;

(ii) the first line therapy comprises both CAR T cell therapy in combination with an anti-CD20 monoclonal antibody and anthracycline-containing regimen; and/or (iii) the method further comprises bridging therapy administered after leukapheresis and completed prior to initiating conditioning chemotherapy).

59. A method of predicting adverse events wherein the method comprises:

(i) predicting NE in response to the treatment of any one of claims 3-11 and 13-58 comprising measuring the peak serum level of IL-6, IL-5, IFN-γ, IL-8, GM-CSF, CCL26, Ferritin, IL-17, IL-10, CCL3, TNF-α, and/or Granzyme B, wherein the higher the peak serum level of one or more of these cytokines the higher the probability of Grade ≥3 NEs; and/or (ii) predicting CRS in response to the treatment of any one of claims 3-11 and 13-58 comprising measuring peak serum levels of IL-6, IL-8, VCAM-1, GM-CSF, IL-17, ICAM-1, IL-4, IL-2, IL-12 P70, CCL17, CCL26, IL-5, and/or peak CAR T cell levels, wherein the higher the peak serum level of one or more of these cytokines or CAR T cells the higher the probability of Grade ≥3 CRS;

and, optionally, administering a therapeutically effective amount of CAR T cells to the subject.

60. A method of reducing NE and/or CRS in response to the treatment of any one of claims any one of claims 3-11 and 13-59, comprising administering to the subject an agent that decreases the serum level and/or activity of any one or more of the cytokines in claims 37-43 and 47-50, after CAR T cell treatment and/or prophylactically.

61. The method of any one of claims 3-11 and 13-60, wherein adverse events are managed by protocol A, protocol B, protocol C, or a combination thereof 62. A method of treating cancer in a subject in need thereof comprising:

(i) administering a T cell product produced according to any one of the methods of claims any one of claims 3-11 and 13-61 as either first line of treatment or a later line of treatment, wherein the T cell product is administered once or more than once; optionally, wherein the T cell product is axicabtagene ciloleucel or brexucabtagene autoleucel;

(ii) using a treatment protocol and/or adverse event management protocol as defined for cohorts 1, 2, 3, 4, 5, or 6, as defined in the Examples section;

(iii) wherein the cancer is NHL; advanced-stage indolent NHL (iNHL), including follicular lymphoma (FL) (optionally, grades 1-3a) and marginal zone lymphoma (MZL) (optionally, R/R after after ≥2 lines of therapy (including an anti-CD20 mAb plus an alkylating agent), and ECOG 0-1); LBCL who relapsed after ≥2 systemic lines of therapy or are chemorefractory—defined as i) a best response of progressive disease (PD) or stable disease (SD) to ≥4 cycles of first-line systemic therapy (SD duration ≤6 months); or ii) a best response of PD or SD after ≥2 cycles of the most recent second-or-later line of systemic therapy; high-risk LBCL: i) double- or triple-hit lymphoma by fluorescent in situ hybridization per investigator or LBCL with International Prognostic Index (IPI) score ≥3; and ii) positive interim positron emission tomography (PET) per Lugano Classification (Deauville criteria [DC] 4 or 5) after 2 cycles of an anti-CD20 monoclonal antibody and anthracycline containing regimen; Mantle Cell Lymphoma (MCL) with documentation of either cyclin D1 overexpression or presence of t(11; 14), optionally, relapsed/refractory to 1-5 prior regimens for MCL, also optionally wherein prior therapy having included anthracycline or bendamustine-containing chemotherapy, an anti-CD20 monoclonal antibody, and ibrutinib or acalabrutinib.

63. The method of any one of claims 3-11 and 13-60 and 62, wherein toxicity/adverse events is/are managed or reduced by one or more of the following:

(i) administration of a steroid and/or an anti-IL6R antibody;

(ii) (iv) one of the two protocols of FIG. 46;

(iii) one or more dosage regimens in Table 12;

(iv) levetiracetam is administered for prophylaxis and at the onset of grade ≥2 neurologic toxicities, if neurologic events occur after the discontinuation of prophylactic levetiracetam and/or levetiracetam is tapered and discontinued if the patient does not experience any grade ≥2 neurologic toxicities;

(v) levetiracetam is administered at 750 mg orally or intravenous twice daily, starting on day 0 of the treatment with engineered lymphocytes and/or at the onset of grade ≥2 neurologic toxicities;

(vi) a method as described in FIG. 56;

(vii) patients receive levetiracetam (750 mg oral or intravenous twice daily) starting on day 0 of administration of T cell therapy; at the onset of grade ≥2 neurologic events, levetiracetam dose is increased to 1000 mg twice daily; if a patient did not experience any grade ≥2 neurologic event, levetiracetam is tapered and discontinued as clinically indicated; patients also receive tocilizumab (8 mg/kg IV over 1 hour [not to exceed 800 mg]) on day 2; further tocilizumab (±corticosteroids) may be recommended at the onset of grade 2 CRS in patients with comorbidities or older age, or otherwise in case of grade ≥3 CRS; for patients experiencing grade ≥2 neurologic events, tocilizumab is initiated, and corticosteroids are added for patients with comorbidities or older age, or if there is any occurrence of a grade ≥3 neurologic event with worsening symptoms despite tocilizumab use;

(viii) patients receive dexamethasone 10 mg PO on Days 0 (prior to T cell therapy infusion), 1, and 2; steroids are also administered starting at Grade 1 NE, and for Grade 1 CRS when no improvement is observed after 3 days of supportive care; tocilizumab is also administered for Grade ≥1 CRS if no improvement is observed after 24 hours of supportive care;

(ix) patients received tocilizumab (8 mg/kg IV over 1 hour [not to exceed 800 mg]) on day 2 of immunotherapy (e.g., CAR T cells), and, optionally, tocilizumab (±corticosteroids) is administered at the onset of grade 2 CRS in patients with comorbidities or older age, or otherwise in case of grade ≥3 CRS; and/or patients experiencing grade ≥2 neurologic events, tocilizumab is initiated, and corticosteroids are added for patients with comorbidities or older age, or if there was any occurrence of a grade ≥3 neurologic event with worsening symptoms despite tocilizumab use; and/or (x) administration of an antibody that depletes and/or neutralizes GM-CSF, preferably wherein the antibody is lenzilumab (optionally, wherein patients receive lymphodepleting chemotherapy on Days −3 to −5 followed by Day 0 administration of lenzilumab (e.g., a single infusion of 600 mg (over 1 h) or 1800 mg (over 2 h)) and, 6 hours later, a single infusion of immunotherapy (e.g., target dose, 2×106 CAR T cells/kg).

64. The method of any one of claims 1 through 63, wherein the cancer is selected from a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

65. The method of any one of claims 1 through 64, wherein the treatment or therapy is any immunotherapy (e.g., T cells, non-T cells, TCR-based therapies, CAR-based therapies, bispecific T-cell engagers (BiTEs), and/or immune checkpoint blockade) and not just CAR T− cells 66. The method of any one of claims 1 through 65, wherein the treatment is CAR T or TCR T cell treatment.

67. The method of claim 66, wherein the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

68. The method of claim 67, wherein the antigen is CD19 or CCL-1.

69. The method of anyone of claims 1 through 68, wherein the cancer is a NHL (e.g., Relapsed/Refractory Large B-cell Lymphoma (R/R LBCL), MCL, iNHL, FL, MZL) or a leukemia.

70. The method of any one of claims 1 through 69, wherein the T cells, CART cells, or immunotherapy are selected from axicabtagene ciloleucel, brexucabtagene autoleucel, tisagenlecleucel, lisocabtagene maraleucel, and bb2121.

BRIEF DESCRIPTION OF THE DRAWINGS

FIGS. 1A-1P. CAR T cell expansion commensurate with baseline tumor burden associates with durable responses after anti-CD19 CART cell treatment. FIG. 1A-FIG. 1F, analysis of CAR T cell expansion by response status. FIG. 1G and FIG. 1H, response (FIG. 1G) and peak CAR T-cell levels (FIG. 1H) by quartiles of tumor burden. FIG. 1I, scatter plot of baseline tumor burden and peak CAR T-cell levels. FIG. 1J and FIG. 1K, analysis of peak CAR T-cell levels normalized to tumor burden by response status. FIG. 1L and FIG. 1M, response by quartiles of peak CAR T cell levels (FIG. 1L) or peak CAR T-cell levels normalized to tumor burden (FIG. 1M). FIG. 1N-FIG. 1P, logistic regression analysis of evaluating the association of durable response with peak CAR T-cell levels (FIG. 1N), baseline tumor burden (FIG. 1O), and peak CAR T-cell levels normalized to tumor burden (FIG. 1P). Line graphs (FIG. 1G, FIG. 1L-FIG. 1M) and bar graphs (FIG. 1H) show medians per quartile for variables as indicated. P values were calculated using Kruskal-Wallis and Dunn's tests for all box plots (FIG. 1A-FIG. 1F, FIG. 1J-FIG. 1K) and logistic regression for line graphs and probability curves (FIG. 1G, FIG. 1L, FIG. 1M and FIG. 1N-FIG. 1P). Spearman's correlation was used to calculate r and P values in FIG. 1H. CAR, chimeric antigen receptor; CR, complete response; NR, no response; PR partial response; Q, quartile. For this figure and other figures, see FIG. 21A through FIG. 21E for Quartile distributions.

FIG. 2A, Heat map showing association between pretreatment inflammatory markers and other laboratory analytes. FIG. 2B-FIG. 2G, peak CAR T-cell expansion and peak CAR T-cell expansion normalized to tumor burden (FIG. 2B-FIG. 2D) and response (FIG. 2E-FIG. 2G) by quartile analyses of pro-inflammatory and myeloid activation markers. Heat map (FIG. 2A) depicts the positive (blue) or negative (red) association between key parameters measured prior conditioning (at baseline). Size of circle represents the amplitude of the association and the numerical values correspond to the regression coefficient r. Bar graphs (FIG. 2B-FIG. 2D) and line graphs (FIG. 2E-FIG. 2G) show medians per quartile. Spearman's correlation was used to calculate r and P values for all bar graphs (FIG. 2B-FIG. 2D), and P values were calculated using logistic regression for line graphs (FIG. 2E-FIG. 2G). CAR, chimeric antigen receptor; CRP, C-reactive protein; IL, interleukin; LDH, lactate dehydrogenase; CCL2, chemokine (C-C motif) ligand 2; Q, quartile.

FIGS. 3A-3H. Higher expansion rate of product T cells measured preinfusion (doubling time) is associated with greater in vivo CAR T-cell levels and efficacy (FIG. 3A-FIG. 3C) and correlates with T cell phenotype (FIG. 3D-FIG. 3H). Line (FIG. 3A) and bar graphs (FIG. 3B-FIG. 3C) show medians per quartile. P values were calculated using logistic regression for the line graph, and Spearman's correlation was used to calculate r and P values for all bar graphs and scatter plots. TCM, central memory T cells (CD45RA–CCR7+); TEFF, effector T cells (CD45RA+CCR7–); TEM, effector memory T cells (CD45RA–CCR7–); TN, naïve-like T cells (CD45RA+CCR7+), which are actually more like stem-like memory cells in the context of axicabtagene ciloleucel.

FIGS. 4A-4S. The proportion of T cells with a more juvenile phenotype in the apheresis material directly associates with a lower product doubling time. Association between T-cell phenotypes in apheresis material pre-gated on live, CD45+ cells and product doubling time (FIG. 4A-FIG. 4O) or product phenotype (FIG. 4P-FIG. 4S). Spearman's correlation was used to calculate r and P values. TCM, central memory T cells (CD45RA–CCR7+); TEFF, effector T cells (CD45RA+CCR7–); TEM, effector memory T cells (CD45RA–CCR7–); TN, naïve-like T cells (CD45RA+CCR7+), which are actually more like stem-like memory cells in the context of axicabtagene ciloleucel.

FIGS. 5A-5I. The number of CD8 and Tn cells, commensurate with tumor burden, is relevant to achieving durable response after anti-CD19 CAR T cell treatment. FIG. 5A-FIG. 5D, Response, peak CAR T-cell levels, and peak CAR-T cell levels normalized to tumor burden by quartile analysis of number of CD8 T cells (FIG. 5A and FIG. 5B) or CD8 T cells normalized to tumor burden (FIG. 5C and FIG. 5D). FIG. 5E, number of CD8 T cells among patient with low tumor burden (below median; left) and high tumor burden (above median, right) by response. FIG. 5F-FIG. 5I, Response, peak CAR T-cell levels, and peak CAR-T cell levels normalized to tumor burden by quartile analysis of number of Tn cells (FIG. 5F and FIG. 5G) or CD8 T cells normalized to tumor burden (FIG. 5H and FIG. 5I). P values were calculated using logistic regression for line graphs (FIG. 5A, FIG. 5C, FIG. 5F, FIG. 5H) and Kruskal-Wallis and Dunn's tests for box plots (FIG. 5E). Spearman's correlation was used to calculate r and P values for bar graphs (FIG. 5B, FIG. 5D, FIG. 5G, FIG. 5I). CAR, chimeric antigen receptor; TN, naïve-like T cells (CD45RA+CCR7+), which are actually more like stem-like memory cells in the context of axicabtagene ciloleucel.

FIGS. 6A-6H. Factors differentially associated with toxicities and efficacy: tumor burden, inflammatory markers, and key product attributes. P values were calculated using logistic regression. CAR, chimeric antigen receptor; CRS, cytokine release syndrome; IFN, interferon; IL, interleukin; LDH, lactate dehydrogenase; MCP-1, monocyte chemoattractant protein-1; NE, neurologic events; TN, naïve-like T cells (CD45RA+CCR7+), which are actually more like stem-like memory cells in the context of axicabtagene ciloleucel.

FIG. 7B-FIG. 7D, Top covariates differentially associated with efficacy and neurotoxicity (B), efficacy and CRS (C), and neurologic events and CRS (D) by random forest analysis (n=XX). CAR, chimeric antigen receptor; CRP, C-reactive protein; CRS, cytokine release syndrome; IFN, interferon; IL, interleukin; LDH, lactate dehydrogenase; NE, neurologic events; TN, naïve-like T cells (CD45RA+ CCR7+), which are actually more like stem-like memory cells in the context of axicabtagene ciloleucel.

FIGS. 9A-9L Association of Day 0 and Day 1 IL-6, ferritin, and CCL2 with in vivo CAR T-cell expansion and rate of response. All graphs show medians per quartile. Spearman's correlation was used to calculate r and P values for all bar graphs (FIG. 9A, FIG. 9C, FIG. 9E, FIG. 9G, FIG. 9I, FIG. 9K), and P values were calculated using logistic regression for line graphs (FIG. 9B, FIG. 9D, FIG. 9F, FIG. 9H, FIG. 9J, FIG. 9L). CAR, chimeric antigen receptor; IL, interleukin; CCL2, monocyte chemoattractant protein-1.

FIGS. 12A-12H. Association was observed between baseline tumor burden (FIG. 12A-FIG. 12B) or pre-treatment inflammatory status (FIG. 12C-FIG. 12H) and T-cell phenotypes. Spearman's correlation was used to calculate r and P values. LDH, lactate dehydrogenase; TEM, effector memory T cells (CD45RA–CCR7–); TN, naïve-like T cells (CD45RA+CCR7+), which are actually more like stem-like memory cells in the context of axicabtagene ciloleucel.

FIGS. 13A-13B. Rapid, intrinsic expansion capability of product T cells is more influential in patients with higher tumor burden. P values were calculated using Kruskal-Wallis and Dunn's tests FIGS. 14A-14J. Association of the number of infused product CD4 cells (FIG. 14A-FIG. 14D), the number of infused product CD3 cells (FIG. 14E-FIG. 14H) and CD4: CD8 ratio with efficacy and engraftment. P values were calculated using logistic regression for line graphs (FIG. 14A, FIG. 14C, FIG. 14E, FIG. 14G, FIG. 14I), and Spearman's correlation was used to calculate r and P values for bar graphs (FIG. 14B, FIG. 14D, FIG. 14F, FIG. 14H, FIG. 14J). CAR, chimeric antigen receptor.

FIGS. 15A-15P. Frequency and proportion of TN and TEM CD8+ or CD4+ T cells in the CAR T-cell product and clinical efficacy. P values were calculated using Kruskal-Wallis and Dunn's tests. CAR, chimeric antigen receptor; CR, complete response; PR, partial response; TEM, effector memory T cells (CD45RA–CCR7–); TN, naïve-like T cells (CD45RA+CCR7+), which are actually more like stem-like memory cells in the context of axicabtagene ciloleucel.

FIGS. 17A-17D. Association of toxicity and efficacy with key cytokines. P values were calculated using logistic regression. CRS, cytokine release syndrome; IL, interleukin; LDH, lactate dehydrogenase; CCL2, monocyte chemoattractant protein-1; NE, neurologic events.

FIGS. 18A-18B. Association between interferon-γ produced in coculture by the product and product T-cell attributes. Spearman's correlation was used to calculate r and P values for all scatter plots. CCR, chemokine receptor; IFN, interferon.

FIG. 20B-FIG. 20C) Top covariates differentially associated with efficacy and neurotoxicity (B), efficacy and CRS (C), and neurologic events and CRS (D) by multivariate analysis. CAR, chimeric antigen receptor; CRP, C-reactive protein; CRS, cytokine release syndrome; IFN, interferon; IL, interleukin; LDH, lactate dehydrogenase; NE, neurologic events; TN, naïve-like T cells (CD45RA+CCR7+), which are actually more like stem-like memory cells in the context of axicabtagene ciloleucel.

FIGS. 21A-21E Analyte Quartiles: FIG. 21A: CAR T-cell expansion, FIG. 21B: Baseline Characteristics, FIG. 21C: Serum Analytes, FIG. 21D: T cell subsets (Infused Naïve-like T cells correspond to T cells that are CCR7+ CD45RA+), and FIG. 21 E: Product Characteristics.

FIG. 22 Random forest multivariate analysis.

FIGS. 23A-23E Evolution of TME gene signatures post-axicabtagene ciloleucel infusion associated with clinical outcomes. Gene expression was compared at baseline (before conditioning chemotherapy and axicabtagene ciloleucel) versus early after axicabtagene ciloleucel infusion in fresh frozen tumor biopsies using the PanCancer Immune Profiling+CAR T gene panel. a, Heatmap of gene expression in patients with CR (n=18 [12 pretreatment; 6 within 2 weeks posttreatment]) versus PR/SD/PD (n=17 [11 pretreatment; 5 within 2 weeks posttreatment; 1 with SD within 4 weeks posttreatment]). Expression of b, B cell-related genes; c, T cell-related genes, T cell growth factors, and effector molecule genes; d, checkpoint genes; and e, myeloid-related genes and chemokine genes. Gene expression was assessed in patients with CR/PR (n=25 [17 pretreatment; 8 post-treatment]) versus SD/PD (n=10; [6 pre-treatment; 3 within 2 weeks post-treatment; 1 within 4 weeks post-treatment]. Abbreviations: axicabtagene ciloleucel, axicabtagene ciloleucel; CAR, chimeric antigen receptor; CR, complete response; PD, progressive disease; PR, partial response; SD, stable disease; TME, tumor microenvironment FIGS. 24A-24E Dynamic changes in TME gene signatures were evident post-axicabtagene ciloleucel and correlated with clinical outcomes. FIG. 24A, Evolution of B cell lineage genes posttreatment. FIG. 24B, Volcano plot of gene expression of B cell lineage markers and CTA genes before (left) versus 2 weeks after (right) axicabtagene ciloleucel infusion in the TME of patients with CR/PR versus SD/PD. The plot was constructed using log 2(fold change) and −log 10(P values) for all genes. Red dots represent the top differentially expressed genes with P<0.01. FIG. 24C, Definition of the Immunosign score cutoff. IS21 scoring function is an algorithm derived from the Immunoscore algorithm (Galon, J. et al. *Science.* 2006; 313(5795): 1960-4), is independent of clinical outcome, and is arbitrarily defined as the 25th percentile of the observed scores among samples. FIG. 24E, Evolution of chemokine genes posttreatment. Abbreviations: axicabtagene ciloleucel, axicabtagene ciloleucel; CAR, chimeric antigen receptor; CR, complete response; CTA, cancer testis antigen; IS, Immunosign; PD, progressive disease; PR, partial response; SD, stable disease; TME, tumor microenvironment.

FIG. 25 Gene-expression profiling panels. Tumor biopsies were performed at baseline (before conditioning chemotherapy and axicabtagene ciloleucel infusion), early after CAR T cell infusion (Day 7-Day 14 post-axicabtagene ciloleucel), or later at relapse. Abbreviations: axicabtagene ciloleucel, axicabtagene ciloleucel; CAR, chimeric antigen receptor.

FIG. 26 Genes interrogated by NanoString panels and Immunosign 15 and 21. Abbreviations: CAR, chimeric antigen receptor.

FIG. 27A, T cell and immune checkpoint genes. P values are from Kruskal-Wallis test. FIG. 27B, Volcano plot of CART and myeloid cell gene signature within 4 weeks after axicabtagene ciloleucel infusion (left) versus at relapse (right). The plot was constructed using log 2(fold change) and −log 10(P value) for all genes analysed by PanCancer Immune Profiling+CAR T gene panel. Red dots represent the top differentially expressed genes with P<0.01. FIG. 27C, Immunosign. P values are from Kruskal-Wallis test. Abbreviations: axicabtagene ciloleucel, axicabtagene ciloleucel; CAR, chimeric antigen receptor; TME, tumor microenvironment FIGS. 28A-28C At relapse, the TME evolved towards an immune-detrimental contexture with upregulation of B cell-, CTA-, and Treg-related genes. Gene expression was compared at baseline (before lymphodepletion and axicabtagene ciloleucel infusion), within 4 weeks after axicabtagene ciloleucel infusion, and at relapse (as indicated) in fresh frozen biopsies analysed by PanCancer Immune Profiling+CAR T gene NanoString panel (unpaired samples, n=23 pretreatment; 12 posttreatment [11 within 2 weeks; 1 within 4 weeks]; 3 relapse) or Immunosign Clinical Research panel (paired samples, n=3).

FIG. 29A-FIG. 29C, Gene expression was compared at pretreatment (prelymphodepletion) in formalin-fixed, paraffin-embedded biopsies from axicabtagene ciloleucel responders (n=18 total [16 CR, 2 PR]) compared to nonresponders (n=6 total [4 SD, 2 PD]) using the PanCancer Immune+Immunosign NanoString panel. Volcano plot of gene expression of a, B cell lineage markers and b, cancer testis antigen genes in responders (left) versus nonresponders (right). Volcano plots were constructed using log 2(fold change) and −log 10(P values) for all genes. Red dots represent the top differentially expressed genes with P<0.01. Expression of b, cancer testis antigen genes and c, T cell markers, immune checkpoints, STAT/IFN program, and chemokine genes in responders versus nonresponders. P values are from Wilcoxon test. d, Low, medium, and high-density patterns of tumor-infiltrating T cells by IHC in patient tumor biopsies before lymphodepletion. e, Immunoscore TL and Immunosign 21 scores before lymphodepletion in patients with CR (n=18 and 13, respectively) versus PR/SD/PD (n=12 and 7, respectively). The red line depicts the high/low score cutoffs. f, Distribution of Immunoscore TL and Immunosign 21 scores in patients with CR/PR (n=22 and 21 total, respectively) versus SD/PD (n=8 and 5 total, respectively). P values are from Fisher exact test. Abbreviations: axicabtagene ciloleucel, axicabtagene ciloleucel; CR, complete response; IFN, interferon; IHC, immunohistochemistry; PD, progressive disease; PR, partial response; SD, stable disease; STAT, signal transducer and activator of transcription; TME, tumor microenvironment.

FIGS. 30A-30E Immunoscore TL correlated with tumor-infiltrating immune cell density and Immunosign 15 and 21 pretreatment (prelymphodepletion). Correlation between Immunoscore TL and FIG. 30A, tumor-infiltrating CD3+ and CD8+ T cells, FIG. 30B, Immunosign 15, and FIG. 30C, Immunosign 21. Distribution of immune cell densities by high versus low FIG. 30D, Immunosign 21 and FIG. 30E, Immunoscore TCE and SC indexes. Abbreviations: CR, complete response; PD, progressive disease; PR, partial response; SD, stable disease; Treg, regulatory T cell.

FIG. 31A, Following selection of a digital image area by a pathologist, CD3 and CD8 IHC staining was scored (high or low) and quantified by the application of a prespecified bioinformatics algorithm that generated a numerical index (Immunoscore TL) and analysis cutoffs. Because the majority of lymph node biopsies lacked identifiable invasive margin, as expected for lymphoma, positive densities were calculated from the core tumor only. FIG. 31B, Raw data included images of successive stainings on the same slide with Immunoscore TCE or SC panel, as indicated (250 μm scale). Abbreviations: CR, complete response; IHC, immunohistochemistry; IS, Immunoscore; PD, progressive disease; PR, partial response; SD, stable disease FIGS. 32A-32B Pretreatment tumor density of Treg and myeloid cells in association with axicabtagene ciloleucel response.

FIGS. 34A-34C FIG. 34A-34B: Immunoscore TCE and SC panels, cell type marker signatures; and FIG. 34C: associations between pretreatment TME immune cell density and clinical outcomes. Abbreviations: CR, complete response; M-MDSC, monocytic myeloid-derived suppressor cell; PD, progressive disease; PMN-MDSC, polymorphonuclear myeloid-derived suppressor cell; PR, partial response; SD, stable disease; Treg, regulatory T cell FIGS. 35A-35C Optimized immune indexes tailored to axicabtagene ciloleucel response. FIG. 35A, Overview of the algorithm optimization methodology. Retrospective machine learning was applied to the Immunosign score calculated from gene expression analysed by Immunosign Clinical Research panel. Three types of parameters were optimized across $1.73 \times 10^{34}$ possible configurations using genetic algorithms. FIG. 35B, Optimized signatures for objective response (CR or PR), best response, and worst grade of neurotoxicity. FIG. 37A-37B: adaptive immunity; FIG. 37C; adhesion and anigen representation; FIG. 37D: CTA, TAA, cellular morphology and transcription factors; FIG. 37E; B cell genes and apoptosis and cell cycle regulation; FIG. 37F: IFN signaling; FIG. 37G-37H: chemotaxis and innate immunity; FIG. 37I-37K: innate immunity (continued); Abbreviations: CTA, cancer testis antigen; IFN, interferon; TAA, tumor-associated antigen.

FIGS. 38A-38C Correlations between pretreatment gene expression of cytokines, cytokine-responsive transcription factors, and T cell markers. Gene expression was measured using the PanCancer Immune+Immunosign NanoString panel FIGS. 39A-39E Correlation studies between pretreatment TME gene expression of cytokines and immune genes or immune cell density. Gene expression was assessed in pretreatment (prelymphodepletion), formalin-fixed, paraffin-embedded tumor biopsies using the PanCancer Immune+ Immunosign NanoString panel. Cell density of immune subsets was determined pretreatment via Immunoscore TL. Correlation between FIG. 39A, CCL5 and FIG. 39B, CCR5 gene expression and T cell gene expression.

FIG. 40A, Distribution of axicabtagene ciloleucel-treated patients who achieved CR (n=11) versus PR/SD/PD (n=7) in function of the tumor burden. FIG. 40B, Checkpoint expression (0, 1, 2, 3) on CD8+ T cells, CD4+ T cells, and Tregs in function of tumor burden. Abbreviations: Axi-cel, axicabtagene ciloleucel; CR, complete response; PD, progressive disease; PR, partial response; SD, stable disease; TME, tumor microenvironment.

FIG. 41A, Correlation between CD3+, CD8+, and CD8+PD-1+ cell density (cell count/mm$^2$) and peak CAR T cell levels (cells/µl), pretreatment tumor burden (mm$^2$; measured using the sum of the products of the diameters for the selected lesions at baseline in absolute numbers), and the ratio of peak CAR T cell levels to pretreatment tumor burden. FIG. 41B, Correlation between Immunosign 21, Immunosign 15, and Immunoscore TL and peak CAR T cell levels, pretreatment tumor burden, and the ratio of peak CART T cell levels to pretreatment tumor burden. Patient data are expressed according to response (CR, PR, or SD/PD) and neurotoxicity grade (1-2 or ≥3A).

FIG. 42 Origin of ZUMA-1 tumoral biopsies analysed in this study with known anatomic location. Abbreviations: axicabtagene ciloleucel, axicabtagene ciloleucel.

FIGS. 55A-55C: Pharmacodynamics and Pharmacokinetics of Cohort 4 Versus Cohorts 1+2.

FIGS. 58A-58B: CAR T-Cell Expansion. The figure summarizes peak levels of CAR T cells (FIG. 58A) or area under the curve (FIG. 58B) of CAR T cells in blood for all patients with available values in Cohorts 1+2 and Cohort 3. Each circle represents 1 patient. The middle line represents the median, box represents the bounds of the first and third quartiles, whiskers show range. P values are for ratio of medians (Cohort 3/Cohorts 1+2). Patients with missing absolute lymphocyte counts are excluded. C, cohort; CAR, chimeric antigen receptor; Ph, phase.

FIG. 63: Details from a case study of a patient with grade 5 cerebral edema. Left panels summarize the patient history (upper) and management (lower); upper right panels show results of head CT scan; lower right panel summarizes findings of post-hoc analysis. Post-hoc translational findings revealed that prior to chemotherapy conditioning and axi-cel infusion, the patient showed high levels of pro-inflammatory markers, cell adhesion/vascular damage markers, and chemokines in serum. axi-cel, axicabtagene ciloleucel; CAR, chimeric antigen receptor; CNS, central nervous system; CRP, C-reactive protein; CRS, cytokine release syndrome; CSF, cerebrospinal fluid; CT, computed tomography; CMV, cytomegalovirus; ECOG, Eastern Cooperative Oncology Group; ICAM, intracellular adhesion molecule; ICH, intracranial hemorrhage; IL, interleukin; IP, IFN-γ-induced protein; IPI, International Prognostic Index; IV, intravenous; MM, magnetic resonance imaging; MRSA, methicillin-resistant *Staphylococcus aureus*; PD, progressive disease; R, receptor; VCAM, vascular cell adhesion molecule.

FIGS. 64A-64K: Associations of CAR T-cell levels during the first month post infusion with clinical response. (FIG. 64A-FIG. 64C) Analysis of CAR T cell expansion by response status at specified times. (FIG. 64D) Peak CAR T cell expansion by best response. (FIG. 64E-FIG. 64F) Cumulative CAR T cell levels (AUC) associate durable and objective response. (FIG. 64I-FIG. 64J) Linear regression analysis of objective response with peak CAR T cell levels and peak CAR T cell levels normalized to tumor burden. Line graphs show medians at each timepoint. P values were calculated using Kruskal-Wallis for line graphs, and Dunn's tests for box plots. AUC, area under the curve from day 0-28; CAR, chimeric antigen receptor; CR, complete response, NR, no response, PR partial response.

FIGS. 65A-65G: Heat map showing association between pretreatment inflammatory markers and other laboratory analytes. (FIG. 65B-FIG. 65D) Quartile analysis of baseline inflammatory markers and objective and durable response. (FIG. 65E-FIG. 65G) Logistic regression analysis of baseline inflammatory markers and objective response. CAR, chimeric antigen receptor; CRP, C-reactive protein; IL, interleukin; LDH, lactate dehydrogenase; MCP-1, monocyte chemoattractant protein-1; Q, quartile.

(FIG. 66A-FIG. 66C) Peak CAR T-cell expansion and peak CAR T-cell expansion normalized to tumor burden were analyzed by quartile analyses of pro-inflammatory and myeloid activation markers. (D-F) Logistic regression analysis of evaluating the association of durable response with baseline pro-inflammatory and myeloid activation markers. Bar graphs show medians per quartile, and Spearman's correlation was used to calculate r and P values for all bar graphs. CAR, chimeric antigen receptor; CRP, C-reactive protein; IL, interleukin; LDH, lactate dehydrogenase; MCP-1, monocyte chemoattractant protein-1; Q, quartile.

FIG. 70: Association between product characteristics and response. All P values were calculated by logistic regression FIGS. 71A-71I: Higher expansion rate of product T cells measured preinfusion (doubling time) is associated with greater in vivo CAR T-cell levels and efficacy, and correlates with T-cell phenotype. Logistic regression analysis showing association of response (FIG. 71A) or durable response (FIG. 71B) with doubling time. Doubling time by peak CAR T-cell expansion and peak CAR T-cell expansion normalized to tumor burden (FIG. 71C) or by CAR AUC (FIG. 71D) were analyzed by quartile analyses. Scatter plots show association of doubling time with specified T-cell populations (FIG. 71E-FIG. 71H) and CD4:CD8 ratio (FIG. 71I). Bar graphs show medians per quartile, and Spearman's correlation was used to calculate r and P values for all bar graphs and scatter plots. AUC, area under the curve; CAR, chimeric antigen receptor.

FIGS. 72A-72C: Quartile and logistic regression analyses show associations of doubling time with response (FIG. 72A), peak CAR T cell expansion (FIG. 72B) and peak CAR T cell expansion normalized to tumor burden (FIG. 72C).

Figures 2A, 2B, 2C, 2D, 2E, 2F, 2G:
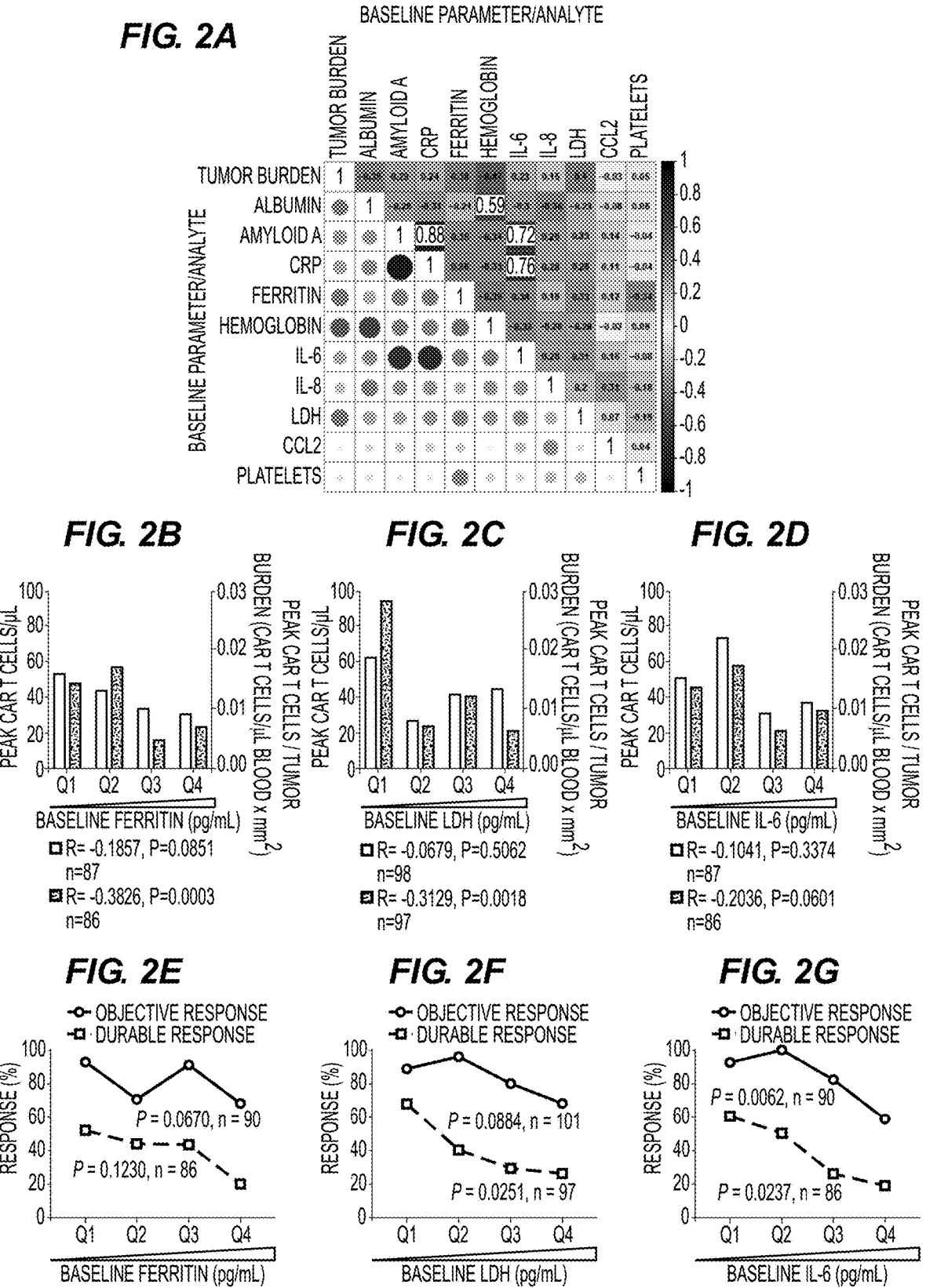
FIGS. 2A-2G. Systemic inflammation is negatively associated with both CAR T-cell expansion relative to pretreatment tumor burden and the rate of durable responses.

Line graph shows medians per quartile, and P values were calculated using logistic regression. Spearman's correlation was used to calculate r and P values for scatter plots. CAR, chimeric antigen receptor; Q, quartile.

FIGS. 73A-73H: The proportion of T cells with a more juvenile phenotype in the apheresis material directly associates with a lower product doubling time. Association between T-cell phenotypes in apheresis material pre-gated on live, CD45+ cells and product phenotype (FIG. 73A-FIG. 73C) or product doubling time (FIG. 73D-FIG. 73H). Spearman's correlation was used to calculate r and P values.

FIGS. 74A-74J: Association between T-cell phenotypes in apheresis material pre-gated on live, CD45+ cells and product doubling time (FIG. 74A-FIG. 74J) or product phenotype. Spearman's correlation was used to calculate r and P values.

FIGS. 75A-75H: Weak association was observed between baseline tumor burden (A-B) or pre-treatment inflammatory status (FIG. 75C-FIG. 75H) and T-cell phenotypes. Spearman's correlation was used to calculate r and P values. LDH, lactate dehydrogenase.

FIGS. 76A-76P: The number of CD8 and CCR7+ CD45RA+ T cells, commensurate with tumor burden, is critical to achieving durable response after axicabtagene ciloleucel. (FIG. 76A-FIG. 76F) Logistic regression analysis of response (right) and durable response (middle) and quartile analysis of peak CAR T-cell levels and peak CAR T-cell levels normalized to tumor burden (left) by the number of CD8 T cells (FIG. 76A-FIG. 76C) or the number of CD8 T cells normalized to tumor burden (FIG. 76D-FIG. 76F), of response and of response and durable response. (FIG. 76G) The number of CD8 T cells among patient with low tumor burden (below median; left) and high tumor burden (above median, right) by response. (FIG. 76H-FIG. 76P) Logistic regression analysis of response (right) and durable response (middle) and quartile analysis of peak CAR T-cell levels and peak CAR T-cell levels normalized to tumor burden (left) by the number of CCR7+CD45RA+ T cells (FIG. 76H-FIG. 76J), the number of CCR7+CD45RA+ T cells normalized to tumor burden (FIG. 76K-FIG. 76M), or CD4:CD8 ratio (FIG. 76N-FIG. 76P). P values were calculated using Kruskal-Wallis and Dunn's tests for box plots. Spearman's correlation was used to calculate r and P values for bar graphs. CAR, chimeric antigen receptor.

FIGS. 77A-77L: Quartile and logistic regression analyses show associations of infused CD8 T cells (FIG. 77A-FIG. 77C), infused CD8 T cells normalized to tumor burden (FIG. 77D-FIG. 77F), infused CCR7+CD45RA+ cells (FIG. 77G-FIG. 77I), infused CCR7+CD45RA+ cells normalized to tumor burden (FIG. 77J-FIG. 77L), with response, peak CAR T cell expansion and peak CAR T cell expansion normalized to tumor burden. Line graph shows medians per quartile, and P values were calculated using logistic regression. Spearman's correlation was used to calculate r and P values for scatter plots. CAR, chimeric antigen receptor; Q, quartile.

FIGS. 78A-78E: Quartile and logistic regression analyses show associations of the number of infused CD4 T cells (FIG. 78A), CD4 T cells normalized to tumor burden (FIG. 78B), CD3 T cells (FIG. 78C), CD3 T cells normalized to tumor burden (FIG. 78D), and CD4:CD8 T cell ratio (FIG. 78E) with objective and durable response. Line graphs show medians per quartile. All P values were calculated using logistic regression. CAR, chimeric antigen receptor; IL, interleukin; Q, quartile.

FIGS. 79A-79E: Association of CD4 T cells (FIG. 79A), CD4 T cells normalized to tumor burden (FIG. 79B), CD3 T cells (FIG. 79C), CD3 T cells normalized to tumor burden (FIG. 79D), and CD4:CD8 T cell ratio (FIG. 79E) with in vivo CAR T-cell expansion. Bar charts show medians per quartile. Spearman's correlation was used to calculate r and P values. CAR, chimeric antigen receptor; Q, quartile.

FIGS. 80A-80Ps: Frequency and proportion of CCR7+ CD45RA+ and CCR7−CD45RA−CD8+ or CD4+ T cells in the CAR T-cell product and clinical efficacy. P values were calculated using Kruskal-Wallis and Dunn's tests. CAR, chimeric antigen receptor; CR, complete response; PR, partial response.

FIGS. 81A-81H: Factors differentially associated with toxicities: tumor burden, inflammatory markers, and key product attributes. P values were calculated using logistic regression. CAR, chimeric antigen receptor; CRS, cytokine release syndrome; IFN, interferon; IL, interleukin; LDH, lactate dehydrogenase; MCP-1, monocyte chemoattractant protein-1; NE, neurologic events.

FIGS. 82A-82F: Association of toxicity and efficacy with key product attributes. Probability curve of durable response presented in the main manuscript figures are repeated here for completeness. P values were calculated using logistic regression. CAR, chimeric antigen receptor; CRS, cytokine release syndrome; NE, neurologic events.

FIGS. 83A-83G: Association of key baseline and product attributes with in vivo CAR T-cell expansion. Bar charts show medians per quartile. Spearman's correlation was used to calculate r and P values. CAR, chimeric antigen receptor; CCL2, chemokine (C-C motif) ligand 2; CRS, cytokine release syndrome; IL, interleukin; LDH, lactate dehydrogenase; NE, neurologic events; Q, quartile.

Figure 84:
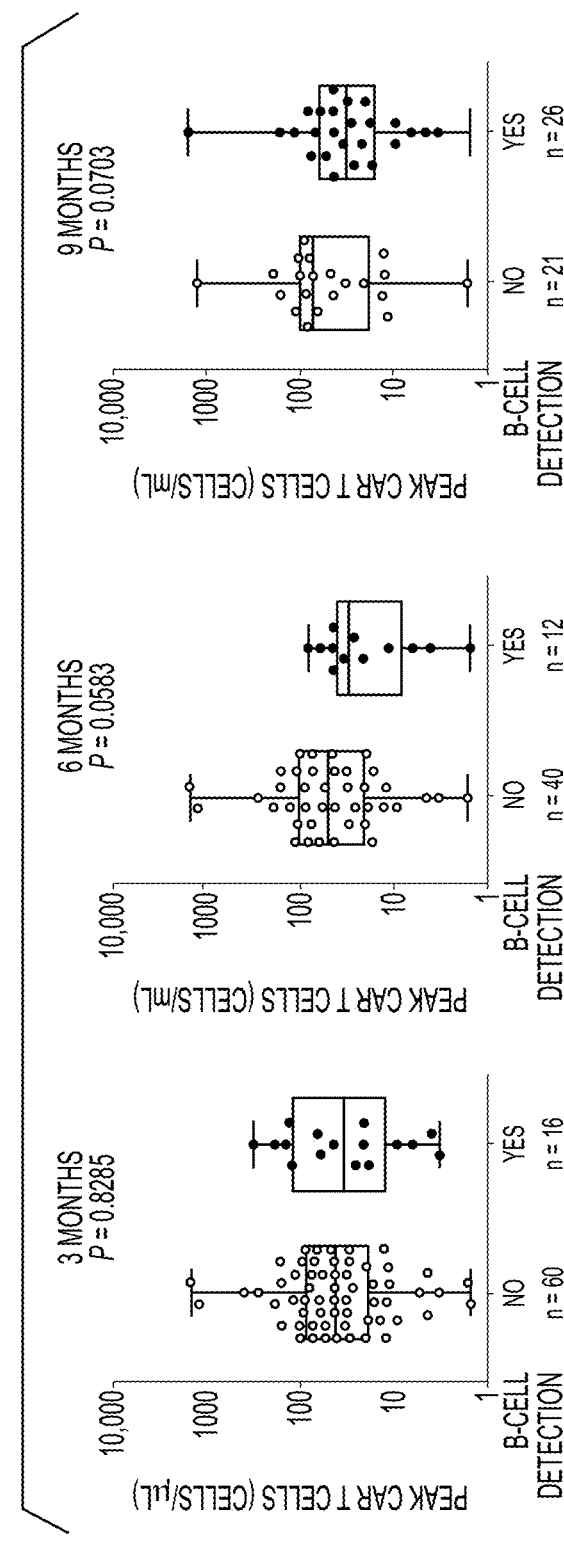
Figures 85A, 85B:
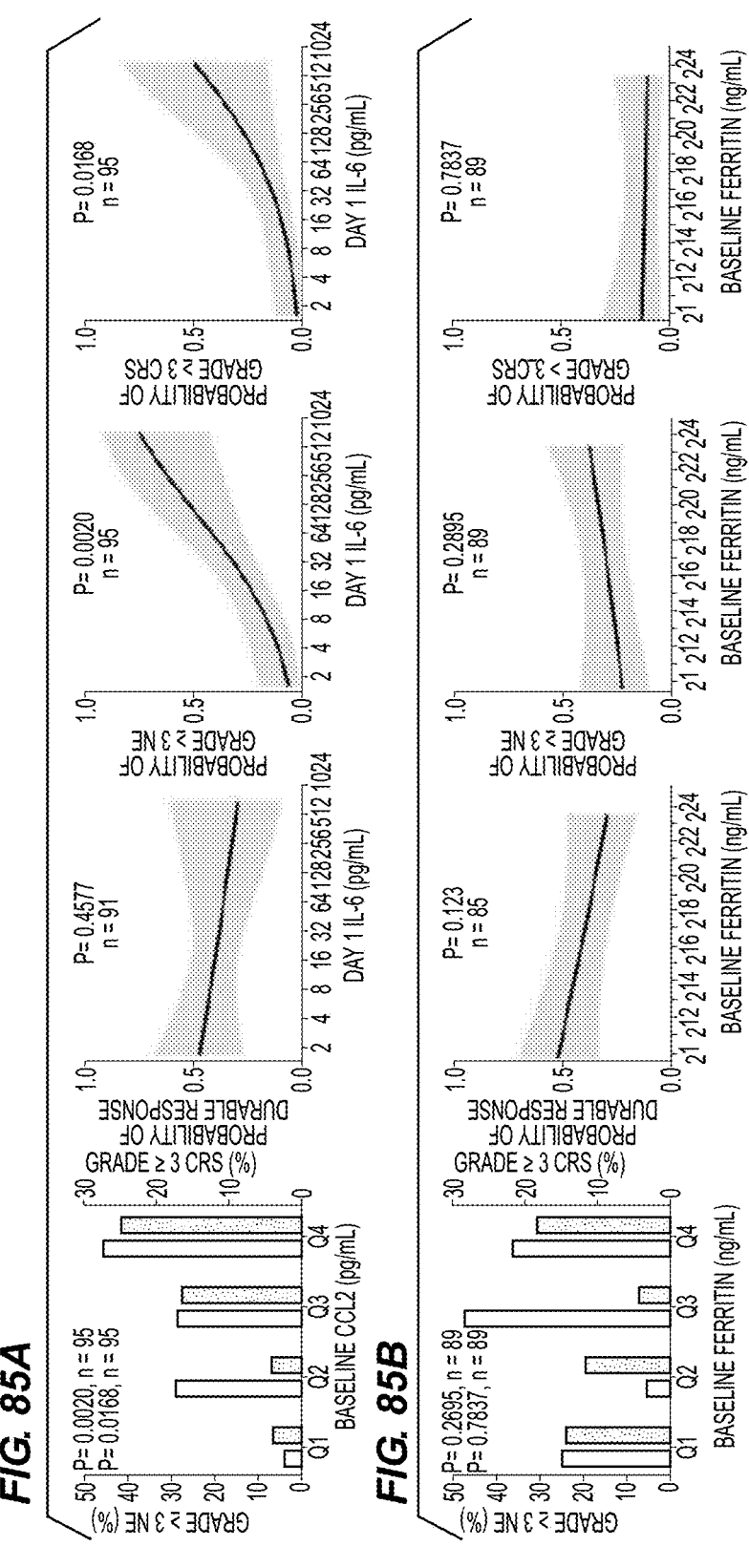

FIG. 84: Association of peak CAR T-cell levels and B-cell aplasia among patients with ongoing response.

FIGS. 85A-85D: Association of toxicity and efficacy with key cytokines. Probability curve of durable response presented in the main manuscript figures are repeated here for completeness. P values were calculated using logistic regression. CCL2, chemokine (C-C motif) ligand 2; CRS, cytokine release syndrome; IL, interleukin; LDH, lactate dehydrogenase; NE, neurologic events.

Figure 86B:
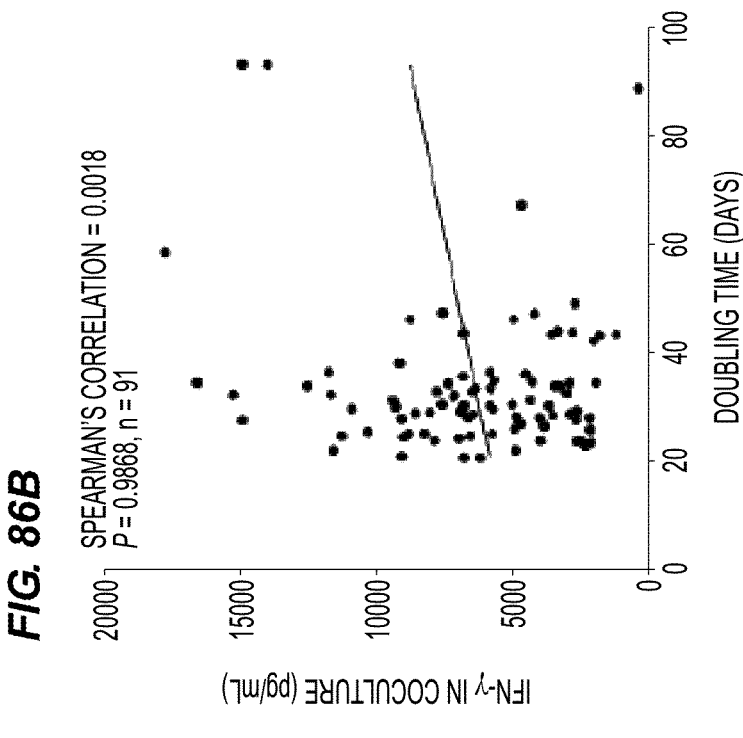
Figure 86A:
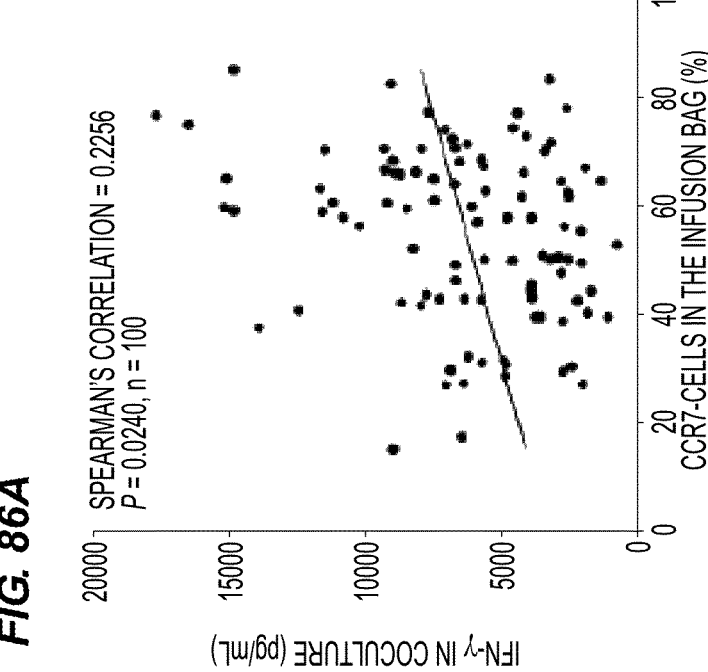

FIGS. 86A-86B: Association between interferon-γ produced in coculture by the product and product T-cell attributes. Spearman's correlation was used to calculate r and P values for all scatter plots. CCR, chemokine receptor; IFN, interferon.

Figures 87A, 87B:
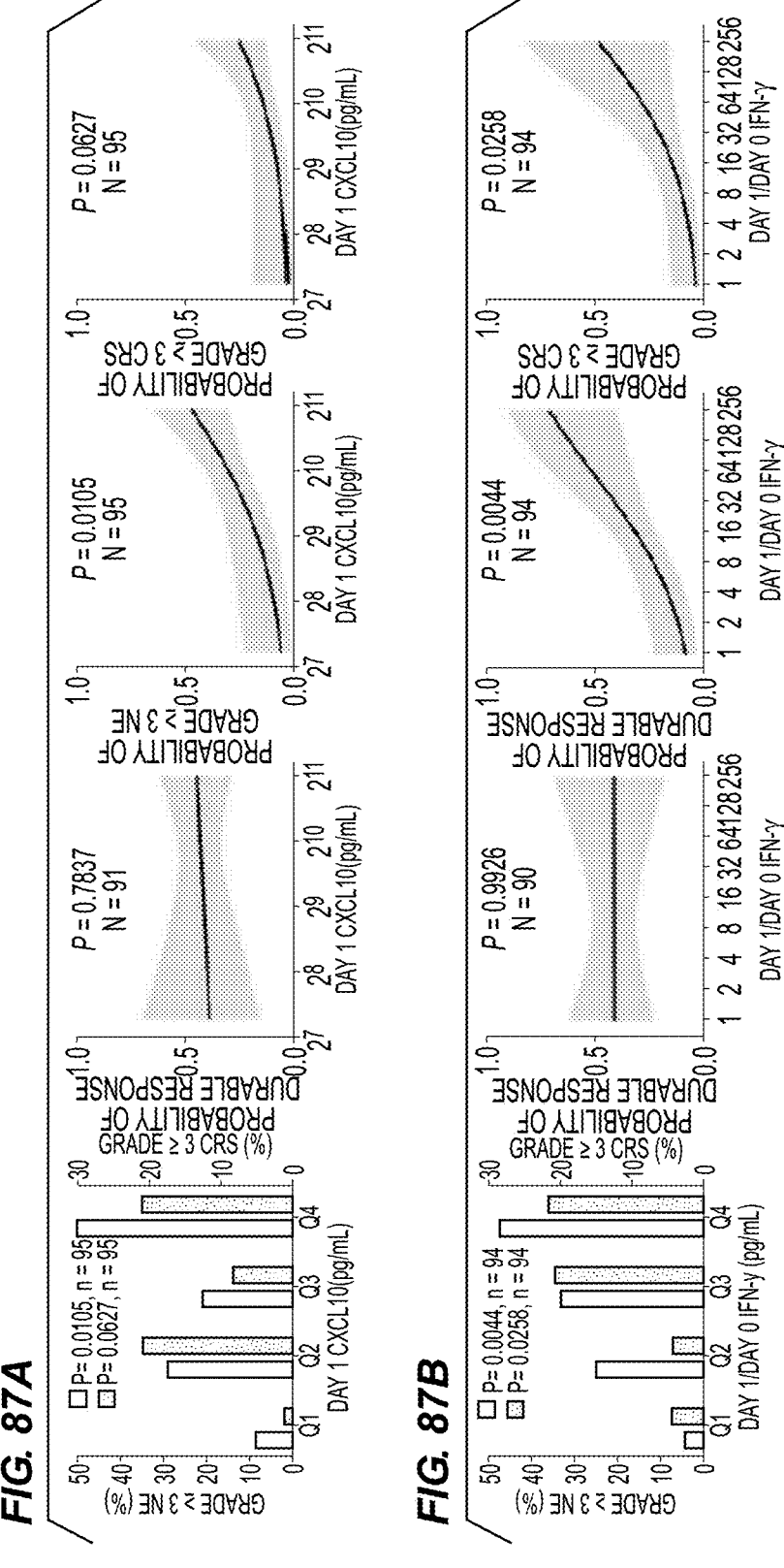
Figures 87C, 87D:
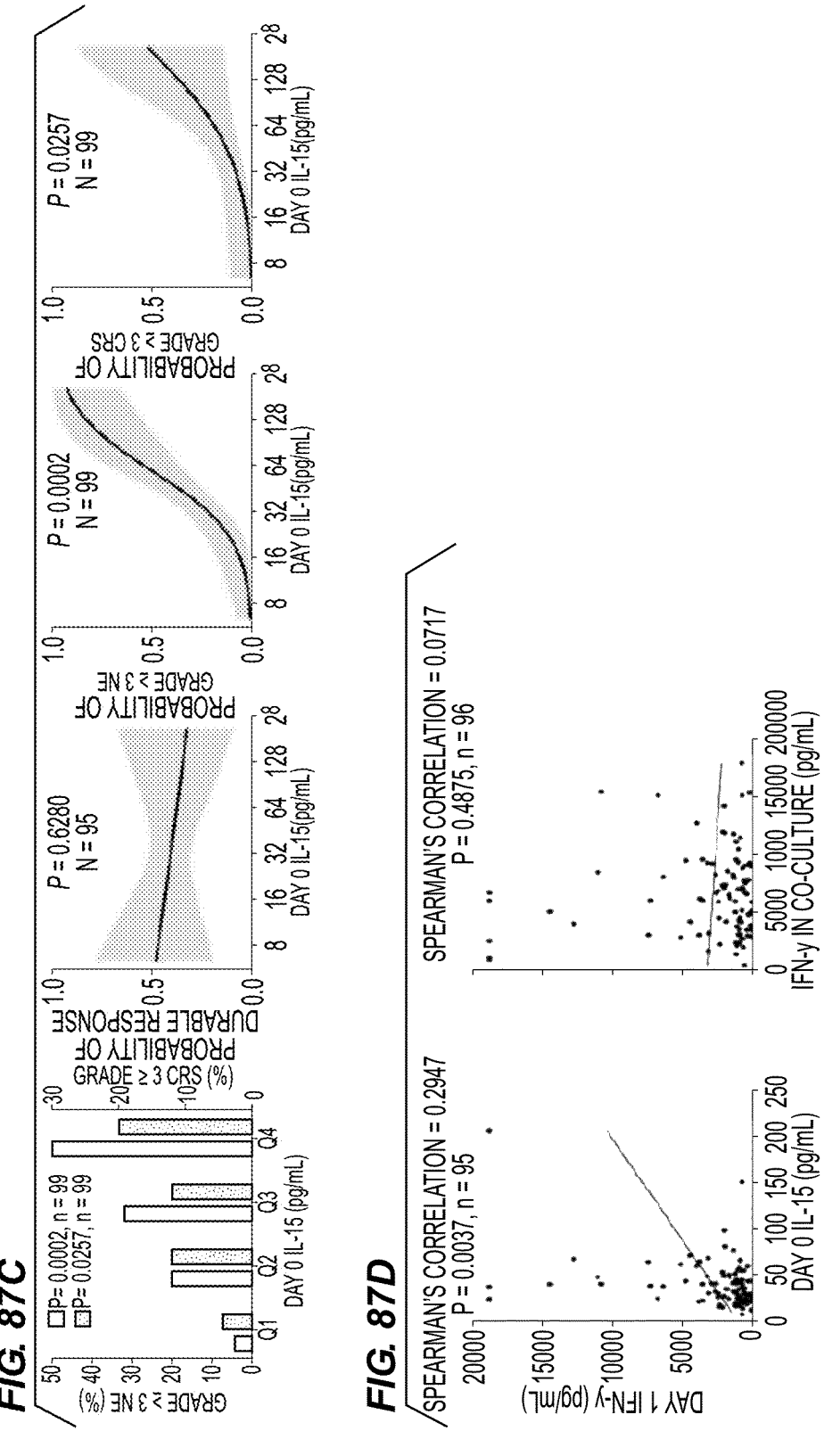
Figure 88B:
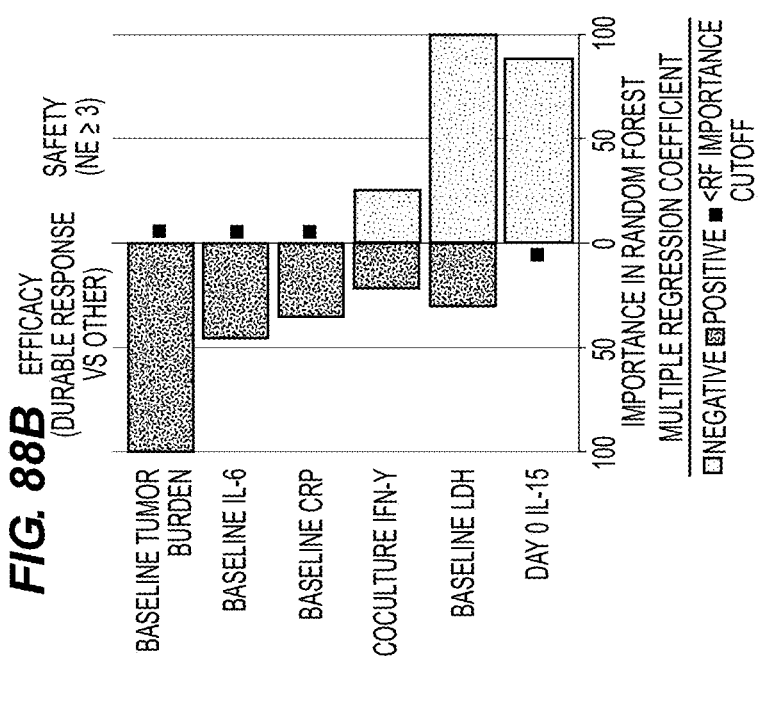
Figure 88A:
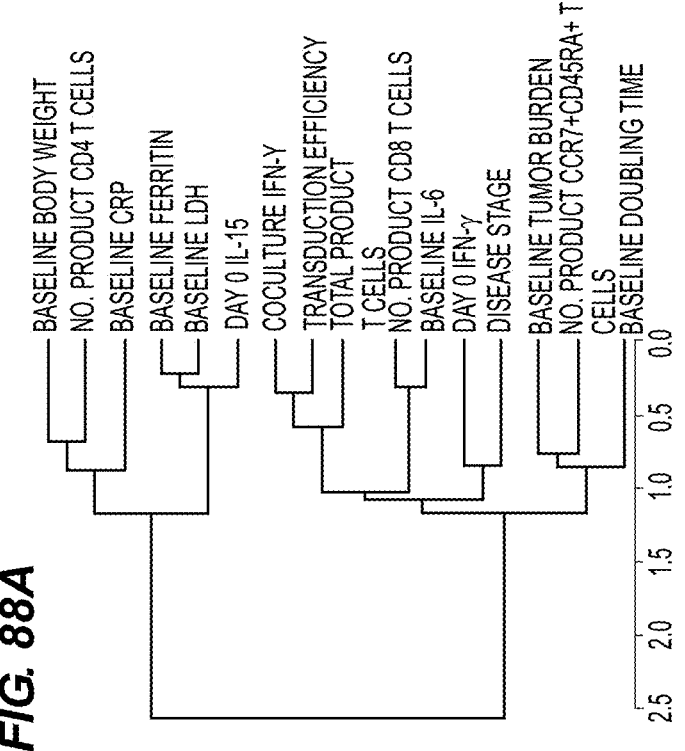
Figures 88C, 88D, 88E:
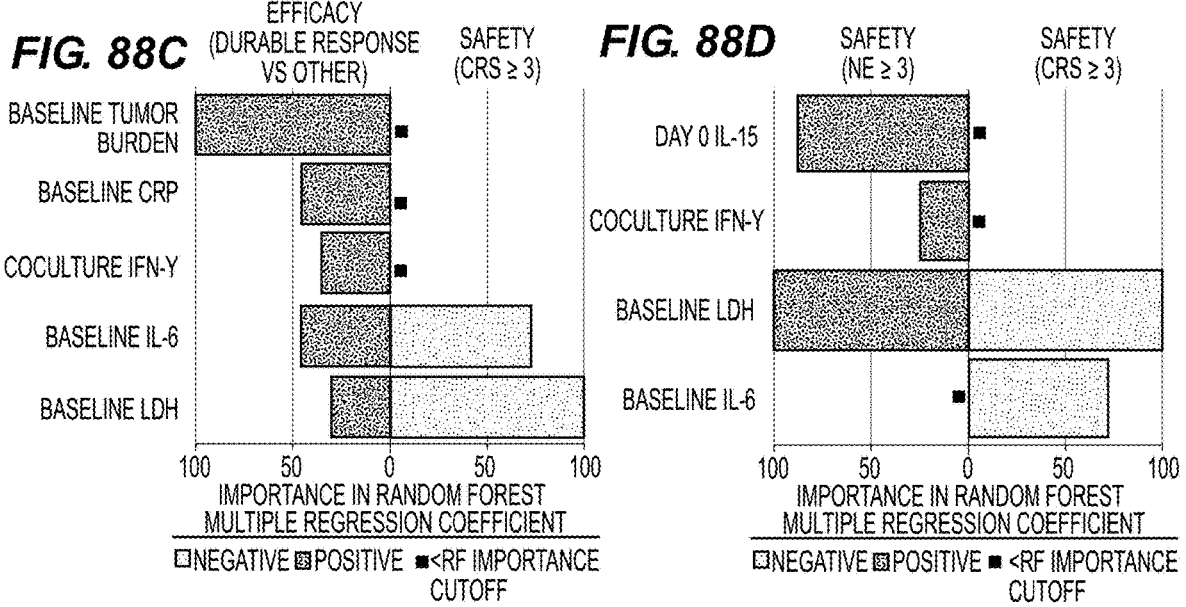

FIGS. 87A-87D: Association of toxicity and efficacy with post-infusion cytokines. P values were calculated using logistic regression for bar graphs and probability curves (FIG. 87A-FIG. 87C), and Spearman's correlation was used to calculate r and P values for scatter plots (FIG. 87D). CXCL, chemokine (C-X-C motif) ligand; IL, interleukin; IFN, interferon.

FIGS. 88A-88E: Tumor burden, LDH, and pro-inflammatory markers measured pre-CAR T-cell infusion associate differentially with clinical outcomes in multivariate analysis. (FIG. 88A) Cluster analysis summarizing the strength of association between covariates from the two major categories: product attributes and pretreatment tumor/inflammatory markers. (FIG. 88B-FIG. 88D) Top covariates differentially associated with efficacy and neurotoxicity (FIG. 88B), efficacy and CRS (FIG. 88C), and neurologic events and CRS (FIG. 88D) by random forest analysis (n=97-101 patients per parameter [supplemental Table 9]). (FIG. 88E) Summary of multivariate findings. CAR, chimeric antigen receptor; CRP, C-reactive protein; CRS, cytokine release syndrome; IFN, interferon; IL, interleukin; LDH, lactate dehydrogenase; NE, neurologic events.

FIGS. 89A-89C: Top covariates differentially associated with peak CAR T cells normalized by tumor burden compared with efficacy (FIG. 89A), neurotoxicity (FIG. 89B) and CRS (FIG. 89C) by multivariate analysis. CAR, chimeric antigen receptor; CRP, C-reactive protein; CRS, cytokine release syndrome; IFN, interferon; IL, interleukin; LDH, lactate dehydrogenase; NE, neurologic events.

FIGS. 90A-90B: Random forest multivariate analysis.

Figures 91A, 91B:
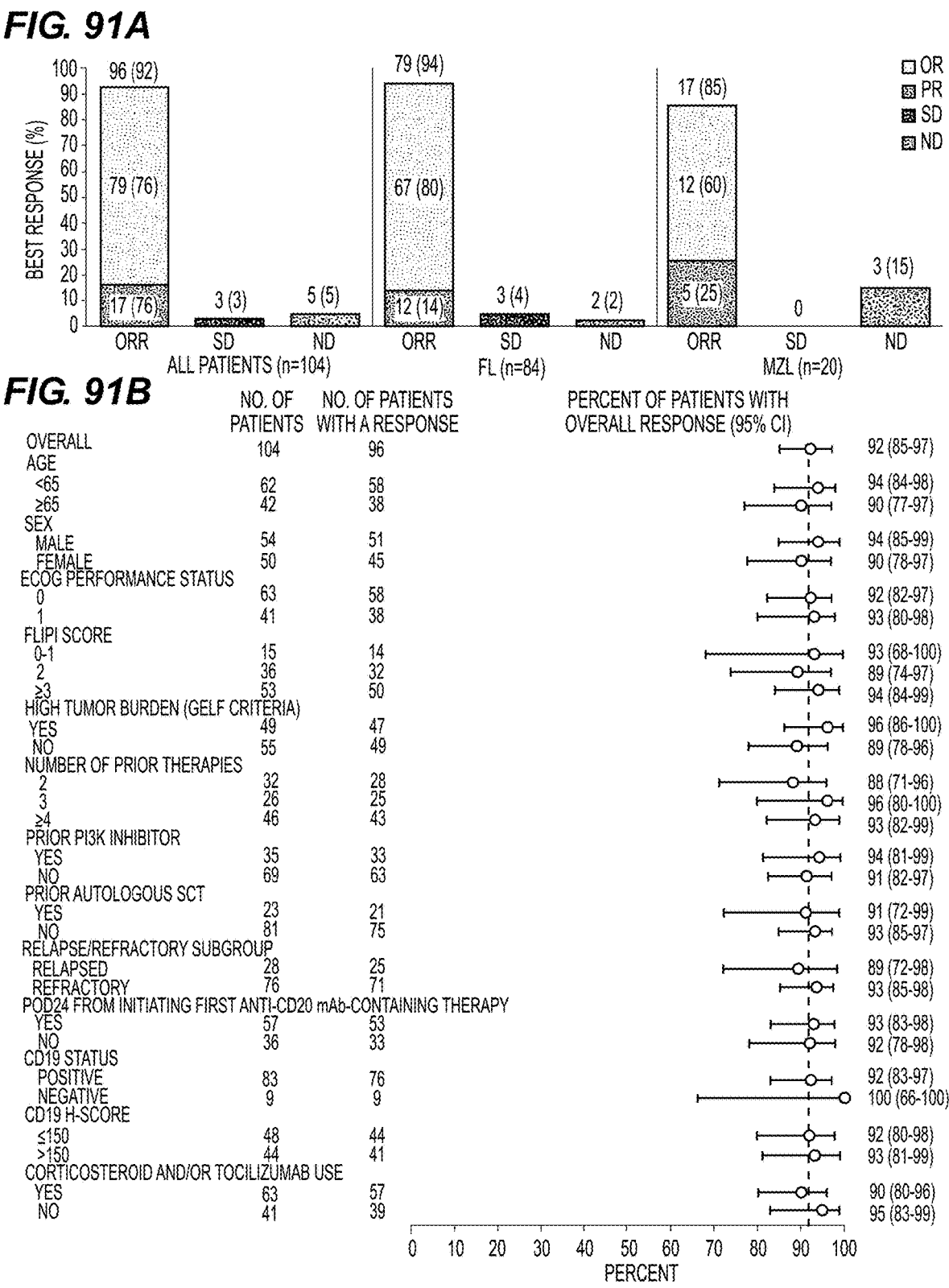

FIGS. 91A-91B: Overall response. Panel A shows the number (percent) of all patients with iNHL (N=104), FL (n=84), and MZL (n=20) who had an overall response to axicabtagene ciloleucel, including a complete response or partial response, as assessed by an independent radiology review committee in the primary efficacy analysis. For the patients classified as ND, 4 patients had no disease at baseline or post-baseline but were considered with disease by the investigator, and 1 patient with FL died prior to the first disease assessment. Panel B is a subgroup analysis for overall response in all patients with iNHL by key patient baseline and clinical covariates. The Clopper-Pearson method was used to calculate the 95% confidence interval. Axi-cel, axicabtagene ciloleucel; CR, complete response; ECOG, Eastern Cooperative Oncology Group; FL, follicular lymphoma; FLIPI, Follicular Lymphoma International Prognostic Index; GELF, Groupe d'Etude des Lymphomes Folliculaires; iNHL, indolent non-Hodgkin lymphoma; MZL, marginal zone lymphoma; ND, undefined/no disease or not done; ORR, overall response rate; PI3Ki, phosphoinositide 3-kinase inhibitor; POD24, Progression <24 months from initiating first anti-CD20 mAb-containing therapy; PR, partial response; SCT, stem cell transplantation; SD, stable disease.

FIG. 92: Subgroup Analysis of Complete Response Rate. Figure shows a subgroup analysis for complete response to axi-cel in all efficacy-evaluable patients with iNHL by key patient baseline and clinical covariates. The Clopper-Pearson method was used to calculate the 95% confidence interval. Axi-cel, axicabtagene ciloleucel; CR, complete response; ECOG, Eastern Cooperative Oncology Group; FLIPI, Follicular Lymphoma International Prognostic Index; GELF, Groupe d'Etude des Lymphomes Folliculaires; iNHL, indolent non-Hodgkin lymphoma; PI3Ki, phosphoinositide 3-kinase inhibitor; POD24, Progression <24 months from initiating first anti-CD20 mAb-containing therapy; SCT, stem cell transplantation.

Figures 93A, 93B, 93C, 93D:
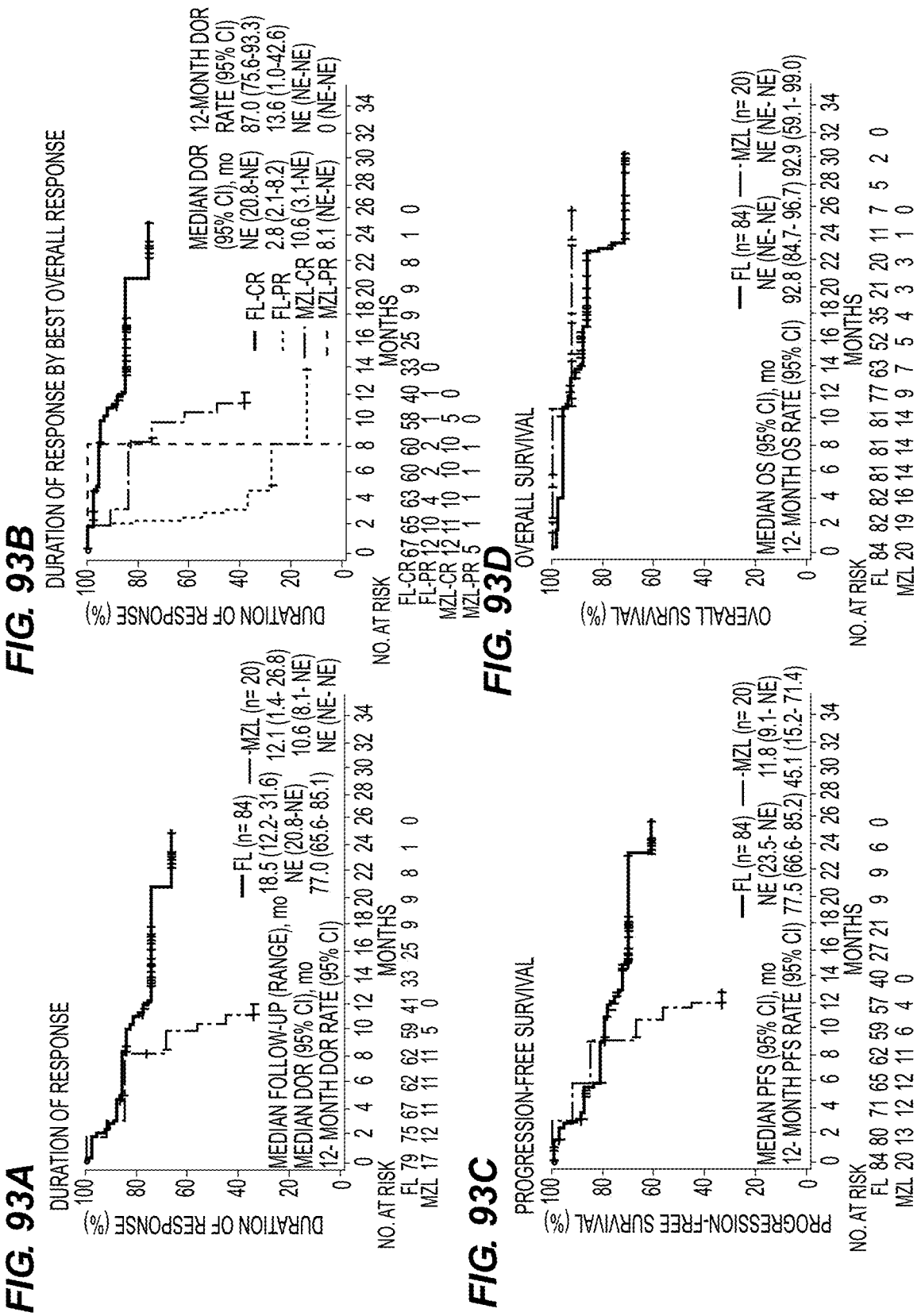

FIGS. 93A-93D: Duration of Response, Progression-free Survival, and Overall Survival. FIG. 93A shows the Kaplan-Meier estimate of the duration of response among the 79/84 patients with FL and 17/20 patients with MZL who were efficacy-evaluable and had a response to axicabtagene ciloleucel. FIG. 93B shows the Kaplan-Meier estimate of the duration of response for those patients who had either a CR or a PR to axicabtagene ciloleucel. FIG. 93C and FIG. 93D show Kaplan-Meier estimates of progression-free survival and overall survival among the 84 patients with FL and 20 patients with MZL who were included in the primary efficacy analysis. Axi-Cel, axicabtagene-ciloleucel; CR, complete response; DOR, duration of response; FL, follicular lymphoma; mo, month; MZL, marginal zone lymphoma; NE, not estimable; OS, overall survival; PFS, progression-free survival; PR, partial response.

Figure 94:
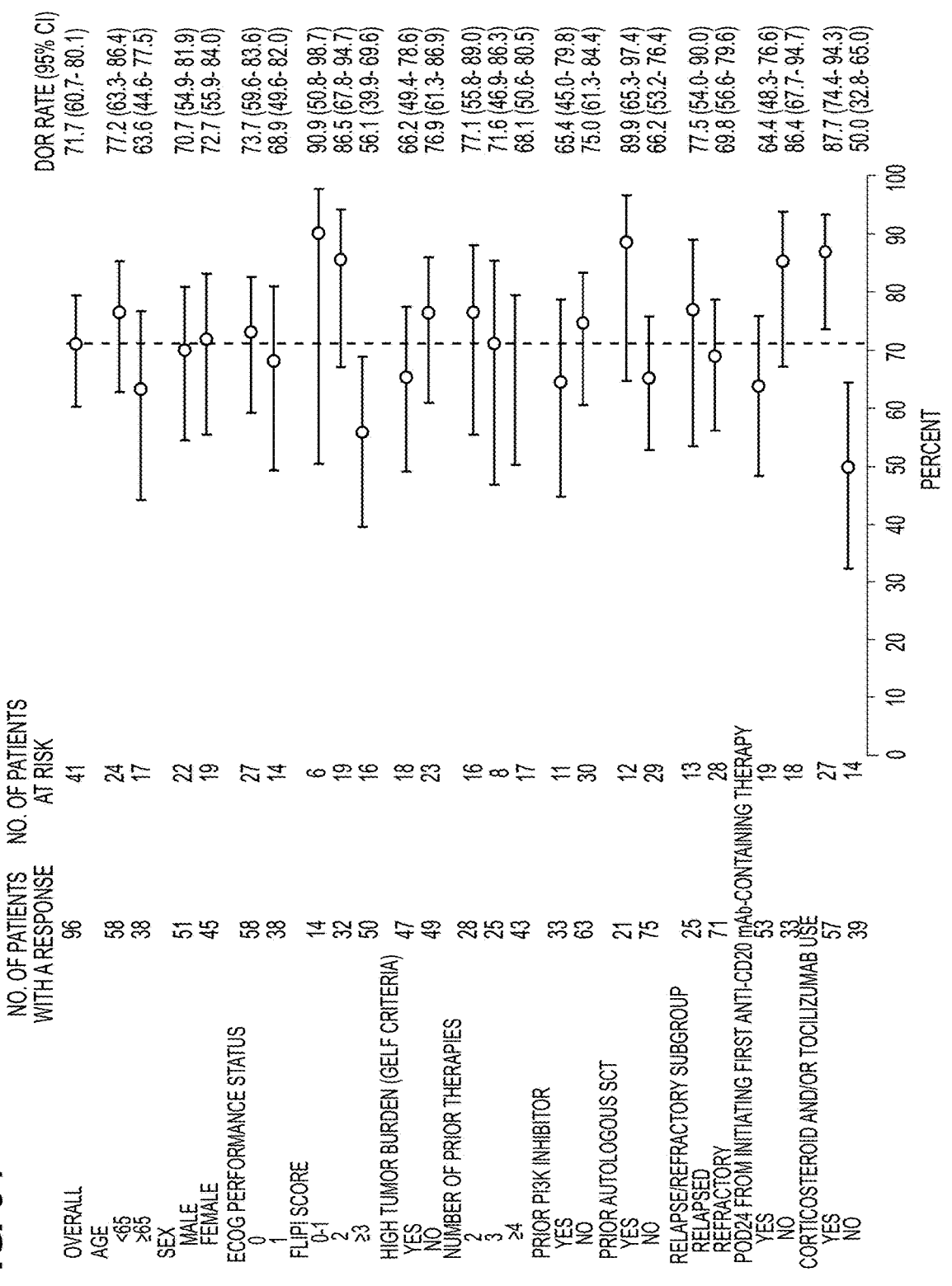

FIG. 94: Subgroup Analysis of 12-Month Duration of Response Rate. Figure shows a subgroup analysis for the estimated rate of duration of response at 12 months in all efficacy-evaluable patients with iNHL who had a response to axicabtagene ciloleucel by key patient baseline and clinical covariates. The Clopper-Pearson method was used to calculate the 95% confidence interval. Axi-cel, axicabtagene ciloleucel; DOR, duration of response; ECOG, Eastern Cooperative Oncology Group; FLIPI, Follicular Lymphoma International Prognostic Index; GELF, Groupe d'Etude des Lymphomes Folliculaires; iNHL, indolent non-Hodgkin lymphoma; PI3Ki, phosphoinositide 3-kinase inhibitor; POD24, Progression <24 months from initiating first anti-CD20 mAb-containing therapy; SCT, stem cell transplantation.

Figure 95:
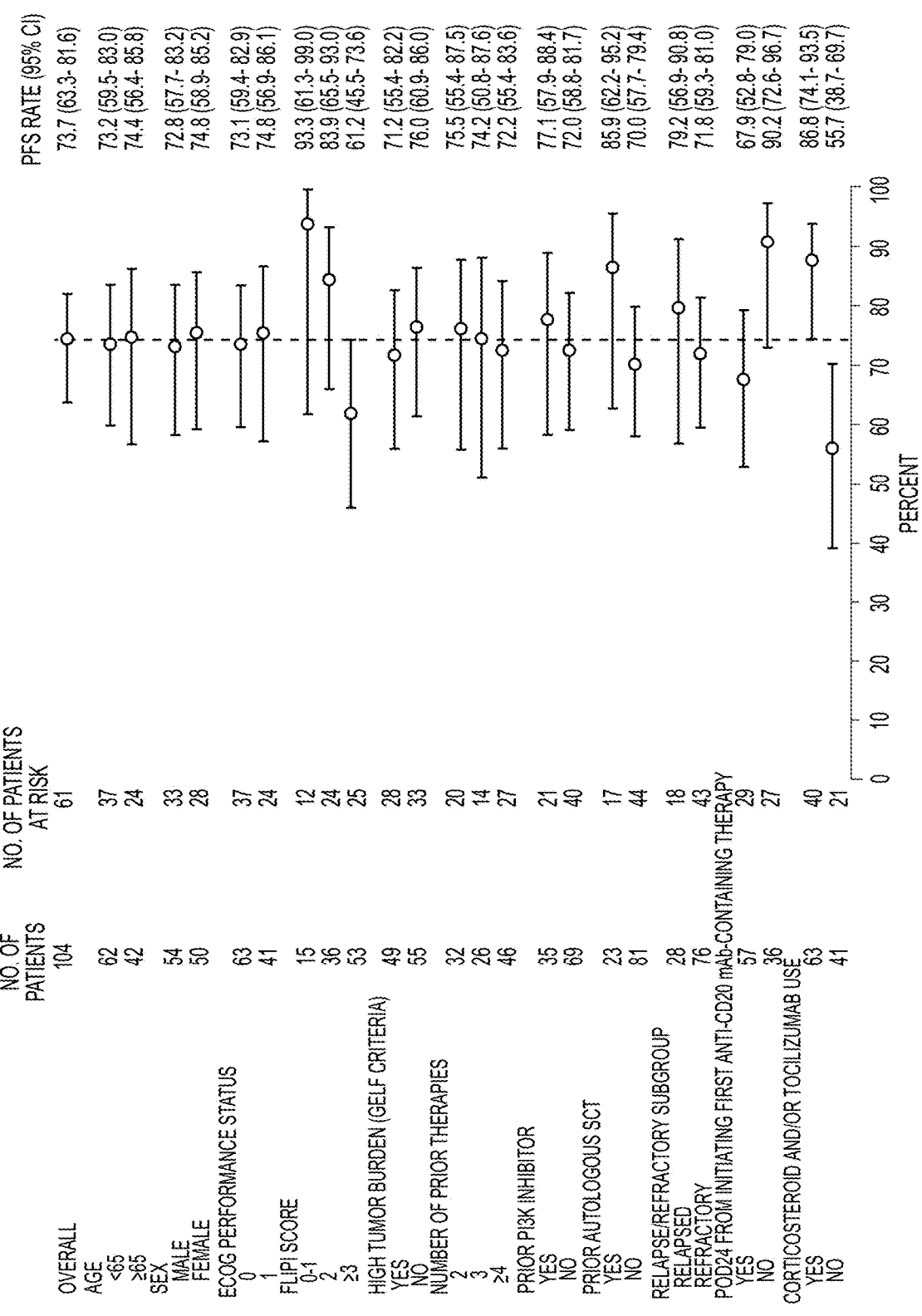

FIG. 95: Subgroup Analysis of 12-Month Progression-Free Survival Rate. Figure shows a subgroup analysis for the estimated rate of progression-free survival at 12 months in all efficacy-evaluable patients with iNHL by key patient baseline and clinical covariates. The Clopper-Pearson method was used to calculate the 95% confidence interval. Axi-cel, axicabtagene ciloleucel; ECOG, Eastern Cooperative Oncology Group; FLIPI, Follicular Lymphoma International Prognostic Index; GELF, Groupe d'Etude des Lymphomes Folliculaires; iNHL, indolent non-Hodgkin lymphoma; PFS, progression-free survival; PI3Ki, phosphoinositide 3-kinase inhibitor; POD24, Progression <24 months from initiating first anti-CD20 mAb-containing therapy; SCT, stem cell transplantation.

Figure 96:
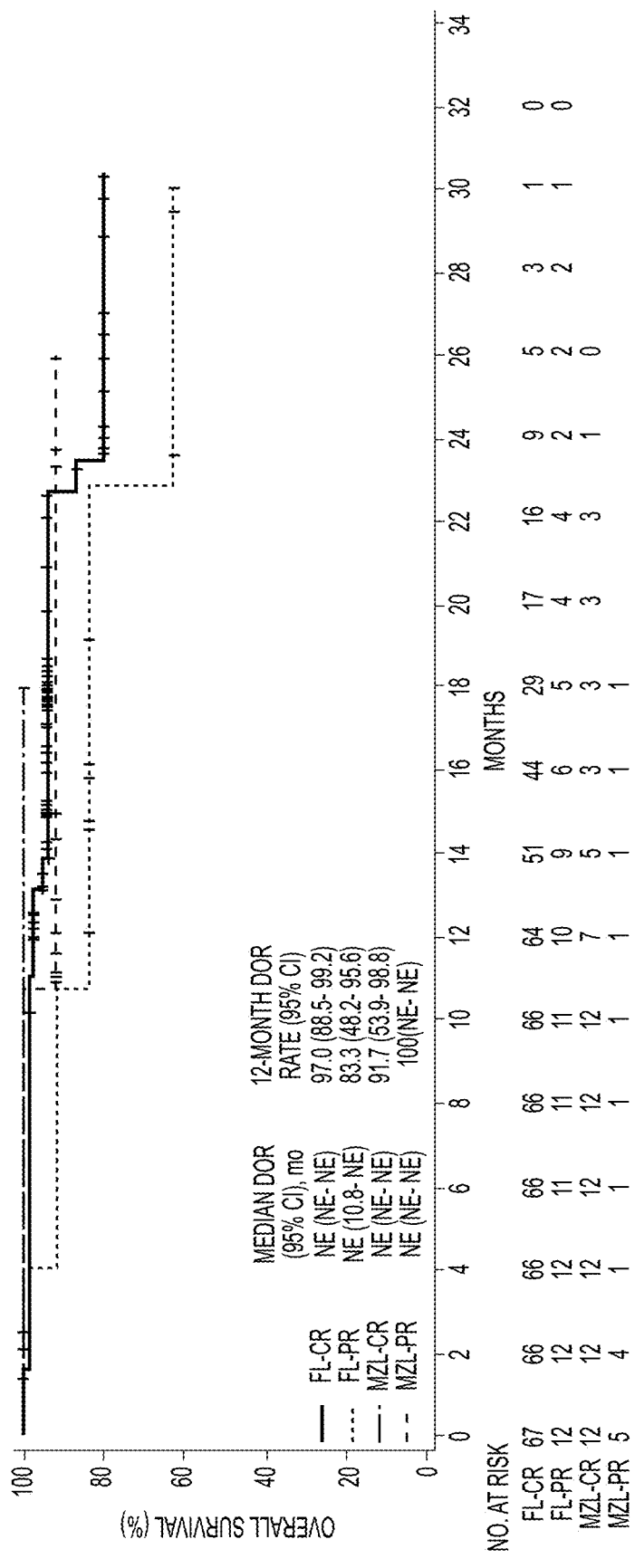
Figures 97A, 97B:
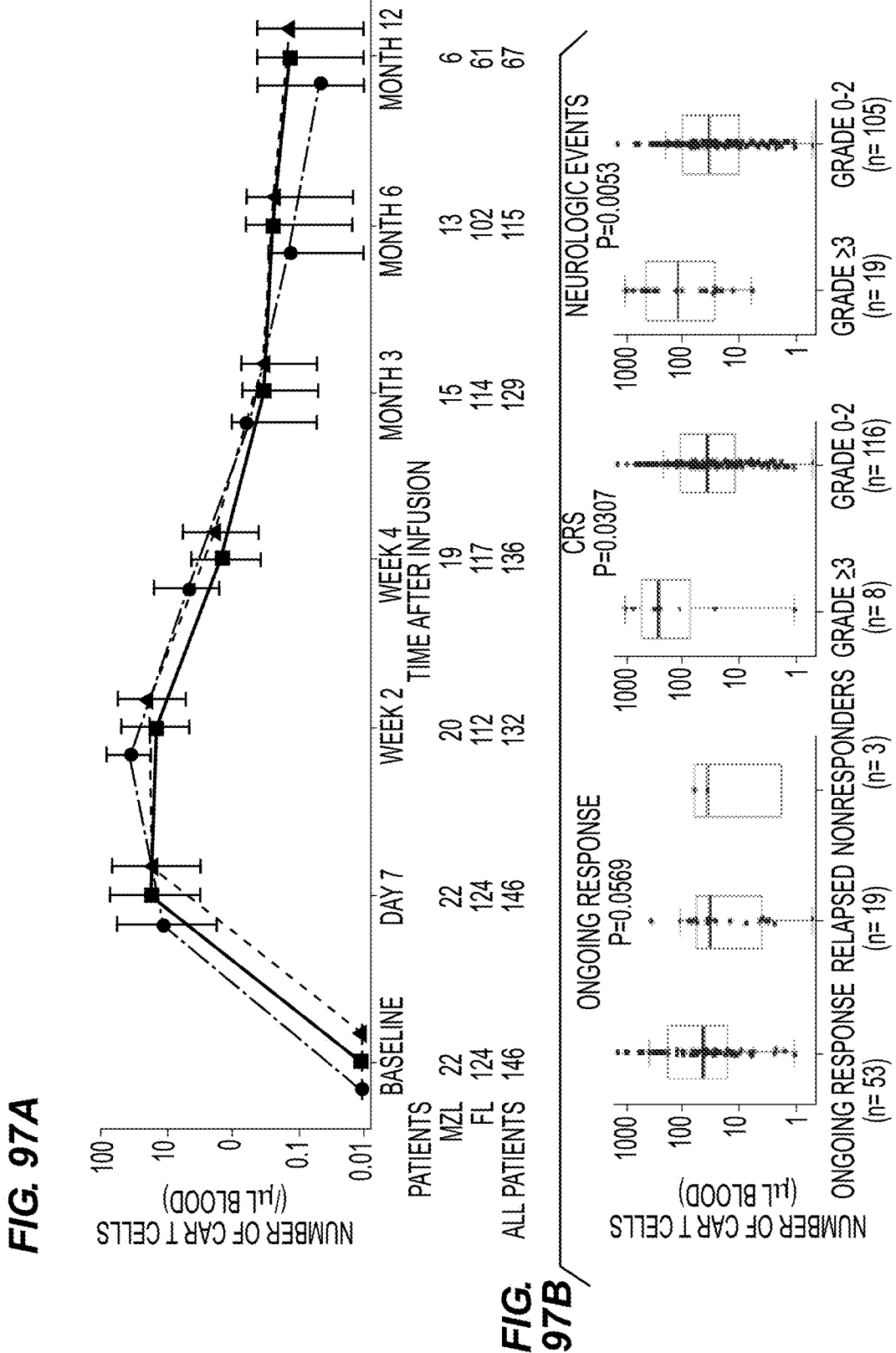
Figure 97C:
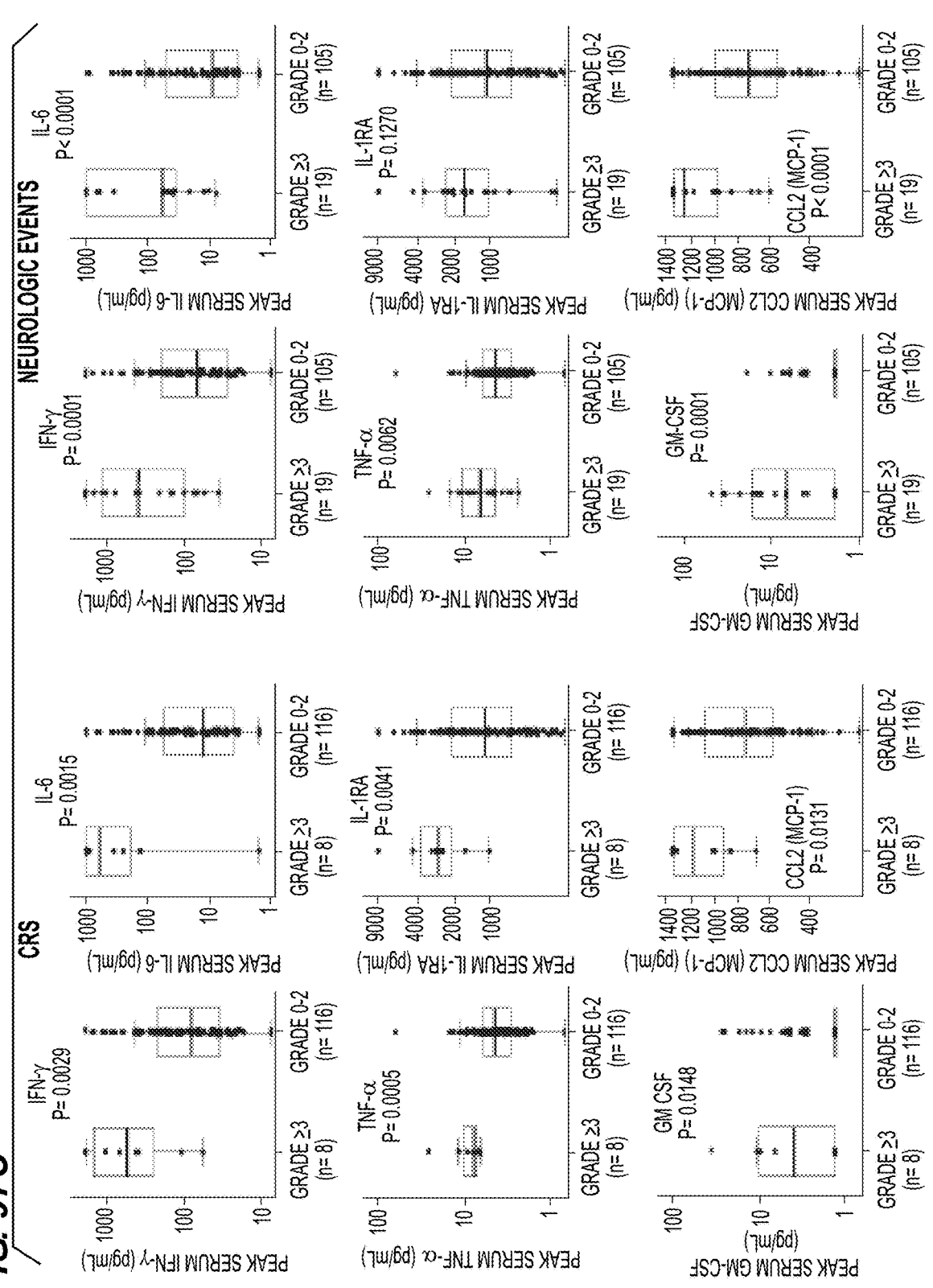

FIG. 96: Overall Survival by Best Overall Response. This figure shows Kaplan-Meier estimates of overall survival in efficacy-evaluable patients with FL or MZL who had a complete response or a partial response to axicabtagene ciloleucel. Confidence intervals were not adjusted for multiplicity. Axi-cel, axicabtagene ciloleucel; CR, complete response; FL, follicular lymphoma; MZL, marginal zone lymphoma; PR, partial response; NE, not estimable FIGS. 97A-97C: CAR T-Cell Expansion, Peak Serum Biomarkers, and Associations With Response and Adverse Events in Patients With FL. FIG. 97A shows expansion and persistence of CAR T-cells in all patients with iNHL, patients with FL, and patients with MZL. FIG. 97B shows the association between CAR T-cell expansion and ongoing response versus relapse in efficacy-evaluable patients with FL, and CRS and neurologic events in all treated patients with FL. FIG. 97C shows associations between key serum biomarkers and CRS and neurologic events in all treated patients with FL. P values were calculated using the Wilcoxon rank-sum test and were not adjusted for multiplicity. The median is represented by the horizontal line within each box, and the 25th and the 75th percentiles are represented by the lower and upper borders of each box. CAR, chimeric antigen receptor; CCL, C-C motif chemokine ligand; CRS, cytokine release syndrome; FL, follicular lymphoma; GM-CSF, granulocyte-macrophage colony-stimulating factor; IFN, interferon; IL, interleukin; iNHL, indolent non-Hodgkin lymphoma; MCP, monocyte chemoattractant protein; MZL, marginal zone lymphoma; TNF, tumor necrosis factor.

Figure 98A:
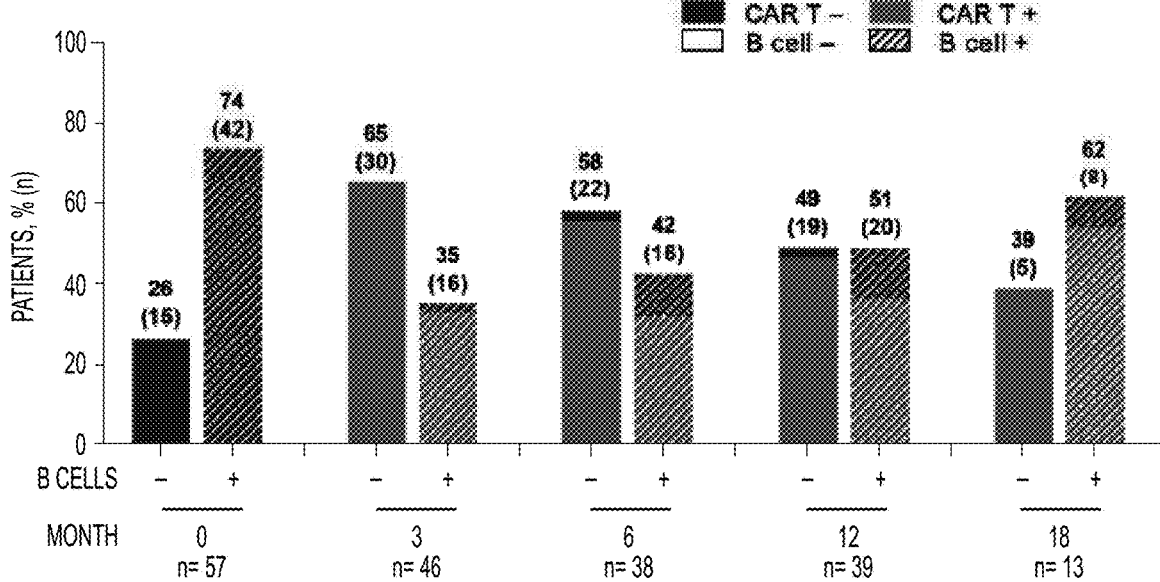
Figure 98B:
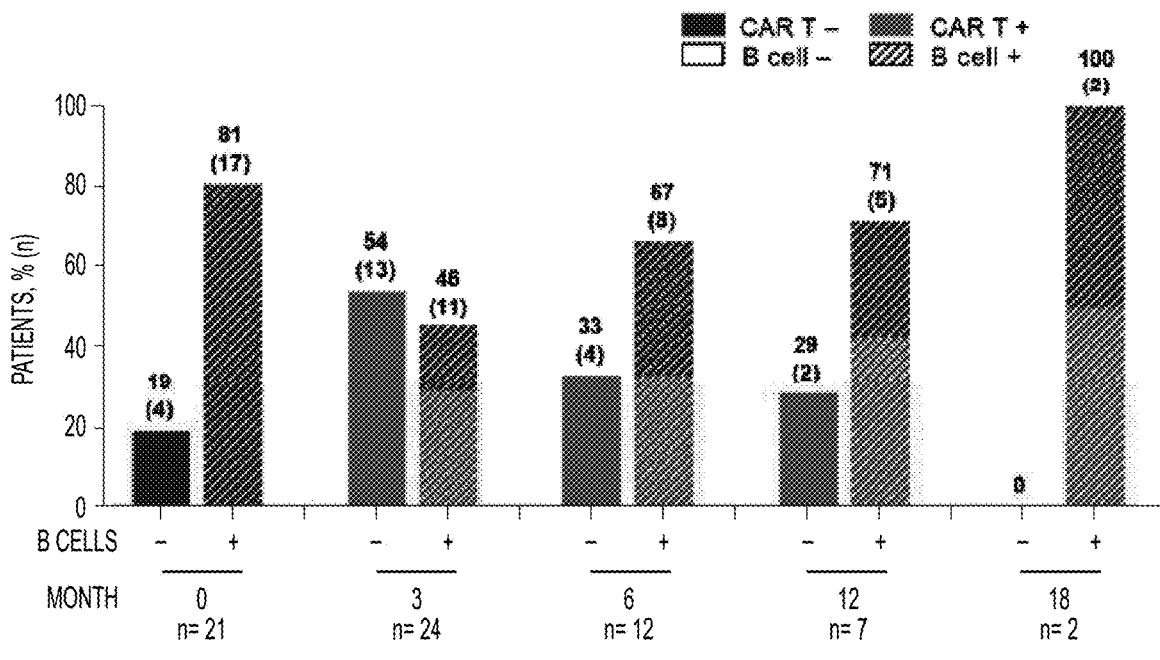

FIGS. 98A-98B: B-Cell Aplasia and CAR T-Cell Persistence at 12 Months in Ongoing Responders and Relapsed Patients. FIG. 98A shows the percentage of patients with or without detectable B cells and with or without detectable anti-CD19 CAR T cells at month 0 (baseline), 3, 6, 12, and 18 for efficacy-evaluable patients with iNHL in ongoing response at 12 months. FIG. 98B shows the percentage of patients with or without detectable B cells and with or without detectable anti-CD19 CAR T cells at month 0 (baseline), 3, 6, 12, and 18 for those patients who have relapsed at 12 months. CAR, chimeric antigen receptor.

FIGS. 99A-99B: Selected Inflammatory Biomarkers in Serum at Baseline and at Post-infusion Peak.

Figures 100A, 100B:
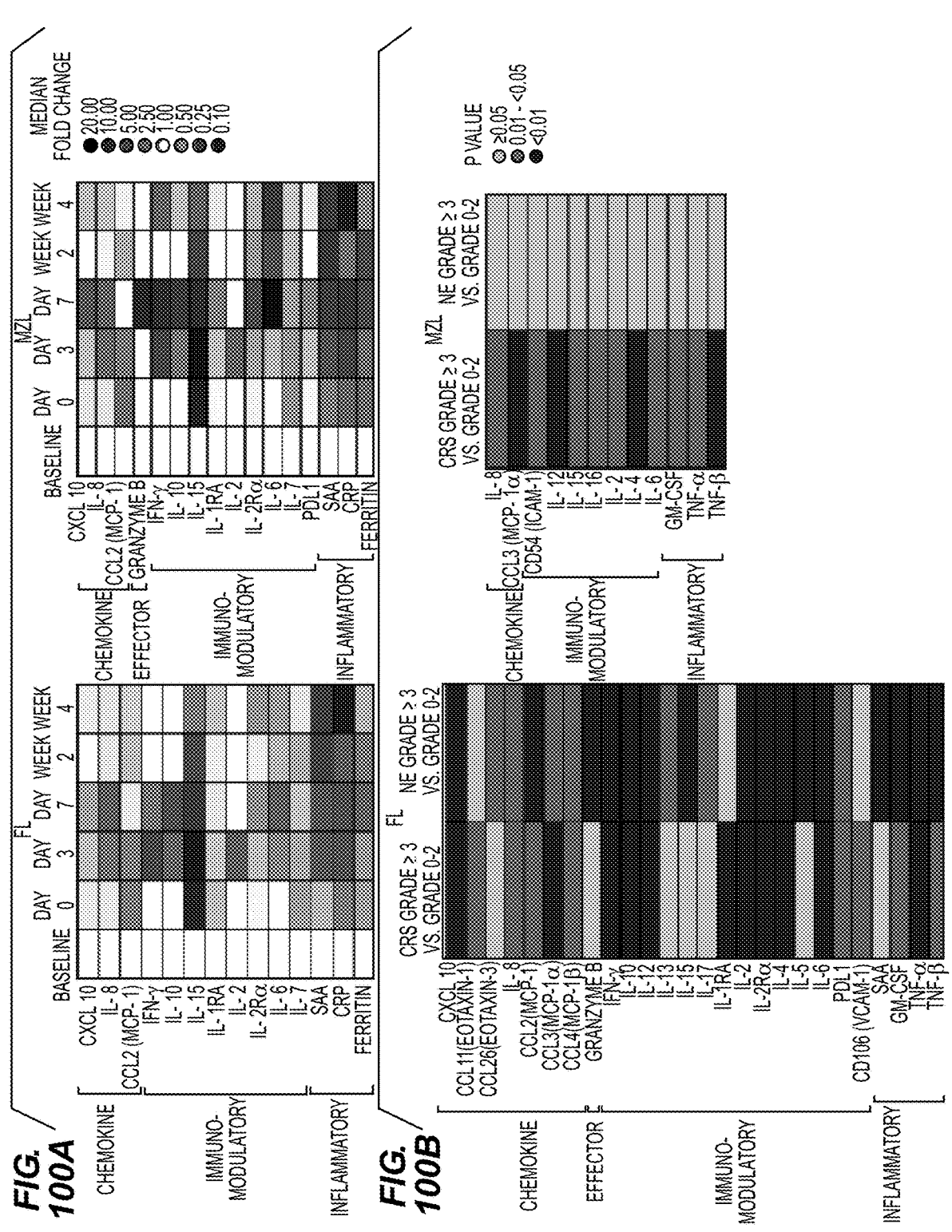

FIGS. 100A-100B: Longitudinal Profile of Cytokines. FIGS. 100A-100B show select key cytokine levels overtime by median fold change at each time point, represented by color, in patients with FL and MZL. Analytes that were elevated in ≥50% of patients with ≥2 fold of induction were selected. The majority of these analytes at peak level are associated with serious adverse events (except for IL-7). CCL, C-C motif chemokine ligand; CRP, C reactive protein; CXCL, C-X-C motif chemokine ligand; FL, follicular lymphoma; GM-CSF, granulocyte-macrophage colony-stimulating factor; IFN, interferon; ICAM, intercellular adhesion molecule; IL, interleukin; MCP-1, Monocyte Chemoattractant Protein-1; MZL, marginal zone lymphoma; PDL1, programmed death-ligand 1; Rα, receptor alpha; RA, receptor agonist; SAA, serum amyloid A; TNF, tumor necrosis factor; VCAM; vascular cell adhesion molecule.

FIG. 101: Association of Selected Serum Biomarkers with Ongoing Response in Patients with FL. *Assigned below the limit of quantification value for cytokine analysis in serum. † Assigned upper limit of quantification value for cytokine analysis in serum. P-values were calculated using Wilcoxon two-sample test. Baseline values were assessed at leukapheresis. CCL, C-C motif chemokine ligand; CRP, C-reactive protein; CXCL, C-X-C motif chemokine ligand; GM-CSF, granulocyte-macrophage colony-stimulating factor; IFN, interferon; IL, interleukin; IP, interferon γ-induced protein; MCP, monocyte attractant protein; MDC, macrophage-derived chemokine; MIP, macrophage inflammatory protein; Ra, receptor alpha; RA, receptor agonist; SAA, serum amyloid A; TARC, thymus and activation regulated chemokine; TNF, tumor necrosis factor.

Figure 102:
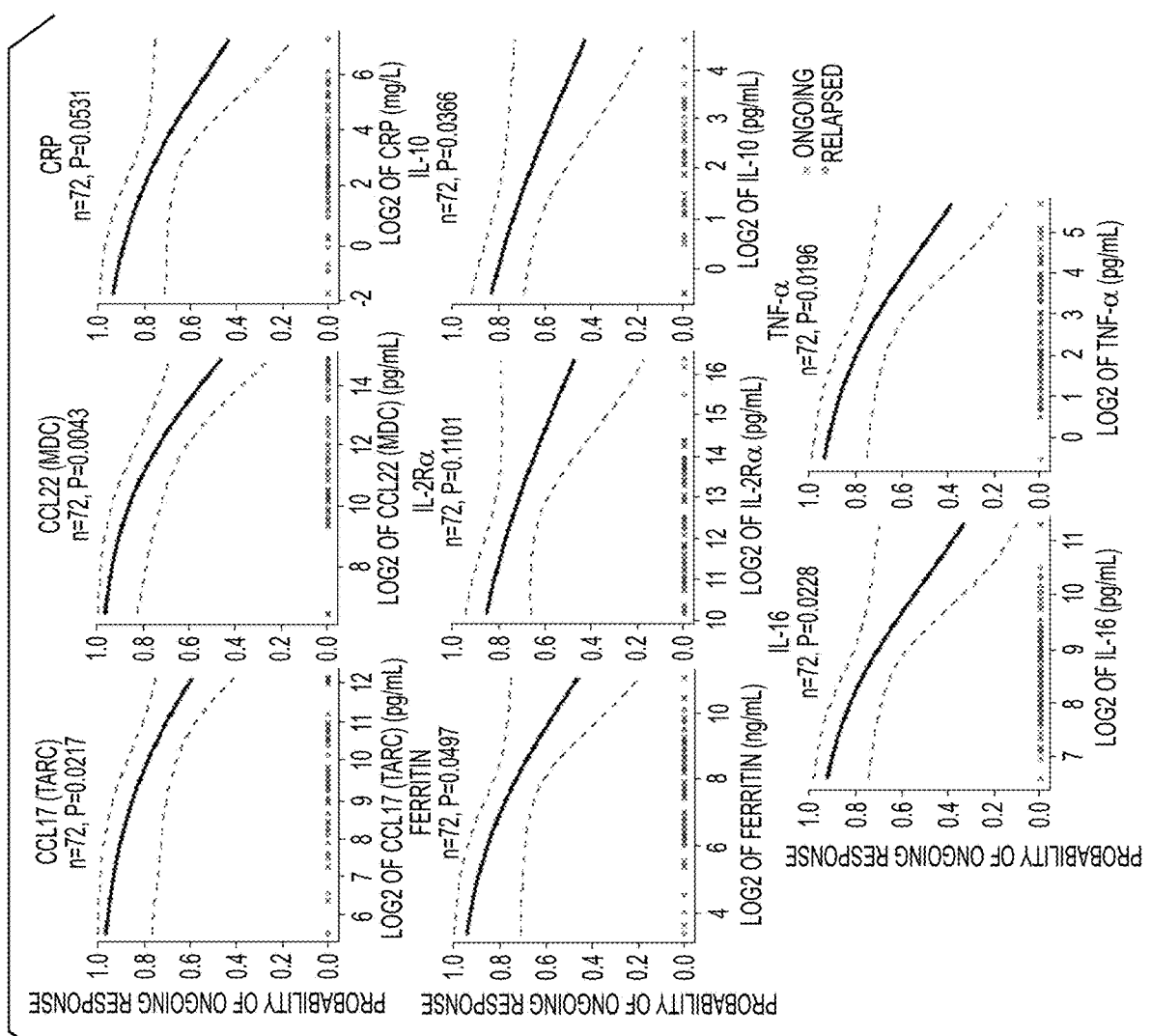

FIG. 102: Associations Between Baseline Cytokine Levels and Ongoing Response in Patients with Follicular Lymphoma. FIG. 102 shows logistic regression curves of key cytokines at baseline and association with ongoing response in efficacy-evaluable patients with follicular lymphoma. CCL, C-C motif chemokine ligand; CRP, C reactive protein; IL, interleukin; TARC, thymus and activation regulated chemokine; MDC, macrophage-derived chemokine; TNF, tumor necrosis factor.

FIG. 103: Association of Selected Serum Biomarkers with Cytokine Release Syndrome and Neurologic Events in Patients with FL.

Figure 104:
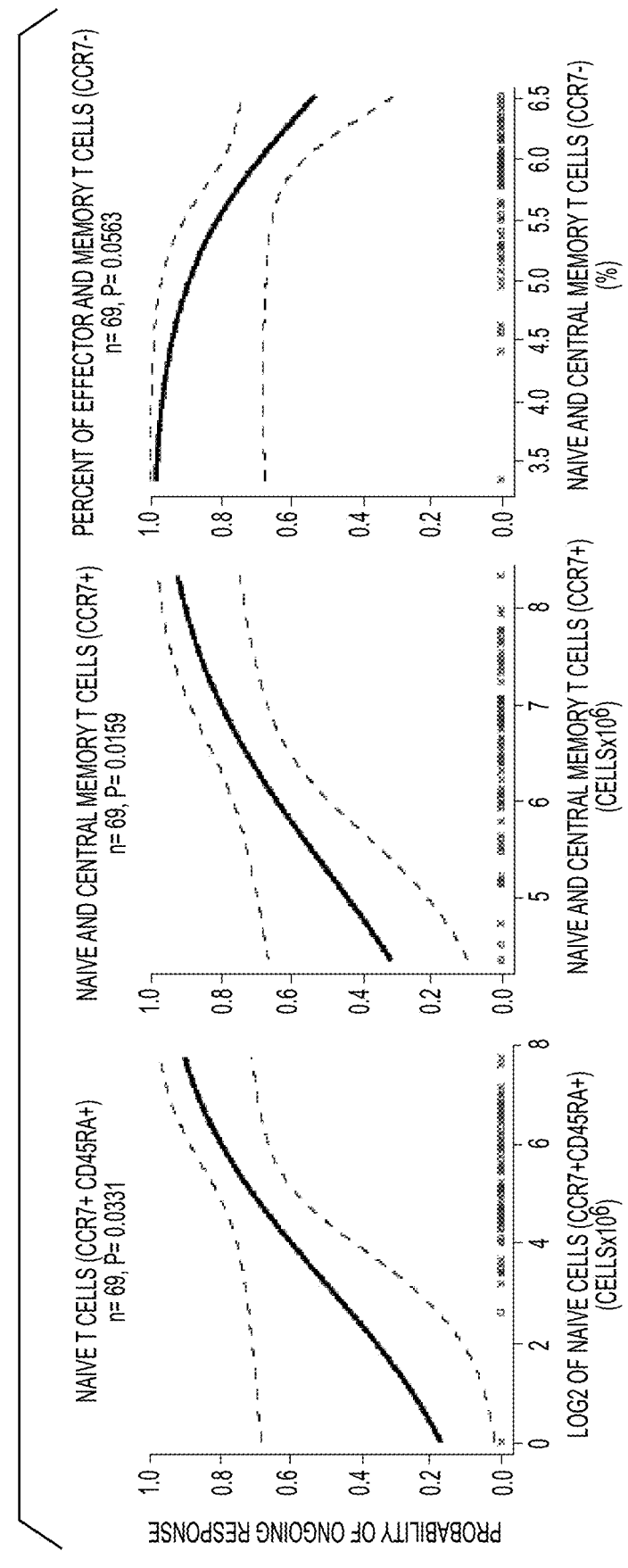

FIG. 104: Axicabtagene ciloleucel Product Characteristics Associated with Ongoing Response in patients with FL. FIG. 104 shows logistic regression curves of the number of naïve cells and memory T cells associated with ongoing response in patients with follicular lymphoma.

Figures 105A, 105B:
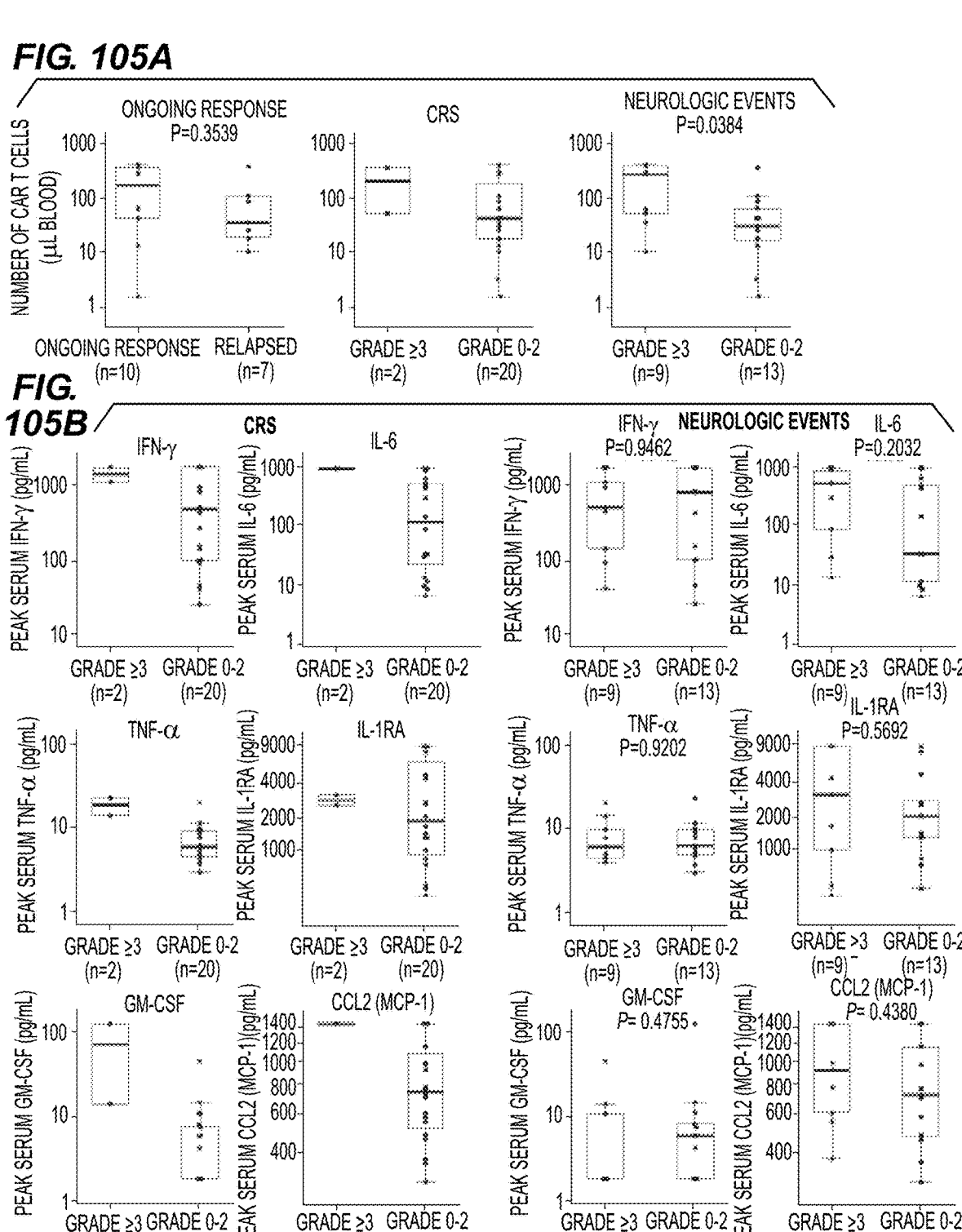

FIGS. 105A-105B: Associations Between CAR T-Cell Expansion, Peak Serum Biomarkers, Response, and Adverse Events in Patients with MZL. Panel A shows the association between CAR T-cell expansion and ongoing response in efficacy-evaluable patients with MZL, and CRS and neurologic events in all treated patients with MZL. Panel B shows associations between key serum biomarkers and CRS and NEs in all treated patients with MZL. P values for associations between cytokines and NEs were calculated using the Wilcoxon rank-sum test and were not adjusted for multiplicity. The median is represented by the horizontal line within each box, and the 25th and the 75th percentiles are represented by the lower and upper borders of each box. CAR, chimeric antigen receptor; CCL, C-C motif chemokine ligand; CRS, cytokine release syndrome; FL, follicular lymphoma; GM-CSF, granulocyte-macrophage colony-stimulating factor; IFN, interferon; IL, interleukin; iNHL, indolent non-Hodgkin lymphoma; MCP, monocyte chemoattractant protein; MZL, marginal zone lymphoma; TNF, tumor necrosis factor.

Figure 106:
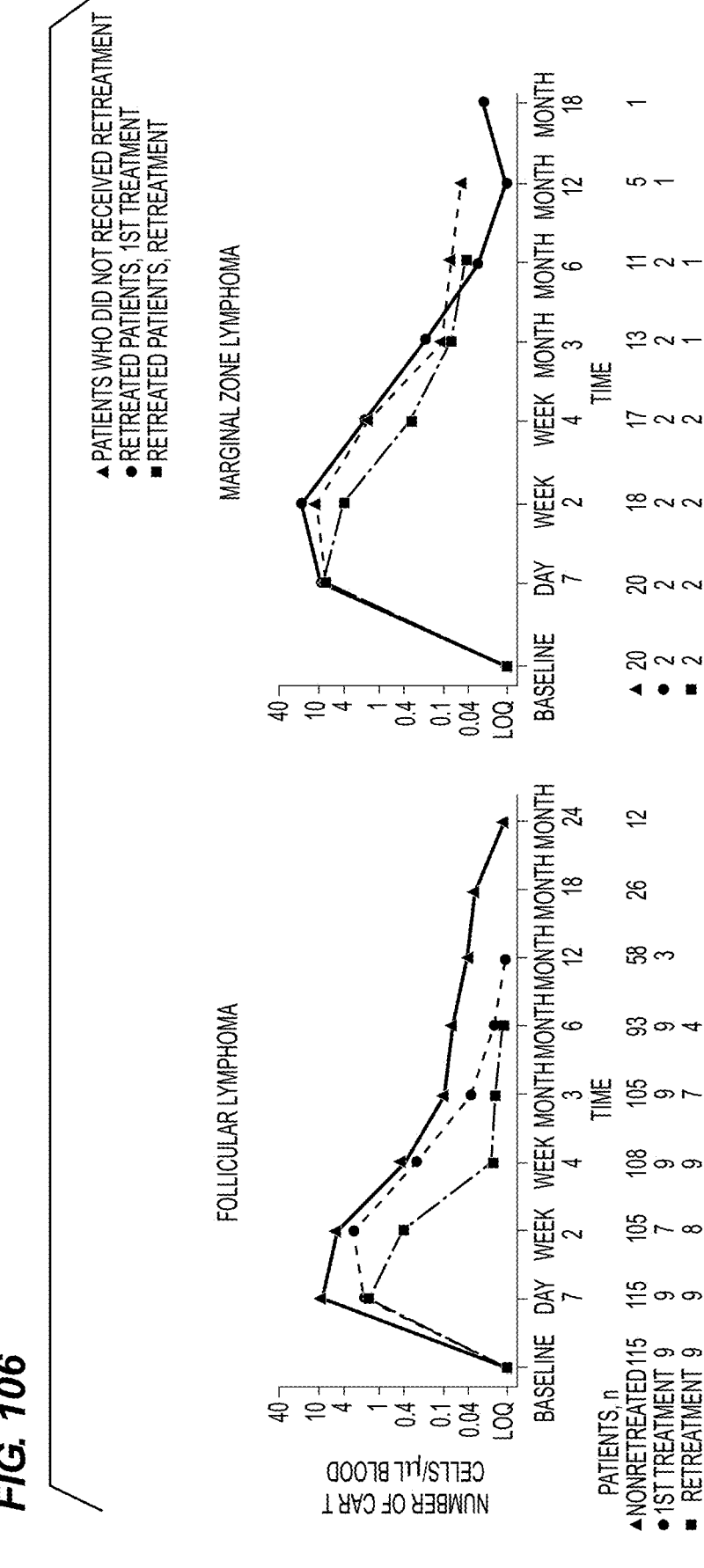

FIG. 106: CAR T Cell Levels Over Time. $AUC_{0-28}$, area under the curve between Day 0 and 28; CAR, chimeric antigen receptor; FL, follicular lymphoma; MZL, marginal zone lymphoma.

Figure 107:
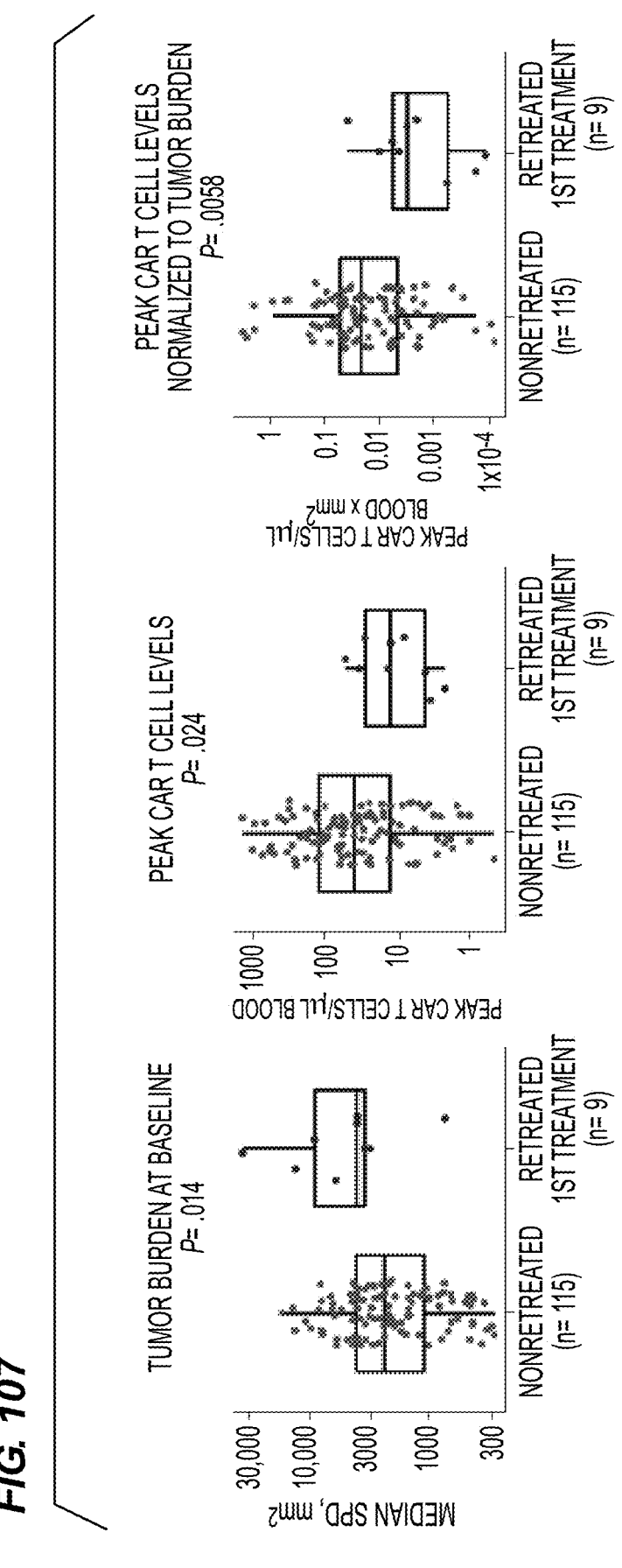

FIG. 107: Baseline Tumor Burden and CAR T Cell Expansion at First Treatment in Patients with FL. Specified groups were compared using the Wilcoxon signed-rank test. P values are descriptive and not adjusted for multiplicity. CAR, chimeric antigen receptor; FL, follicular lymphoma; SPD, sum of product diameters.

Figure 108:
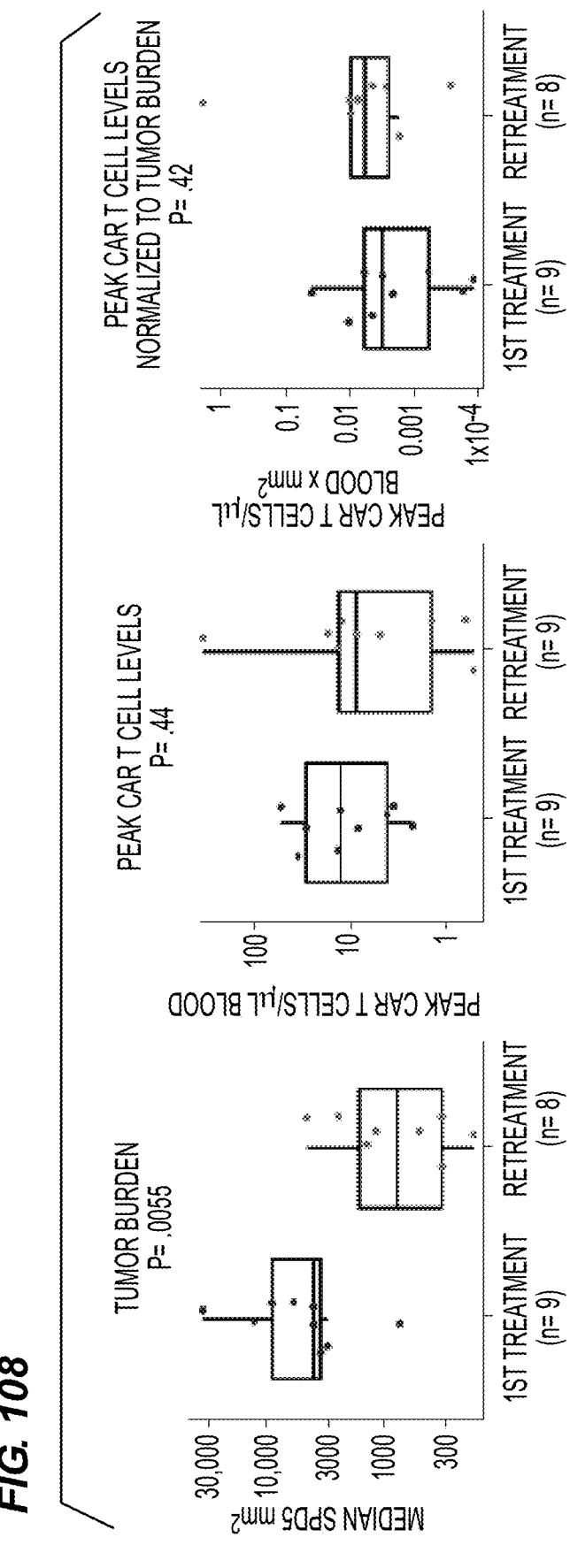

FIG. 108: Tumor Burden and CAR T Cell Expansion at Retreatment in Patients with FL. Specified groups were compared using the Wilcoxon signed-rank test. P values are descriptive and not adjusted for multiplicity. CAR, chimeric antigen receptor; FL, follicular lymphoma; IL, interleukin; SPD, sum of product diameters; TNF, tumor necrosis factor.

Figure 109:
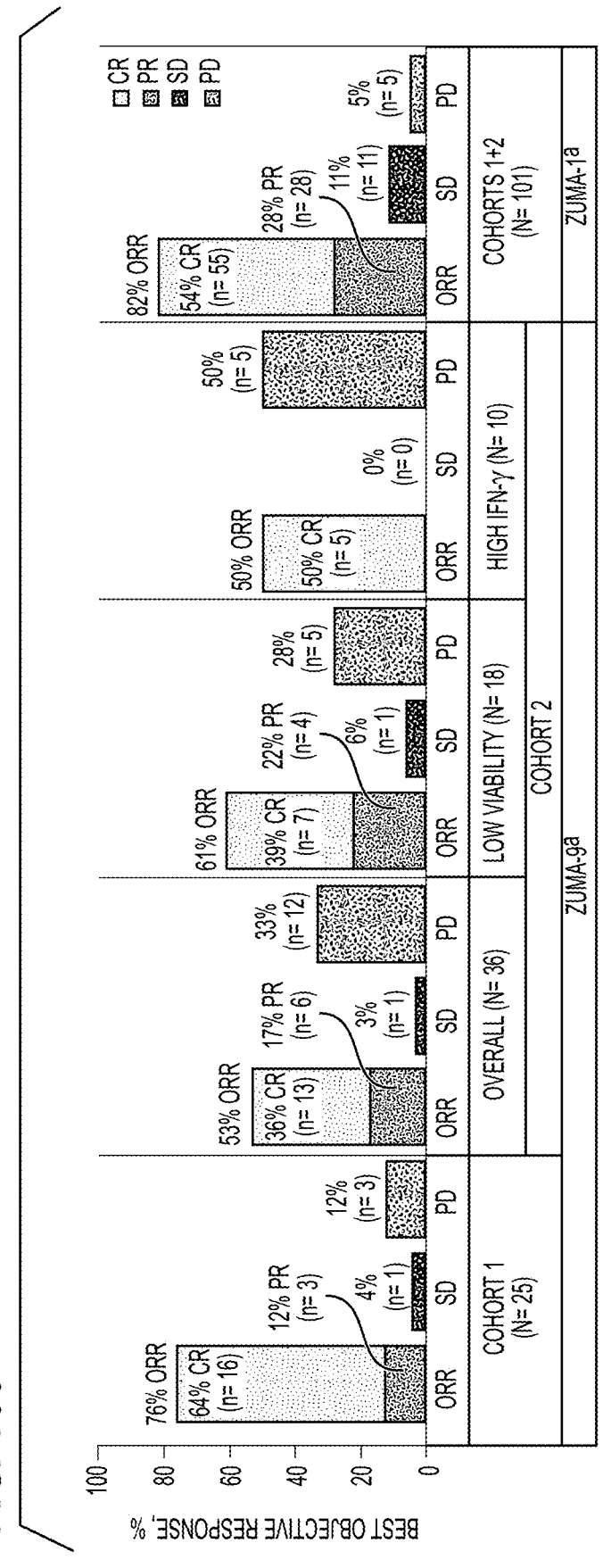

FIG. 109: Objective Response Rate for ZUMA-9 and ZUMA-1. [a] Does not show 2 patients in ZUMA-9 Cohort 1, 4 in ZUMA-9 Cohort 2 (1 with low viability), and 2 in ZUMA-1 Cohorts 1+2 for whom response was not done or not evaluable. CR, complete response; IFN-γ, interferon gamma; IRRC, independent radiology review committee; ORR, objective response rate; PD, progressive disease; PR, partial response; SD, stable disease.

Figure 110:
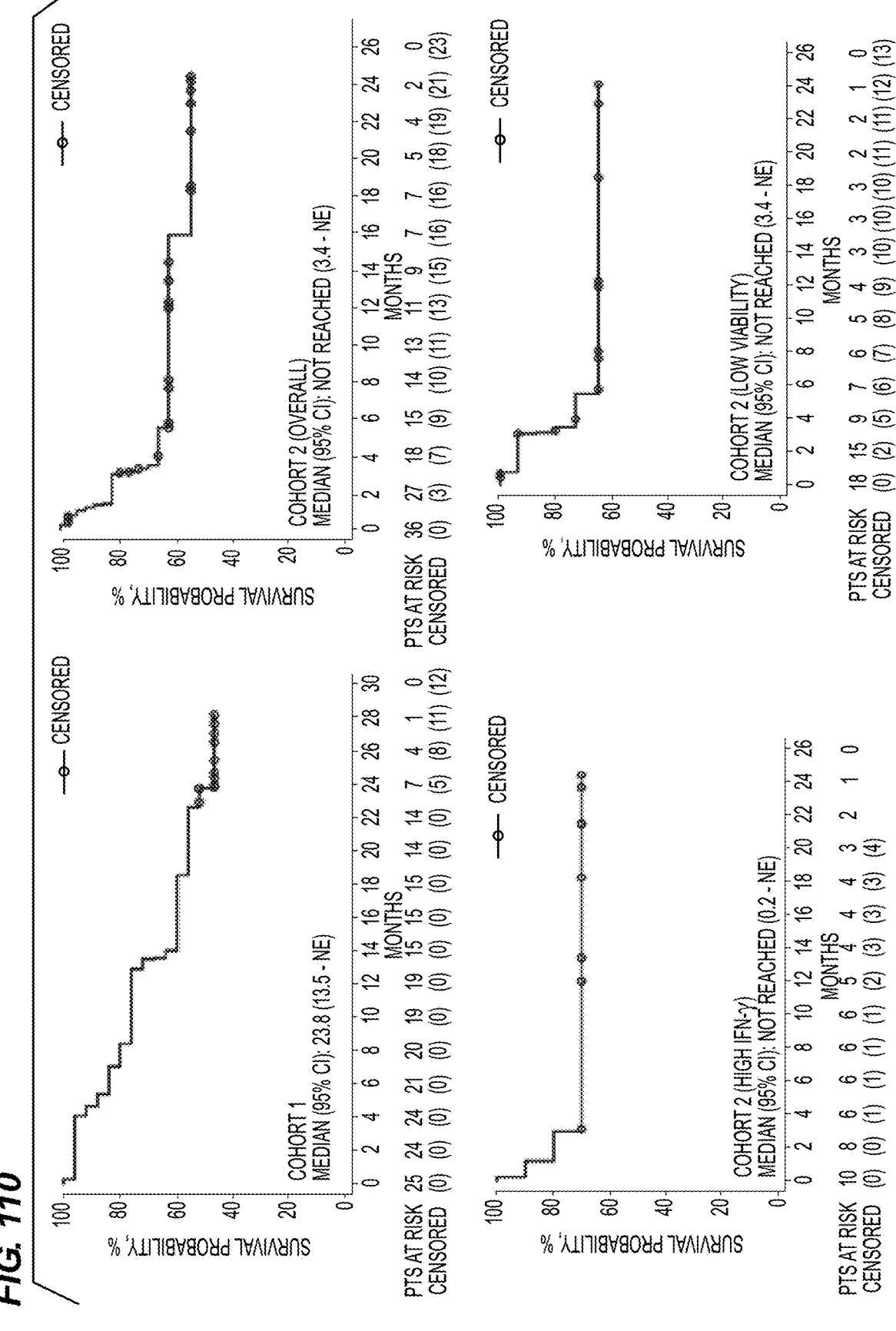

FIG. 110: Overall Survival for ZUMA-9. IFN-γ, interferon gamma; NE, not evaluable; NR, not reached; OS, overall survival; Pts, patients.

Figure 111:
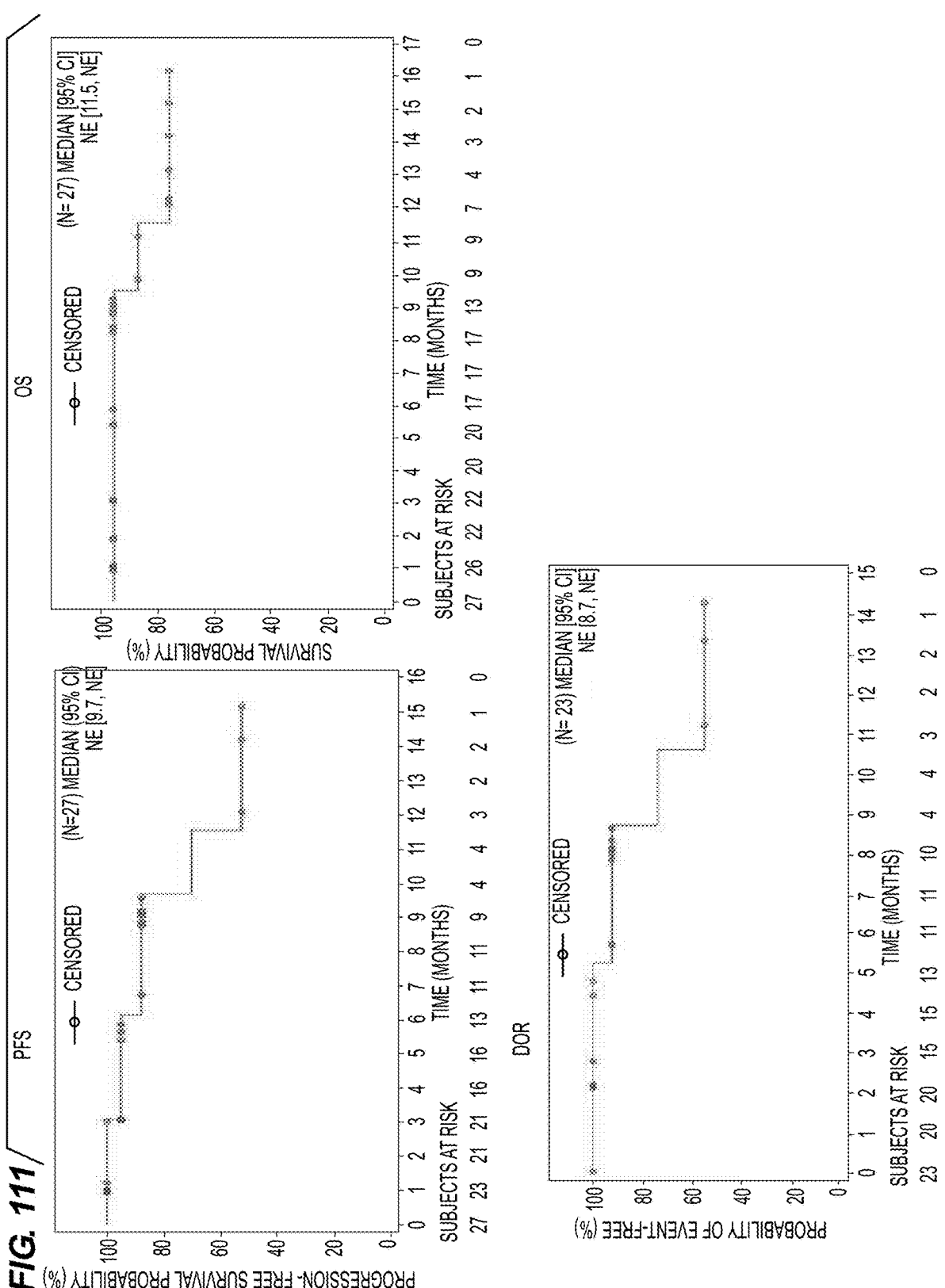
Figure 112:
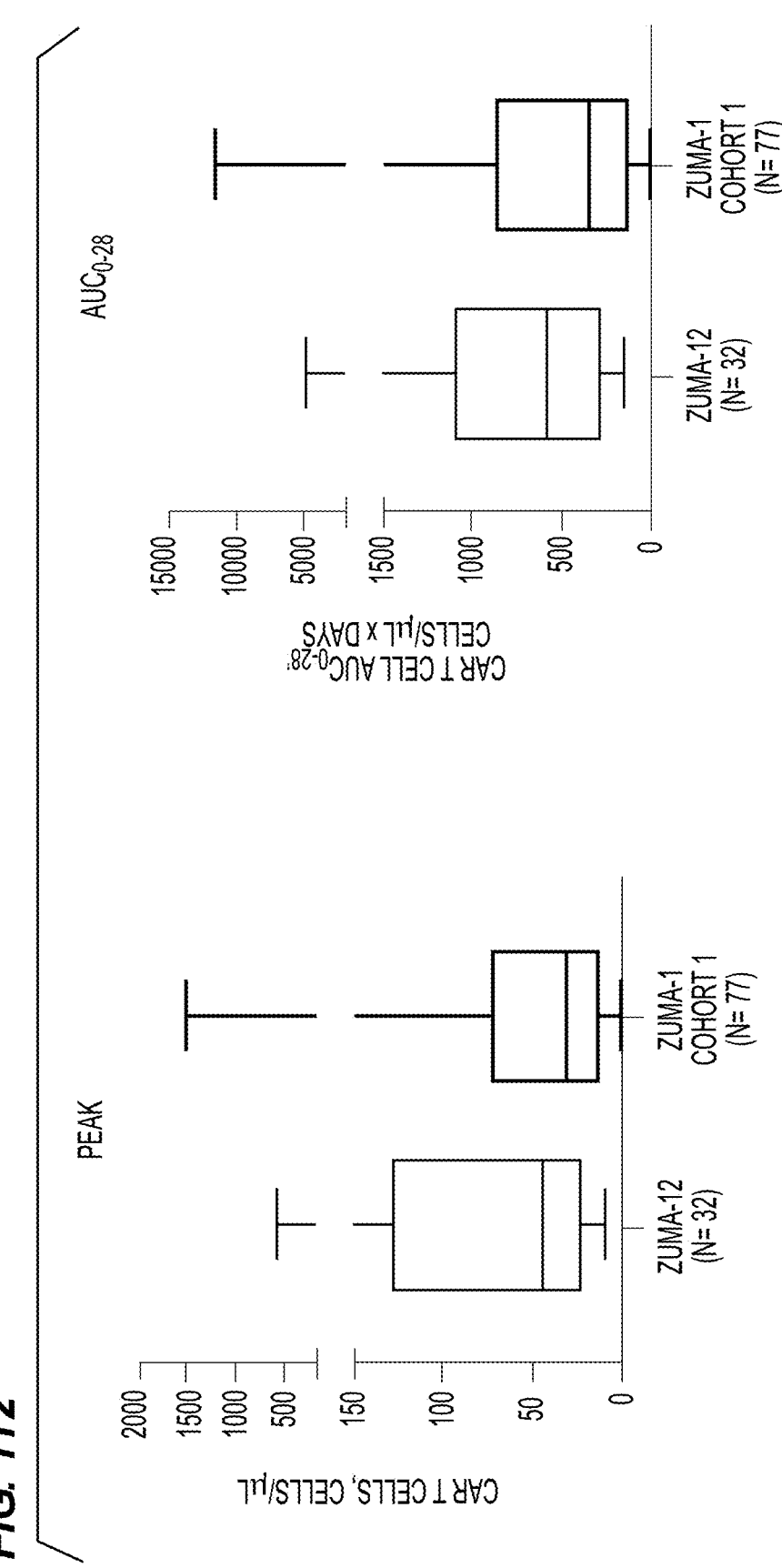

FIG. 111: Duration of Response and Survival Endpoints. DOR, duration of response; NE, not estimable; OS, overall survival; PFS, progression-free survival. FIG. 112: Overall Peak and AUC0-28. ZUMA-1 Cohort 1 includes all treated patients who received any dose of axicabtagene ciloleucel and have ≥24 months of follow-up. Blood draws for CAR T cell levels were collected prior to leukapheresis and on Day 7, Weeks 2 and 4, and Month 3. CART cell concentrations were assessed by validated polymerase chain reaction enumerating gene-marked cells in blood. Tumor burden median was determined by the SPD of target lesions and is based on that of ZUMA-1 Cohort 1. P values were calculated using Wilcoxon rank sum test. $AUC_{0-28}$, area under the curve from Day 0 to Day 28; CAR, chimeric antigen receptor; DLBCL, diffuse large B cell lymphoma; IPI, International Prognostic Index; SPD, sum of product diameters.

FIG. 112: Peak levels of CART cells in blood for ZUMA-12 and ZUMA-1.

Figure 113:
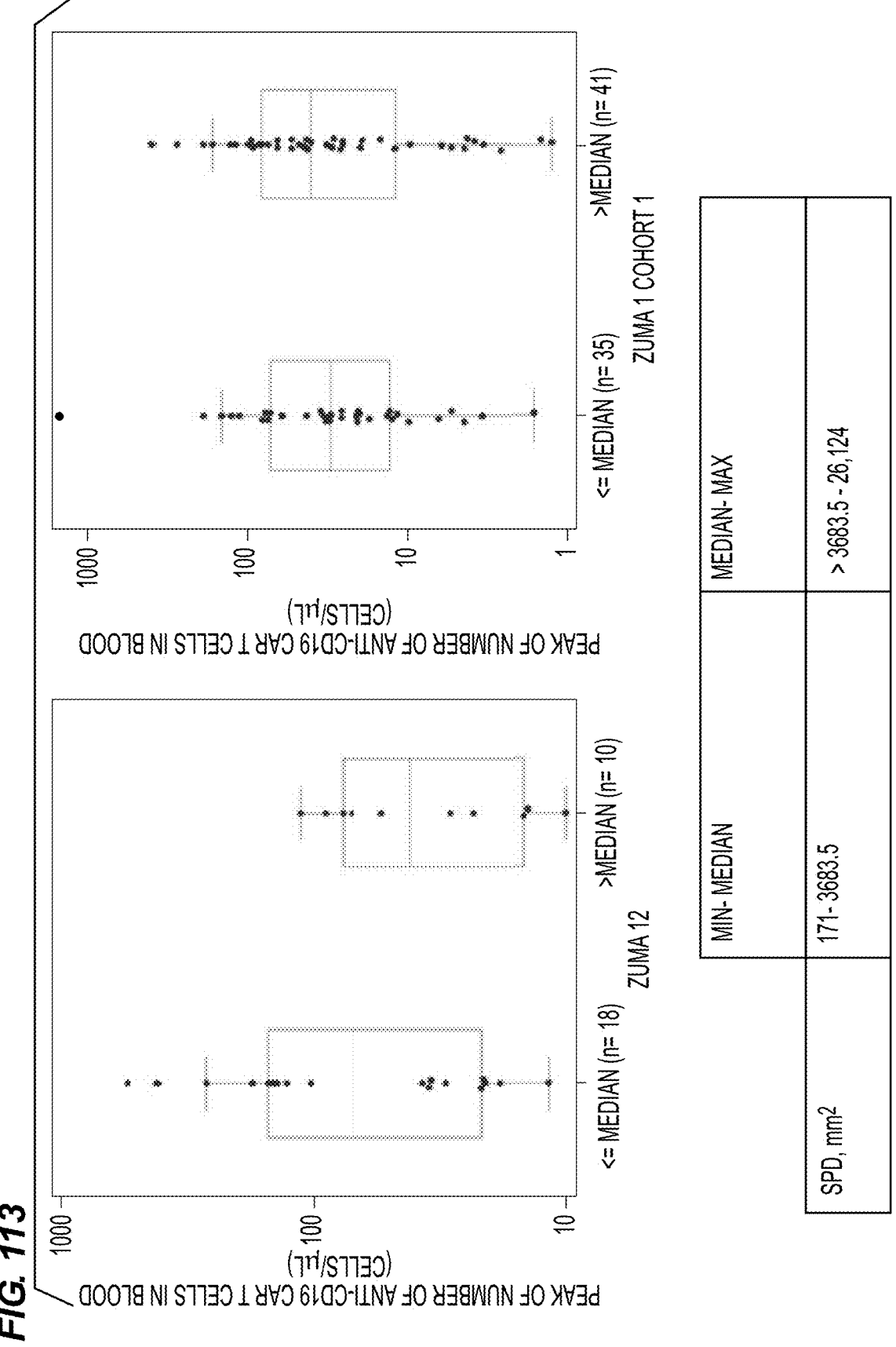

FIG. 113: Peak by Tumor Burden Median. Peak of number of anti-CD19 CART cells in blood (cells/μL).

Figure 114:
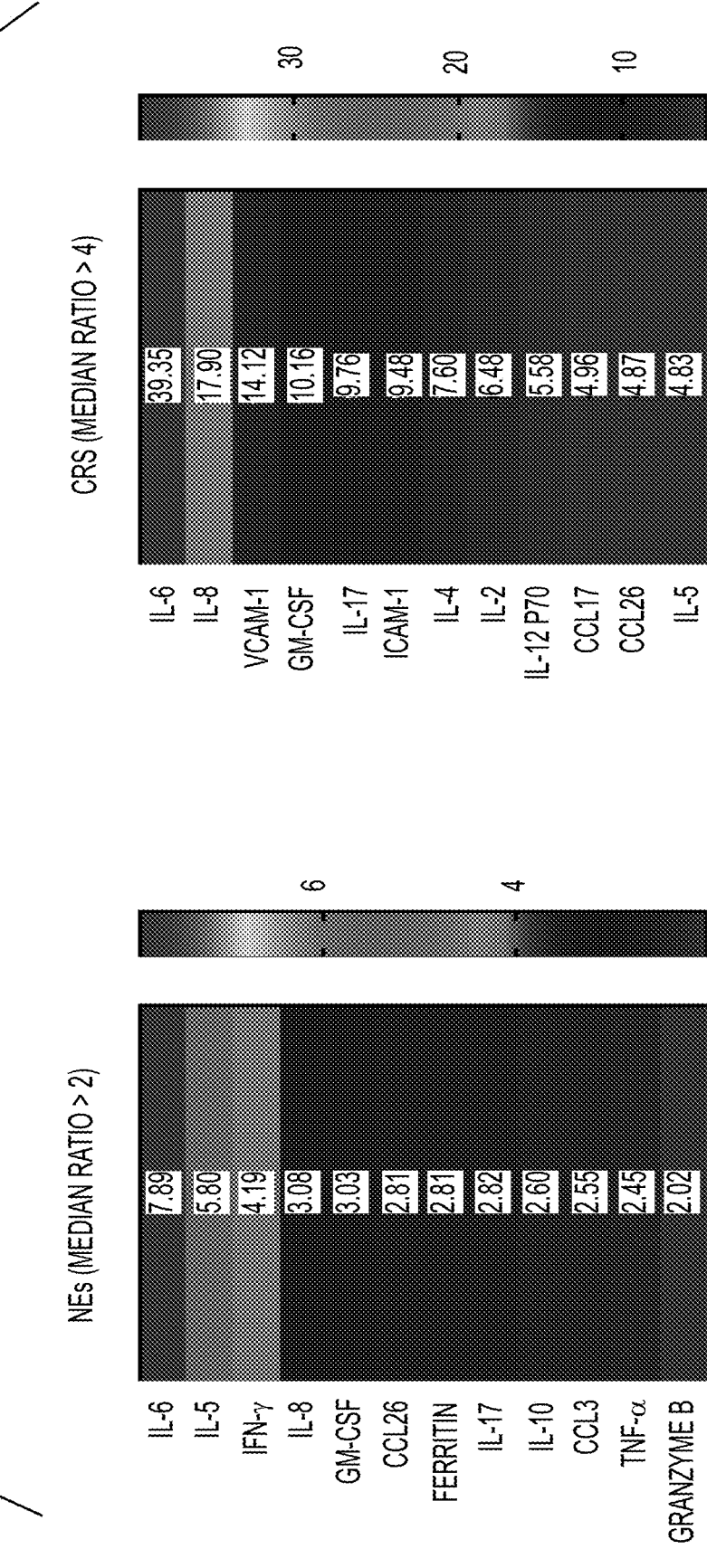

FIG. 114: Median Peak Serum Cytokines Associated with Severe NEs or CRS in ZUMA-12. Bloods draws for cytokines were collected prior to leukapheresis, on Day 0 prior to administration of axicabtagene ciloleucel, and on Days 1, 3, and 7, and Weeks 2 and 4. Cytokines associated with NEs and CRS were selected for having median ratio >2 after taking the ratio of median peak levels in Grade ≥3 events to Grade <3 events. The resultant values with ratio >2 for NEs and >4 for CRS are depicted. Bloods draws for cytokines were collected prior to leukapheresis, on Day 0 prior to administration of axicabtagene ciloleucel, and on Days 1, 3, and 7, and Weeks 2 and 4. Cytokines associated with NEs and CRS were selected for having median ratio >2 after taking the ratio of median peak levels in Grade ≥3 events to Grade <3 events. The resultant values with ratio >2 for NEs and >4 for CRS are depicted.

FIG. 115: Summary of ZUMA-1 Study Design. [a] Includes adult patients with DLBCL, PMBCL, TFL, and high-grade B cell lymphoma after >2 systemic lines of therapy. [b] 20 to 40 mg/d or equivalent daily for 1 to 4 days, completed before conditioning chemotherapy. [c] Methylprednisolone 1 g/m$^2$ daily for 3 days+rituximab (375 mg/m$^2$ weekly), completed at least 7 days before conditioning chemotherapy. [d] Bendamustine 90 mg/m$^2$ daily for 2 days+rituximab (375 mg/m$^2$ for 1 day), completed at least 14 days before conditioning chemotherapy. [e] Flat dose of 2×10$^8$ CAR+ T cells/kg for patients with body weight >100 kg. AE, adverse event; ASCT, autologous stem cell transplantation; axi-cel, axicabtagene ciloleucel; CAR, chimeric antigen receptor; CRS, cytokine release syndrome; DLBCL, diffuse large B-cell lymphoma; LBCL, large B-cell lymphoma; NE, neurologic event; PMBCL, primary mediastinal B-cell lymphoma; R/R, relapsed/refractory; TFL, transformed follicular lymphoma FIG. 116: Adverse Events Management in ZUMA-1. [a] Only in case of comordbidities or older age. [b] Only if no improvement with tocilizumab; use standard dose. [c] If no improvement after 24 hours of supportive care in Cohort 6. [d] If no improvement after 3 days. [e] Only for Grade ≥2 NEs with concurrent CRS in Cohort 6. AE, adverse event; CRS, cytokine release syndrome; HD, high dose; mgmt, management; NE neurologic event. 1. Neelapu S S, et al. *N Engl J Med.* 2017; 377:2531-2544. 2. Oluwole O O, et al. Manuscript under review.

Figure 117:
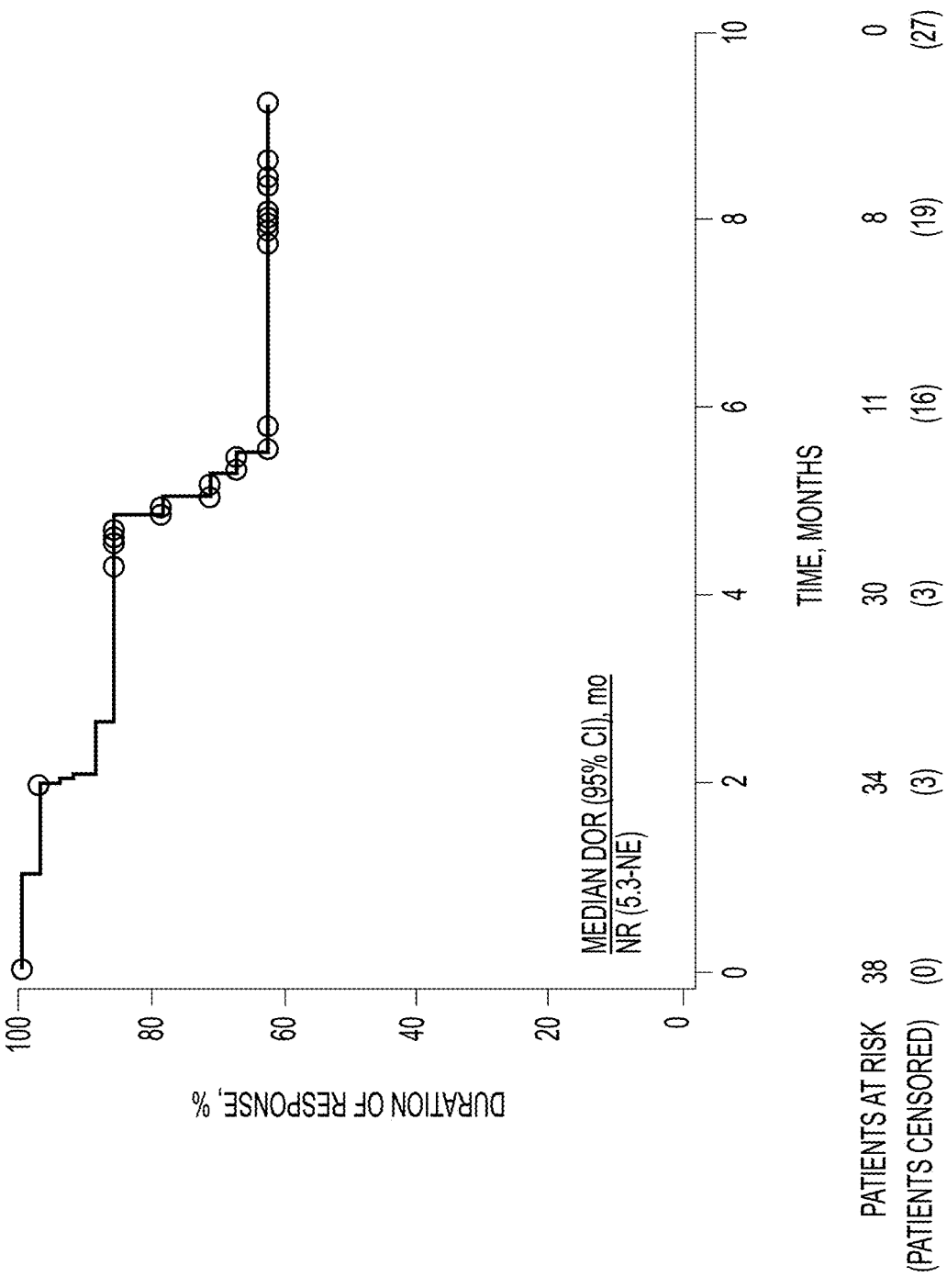

FIG. 117: Duration of Response

DETAILED DESCRIPTION

The present disclosure is based in part on the discovery that pre-infusion attributes (e.g., T cell fitness) of apheresis material and engineered CAR T cells, as well as pretreatment characteristics of patients' immune factors and tumor burden may be associated with clinical efficacy and toxicity including durable responses, grade cytokine release syndrome, and grade 3 neurologic events.

Definitions

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided. The term "consisting of" excludes any element, step, or ingredient not specified in the claim. *In re Gray*, 53 F.2d 520, 11 USPQ 255 (CCPA 1931); *Ex parte Davis*, 80 USPQ 448, 450 (Bd. App. 1948) ("consisting of" defined as "closing the claim to the inclusion of materials other than those recited except for impurities ordinarily associated therewith"). The term "consisting essentially of" limits the scope of a claim to the specified materials or steps "and those that do not materially affect the basic and novel characteristic(s)" of the claimed invention.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Systeme International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. Exemplary routes of administration for the compositions disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods. In one embodiment, the CAR T cell treatment is administered via an "infusion product" comprising CAR T cells.

The term "antibody" (Ab) includes, without limitation, a glycoprotein immunoglobulin which binds specifically to an antigen. In general, an antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocks a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

In one embodiment, the CAR T cell treatment comprises "axicabtagene ciloleucel treatment". "Axicabtagene ciloleucel treatment" consists of a single infusion of anti-CD19 CAR transduced autologous T cells administered intravenously at a target dose of $2 \times 106$ anti-CD19 CAR T cells/kg. For subjects weighing greater than 100 kg, a maximum flat dose of $2 \times 108$ anti-CD19 CAR T cells may be administered. The anti-CD19 CAR T cells are autologous human T cells that have been engineered to express an extracellular single-chain variable fragment (scFv) with specificity for CD19 linked to an intracellular signaling part comprised of signaling domains from CD28 and CD3 (CD3-zeta) molecules arranged in tandem anti-CD19 CAR vector construct has been designed, optimized and initially tested at the Surgery Branch of the National Cancer Institute (NCI, IND 13871) (Kochenderfer et al, *J Immunother.* 2009; 32(7):689-702; Kochenderfer et al, *Blood.* 2010; 116(19):3875-86). The scFv is derived from the variable region of the anti-CD19 monoclonal antibody FMC63 (Nicholson et al, *Molecular Immunology.* 1997; 34(16-17):1157-65). A portion of the CD28 costimulatory molecule is added, as murine models suggest this is important for the anti-tumor effect and persistence of anti-CD19 CAR T cells (Kowolik et al, *Cancer Res.* 2006; 66(22):10995-1004). The signaling domain of the CD3-zeta chain is used for T cell activation. These fragments were cloned into the murine stem cell virus-based (MSGV1) vector, utilized to genetically engineer the autologous T cells. The CAR construct is inserted into the T cells' genome by retroviral vector transduction. Briefly, peripheral blood mononuclear cells (PBMCs) are obtained by leukapheresis and Ficoll separation. Peripheral blood mononuclear cells are activated by culturing with an anti-CD3 antibody in the presence of recombinant interleukin 2 (IL-2). Stimulated cells are transduced with a retroviral vector containing an anti-CD19 CAR gene and propagated in culture to generate sufficient engineered T cells for administration. Axicabtagene ciloleucel is a subject-specific product.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. In this application, the term cancer is synonymous with malignancy. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, [add other solid tumors] multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. In some embodiments, the cancer is NHL. The particular cancer may be responsive to chemo- or radiation therapy or the cancer may be refractory. A refractory cancer refers to a cancer that is not amenable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p'70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, "chimeric receptor" refers to an engineered surface expressed molecule capable of recognizing a particular molecule. Chimeric antigen receptors (CARs) and engineered T cell receptors (TCRs), which comprise binding domains capable of interacting with a particular tumor antigen, allow T cells to target and kill cancer cells that express the particular tumor antigen. In one embodiment, the T cell treatment is based on T cells engineered to express a chimeric antigen receptor (CAR) or a T cell receptor (TCR), which comprises (i) an antigen binding molecule, (ii) a costimulatory domain, and (iii) an activating domain. The costimulatory domain may comprise an extracellular domain, a transmembrane domain, and an intracellular domain, wherein the extracellular domain comprises a hinge domain, which may be truncated.

A "therapeutically effective amount," "effective dose," "effective amount," or "therapeutically effective dosage" of a therapeutic agent, e.g., engineered CAR T cells, small molecules, "agents" described in the specification, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. Such terms may be used interchangeably. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays. Therapeutically effective amounts and dosage regimens can be determined empirically by testing in known in vitro or in vivo (e.g. animal model) systems.

The term "combination" refers to either a fixed combination in one dosage unit form, or a combined administration where a compound of the present invention and a combination partner (e.g. another drug as explained below, also referred to as "therapeutic agent" or "agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The terms "product" or "infusion product" are used interchangeably herein and refer to the T cell composition that is administered to the subject in need thereof. Typically, in CAR T-cell therapy, the T cell composition is administered as an infusion product.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naïve cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

In the context of this disclosure, the term "TN," "T naïve-like", and CCR7+CD45RA+ actually refers to cells that are more like stem-like memory cells than like canonical naïve T cells. Accordingly, all references in the Examples and Claims to $T_N$ refers to cells that were experimentally selected only by their characterization as CCR7+CD45RA+ cells and should be interpreted as such. Their better name in the context of this disclosure is stem-like memory cells, but they shall be referred to as CCR7+CD45RA+ cells. Further characterization into stem-like memory cells can be done for example using the methods described in Arihara Y, Jacobsen C A, Armand P, et al. *Journal for ImmunoTherapy of Cancer.* 2019; 7(1):P210.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Publication No. WO 2008/081035. In some embodiments, the immunotherapy comprises CAR T cell treatment. In some embodiments, the CAR T cell treatment product is administered via infusion.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by reference in its entirety.

The term "engineered Autologous Cell Therapy," or "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv may be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CAR T cell therapies and constructs are described in U.S. Patent Publication Nos. 2013/0287748, 2014/0227237, 2014/0099309, and 2014/0050708, and these references are incorporated by reference in their entirety.

A "patient" or a "subject" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell. The term "in vivo" means within the patient.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex that specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. In certain embodiments, a co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD33, CD45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD11a, CD11b, CD11c, CD11d, CDS, CEACAM1, CRT AM, DAP-10, DNAM1 (CD226), Fc gamma receptor, GADS, GITR, HVEM (LIGHTR), IA4, ICAM-1, ICOS, Ig alpha (CD79a), IL2R beta, IL2R gamma, IL7R alpha, integrin, ITGA4, ITGA6, ITGAD, ITGAE, ITGAL, ITGAM, ITGAX, ITGB2, ITGB7, ITGB1, KIRDS2, LAT, LFA-1, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions. Similarly, the term "increasing" indicates any change that is higher than the original value. "Increasing," "higher," and "lower" are relative terms, requiring a comparison between pre- and post-measurements and/or between reference standards. In some embodiments, the reference values are obtained from those of a general population, which could be a general population of patients. In some embodiments, the reference values come quartile analysis of a general patient population.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission. In some embodiments, the treatment may be prophylactic, in which case the treatment is administered before any symptoms of the condition are observed. The term "prophylaxis" as used herein means the prevention of or protective treatment for a disease or disease state. Prevention of a symptom, disease, or disease state can include reduction (e.g., mitigation) of one or more symptoms of the disease or disease state, e.g., relative to a reference level (e.g., the symptom(s) in a similar subject not administered the treatment). Prevention can also include delaying onset of one or more symptoms of the disease or disease state, e.g., relative to a reference level (e.g., the onset of the symptom(s) in a similar subject not administered the treatment). In embodiments, a disease is a disease described herein. In some embodiments, the disease is cancer. In some embodiments, the diseased state is CRS or neurotoxicity. In some embodiments, indicators of improvement or successful treatment include determination of the failure to manifest a relevant score on toxicity grading scale (e.g. CRS or neurotoxicity grading scale), such as a score of less than 3, or a change in grading or severity on the grading scale as discussed herein, such as a change from a score of 4 to a score of 3, or a change from a score of 4 to a score of 2, 1 or 0.

As used herein, the term "polyfunctional T cells" refers to cells co-secreting at least two proteins from a pre-specified panel per cell coupled with the amount of each protein produced (i.e., combination of number of proteins secreted and at what intensity). In some embodiments, a single cell functional profile is determined for each evaluable population of engineered T cells. Profiles may be categorized into effector (Granzyme B, IFN-γ, MIP-1α, Perforin, TNF-α, TNF-β), stimulatory (GM-CSF, IL-2, IL-5, IL-7, IL-8, IL-9, IL-12, IL-15, IL-21), regulatory (IL-4, IL-10, IL-13, IL-22, TGF-β1, sCD137, sCD40L), chemoattractive (CCL-11, IP-10, MIP-1β, RANTES), and inflammatory (IL-1b, IL-6, IL-17A, IL-17F, MCP-1, MCP-4) groups. In some embodiments, the functional profile of each cell enables the calculation of other metrics, including a breakdown of each sample according to cell polyfunctionality (i.e., what percentage of cells are secreting multiple cytokines versus non-secreting or monofunctional cells), and a breakdown of the sample by functional groups (i.e., which mono- and polyfunctional groups are being secreted by cells in the sample, and their frequency).

As used herein, "myeloid cells" are a subgroup of leukocytes that includes granulocytes, monocytes, macrophages, and dendritic cells.

As used herein, the term "quartile" is a statistical term describing a division of observations into four defined intervals based upon the values of the data and how they compare to the entire set of observations. Examples of the quartiles described in this disclosure are presented in FIGS. 21A through 21E. In one exemplary embodiment (for the set of observations related to the treatment described in the EXAMPLES), the values observed for the peak CAR T cells/tumor burden in the population of patients described in the Examples and measured in cells/microliter of blood× mm2, are divided into the quartiles described in FIG. 21A. In FIG. 1M, the association between the peak CAR T cells/tumor burden quartiles and objective response and durable response is shown. In another exemplary embodiment, the values observed for baseline IL6 in the population of patients described in the Examples and measured in pg/microliter of blood, are divided into the quartiles described in FIG. 21C. The quartiles for various attributes are described in FIG. 21 and may be broken down into specific median and ranges of values based on the respective tables.

As used herein, the term "Study day 0" is defined as the day the subject received the first CAR T cell infusion. The day prior to study day 0 will be study day −1. Any days after enrollment and prior to study day −1 will be sequential and negative integer-valued.

As used herein, the term "durable response" refers to the subjects who were in ongoing response at least by one year follow up post CAR T cell infusion. In one embodiment, "duration of response" is defined as the time from the first objective response to disease progression or to death due to disease relapse.

As used herein, the term "relapse" refers to the subjects who achieved a complete response (CR) or partial response (PR) and subsequently experienced disease progression.

As used herein, the term "non-response" refers to the subjects who had never experienced CR or PR post CAR T cell infusion.

As used herein, the term "objective response" refers to complete response (CR), partial response (PR), or non-response. It may be assessed per revised IWG Response Criteria for Malignant Lymphoma (Cheson et al., *J Clin Oncol.* 2007; 25(5):579-86)

As used herein, the term "complete response" refers to complete resolution of disease, which becomes not detectable by radio-imaging and clinical laboratory evaluation. No evidence of cancer at a given time.

As used herein, the term "partial response" refers to a reduction of greater than 30% of tumor without complete resolution.

As used herein "objective response rate" (ORR) is determine per International Working Group (IWG) 2007 criteria (Cheson et al. J Clin Oncol. 2007; 25(5):579-86).

As used herein "progression-free survival (PFS)" may be defined as the time from the T cell infusion date to the date of disease progression or death from any cause. Progression is defined per investigator's assessment of response as defined by IWG criteria (Cheson et al., *J Clin Oncol.* 2007; 25(5):579-86).

The term "overall survival (OS)" may be defined as the time from the T cell infusion date to the date of death from any cause.

As used herein, the expansion and persistence of CART cells in peripheral blood may be monitored by qPCR analysis, for example using CAR-specific primers for the scFv portion of the CAR (e.g., heavy chain of a CD19 binding domain) and its hinge/CD28 transmembrane domain. Alternatively, it may be measured by enumerating CAR cells/unit of blood volume.

As used herein, the scheduled blood draw for CAR T cells may be before CAR T cell infusion, Day 7, Week 2 (Day 14), Week 4 (Day 28), Month 3 (Day 90), Month 6 (Day 180), Month 12 (Day 360), and Month 24 (Day 720).

As used herein, the "peak of CART cell" is defined as the maximum absolute number of CAR+ PBMC/µL in serum attained after Day 0.

As used herein, the "time to Peak of CART cell" is defined as the number of days from Day 0 to the day when the peak of CAR T cell is attained.

As used herein, the "Area Under Curve (AUC) of level of CAR T cell from Day 0 to Day 28" is defined as the area under the curve in a plot of levels of CAR T cells against scheduled visits from Day 0 to Day 28. This AUC measures the total levels of CART cells overtime.

As used herein, the scheduled blood draw for cytokines is before or on the day of conditioning chemotherapy (Day −5), Day 0, Day 1, Day 3, Day 5, Day 7, every other day if any through hospitalization, Week 2 (Day 14), and Week 4 (Day 28).

As used herein, the "baseline" of cytokines is defined as the last value measured prior to conditioning chemotherapy.

As used herein, the fold change from baseline at Day X is defined as $$\frac{\text{Cytokine level at Day } X - \text{Baseline}}{\text{Baseline}}$$

As used herein, the "peak of cytokine post baseline" is defined as the maximum level of cytokine in serum attained after baseline (Day −5) up to Day 28.

As used herein, the "time to peak of cytokine" post CAR T cell infusion is defined as the number of days from Day 0 to the day when the peak of cytokine was attained.

As used herein, the "Area Under Curve (AUC) of cytokine levels" from Day −5 to Day 28 is defined as the area under the curve in a plot of levels of cytokine against scheduled visits from Day −5 to Day 28. This AUC measures the total levels of cytokine overtime. Given the cytokine and CAR+ T cell are measured at certain discrete time points, the trapezoidal rule may be used to estimate the AUCs.

As used herein, treatment-emergent adverse events (TEAEs) are defined as adverse events (AE) with onset on or after the first dose of conditioning chemotherapy. Adverse events may be coded with the Medical Dictionary for Regulatory Activities (MedDRA) version 22.0 and graded using the National Cancer Institute (NCI) Common Terminology Criteria for Adverse Events (CTCAE) version 4.03. Cytokine Release Syndrome (CRS) events may be graded on the syndrome level per Lee and colleagues (Lee et al, 2014 *Blood.* 2014; 124(2):188-95. Individual CRS symptoms may be graded per CTCAE 4.03. Neurologic events may be identified with a search strategy based on known neurologic toxicities associated with CAR T immunotherapy, as described in, for example, Topp, M S et al. *Lancet Oncology*. 2015; 16(1):57-66.

Various aspects of the disclosure are described in further detail in the following subsections.

Pre-Treatment Attributes

Pre-treatment attributes of the apheresis and engineered cells (T cell attributes) and patient immune factors measured from a patient sample may be used to assess the probability of clinical outcomes including response and toxicity. Attributes associated with clinical outcomes may be tumor related parameters (e.g., tumor burden, serum LDH as hypoxic/cell death marker, inflammatory markers associated with tumor burden and myeloid cell activity), T cell attributes (e.g., T cell fitness, functionality especially T1 related IFNgamma production, and the total number of CD8 T cells infused) and CAR T cell engraftment measured by peak CAR T cell levels in blood at early time points.

Information extrapolated from T cell attributes and patient pre-treatment attributes may be used to determine, refine or prepare a therapeutically effective dose suitable for treating a malignancy (e.g., cancer). Furthermore, some T cell attributes and patient pre-treatment attributes may be used to determine whether a patient will develop adverse events after treatment with an engineered chimeric antigen receptor (CAR) immunotherapy (e.g., neurotoxicity (NT), cytokine release syndrome (CRS)). Accordingly, an effective adverse event management strategy may be determined (e.g., administration of tocilizumab, a corticosteroid therapy, or an anti-seizure medicine for toxicity prophylaxis based on the measured levels of the one or more attributes).

In some embodiments, the pre-treatment attributes are attributes of the engineered T cells comprising one or more chimeric antigen receptors. In some embodiments, the pre-treatment attributes are T cell transduction rate, major T cell phenotype, numbers of CAR T cells and T cell subsets, fitness of CAR T cells, T cell functionality, T cell polyfunctionality, number of differentiated CAR+CD8+ T cells.

In some embodiments, the pre-treatment attributes are measured from a sample obtained from the patient (e.g., cerebrospinal fluid (CSF), blood, serum, or tissue biopsy). In some embodiments, the one or more pre-treatment attributes is tumor burden, levels of IL-6, or levels of LDH.

T Cell Fitness

In some embodiments, the intrinsic cell fitness is assessed based on the capacity of the CAR T cells to expand during nonspecific stimulation in vitro (e.g., shorter doubling time), the differentiation state of the CAR T cells (favorable juvenile phenotype), the levels of specialized CAR T-cell subsets in the CAR T-cell population (e.g., the numbers of CD8 and naïve-like CD8 cells (e.g., CD8+ CCR7+ CD45RA+ T Cells) in the infusion product), and the in vivo CAR T cell expansion rate.

In one embodiment, T cell fitness is the capability of cells to rapidly expand. In the context of engineered T cells, in one embodiment, T cell fitness is a measurement of how fast the engineered T cell population expand pre-treatment. As described herein, T cell fitness is an attribute of engineered T cells that associates with clinical outcome. In some embodiments, T cell fitness is measured by doubling time or expansion rate. An exemplary derivation of T cell "fitness" measured as T cell population doubling time (DT) during the manufacturing process is shown below.

$$\text{Doubling Time} = \frac{\ln(2) \times \text{duration}}{\ln\left(\dfrac{\text{total viable cells at harvest}}{\text{total viable cells at Day 3}}\right)}$$

Duration may be defined as total manufacturing timeframe MINUS three days (essentially the number of days for the product cells in culture post transduction and before harvest and cryopreservation). Recombinant IL-2 (after nonspecific stimulation with, for example, anti-CD3 antibodies) may be used to drive polyclonal T cell expansion towards achieving the target dose. The shorter the DT, the higher engineered T cell fitness. In vitro expansion rate may be calculated using the formula below.

$$\text{Expansion rate} = \ln(2)/\text{Doubling Time}$$

In the instances described above, the expansion rate is provided in units of "rate/day" or "/day."

In some embodiments, in vivo expansion rate is measured by enumerating CAR cells/unit of blood volume. In some embodiments, the in vivo expansion rate is measured by the number of CAR gene copies/µg of host DNA. In some embodiments, the in vivo expansion rate is measured by of enumerating CAR cells/unit of blood volume.

In one aspect, the present disclosure provides a method of treating a malignancy in a patient comprising measuring the doubling time (DT) in a population of engineered T cells comprising a chimeric antigen receptor (CAR). In some embodiments, the method further comprises determining whether the patient will respond to chimeric antigen receptor treatment based on the measured doubling time compared to a reference level. In some embodiments, the doubling time is measured during the manufacturing process. In some embodiments, the measured level or the reference level of doubling time is 1.5 days. In some embodiments, the measured level or the reference level of doubling time is 2 days. In some embodiments, the measured level or the reference level of doubling time is 2.5 days. In some embodiments, the measured level or the reference level of doubling time is about 1 day, about 1.1 days, about 1.2 days, about 1.3 days, about 1.4 days, about 1.5 days, about 1.6 days, about 1.7 days, about 1.8 days, about 1.9 days, about 2 days, about 2.1 days, about 2.2 days, about 2.3 days, about 2.4 days, about 2.5 days, about 2.6 days, about 2.7 days, about 2.8 days, about 2.9 days, about 3 days, about 3.1 days, about 3.2 days, about 3.3 days, about 3.4 days, about 3.5 days, about 3.6 days, about 3.7 days, about 3.8 days, about 3.9 days, about 4 days, about 4.1 days, about 4.2 days, about 4.3 days, about 4.4 days, about 4.5 days, about 4.6 days, about 4.7 days, about 4.8 days, about 4.9 days, about 5 days, about 6 days, or about 7 days.

In some embodiments, the measured level or the reference level of doubling time is less than about 1 day, about 1.1 days, about 1.2 days, about 1.3 days, about 1.4 days, about 1.5 days, about 1.6 days, about 1.7 days, about 1.8 days, about 1.9 days, about 2 days, about 2.1 days, about 2.2 days, about 2.3 days, about 2.4 days, about 2.5 days, about 2.6 days, about 2.7 days, about 2.8 days, about 2.9 days, about 3 days, about 3.1 days, about 3.2 days, about 3.3 days, about 3.4 days, about 3.5 days, about 3.6 days, about 3.7 days, about 3.8 days, about 3.9 days, about 4 days, about 4.1 days, about 4.2 days, about 4.3 days, about 4.4 days, about 4.5 days, about 4.6 days, about 4.7 days, about 4.8 days, about 4.9 days, about 5 days, about 6 days, or about 7 days.

In some embodiments, the measured level or the reference level of doubling time is greater than about 1 day, about 1.1 days, about 1.2 days, about 1.3 days, about 1.4 days, about 1.5 days, about 1.6 days, about 1.7 days, about 1.8 days, about 1.9 days, about 2 days, about 2.1 days, about 2.2 days, about 2.3 days, about 2.4 days, about 2.5 days, about 2.6 days, about 2.7 days, about 2.8 days, about 2.9 days, about 3 days, about 3.1 days, about 3.2 days, about 3.3 days, about 3.4 days, about 3.5 days, about 3.6 days, about 3.7 days, about 3.8 days, about 3.9 days, about 4 days, about 4.1 days, about 4.2 days, about 4.3 days, about 4.4 days, about 4.5 days, about 4.6 days, about 4.7 days, about 4.8 days, about 4.9 days, about 5 days, about 6 days, or about 7 days.

In some embodiments, the measured level or the reference level of doubling time is lower than about 2 days, or about 1 day, about 1.1 days, about 1.2 days, about 1.3 days, about 1.4 days, about 1.5 days, about 1.6 days, about 1.7 days, about 1.8 days, about 1.9 days, about 2 days.

In some embodiments, the engineered T cells with a doubling time (DT) greater than about 1.5 days, about 1.6 days, about 1.7 days, about 1.8 days, about 1.9 days, or about 2 days, may result in primary treatment failure. In some embodiments, engineered CAR T cells with a doubling time (DT) less than about 1.2 days, 1.3 days, 1.4 days, 1.5 days, about 1.6 days, about 1.7 days, about 1.8 days, about 1.9 days, or about 2 days, result in objective response in patients with high tumor burden.

In some embodiments, the engineered CAR T cells with a doubling time (DT) greater than about 2 days are associated with relapse and/or no response to CAR T cell treatment. In some embodiments, engineered CAR T cells with a doubling time (DT) less than about 2 days, are associated with objective response or durable response, in patients with high tumor burden.

In another aspect, the present disclosure provides a method of treating a malignancy in a patient comprising measuring the expansion rate of a population of engineered T cells comprising a chimeric antigen receptor (CAR). In some embodiments, the method further comprises determining whether the patient may respond to chimeric antigen receptor treatment based on the measured expansion rate compared to a reference level. In some embodiments, the expansion rate is measured during the manufacturing process. In some embodiments, measured level or the reference level of expansion rate is 0.4/day, 0.45/day or 0.5/day. In some embodiments, the reference level of expansion rate is 0.3/day, 0.35/day or 0.4/day. In some embodiments, the reference level of expansion rate is 0.28/day. In some embodiments, the reference level of expansion rate is about 0.7/day, about 0.65/day, about 0.6/day, about 0.55/day, about 0.5/day, about 0.45/day, about 0.4/day, about 0.35/day, about 0.3/day, about 0.25/day, about 0.2/day, about 0.15/day, or about 0.1/day.

In some embodiments, the measured level or the reference level of expansion rate is less than about 0.7/day, about 0.65/day, about 0.6/day, about 0.55/day, about 0.5/day, about 0.45/day, about 0.4/day, about 0.35/day, about 0.3/day, about 0.25/day, about 0.2/day, about 0.15/day, or about 0.1/day.

In some embodiments, the measured level or the reference level of expansion rate is greater than about 0.7/day, about 0.65/day, about 0.6/day, about 0.55/day, about 0.5/day, about 0.45/day, about 0.4/day, about 0.35/day, about 0.3/day, about 0.25/day, about 0.2/day, about 0.15/day, or about 0.1/day.

In some embodiments, the engineered T cells with an expansion rate less than about 0.45/day, about 0.44/day, about 0.43/day, about 0.42/day, about 0.41/day, about 0.40/day, about 0.39/day, about 0.38/day, about 0.37/day, about 0.36/day, or about 0.35/day result in primary treatment failure. In some embodiments, engineered CAR T cells with an expansion rate greater than about 0.45/day, about 0.44/day, about 0.43/day, about 0.42/day, about 0.41/day, about 0.40/day, about 0.39/day, about 0.38/day, about 0.37/day, about 0.36/day, or about 0.35/day, result in objective response in patients with high tumor burden.

As described herein, during manufacturing, T cells may be initially non-specifically stimulated with anti-CD3 antibodies in the presence of IL2 and then expanded with growth medium supplemented with IL2. As described herein, low doubling time associates positively with objective response as compared to nonresponse. The median DT in responders was 1.6 days, while nonresponders had a median DT time of 2.1 days. Quartile analysis of response by DT showed that all patients (100%) in the lowest DT quartile achieved an objective response, while 80% of all nonresponders were in the third and fourth quartile of DT. Accordingly, the disclosure provides a method to assess primary treatment resistance comprising (a) measuring the doubling time of the population of T-cells in the infusion product to obtain a value and (b) assessing primary treatment resistance based on the value. In some embodiments, the assessment involves determining in which quartile of the population does the patient fall. In some embodiments, the assessment is done relative to a reference standard. In some embodiments, the method further comprises administering an effective dose of CAR T-cells to the patient, wherein the effective dose is determined using said/the value. In some embodiments, the higher doubling time is associated with primary treatment resistance. In some embodiments, a product doubling time >1.6 days is associated with non-response. In some embodiments, in patients with high tumor burden, patients with objective response or a durable response have doubling times <2 days. In some embodiments, a doubling time >2 days is associated with relapse or non-response. In some embodiments, the higher the number of CD28+CD27+ $T_N$ cells in the apheresis starting material the better (shorter) the infusion product doubling time.

As described herein, higher peak expansion of CAR T cells in the peripheral blood, generally occurring within 2 weeks of post-CAR T-cell infusion, associates with both objective response and durable response, defined as ongoing response with a minimum follow-up of 1 year. Peak number of CAR T cells in the blood correlated with response. Cumulative CAR T-cell levels over the first 28 days, as measured in blood by area under the curve (AUC), were also associated with better objective and durable response to therapy. Accordingly, the disclosure provides a method to assess response to CART cell treatment comprising (a) measuring the peak expansion of CART cells in the peripheral blood to obtain a value and (b) assessing treatment response based on the value. In another aspect, the disclosure provides a method of determining whether a patient will respond to CAR T cell therapy comprising: (a) measuring the peak CAR T-cell levels in the blood post CAR T-administration to obtain a value (b) normalizing the value to pretreatment tumor burden; and (c) determining if the patient will achieve durable response based on the normalized value. In some embodiments, the value is positively associated with durable response and separates subsets of patients with higher (~60%) vs. lower (~10%) probability of achieving a durable response. In some embodiments, the CAR T-cell levels are calculated by enumerating the number of CAR T-cells per unit of blood volume. In one embodiment, higher peak expansion of CAR T cells in the peripheral blood means peak expansion values falling within the higher quartiles. In some embodiments, in vivo expansion rate is measured by enumerating CAR cells/unit of blood volume. In some embodiments, the in vivo expansion rate is measured by the number of CAR gene copies/μg of host DNA. In some embodiments, the assessment or determination involves determining in which quartile of the population does the patient fall. In some embodiments, the assessment is done relative to a reference standard As described herein, higher peak CAR T-cell expansion is associated with severe neurotoxicity but not CRS. Accordingly, in one embodiment, the disclosure provides a method of predicting severe neurotoxicity comprising (a) measuring the peak CAR T-cell expansion after CAR T cell treatment and to obtain a value and (b) predicting neurotoxicity based on the value. In one embodiment, the method further comprises administering an agent that prevents or reduces neurotoxicity in combination with the CAR T cell treatment.

As described herein, higher expansion rate of CAR T cells during manufacturing associates with greater in vivo CAR T-cell expansion and higher probability of durable remission (durable remission/durable response means being in response at 1 year and beyond). As described herein, product doubling time negatively associates with expansion of CAR T cells in vivo after infusion. As described herein, product doubling time negatively associates with peak CAR T cells normalized to tumor burden. As described herein, product doubling time negatively associates with CAR T-cell AUC. In some embodiments, in vivo expansion rate is measured by enumerating CAR cells/unit of blood volume. In some embodiments, the in vivo expansion rate is measured by the number of CAR gene copies/µg of host DNA. Accordingly, in some embodiments, the disclosure provides a method of determining whether a patient will respond to CAR T cell therapy comprising: (a) measuring the expansion rate of CAR T cells during manufacturing or peak CAR T-cell levels in the blood post CAR T-administration to obtain a value (b) determining whether the patient will achieve durable response based on the value.

As described herein, among patients with high tumor burden, a greater proportion of patients who achieved an objective response or a durable response have a shorter product doubling time (<2 days) compared with patients who relapsed or had no response. Accordingly, in some embodiments, the disclosure provides a method of determining whether a patient will respond to CAR T cell therapy comprising: (a) measuring the peak CAR T-cell levels in the blood post CAR T-administration to obtain a value (b) normalizing the value to pretreatment tumor burden; and (c) determining if the patient will achieve durable response based on the normalized value. In some embodiments, the value is positively associated with durable response and separates subsets of patients with higher (~60%) vs. lower (~10%) probability of achieving a durable response. In some embodiments, the CAR T-cell levels are calculated by enumerating the number of CAR T-cells per unit of blood volume. In some embodiments, the assessment involves determining in which quartile of the population does the patient fall. In some embodiments, the assessment is done relative to a reference standard.

As described herein, doubling time positively associates with the frequency of T-cell differentiation subsets in the final infusion bag. Doubling time is positively associated with the frequency of effector memory T ($T_{EM}$) cells and negatively associated with the frequency of naïve-like T ($T_N$) cells. In one embodiment (e.g., axicabtagene ciloleucel), the $T_N$ cells that are identified as CCR7+CD45RA+ cells are actually stem-like memory cells and not canonical naïve T cells.

As described herein, intrinsic product T-cell fitness, as measured by the product doubling time, is positively associated with a less differentiated product and influences the ability of CAR T cells to expand in vivo to a sufficient effector-to-target ratio that supports tumor eradication.

Accordingly, in one embodiment, the disclosure provides a method for improving response to CAR T cell treatment in a patient with an infusion product comprising manipulating the cell population to decrease the doubling time of the infusion product and/or administering to the patient an infusion product with a lower doubling time relative to a reference value.

As described herein, the intrinsic capability of T-cell expansion measured pretreatment, as measured by product doubling time, is a major attribute of product T-cell fitness. Relative to other product characteristics, DT was most strongly associated with the frequency of T-cell differentiation subsets in the final infusion bag. Specifically, DT was positively associated with the frequency of effector memory T (TEM) cells and negatively associated with the frequency of naïve-like T (TN) cells. In one embodiment (e.g., axicabtagene ciloleucel), the $T_N$ cells that are identified as CCR7+CD45RA+ cells are actually stem-like memory cells and not canonical naïve T cells. As described herein, baseline tumor burden is positively associated with the differentiation phenotype in the final infusion product. As described herein, product composition and clinical performance associate with the pretreatment immune status of the patient. Accordingly, in one embodiment, the disclosure provides a method of reducing post-treatment tumor burden with treatment with CAR T cells comprising administering an infusion product comprising increased frequency of naïve-like T (TN) cells in the infusion product relative to a reference value. In another embodiment, the disclosure provides a method to predict or estimate the differentiation phenotype of the final infusion product comprising measuring the baseline tumor burden in the patient to obtain a value and estimating or predicting the differentiation phenotype based on the value. In one embodiment, the measure further comprises preparing an effective dose of CAR T cells in the final product based on the value.

T Cell Phenotypes

As described herein, the T cell phenotypes in manufacturing starting material (apheresis) may be associated with T cell fitness (DT). Total % of Tn-like and Tcm cells (CCR7+ cells) is inversely related to DT. The % of Tem (CCR7-CD45RA-) cells is directly associated with DT. Accordingly, in some embodiments, the pre-treatment attribute is the % of Tn-like and Tcm cells. In some embodiments, the % of Tn-like and Tcm cells is determined by the percentage of CCR7+ cells. In some embodiments, the percentage of CCR7+ cells is measured by flow cytometry.

In some embodiments, the pre-treatment attribute is the % of Tem (CCR7-CD45RA-) cells. In some embodiments, the % of Tem cells is determined by the percentage of CCR7-CD45RA- cells. In some embodiments, the percentage of CCR7-CD45RA- cells is measured by flow cytometry.

As described herein, manufacturing doubling time and product T-cell fitness associate directly with the differentiation state of patients' T cells prior to enrollment in CAR T cell treatment. Accordingly, the disclosure provides a method of predicting the T-cell fitness of the manufactured product comprising determining the differentiation state of the patients' T cells prior to CAR T cell treatment (e.g., in the apheresis product) and predicting T-cell fitness during manufacturing based on the differentiation state.

As described herein, the greater the proportions of effector memory T cells in the apheresis product, within total CD3+ T cells or CD4 and CD8 subsets, the higher the product doubling time. As described herein, the more juvenile the T-cell phenotype in the starting material but better the product T-cell fitness. As described herein, CD27+CD28+

$T_N$ cells, which represent immunologically competent subset of $T_N$ cells that express key costimulatory molecules, associate positively with product doubling time. As described herein, there is a direct association across all major phenotypic groups, including proportions of T-cell subsets defined by differentiation markers in CD3, CD4, and CD8 subpopulations, in the apheresis product relative to the final product phenotype. As described herein, the proportion of T cells with CD25$^{hi}$ CD4 expression, possibly representing regulatory T cells in the apheresis material, negatively correlates with the CD8 T-cell output in the product. As described herein, tumor burden after CAR T cell treatment is positively associated with the differentiation phenotype of the final product.

As described herein, the number of infused CD8+ T cells normalized to tumor burden is associated with durable response and expansion of CAR T cells relative to tumor burden. More specifically, quartile analysis of the number of infused CD8 T cells/pretreatment tumor burden, showed a durable response rate of 16% in the lowest quartile vs. 58% in the top quartile.

As described herein, the number of infused specialized T cells, primarily the CD8+ $T_N$-cell population, has a positive influence on durable clinical efficacy with CAR T-cell therapy. As described herein, higher numbers of product CD8+ T cells are needed to achieve complete tumor resolution and establish a durable response in patients with higher tumor burden. As described herein, in patients with high tumor burden, durable response is associated with significantly higher number of infused CD8 T cells compared with patients who respond and then relapse. As described herein, the number of infused TN cells normalized to tumor burden positively associates with durable response. As described herein, the CD4:CD8 ratio positively associates with durable response. As described herein, the total number of CD8 T cells in the product normalized to pretreatment tumor burden positively associates with durable response. Among CD8 T cells, the number of $T_N$ cells is most significantly associated with durable response. In one embodiment (e.g., axicabtagene ciloleucel), the $T_N$ cells that are identified as CCR7+CD45RA+ cells are actually stem-like memory cells and not canonical naïve T cells. The disclosure provides some additional associations, which may be used for one or more of methods of improvement of CAR T cell infusion product, determination of effective dose, and/or predicting durable response based on one or more of these associations. See Table 1.

TABLE 1

Association between product phenotypes and ongoing response or peak CAR T-cell levels. P values were calculated using logistic regression for durable response and by Spearman correlation for CAR T-cell levels.

| Parameter | Association With Durable Response | | Association With Peak CAR T-cell Levels | |
|---|---|---|---|---|
| | P value | Direction of association | P value | Direction of association |
| CD3 infused (%) | 0.201 | Negative | 0.762 | Positive |
| Number of CD3 infused[a] | 0.654 | Positive | 0.441 | Positive |
| Number of CD3 infused/tumor burden[a] | 0.030 | Positive | 0.443 | Positive |
| +T$_n$ infused (%) | 0.454 | Positive | 0.099 | Positive |
| Number of +Tn infused[a] | 0.182 | Positive | 0.091 | Positive |
| Number of +Tn infused/tumor burden[a] | 0.025 | Positive | 0.114 | Positive |
| % CD8 infused | 0.21 | Positive | 0.126 | Positive |
| Number of CD8[a] | 0.116 | Positive | 0.154 | Positive |
| Number of CD8 infused/tumor burden[a] | 0.009 | Positive | 0.273 | Positive |
| CD4 infused (%) | 0.21 | Negative | 0.124 | Negative |
| Number of CD4 infused[a] | 0.930 | Negative | 0.257 | Negative |
| Number of CD4 infused/tumor burden[a] | 0.059 | Positive | 0.841 | Positive |

[a]Denote analytes in LOG2 transformation.

+The cells referred to as $T_N$ in the EXAMPLES were identified simply as CCR7 + CD45RA + T-cells and have been further characterized as stem-like memory cells.

Accordingly, the disclosure provides a method of improving durable clinical efficacy (e.g., durable response) of CAR T-cell therapy in a patient comprising preparing and/or administering to the patient an effective dose of CAR T cell treatment, wherein the effective dose is determined based on the number of specialized T cells in the infusion product and/or the CD4:CD8 ratio. In some embodiments, the specialized T cells are CD8+ T cells, preferably $T_N$ cells. In one embodiment (e.g., axicabtagene ciloleucel), the cells referred to as $T_N$ are identified as CCR7+ CD45RA+ T-cells and have been further characterized as stem-like memory cells.

In another embodiment, the disclosure provides a method of determining how a patient will respond to treatment comprising (a) characterizing the number of specialized T cells in the infusion product to obtain one or more values and (b) determining how the patient will respond based on the one or more values. In another embodiment, the present disclosure provides a method of treating a malignancy in a patient comprising measuring the T cell phenotypes in a population of T cells obtained from a patient (e.g., apheresis material). In some embodiments, the method further comprises determining whether the patient will respond to chimeric antigen receptor treatment based on the measured percentage of specific T cell types. In some embodiments, the T cell phenotype is measured prior to engineering the cells to express a chimeric antigen receptor (CAR) (e.g., apheresis material). In some embodiments, the T cell phenotype is measured after engineering the cells to express a chimeric antigen receptor (CAR) (e.g., engineered T cells comprising a CAR).

As described herein, the number of CCR7+CD45RA+ cells in the product infusion bag is associates positively with a ("rapid") response (approximately two weeks) to axicabtagene ciloleucel treatment. Accordingly, the percentage or total number of these cells in the T cell product may be manipulated to improve response to T cell therapy.

As described herein, the higher the frequency of CCR7+ CD45RA+ T cells in the product infusion bag, the higher the product T-cell fitness. As described herein, the higher the frequency of CCR7+CD45RA+ T cells in the product infusion bag, the lower the product doubling time. Accordingly, the percentage or total number of these cells in the T cell product may be manipulated to decrease DT and improve response to T cell therapy.

As described herein, the majority of CCR7+ CD45RA+ T cells in the axicabtagene ciloleucel product infusion bag were stem-like memory cells, not canonical naïve T cells. As described herein, CCR7+ CD45RA+ T cells from peripheral blood may differentiate in vitro into stem-like memory cells.

As described herein, the T cell subpopulation that best associates with DT was CCR7+CD45RA+CD27+CD28+ T cells. Accordingly, the percentage or total number of these cells in the T cell product may be manipulated to decrease DT and improve response to T cell therapy.

As described herein, CCR7+ CD45RA+ T cells are drivers of anti-tumor activity in the context of T-cell therapies. Accordingly, the percentage or total number of these cells in the T cell product may be manipulated to improve response to T cell therapy.

As described herein, the total number of specialized T cells normalized to pretreatment tumor burden associates better with clinical efficacy than the number of product T cells of CAR T cells. Accordingly, the percentage or total number of these cells in the T cell product may be manipulated to improve response to T cell therapy.

T1 Functionality

Engineered T cells may be characterized by their immune function characteristics. Methods of the present disclosure provide measuring levels of cytokine production ex vivo. In some embodiments, the cytokines are selected from the group consisting of IFNgamma, TNFa, IL-12, MIP1β, MIP1α, IL-2, IL-4, IL-5, and IL-13. In some embodiments, the T cell functionality is measured by levels of Th1 cytokines.

In some embodiments, the Th1 cytokines are selected from the group consisting of IFNgamma, TNFa, and IL-12. In some embodiments, T cell functionality is measured by levels of IFNgamma production. In some embodiments, excess T cell IFNgamma (pre-treatment attribute), and post-treatment T1 activity, are attributes that may be used to determine whether a patient will develop adverse events (e.g., neurotoxicity). In some embodiments, IFNgamma levels produced by engineered CAR T cells are measured by co-culture prior to administration of engineered CAR T cells.

In some embodiments, engineered CAR T cells with lower co-culture IFNgamma result in positive clinical efficacy outcome and reduced grade 3+ neurotoxicity. In one aspect, the present disclosure provides a method of treating a malignancy in a patient comprising measuring the levels of IFNgamma produced by a population of engineered T cells comprising a chimeric antigen receptor (CAR). In some embodiments, the method further comprises determining whether the patient will respond to chimeric antigen receptor treatment based on the measured levels of IFNgamma compared to a reference level. In some embodiments, the reference level is less than about 1 ng/ml, about 2 ng/ml, about 3 ng/ml, about 4 ng/ml, about 5 ng/ml, about 6 ng/ml, about 7 ng/ml, or about 8 ng/ml.

In some embodiments, engineered CAR T cells with excess IFNgamma production show rapidly elevating rate of grade 3+ neurotoxicity and diminution of objective response rate. In one aspect, the present disclosure provides a method of treating a malignancy in a patient comprising measuring the levels of IFNgamma produced by a population of engineered T cells comprising a chimeric antigen receptor (CAR). In some embodiments, the method further comprises determining whether the patient will develop an adverse event to chimeric antigen receptor treatment based on the measured levels of IFNgamma compared to a reference level. In some embodiments, the reference level is greater than about 5 ng/ml, about 6 ng/ml, about 7 ng/ml, or about 8 ng/ml, about 9 ng/ml, about 10 ng/ml, or about 11 ng/ml.

As described herein, there is a direct association of early elevation of IFNgamma in serum after CAR T cell infusion and rate of grade 3+ toxicities. In some embodiments, IFNgamma elevation in serum post CAR T cell infusion (day 1/day 0 fold change) is measured. In some embodiments, day 1/day 0 serum IFNgamma fold change greater than about 25 results in grade 3+ neurotoxicity. In some embodiments, day 1/day 0 serum IFNgamma fold change greater than about 30, about 35, about 40, about 45, or about 50 results in grade 3+ neurotoxicity.

There is a direct association of early elevation of IFNgamma related CXCL10 (IP-10) elevation in serum after CAR T cell infusion and rate of grade 3+ toxicities. In some embodiments, IFNgamma related CXCL10 (IP-10) elevation in serum post CAR T cell infusion (day 1/day 0 fold change) is measured. In some embodiments, day 1/day 0 serum IFNgamma related CXCL10 (IP-10) fold change a greater than about 2.5 results in grade 3+ neurotoxicity. In some embodiments, day 1/day 0 serum IFNgamma related CXCL10 (IP-10) fold change greater than about 3.0, about 3.5, about 4.0, about 4.5, or about 5.0 results in grade 3+ neurotoxicity.

As described herein, pretreatment product T-cell IFNγ production is linked to the more differentiated T cells in the infusion bag and associated positively with severe neurologic toxicities and to a lesser degree with decreased efficacy. Accordingly, in one embodiment, the disclosure provides a method of predicting neurologic toxicities comprising measuring the pretreatment product T-cell IFNγ production level and predicting neurologic toxicities based on that level. In one embodiment, the method further comprises modulating the pretreatment product T-cell IFNγ production level to improve the effectiveness and/or toxicity of the CAR T cell treatment. In some embodiments, the method further comprises administering an effective dose of CAR T cell treatment wherein the effective dose is determined based on the product T-cell IFNγ production level.

Pre-Treatment Levels of Systemic Pro-Inflammatory and Myeloid Activation Markers Systemic inflammatory conditions have been associated with elevated serum ferritin, C-reactive protein (CRP), IL6, IL8, CCL2, as well as decreased serum albumin and indicate a generalized myeloid activation state. Myeloid-derived suppressor cells are known to be induced by IL8 and CCL2 within tumors and mobilized by IL6 from the bone marrow.

As described herein, pro-inflammatory and myeloid activation markers (e.g., IL6, ferritin, CCL2) in the serum measured prior to conditioning (at baseline) correlate with impaired in vivo CAR T-cell expansion and decreased rate of durable response. Accordingly, in one embodiment, the disclosure provides a method of increasing the rate of durable response after CART cell treatment comprising decreasing the baseline levels of pro-inflammatory and myeloid activation markers in the patient prior to CAR T cell treatment administration. The disclosure also provides a method of determining whether or not a patient will have a durable response to CAR T cell treatment comprising measuring the baseline levels of pro-inflammatory and myeloid activation markers and making the determination based on those levels. In some embodiments, the method further comprises administering an effective dose of CAR T cell treatment wherein the effective dose is determined based on the baseline levels of pro-inflammatory and myeloid activation markers. As described herein, persisting systemic inflammation after CAR T-cell infusion associates with a failure of the CAR T cells to completely eliminate the tumor.

As described herein, pretreatment levels measured prior conditioning (at baseline) of pro-inflammatory markers associated positively with each other and negatively with hemoglobin and platelet levels. As described herein, pretreatment tumor burden correlates with baseline serum LDH, ferritin, and IL6 but not with CCL2. As described herein, pretreatment ferritin and LDH negatively associate with CAR T-cell expansion normalized to pretreatment tumor burden (peak CAR T-cell expansion/tumor burden). As described herein, pretreatment tumor burden and systemic inflammation negatively associate with the rate of durable responses; this effect may be mediated by decreased CAR-T-cell expansion relative to the pretreatment tumor burden. Accordingly, in one embodiment, the disclosure provides a method of increasing the rate of durable response after CAR T cell treatment comprising decreasing the systemic inflammation in the patient prior to CAR T cell treatment administration. The disclosure also provides a method of determining whether or not a patient will have a durable response to CAR T cell treatment comprising measuring pretreatment tumor burden and inflammation to obtain their levels and making the determination based on those levels. In some embodiments, the method further comprises administering an effective dose of CAR T cell treatment wherein the effective dose is calculated based on those levels.

As described herein, elevated LDH associates with decreased durable response. Accordingly, the disclosure also provides a method of determining whether or not a patient will have a durable response to CAR T cell treatment comprising measuring the baseline level of LDH and making the determination based on those levels. In some embodiments, the method further comprises administering an effective dose of CAR T cell treatment wherein the effective dose is determined based on the baseline levels of LDH.

As described herein, baseline IL6 elevation associates with both decreased response rates and durable response rates. Accordingly, the disclosure provides a method of increasing the response and durable response after CAR T cell treatment comprising decreasing the baseline levels of IL6 prior to CAR T cell treatment administration. The disclosure also provides a method of determining whether or not a patient will have a durable response to CAR T cell treatment comprising measuring the baseline levels of IL6 and making the determination based on those levels. In some embodiments, the method further comprises administering an effective dose of CAR T cell treatment wherein the effective dose is determined based on the baseline levels of IL6. In one embodiment, baseline IL6 activation or levels are decreased with an agent like tocilizumab (or another anti-IL6/IL6R agent/antagonist).

As described herein, high peak and cumulative ferritin levels within the first 28 days after infusion associate with lower in vivo CAR T-cell expansion and lower rates of durable response. Accordingly, the disclosure provides a method of increasing the response and durable response after CAR T cell treatment comprising decreasing the high peak and cumulative ferritin levels after CAR T cell treatment administration during the first 28 days. The disclosure also provides a method of determining whether or not a patient will have a durable response to CAR T cell treatment comprising measuring the high peak and cumulative ferritin levels within the first 28 days after infusion and making the determination based on those levels.

As described herein, there is an association between ferritin levels over the first 28 days, and peak CAR T-cell levels normalized to tumor burden. As described herein, higher levels of serum ferritin at most time points after CAR T-cell infusion are seen in patients who relapse or have no response compared with those who have durable response. Accordingly, the disclosure also provides a method of determining whether or not a patient will relapse or have no response to CAR T cell treatment comprising measuring the levels of serum ferritin at a time point after CAR T-cell infusion and making the determination based on those levels (e.g., relative to a reference value).

As described herein, elevated pretreatment or posttreatment pro-inflammatory, myeloid-related cytokines (IL6, ferritin, CCL2), as well as LDH, are positively associated with grade ≥3 NE or CRS. Accordingly, the disclosure provides a method of decreasing grade ≥3 NE and/or CRS comprising decreasing the pretreatment and/or posttreatment levels of one or more pro-inflammatory, myeloid-related cytokines (e.g., IL6, ferritin, CCL2) and/or LDH. The disclosure also provides a method of determining whether or not a patient will have ≥3 NE or CRS after administration of CAR T cell treatment comprising measuring the baseline levels of pro-inflammatory, myeloid-related cytokines (IL6, ferritin, CCL2), and/or LDH and making the determination based on those levels. In some embodiments, the method further comprises administering an effective dose of CAR T cell treatment wherein the effective dose is determined based on the baseline levels of pro-inflammatory, myeloid-related cytokines (IL6, ferritin, CCL2), as well as LDH.

As described herein, serum levels of IFNγ, CXCL10, and IL15, measured early posttreatment, associate positively with neurotoxicity but are not associated with durable response rate. Accordingly, the disclosure provides a method of decreasing neurotoxicity comprising decreasing the early posttreatment serum levels of IFNγ, CXCL10, and/or IL15. As described herein, day 0 IL15 serum levels significantly associate with day 1 IFNγ serum levels, rather than product co-culture IFNγ.

The disclosure also provides a method of determining whether or not a patient will show neurotoxicity after administration of CAR T cell treatment comprising measuring the serum levels of IFNγ, CXCL10, and IL15, measured early posttreatment and making the determination based on those levels. In some embodiments, the method further comprises administering an effective dose of agents that decrease neurotoxicity wherein the effective dose is determined based on the baseline levels of IFNγ, CXCL10, and IL15. In some embodiments, the levels are measured at day 0 and/or day 1, posttreatment. In some embodiments, the agents are selected from agents that decrease the levels or activity of IFNγ, CXCL10, and IL15 and/or other cytokines.

Tumor Burden

Tumor related parameters (e.g., tumor burden, serum LDH as hypoxic/cell death marker, inflammatory markers associated with tumor burden and myeloid cell activity) may be associated with clinical outcomes. In one aspect, the present disclosure provides a method of treating a malignancy in a patient comprising measuring the tumor burden in a patient prior to administration of a CAR T cell treatment. In some embodiments, the method further comprises determining whether the patient will respond to CAR T cell treatment based on the levels of tumor burden compared to a reference level. In some embodiments, the reference level is less than about 1,000 mm$^2$, about 2,000 mm$^2$, about 3,000 mm$^2$, about 4,000 mm$^2$.

As described herein, the higher the tumor burden, the higher the probability of relapse within 1 year post treatment in subjects who achieved an OR, and the higher the probability of grade 3+ neurotoxicity. In some embodiments, tumor burden may be used to assess the probability of relapse in patients who respond, if the pre-treatment tumor burden is greater than about 4,000 mm$^2$, about 5,000 mm$^2$, about 6,000 mm$^2$, about 7,000 mm$^2$, or about 8,000 mm$^2$.

As described herein, low tumor burden pre-CAR T-cell therapy is a positive predictor of durable response. As described herein, in the highest tumor burden quartile, patients who achieved a durable response had a greater than 3-fold higher peak CAR T-cell expansion compared with patients who relapsed or had no response. As described herein, there is a lower durable response rate at comparable peak CAR T-cell levels in patients with higher tumor burden compared with patients who had lower tumor burden. As described herein, durable responders had a higher peak CAR T-cell/tumor burden ratio compared with nonresponders or responders who subsequently relapsed within one year post-treatment. As described herein, complete responders had a higher peak CAR T-cell/tumor burden ratio compared with partial responders or nonresponders. Accordingly, the disclosure also provides a method of determining whether or not a patient will be a nonresponder, have a durable response, or relapse within one year after administration of CAR T cell treatment comprising measuring the peak CAR T-cell/tumor burden ratio and making the determination based on those levels. As described herein, objective and durable response rate correlate with increasing peak CAR T-cell levels. As described herein, there is a lower durable response rate (12%) in patients within the lowest quartile of peak CAR T-cell/tumor burden ratio than in the top quartiles (>50%). As described herein, durable response in refractory large cell lymphoma treated with anti-CD19 CAR T-cell therapy containing a CD28 costimulatory domain, benefits from early CAR T cell expansion, commensurate with tumor burden.

As described herein, tumor burden positively associates with severe neurotoxicity: while rates increase from quartile 1 to quartile 3, they decline in the highest quartile, generally mirroring the association between CAR T-cell expansion and tumor burden in the overall population.

As described herein, peak CAR T-cell levels that are normalized to either pretreatment tumor burden or body weight associate strongly with efficacy, and the latter associate with grade ≥3 NE. Accordingly, the disclosure also provides a method of determining whether or not a patient will show durable response after administration of CAR T cell treatment comprising measuring the peak CAR T-cell levels normalized to either pretreatment tumor burden or body weight and making the determination based on those levels. Also, the disclosure also provides a method of determining whether or not a patient will show grade ≥3 NE after administration of CAR T cell treatment comprising measuring the peak CAR T-cell levels normalized to pretreatment tumor body weight and making the determination based on those levels.

As described herein, in vivo CAR T-cell expansion commensurate with pretreatment tumor burden and influenced by intrinsic product T-cell fitness, dose of specialized T-cell subsets, and host systemic inflammation, were determining factors for durable response. Accordingly, these parameters may be used as biomarkers for durable response and may also be manipulated experimentally to improve response to T cell therapy.

As described herein, suboptimal product T-cell fitness was a major factor related to primary treatment resistance, and limited numbers of CCR7+CD45RA+ or CD8 T cells in proportion to tumor burden were associated with a failure to achieve durable response. Accordingly, these parameters may be used as biomarkers for durable response and may also be manipulated experimentally to improve response to T cell therapy.

As described herein, high tumor burden, pronounced inflammatory status (reflected by myeloid activation markers pre- and post-CAR T-cell infusion), and excess type-1 cytokines associated negatively with durable efficacy and positively with severe toxicities. Accordingly, these parameters may be used as biomarkers for durable response and may also be manipulated experimentally to improve response to T cell therapy.

Characterization of the Tumor Microenvironment (TME)

The present disclosure also provides methods to characterize the tumor microenvironment (TME) using gene expression profiling and/or intratumoral T cell density measurement prior to treatment with a chimeric receptor therapy (e.g., axicabtagene ciloleucel (axi-cel)). As described herein, the TME characteristics utilizing pre-specified gene sets (e.g., Immunosign®21, Pan Cancer) and immune scores (e.g., Immunosign®21) and/or intratumoral T cell density measurements or indices (e.g., Immunoscore®) associate with clinical outcomes of chimeric receptor therapy (e.g., axicabtagene ciloleucel (axi-cel)).

Patient biopsies may be used as starting material to analyze the tumor microenvironment using gene expression profiling (e.g., digital gene expression using NanoString™) and immunohistochemistry (IHC). In some embodiments, the patient biopsy is obtained prior to treatment with a chimeric receptor therapy (e.g., axicabtagene ciloleucel (axi-cel)). In some embodiments, the biopsy is obtained just prior to the beginning of conditioning therapy.

A bioinformatics method may be used to generate an immune score or scores to characterize the TME. In some embodiments, the immune score is a measure of immune related genes that provides information regarding adaptive immunity including T cell cytotoxicity, T cell differentiation, T cell attraction, T cell adhesion and immune suppression including immune orientation, angiogenesis suppression, immune co-inhibition, and cancer stem cells. The bioinformatics method may also include T cell-specific (effector T cell, Th1) genes, interferon pathway-related genes, chemokines, and immune checkpoints.

An expression profiling assay (e.g., The Immunosign® Clinical Research assay utilizes the nCounter® technology (NanoString)) may be used to measure the gene expression level of multiple immune genes in a multiplex format. In some embodiments, a high/low immune score (e.g., Immunosign®21 score) cut-off may be defined as the 25th percentile of the observed scores among samples. In some embodiments, the high score indicates expression of immune-related genes potentially associated with tumor response.

In some embodiments, the immune score is a measure of intratumoral T cell density. Intratumoral T cell density may be determined by, for example, detecting and quantifying T cells, such as CD3+ T cells and/or CD8+ T cells, in the tumor microenvironment. For example, tumor biopsies may be sectioned and stained or labeled for T cell markers such as CD3 and/or CD8, and the relative or absolute abundance of T cells may be quantified by a pathologist or determined using dedicated digital pathology software. In some embodiments, a high/low immune score (e.g., Immunoscore®) is assigned based on intratumoral T cell density. A high/low immune score threshold may be defined, for example, as the median score observed among samples. In some embodiments, intratumoral T cell density is determined using flow cytometry and/or protein-based assays such as western blotting and ELISA.

Expression and tumor-infiltrating T lymphocyte analysis and scoring may be used to examine associations between TME features and response. In some embodiments, objective response (OR) is determined per the revised IWG Response Criteria for Malignant Lymphoma (Cheson, 2007) and determined by IWG Response Criteria for Malignant Lymphoma (Cheson et al. Journal of Clinical Oncology 32, no. 27 (September 2014) 3059-3067). In some embodiments, Duration of Response is assessed. In some embodiments, Progression-Free Survival (PFS) by investigator assessment per Lugano Response Classification Criteria is evaluated.

In some embodiments, the present disclosure provides a predictive tool for clinical efficacy of T cell therapy, by analyzing tumor microenvironment prior to treatment (e.g., pre-conditioning) and changes occurring after T cell therapy administration (e.g., two weeks after, four weeks after).

Methods of the present invention may also be used in companion testing to inform on whether additional therapies, in combination or used sequentially, will be more effective in subjects with certain tumor microenvironment characteristics. In some embodiments, additional treatments may be cytokines (e.g., IL-2, IL-15), stimulating antibodies (e.g., anti-41BB, OX-40), checkpoint blockade (e.g., CTLA4, PD-1), or innate immune stimulators (e.g., TLR, STING agonists). In some embodiments, additional treatments may be T cell-recruiting chemokines (e.g., CCL2, CCL1, CCL22, CCL17, and combinations thereof) and/or T cells. In some embodiments, the additional therapy or therapies are administered systemically or intratumorally.

One aspect of the present disclosure relates to methods of treating malignancy comprising measuring immune-related gene expression and/or T cell density at one or more site(s) of malignancy (i.e., the tumor microenvironment) prior to administration (e.g., at least one infusion) of CAR-T cells or T cells expressing an exogenous TCR. In some embodiments, said measurement is performed prior to chemotherapeutic conditioning and engineered T cell (e.g., CAR-T cell) administration.

In some embodiments, said measurement comprises determining a composite immune score based on immune-related gene expression, such as an ImmunoSign®21 or Immunosign®15 score. In some embodiments, said measurement comprises determining an immune score based on intratumoral density of T cells, including CD3+ and/or CD8+ T cells, such as Immunoscore®. In some embodiments, said measurement further comprises determining and assigning relative score(s), such as High or Low, based on comparison of a subject's immune score(s) to a predetermined threshold. In some embodiments, such predetermined threshold is or has been determined to have prognostic value with respect to the treatment of the malignancy with the engineered T cell.

In some embodiments, the disclosed methods further comprise a step of treatment optimization based on said measurement(s). For example, in some embodiments, the dose and/or schedule of engineered T cell (e.g., CAR-T cell) administration is optimized based on the immune score(s) of the tumor microenvironment. In exemplary embodiments, a subject with a low immune score, such as a low ImmunoSign®21 score, is administered a higher dose of CAR-T cells than a subject with a High immune score. In some embodiments, a subject with a low immune score is administered a dose that is about 25% higher, or about 50% higher, or about 100% higher, than a subject with a high immune score.

In additional and alternative exemplary embodiments, a subject with a Low immune score receives one or more additional CAR-T cell infusions. In some embodiments, a subject with a Low pretreatment immune score is administered a first dose of CAR-T cells, treatment response is assessed, and, if incomplete response is observed, an additional TME immune score measurement step is conducted. In some embodiments, an additional administration of CAR-T cells is performed if the subject's immune score is high following the first administration.

In some embodiments, the disclosed methods additionally or alternatively comprise a 'pre-treatment' step in which subjects with a low immune score are treated with the objective of improving their immune score prior to CAR-T administration. For example, in some embodiments, a patient with a Low immune score is administered one or more immunostimulants, such as cytokines, chemokines, or immune checkpoint inhibitors. In some embodiments, an additional measurement of immune score is performed prior to treatment.

In some embodiments, the prognostic value of a High immune score with respect to complete response based on CAR-T therapy is considered when evaluating treatment options. For example, in some embodiments, a subject with a high immune score receives CAR-T administration as an earlier line of therapy than a subject with a low immune score.

Tumor Immune Contexture is a Determinant of Anti-CD19 CAR T Cell Efficacy in Large B Cell Lymphoma As listed below, the disclosure provides a number of associations between the properties of the TME in a subject's cancer and CART treatment efficacy and other parameters. These associations have multiple applications including biomarker use, treatment selection guidelines, treatment improvements, and T cell therapy design. Clinically, these findings may yield new predictive/prognostic markers and new strategies to overcome primary treatment resistance in patients with immune detrimental TME pretreatment via local or systemic provision of T cell chemokines, γ-chain receptor cytokines, or IFN program-stimulating factors through T cell engineering or combinatorial approaches. In addition, the inverse associations between efficacy and tumor expression of CTAs and transcriptional factors (master switch PAX5, B cell specific transcriptional coactivator POU2AF143, marker of epigenetic heterogeneity AICDA44, surface sialyltransferase B cell antigen CD75 [ST6GAL145,46]) suggest possible epigenetic dysregulation as a primary resistance mechanism to T cell intervention, similar to that observed in other cancer types, that may be actionable via epigenetic modulators (DNA methylation inhibitors, histone deacetylases, methylases and demethylases), checkpoint blocking agents, agonists, or CAR T cell design improvements. In one embodiment, the pretreatment/baseline measurements are taken prior to pre-conditioning therapy (e.g., cyclophosphamide, fludarabine). In one embodiment, the tumor is large B cell lymphoma.

As described herein, the expression levels of the CD3D, CD69, IRF1, CXCL9, CXCL10, STAT1 genes correlate positively with objective response (CR/PR) and the expression levels of the VEGFA, PDCD1, and/or CD274 genes correlate negatively with objective response (CR/PR). Accordingly, in one embodiment, the disclosure provides a method of predicting efficacy in response to CAR T cell therapy in a subject having a tumor in need thereof comprising measuring the baseline (preconditioning) levels of CD3D, CD69, IRF1, CXCL9, CXCL10, STAT1, VEGFA, PDCD1, and/or CD274 genes in a sample of the subject's tumor, and predicting the tumor's response based on one or more of those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, the expression levels of the GZMA, CD69, IRF1, CXCL9, CXCL10, STAT1 genes correlate positively with best response and the expression levels of the VEGFA gene correlates negatively with best response. Accordingly, the disclosure provides a method of predicting efficacy in response to CAR T cell therapy in a subject having a tumor in need thereof comprising measuring baseline (preconditioning) levels of GZMA, CD69, IRF1, CXCL9, CXCL10, STAT1, and/or VEGFA genes in a sample of the subject's tumor and predicting the tumor's best response based on one or more of those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, the lower the expression levels of at least one of CD8A, PRF1, IRF1, CCL5, CXCL9, CCL2, STAT1, STAT4, VEGFA, CTLA4, PDCD1, and/or CD274 in a sample of a subject's tumor, the worse the grade of neurologic events after CAR T cell therapy. Accordingly, the disclosure provides a method of predicting adverse events in response to CAR T cell therapy in a subject in need thereof comprising measuring the baseline (preconditioning) levels of CD8A, PRF1, IRF1, CCL5, CXCL9, CCL2, STAT1, STAT4, VEGFA, CTLA4, PDCD1, and/or CD274 in a sample of the subject's tumor and predicting the grade of neurologic events based on one or more of those measurements. In one embodiment, the disclosure provides a method of selecting a subject for CAR T cell treatment based on these results. In one embodiment, the disclosure provides a method that further comprises administering the treatment to the subject with a TME favorable to treatment response without neurotoxicity. In one embodiment, the disclosure provides a method further comprising administering to the subject the appropriate treatments to reduce neurotoxicity in advance of treatment or during treatment.

As disclosed herein, the profile of pretreatment tumor immune infiltrates in a subject's tumor may fall in one of two clusters: if a subject's tumor measurements fall within cluster A (FIG. 36), the subject will fall within those having a complete response whereas if the measurements fall within cluster B (FIG. 36), the subject will fall among those having progressive disease. Accordingly, the disclosure provides a method of predicting efficacy in response to CAR T cell therapy in a subject having a tumor in need thereof comprising measuring the baseline (preconditioning) profile of pretreatment tumor immune infiltrates in a sample of the subject's tumor and predicting the subject's response to the treatment based on one or more of those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, the lower the density of Treg and polymorphonuclear myeloid-derived suppressor cells (PMN-MDSC cells), the worse the neurotoxicity (Grade ≥3). Accordingly, the disclosure provides a method of predicting neurotoxicity in response to CAR T cell therapy in a subject in need thereof comprising measuring the baseline (preconditioning) density of Treg cells and PMN-MDSCs in a sample of the subject's tumor and predicting the treatment's neurotoxicity based on one or more of those measurements. In one embodiment, the disclosure provides a method of selecting a subject for CAR T cell treatment based on these results. In one embodiment, the disclosure provides a method that further comprises administering the treatment to the subject with a TME favorable to treatment response without neurotoxicity. In one embodiment, the disclosure provides a method further comprising administering to the subject the appropriate treatments to reduce neurotoxicity in advance of treatment or during treatment.

As disclosed herein, pretreatment density of Treg (CD3+CD8−FoxP3+) in a sample of the subject's tumor correlates positively with tumor microenvironment features that are desirable for efficacy, including CD8+PD-1+ T cell density.

Accordingly, the disclosure provides a method of predicting efficacy in response to CAR T cell treatment in a subject having a tumor in need thereof comprising measuring pretreatment density of Treg (CD3+CD8−FoxP3+) in a sample of the subject's tumor and predicting efficacy based on that measurement. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, the levels of CD3+, CD8+, and activated CD8+ T cells associate positively with response to treatment. Accordingly, the disclosure provides a method of predicting efficacy in response to CAR T cell therapy in a subject having a tumor in need thereof comprising measuring the baseline (preconditioning) density of CD3+, CD8+, and activated CD8+ T cells in a sample of the subject's tumor and predicting the treatment efficacy based on that measurements. In one embodiment, the activated CD8+ T cells have expression of one checkpoint gene selected from PD-1 and LAG-3. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, low tumor burden and high tumor-infiltrating T cell density correlate positively with complete response. Accordingly, the disclosure provides a method of predicting efficacy in response to CAR T cell therapy in a subject having a tumor in need thereof comprising measuring the baseline (preconditioning) tumor burden and/or tumor-infiltrating T cell density in a sample of the subject's tumor and predicting the treatment efficacy based on those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment expression levels in a sample of the subject's tumor of IL-7/IL-7R, IL-18, and CCL5 correlate with CD3δ, CD8α, CD4; CCR5 and IL-15 correlate with CD3δ, CD8α; and IL-21 correlates with CD3δ. Accordingly, the disclosure provides a method of predicting T cell gene expression and density as a surrogate for T cell involvement, which correlates positively with response in CART cell treatment of a tumor in a subject in need thereof, comprising measuring the baseline (preconditioning) levels of IL-7/IL-7R, IL-18, CCL5, CCR5, IL-15 and IL-21 and predicting T cell gene expression and density based on those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment expression in a sample of the subject's tumor of CCL5 and CCR5 correlates positively with density of CD8+ and CD4+ T cells by IHC. Accordingly, the disclosure provides a method of predicting T cell gene expression and density as a surrogate for T cell involvement in CART cell treatment of a tumor in a subject in need thereof comprising measuring pretreatment expression levels in a sample of the subject's tumor of CCL5 and CCR5 and correlating those levels with density of CD8+ and CD4+ T cells by IHC based on the measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment expression in a sample of the subject's tumor of CCR5, IL-1R, STAT1, FPR2, and CXCL9 correlates positively with myeloid cell density (CD11b+ and CD14+). Accordingly, the disclosure provides a method of predicting myeloid cell density in a tumor in a subject in need of CAR T cell treatment, comprising measuring pretreatment expression in a sample of the subject's tumor of CCR5, IL-1R, STAT1, FPR2, and CXCL9 and predicting myeloid cell density (CD11b+ and CD14+) based on those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment CD8+PD-1+ T cell density associates positively with CART cell levels. Accordingly, the disclosure provides a method of predicting peak CAR T cell levels normalized to tumor burden after CAR T cell administration to a subject having a tumor in need thereof comprising measuring pretreatment CD8+PD-1+ T cell density and predicting CART cell levels based on those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment density of activated CD8+PD-1+LAG-3+/−TIM-3− T cells associates positively with clinical efficacy. Accordingly, the disclosure provides a method of predicting efficacy in response to CAR T cell treatment in a subject having a tumor in need thereof comprising measuring pretreatment density of activated CD8+PD-1+LAG-3+/−TIM-3− T cells in a sample of the subject's tumor and predicting efficacy based on that measurement. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment density of CD3+CD8−FoxP3+ (Treg) cells and/or CCL22 gene expression associate positively with low-grade neurotoxicity and high activated T cell density. Accordingly, the disclosure provides a method of predicting neurotoxicity and activated T cell density in response to CART cell treatment in a subject having a tumor in need thereof comprising measuring pretreatment density of CD3+CD8−FoxP3+ (Treg) cells and/or CCL22 gene expression in a sample of the subject's tumor and predicting neurotoxicity and activated T cell density based on that measurement. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, Immunosign 21 score is predictive of objective response (CR/PR). Accordingly, the disclosure provides a method of predicting objective response to CAR T cell treatment in a subject having a tumor in need thereof, comprising measuring the pretreatment Immunosign 21 score in a sample of the subject's tumor and predicting objective response based on that measurement. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, pretreatment Immunoscore TL, Immunosign 15 and Immunosign 21 associate positively with T cell density. Accordingly, the disclosure provides a method of predicting pretreatment T cell density in a sample of the subject's tumor comprising measuring the pretreatment Immunoscore TL, Immunosign 15 and/or Immunosign 21 scores in a sample of the subject's tumor and predicting T cell density based on those measurements. In one embodiment, the disclosure provides a method of selecting a subject for CAR T cell treatment based on these results. In one embodiment, the disclosure provides a method that further comprises administering the treatment to the subject with a TME favorable to treatment response.

As disclosed herein, gene expression across all B cell lineage markers, including CD19, CD20, CD22, and CD75 (ST6GAL1), B cell transcriptional master switch PAX5, and transcriptional coactivator POU2AF1, markedly decreased in the TME of responders early post CAR T cell treatment (e.g., within 1-2 weeks). In one embodiment, decreased expression of CTAG1B (NY-ESO-1) and MAGE-C2 were observed only in responders. Accordingly, the disclosure provides a method of predicting CAR T cell efficacy by measuring, early post treatment, the decrease of B cell related genes and predicting efficacy based on the measurement.

As disclosed herein, responders, but not nonresponders, show early and brisk elevation of cytotoxic T cell-related genes, including CD8α, immune effector molecules (granzyme A), key T cell growth factors and chemokines (IL-15), interferon (IFN)γ-regulated immune checkpoints (PD-L1, B7-H3, CTLA-4), and myeloid-related genes and corresponding chemokines (CD14, CCL2). Accordingly, the disclosure provides a method of predicting CAR T cell efficacy by measuring, early post treatment (within 1-2 weeks) the increase in T cell related genes and predicting efficacy based on that measurement. In one embodiment, the method further comprises adjusting treatment based on the measurements.

In one embodiment, the disclosure provides a method of decreasing primary resistance to CART cell treatment comprising administering to a subject having a tumor in need thereof an agent that modulates the methylation state of the tumor (e.g. DNA demethylating inhibitors (DDMTi) 5-aza-2'-deoxycytidine (decitabine) and 5-azacytidine or other cytosine analogs), and/or the acetylation state of the tumor (e.g., HDAC inhibitors) prior to, during, or after administration of CART cell treatment.

In one embodiment, the disclosure provides a method of decreasing primary resistance to CAR T cell treatment comprising administering to a subject having a tumor in need thereof a checkpoint blocking agent such as agents that block immune checkpoint receptors on the surface of T cells, such as cytotoxic T lymphocyte antigen 4 (CTLA-4), lymphocyte activation gene-3 (LAG-3), T-cell immunoglobulin mucin domain 3 (TIM-3), B- and T-lymphocyte attenuator (BTLA), T-cell immunoglobulin and T-cell immunoreceptor tyrosine-based inhibitory motif (ITIM) domain, and programmed cell death 1 (PD-1/PDL-1) prior to, during, or after administration of CAR T cell treatment. In one embodiment, the checkpoint inhibitor is selected from Pembrolizumab (Keytruda), Nivolumab (Opdivo), Cemiplimab (Libtayo), Atezolizumab (Tecentriq), Avelumab (Bavencio), Durvalumab (Imfinzi), and Ipilimumab (Yervoy).

In one embodiment, the disclosure provides a method of decreasing primary resistance to CAR T cell treatment comprising administering to a subject having a tumor in need thereof an agonist of 41BB, OX40, and/or TLR prior to, during, or after administration of CAR T cell treatment.

In one embodiment, the disclosure provides a method of decreasing or overcoming primary resistance to CAR T cell treatment comprising improving CAR T cells by co-expressing gamma chain receptor cytokines under constitutive or inducible promoters.

In one embodiment, the disclosure provides a method of improving CAR T cell treatment by optimization of bridging therapy to modulate the tumor microenvironment to a more favorable immune permissive state. In one embodiment, the optimization comprises administering bridging therapy with Immunomodulatory imide drugs (IMIDs)/cereblon modulators (e.g., lenoalidomide, pomalidomide, iberdomide, and apremilast). In one embodiment, the optimization comprises administering bridging therapy with local radiation.

In one embodiment, the disclosure provides a method of improving CAR T cell treatment by optimization of bridging therapy to diminish tumor burden prior to CAR T cell treatment administration. In one embodiment, the optimization comprises administering bridging therapy with R-CHOP, bendamustine, alkylating agents, and/or platinum-based agents. Other exemplary bridging therapies are described elsewhere in this application.

In one embodiment, the disclosure provides a method of improving CAR T cell treatment by optimization of conditioning treatment to modulate the tumor microenvironment to a more favorable immune permissive state. In one embodiment, the optimization comprises addition of local irradiation to cyclophosphamide/fludarabine conditioning. In one embodiment, the optimization comprises administration of platinum-based agents as conditioning agents.

In one embodiment, the disclosure provides a method of improving CAR T cell treatment by coadministration of biological response modifiers together or post-CAR T cell administration to enable CAR T cell activity. In one embodiment, the method comprises administration of gamma chain cytokines (e.g., IL-2, IL-4, IL-7, IL-9, IL-15, and IL-21). In one embodiment, the method comprises administration of checkpoint blocking agents (e.g. anti-CTLA-4).

In one embodiment, the disclosure provides a method of improving CAR T cell treatment by reprogramming of CAR T cells to overcome detrimental tumor microenvironments. In one embodiment, the CAR T cells are engineered to express gamma chain receptor cytokines. In one embodiment, the gamma chain receptor cytokines are expressed under constitutive or inducible promoters.

In one embodiment, the disclosure provides a method of improving CAR T cell treatment by optimizing T cell manufacturing to help CAR T cells overcome detrimental tumor microenvironments. In one embodiment, the method comprises engineering CAR T cells to express gamma chain receptor cytokines. In one embodiment, the gamma chain receptor cytokines are expressed under constitutive or inducible promoters. In one embodiment, the method comprises growing the T cells in the presence of gamma chain cytokines such as IL-15.

In one embodiment, the disclosure provides a method of treating a malignancy in a patient comprising:

(a) analyzing a tumor biopsy from the patient to characterize the tumor microenvironment; and (b) administering an effective dose of T cells comprising one or more chimeric receptors to the patient, wherein the effective dose is determined using the characteristics of the tumor microenvironment.

In one embodiment, the tumor microenvironment is characterized using gene expression profiling, intratumoral T cell density measurement, or a combination thereof.

In one embodiment, the gene expression profiling comprises determining the expression level of a specified panel of genes (herein used as biomarkers) and/or a specific subset of T cells, many of which are exemplified in this section of the disclosure and in the Examples.

In one embodiment, the disclosure provides method of determining whether a patient will respond to chimeric receptor treatment comprising:

(a) analyzing a tumor biopsy (before and/or after treatment) from the patient to characterize the tumor microenvironment using a gene expression profile or a T cell profile;

(b) determining an immune score based on the gene expression profile; and (c) determining if the patient will respond to chimeric receptor treatment based on the immune score.

In one embodiment, the disclosure provides a method of determining whether a patient will respond to chimeric receptor treatment comprising:

(a) obtaining a tumor biopsy from a patient prior to treatment and after treatment;

(b) analyzing the tumor biopsy to characterize the tumor microenvironment; and (c) determining if the patient will respond to chimeric receptor treatment based on the characteristics of the tumor microenvironment.

In one embodiment, the disclosure provides a method of treating a malignancy in a patient comprising:

(a) analyzing a tumor biopsy from the patient prior to chimeric receptor treatment to characterize the tumor microenvironment;

(b) determining if the patient will respond to chimeric receptor treatment based on the characteristics of the tumor microenvironment; and (c) administering an effective dose of T cells comprising one or more chimeric receptors to the patient, wherein the effective dose is determined using the characteristics of the tumor microenvironment.

In one embodiment, the characteristics of the tumor microenvironment are any of the characteristics analyzed and described in the Examples and in this section of the disclosure.

Measuring Response and Efficacy

In some embodiments, methods described herein may provide a clinical benefit to a subject. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, approximately 1%, 2%, 3%, 4%, 5%, 6%, 7%, 8%, 9%, 10%, 15%, 20%, 25%, 30%, 35%, 40%, 45%, 0%, 55%, 60%, 65%, 70%, 75%, 80%, 85%, 90% or 95% and any unenumerated % in between of patients achieve a clinical benefit. In some embodiments, the response rate is 1%, 2%, 3%, 4%, 5%, 6%, 7%, 8%, 9%, 9.5%, 10.5%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 25 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81, 82, 83, 84, 85, 86, 87, 88, 89, 90, 91, 92, 93, 94, 95, 96, 97, 98, 99, or 100% or some other unenumerated percentage and range in between 1% and 100%. In some embodiments, the response rate is between 0%-10%, 10%-20%, 20%-30%, 30%-40%, 40%-50%, 50%-60%, 60%-70%, 70%-80%, 80%-90%, or 90%-100%. In some embodiments, the response rate is between 0%-1.%, 1%-1.5%, 1.5%-2%, 2%-3%, 3%-4%, 4%-5%, 5%-6%, 6%-7%, 7%-8%, 8%-9%, 9%-10%, 10%-15%, 15%-20%, 20-25%, 25%-30%, 35-40%, and so one and so forth, through 95%-100%.

In some embodiments, the quartiles for peak CAR T cells ranges are those in the FIGS. and Tables and 0-15, 15-35, and so on and so forth, 40-100, 0-40 40-50 40-60 40-70, 40-80, 40-90, 40-100, 40-110, 40-120, 40-130, 40-140, 40-150, 40-300, 40-1000, 80-160, 50-100, 50-110, 50-120, 50-130, 50-140, 50-150, 50-160, 50-170, 50-180, 50-190, 50-200, 60-100, 60-110, 60-120, 60-130, 60-140, 60-150, 60-160, 60-170, 60-180, 60-190, 60-200, 70-100, 70-110, 70-120, 70-130, 70-140, 70-150, 70-160, 70-170, 70-180, 70-190, 70-200, 80-100, 80-110, 80-120, 80-130, 80-140, 80-150, 80-160, 80-170, 80-180, 80-190, 80-200, 90-100, 90-110, 90-120, 90-130, 90-140, 90-150, 90-160, 90-170, 90-180, 90-190, 90-200, 100-110, 100-120, 100-130, 100-140, 100-150, 100-160, 100-170, 100-180, 100-190, 100-200, and so on and so forth, 50-70, 60-80, 70-90, 80-100, 90-110, 100-120, 110-130, 120-150, 130-160, 140-170, 150-180, 160-190, 170-200, 180-210, 190-210, 200-220, 210-230, 220-240, or 230-250, and so on and so forth, and any unenumerated ranges in between. In some embodiments, the quartiles for CCL2 and CXCL10 ranges are those in the FIGS. and Tables and 0-100, 100-200, 200-300, 400-500 500-600 600-700, or so on and so forth or any other unenumerated ranges in between, 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, 1900-2000, 2000-2200, 2200-2300, 2300-2400, 2400-2600, 2600-2800, 2800-3000, or so on and so forth, or any other unenumerated ranges in between. In some embodiments, the quartiles for Tumor Burden are those in the FIGS. and Tables and 0-500, 500-1000, 1000-1500 and so on and so forth, 1000-2000, 2000-3000, 3000-4000, 4000-5000, 5000-6000, 6000-7000 and so on and so forth, 8000-10000, 10000-20000 and so on and so forth, and any other unenumerated ranges in between. In some embodiments, the quartiles for Ferritin ranges are those in the FIGS. and Tables and 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200 and so on and so forth, 100,000-200,000, 200,000-500,000, 500,000, or 400,000-500,000, and so on and so forth, 1000000-1500000, 1500000-1600000, and so on and so forth, 2000000-10000000, 2000000-15000000, and so on and so forth, and any other unenumerated ranges in between. In some embodiments, the quartiles for IFNγ, Infused Naïve-like T Cells, Infused CD8 T Cells, Infused CD4 T cells ranges, are those in the FIGS. and Tables an <0.1, 0.1-0.2, 0.2-0.3, 0.3-0.4, 0.4-0.5, 0.6-0.7, 0.7-0.8, 0.8-0.9, 0.91-1.0, 1.0-1.1 so on and so forth through 99.9-100, 1-5, 5-10, 10-15, 15-20, 25-30, 30-35, 35-40, 40-45, 45-50, 50-60, 60-70, 70-80, 80-90, 90-100, 100-125, 125-150, 150-175, or 175-200, 10-30 30-50 50-70, 70-90 and so on and so forth, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48, 48-49, 49-50, 50-51, 51-52, 52-53, 53-54, 54-55, 55-56, 56-57, 57-58, 58-59, 59-60 and so on and so forth units and so on and so forth, and any other unenumerated ranges in between. In some embodiments, the quartiles for peak CAR T cells/tumor burden, peak CAR T cells/body weight, Infused Naïve-like T Cells/Tumor Burden, Infused CD8 T Cells/Tumor Burden, Infused CD4 T Cells/Tumor Burden, and Infused CD3 T Cells/Tumor Burden ranges are those in the FIGS. and Tables and 0.001-0.005, 0.005-0.010, 0.010-0.020, 0.020-0.030, 0.030-0.040, 0.040-0.050, 0.05-0.06, 0.06-0.07, 0.07-0.08, 0.08-0.09, 0.09-0.10, 0.1-0.11, 0.11-0.12, 0.12-0.13, 0.13-0.14, 0.14-0.15, 0.15-0.16, 0.16-0.17, 0.17-0.18, 0.18-0.19, 0.19-0.20, 0.5-2.5, 0.05-0.1, 0.1-0.2, 0.2-0.3, 0.3-0.4, 0.4-0.5, 0.5-0.6, 0.6-0.7, 0.7-0.8, 0.8-0.9, 0.9-1.0, 1-2, 2-3, 3-4, 4-5, and so on and so forth, and any unenumerated ranges in between, and the median is 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 012, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, or 10 units and any other values in between. In some embodiments, the quartiles for LDH and Infused CD3 T Cells ranges are those in the FIGS. and Tables and 0-50, 50-100, 100-150, 150-200, 200-250, 250-300, 300-350, 350-400, 400-450 or 450-500 and so on and so forth up to 1000, 150-250, 250-350, 350-450, 450-550, and so on and so forth, 1-500, 1-1000, 25-100, 25-200, 25-300, 25-400, 25-500, 25-1000, 100-150, 100-200, 100-300, 100-400, 100-500, 100-1000 and so on and so forth, 100-5000, 100-4900, 100-4800, 100-4700, 100-4600, 100-4500, 100-4400, 100-4300, 100-4200, 100-4100, 100-4000, 100-3900, 100-3800, 100-3700, 100-3600, 100-3500, 100-3400, 100-3300, 100-3200, 100-3100, 100-3000, 100-2900, 100-2800, 100-2700; 100-2600; 100-2500, 100-2400, 100-2300, 100-2200, 100-2100, 100-2000, 100-1900, 100-1800, 100-1700, 100-1600, 100-1500, 100-1400, 100-1300, 100-1200, 100-1100, 100-1000, 100-900, 100-800, 100-700; 100-600, 100-500, 100-400; 100-300, 100-200, 500-10,000, 500-7500, 500-5000, 500-4900, 500-4800, 500-4700, 500-4600, 500-4500, 500-4400, 500-4300, 500-4200, 500-4100, 500-4000; 500-3900, 500-3800, 500-3700, 500-3600, 500-3500, 500-3400, 500-3300, 500-3200; 500-3100; 500-3000, 500-2900, 500-2800, 500-2700, 500-2600, 500-2500, 500-2400, 500-2300, 500-2200, 500-2100, 500-2000, 500-1900, 500-1800, 500-1700, 500-1600, 500-1500; 500-1400; 500-1300, 500-1200, 500-1100, 500-1000, 500-900, 500-800; 500-700, or 500-600, and so on and so forth, and any other unenumerated ranges in between. In some embodiments, the quartiles for IL-6 ranges are those in the FIGS. and Tables and 0-1, 1-2; 2-3, 3-4; 4-5, 5-6, 6-7, 7-8, 8-9, 9-10, and so on and so forth, 3-4, 3-5, 3-6, 3-7, 3-8, 3-9, and so on and so forth, 6-1; 6-2, 6-3, 6-4, 6-6, 6-6; 6-7 and so on and so forth; 6.7-10, 6.7-20, 6.7-30, 6.7-80, 6.7-90, 6.7-100, 6.7-110, 6.77-120, 6.7-130, and so on and so forth, and any other unenumerated ranges in between. In some embodiments, the quartiles for infused CD3 T cells ranges are those in the FIGS. and Tables and 0-100, 100-200, 200-300, 300-400, 400-500; 500-600, 600-700, and so on and so forth; 100-240, 100-150, 100-260, and so on and so forth, 300-400, 300-500, 300-600, 300-700, 300-800, and so on and so forth, and any other unenumerated ranges in between. In some embodiments, the quartiles for Doubling Time are those in the FIGS. and Tables and <2, <2.1, <2.2, <2.3, <2.4, <2.5 and so on and so forth, more than 1.1, 1.2, 1.3, 1.4, 1.5, 1.6, 1.7, 1.8, 1.9 and less than 2, and so on and so forth, and any other ranges in between. In some embodiments, the quartiles for IFNγ in coculture ranges are 200-300, 300-400, 400-500, 500-600 and so on and so forth, 300-500, 300-1000, 300-1500, 300-2000, 300-2500, 300-3000, 300-3500, 300-3600 and so on and so forth, 2000-3000, 3000-4000, 4000-5000, 4000-6000, and so on and so forth, 6000-7000, 6000-8000, 6000-9000 and so on and so forth, 8000-15000, 8000-16000, 8000-17000, 8000-18000 and so on and so forth and any other unenumerated ranges in between. In some embodiments, any of these ranges may be qualified by the terms about or approximately.

Clinical benefit may be objective response or durable clinical response defined as ongoing response at a median follow up time of 1 year. In some embodiments, response, levels of CAR T cells in blood, or immune related factors is determined by follow up at about 1 day, about 2 days, about 3 days, about 4 days, about 5 days, about 6 days, or about 7 days after administration of engineered CAR T cells. In some embodiments, response, levels of CAR T cells in blood, or immune related factors is determined by follow up at about 1 week, about 2 weeks, about 3 weeks, or about 4 weeks after administration of engineered CART cells. In some embodiments, response, levels of CAR T cells in blood and/or immune related factors are determined by follow up at about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months after administration of a engineered CAR T cells. In some embodiments, response, levels of CAR T cells in blood and/or immune related factors are determined by follow up at about 1 year, about 1.5 years, about 2 years, about 2.5 years, about 3 years, about 4 years, or about 5 years after administration of engineered CAR T cells.

Additional Attributes that Improve the Product Safety Profile and their Impact in Efficacy of CAR T-Cell Therapy As described herein, efficacy decreases and toxicity increases with increasing lines of prior therapy. Tumor burden, markers of baseline inflammation, and product doubling time increases with increasing lines of therapy, while the proportion and absolute numbers of $T_N$ cells in the product decreases. The cells referred to as $T_N$ in the EXAMPLES were identified as CCR7+ CD45RA+ T-cells and have been further characterized as stem-like memory cells. As described herein, product CAR T-cell doubling time closely associates with efficacy and is not associated with severe toxicities.

As described herein, the total number of infused CD8+ cells, TN cells, and CD8 TN cells, all normalized to tumor burden, associate with durable response but not with toxicity. Accordingly, the disclosure provides methods of improving efficacy of CART cell therapy in a patient comprising increasing the total number of infused CD8+ cells, TN cells, and CD8 TN cells, all normalized to tumor burden in the infusion product, and administering the infusion product to the patient. The cells referred to as $T_N$ in the EXAMPLES were identified as CCR7+ CD45RA+ T-cells and may be further characterized as stem-like memory cells.

As described herein, IFNγ secretion levels of the final product after co-culture with CD19-expressing targets positively associated with grade ≥3 NE but not efficacy or grade ≥3 CRS. As described herein, there is an association between product co-culture IFNγ levels and the proportion of differentiated CCR7-negative T cells in the infusion bag and product doubling time. As described herein, tumor burden and pretreatment inflammatory markers levels negatively associate with durable response rate. As described herein, the levels of pretreatment inflammatory markers are positively associated with toxicity, such as grade ≥3 neurotoxicity. Accordingly, in one embodiment, the disclosure provides a method of reducing (e.g., prophylactically) neurotoxicity of CAR T cell treatment based on those levels. As described herein, in addition to pretreatment tumor burden, baseline serum LDH, and the baseline inflammatory markers IL6 and CRP negatively associated with efficacy. As described herein, baseline serum LDH and day 0 IL15 measured postconditioning but prior to CAR T-cell infusion, associate positively with grade ≥3 NE. As described herein, baseline serum IL6 and LDH associate positively with grade ≥3 CRS. Accordingly, in one embodiment, the disclosure provides a method of predicting and reducing neurotoxicity based on the baseline serum LDH and day 0 IL15 measured postconditioning but prior to CAR T-cell infusion, and/or baseline serum IL6 levels. In another embodiment, the disclosure provides a method of determining the effective dose of CAR T cell treatment based on these levels. In another embodiment, the disclosure provides a method of reducing (e.g., prophylactically) neurotoxicity of CAR T cell treatment based on those levels.

Accordingly, the disclosure provides for methods of improving response to CAR T cell therapy and/or decreasing toxicity comprising decreasing the pre-treatment levels of inflammatory markers, day 0 IL15 postconditioning but prior to CAR T cell infusion, and/or baseline serum IL6. The disclosure also provides methods for predicting patient response to CAR T cell treatment comprising (a) measuring the levels of pre-treatment serum levels of inflammatory markers, day 0 serum levels of IL15 postconditioning but prior to CART cell infusion, and/or baseline serum IL6 and (b) predicting response based on those levels.

Measuring Response and Efficacy

In some embodiments, methods described herein may provide a clinical benefit to a subject. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, approximately 1%, 2%, 3%, 4%, 5%, 6%, 7%, 8%, 9%, 10%, 15%, 20%, 25%, 30%, 35%, 40%, 45%, 0%, 55%, 60%, 65%, 70%, 75%, 80%, 85%, 90% or 95% and any unenumerated % in between of patients achieve a clinical benefit. In some embodiments, the response rate is 1%, 2%, 3%, 4%, 5%, 6%, 7%, 8%, 9%, 9.5%, 10.5%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 25 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81, 82, 83, 84, 85, 86, 87, 88, 89, 90, 91, 92, 93, 94, 95, 96, 97, 98, 99, or 100% or some other unenumerated percentage and range in between 1% and 100%. In some embodiments, the response rate is between 0%-10%, 10%-20%, 20%-30%, 30%-40%, 40%-50%, 50%-60%, 60%-70%, 70%-80%, 80%-90%, or 90%-100%. In some embodiments, the response rate is between 0%-1.%, 1%-1.5%, 1.5%-2%, 2%-3%, 3%-4%, 4%-5%, 5%-6%, 6%-7%, 7%-8%, 8%-9%, 9%-10%, 10%-15%, 15%-20%, 20-25%, 25%-30%, 35-40%, and so one and so forth, through 95%-100%.

In some embodiments, the quartiles for peak CAR T cells ranges are those in the FIGS. and Tables and 0-15, 15-35, and so on and so forth, 40-100, 0-40 40-50 40-60 40-70, 40-80, 40-90, 40-100, 40-110, 40-120, 40-130, 40-140, 40-150, 40-300, 40-1000, 80-160, 50-100, 50-110, 50-120, 50-130, 50-140, 50-150, 50-160, 50-170, 50-180, 50-190, 50-200, 60-100, 60-110, 60-120, 60-130, 60-140, 60-150, 60-160, 60-170, 60-180, 60-190, 60-200, 70-100, 70-110, 70-120, 70-130, 70-140, 70-150, 70-160, 70-170, 70-180, 70-190, 70-200, 80-100, 80-110, 80-120, 80-130, 80-140, 80-150, 80-160, 80-170, 80-180, 80-190, 80-200, 90-100, 90-110, 90-120, 90-130, 90-140, 90-150, 90-160, 90-170, 90-180, 90-190, 90-200, 100-110, 100-120, 100-130, 100-140, 100-150, 100-160, 100-170, 100-180, 100-190, 100-200, and so on and so forth, 50-70, 60-80, 70-90, 80-100, 90-110, 100-120, 110-130, 120-150, 130-160, 140-170, 150-180, 160-190, 170-200, 180-210, 190-210, 200-220, 210-230, 220-240, or 230-250, and so on and so forth, and any unenumerated ranges in between. In some embodiments, the quartiles for CCL2 and CXCL10 ranges are those in the FIGS. and Tables and 0-100, 100-200, 200-300, 400-500 500-600 600-700, or so on and so forth or any other unenumerated ranges in between, 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-1800, 1800-1900, 1900-2000, 2000-2200, 2200-2300, 2300-2400, 2400-2600, 2600-2800, 2800-3000, or so on and so forth, or any other unenumerated ranges in between. In some embodiments, the quartiles for Tumor Burden are those in the FIGS. and Tables and 0-500, 500-1000, 1000-1500 and so on and so forth, 1000-2000, 2000-3000, 3000-4000, 4000-5000, 5000-6000, 6000-7000 and so on and so forth, 8000-10000, 10000-20000 and so on and so forth, and any other unenumerated ranges in between. In some embodiments, the quartiles for Ferritin ranges are those in the FIGS. and Tables and 0-50, 50-100, 100, 150, 200, 300, 400, 500, 549, 549-600, 600-650, 650-700, 700-750, 750-800, 800-850, 850-900, 900-950, 950-1000, 1000-1100, 1100-1200 and so on and so forth, 100,000-200,000, 200,000-500,000, 500,000, or 400,000-500,000, and so on and so forth, 1000000-1500000, 1500000-1600000, and so on and so forth, 2000000-10000000, 2000000-15000000, and so on and so forth, and any other unenumerated ranges in between. In some embodiments, the quartiles for IFNγ, Infused Naïve-like T Cells, Infused CD8 T Cells, Infused CD4 T cells ranges, are those in the FIGS. and Tables an <0.1, 0.1-0.2, 0.2-0.3, 0.3-0.4, 0.4-0.5, 0.6-0.7, 0.7-0.8, 0.8-0.9, 0.91-1.0, 1.0-1.1 so on and so forth through 99.9-100, 1-5, 5-10, 10-15, 15-20, 25-30, 30-35, 35-40, 40-45, 45-50, 50-60, 60-70, 70-80, 80-90, 90-100, 100-125, 125-150, 150-175, or 175-200, 10-30 30-50 50-70, 70-90 and so on and so forth, 30-31, 31-32, 32-33, 33-34, 34-35, 35-36, 36-37, 37-38, 38-39, 39-40, 40-41, 41-42, 42-43, 43-44, 44-45, 45-46, 46-47, 47-48 48-49, 49-50, 50-51, 51-52, 52-53, 53-54, 54-55, 55-56, 56-57, 57-58, 58-59, 59-60 and so on and so forth units and so on and so forth, and any other unenumerated ranges in between. In some embodiments, the quartiles for peak CAR T cells/tumor burden, peak CAR T cells/body weight, Infused Naïve-like T Cells/Tumor Burden, Infused CD8 T Cells/Tumor Burden, Infused CD4 T Cells/Tumor Burden, and Infused CD3 T Cells/Tumor Burden ranges are those in the FIGS. and Tables and 0.001-0.005, 0.005-0.010, 0.010-0.020, 0.020-0.030, 0.030-0.040, 0.040-0.050, 0.05-0.06, 0.06-0.07, 0.07-0.08, 0.08-0.09, 0.09-0.10, 0.1-0.11, 0.11-0.12, 0.12-0.13, 0.13-0.14, 0.14-0.15, 0.15-0.16, 0.16-0.17, 0.17-0.18, 0.18-0.19, 0.19-0.20, 0.5-2.5, 0.05-0.1, 0.1-0.2, 0.2-0.3, 0.3-0.4, 0.4-0.5, 0.5-0.6, 0.6-0.7, 0.7-0.8, 0.8-0.9, 0.9-1.0, 1-2, 2-3, 3-4, 4-5, and so on and so forth, and any unenumerated ranges in between, and the median is 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 2, 3, 4, 5, 6, 7, 8, 9, or 10 units and any other values in between. In some embodiments, the quartiles for LDH and Infused CD3 T Cells ranges are those in the FIGS. and Tables and 0-50, 50-100, 100-150, 150-200, 200-250, 250-300, 300-350, 350-400, 400-450 or 450-500 and so on and so forth up to 1000, 150-250, 250-350, 350-450, 450-550, and so on and so forth, 1-500, 1-1000, 25-100, 25-200, 25-300, 25-400, 25-500, 25-1000, 100-150, 100-200, 100-300, 100-400, 100-500, 100-1000 and so on and so forth, 100-5000, 100-4900, 100-4800, 100-4700, 100-4600, 100-4500, 100-4400, 100-4300, 100-4200, 100-4100, 100-4000, 100-3900, 100-3800, 100-3700, 100-3600, 100-3500, 100-3400, 100-3300, 100-3200, 100-3100, 100-3000, 100-2900, 100-2800, 100-2700, 100-2600, 100-2500, 100-2400, 100-2300, 100-2200, 100-2100, 100-2000, 100-1900, 100-1800, 100-1700, 100-1600, 100-1500, 100-1400, 100-1300, 100-1200, 100-1100, 100-1000, 100-900, 100-800, 100-700, 100-600, 100-500, 100-400, 100-300, 100-200, 500-10,000, 500-7500, 500-5000, 500-4900, 500-4800, 500-4700, 500-4600, 500-4500, 500-4400, 500-4300, 500-4200, 500-4100, 500-4000, 500-3900, 500-3800, 500-3700, 500-3600, 500-3500, 500-3400, 500-3300, 500-3200, 500-3100, 500-3000, 500-2900, 500-2800, 500-2700, 500-2600, 500-2500, 500-2400, 500-2300, 500-2200, 500-2100, 500-2000, 500-1900, 500-1800, 500-1700, 500-1600, 500-1500, 500-1400, 500-1300, 500-1200, 500-1100, 500-1000, 500-900, 500-800, 500-700, or 500-600, and so on and so forth, and any other unenumerated ranges in between. In some embodiments, the quartiles for IL-6 ranges are those in the FIGS. and Tables and 0-1, 1-2, 2-3, 3-4, 4-5, 5-6, 6-7, 7-8, 8-9, 9-10, and so on and so forth, 3-4, 3-5, 3-6, 3-7, 3-8, 3-9, and so on and so forth, 6-1, 6-2, 6-3, 6-4, 6-6, 6-6, 6-7 and so on and so forth, 6.7-10, 6.7-20, 6.7-30, 6.7-80, 6.7-90, 6.7-100, 6.7-110, 6.77-120, 6.7-130, and so on and so forth, and any other unenumerated ranges in between. In some embodiments, the quartiles for Infused CD3 T cells ranges are those in the FIGS. and Tables and 0-100, 100-200, 200-300, 300-400, 400-500, 500-600, 600-700, and so on and so forth, 100-240, 100-150, 100-260, and so on and so forth, 300-400, 300-500, 300-600, 300-700, 300-800, and so on and so forth, and any other unenumerated ranges in between. In some embodiments, the quartiles for Doubling Time are those in the FIGS. and Tables and <2, <2, <2.1, <2.2, <2.3, <2.4, <2.5 and so on and so forth, more than 1.1, 1.2, 1.3, 1.4, 1.5, 1.6, 1.7, 1.8, 1.9 and less than 2, and so on and so forth, and any other ranges in between. In some embodiments, the quartiles for IFNγ in coculture ranges are 200-300, 300-400, 400-500, 500-600 and so on and so forth, 300-500, 300-1000, 300-1500, 300-2000, 300-2500, 300-3000, 300-3500, 300-3600 and so on and so forth, 2000-3000, 3000-4000, 4000-5000, 4000-6000, and so on and so forth, 6000-7000, 6000-8000, 6000-9000 and so on and so forth, 8000-15000, 8000-16000, 8000-17000, 8000-18000 and so on and so forth and any other unenumerated ranges in between. In some embodiments, any of these ranges may be qualified by the terms about or approximately.

Clinical benefit may be objective response or durable clinical response defined as ongoing response at a median follow up time of 1 year. In some embodiments, response, levels of CAR T cells in blood, or immune related factors is determined by follow up at about 1 day, about 2 days, about 3 days, about 4 days, about 5 days, about 6 days, or about 7 days after administration of engineered CAR T cells. In some embodiments, response, levels of CAR T cells in blood, or immune related factors is determined by follow up at about 1 week, about 2 weeks, about 3 weeks, or about 4 weeks after administration of engineered CART cells. In some embodiments, response, levels of CAR T cells in blood and/or immune related factors are determined by follow up at about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months after administration of a engineered CAR T cells. In some embodiments, response, levels of CAR T cells in blood and/or immune related factors are determined by follow up at about 1 year, about 1.5 years, about 2 years, about 2.5 years, about 3 years, about 4 years, or about 5 years after administration of engineered CAR T cells.

Chimeric Antigen Receptors

Chimeric antigen receptors (CARs) are genetically engineered receptors. These engineered receptors may be inserted into and expressed by immune cells, including T cells and other lymphocytes in accordance with techniques known in the art. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci. Transl. Med. 3:95 (2011); Porter et al., N. Engl. J. Med. 365:725-33 (2011), and Gross et al., Annu. Rev. Pharmacol. Toxicol. 56:59-83 (2016).

In some embodiments, a costimulatory domain which includes a truncated hinge domain ("THD") further comprises some or all of a member of the immunoglobulin family such as IgG1, IgG2, IgG3, IgG4, IgA, IgD, IgE, IgM, or fragment thereof.

In some embodiments, the THD is derived from a human complete hinge domain ("CHD"). In other embodiments, the THD is derived from a rodent, murine, or primate (e.g., non-human primate) CHD of a costimulatory protein. In some embodiments, the THD is derived from a chimeric CHD of a costimulatory protein.

The costimulatory domain for the CAR of the disclosure may further comprise a transmembrane domain and/or an intracellular signaling domain. The transmembrane domain may be fused to the extracellular domain of the CAR. The costimulatory domain may similarly be fused to the intracellular domain of the CAR. In some embodiments, the transmembrane domain that naturally is associated with one of the domains in a CAR is used. In some instances, the transmembrane domain is selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this disclosure may be derived from (i.e., comprise) 4-1BB/ CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD29, CD3 delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1; CD11a/ CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Optionally, short linkers may form linkages between any or some of the extracellular, transmembrane, and intracellular domains of the CAR. In some embodiments, the linker may be derived from repeats of glycine-glycine-glycine-glycine-serine (SEQ ID NO: 2) (G4S)n or GST-SGSGKPGSGEGSTKG (SEQ ID NO: 1). In some embodiments, the linker comprises 3-20 amino acids and an amino acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to GST-SGSGKPGSGEGSTKG (SEQ ID NO: 1).

The linkers described herein, may also be used as a peptide tag. The linker peptide sequence may be of any appropriate length to connect one or more proteins of interest and is preferably designed to be sufficiently flexible so as to allow the proper folding and/or function and/or activity of one or both of the peptides it connects. Thus, the linker peptide may have a length of no more than 10, no more than 11, no more than 12, no more than 13, no more than 14, no more than 15, no more than 16, no more than 17, no more than 18, no more than 19, or no more than 20 amino acids. In some embodiments, the linker peptide comprises a length of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the linker comprises at least 7 and no more than 20 amino acids, at least 7 and no more than 19 amino acids, at least 7 and no more than 18 amino acids, at least 7 and no more than 17 amino acids, at least 7 and no more than 16 amino acids, at least 7 and no more 15 amino acids, at least 7 and no more than 14 amino acids, at least 7 and no more than 13 amino acids, at least 7 and no more than 12 amino acids or at least 7 and no more than 11 amino acids. In certain embodiments, the linker comprises 15-17 amino acids, and in particular embodiments, comprises 16 amino acids. In some embodiments, the linker comprises 10-20 amino acids. In some embodiments, the linker comprises 14-19 amino acids. In some embodiments, the linker comprises 15-17 amino acids. In some embodiments, the linker comprises 15-16 amino acids. In some embodiments, the linker comprises 16 amino acids. In some embodiments, the linker comprises 3, 4, 5, 6, 7, 8, 9, 10, 11, 12, 13, 14, 15, 16, 17, 18, 19 or 20 amino acids.

In some embodiments, a spacer domain is used. In some embodiments, the spacer domain is derived from CD4, CD8a, CD8b, CD28, CD28T, 4-1BB, or other molecule described herein. In some embodiments, the spacer domains may include a chemically induced dimerizer to control expression upon addition of a small molecule. In some embodiments, a spacer is not used.

The intracellular (signaling) domain of the engineered T cells of the disclosure may provide signaling to an activating domain, which then activates at least one of the normal effector functions of the immune cell. Effector function of a T cell, for example, may be cytolytic activity or helper activity including the secretion of cytokines.

In certain embodiments, suitable intracellular signaling domain include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8, CD8alpha, CD8beta, CD96 (Tactile), CD11a, CD11b, CD11c, CD11d, CD S, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, ligand that specifically binds with CD83, LIGHT, LTBR, Ly9 (CD229), Ly108), lymphocyte function-associated antigen-1 (LFA-1; CD11a/ CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Antigen Binding Molecules

Suitable CARs may bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). A scFv is a single chain antibody fragment having the variable regions of the heavy and light chains of an antibody linked together. See U.S. Pat. Nos. 7,741,465 and 6,319,494, as well as Eshhar et al., Cancer Immunol Immunotherapy (1997) 45: 131-136. A scFv retains the parent antibody's ability to interact specifically with target antigen. scFv's are useful in chimeric antigen receptors because they may be engineered to be expressed as part of a single chain along with the other CAR components. Id. See also Krause et al., J. Exp. Med., Volume 188, No. 4, 1998 (619-626); Finney et al., *Journal of Immunology*, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the disclosure, with specificity to more than one target of interest.

In some embodiments, the polynucleotide encodes a CAR comprising a (truncated) hinge domain and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

Engineered T Cells and Uses

The cell of the present disclosure may be obtained through T cells obtained from a subject. T cells may be obtained from, e.g., peripheral blood mononuclear cells, bone marrow, lymph node tissue, cord blood, thymus tissue, tissue from a site of infection, ascites, pleural effusion, spleen tissue, tumors, or differentiated in vitro. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step may be used, such as by using a semi-automated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naïve, memory, and effector T cell subpopulations either before or after genetic modification and/or expansion.

In some embodiments, CD8+ cells are further sorted into naïve, central memory, and effector cells by identifying cell surface antigens that are associated with each of these types of CD8+ cells. In some embodiments, the expression of phenotypic markers of central memory T cells includes expression of CCR7, CD3, CD28, CD45RO, CD62L, and CD127 and negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+ T helper cells may be sorted into naïve, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor.

In some embodiments, a composition comprising engineered T cells comprises a pharmaceutically acceptable carrier, diluent, solubilizer, emulsifier, preservative and/or adjuvant. In some embodiments, the composition comprises an excipient. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method may include collecting blood cells from the patient. The isolated blood cells (e.g., T cells) may then be engineered to express a CAR disclosed herein. In a particular embodiment, the CAR T cells are administered to the patient. In some embodiments, the CAR T cells treat a tumor or a cancer in the patient. In some embodiments the CAR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient. In certain embodiments, the T cell is a tumor-infiltrating lymphocyte (TIL), engineered autologous T cell (eACT™), an allogeneic T cell, a heterologous T cell, or any combination thereof.

In some embodiments, the engineered T cells are administered at a therapeutically effective amount. For example, a therapeutically effective amount of the engineered T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, the therapeutically effective amount of the engineered viable T cells is between about $1\times10^6$ and about $2\times10^6$ engineered viable T cells per kg body weight up to a maximum dose of about $1\times10^8$ engineered viable T cells.

In some embodiments, the engineered T cells are anti-CD19 CAR T T cells. In some embodiments, the anti-CD19 CAR T cells are the axicabtagene ciloleucel product. In some embodiments, the product meets commercial specifications. In some embodiments, the product does not meet commercial specifications (out-of-specification product, OOS). In some embodiments, the OOS product comprises fewer, less differentiated CCR7+ $T_N$ and $T_{CM}$ and a greater proportion of more differentiated CCR7− $T_{EM}$+ $T_{EFF}$ cells than the axicabtagene ciloleucel product that meets commercial specifications. In some embodiments, the OOS product results in a median peak CAR T cell level after administration that is lower than that of the commercial product. In some embodiments, the OOS product still showed a manageable safety profile and meaningful clinical benefit (Examples 18 and 9).

Methods of Treatment

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is leukemia. In some embodiments, the cancer is acute myeloid leukemia.

In some embodiments, the cancer is Non-Hodgking lymphoma. In some embodiments, the cancer is relapsed/refractory NHL. In some embodiments, the cancer is mantle cell lymphoma.

In some embodiments, the cancer is advanced-stage indolent non-Hodgkin lymphoma (iNHL), including follicular lymphoma (FL) and marginal zone lymphoma (MZL). In some embodiments, the patient has had relapsed/refractory disease after ≥2 prior lines of therapy, including an anti-CD20 monoclonal antibody with an alkylating agent. In some embodiments, the patient may have received a PI3K inhibitor. In some embodiments, the patient may (also) have received autologous stem cell transplantation. In some embodiments, the patient undergoes leukapheresis to obtain T cells for CAR T cell manufacturing, followed by conditioning chemotherapy with cyclophosphamide at 500 mg/m²/day and fludarabine at 30 mg/m²/day administered on days −5, −4, and −3; on day 0, the patient may receive a single intravenous infusion of CART cell therapy (e.g., axicabtagene ciloleucel) at a target dose of $2 \times 10^6$ CAR T cells/kg. In some embodiments, additional infusions may be given at a later period. In some embodiments, if the patient progresses after responding at the month 3 assessment after initial administration, the patient may receive retreatment with CAR T cell treatment (e.g., axicabtagene ciloleucel). In some embodiments, the patient may receive bridging therapy. Examples of bridging therapies are provided elsewhere in the specification, including the Examples. In some embodiments, the patient experiences CRS. In some embodiments, CRS is managed using any one of the protocols described in this application, including the Examples. In some embodiments, CRS is managed with tocilizumab, corticosteroids and/or vasopressor.

In some embodiments, the cancer is relapsed/refractory indolent Non-Hodgkin Lymphoma and the method of treating a subject in need thereof comprises administering to the subject a therapeutically effective amount of CART cells as a retreatment, wherein the subject has previously received a first treatment with CAR T cells. In some embodiments, the first treatment with CAR T cells may have been administered as a first line therapy or a second line therapy, optionally wherein the lymphoma is R/R follicular lymphoma (FL) or marginal zone lymphoma (MZL) and optionally wherein the previous prior lines of therapy included anti-CD20 monoclonal antibody combined with an alkylating agent. In some embodiments, the conditioning therapy comprises fludarabine 30 mg/m² IV and cyclophosphamide 500 mg/m² IV on Days −5, −4, and −3. In some embodiments, the CAR T cell treatment comprises single IV infusion of $2 \times 10^6$ CAR T cells/kg on Day 0. In some embodiments, at least about $10^4$ cells, at least about $10^5$ cells, at least about $10^6$ cells, at least about $10^7$ cells, at least about $10^8$ cells, at least about $10^9$, or at least about $10^{10}$ CAR T cells are administered. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the T cells is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg In some embodiments, the CAR T cells are anti-CD19 CAR T cells. In some embodiments, the CAR T cells are axicabtagene ciloleucel CAR T cells. In some embodiments, the retreatment eligibility criteria include response of a CR or PR at the month 3 disease assessment with subsequent progression; no evidence of CD19 loss in progression biopsy by local review; and/or no Grade 4 CRS or neurologic events, or life-threatening toxicities with the first treatment with CAR T cells. In some embodiments, the method of treatment is that followed by the ZUMA-5 clinical trial (NCT03105336).

In some embodiments, the cancer is NHL and the CART cell treatment is administered as a first line therapy. In some embodiments, the cancer is LBCL. In some embodiments, the LBCL is high risk/high grade LBCL with MYC and BCL2 and/or BCL6 translocations or DLBCL with IPI score ≥3 any time before enrollment. In some embodiments, the first line therapy comprises CAR T cell treatment in combination with an anti-CD20 monoclonal antibody and anthracycline-containing regimen. In some embodiments, the CAR T cell treatment is administered first. In some embodiments, the anti-CD20 monoclonal antibody/anthracycline-containing regimen is administered first. In some embodiments, the treatments are administered at least 2 weeks, at least 4 weeks, at least 6 weeks, at least 1 month, at least 2 months, at least 3 months, at least 4 months, at least 5 months, less than a year apart, etc. In some embodiments, the method further comprises bridging therapy administered after leukapheresis and completed prior to initiating conditioning chemotherapy. In some embodiments, additional inclusion criteria include age ≥18 years and ECOG PS 0-1. In some embodiments, the conditioning therapy comprises fludarabine 30 mg/m$^2$ IV and cyclophosphamide 500 mg/m$^2$ IV on Days −5, −4, and −3. Other exemplary beneficial preconditioning treatment regimens are described in U.S. Provisional Patent Applications 62/262,143 and 62/167,750 and U.S. Pat. Nos. 9,855,298 and 10,322,146, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. Another embodiment comprises serum cyclophosphamide and fludarabine at days −4, −3, and −2 prior to T cell administration at a dose of 500 mg/m$^2$ of body surface area of cyclophosphamide per day and a dose of 30 mg/m$^2$ of body surface area per day of fludarabine during that period of time. Another embodiment comprises cyclophosphamide at day −2 and fludarabine at days −4, −3, and −2 prior to T cell administration, at a dose of 900 mg/m$^2$ of body surface area of cyclophosphamide and a dose of 25 mg/m$^2$ of body surface area per day of fludarabine during that period of time. In another embodiment, the conditioning comprises cyclophosphamide and fludarabine at days −5, −4 and −3 prior to T cell administration at a dose of 500 mg/m$^2$ of body surface area of cyclophosphamide per day and a dose of 30 mg/m$^2$ of body surface area of fludarabine per day during that period of time. Other preconditioning embodiments comprise 200-300 mg/m$^2$ of body surface area of cyclophosphamide per day and a dose of 20-50 mg/m$^2$ of body surface area per day of fludarabine for three days. In some embodiments, the CAR T cell treatment comprises single IV infusion of 2×10$^6$ CAR T cells/kg on Day 0. In some embodiments, at least about 10$^4$ cells, at least about 10$^5$ cells, at least about 10$^6$ cells, at least about 10$^7$ cells, at least about 10$^8$ cells, at least about 10$^9$, or at least about 10$^{10}$ CAR T cells are administered. In another embodiment, the therapeutically effective amount of the T cells is about 10$^4$ cells, about 10$^5$ cells, about 10$^6$ cells, about 10$^7$ cells, or about 10$^8$ cells. In some embodiments, the therapeutically effective amount of the T cells is about 2×10$^6$ cells/kg, about 3×10$^6$ cells/kg, about 4×10$^6$ cells/kg, about 5×10$^6$ cells/kg, about 6×10$^6$ cells/kg, about 7×10$^6$ cells/kg, about 8×10$^6$ cells/kg, about 9×10$^6$ cells/kg, about 1×10$^7$ cells/kg, about 2×10$^7$ cells/kg, about 3×10$^7$ cells/kg, about 4×10$^7$ cells/kg, about 5×10$^7$ cells/kg, about 6×10$^7$ cells/kg, about 7×10$^7$ cells/kg, about 8×10$^7$ cells/kg, or about 9×10$^7$ cells/kg In some embodiments, the CAR T cells are anti-CD19 CAR T cellsIn some embodiments, the CAR T cell treatment comprises anti-CD19 CAR T cells. In some embodiments, the CAR T cell treatment comprises axicabtagene ciloleucel. In some embodiments, the method of treatment is the method used in the ZUMA-12 clinical trial (NCT03761056). In some embodiments, the median peak serum levels of several cytokines associate with severe NEs or CRS in the patients subject to these treatments. In some embodiments, these serum levels may be used to predict NE and CRS, wherein the higher the peak serum level of one or more of these cytokines the higher the probability of Grade ≥3 NEs or Grade ≥3 CRS. Reference levels may be established by one of ordinary skill in the art. In some embodiments, cytokines associated with NEs (IL-6, IL-5, IFN-γ, IL-8, GM-CSF, CCL26, Ferritin, IL-17, IL-10, CCL3, TNF-α, and Granzyme B) and CRS (IL-6, IL-8, VCAM-1, GM-CSF, IL-17, ICAM-1, IL-4, IL-2, IL-12 P70, CCL17, CCL26, and IL-5) have a median ratio >2 after taking the ratio of median peak levels in Grade ≥3 events to Grade <3 events In some embodiments, the axicabtagene ciloleucel product comprises a higher frequency of naïve T cells than the axicabtagene ciloleucel product prepared according to the ZUMA-1 clinical trial. ZUMA-1 (NCT02348216) clinical trial has been described in detail in the Examples and in Neelapu, S S et al. 2017, *N Engl J Med* 2017; 377(26):2531-44) and Locke, et al. *Lancet Oncol.* 2019; 20:31-42.

In some embodiments, the methods of treatment comprise the administration of the immune cells in combination with other therapeutic agents or treatments (e.g., radiation, debulking). In some embodiments, the additional therapeutic agents or treatments are included to manage adverse events. In some embodiments, the additional therapeutic agents or treatments are included to improve therapeutic efficacy of the cell treatment. In some examples, they achieve both. Examples of therapeutic agents that can be used together with (before, after, and/or concurrently with) the immune cells are provided below and elsewhere in the specification.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 and U.S. Pat. Nos. 9,855, 298 and 10,322,146, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. Another embodiment comprises serum cyclophosphamide and fludarabine at days −4, −3, and −2 prior to T cell administration at a dose of of 500 mg/m$^2$ of body surface area of cyclophosphamide per day and a dose of 30 mg/m$^2$ of body surface area per day of fludarabine during that period of time. Another embodiment comprises cyclophosphamide at day −2 and fludarabine at days −4, −3, and −2 prior to T cell administration, at a dose of 900 mg/m$^2$ of body surface area of cyclophosphamide and a dose of 25 mg/m$^2$ of body surface area per day of fludarabine during that period of time. In another embodiment, the conditioning comprises cyclophosphamide and fludarabine at days −5, −4 and −3 prior to T cell administration at a dose of 500 mg/m$^2$ of body surface area of cyclophosphamide per day and a dose of 30 mg/m$^2$ of body surface area of fludarabine per day during that period of time.

In some embodiments, the antigen binding molecule, transduced (or otherwise engineered) cells (such as CARs), and the chemotherapeutic agent are administered each in an amount effective to treat the disease or condition in the subject.

In some embodiments, compositions comprising CAR-expressing immune effector cells disclosed herein may be administered in conjunction (before, after, and/or concurrently with T cell administration) with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylol melamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; Polysaccharide K (PSK); razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone, R-CHOP (CHOP plus Rituximab), and G-CHOP (CHOP plus obinutuzumab).

In some embodiments, the chemotherapeutic agent is administered at the same time or within one week after the administration of the engineered cell. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein (before, after, and/or concurrently with T cell administration). For example, potentially useful additional therapeutic agents include PD-1 inhibitors such as nivolumab (OPDIVO®), pembrolizumab (KEYTRUDA®), Cemiplimab (Libtayo), pidilizumab (CureTech), and atezolizumab (Roche), and PD-L1 inhibitors such as atezolizumab, durvalumab, and avelumab.

Additional therapeutic agents suitable for use in combination (before, after, and/or concurrently with T cell administration) with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib), inhibitors of GM-CSF, CSF1, GM-CSFR, or CSF1R, in addition to anti-thymocyte globulin, lenzilumab and mavrilimumab.

In one embodiment, the GM-CSF inhibitor is selected from lenzilumab; namilumab (AMG203); GSK3196165/MOR103/otilimab (GSK/MorphoSys); KB002 and KB003 (KaloBios); MT203 (Micromet and Nycomed); MORAb-022/gimsilumab (Morphotek); or a biosimilar of any one of the same; E21R; and a small molecule. In one embodiment, the CSF1 inhibitor is selected from RG7155, PD-0360324, MCS110/lacnotuzumab), or a biosimilar version of any one of the same; and a small molecule. In one embodiment, the GM-CSFR inhibitor and the CSF1R inhibitor is/are selected from Mavrilimumab (formerly CAM-3001; MedImmune, Inc.); cabiralizumab (Five Prime Therapeutics); LY3022855 (IMC-CS4)(Eli Lilly), Emactuzumab, also known as RG7155 or RO5509554; FPA008 (Five Prime/BMS); AMG820 (Amgen); ARRY-382 (Array Biopharma); MCS110 (Novartis); PLX3397 (Plexxikon); ELB041/AFS98/TG3003 (ElsaLys Bio, Transgene), SNDX-6352 (Syndax); a biosimilar version of any one of the same; and a small molecule.

In some embodiments, the agent is administered by injection, e.g., intravenous or subcutaneous injections, intraocular injection, periocular injection, subretinal injection, intra-vitreal injection, trans-septal injection, subscleral injection, intrachoroidal injection, intracameral injection, subcon-jectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

In some embodiments, the treatment further comprises bridging therapy, which is therapy between conditioning and the compositions disclosed herein or therapy administered after leukapheresis and completed prior to initiating conditioning chemotherapy. In some embodiments, the bridging therapy comprises, CHOP, G-CHOP, R-CHOP (rituximab, cyclophosphamide, doxorubicin, vincristine, and predniso-lone), corticosteroids, bendamustine, platinum compounds, anthracyclines, and/or phosphoinositide 3-kinase (PI3K) inhibitors. In some embodiments, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032). In some embodiments, the AKT inhibitor is perifosine, MK-2206. In one embodiment, the mTOR inhibitor is selected from everolimus, sirolimus, temsirolimus, ridaforolimus. In some embodiments, the dual PI3K/mTOR inhibitor is selected from BEZ235, XL765, and GDC-0980. In some embodiments, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032).

In some embodiments, the bridging therapy comprises acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denile-ukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin diftitox, pembrolizumab, plerixafor, polatuzumab vedotin-piiq, mogamulizumab-kpc, prednisone, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

In some embodiments, the cell immunotherapy is administered in conjunction with debulking therapy, which is used with the aim of reducing tumor burden. In one embodiment, debulking therapy is to be administered after leukapheresis and prior to administration of conditioning chemotherapy or cell infusion. Examples of debulking therapy include the following:

| Type | Proposed Regimen[a] | Timing/Washout |
|---|---|---|
| R-CHOP | Rituximab 375 mg/m2 Day 1<br>Doxorubicin 50 mg/m2 Day 1<br>Prednisone 100 mg Day 1 through Day 5<br>Cyclophosphamide 750 mg/m2 Day 1<br>Vincristine 1.4 mg/m2 Day 1 | Should be administered after leukapheresis/enrollment and should be completed at least 14 days prior to the start of conditioning chemotherapy |
| R-ICE | Rituximab 375 mg/m2 Day 1<br>Ifosfamide 5 g/m2 24 h-CI Day 2<br>Carboplatin AUC5 Day 2 maximum dose 800 mg<br>Etoposide 100 mg/m2/d Days 1 through Day 3 | |
| R-GEMOX | Rituximab 375 mg/m2 Day 1<br>Gemcitabine 1000 mg/m2 Day<br>2 Oxaliplatin 100 mg/m2 Day 2 | |
| R-GDP | Rituximab 375 mg/m2 Day 1 (or Day 8)<br>Gemcitabine 1 g/m2 on Day 1 and Day 8<br>Dexamethasone 40 mg on Day 1 through Day 4<br>Cisplatin 75 mg/m2 on Day 1<br>(or carboplatin AUC5 on Day 1) | |
| RADIOTHERAPY[b] | Per local standard up to 20 to 30 Gy | Should be administered after leukapheresis/enrollment and should be completed at least 5 days prior to the start of conditioning chemotherapy |

Abbreviations: AUG, area under the curve

[a]Other debulking treatment options may be used, to be discussed with the medical monitor. Supportive care with hydration, anti-emesis, mesna, growth factor support, and tumor lysis prophylaxis according to local standard may be used. More than 1 cycle allowed.

[b]At least 1 target lesion should remain outside of the radiation field to allow for tumor measurements

In some embodiments, a composition comprising engineered CAR T cells are administered with an anti-inflammatory agent (before, after, and/or concurrently with T cell administration). Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine (before, after, or concurrently with T cell administration). Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In some embodiments, the administration of the cells and the administration of the additional therapeutic agent are carried out on the same day, are carried out no more than 36 hours apart, no more than 24 hours apart, no more than 12 hours apart, no more than 6 hours apart, no more than 4 hours apart, no more than 2 hours apart, or no more than 1 hour apart or no more than 30 minutes apart. In some embodiments, the administration of the cells and the administration of the additional therapeutic agent are carried out between at or about 0 and at or about 48 hours, between at or about 0 and at or about 36 hours, between at or about 0 and at or about 24 hours, between at or about 0 and at or about 12 hours, between at or about 0 and at or about 6 hours, between at or about 0 and at or about 2 hours, between at or about 0 and at or about 1 hours, between at or about 0 and at or about 30 minutes, between at or about 30 minutes and at or about 48 hours, between at or about 30 minutes and at or about 36 hours, between at or about 30 minutes and at or about 24 hours, between at or about 30 minutes and at or about 12 hours, between at or about 30 minutes and at or about 6 hours, between at or about 30 minutes and at or about 4 hours, between at or about 30 minutes and at or about 2 hours, between at or about 30 minutes and at or about 1 hour, between at or about 1 hours and at or about 48 hours, between at or about 1 hour and at or about 36 hours, between at or about 1 hour and at or about 24 hours, between at or about 1 hour and at or about 12 hours, between at or about 1 hour and at or about 6 hours, between at or about 1 hour and at or about 4 hours, between at or about 1 hour and at or about 2 hours, between at or about 2 hours and at or about 48 hours, between at or about 2 hours and at or about 36 hours, between at or about 2 hours and at or about 24 hours, between at or about 2 hours and at or about 12 hours, between at or about 2 hours and at or about 6 hours, between at or about 2 hours and at or about 4 hours, between at or about 4 hours and at or about 48 hours, between at or about 4 hours and at or about 36 hours, between at or about 4 hours and at or about 24 hours, between at or about 4 hours and at or about 12 hours, between at or about 4 hours and at or about 6 hours, between at or about 6 hours and at or about 48 hours, between at or about 6 hours and at or about 36 hours, between at or about 6 hours and at or about 24 hours, between at or about 6 hours and at or about 12 hours, between at or about 12 hours and at or about 48 hours, between at or about 12 hours and at or about 36 hours, between at or about 12 hours and at or about 24 hours, between at or about 24 hours and at or about 48 hours, between at or about 24 hours and at or about 36 hours or between at or about 36 hours and at or about 48 hours. In some embodiments, the cells and the additional therapeutic agent are administered at the same time.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg.

In some embodiments, the agent is administered in a dosage amount from 0.5 mg/kg to 100 mg/kg, 1 mg/kg to 50 mg/kg, 1 mg kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount from 1 mg/kg to 10 mg/kg, 2 mg kg/to 8 mg/kg, 2 mg/kg to 6 mg/kg, 2 mg/kg to 4 mg/kg or 6 mg/kg to 8 mg/kg, each In some aspects, the agent is administered in a dosage amount of at least 1 mg/kg, 2 mg/kg, 4 mg/kg, 6 mg/kg, 8 mg/kg, 10 mg/kg or more.

Monitoring

In some embodiments, administration of chimeric receptor T cell immunotherapy occurs at a certified healthcare facility.

In some embodiments, the methods disclosed herein comprise monitoring patients at least daily for 7 days at the certified healthcare facility following infusion for signs and symptoms of CRS and neurologic toxicities and other adverse reactions to CAR T cell treatment. In some embodiments, the symptom of neurologic toxicity is selected from encephalopathy, headache, tremor, dizziness, aphasia, delirium, insomnia, and anxiety. In some embodiments, the symptom of adverse reaction is selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia. In some embodiments, patients are instructed to remain within proximity of the certified healthcare facility for at least 4 weeks following infusion.

Clinical Outcomes

In some embodiments, the clinical outcome is complete response. In some embodiments, the clinical outcome is durable response. In some embodiments, the clinical outcome is complete response. In some embodiments, the clinical outcome is no response. In some embodiments, the clinical outcome is partial response. In some embodiments, the clinical outcome is objective response. In some embodiments, the clinical outcome is survival. In some embodiments, the clinical outcome is relapse.

In some embodiments, objective response (OR) is determined per the revised IWG Response Criteria for Malignant Lymphoma (Cheson, 2007) and determined by IWG Response Criteria for Malignant Lymphoma (Cheson et al. Journal of Clinical Oncology 32, no. 27 (September 2014) 3059-3067). Duration of Response is assessed. The Progression-Free Survival (PFS) by investigator assessment per Lugano Response Classification Criteria is evaluated.

Prevention or Management of Severe Adverse Reactions

In some embodiments, the present disclosure provides methods of preventing the development or reducing the severity of adverse reactions based on the levels of one or more attributes. In some embodiments, the cell therapy is administered in with one or more agents that prevents, delays the onset of, reduces the symptoms of, treats the adverse events, which include cytokine release syndromes and neurologic toxicity. In one embodiment, the agent has been described above. In other embodiments, the agent is described below. In some embodiments, the agent is administered by one of the methods and doses described elsewhere in the specification, before, after, or concurrently with the administration of the cells. In one embodiment, the agent(s) are administered to a subject that may be predisposed to the disease but has not yet been diagnosed with the disease.

In this respect, the disclosed method may comprise administering a "prophylactically effective amount" of tocilizumab, of a corticosteroid therapy, and/or of an anti-seizure medicine for toxicity prophylaxis. In some embodiments, the method comprises administering inhibitors of GM-CSF, CSF1, GM-CSFR, or CSF1R, lenzilumab, mavrilimumab, cytokines, and/or anti-inflammatory agents. The pharmacologic and/or physiologic effect may be prophylactic, i.e., the effect completely or partially prevents a disease or symptom thereof. A "prophylactically effective amount" may refer to an amount effective, at dosages and for periods of time necessary, to achieve a desired prophylactic result (e.g., prevention of onset of adverse reactions).

In some embodiments, the method comprises management of adverse reactions in any subject. In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

In some embodiments, the patient has been identified and selected based on one or more of the biomarkers described in this application. In some embodiments, the patient has been identified and selected simply by the clinical presentation (e.g., presence and grade of toxicity symptom).

Cytokine Release Syndrome (CRS)

In some embodiments, the method comprises preventing or reducing the severity of CRS in a chimeric receptor treatment. In some embodiments, the engineered CAR T cells are deactivated after administration to the patient.

In some embodiments, the method comprises identifying CRS based on clinical presentation. In some embodiments, the method comprises evaluating for and treating other causes of fever, hypoxia, and hypotension. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered.

In some embodiments, the method comprises monitoring patients at least daily for 7 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

Neurologic Toxicity (NT)

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. In some embodiments, the symptom of neurologic toxicity is selected from encephalopathy, headache, tremor, dizziness, aphasia, delirium, insomnia, and anxiety.

Management of Adverse Events

In some embodiments, the cell treatment is administered before, during/concurrently, and/or after the administration of one or more agents (e.g., steroids) or treatments (e.g., debulking) that treat and or prevent (are prophylactic) one or more symptoms of adverse events. A "prophylactically effective amount" refers to an amount effective, at dosages and for periods of time necessary, to achieve the desired prophylactic result. In one embodiment, a prophylactically effective amount is used in subjects prior to or at an earlier stage of disease. In one embodiment, the prophylactically effective amount will be less than the therapeutically effective amount. In some embodiments, the patient is selected for management of adverse events based on the expression of one of more of the markers described herein in this specification. In one embodiment, the adverse event treatment or prophylaxis is administered to any patient that will receive, is receiving, or has received cell therapy.

In some embodiments, the method of managing adverse events comprises monitoring patients at least daily for 7 days at the certified healthcare facility following infusion for signs and symptoms of neurologic toxicities. In some embodiments, the method comprises monitoring patients for signs or symptoms of neurologic toxicities and/or CRS for 4 weeks after infusion In some embodiments, the disclosure provides two methods of managing adverse events in subjects receiving CAR T cell treatment with steroids and anti-IL6/anti-IL-6R antibody/ies. In one embodiment, the methods are described in FIG. 46. In one embodiment, the disclosure provides that early steroid intervention in Cohort 4 is associated with lower rates of severe CRS and neurologic events than what was observed in Cohorts 1+2. In one embodiment, the disclosure provides that earlier use of steroids in Cohort 4 was associated with a median cumulative cortisone-equivalent dose approximately 15% of that in Cohorts 1+2, suggesting that earlier steroid use may allow reduction of overall steroid exposure. Accordingly, in one embodiment, the disclosure provides a method of adverse event management whereby corticosteroid therapy is initiated for management of all cases of grade 1 CRS if there was no improvement after 3 days and for all grade ≥1 neurologic events. In one embodiment, tocilizumab is initiated for all cases of grade 1 CRS if there is no improvement after 3 days and for all grade ≥2 neurologic events. In one embodiment, the disclosure provides a method of reducing overall steroid exposure in patients receiving adverse event management after CAR T cell administration, the method comprising initiation of corticosteroid therapy for management of all cases of grade 1 CRS if there was no improvement after 3 days and for all grade ≥1 neurologic events and/or initiation of tocilizumab for all cases of grade 1 CRS if there is no improvement after 3 days and for all grade ≥2 neurologic events. In one embodiment, the corticosteroid and tocilizumab are administering in a regimen selected from those exemplified in Table 12. In one embodiment, the disclosure provides that earlier steroid use is not associated with increased risk for severe infection, decreased CAR T-cell expansion, or decreased tumor response.

In one embodiment, the disclosure supports the safety of levetiracetam prophylaxis in CAR T cell cancer treatment. In one embodiment, the cancer is NHL. In one embodiment, the cancer is R/R LBCL and the patients receive axicabtagene ciloleucel. Accordingly, in one embodiment, the disclosure provides a method of managing adverse events in patients treated with CAR T cells comprising administering to the patient a prophylactic dosage of an anti-seizure medication. In some embodiments, the patients receive levetiracetam (for example, 750 mg orally or intravenous twice daily) starting on day 0 of the CAR T cell treatment (after conditioning) and also at the onset of grade ≥2 neurologic toxicities, if neurologic events occur after the discontinuation of prophylactic levetiracetam. In one embodiment, if a patient does not experience any grade ≥2 neurologic toxicities, levetiracetam is tapered and discontinued as clinically indicated. In one embodiment, levetiracetam prophylaxis is combined with any other adverse event management protocol.

In one embodiment, the disclosure provides that CAR T-cell levels in the patients subject to the adverse management protocol of Cohort 4 were comparable to those of Cohorts 1+2. In one embodiment, the disclosure provides that the numerical levels of key inflammatory cytokines associated with CAR-related inflammatory events (e.g., IFNγ, IL-2 and GM-CSF) are lower in Cohort 4 than in Cohorts 1+2. Accordingly, the disclosure provides a method of reducing CAR T cell treatment-related inflammatory events without impact on CAR T cell levels comprising administering to the patient the adverse event management protocol of Cohort 4. The disclosure also provides a method of reducing cytokine production by immune cells after CAR T cell therapy comprising administering to the patient the adverse event management protocol of Cohort 4. In one embodiment, this effect is obtained without affecting CAR T-cell expansion and response rates. In one embodiment, the patient has R/R LBCL. In one embodiment, the CAR T cell treatment is anti-CD19 CAR T cell treatment. In one embodiment, the CAR T cell treatment comprises axicabtagene ciloleucel.

In one embodiment, the disclosure provides that early or prophylactic use of tocilizumab following axicabtagene ciloleucel for adverse event management decreased grade ≥3 cytokine release syndrome but increased grade ≥3 neurologic events. Accordingly, the disclosure provides a method for adverse event management in CAR T-cell therapy as described in FIG. 56. In one embodiment, patients receive levetiracetam (750 mg oral or intravenous twice daily) starting on day 0. At the onset of grade ≥2 neurologic events, levetiracetam dose is increased to 1000 mg twice daily. If a patient did not experience any grade ≥2 neurologic event, levetiracetam is tapered and discontinued as clinically indicated. Patients also receive tocilizumab (8 mg/kg IV over 1 hour [not to exceed 800 mg]) on day 2. Further tocilizumab (±corticosteroids) may be recommended at the onset of grade 2 CRS in patients with comorbidities or older age, or otherwise in case of grade ≥3 CRS. For patients experiencing grade ≥2 neurologic events, tocilizumab is initiated, and corticosteroids are added for patients with comorbidities or older age, or if there is any occurrence of a grade ≥3 neurologic event with worsening symptoms despite tocilizumab use.

In one embodiment, the disclosure provides that prophylactic steroid use appears to reduce the rate of severe CRS and NEs to a similar extent as early steroid use following axicabtagene ciloleucel administration. Accordingly, the disclosure provides a method for adverse event management in CAR T-cell therapy wherein patients receive dexamethasone 10 mg PO on Days 0 (prior to axicabtagene ciloleucel infusion), 1, and 2. Steroids are also administered starting at Grade 1 NE, and for Grade 1 CRS when no improvement is observed after 3 days of supportive care. Tocilizumab is also administered for Grade ≥1 CRS if no improvement is observed after 24 hours of supportive care.

In one embodiment, the disclosure provides that adverse event management of CAR T-cell therapy with an antibody that neutralizes and/or depletes GM-CSF prevents or reduces treatment-related CRS and/or NEs in treated patients. In one embodiment, the antibody is lenzilumab.

In some embodiments, the adverse events are managed by the administration of an agent/agents that is/are an antagonist or inhibitor of IL-6 or the IL-6 receptor (IL-6R). In some embodiments, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-TL-6 antibody, such as siltuximab, elsilimomab, ALD518/BMS-945429, sirukumab (CNTO 136), CPSI-2634, ARGX 109, FE301, FM101, or olokizumab (CDP6038), and combinations thereof. In some embodiments, the agent may neutralize IL-6 activity by inhibiting the ligand-receptor interactions. In some embodiments, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, other agents that can be used to manage adverse reactions and their symptoms include an antagonist or inhibitor of a cytokine receptor or cytokine. In some embodiments, the cytokine or receptor is IL-10, TL-6, TL-6 receptor, IFNγ, IFNGR, IL-2, IL-2R/CD25, MCP-1, CCR2, CCR4, MIP13, CCR5, TNFalpha, TNFR1, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R), IL-1, and IL-1Ralpha/IL-1beta. In some embodiments, the agent comprises situximab, sarilumab, olokizumab (CDP6038), elsilimomab, ALD518/BMS-945429, sirukumab (CNTO 136), CPSI-2634, ARGX 109, FE301, or FM101. In some embodiments, the agent, is an antagonist or inhibitor of a cytokine, such as transforming growth factor beta (TGF-beta), interleukin 6 (TL-6), interleukin 10 (IL-10), IL-2, MIP13 (CCL4), TNF alpha, IL-1, interferon gamma (IFN-gamma), or monocyte chemoattractant protein-I (MCP-1). In some embodiments, the is one that targets (e.g. inhibits or is an antagonist of) a cytokine receptor, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R) and combinations thereof. In some embodiments, the agent is administered by one of the methods and doses described elsewhere in the specification, before, after, or concurrently with the administration of the cells.

In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the agent is administered in a dosage amount of at least or at least about or about 2 mg/kg, 4 mg/kg, 6 mg/kg or 8 mg/kg. In some embodiments, is administered in a dosage amount from about 1 mg/kg to 12 mg/kg, such as at or about 10 mg/kg. In some embodiments, the agent is administered by intravenous infusion. In one embodiment, the agent is tocilizumab. In some embodiments, the (agent(s), e.g, specifically tocilizumab) is/are administered by one of the methods and doses described elsewhere in the specification, before, after, or concurrently with the administration of the cells.

In some embodiments, the method comprises identifying CRS based on clinical presentation. In some embodiments, the method comprises evaluating for and treating other causes of fever, hypoxia, and hypotension. If CRS is observed or suspected, it may be managed according to the recommendations in protocol A, which may also be used in combination with the other treatments of this disclosure, including Neutralization or Reduction of the CSF/CSFR1 Axis. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered. In some embodiments, a biosimilar or equivalent of tocilizumab may be used instead of tocilizumab in the methods disclosed herein. In other embodiments, another anti-IL6R may be used instead of tocilizumab.

In some embodiments, adverse events are managed according to the following protocol (protocol A):

| CRS Grade (a) | Tocilizumab | Corticosteroids |
| --- | --- | --- |
| Grade 1 Symptoms require symptomatic treatment only (e.g., fever, nausea, fatigue, headache, myalgia, malaise). | N/A | N/A |
| Grade 2 Symptoms require and respond to moderate intervention. Oxygen requirement less than 40% FiO$_2$ or hypotension responsive to fluids or low-dose of one vasopressor or Grade 2 organ toxicity (b). | Administer tocilizumab (c) 8 mg/kg IV over 1 hour (not to exceed 800 mg). Repeat tocilizumab every 8 hours as needed if not responsive to IV fluids or increasing supplemental oxygen. Limit to a maximum of 3 doses in a 24-hour period; maximum total of 4 doses if no clinical improvement in the signs and symptoms of CRS. | Manage per Grade 3 if no improvement within 24 hours after starting tocilizumab. |
| Grade 3 Symptoms require and respond to aggressive intervention. Oxygen requirement greater than or equal to 40% FiO$_2$ or hypotension requiring high- | Per Grade 2 | Administer methylprednisolone 1 mg/kg IV twice daily or equivalent dexamethasone (e.g., 10 mg IV every 6 hours). Continue corticosteroids use until the event is Grade 1 or |

-continued

| CRS Grade (a) | Tocilizumab | Corticosteroids |
|---|---|---|
| dose or multiple vasopressors or Grade 3 organ toxicity or Grade 4 transaminitis. | | less, then taper over 3 days. If not improving, manage as Grade 4. |
| Grade 4 Life-threatening symptoms. Requirements for ventilator support, continuous veno-venous hemodialysis (CVVHD) or Grade 4 organ toxicity (excluding transaminitis). | Per Grade 2 | Administer methylprednisolone 1000 mg IV per day for 3 days; if improves, then manage as above. Consider alternate immunosuppressants if no improvement or if condition worsens. |

(a) Lee D W et al., (2014). Current concepts in the diagnosis and management of cytokine release syndrome. Blood. 2014 Jul. 10; 124(2): 188-195.
(b) Refer to Table 2 for management of neurologic toxicity.
(c) Refer to ACEMTRA ® (tocilizumab) Prescribing Information for details, https://www.gene.com/download/pdf/actemra_prescribing.pdf (last accessed Oct. 18, 2017). Initial U.S. approval is indicated to be in 2010.

Neurologic Toxicity

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threat-ening neurologic toxicities. Consider non-sedating, anti-seizure medicines (e.g., levetiracetam) for seizure prophy-laxis for any ≥Grade 2 neurologic toxicities. The following treatments may be used in combination with the other treatments of this disclosure, including Neutralization or Reduction of the CSF/CSFR1 Axis.

In some embodiments, adverse events are managed according to the following protocol (protocol B):

| Grading Assessment | Concurrent CRS | No concurrent CRS |
|---|---|---|
| Grade 2 | Administer tocilizumab per table above (protocol A) for management of Grade 2 CRS. If no improvement within 24 hours after starting tocilizumab, administer dexamethasone 10 mg IV every 6 hours if not already taking other steroids. Continue dexamethasone use until the event is Grade 1 or less, then taper over 3 days. Consider non-sedating, anti-seizure medicines (e.g., levetiracetam) for seizure prophylaxis. | Administer dexamethasone 10 mg IV every 6 hours. Continue dexamethasone use until the event is Grade 1 or less, then taper over 3 days. |
| Grade 3 | Administer tocilizumab per (protocol A) for management of Grade 2 CRS. In addition, administer dexamethasone 10 mg IV with the first dose of tocilizumab and repeat dose every 6 hours. Continue dexamethasone use until the event is Grade 1 or less, then taper over 3 days. Consider non-sedating, anti-seizure medicines (e.g., levetiracetam) for seizure prophylaxis. | Administer dexamethasone 10 mg IV every 6 hours. Continue dexamethasone use until the event is Grade 1 or less, then taper over 3 days. |
| Grade 4 | Administer tocilizumab per (protocol A) for management of Grade 2 CRS. Administer methylprednisolone 1000 mg IV per day with first dose of tocilizumab and continue methylprednisolone 1000 mg IV per day for 2 more days; if improves, then manage as above. Consider non-sedating, anti-seizure medicines (e.g., levetiracetam) for seizure prophylaxis. | Administer methylprednisolone 1000 mg IV per day for 3 days; if improves, then manage as above. |

Additional Safety Management Strategies with Corticosteroids

Administration of corticosteroids and/or tocilizumab at Grade 1 may be considered prophylactic. Supportive care may be provided in all protocols at all CRS and NE severity grades.

In one embodiment of a protocol for management of adverse events related to CRS, tocilizumab and/or corticosteroids are administered as follows: Grade 1 CRS: no tocilizumab; no corticosteroids; Grade 2 CRS: tocilizumab (only in case of comorbidities or older age); and/or corticosteroids (only in case of comorbidities or older age); Grade 3 CRS: tocilizumab; and/or corticosteroids; Grade 4 CRS: tocilizumab; and/or corticosteroids. In another embodiment of a protocol for management of adverse events related to CRS, tocilizumab and/or corticosteroids are administered as follows: Grade 1 CRS: tocilizumab (if no improvement after 3 days); and/or corticosteroids (if no improvement after 3 days); Grade 2 CRS: tocilizumab; and/or corticosteroids; Grade 3 CRS: tocilizumab; and/or corticosteroids; Grade 4 CRS: tocilizumab; and/or corticosteroids, high dose.

In one embodiment of a protocol for management of adverse events related to NE, tocilizumab and/or corticosteroids are administered as follows: Grade 1 NE: no tocilizumab; no corticosteroids;

Grade 2 NE: no tocilizumab; no corticosteroids; Grade 3 NE: tocilizumab; and/or corticosteroids (only if no improvement to tocilizumab, standard dose); Grade 4 NE: tocilizumab; and/or corticosteroids.

In another embodiment of a protocol for management of adverse events related to NE, tocilizumab and/or corticosteroids are administered as follows: Grade 1 NE: no tocilizumab; and/or corticosteroids; Grade 2 NE: tocilizumab; and/or corticosteroids; Grade 3 NE: tocilizumab; and/or corticosteroids, high dose; Grade 4 NE: tocilizumab; and/or corticosteroids, high dose.

In one embodiment, corticosteroid treatment is initiated at CRS grade ≥2 and tocilizumab is initiated at CRS grade ≥2. In one embodiment, corticosteroid treatment is initiated at CRS grade ≥1 and tocilizumab is initiated at CRS grade ≥1. In one embodiment, corticosteroid treatment is initiated at NE grade ≥3 and tocilizumab is initiated at CRS grade ≥3. In one embodiment, corticosteroid treatment is initiated at CRS grade ≥1 and tocilizumab is initiated at CRS grade ≥2. In some embodiments, prophylactic use of tocilizumab administered on Day 2 may decrease the rates of Grade ≥3 CRS.

In one embodiment, adverse events may be managed by a method comprising protocol C:

| CRS Grade | Tocilizumab Dose[a] | Corticosteroid Dose[a] |
|---|---|---|
| 1 | 8 mg/kg over 1 hour[b] if no improvement after 24 hours of supportive care; repeat every 4-6 hours as needed | Dexamethasone 10 mg × 1 if no improvement after 3 days |
| 2 | 8 mg/kg over 1 hour[b]; repeat every 4-6 hours as needed | Dexamethasone 10 mg × 1 |
| 3 | Per Grade 2 | Methylprednisolone 1 mg/kg IV twice daily or equivalent dexamethasone dose |
| 4 | Per Grade 2 | Methylprednisolone 1000 mg/d IV for 3 days |

-continued

| NE Grade | Tocilizumab Dose | Corticosteroid Dose |
|---|---|---|
| 1 | N/A | Dexamethasone 10 mg × 1 |
| 2 | Only in the case of concurrent CRS; 8 mg/kg over 1 hour; repeat every 4-6 hours as needed | Dexamethasone 10 mg 4×/day |
| 3 | Per Grade 2 | Methylprednisolone 1 g once daily |
| 4 | Per Grade 2 | Methylprednisolone 1 g twice daily |

[a]Therapy to be tapered on improvement of symptoms at investigator's discretion;
[b]Not to exceed 800 mg;
AE, adverse event;
CRS, cytokine release syndrome;
IV, intravenous;
N/A, not applicable;
NE, neurologic event Any corticosteroid may be appropriate for this use. In one embodiment, the corticosteroid is dexamethasone. In some embodiments, the corticosteroid is methylprednisolone. In some embodiments, the two are administered in combination. In some embodiments, glucocorticoids include synthetic and non-synthetic glucocorticoids. Exemplary glucocorticoids include, but are not limited to: alclomethasones, algestones, beclomethasones (e.g. beclomethasone dipropionate), betamethasones (e.g. betamethasone 17 valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones and hydrocortisones (e.g. hydrocortisone acetate), cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemi succinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21 palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980) and Remington: The Science and Practice of Pharmacy, 22nd Edition, Lippincott Williams & Wilkins, Philadelphia, Pa. (2013) and any other editions, which are hereby incorporated by reference. In some embodiments, the glucocorticoid is selected from among cortisones, dexamethasones, hydrocortisones, methylprednisolones, prednisolones and prednisones. In an embodiment, the glucocorticoid is dexamethasone. In other embodiments, the steroid is a mineralcorticoid. Any other steroid may be used in the methods provided herein.

The one or more corticosteroids may be administered at any dose and frequency of administration, which may be adjusted to the severity/grade of the adverse event (e.g., CRS and NE). Tables 1 and 2 provide examples of dosage regimens for management of CRS and NE, respectively. In another embodiment, corticosteroid administration comprises oral or IV dexamethasone 10 mg, 1-4 times per day. Another embodiment, sometimes referred to as "high-dose" corticosteroids, comprises administration of IV methylprednisone 1 g per day alone, or in combination with dexamethasone. In some embodiments, the one or more cortico steroids are administered at doses of 1-2 mg/kg per day.

The corticosteroid may be administered in any amount that is effective to ameliorate one or more symptoms associated with the adverse events, such as with the CRS or neurotoxicity. The corticosteroid, e.g., glucocorticoid, can be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid may be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

Generally, the dose of corticosteroid administered is dependent upon the specific corticosteroid, as a difference in potency exists between different corticosteroids. It is typically understood that drugs vary in potency, and that doses can therefore vary, in order to obtain equivalent effects. Equivalence in terms of potency for various glucocorticoids and routes of administration, is well known. Information relating to equivalent steroid dosing (in a non-chronotherapeutic manner) may be found in the British National Formulary (BNF) 37, March 1999.

In some embodiments, the adverse events are managed by the following protocol: patients receive levetiracetam (750 mg oral or intravenous twice daily) starting on day 0 of administration of T cell therapy; at the onset of grade ≥2 neurologic events, levetiracetam dose is increased to 1000 mg twice daily; if a patient did not experience any grade ≥2 neurologic event, levetiracetam is tapered and discontinued as clinically indicated; patients also receive tocilizumab (8 mg/kg IV over 1 hour [not to exceed 800 mg]) on day 2; further tocilizumab (±corticosteroids) may be recommended at the onset of grade 2 CRS in patients with comorbidities or older age, or otherwise in case of grade ≥3 CRS; for patients experiencing grade ≥2 neurologic events, tocilizumab is initiated, and corticosteroids are added for patients with comorbidities or older age, or if there is any occurrence of a grade ≥3 neurologic event with worsening symptoms despite tocilizumab use. In sone embodiments, levetiracetam is administered for prophylaxis and at the onset of grade ≥2 neurologic toxicities, if neurologic events occur after the discontinuation of prophylactic levetiracetam and/ or levetiracetam is tapered and discontinued if the patient does not experience any grade ≥2 neurologic toxicities.

In some embodiments, the adverse events are managed by the following protocol: patients receive dexamethasone 10 mg PO on Days 0 (prior to T cell therapy infusion), 1, and 2; steroids are also administered starting at Grade 1 NE, and for Grade 1 CRS when no improvement is observed after 3 days of supportive care; tocilizumab is also administered for Grade ≥1 CRS if no improvement is observed after 24 hours of supportive care.

In some embodiments, the adverse events are managed by the following protocol:

Secondary Malignancies

In some embodiments, patients treated with CART cells (e.g., CD19-directed) or other genetically modified autologous T cell immunotherapy may develop secondary malignancies. In certain embodiments, patients treated with CAR T cells (e.g, CD19-directed) or other genetically modified allogeneic T cell immunotherapy may develop secondary malignancies. In some embodiments, the method comprises monitoring life-long for secondary malignancies.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control.

The present disclosure is further illustrated by the following examples, which should not be construed as further limiting. The contents of all references cited throughout this application are expressly incorporated herein by reference.

The disclosures provided by this application may be used in a variety of methods in additional to, or as a combination of, the methods described above. The following is a compilation of exemplary methods that can be derived from the disclosures provided in this application.

Methods and Compositions to Generate and Optimize a Product for Increased Clinical Efficacy and/or Decreased Toxicity In one embodiment, the disclosure provides a method of manufacturing an immunotherapy product with improved clinical efficacy and/or decreased toxicity. In some embodiments, the immunotherapy product comprises blood cells. In some embodiments, blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some embodiments, a washing step is accomplished a semi-automated"flow-through" centrifuge (for example, the Cobe 2991 cell processor, Baxter) according to the manufacturer's instructions. In some embodiments, a washing step is accomplished by tangential flow filtration (TFF) according to the manufacturer's instructions. In some embodiments, the cells are resuspended in a variety of biocompatible buffers after washing, such as, for example, Ca++Mg++free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient. In some embodiments, the methods include leukapheresis.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some embodiments includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some embodiments of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a chamber, for example, under centrifugal rotation. In some embodiments, incubation of cells with selection reagents, such as immunoaffinity-based selection reagents, is performed in a chamber.

In some embodiments, by conducting such selection steps or portions thereof (e.g., incubation with antibody-coated particles, e.g., magnetic beads) in the cavity of a chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection.

In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a chamber, which includes incubation of cells with a selection reagent. In some embodiments of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some embodiments also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some embodiments includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use.

In some embodiments, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some embodiments, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. For example, CD3+, CD28+ T cells can be positively selected using anti-CD3/anti-CD28 conjugated magnetic beads (e.g., DYNABEADS® M-450 CD3/CD28 T Cell Expander). In some embodiments, the population of cells is enriched for T cells with naïve phenotype (CD45RA+ CCR7+).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (markerhlgh) on the positively or negatively selected cells, respectively.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In some embodiments, T cells are separated from a PBMC sample by negative selection of markers expressed on non-T cells, such as B cells, monocytes, or other white blood cells, such as CD14. In some embodiments, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naïve, memory, and/or effector T cell subpopulations.

In some embodiments, CD8+ cells are further enriched for or depleted of naïve, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long term survival, expansion, and/or engraftment following administration, which in some embodiments is particularly robust in such sub-populations. In some embodiments, combining TcM-enriched CD8+ T cells and CD4+ T cells further enhances efficacy. In some embodiments, enriching for T cells with naïve phenotype (CD45RA+ CCR7+) enhances efficacy.

In embodiments, memory T cells are present in both CD62L+ and CD62L subsets of CD8+ peripheral blood lymphocytes. PBMC can be enriched for or depleted of CD62L CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD127; in some embodiments, it is based on negative selection for cells expressing or highly expressing CD45RA and/or granzyme B. In some embodiments, isolation of a CD8+ population enriched for TCM cells is carried out by depletion of cells expressing CD4, CD 14, CD45RA, and positive selection or enrichment for cells expressing CD62L. In one embodiment, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some embodiments are carried out simultaneously and in other embodiments are carried out sequentially, in either order. In some embodiments, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naïve CD4+ T lymphocytes are CD45RO, CD45RA+, CD62L+, CD4+ T cells. In some embodiments, central memory CD4+ cells are CD62L+ and CD45RO+. In some embodiments, effector CD4+ cells are CD62L and CD45RO. In some embodiments, T cells with naïve phenotype are CD45RA+ CCR7+.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques.

In some embodiments, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some embodiments, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some embodiments, a combination of positive and negative selection is performed during the same selection step, where the positive and negative fractions are retained and further processed or subject to further separation steps.

In some embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some embodiments, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the isolation or separation is carried out using a system, device, or apparatus that carries out one or more of the isolation, cell preparation, separation, processing, incubation, culture, and/or formulation steps of the methods. In some embodiments, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., ah, of the isolation, processing, engineering, and formulation steps in an integrated or self-contained system, and/or in an automated or programmable fashion. In some embodiments, the system or apparatus includes a computer and/or computer program in communication with the system or apparatus, which allows a user to program, control, assess the outcome of, and/or adjust various embodiments of the processing, isolation, engineering, and formulation steps.

In some embodiments, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some embodiments controls ah components of the instrument and directs the system to perform repeated procedures in a standardized sequence. The magnetic separation unit in some embodiments includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some embodiments uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some embodiments is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some embodiments may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the isolation and/or selection results in one or more input compositions of enriched T cells, e.g., CD3+ T cells, CD4+ T cells, and/or CD8+ T cells.

In some embodiments, two or more separate input composition are isolated, selected, enriched, or obtained from a single biological sample. In some embodiments, separate input compositions are isolated, selected, enriched, and/or obtained from separate biological samples collected, taken, and/or obtained from the same subject.

In certain embodiments, the one or more input compositions is or includes a composition of enriched T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD3+ T cells. In one embodiment, the input composition of enriched T cells consists essentially of CD3+ T cells.

In certain embodiments, the one or more input compositions is or includes a composition of enriched CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the composition of enriched T cells consists essentially of CD4+ T cells.

In certain embodiments, the one or more compositions is or includes a composition of CD8+ T cells that is or includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the composition of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the composition of enriched T cells consists essentially of CD8+ T cells.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of stimulating or activating an intracellular signaling domain of a TCR complex. In some embodiments, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/mL). In some embodiments, the stimulating agents include IL-2, IL-15 and/or IL-7. In some embodiments, the IL-2 concentration is at least about 10 units/mL. In some embodiments, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some embodiments, the non-dividing feeder cells can comprise gamma-irradiated PBMC feeder cells. In some embodiments, the PBMC are irradiated with gamma rays in the range of about 3000 to 3600 rads to prevent cell division. In some embodiments, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some embodiments is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naïve or antigen specific T lymphocytes with antigen. Lor example, antigen-specific T cell lines or clones can be generated to cytomegalovirus antigens by isolating T cells from infected subjects and stimulating the cells in vitro with the same antigen.

In some embodiments, at least a portion of the incubation in the presence of one or more stimulating conditions or a stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some embodiments of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In some embodiments, the stimulating conditions include incubating, culturing, and/or cultivating a composition of enriched T cells with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, inter-leukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the stimulation results in activation and/or proliferation of the cells, for example, prior to transduction.

In some embodiments, engineered cells, such as T cells, used in connection with the provided methods, uses, articles of manufacture or compositions are cells have been genetically engineered to express a recombinant receptor, e.g., a CAR or a TCR described herein. In some embodiments, the cells are engineered by introduction, delivery or transfer of nucleic acid sequences that encode the recombinant receptor and/or other molecules.

In some embodiments, methods for producing engineered cells includes the introduction of a polynucleotide encoding a recombinant receptor (e.g. anti-CD19 CAR) into a cell, e.g., such as a stimulated or activated cell. In particular embodiments, the recombinant proteins are recombinant receptors, such as any described. Introduction of the nucleic acid molecules encoding the recombinant protein, such as recombinant receptor, in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g. retroviral or lentiviral, transduction, transposons, and electroporation. In some embodiments, the engineering produces one or more engineered compositions of enriched T cells.

In certain embodiments, the one or more compositions of stimulated T cells are or include two separate stimulated compositions of enriched T cells. In some embodiments, two separate compositions of enriched T cells, e.g., two separate compositions of enriched T cells that have been selected, isolated, and/or enriched from the same biological sample, are separately engineered. In certain embodiments, the two separate compositions include a composition of enriched CD4+ T cells. In some embodiments, the two separate compositions include a composition of enriched CD8+ T cells. In some embodiments, two separate compositions of enriched CD4+ T cells and enriched CD8+ T cells are genetically engineered separately. In some embodiments, the same composition is enriched for both CD4+ T cells and CD8+ T cells and these are genetically engineered together.

In one embodiment, the disclosure provides (i) a method of manufacturing an immunotherapy product with improved clinical efficacy and/or decreased toxicity and/or (ii) manipulating the composition of a T cell immunotherapy infusion product comprising:

Preparing a T cell product from a population of lymphocytes comprising T cells with various baseline T cell phenotypes, wherein no specific T cell phenotype has been enriched during the preparation of the product;

Increasing or maximizing the percentage of T cells with naïve phenotype (CD45RA+CCR7+) in the product;

Increasing or maximizing the percentage of CD8+ T cells with naïve phenotype (CD45RA+ CCR7+) in the product;

Decreasing or minimizing the percentage and number of T cells with differentiated phenotype (CCR7−) in the product;

Including at least $20 \times 10^6$ T cells with naïve phenotype in the product;

Including at least $100 \times 10^6$ CD8+ T cells in the product.

In some embodiments, the product is an immunotherapy infusion product and the various baseline T cell phenotypes comprise $T_{CM}$, central memory T cells (CD45RA−CCR7+); $T_{EFF}$, effector T cells (CD45RA+CCR7−); $T_{EM}$, effector memory T cells (CD45RA−CCR7−); and/or $T_N$, naïve-like T cells (CD45RA+CCR7+). The cells referred to as $T_N$ in the EXAMPLES were identified as CCR7+ CD45RA+ T-cells and have been further characterized as stem-like memory cells.

In one embodiment, increasing or maximizing the percentage of T cells with naïve phenotype (CD45RA+ CCR7+) in the product increases product efficacy without increasing toxicity. In one embodiment, increasing or maximizing the percentage of CD8+ T cells with naïve phenotype (CD45RA+ CCR7+) in the product increases product efficacy without increasing toxicity. In one embodiment, decreasing or minimizing the percentage and number of T cells with differentiated phenotype (CCR7−) in the product improves safety profile. In one embodiment, decreasing or minimizing the percentage and number of IFNgamma producing cells in the product improves safety profile. In one embodiment, including at least $20 \times 10^6$ T cells with naïve phenotype in the product improves efficacy without increasing toxicity. In one embodiment, including at least $100 \times 10^6$ CD8 T cells in the product improves efficacy. In one embodiment, including at least $15 \times 10^6$ CD8 T cells of naïve phenotype in the product improves efficacy without increasing toxicity. The cells referred to as $T_N$ in the EXAMPLES were identified only as CCR7+ CD45RA+ T-cells and may be further characterized as stem-like memory cells.

In some embodiments, the method enhances the efficacy of the immunotherapy product. In some embodiments, the population of lymphocytes from which the T cell product is prepared is the product of leukapheresis of Peripheral Blood Mononuclear Cells (PBMCs). The samples, in some embodiments, contain lymphocytes, including T cells, monocytes, granulocytes, B cells, other nucleated white blood cells, red blood cells, and/or platelets, and in some embodiments contains cells other than red blood cells and platelets.

In some embodiments, the population of lymphocytes from which the T cell product is prepared is a population of lymphocytes prepared by in vitro differentiation of stem cells. In some embodiments, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources. In some embodiments, the cells are derived from cell lines, e.g., T cell lines. The cells in some embodiments are obtained from a xenogeneic source, for example, from mouse, rat, non-human primate, and pig. In some embodiments, T cells are genetically modified. In some embodiments, the cells are autologous, allogeneic, or differentiated in vitro from a universal perpetually renewable cell population. In some embodiments, the universal perpetually renewable cell population is a population of stem cells. In one embodiment, the lymphocytes are engineered T lymphocytes engineered to comprise a CAR or an exogenous TCR. Examples of CARs and TCRs and methods of engineering lymphocytes are described elsewhere in the disclosure. In one embodiment, the method comprises expanding the engineered lymphocytes to produce the infusion product in the presence of IL-2. In one embodiment, the engineered lymphocytes are expanded for about 2-7 days in the presence of IL-2.

In one embodiment, the disclosure provides a method of preparing a personalized immunotherapy product for infusion to a subject in need thereof comprising:

Preparing a population of lymphocytes comprising CD8+ T cells and naïve T cells;

Determining the subject's tumor burden; and

Increasing the cumulative cell dose to be infused to the subject based on the measured tumor burden to increase the ratio of infused CD8+ T cells/tumor burden; and/or Increasing the cumulative cell dose to be infused based on the measured tumor burden to increase the ratio of infused naïve T cells/tumor burden.

In some embodiments, the method enhances the efficacy of the immunotherapy product. In some embodiments, the population of lymphocytes from which the T cell product is prepared is the product of leukapheresis of Peripheral Blood Mononuclear Cells (PBMCs). In some embodiments, the population of lymphocytes from which the T cell product is prepared is a population of lymphocytes prepared by in vitro differentiation of stem cells. In some embodiments, T cells are genetically modified. In some embodiments, the cells are autologous, allogeneic, or differentiated in vitro from a universal perpetually renewable cell population. In some embodiments, the universal perpetually renewable cell population is a population of stem cells. In one embodiment, the lymphocytes are engineered T lymphocytes engineered to comprise a CAR or an exogenous TCR. Examples of CARs and TCRs and methods of engineering lymphocytes are described elsewhere in the disclosure. In one embodiment, the method comprises expanding the engineered lymphocytes to produce the infusion product in the presence of IL-2. In one embodiment, the engineered lymphocytes are expanded for about 2-7 days in the presence of IL-2.

In some embodiments, the disclosure provides a method of manufacturing an effective dose of engineered lymphocytes comprising:

preparing a population of engineered lymphocytes, optionally comprising a chimeric antigen receptor (CAR), and optionally starting with an apheresis product;

measuring the expansion capability of the population of engineered lymphocytes during manufacturing of an infusion product, or in the infusion product, comprising the engineered lymphocytes; and preparing an effective dose of engineered lymphocytes in an infusion product for treating a malignancy in a patient in need thereof based on the expansion capability of the engineered lymphocyte population.

In one embodiment, the engineered lymphocyte population expansion capability is determined by measuring doubling time. In one embodiment, the doubling time is measured by determining the number of total viable cells at the start of expansion and at the time of harvesting the engineered lymphocytes. In one embodiment, the doubling time is about 1.0, 1.1, about 1.2, about 1.3, about 1.4 days, about 1.5 days, about 1.6, about 1.7 days, about 1.8, about 1.9, and about 2. In one embodiment, the doubling time is about 2.1 days. In one embodiment, the doubling time is about 1.6 or >1.6 days. In one embodiment, the doubling time is <2 days. In one embodiment, the doubling time is >2 days. In one embodiment, the doubling time is greater than about 2 days. In one embodiment, the doubling time is less than about 2 days. In one embodiment, the doubling time of the population of engineered lymphocytes (e.g., CART cells) is measured during preparation of the infusion product. In one embodiment, the method further comprises manipulating the population of engineered lymphocytes during manufacturing of the infusion product to produce an infusion product with a predetermined engineered lymphocyte population doubling time. In one embodiment, the predetermined doubling time is about 1.6 or >1.6 days, about 2 days, or greater than about 2 days. In one embodiment, the predetermined doubling time is about <1.6 days, about 2 days, or smaller than about 2 days.

In some embodiments, the method enhances the efficacy of the immunotherapy product. In some embodiments, the population of lymphocytes from which the T cell product is prepared is the product of leukapheresis of Peripheral Blood Mononuclear Cells (PBMCs). In some embodiments, the population of lymphocytes from which the T cell product is prepared is a population of lymphocytes prepared by in vitro differentiation of stem cells. In some embodiments, T cells are genetically modified. In some embodiments, the cells are autologous, allogeneic, or differentiated in vitro from a universal perpetually renewable cell population. In some embodiments, the universal perpetually renewable cell population is a population of stem cells. In one embodiment, the engineered lymphocytes are T lymphocytes engineered to comprise a CAR or an exogenous TCR. Examples of CARs and TCRs and methods of engineering lymphocytes are described elsewhere in the disclosure.

In one embodiment, manipulating the population of engineered lymphocytes comprises manipulating the composition of the final infusion product in terms of numbers of $T_{CM}$, central memory T cells (CD45RA–CCR7+); $T_{EFF}$, effector T cells (CD45RA+CCR7–); $T_{EM}$, effector memory T cells (CD45RA–CCR7–); and/or $T_N$, naïve-like T cells (CD45RA+CCR7+). In one embodiment, the greater the percentage of $T_{EM}$ cells in the infusion product the higher the doubling time. In one embodiment, the higher the percentage of $T_N$ cells in the infusion product, the lower the doubling time. In one embodiment, the lower the doubling time of the population of engineered lymphocytes in the final infusion product, the greater the in vivo engineered lymphocyte (e.g., CAR T cells) levels after administration. In one embodiment, the lower the doubling time of the population of engineered lymphocytes in the final infusion product, the greater the efficacy of the final infusion product. In one embodiment, the method further comprises measuring the proportion of T cells with a juvenile phenotype in the apheresis product from which the population of engineered lymphocytes is prepared, wherein the higher the proportion of cells with a juvenile phenotype (e.g., CD28+CD27+ $T_N$ cells, CD45RA+CCR7+ cells) the lower the doubling time of the infusion product. In one embodiment, the method comprises expanding the engineered lymphocytes to produce the infusion product in the presence of IL-2. In one embodiment, the engineered lymphocytes are expanded for about 2-7 days in the presence of IL-2. In one embodiment, the doubling time is measured by determining the number of total viable cells at the start of expansion and at the time of harvesting the engineered lymphocytes. The cells referred to as $T_N$ in the EXAMPLES were identified only as CCR7+ CD45RA+ T-cells and may be further characterized as stem-like memory cells.

In one embodiment, the disclosure provides a T cell product produced according to any one of the methods of the disclosure. In one embodiment, the T cell product is an immunotherapy product. In one embodiment, the T cell product is an infusion product.

In one embodiment, the disclosure provides a method of selecting a donor for allogeneic T cell immunotherapy comprising:

Collecting a sample of T lymphocytes from a subject;

Selecting the subject to be a donor for allogeneic T cell immunotherapy based on one or more of the following:

a. the percentage of T cells with naïve phenotype (CD45RA+ CCR7+) in the sample;

b. the percentage of CD8+ T cells with naïve phenotype (CD45RA+ CCR7+) in the sample;

c. the percentage and number of T cells with differentiated phenotype (CCR7–) in the sample;

d. the percentage and number of IFNgamma producing cells in the sample; and, optionally, Preparing an allogeneic T cell product from the selected subject; and Administering the product to a patient in need thereof.

In one embodiment, the sample of T lymphocytes is prepared by leukapheresis of PBMCs from the subject. In one embodiment, the leukapheresis sample is further subject to T lymphocyte enrichment through positive selection for CD4+ and/or CD8+ cells. In one embodiment, the lymphocytes are further engineered to comprise a CAR or an exogenous TCR. Examples of CARs and TCRs and methods of engineering lymphocytes are described elsewhere in the disclosure. In one embodiment, the method comprises expanding the engineered lymphocytes to produce a T cell infusion product in the presence of IL-2. In one embodiment, the engineered lymphocytes are expanded for about 2-7 days in the presence of IL-2.

Under circumstances where subjects initially respond and subsequently relapse, subjects may be eligible for a second course of conditioning chemotherapy and axicabtagene ciloleucel. Retreatment may be administered under conditions such as: subject has a PR or CR; subject's disease subsequently progresses; CD19 tumor expression confirmed locally by biopsy after disease progression and prior to re-treatment; Subject continues to meet the original study eligibility criteria with exception of prior axicabtagene ciloleucel use. Screening assessments should be repeated if clinically indicated, as determined by the investigator, to confirm eligibility; Subject has not received subsequent therapy for the treatment of lymphoma; Toxicities related to conditioning chemotherapy (fludarabine and cyclophosphamide), with the exception of alopecia, have resolved to ≤Grade 1 or returned to baseline prior to retreatment; and Subject does not have known neutralizing antibodies (exception: if a non-neutralizing antibody develops subject may be retreated if they meet the original study eligibility criteria).

Methods of Increasing the Efficacy and/or Diminishing the Toxicity of T Cell Therapy In one embodiment, the disclosure provides a method of increasing the efficacy and/or reducing the toxicity of T cell immunotherapy (e.g., CAR T cell immunotherapy) comprising decreasing the subject's tumor burden prior to CAR T-cell immunotherapy. In one embodiment, the decrease of the subject's tumor burden comprises administration of bridging therapy. In one embodiment, bridging therapy comprises therapy between conditioning and T cell administration. In one embodiment, the bridging therapy comprises CHOP, R-CHOP (rituximab, cyclophosphamide, doxorubicin, vincristine, and prednisolone), G-CHOP (obinutuzumab, cyclophosphamide, doxorubicin, vincristine, and prednisolone), corticosteroids, bendamustine, platinum compounds, anthracyclines, venetoclax, zanubrutinib, and/or phosphoinositide 3-kinase (PI3K) inhibitors, and inhibitors of the PI3K/Akt/mTOR pathway. In one embodiment, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032). In one embodiment, the bridging therapy comprises acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denileukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin diftitox, pembrolizumab, plerixafor, polatuzumab vedotin-piiq, mogamulizumab-kpc, prednisone, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

In one embodiment, bridging therapy may be considered for subjects with particularly high disease burden at screening or baseline assessment (e.g., bulky disease or rapidly progressing disease). An example of a bridging therapy protocol may be found in Table 11.

In one embodiment, the disclosure provides a method of increasing the efficacy and/or reducing the toxicity of T cell immunotherapy (e.g., CAR T cell immunotherapy) comprising decreasing the subject's systemic inflammatory state prior to T-cell immunotherapy. In one embodiment, the therapy is CAR T cell therapy. In one embodiment, the method comprises administering anti-inflammatory treatment to the subject prior to CAR T-cell immunotherapy. Examples of anti-inflammatory treatments are provided elsewhere in this disclosure.

In one embodiment, the disclosure provides a method of increasing the efficacy and/or reducing the toxicity of T cell immunotherapy (e.g., CART cell immunotherapy) comprising reducing myeloid cell activity in the subject prior to CAR T-cell immunotherapy. In one embodiment, the disclosure provides a method of increasing the efficacy and/or reducing the toxicity of T cell immunotherapy (e.g., CAR T cell immunotherapy) comprising reducing the MCP-1 and/or IL-6 activity prior to, or early after CAR T-cell administration. In one embodiment, reducing myeloid cell activity, MCP-1, and/or IL-6 activity comprises administering to the subject a monoclonal antibody against MCP-1, IL-6, IL-1, CSF1R, GM-CSF and/or a small molecule. Examples of such agents are described elsewhere in the disclosure. In one embodiment, the small molecule is a JAK/STAT inhibitor. In one embodiment, the JAK/STAT inhibitor is selected from tofacitinib, ruxolitinib, filgotinib, baricitinib, peficitinib, oclacitinib, upadicitinib, solcitinib, decernotinib, SHR0302, AC430, PF-06263276, BMS-986165, lestaurtinib, PF-06651600, PF-04965841, abrocitinib, sttatic, peptidomimetics, and combinations thereof.

In one embodiment, the disclosure provides a method of increasing the efficacy and/or reducing the toxicity of T cell immunotherapy (e.g., CART cell immunotherapy) comprising reducing the activity of activated T cells in the subject/product prior to CAR T-cell immunotherapy. In one embodiment, this may be achieved by separation/removal of differentiated cells (effector memory and/or effector cells, enriching the product for juvenile T cells (CCR7+), removing or diminishing the percentage and number of differentiated T cells in the T cell product infusion bag through separation techniques; and/or treating the product T cells during or after manufacturing process with pharmacological agents or biological response modifiers that would reduce excessive T cell activity (e.g. JAK/STAT inhibitors).

In one embodiment, the disclosure provides a method of increasing the efficacy and/or reducing the toxicity of T cell immunotherapy (e.g., CAR T cell immunotherapy) comprising increasing the dosage of the T cell immunotherapy in a manner commensurate with tumor burden and/or re-dosing patients with high tumor burden. Methods of measuring and classifying tumor burden are described elsewhere in the disclosure.

In one embodiment, the disclosure provides a method of increasing the efficacy and/or reducing the toxicity of T cell immunotherapy (e.g., CAR T cell immunotherapy) comprising (a) identifying a subject positive for marker(s) of toxicity in response to T-cell immunotherapy; and (b) reducing IL-15 elevation post-conditioning and pre-T cell immunotherapy in the subject. In one embodiment, the marker of toxicity in response to T-cell immunotherapy is high tumor burden. In one embodiment, the marker of toxicity in response to T-cell immunotherapy is increased pre-treatment levels of an inflammatory marker. In one embodiment, the inflammatory marker is selected from IL6, CRP, and ferritin. In one embodiment, reduction of IL-15 elevation post-conditioning and pre-T cell immunotherapy is accomplished by selection of a pre-conditioning protocol. In one embodiment, the pre-conditioning protocol comprises cyclophosphamide, fludarabine, bendamustine, Anti-Human Thymocyte Globulin, carmustine, radiation, etoposide, cytarabine, melphalan, rituximab, or combinations thereof.

Methods to Predict Toxicity to Optimize Management of Patients by Measurement of Subject Attributes In one embodiment, the disclosure provides a method of predicting toxicity in response to T cell therapy in a subject in need thereof comprising (a) measuring pre-treatment tumor burden in the subject and (b) predicting toxicity in response to T cell therapy based on the pre-treatment tumor burden. In one embodiment, the larger the tumor burden, the higher/more severe the toxicity. In one embodiment, the T cell therapy is CAR T cell therapy.

In one embodiment, the disclosure provides a method of predicting toxicity in response to T cell therapy in a subject in need thereof comprising (a) measuring tumor burden changes between pre and post-conditioning in the subject and (b) predicting toxicity in response to T cell therapy based on the changes. In one embodiment, the higher the change the less severe the toxicity.

In one embodiment, the disclosure provides a method of predicting toxicity in response to T cell therapy in a subject in need thereof comprising (a) measuring changes in tumor burden between day 1 and day 0 in the subject and (b) predicting toxicity in response to T cell therapy based on the changes. In one embodiment, the higher the change the less severe the toxicity.

In one embodiment, the disclosure provides a method of predicting toxicity in response to T cell therapy in a subject in need thereof comprising (a) measuring changes in tumor burden between day 0 and baseline in the subject and (b) predicting toxicity in response to T cell therapy based on the changes. In one embodiment, the higher the change the less severe the toxicity.

In one embodiment, the disclosure provides a method of predicting toxicity in response to T cell therapy in a subject in need thereof comprising (a) measuring changes in tumor burden between day 1 and baseline in the subject and (b) predicting toxicity in response to T cell therapy based on the changes. In one embodiment, the higher the change the less severe the toxicity.

In one embodiment, the disclosure provides a method of predicting toxicity in response to T cell therapy in a subject in need thereof comprising (a) measuring pre-treatment blood levels of LDH, ferritin, and/or IL-6 in the subject and (b) predicting toxicity in response to T cell therapy based on the pre-treatment blood levels of LDH, ferritin, and/or IL-6. In one embodiment, larger the pre-treatment blood levels of LDH, ferritin, and/or IL-6, the higher/more severe the toxicity. In one embodiment, the T cell therapy is CAR T cell therapy.

In one embodiment, the disclosure provides a method of predicting toxicity in response to T cell therapy in a subject in need thereof comprising (a) measuring changes in blood levels of LDH, ferritin, and/or IL-6 between pre and post-conditioning in the subject and (b) predicting toxicity in response to T cell therapy based on the changes. In one embodiment, the—larger the increase the—higher/more severe the toxicity In one embodiment, the disclosure provides a method of predicting toxicity in response to T cell therapy in a subject in need thereof comprising (a) measuring changes in blood levels of LDH, ferritin, and/or IL-6 between day 1 and day 0 in the subject and (b) predicting toxicity in response to T cell therapy based on the changes. In one embodiment, the larger the increase the higher/more severe the toxicity In one embodiment, the disclosure provides a method of predicting toxicity in response to T cell therapy in a subject in need thereof comprising (a) measuring changes in blood levels of LDH, ferritin, and/or IL-6 between day 0 and baseline in the subject and (b) predicting toxicity in response to T cell therapy based on the changes. In one embodiment, the larger the increase—higher/more severe the toxicity In one embodiment, the disclosure provides a method of predicting toxicity in response to T cell therapy in a subject in need thereof comprising (a) measuring changes in blood levels of LDH, ferritin, and/or IL-6 between day 1 and baseline in the subject and (b) predicting toxicity in response to T cell therapy based on the changes. In one embodiment, the larger the increase the higher/more severe the toxicity.

In one embodiment, the disclosure provides a method of predicting toxicity in response to T cell therapy in a subject in need thereof comprising (a) measuring blood levels of IL-15 post-conditioning therapy and pre-CAR T cell treatment in the subject and (b) predicting toxicity in response to T cell therapy based on the blood levels of IL-15 post-conditioning therapy and pre-T cell treatment. In one embodiment, the larger the blood levels of IL-15 post-conditioning therapy and pre-T cell treatment, the higher/more severe the toxicity. In one embodiment, the T cell therapy is CAR T cell therapy.

In one embodiment, the disclosure provides a method of predicting toxicity in response to T cell therapy in a subject in need thereof comprising (a) measuring changes in blood levels of IL-15 between pre and post-conditioning in the subject and (b) predicting toxicity in response to T cell therapy based on the changes. In one embodiment, the—larger the increase the—higher/more severe the toxicity.

In one embodiment, the disclosure provides a method of predicting toxicity in response to T cell therapy in a subject in need thereof comprising (a) measuring changes in blood levels of IL-15 between day 1 and day 0 in the subject and (b) predicting toxicity in response to T cell therapy based on the changes. In one embodiment, the larger the increase the higher/more severe the toxicity In one embodiment, the disclosure provides a method of predicting toxicity in response to T cell therapy in a subject in need thereof comprising (a) measuring changes in blood levels of IL-15 between day 0 and baseline in the subject and (b) predicting toxicity in response to T cell therapy based on the changes. In one embodiment, the larger the increase the higher/more severe the toxicity In one embodiment, the disclosure provides a method of predicting toxicity in response to T cell therapy in a subject in need thereof comprising (a) measuring changes in blood levels of IL-15 between day 1 and baseline in the subject and (b) predicting toxicity in response to T cell therapy based on the changes. In one embodiment, the larger the increase the higher/more severe the toxicity.

In one embodiment, the disclosure provides a method of predicting toxicity in response to T cell therapy in a subject in need thereof comprising (a) measuring blood levels of MCP-1, IL-6, IFNgamma, and/or CXCL10 one day post CAR T cell treatment in the subject and (b) predicting toxicity in response to T cell therapy based on the blood levels of MCP-1, IL-6, IFNgamma, and/or CXCL10 one day post T cell treatment. In one embodiment, the larger the blood levels of MCP-1, IL-6, IFNgamma, and/or CXCL10 one day post CART cell treatment, the higher/more severe the toxicity. In one embodiment, the T cell therapy is CAR T cell therapy.

In one embodiment, the disclosure provides a method of predicting toxicity in response to T cell therapy in a subject in need thereof comprising (a) measuring changes in blood levels of MCP-1, IL-6, IFNgamma, and/or CXCL10 between pre and post-conditioning in the subject and (b) predicting toxicity in response to T cell therapy based on the changes. In one embodiment, the larger the increase the higher/more severe the toxicity In one embodiment, the disclosure provides a method of predicting toxicity in response to T cell therapy in a subject in need thereof comprising (a) measuring changes in blood levels of MCP-1, IL-6, IFNgamma, and/or CXCL10 between day 1 and day 0 in the subject and (b) predicting toxicity in response to T cell therapy based on the changes. In one embodiment, the larger the increase the higher/more severe the toxicity In one embodiment, the disclosure provides a method of predicting toxicity in response to T cell therapy in a subject in need thereof comprising (a) measuring changes in blood levels of MCP-1, IL-6, CRP, IFNgamma, and/or CXCL10 between day 0 and baseline in the subject and (b) predicting toxicity in response to T cell therapy based on the changes. In one embodiment, the larger the increase the higher/more severe the toxicity In one embodiment, the disclosure provides a method of predicting toxicity in response to T cell therapy in a subject in need thereof comprising (a) measuring changes in blood levels of MCP-1, IL-6, CRP, IFNgamma, and/or CXCL10 between day 1 and baseline in the subject and (b) predicting toxicity in response to T cell therapy based on the changes. In one embodiment, the higher/more severe the toxicity.

In one embodiment, the disclosure provides a method of predicting toxicity in response to T cell therapy in a subject in need thereof comprising (a) measuring the subject's inflammatory status reflected by myeloid activation markers pre- and post-treatment in the subject and (b) predicting toxicity in response to T cell therapy based on inflammatory status reflected by myeloid activation markers pre- and post-treatment. In one embodiment, the higher the inflammatory status reflected by myeloid activation markers pre- and post-treatment, the higher/more severe the toxicity.

In one embodiment, the disclosure provides a method of predicting toxicity in response to T cell therapy in a subject in need thereof comprising (a) measuring treatment-related type-1 cytokines in the subject and (b) predicting toxicity in response to T cell therapy based on treatment-related type-1 cytokines. In one embodiment, the higher the treatment-related type-1 cytokines levels, the higher/more severe the toxicity.

In one embodiment, the disclosure provides a method of predicting toxicity in response to CART cell therapy in a subject in need thereof comprising (a) measuring the peak CART cell level after treatment in the subject and (b) predicting toxicity in response to T cell therapy based on the peak CAR T cell level after treatment. In one embodiment, the higher the peak CAR T cell level after treatment, the higher/more severe the toxicity.

In one embodiment, the disclosure provides a method of predicting Grade ≥3 NE in response to T cell therapy in a subject in need thereof comprising (a) measuring baseline LDH and/or day 0 IL-15 and (b) predicting Grade ≥3 NE in response to T cell therapy based on baseline LDH and/or day 0 IL-15. In one embodiment, the larger the baseline LDH and/or day 0 IL-15 level the higher the number of Grade ≥3 NE.

In one embodiment, the disclosure provides a method of predicting Grade 3+ neurotoxicity in response to T cell therapy in a subject in need thereof comprising (a) measuring day 1/day 0 serum IFNgamma fold change and (b) predicting Grade 3+ neurotoxicity in response to T cell therapy based on day 1/day 0 serum IFNgamma fold change. In one embodiment, a day 1/day 0 serum IFNgamma fold change greater than about 25 results in Grade 3+ neurotoxicity. In one embodiment, day 1/day 0 serum IFNgamma fold change greater than about 30, about 35, about 40, about 45, or about 50 results in Grade 3+ neurotoxicity.

In one embodiment, the disclosure provides a method of predicting Grade ≥3 CRS in response to T cell therapy in a subject in need thereof comprising (a) measuring baseline LDH and/or baseline IL-6 and (b) predicting Grade ≥3 CRS in response to T cell therapy based baseline LDH and/or baseline IL-6. In one embodiment, the larger the baseline LDH and/or baseline IL-6 level the larger the Grade ≥3 CRS.

In one embodiment of the above methods to predict toxicity or response (or treatment failure) to optimize management of patients by measurement of subject attributes, the comparisons are made between the subject's attribute levels and those of a reference standard for each attribute. In one embodiment, the reference standards are classified in quartiles. In one embodiment, the comparisons require determining the quartile in which the subject's attribute levels fit. In one embodiment, the quartiles are those exemplified in the Figures of this disclosure.

In one embodiment of the above methods to predict toxicity or response (or treatment failure) to optimize management of patients by measurement of subject attributes, the method further comprises administering to the subject one or more agents capable of reducing the adverse effects, optionally selected from agents that have a direct relation to or a direct effect on the measured attributes. In one embodiment, the agent is administered prior to T cell treatment. In one embodiment, the agent is administered concurrently with or after administration of the CAR T cell treatment. In one embodiment, the agent is selected from tocilizumab (or another anti-IL6/IL6R agent/antagonist), a corticosteroid therapy, or an anti-seizure medicine for toxicity prophylaxis based on the measured levels of the one or more attributes, or combinations thereof. In one embodiment, the agent is selected from inhibitors of GM-CSF, CSF1, GM-CSFR, or CSF1R, anti-thymocyte globulin, lenzilumab, mavrilimumab, cytokines, and/or anti-inflammatory agents.

Methods to Predict Toxicity to Optimize Management of Patients and Product by Measurement of Product Attributes In one embodiment, the disclosure provides a method of predicting neurologic toxicity in response to CAR T cell treatment in a subject in need thereof comprising (a) measuring the IFN gamma production by the T cell product to obtain a value and (b) predicting neurologic toxicity based on the value. In one embodiment, the higher the value the more severe the toxicity.

Methods to Predict Toxicity or Response (or Treatment Failure) to Optimize Management of Patients by Measurement of T Cell Product and Subject Attributes In one embodiment, the disclosure provides a method to predict response to a T cell treatment in a subject in need thereof comprising (a) measuring the IFN gamma production by the T cell product to obtain a value and (b) predicting response based on the value. In one embodiment, the higher the value the lower the efficacy of the T cell treatment with the T cell product.

In one embodiment, the disclosure provides a method to predict response to a T cell treatment in a subject in need thereof comprising (a) measuring the dose of CD8+ T cells administered or to be administered to the subject to obtain a value and (b) predicting treatment response based on the value. In one embodiment, the higher the dose, the higher the response.

In one embodiment, the disclosure provides a method to predict response to a T cell treatment in a subject in need thereof comprising (a) measuring the dose of naïve T cells (CCR7+CD45RA+) administered or to be administered to the subject to obtain a value and (b) predicting treatment response based on the value. In one embodiment, the higher the dose, the higher the response.

In one embodiment, the disclosure provides a method to predict response to a T cell treatment in a subject in need thereof comprising (a) measuring the pre-treatment tumor burden to obtain a value and (b) predicting treatment response based on the value. In one embodiment, the lower the tumor burden the higher the response.

In one embodiment, the disclosure provides a method of predicting peak CAR T cell levels in the blood after administration of a CAR T cell infusion product to a subject. In one embodiment, the higher the number of naïve T cells in the infusion product, the higher the peak CAR T cell levels in the blood after administration of the T cell infusion product to a subject. In one embodiment, the higher the number of naïve T cells in the infusion product, the higher the peak CAR T cell levels normalized to pre-treatment tumor burden in the blood after administration of the T cell infusion product to a subject. In one embodiment, the lower the baseline doubling time of the CAR T cells in the infusion product, the higher the peak CAR T cell levels in the blood after administration of the T cell in fusion product to a subject. In one embodiment, the lower the coculture IFN-γ of the CAR T cells in the infusion product, the higher the peak CAR T cell levels in the blood after administration of the T cell in fusion product to a subject.

In one embodiment, the lower the baseline ferritin levels in the blood of the subject, the higher the peak engineered lymphocytes normalized to pre-treatment tumor burden in the subject after administration of an infusion product of engineered lymphocytes to the subject. In one embodiment, the lower the baseline LDH levels in the blood of the subject, the higher the peak engineered lymphocytes normalized to tumor burden in the subject after administration of an infusion product of engineered lymphocytes to the subject. In one embodiment, the lower the baseline CRP levels in the blood of the subject, the higher the peak engineered lymphocytes normalized to tumor burden in the subject after administration of an infusion product of engineered lymphocytes to the subject.

In one embodiment, the disclosure provides a method to predict response to a CAR T cell treatment in a subject in need thereof comprising (a) measuring the peak CAR T cell levels in the blood after CAR T cell therapy (optionally normalized to pre-treatment tumor burden) to obtain a value and (b) predicting treatment response based on the value. In one embodiment, the higher the value the higher the durable response.

In one embodiment, the disclosure provides a method to predict response to a CAR T cell treatment in a subject in need thereof comprising (a) measuring the rate of in vivo CAR T cell expansion relatively to pretreatment tumor burden to obtain a value and (b) predicting treatment response based on the value. In one embodiment, the higher the value the higher the durable response.

In one embodiment, the disclosure provides a method to predict response to a CAR T cell treatment in a subject in need thereof comprising (a) measuring the intrinsic product T-cell fitness (optionally relatively to pretreatment tumor burden) to obtain a value and (b) predicting treatment response based on the value. In one embodiment, the higher the value the higher the durable response. In one embodiment, suboptimal product T-cell fitness is associated with primary treatment resistance.

In one embodiment, the disclosure provides a method to predict response to a CAR T cell treatment in a subject in need thereof comprising (a) measuring the dose of specialized T cell subsets in the T cell product (optionally in proportion to tumor burden) to obtain a value and (b) predicting treatment response based on the value. In one embodiment, the higher the value the higher the durable response. In one embodiment, limited numbers of naïve-like or CD8+ T cells in proportion to tumor burden are associated with a failure to achieve durable response In one embodiment, the disclosure provides a method to predict response to a CAR T cell treatment in a subject in need thereof comprising (a) measuring pre-treatment and/or post-treatment host systemic inflammation to obtain a value to obtain a value and (b) predicting treatment response based on the value. In one embodiment, the higher the value the lower the durable response.

In one embodiment, the disclosure provides a method to predict response to a CAR T cell treatment in a subject in need thereof comprising (a) measuring the rate of in vivo CAR T cell expansion relatively to pretreatment tumor burden to obtain a value and (b) predicting treatment response based on the value. In one embodiment, the higher.

In one embodiment, the disclosure provides a method to predict response to a CAR T cell treatment in a subject in need thereof comprising (a) measuring the levels of type-1 cytokines in the blood of the patient post-treatment to obtain a value and (b) predicting treatment response based on the value. In one embodiment, the lower the value the higher the response/efficacy.

In one embodiment, the disclosure provides a method to predict response to a CAR T cell treatment in a subject in need thereof comprising (a) measuring baseline tumor burden, baseline IL6, baseline CRP, baseline LDH, and T cell product coculture IFN-γ to obtain a value and (b) predicting treatment response based on the value. In one embodiment, the higher the baseline tumor burden, baseline IL6, baseline CRP, baseline LDH, and/or T cell product coculture IFN-γ, the lower the durable response.

In one embodiment, the disclosure provides that baseline serum levels of CCL17 (TARC), CCL22 (MDC), Ferritin, IL-16, IL-10, TNFα, IL-2Rα, and CRP in serum were negatively associated with response. Accordingly, the disclosure provides a method to predict response to CAR T cell treatment in a subject in need thereof comprising (a) measuring baseline serum levels of one or more of CCL17 (TARC), CCL22 (MDC), Ferritin, IL-16, IL-10, TNFα, IL-2Rα, and CRP, and (b) predicting response based on the measured level(s) wherein the higher the level(s) the poorer/worse the response to treatment. In some embodiments, the subject has follicular lymphoma.

In one embodiment, the disclosure provides that peak serum levels of IL-1RA associated positively with Grade ≥3 CRS. Accordingly, the disclosure provides a method of predicting Grade ≥3 CRS in response to T cell therapy in a subject in need thereof comprising (a) measuring peak serum levels of IL-1RA and predicting Grade ≥3 CRS in response to T cell therapy based the level. In one embodiment, the larger the peak serum level of IL-1RA, the higher/more likely the Grade ≥3 CRS in response to treatment. In some embodiments, the subject has follicular lymphoma In one embodiment, the disclosure provides that peak serum levels of IL-15, CRP, Granzyme B, CCL26 [Eotaxin-3], and IL-17 associated positively with neurologic toxicity in response to CAR T cell treatment. Accordingly, the disclosure provides a method of predicting neurologic toxicity in response to T cell therapy in a subject in need thereof comprising (a) measuring peak serum levels of IL-15, CRP, Granzyme B, CCL26 [Eotaxin-3], and/or IL-17 and predicting neurologic toxicity in response to T cell therapy based on the level(s). In one embodiment, the larger the peak serum level of IL-15, CRP, Granzyme B, CCL26 [Eotaxin-3], and/or IL-17, the larger/the more likely the neurologic toxicity in response to treatment. In some embodiments, the subject has follicular lymphoma In one embodiment, the disclosure provides that peak serum levels of IL-2, IL-6, IL-2Rα, GM-CSF, IFN-γ, IL-8, CXCL10 [IP-10], CCL2 [MCP-1], IL-10, CCL4 [MIP-1β], and TNF-α associated positively with both Grade ≥3 CRS and neurologic toxicity in response to CAR T cell treatment. Accordingly, the disclosure provides a method of predicting neurologic toxicity in response to T cell therapy in a subject in need thereof comprising (a) measuring peak serum levels of IL-2, IL-6, IL-2Rα, GM-CSF, IFN-γ, IL-8, CXCL10 [IP-10], CCL2 [MCP-1], IL-10, CCL4 [MIP-1β], and/or TNF-α and predicting Grade ≥3 CRS and/or neurologic toxicity in response to T cell therapy based the level. In one embodiment, the larger the peak serum level of IL-2, IL-6, IL-2Rα, GM-CSF, IFN-γ, IL-8, CXCL10 [IP-10], CCL2 [MCP-1], IL-10, CCL4 [MIP-1β], and/or TNF-α, the higher/more likely the Grade ≥3 CRS and the higher/more likely the neurologic toxicity in response to treatment. In some embodiments, the subject has follicular lymphoma.

In one embodiment, the disclosure provides that high numbers of naïve and central memory T cells (CCR7+ cells) in the CAR T cell product were positively associated with ongoing response in patients with FL. Accordingly, the disclosure provides a method of improving FL patient response to CART cell treatment comprising increasing/maximizing the numbers of naïve and central memory T cells (CCR7+ cells) in the CAR T cell product administered to the patient.

Methods of Manipulating the Composition of Specific T Cell Subsets in a T Cell Product to Improve Methods of Treating a Subject with a T Cell Product In one embodiment, the disclosure provides methods of treatment of malignancies that combine any of the above methods of predicting response and/or toxicity, and methods of manipulating the composition of the T cell product with administration of T cell treatment (e.g., T cell infusion products).

In one embodiment, the disclosure provides a method of improving an infusion product comprising engineered lymphocytes and, optionally, treating a cancer in a subject with an infusion product comprising engineered lymphocytes comprising:

measuring levels of one or more attributes in a population of lymphocytes from an apheresis product; and/or measuring levels of one or more attributes in a population of engineered lymphocytes (e.g., CAR T cells) during manufacturing of a final infusion product and/or in the final infusion product; and/or manipulating the composition of the T cell infusion product to improve effectiveness and reduce treatment-associated toxicity; and/or determining or predicting a patient's response to treatment with the engineered lymphocytes based on the measured levels of one or more attributes compared to a reference level; and, optionally, administering a therapeutically effective dose of the engineered lymphocytes to the subject, wherein the therapeutically effective dose is determined based on the levels of one or more attributes of the population of engineered lymphocytes in the infusion product and/or of the T cells in the apheresis product.

In one embodiment, the engineered lymphocytes are CAR-T lymphocytes. In one embodiment, the T cell composition of the final infusion product is manipulated during its manufacturing to achieve pre-determined levels of engineered lymphocytes with select attributes in the infusion product. In one embodiment, the one or more attributes is T cell fitness, including doubling time and T cell phenotype (e.g., the levels of specialized CAR T-cell subsets in the CAR T-cell population). In one embodiment, the T cell phenotype that is measured is that of the population of engineered lymphocytes in the final infusion product. In one embodiment, the T cell phenotype that is measured is that of the population of engineered lymphocytes during manufacturing of the final infusion product, and the T cell phenotype of the final infusion product. In one embodiment, the population of engineered lymphocytes (e.g., CAR T cells) is to be infused into the patient and the phenotype is determined by measuring the percentage of CD3 positive cells infused, the number of CD3 cells infused, the number of CD3 cells infused/tumor burden; the percentage of Tn cells infused, the number of Tn cells infused, the number of Tn cells infused/tumor burden; the percentage of CD8 positive cells infused, the number of CD8 positive cells infused, the number of CD8 positive cells infused/tumor burden; the percentage of CD4 positive cells infused, the number of CD4 positive cells infused, the number of CD4 positive cells infused/tumor burden; and/or the CD4:CD8 ratio in the cells infused. In one embodiment, the number of CD3 cells infused, the number of CD3 cells infused/tumor burden; the percentage of $T_n$ cells infused, the number of $T_n$ cells infused, the number of $T_n$ cells infused/tumor burden; the percentage of CD8 positive cells infused, the number of CD8 positive cells infused/tumor burden; and the number of CD4 positive cells infused/tumor burden associate positively with or are predictive of durable response to treatment the percentage of CD3 cells infused, the percentage of CD4 cells infused, and the number of CD4 cells infused associate negatively with are predictive of no durable response. In one embodiment, the frequency and proportion of TN (CD45RA+CCR7+) and TEM CD8+ or CD4+ T cells (CD45RA−CCR7−) in the CAR T-cell infusion product associate with clinical efficacy, positively and negatively, respectively. In one embodiment, the frequency and proportion of TN (CD45RA+CCR7+) and TEM CD8+ or CD4+ T cells (CD45RA−CCR7−) in the engineered lymphocyte (CAR T cells) infusion product are manipulated during manufacturing of the infusion product to improve clinical efficacy. In one embodiment, the % of CD3 cells infused, the number of CD3 cells infused, the number of CD3 cells infused/tumor burden; the percentage of Tn cells infused, the number of Tn cells infused, the number of Tn cells infused/tumor burden; the percentage of CD8 positive cells infused, the number of CD8 positive cells infused, the number of CD8 positive cells infused/tumor burden; and the number of CD4 positive cells infused/tumor burden associate positively with or are predictive of peak engineered lymphocyte (e.g., peak engineered lymphocyte (CAR T cells)) levels in the blood past administration of the infusion product. In one embodiment, the percentage of CD4 cells infused and the number of CD4 cells infused associate negatively with, or are predictive of lower, peak engineered lymphocyte (e.g., peak engineered lymphocyte (CAR T cells)) levels past administration of the infusion product. In one embodiment, the number and percentage of naïve-like CD8 positive T cells (e.g., CD8+ CCR7+ CD45RA+ T Cells) in the infusion product associates positively, or is predictive of, durable response whereas the number of effector memory CD4 positive T cells associates negatively with durable response to CAR T cell therapy. In one embodiment, the attributes that are measured are attributes of the population of T cells in the apheresis product. In one embodiment, the attributes of the apheresis product are the proportion of effector memory T cells within total CD3+ T cells or CD4 and CD8 subsets, the number of CD27+CD28+ TN cells, and/or the proportion of T cells with CD25hi CD4 expression. In one embodiment, the more juvenile the phenotype of the T cells (e.g., the higher the number of CD28+CD27+ TN cells) in the apheresis starting material the better (shorter) the doubling time of the engineered lymphocytes in the infusion product.

In one embodiment, the measured attribute is the doubling time of the population of engineered lymphocytes in the infusion product. In one embodiment, the doubling time is about 1.0, 1.1, about 1.2, about 1.3, about 1.4 days, about 1.5 days, about 1.6, about 1.7 days, about 1.8, about 1.9, and about 2. In one embodiment, the doubling time is about 2.1 days. In one embodiment, the doubling time is about 1.6 or >1.6 days. In one embodiment, the doubling time is <2 days. In one embodiment, the doubling time is >2 days. In one embodiment, the doubling time is greater than about 2 days. In one embodiment, the doubling time is less than about 2 days. In one embodiment, a doubling time <2 days associates positively with or is predictive of objective response (complete response, partial response, or non-response) or durable response in patients with high tumor burden. In one embodiment, a doubling time of about 2.1 days associates with nonresponse to the CAR T cell therapy. In one embodiment, a doubling time >2 days associates with relapse or non-response. In one embodiment, relapse is measured within 1 year post treatment. In one embodiment, a doubling time of about 2.1 associates with non-response. In one embodiment, a doubling time of about 1.6 or >1.6 days associates with non-response. In one embodiment, a CD4:CD8 ratio positively associates with durable response.

In one embodiment, the therapeutically effective dose is calculated and/or manipulated by calculating or manipulating the doubling time, phenotype, and other attributes of the cells in the infusion product used to prepare the therapeutically effective dose. In one embodiment, the attributes of the population of engineered lymphocyte (e.g., CAR T cells) in the product that are manipulated during manufacturing to improve patient response and/or reduce therapeutic dose are selected from the following attributes: the doubling time, the percentage of CD3 positive cells infused, the number of CD3 cells infused, the number of CD3 cells infused/tumor burden; the percentage of $T_n$ cells infused, the number of $T_n$ cells infused, the number of $T_n$ cells infused/tumor burden; the percentage of CD8 positive cells infused, the number of CD8 positive cells infused, the number of CD8 positive cells infused/tumor burden; the percentage of CD4 positive cells infused, the number of CD4 positive cells infused, the number of CD4 positive cells infused/tumor burden; CD4:CD8 ratio in the cells infused, the frequency and proportion of $T_N$ and $T_{EM}$ CD8+ or CD4+ T cells, and/or the number of percentage of naïve-like T cells.

In one embodiment, the disclosure provides a method of treating a cancer with engineered lymphocytes (e.g., CAR T cells) in a subject in need thereof comprising:
    measuring levels of one or more pretreatment attributes of the subject,
    determining or predicting a subject's response to treatment with engineered lymphocytes based on the measured levels of one or more attributes compared to a reference level; and, optionally,
    administering a therapeutically effective dose of the engineered lymphocytes to the subject, wherein the therapeutically effective dose is determined based on the level of one or more pre-treatment attributes of the subject.

In one embodiment, the pretreatment attributes are reflective of or are markers of the subject's systemic inflammation. In one embodiment, the pretreatment attributes show pronounced inflammatory status reflected by the levels of myeloid activation markers (e.g., IL6, ferritin, CCL2) in the serum of the subject. In one embodiment, the pretreatment attributes are selected from baseline tumor burden, baseline IL-6, baseline CRP, baseline LDH, baseline ferritin, disease stage, Day 0 IL-15, Day 0 IFN-γ, baseline weight, baseline CCL2, wherein Day 0 is the day of administration of the engineered lymphocytes. In one embodiment, baseline levels are the last values measured prior to conditioning therapy.

In one embodiment, the engineered lymphocytes target a tumor antigen. In one embodiment, the tumor antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens. In one embodiment, the target antigen is CD19.

In one embodiment, the cancer is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell-or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof. In one embodiment, the cancer is (relapsed or refractory) diffuse large B-cell lymphoma (DLBCL) not otherwise specified, primary mediastinal large B-cell lymphoma, high grade B-cell lymphoma, DLBCL arising from follicular lymphoma, or mantle cell lymphoma.

In one embodiment, the therapeutically effective amount or effective dose of the engineered lymphocytes (e.g., CAR T cells) may be at least about $10^4$ cells, at least about $10^5$ cells, at least about $10^6$ cells, at least about $10^7$ cells, at least about $10^8$ cells, at least about $10^9$, or at least about $10^{10}$ cells.

In one embodiment, the therapeutically effective amount or effective dose of the engineered lymphocytes (e.g., CAR T cells) is about $10^4$ cells, about $10^5$ cells, about $10^6$ cells, about $10^7$ cells, or about $10^8$ cells. In one embodiment, the therapeutically effective amount or effective dose of the engineered lymphocytes (e.g., CAR T cells) may be about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In one embodiment, the therapeutically effective amount or effective dose of the engineered lymphocytes (e.g., CAR T cells) may be between about $1\times10^6$ and about $2\times10^6$ engineered viable lymphocytes (e.g., CAR T cells) per kg body weight up to a maximum dose of about $1\times10^8$ engineered viable lymphocytes (e.g., CAR T cells). In one embodiment, the therapeutically effective dose is between 75 and $200\times10^6$ engineered lymphocytes.

EXAMPLES

ZUMA-1 is a clinical study wherein patients with relapsed/refractory NHL have been treated with axicabtagene ciloleucel. Axicabtagene ciloleucel is a CD19-directed genetically modified autologous T cell immunotherapy, comprising the patient's own T cells harvested and genetically modified ex vivo by retroviral transduction to express a chimeric antigen receptor (CAR) comprising an anti-CD19 single chain variable fragment (scFv) linked to CD28 and CD3-zeta co-stimulatory domains.

Patients may have had diffuse large B-cell lymphoma, primary mediastinal B-cell lymphoma, or transformed follicular lymphoma with refractory disease despite undergoing recommended prior therapy. Patients received a target dose of $2\times10^6$ anti-CD19 CAR T cells per kilogram of body weight after receiving a conditioning regimen of low-dose cyclophosphamide and fludarabine. (Neelapu, S S et al. 2017, N Engl J Med 2017; 377(26):2531-44).

In the following EXAMPLES, biomarker data from ZUMA-1 patients were analyzed according to an expanded statistical analysis plan for correlates of durable response and parameters differentially associated with efficacy and toxicities. Several correlations were revealed. Available samples from patients in ZUMA-1 (NCT02348216) were analyzed. Safety and efficacy results were previously reported. (Neelapu, S S et al. 2017, N Engl J Med 2017; 377(26):2531-44). Durable response refers to those patients who were in ongoing response at least 1 year post-axicabtagene ciloleucel infusion. Relapse refers to those patients who achieved a CR or PR and subsequently experienced disease progression. Patients who achieved stable disease as best response are included in no response category.

Example 1

High Tumor Burden is Associated with a Lower Probability of Durable Response, a Phenomenon which May be Overcome by Commensurate In Vivo CAR T-Cell Expansion

Consistent with previous reports (Locke F L, et al Lancet Oncol 2019; 20(1):31-42), higher peak expansion of CAR T cells in the peripheral blood, generally occurring within 2 weeks post CAR T-cell infusion, associated with both objective response and durable response, defined as ongoing response with a minimum follow-up of 1 year (FIG. 1A-FIG. 1F). While peak number of CAR T cells in blood correlated with response, neither the peak frequency nor the peak number of CAR gene copies/μg of DNA associated with the clinical response (Table 2).

TABLE 2

PK measurements in association with clinical efficacy. CAR T cells were quantified using TaqMan quantitative PCR and confirmed ddPCR. CAR+ cell frequencies, cells per microliter were calculated by normalizing CAR gene expression to actin expression in peripheral blood mononuclear cells.

| Measurement, n \| median (Q1-Q3) | Method | Response Category | | | P Values from Dunn's Test | | | P Value from |
|---|---|---|---|---|---|---|---|---|
| | | Durable Response | Relapsed | No Response | Durable vs Relapsed | Durable vs No Response | Relapsed vs No Response | KW Test |
| Peak number of CAR cells/μL blood | TaqMan | 39 \| 58.63 (20.9454-92.115) | 40 \| 33.3881 (16.7621-79.79) | 16 \| 15.6318 (3.0162-35.3708) | 0.088 | 0.0036 | 0.0437 | 0.0098 |
| Peak % CAR cells | | 40 \| 7.52 (2.92-14.305) | 40 \| 6.445 (4.355-14.46) | 16 \| 3.975 (1.56-8) | 0.4275 | 0.0621 | 0.0572 | 0.1021 |
| Peak CAR gene copies/μg DNA | ddPCR | 39 \| 50382 (17577-84078) | 37 \| 50463 (15633-77679) | 15 \| 25920 (11178-52974) | 0.4324 | 0.1985 | 0.1719 | 0.296 |

TABLE 2-continued

PK measurements in association with clinical efficacy. CAR T cells were
quantified using TaqMan quantitative PCR and confirmed ddPCR. CAR+ cell frequencies, cells per
microliter were calculated by normalizing CAR gene expression to actin expression in peripheral
blood mononuclear cells.

| Measurement,<br><br>n \| median<br>(Q1-Q3) | Method | Response Category | | | | P Values from Dunn's Test | | | P Value<br><br>from<br><br>KW<br>Test |
| | | Complete<br>Response | Partial<br>Response | No<br>Response | CR vs PR | CR vs<br>No<br>Response | PR vs No<br>Response | |
| Peak number<br>of<br>CAR cells/μL<br>blood | TaqMan | 57 \| 47.1073<br>(21.6104-<br>87.9564) | 25 \|<br>26.1504<br>(12.2698-<br>84.916) | 16 \|<br>15.6318<br>(3.0162-<br>35.3708) | 0.0664 | 0.0041 | 0.1278 | 0.0084 |
| Peak % CAR<br>cells | | 59 \| 8.2312<br>(3.38-15.1) | 25 \| 6.06<br>(4.33-<br>11.8) | 16 \| 3.975<br>(1.56-8) | 0.2395 | 0.0419 | 0.1592 | 0.0881 |
| Peak CAR<br>gene<br>copies/μg<br>DNA | ddPCR | 57 \| 50382<br>(18873-<br>81972) | 23 \| 49734<br>(14499-<br>77679) | 15 \| 25920<br>(11178-<br>52974) | 0.2329 | 0.1632 | 0.3902 | 0.2603 |

Abbreviations: CAR, chimeric antigen receptor; CR, complete response; ddPCR, droplet digital polymerase chain reaction; KW, Kruskal-Wallis test; PK, pharmacokinetics; PR, partial response; Q, quartile.

Figures 8A, 8B, 8C, 8D:
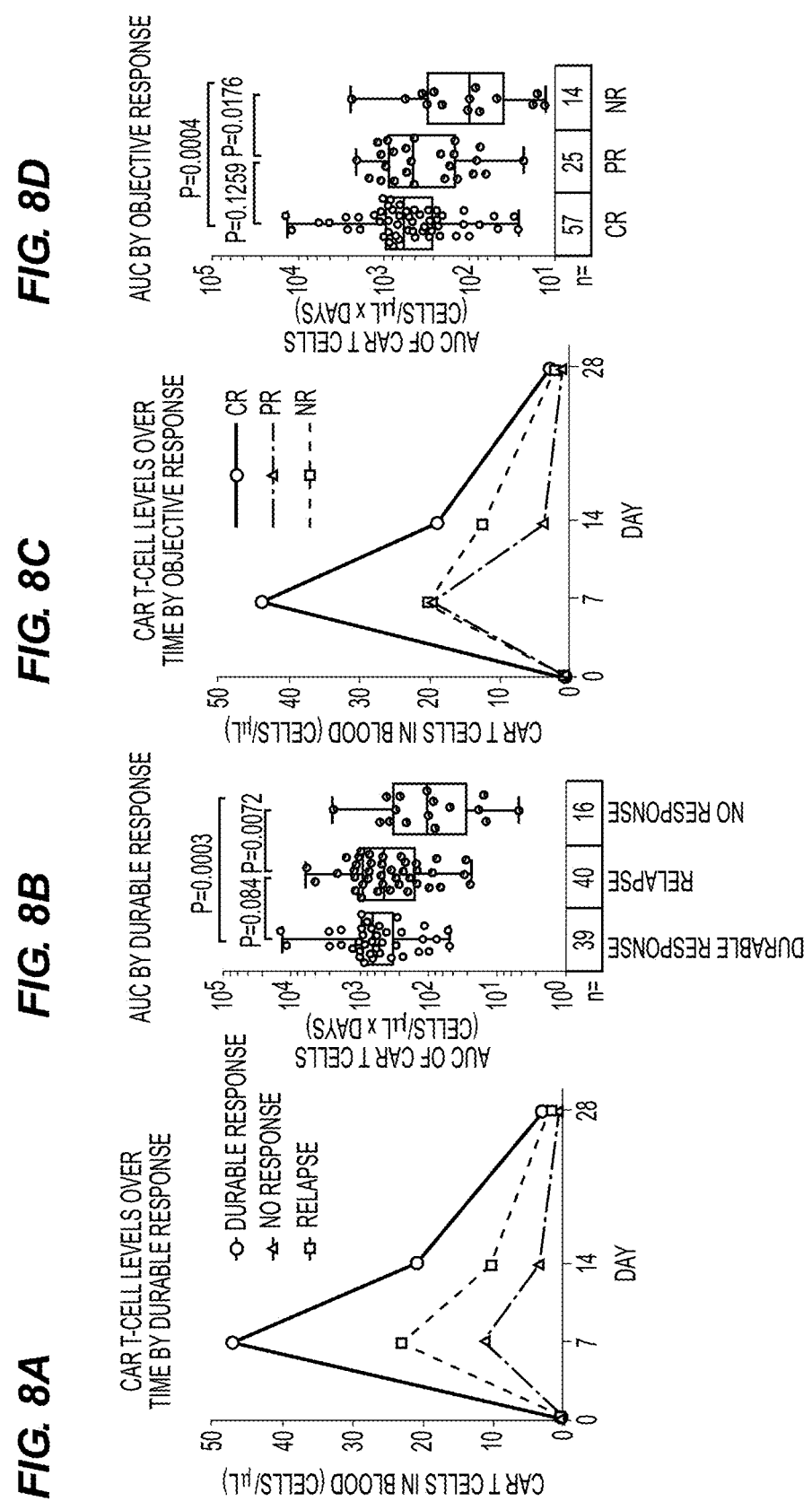
FIGS. 8A-8C. Cumulative CAR T-cell levels during the first month post infusion associate with clinical response. Line graphs (FIG. 8A, FIG. 8C) show medians at each timepoint. P values were calculated using Kruskal-Wallis and Dunn's tests for all box plots (FIG. 8B, FIG. 8D). AUC, area under the curve from day 0 to 28; CAR, chimeric antigen receptor; CR, complete response, NR, no response, PR partial response.

Similar to peak numbers of CAR T cells, cumulative CAR T-cell levels over the first 28 days as measured in blood by area under the curve (AUC) was also associated with better objective and durable response to therapy (FIG. 8).

In contrast to peak and cumulative CAR T-cell levels, levels of CART cells at 3 months and beyond were very low or non-measurable (Neelapu, S S et al. 2017, *N Engl J Med* 2017; 377(26):2531-44), and did not correlate with durable response (FIG. 1E). Baseline tumor burden and CAR T-cell numbers in the peripheral blood shortly after axicabtagene ciloleucel infusion in association with the clinical outcome were examined. Low tumor burden pre-CAR T-cell therapy was a positive predictor of durable response (FIG. 1G). As CD19 antigen is expected to drive CAR T-cell proliferation and expansion in vivo, it was hypothesized that higher tumor burden would associate with increased CAR T-cell numbers in the peripheral blood. Examining the entire cohort, tumor burden itself was not associated with expansion of CART cells. However, in the highest tumor burden quartile, patients who achieved a durable response had a greater than 3-fold higher peak CAR T-cell expansion compared with patients who relapsed or had no response (median, 74.4 vs 20.2 CAR T cells/μL blood; FIG. 1H). Concordant with this observation, there was a lower durable response rate at comparable peak CAR T-cell levels in patients with higher tumor burden compared to patients with lower tumor burden (FIG. 1I). Durable responders had a higher peak CAR T cell/tumor burden ratio compared to non-responders (P=0.005), or responders who subsequently relapsed within 1 year post-treatment (P=0.01; FIG. 1J). Similar differences were observed between peak CAR T-cell levels and tumor burden ratio in complete responders compared with partial responders (P=0.001) or non-responders (P=0.004; FIG. 1K). While a trend in objective and durable response rate was observed with increasing peak CAR T-cell levels (FIG. 1L), there was 12% durable response rate in patients within the lowest quartile of peak CAR T cell/tumor burden ratio, contrasting with >50% durable responses in the top quartiles (FIG. 1M), suggesting a role for effector-to-target ratio in CAR T-cell therapy. These findings are supported by probabilistic logistic regression curves showing associations of durable response rate with tumor burden, peak CAR T-cell levels, and peak CART cells normalized to tumor burden (FIG. 1N-P).

Taken together these findings showed that early expansion, commensurate with tumor burden, rather than long-term persistence of functional circulating CAR T cells, results in durable responses of refractory large cell lymphomas to CD19 CAR T-cell therapy with a CD28 costimulatory domain.

Example 2

Pro-Inflammatory and Myeloid Activation Markers are Correlated with Impaired In Vivo CAR T-Cell Expansion and Decreased Rate of Durable Response The association between pro-inflammatory markers in the serum and tumor burden was evaluated. Generally, pretreatment levels of pro-inflammatory markers associated positively with each other and negatively with hemoglobin and platelet levels (FIG. 2A). There was statistically significant correlation between tumor burden and baseline serum LDH (R=0.4; P<0.0001), ferritin (R=0.38; P=0.0002) and IL-6 (R=0.23; P=0.028), and no significant association between tumor burden and CCL2 (R=−0.03; P=0.8) or IL-8 (R=0.15; P=0.149). Pretreatment tumor biopsy were interrogate for expression of myeloid and inflammation associated genes in relation to tumor burden. While there was significant tumor expression of myeloid-related inflammatory molecules, no significant association was observed between tumor burden and their expression at the gene level: ILIA (R=0.036; P=0.84), CD68 (R=0.13; P=0.45), IL-6 (R=−0.02; P=0.91), and CD14 (R=0.04; P=0.81).

Inflammation-related biomarkers associated with CAR T-cell expansion and response were studied. Pretreatment ferritin and LDH were not associated directly with in vivo expansion of CAR T cells, however each was significantly (P<0.01) but modestly (r<−0.3) negatively associated with expansion of CAR T cells normalized to pretreatment tumor burden (peak CAR T expansion/tumor burden) (FIG. 2B-FIG. 2C). A similar non-significant trend was noted between CAR T-cell expansion/tumor burden and serum IL-6 (FIG. 2D). Elevated serum ferritin showed a non-significant association with decreased response rate, while elevated LDH significantly associated with decreased durable responses (FIG. 2E-F). Baseline IL-6 elevation associated with both decreased response rates and durable response rates (FIG. 2G). Patients in the top quartile, with highest levels of any one of these proinflammatory markers, showed durable response rates of 19-26%, 2.6-3.2-fold lower than first quartile (FIG. 2E-G). Similar associations were seen when day 0 or day 1 levels of ferritin and IL-6 were evaluated (FIG. 9; Table 3).

TABLE 3

Response rates, pairwise comparisons, and overall significance of specified
analytes at baseline, on Day 0, and on Day 1.

| Analyte, n \| median (Q1-Q3), pg/mL | Response Category | | | P Values from Dunn's Test | | | P Value from KW Test |
|---|---|---|---|---|---|---|---|
| | Durable Response | Relapsed | No Response | Durable vs Relapsed | Durable vs No Response | Relapsed vs No Response | from KW Test |
| Baseline IL-6 | 35 \| 1.6 (1.6-4.53) | 35 \| 4.1 (1.6-6.7) | 16 \| 7.48 (4.7-16.7) | 0.0242 | 5.00E-04 | 0.0421 | 0.0013 |
| Day 0 IL-6 | 39 \| 1.6 (1.6-4.6) | 40 \| 3.65 (1.6-6.765) | 17 \| 3.8 (1.6-15.14) | 0.0505 | 0.0378 | 0.2337 | 0.0411 |
| Day 1 IL-6 | 38 \| 13.235 (4.4-42.8) | 39 \| 14.85 (9.39-46.69) | 15 \| 18.17 (11-31.01) | 0.5421 | 0.3663 | 0.4122 | 0.5498 |
| Baseline ferritin | 35 \| 567200 (800-1174800) | 35 \| 867200 (800-1464050) | 16 \| 1000270 (611200-2348615) | 0.1359 | 0.0461 | 0.1971 | 0.0936 |
| Day 0 ferritin | 39 \| 737910 (800-1185080) | 40 \| 1438995 (658250-2514250) | 17 \| 1116640 (760500-2854770) | 0.0043 | 0.0052 | 0.3132 | 0.0024 |
| Day 1 ferritin | 38 \| 773200 (542100-1040400) | 39 \| 1411950 (798200-2430500) | 15 \| 1169600 (773100-3240890) | 0.0044 | 0.015 | 0.4166 | 0.0045 |
| Baseline CCL2 | 35 \| 314.6 (277.25-426.04) | 35 \| 356.5 (293.7-445.6) | 16 \| 331.52 (265.105-370.5) | 0.3334 | 0.4941 | 0.341 | 0.4168 |
| Day 0 CCL2 | 39 \| 766.5 (534.52-1274.8) | 40 \| 929.65 (622.05-1346.905) | 17 \| 904 (644.78-1282.2) | 0.4975 | 0.617 | 0.4003 | 0.619 |
| Day 1 CCL2 | 38\| 1292.85 (691.85-1500) | 39 \| 1500 (1086.6-1500) | 15 \| 1132.27 (599.2-1500) | 0.1014 | 0.4137 | 0.1118 | 0.116 |
| Baseline LDH | 40 \| 239.5 (184-578) | 40 \| 367 (254-607.5) | 17 \| 537 (454-977) | 0.0239 | 0.0053 | 0.1207 | 0.0067 |
| Day 0 LDH | 35 \| 226 (178- 609) | 36 \| 288.5 (204.5-465.5) | 17 \| 372 (205-617) | 0.5141 | 0.3822 | 0.4552 | 0.5529 |
| Day 1 LDH | 35 \| 202 (154-518) | 39 \| 272 (198-403) | 17 \| 340 (254-520) | 0.2154 | 0.1811 | 0.2789 | 0.2423 |

Figure 10:
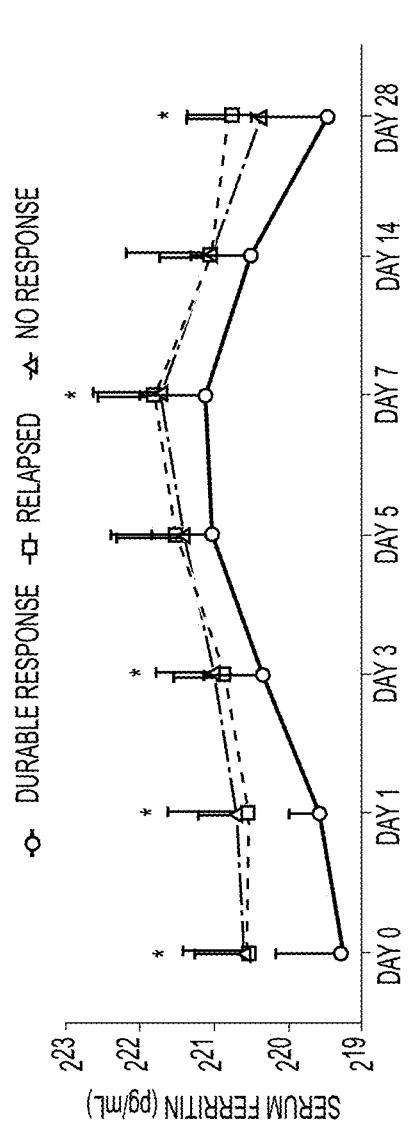
FIG. 10. Association between response group and ferritin over time. Symbols represent median serum ferritin levels for the specified population and bars represent interquartile range. Samples were available for 35-40 (each durable responders or relapsed) or 12-17 (no response) patients at each timepoint. AUC, area under the curve from Day 0 to 28; KW, Kruskal-Wallis. *, P<0.05.
Figure 11:
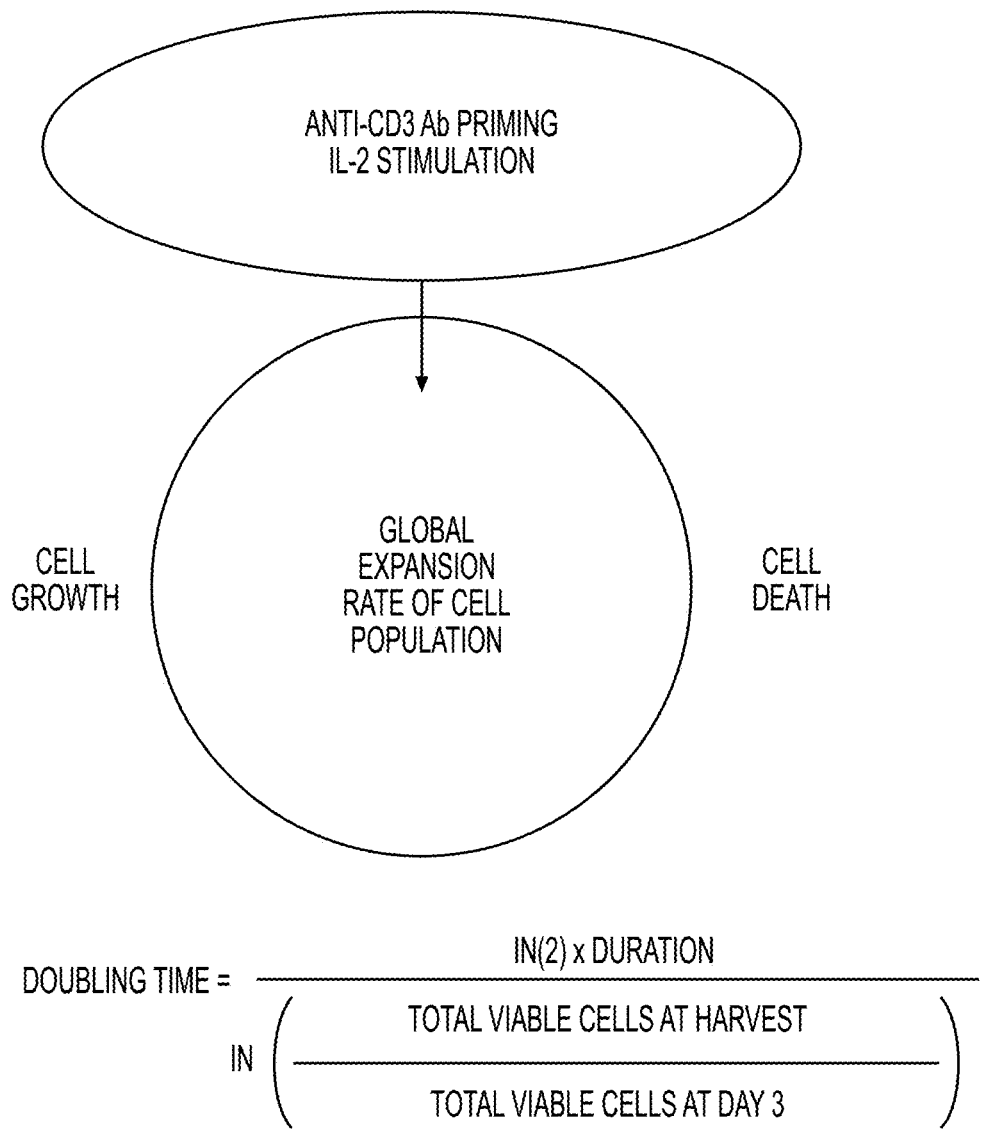
FIG. 11. Definition of product doubling time measured pre-treatment. Ab, antibody; IL, interleukin.
Figure 14A:
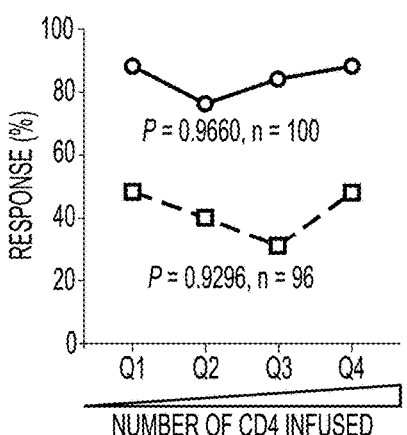
Figure 14B:
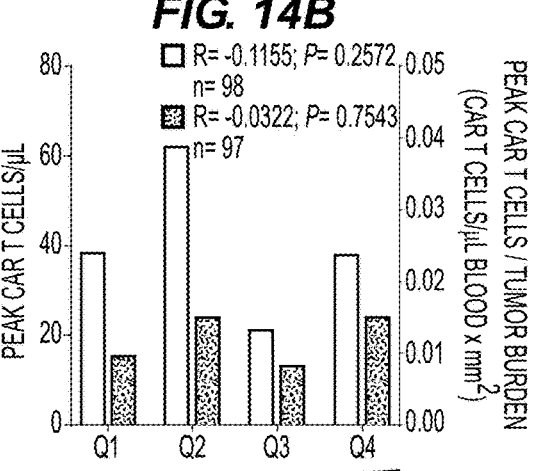
Figure 14C:
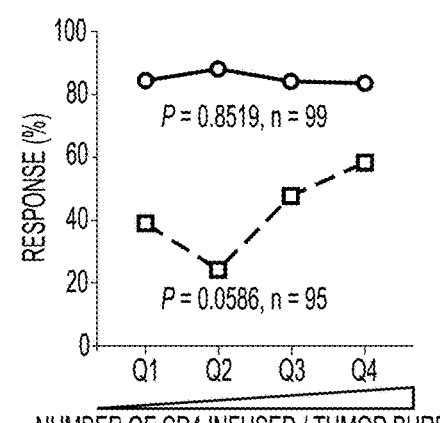
Figure 14D:
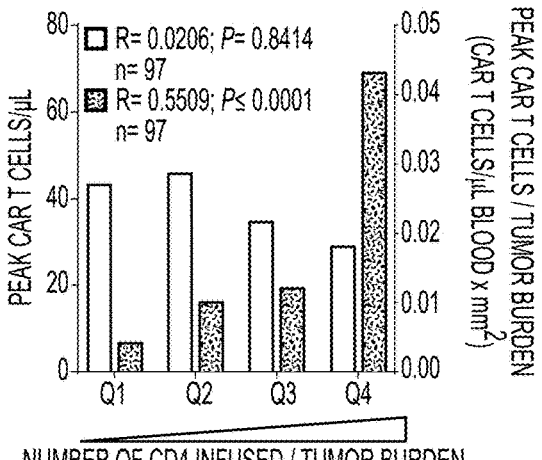
Figure 14E:
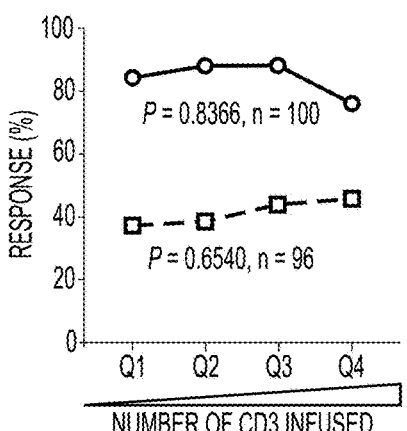
Figure 14F:
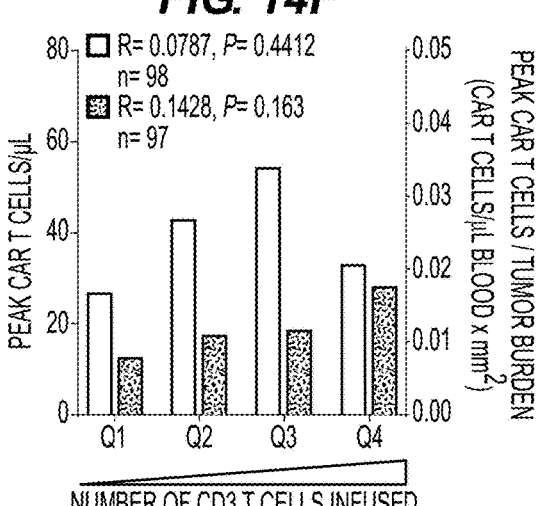
Figure 14G:
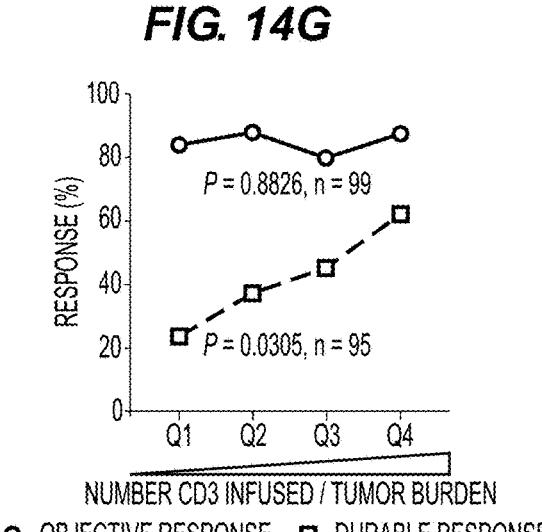
Figure 14H:
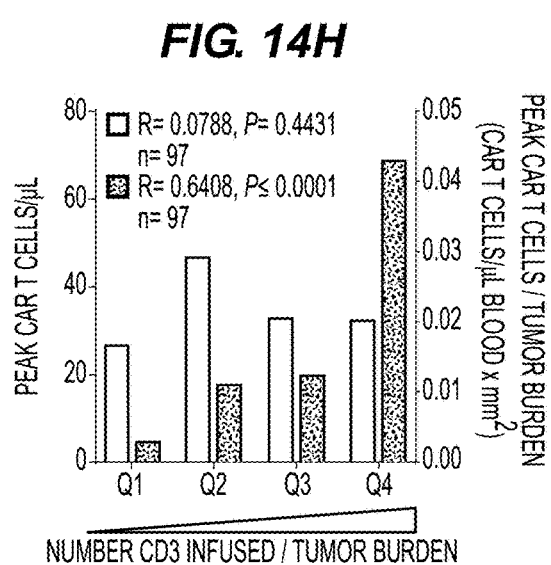
Figure 14I:
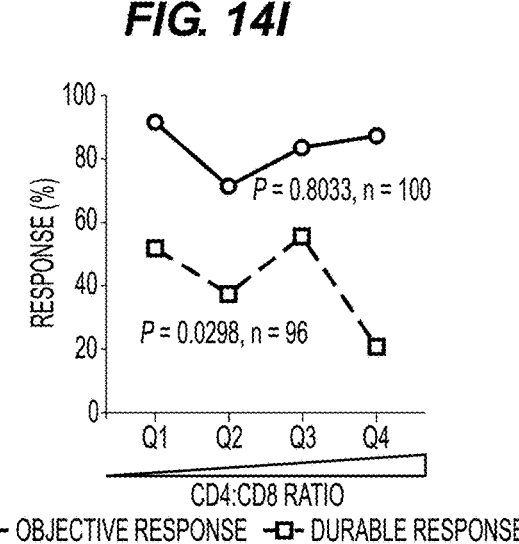
Figure 14J:
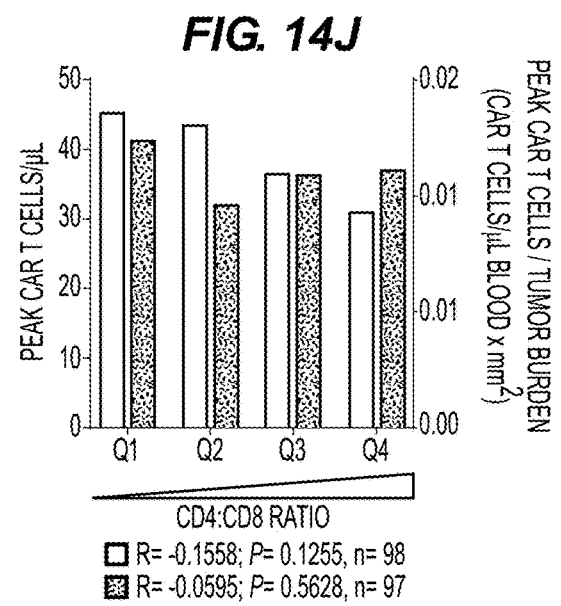

CAR T-cell therapy induces systemic inflammation, which in its most serious form may manifest as cytokine release syndrome. (Lee D W, et al. *Blood* 2014; 124(2):188-95) Both high peak and cumulative ferritin levels within the first 28 days after infusion associated with lower in vivo CAR T-cell expansion and lower rates of durable response (FIG. 10). There was a weak but significant association between ferritin levels over the first 28 days and peak CAR T-cell levels normalized to tumor burden (R=−0.2236; P=0.0277). Higher levels of serum ferritin were observed at most timepoints after CAR T-cell infusion in patients who relapsed or had no response compared with those who had durable responses. (FIG. 10). This shows that persisting systemic inflammation after CAR T-cell infusion may be associated with a failure of the CAR T cells to completely eliminate the tumor. Taken together, these data show that pretreatment tumor burden and systemic inflammation were both negatively associated with the rate of durable responses and that this effect was mediated by decreased CAR-T-cell expansion relative to the pretreatment tumor burden.

Example 3

Higher Expansion Rate of CAR T Cells During Manufacturing Associated with Greater In Vivo CAR T-Cell Expansion and Higher Probability of Durable Remission Based on the importance of early in vivo CAR T-cell expansion in relation to durable clinical response, key CAR T-cell product characteristics associated with improved in vivo expansion and tumor responses were determined. During manufacturing, T cells are initially stimulated with anti-CD3 antibodies in the presence of IL-2 and then expanded with growth medium supplemented with IL-2. A component of the fitness of the final product may be the capacity of T cells to rapidly expand in response to this non-specific stimulation. The intrinsic ability of CAR-T-cells to expand during non-specific stimulation in vitro (during manufacturing) as exemplified by the culture doubling time (DT) was evaluated statistically for correlations with in vivo outcome. Phenotypic and functional product characteristics were evaluated for association with responses and it was found that low DT was one of the product characteristics most significantly associated with objective response as compared to non-response (Table 4).

TABLE 4

Association between product characteristics and response. All P values were
calculated by logistic regression.

| Characteristics | Responder, n | Non-responder, n | Responder, median | Non-responder, median | Ratio of responder: non-responder | P value | Odds Ratio |
|---|---|---|---|---|---|---|---|
| Doubling time in days | 76 | 15 | 1.490 | 1.730 | 1.161 | 0.025 | 0.582 |
| LOG2(Total # of $T_N$ Cells (10^6)) | 84 | 16 | 5.421 | 4.820 | 0.889 | 0.033 | 1.790 |
| $T_N$ Cells (%) | 84 | 16 | 15.450 | 9.500 | 0.615 | 0.093 | 2.021 |
| $T_{EM}$ Cells (%) | 84 | 16 | 37.500 | 39.550 | 1.055 | 0.109 | 0.631 |
| Total $T_N$ cells (n) | 84 | 16 | 42.868 | 28.817 | 0.672 | 0.119 | 1.832 |
| Viability (%) | 84 | 17 | 94.500 | 93.600 | 0.990 | 0.166 | 1.383 |
| LOG2(Total # of $T_{EM}$ Cells (10^6)) | 84 | 16 | 6.784 | 7.012 | 1.034 | 0.169 | 0.651 |
| $T_N$ + $T_{CM}$ Cells/$T_{EFF}$ + $T_{EM}$ Cells | 84 | 16 | 0.733 | 0.691 | 0.943 | 0.186 | 1.795 |
| $T_{EFF}$ + $T_{EM}$ Cells, (%) | 84 | 16 | 57.800 | 59.200 | 1.024 | 0.204 | 0.686 |
| $T_N$ + $T_{CM}$ Cells, (%) | 84 | 16 | 42.350 | 40.900 | 0.966 | 0.263 | 1.388 |
| LOG2(Number of $T_{EFF}$ + $T_{EM}$ Cells (10^6)) | 84 | 16 | 7.270 | 7.567 | 1.041 | 0.289 | 0.732 |
| Interferon-γ by coculture (pg/mL) | 84 | 17 | 5834.500 | 7801.000 | 1.337 | 0.308 | 0.773 |
| LOG2(Number of $T_{CM}$ Cells (10^6)) | 84 | 16 | 6.175 | 6.347 | 1.028 | 0.359 | 0.772 |
| CD3- Cells (%) | 84 | 16 | 2.250 | 2.700 | 1.200 | 0.367 | 0.795 |
| T Cells (%) | 84 | 16 | 97.750 | 97.300 | 0.995 | 0.367 | 1.258 |
| $T_{CM}$ Cells (10^6), n | 84 | 16 | 72.241 | 81.496 | 1.128 | 0.371 | 0.793 |
| $T_{EM}$, n | 84 | 16 | 110.217 | 129.143 | 1.172 | 0.380 | 0.806 |
| No. $T_N$ T Cells (10^6)/ tumor burden at baseline | 84 | 15 | 0.010 | 0.007 | 0.704 | 0.390 | 1.655 |
| $T_{CM}$ Cells, (%) | 84 | 16 | 24.950 | 30.800 | 1.234 | 0.425 | 0.808 |
| LOG2(No. CD8 T cells in product/(Doubling Time × Tumor Burden at baseline (local) | 76 | 14 | −5.439 | −5.899 | 1.085 | 0.433 | 1.280 |
| No. CD4 T cells infused/ tumor burden at baseline | 84 | 15 | 0.038 | 0.045 | 1.190 | 0.456 | 1.573 |
| Interferon-γ Normalized by Transduction Efficiency (pg/mL) | 84 | 17 | 10126.823 | 12313.290 | 1.216 | 0.467 | 0.831 |
| LOG2(No. CD8 T cells infused/Doubling time at baseline) | 76 | 14 | 6.547 | 6.532 | 0.998 | 0.471 | 1.231 |
| LOG2(Number of CD3- T Cells (1e6)) | 84 | 16 | 2.738 | 3.255 | 1.189 | 0.485 | 0.824 |
| LOG2(No. $T_N$ + $T_{CM}$ Cells (10^6)) | 84 | 16 | 7.029 | 6.847 | 0.974 | 0.485 | 1.206 |
| Number of CD8 T cells infused/Doubling time at baseline | 76 | 14 | 93.512 | 92.519 | 0.989 | 0.501 | 1.249 |
| Number of CD3-T Cells (1e6) | 84 | 16 | 6.674 | 9.603 | 1.439 | 0.510 | 0.848 |
| No. $T_N$ + $T_{CM}$ Cells (10^6)/tumor burden at baseline | 84 | 15 | 0.033 | 0.037 | 1.136 | 0.532 | 1.282 |
| $T_N$ + $T_{CM}$ Cells (10^6), n | 84 | 16 | 130.601 | 115.147 | 0.882 | 0.543 | 1.193 |
| $T_{EFF}$ + $T_{EM}$ Cells (10^6), n | 84 | 16 | 154.312 | 189.827 | 1.230 | 0.585 | 0.870 |
| Total CAR + T Cells in Product Bag (1e6) | 84 | 17 | 160.000 | 170.000 | 1.063 | 0.596 | 0.864 |
| $T_{EFF}$ Cells (10^6), n | 84 | 16 | 43.152 | 55.506 | 1.286 | 0.713 | 1.111 |
| LOG2(Total T Cells (1e6)) | 84 | 17 | 8.217 | 8.405 | 1.023 | 0.732 | 0.913 |
| LOG2(Number of CD8 T cells (1e6)) | 84 | 16 | 7.219 | 7.351 | 1.018 | 0.733 | 0.910 |
| LOG2(Total CAR + T Cells in Product Bag (1e6)) | 84 | 17 | 7.322 | 7.409 | 1.012 | 0.755 | 0.918 |
| CD4 T Cells (%) | 84 | 16 | 49.500 | 44.550 | 0.900 | 0.777 | 1.080 |
| CD8 T Cells (%) | 84 | 16 | 50.550 | 55.500 | 1.098 | 0.778 | 0.926 |
| $T_{EFF}$ Cells (%) | 84 | 16 | 15.250 | 15.900 | 1.043 | 0.792 | 1.077 |
| CD4/CD8 ratio | 84 | 16 | 0.985 | 0.803 | 0.815 | 0.803 | 1.074 |
| LOG2(No. T Cells (1e6)) | 84 | 16 | 8.175 | 8.321 | 1.018 | 0.837 | 0.945 |
| LOG2(No. CD4 T cells infused/tumor burden at baseline) | 84 | 15 | −4.711 | −4.459 | 0.947 | 0.852 | 1.054 |

TABLE 4-continued

| Characteristics | Responder, n | Non-responder, n | Responder, median | Non-responder, median | Ratio of responder: non-responder | P value | Odds Ratio |
|---|---|---|---|---|---|---|---|
| LOG2(Interferon-γ by coculture (pg/mL)) | 84 | 17 | 12.510 | 12.929 | 1.033 | 0.853 | 0.951 |
| Transduction Efficiency or Transduction Rate (%) | 84 | 17 | 53.750 | 52.100 | 0.969 | 0.874 | 1.043 |
| No. $T_{EM}$ T Cells (10^6)/tumor burden at baseline | 84 | 15 | 0.028 | 0.035 | 1.264 | 0.881 | 1.046 |
| No. CD4 T Cells (1e6) | 84 | 16 | 162.309 | 143.657 | 0.885 | 0.914 | 0.971 |
| Total T Cells (1e6) | 84 | 17 | 297.482 | 338.983 | 1.140 | 0.919 | 0.974 |
| LOG2(No $T_{EFF}$ Cells (10^6)) | 84 | 16 | 5.431 | 5.795 | 1.067 | 0.924 | 1.027 |
| No $T_{EFF}$ Cells (10^6)/ tumor burden at baseline | 84 | 15 | 0.011 | 0.010 | 0.910 | 0.930 | 1.026 |
| Number of CD8 T cells (1e6) | 84 | 16 | 148.958 | 163.281 | 1.096 | 0.943 | 1.020 |
| Number of CD8 T cells in product/(Doubling Time × Tumor Burden at baseline (local)) | 76 | 14 | 0.023 | 0.017 | 0.727 | 0.957 | 1.016 |
| LOG2(Number of CD8 T cells infused/tumor burden at baseline) | 84 | 15 | −4.820 | −4.974 | 1.032 | 0.964 | 1.013 |
| LOG2(Number of CD4 T Cells (1e6)) | 84 | 16 | 7.343 | 7.166 | 0.976 | 0.966 | 0.988 |
| Number of CD8 T cells infused/tumor burden at baseline | 84 | 15 | 0.035 | 0.032 | 0.899 | 0.991 | 0.997 |
| Number of T Cells (1e6) | 84 | 16 | 289.029 | 319.723 | 1.106 | 0.993 | 0.998 |
| Vector Copy Number | 82 | 15 | 0.200 | 0.210 | 1.050 | 0.995 | 0.998 |

Abbreviations: TCM, central memory T cells (CD45RA− CCR7+); TEFF, effector T cells (CD45RA+ CCR7−); TEM, effector memory T cells (CD45RA− CCR7−); TN, naïve-like T cells (CD45RA+ CCR7+).

The median DT in responders was 1.6 days, while non-responders had a median DT time of 2.1 days. Quartile analysis of response by DT showed that all patients (100%) in the lowest DT quartile achieved an objective response, while 80% of all non-responders were in the $3^{rd}$ and $4^{th}$ quartile of DT (FIG. 3A).

The association of DT with durable response, in vivo CAR T-cell expansion, and the phenotype of T cells in the final infusion product was next evaluated. Durable response was achieved in 27% of patients in the highest DT quartile, lower than the durable response rate of 40% across the entire study (FIG. 3A). Additionally, there was a correlation between product DT and expansion of CAR T cells in vivo after infusion (FIG. 3B). This was mirrored by a similar negative association between DT and peak CAR T cells normalized to tumor burden, as well as between DT and CAR T-cell AUC (FIG. 3B-FIG. 3C)

Relative to other product characteristics, DT was most strongly associated with the frequency of T-cell differentiation subsets in the final infusion bag. Specifically, DT was positively associated with the frequency of effector memory T ($T_{EM}$) cells (R=0.4341, P<0.0001) and negatively associated with the frequency of naïve-like T ($T_N$) cells (R=− 3.837, p=0.0002) (FIG. 3D-FIG. 3E). DT was not associated with CD4:CD8 ratio (FIG. 3F-FIG. 3H). Together these results suggest that intrinsic product T-cell fitness, as measured by the product DT, is positively associated with a less differentiated product, and influences the ability of CAR T cells to expand in vivo to a sufficient effector-to-target ratio that supports tumor eradication It was hypothesized that manufacturing DT, and product T-cell fitness in general, may be a direct result of the differentiation state of patients' T cells prior to enrollment. As such, the association between DT, starting apheresis material and key baseline patient characteristics such as tumor burden and inflammation markers was studied.

The association between DT and characteristics of the premanufacturing starting material (i.e., the baseline apheresis collection product) was first evaluate by examining banked samples by flow cytometry. The phenotype of T cells in the apheresis product associated with DT: greater proportions of effector memory cells, within total CD3+ T cells or CD4 and CD8 subsets, associated positively with product DT (FIG. 4A-FIG. 4O), suggesting that a more juvenile T-cell phenotype in the starting material favors increased product T-cell fitness. This was underscored by the modest association between CD27+CD28+ $T_N$ cells, which represent a more immunologically competent subset of $T_N$ cells (35), and product DT (FIG. 4B). The apheresis T-cell phenotypes was evaluated as it related to the final product phenotype. There was a direct association across all major phenotypic groups, including proportions of T-cell subsets defined by differentiation markers in CD3, CD4 and CD8 subpopulations (FIG. 4P-FIG. 4R). It was also found that the proportion of T cells with CD25$^{hi}$ CD4 expression, possibly representing regulatory T cells in the apheresis material, negatively correlated with the CD8 T-cell output in the product (R=−0.2291; P=0.0225; FIG. 4S Given the impact of tumor burden and pro-inflammatory state on CAR T-cell in vivo expansion and durable response, these variables were compared to product phenotype. Tumor burden and baseline ferritin were positively associated with the differentiation phenotype of the final product (FIG. 12)

Because a subset of patients with the highest tumor burden had inadequate in vivo CAR T-cell expansion (FIG. 1H), and to further characterize the relative importance of product T-cell fitness to outcomes product DT was examined separately in patients with higher or lower tumor burden in relation to response. Among patients with high tumor burden, a greater proportion of patients who achieved an objective response or a durable response had shorter product DT (<2 days) compared with patients who relapsed or had no response (FIG. 13). A similar association was not seen in patients with lower tumor burden, suggesting that a rapid, intrinsic expansion capability of product T cells is more influential in patients with higher tumor burden. Altogether, these findings indicate that the intrinsic capability of T-cell expansion measured pretreatment, as measured by product DT, is a major attribute of product T-cell fitness, and this characteristic connects product composition and clinical performance to the pretreatment immune status of the patient

Example 4

The Number of Infused Product CD8 and Naïve-Like CD8 CCR7+CD45RA+ T Cells are Relevant to Achieving Durable Response CAR T product characteristics other than DT associated with durable response, such as number of infused specialized T-cell subsets, particularly for patients with higher tumor burden. The total number of infused CD8+ T cells was not statistically associated with durable response or peak CAR T-cell levels (FIG. 5A-FIG. 5B). In seeking to account for the effector-to-target ratio it was found that the number of infused CD8+ T cells normalized to tumor burden was strongly associated with durable response and expansion of CAR T cells relative to tumor burden (FIG. 5C-FIG. 5D). More specifically, quartile analysis of the number of infused CD8 T cells/pretreatment tumor burden, showed a durable response rate of 16% in the lowest quartile vs 58% in the top quartile (FIG. 5C). This suggests that higher numbers of product CD8+ T cells are needed to achieve complete tumor resolution and establish a durable response in patients with higher tumor burden. Indeed, in patients with high tumor burden, those who achieved durable responses showed a significantly higher number of infused CD8 T cells compared to patients who responded and then relapsed (FIG. 5E). This association was not seen in subjects with low tumor burden.

Figure 5F:
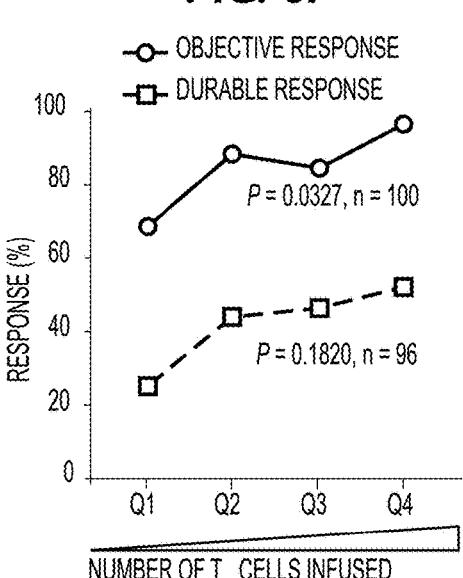
Figure 5G:
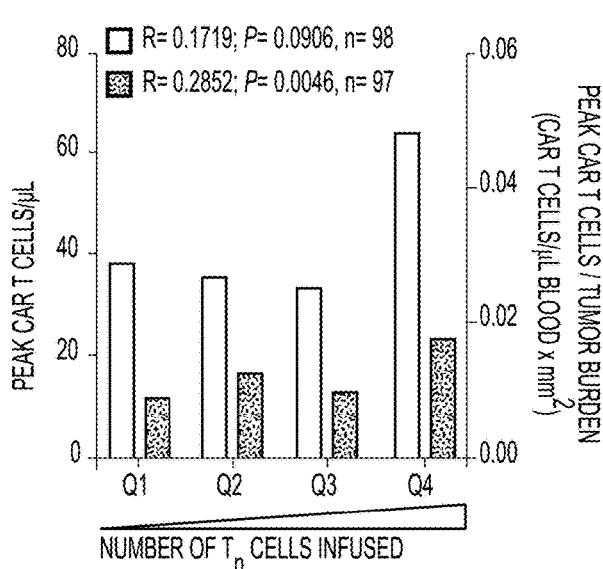
Figure 5H:
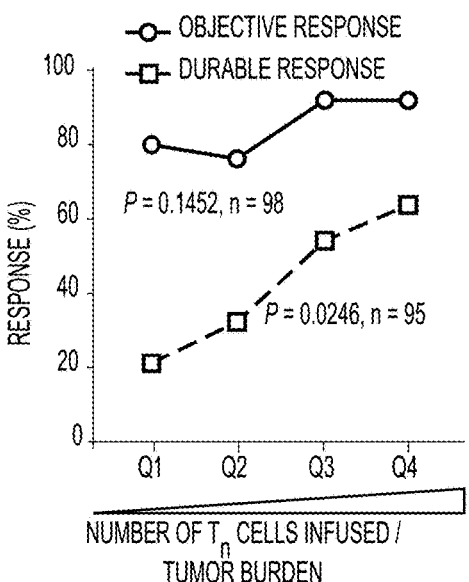
Figure 5I:
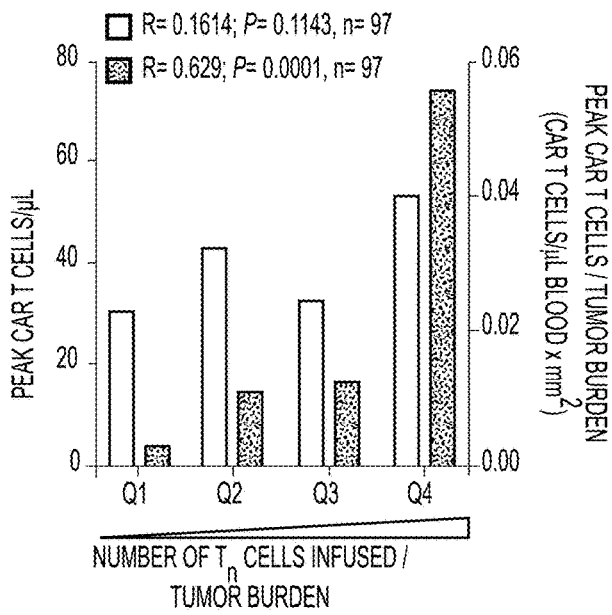

In addition, the number of infused TN cells associated with objective responses and peak CAR T-cell levels (FIG. 5F-FIG. 5G). When the total number of TN cells was normalized to tumor burden, a more significant association with durable response emerged (FIG. 5H-FIG. SI). In contrast, the number of infused cells of other subsets were not associated with peak CAR T-cell levels (FIG. 14). The CD4:CD8 ratio did not strongly associate with peak CAR T-cell levels but was associated with durable response (FIG. 14). Out of all subsets it was found that total number of CD8 T cells normalized to pretreatment tumor burden in the product was most significantly associated with durable response (Table 1; FIG. 15).

Based on these findings, it was hypothesized that the naïve-like subset of CD8+ product T cells were most responsible for achieving durable response. A more detailed subset analysis was done in all patients with evaluable product samples (n=45 patients) and it was found that among CD8 T cells, the number of TN cells were most significantly associated with durable response (Table 5). Taken together, these results suggest that the number of infused specialized T cells, primarily the CD8+ TN-cell population, have a positive influence on durable clinical efficacy with CAR T-cell therapy.

TABLE 5

Association between product phenotypes and durable response. P values were calculated using logistic regression

|  | P value | Direction of association |
|---|---|---|
| Product CD8 T-cell phenotypes | | |
| Naïve-like, n[a] | 0.048 | Positive |
| Central memory, n[a] | 0.22 | NS |
| Effector memory, n[a] | 0.82 | NS |
| Effector, n[a] | 0.28 | NS |
| Naïve-like (%) | 0.041 | Positive |
| Central memory (%) | 0.34 | NS |
| Effector memory (%) | 0.76 | NS |
| Effector (%) | 0.36 | NS |
| Product CD4 T-cell phenotypes | | |
| Naïve-like, n[a] | 0.77 | NS |
| Central memory, n[a] | 0.85 | NS |
| Effector memory, n[a] | 0.043 | Negative |
| Effector, n[a] | 0.07 | NS |
| Naïve-like (%) | 0.29 | NS |
| Central memory (%) | 0.43 | NS |
| Effector memory (%) | 0.01 | NS |
| Effector (%) | 0.039 | NS |

[a]Denote analytes in LOG2 transformation.
Abbreviations: NS, not significant.

Example 5

Product T-Cell Attributes, Tumor Burden, Host/Patient Inflammatory Markers and Treatment-Related Type-1 Activity Associate Differentially with Efficacy and Toxicities CAR T-cell therapy may cause two categories of toxicity, cytokine release syndrome and neurologic toxicities. In ZUMA-1, grade ≥3 CRS or neurologic events were observed in 13% and 28% of patients, respectively (Neelapu S S, et al. 2017 *N Engl J Med;* 377:2531-44). The patient- and product-related markers that associated with efficacy were evaluated for their associations to severe toxicities with the aim to define actionable targets and approaches to improve on the product safety profile without negatively impacting efficacy.

Figures 16A, 16B, 16C:
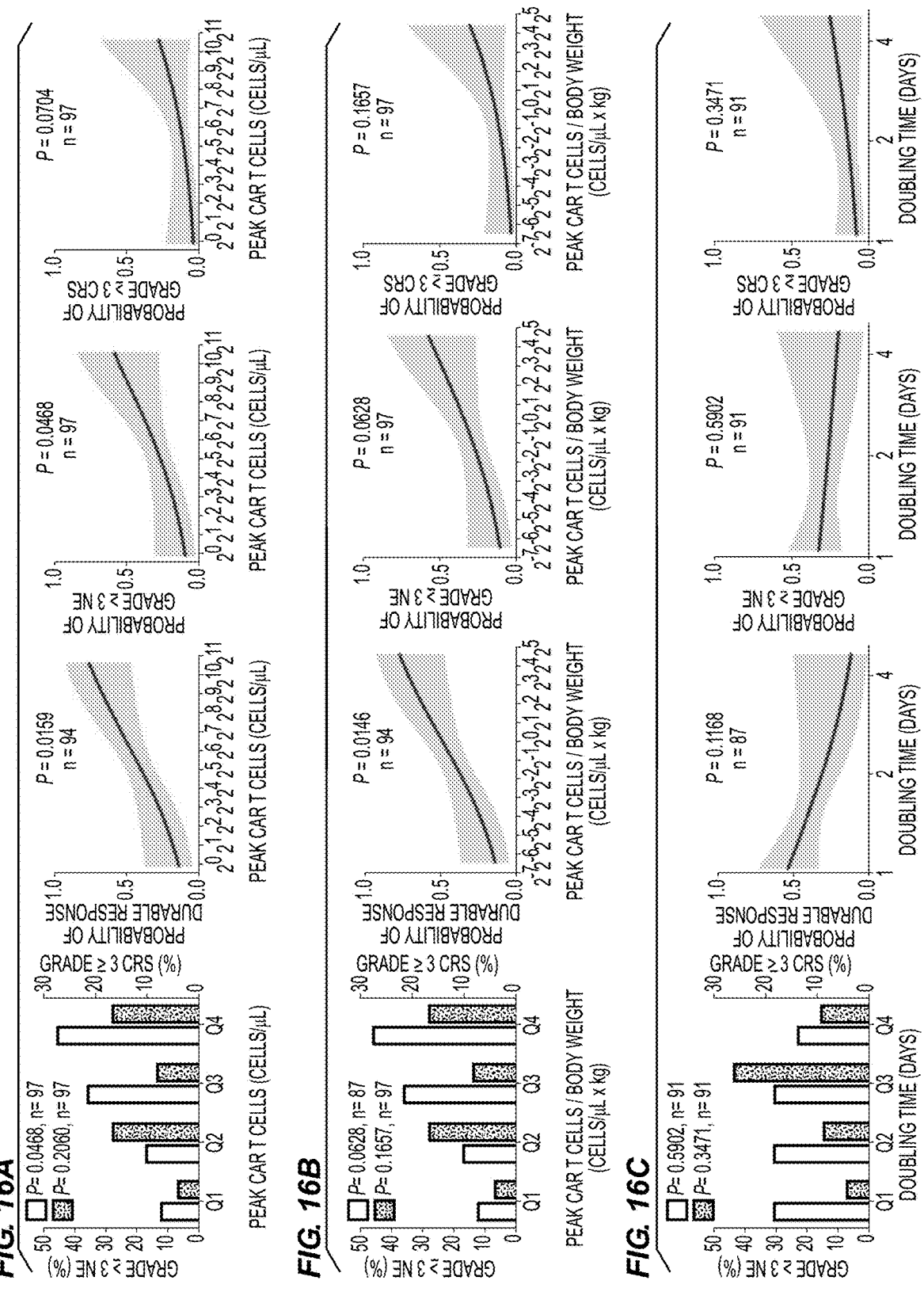
FIGS. 16A-16E. Association of toxicity and efficacy with key product attributes. CAR, chimeric antigen receptor; P values were calculated using logistic regression. CRS, cytokine release syndrome; NE, neurologic events; TN, naïve-like T cell, which are actually more like stem-like memory cells in the context of axicabtagene ciloleucel CD45RA+ CCR7+.
Figures 16D, 16E:
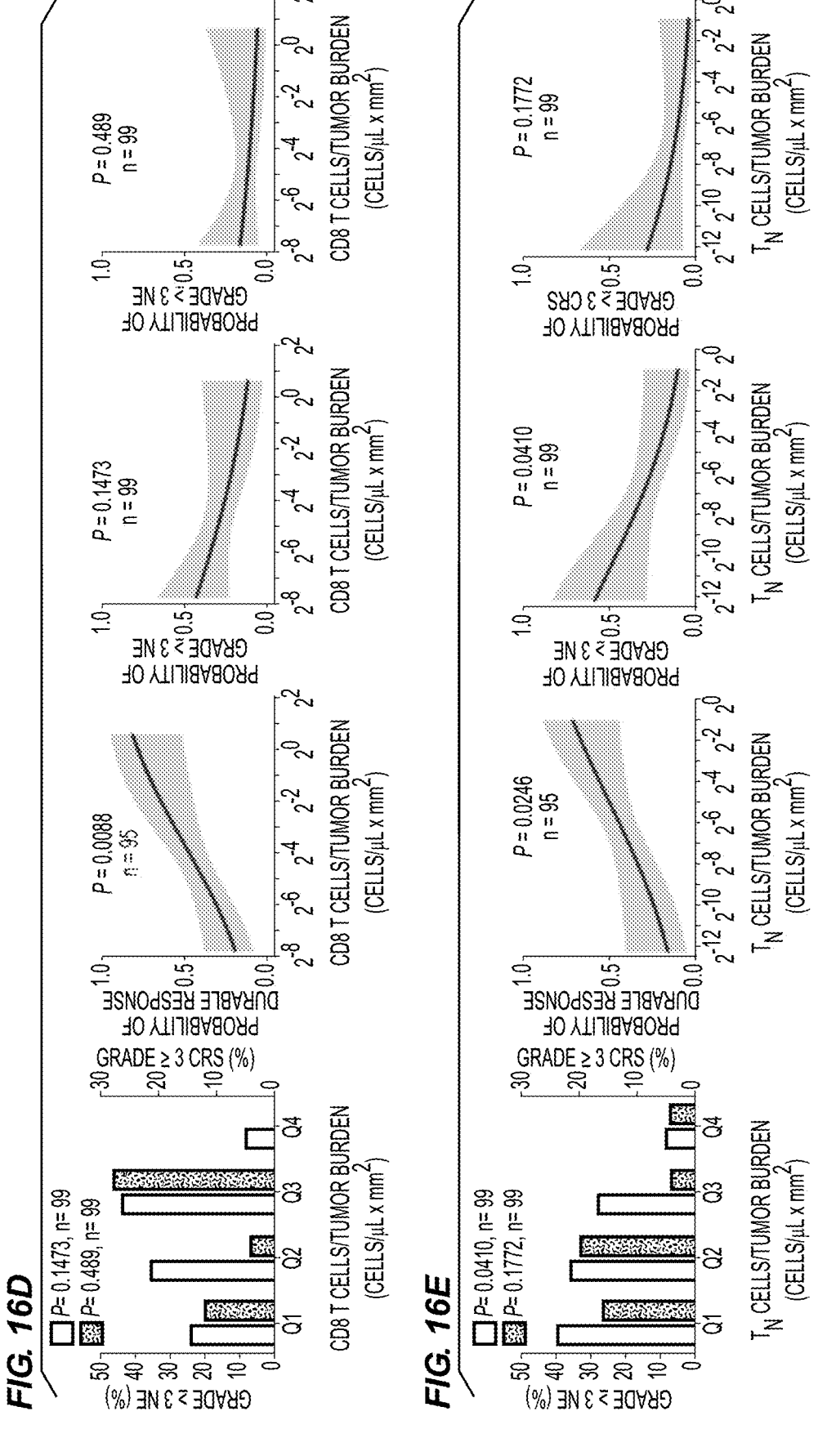
Figures 17C, 17D:
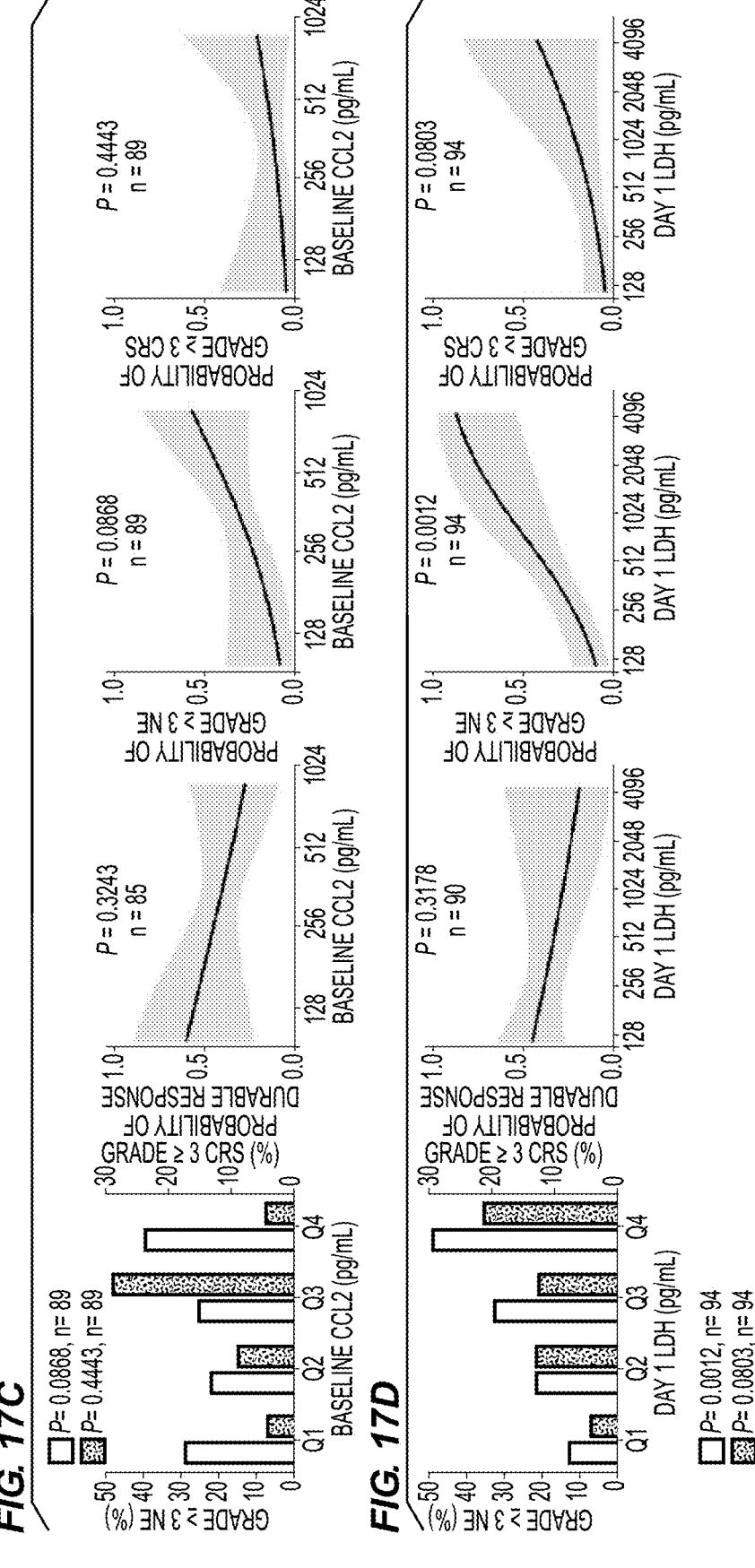

Higher peak CAR T-cell expansion was associated with severe neurotoxicity but not CRS (FIG. 16A). Tumor burden positively association with severe neurotoxicity: while rates increased through Q1-3, they declined in the highest quartile (FIG. 6A), generally mirroring the association between CAR T-cell expansion and tumor burden in the overall population (FIG. 1H). Notably, CAR T-cell levels normalized to either pretreatment tumor burden or body weight associated with efficacy, and the latter associated with grade ≥3 neurologic events (FIG. 6B; FIG. 16B). While DT was closely associated with efficacy, it was not associated with severe toxicities (FIG. 16C). In addition, total number of infused CD8+ cells, TN cells, and CD8 TN cells, normalized to tumor burden, associated with durable response but not with toxicity (FIG. 6C; FIG. 16D-FIG. 16E). Elevated pretreatment or post-treatment proinflammatory, myeloid-related cytokines, including IL-6, ferritin, CCL2, as well as LDH, were positively associated with grade ≥3 neurologic events or CRS (FIG. 6D-FIG. 6G and FIG. 17).

Key features were evaluated by the number of prior lines of therapy. Tumor burden, markers of baseline inflammation, and doubling time increased with increasing lines of therapy while the proportion and absolute numbers of TN cells decreased (Table 6). These findings support the observation that efficacy decreases and toxicity increases with increasing lines of prior therapy (Locke F L, et al. 2017 Mol Ther; 25:285-95).

TABLE 6

| Product and baseline characteristics by prior line of therapy | | | |
|---|---|---|---|
| | Prior Lines of Therapy Before Enrollment on ZUMA-1 Median (range) | | | |
| | 1-2 (n = 32) | 3 (n = 33) | 4 (n = 30) | ≥5 (n = 13) |
| Tumor Burden at Baseline, SPD | 2993 (180-12795) | 3355 (171-19201) | 4248 (268-23297) | 5106 (310-14354) |
| Ferritin at Baseline (mg/L) | 0.6 (LLOQ-2.8) | 0.8 (LLOQ-5.0) | 1.0 (LLOQ-10.6) | 1.2 (LLOQ-8.8) |
| LDH at Baseline (U/L) | 327 (148-2105) | 376 (153-2165) | 338 (150-7802) | 806 (116-3062) |
| Doubling time (days) | 1.4 (1.0-3.4) | 1.5 (1.1-2.4) | 1.7 (1.1-4.7) | 1.7 (1.3-4.7) |
| Transduction rate (%) | 60 (22-85) | 50 (11-72) | 50 (26-76) | 52 (17-67) |
| $T_N + T_{CM}$ (%) | 49 (26-85) | 47 (17-83) | 40 (18-72) | 38 (15-61) |
| $T_N$ Cells in product (%) | 19.2 (4.9-76.0) | 13.8 (3.4-52.8) | 11.1 (1.0-52.2) | 7.6 (1.6-38.9) |
| $T_N$ Cells in product bag ($\times 10^6$ cells) | 53.4 (10.6-214.9) | 39.7 (11.3-158.0) | 31.6 (2.1-200.6) | 30.2 (5.5-110.1) |

Abbreviations: LDH, lactate dehydrogenase; LLOQ, lower limit of quantification; SPD, sum of product diameters; $T_{CM}$, central memory T cells (CD45RA–CCR7+); Tn, naïve-like T cells (CD45RA+CCR7+).

Figures 6G, 6H:
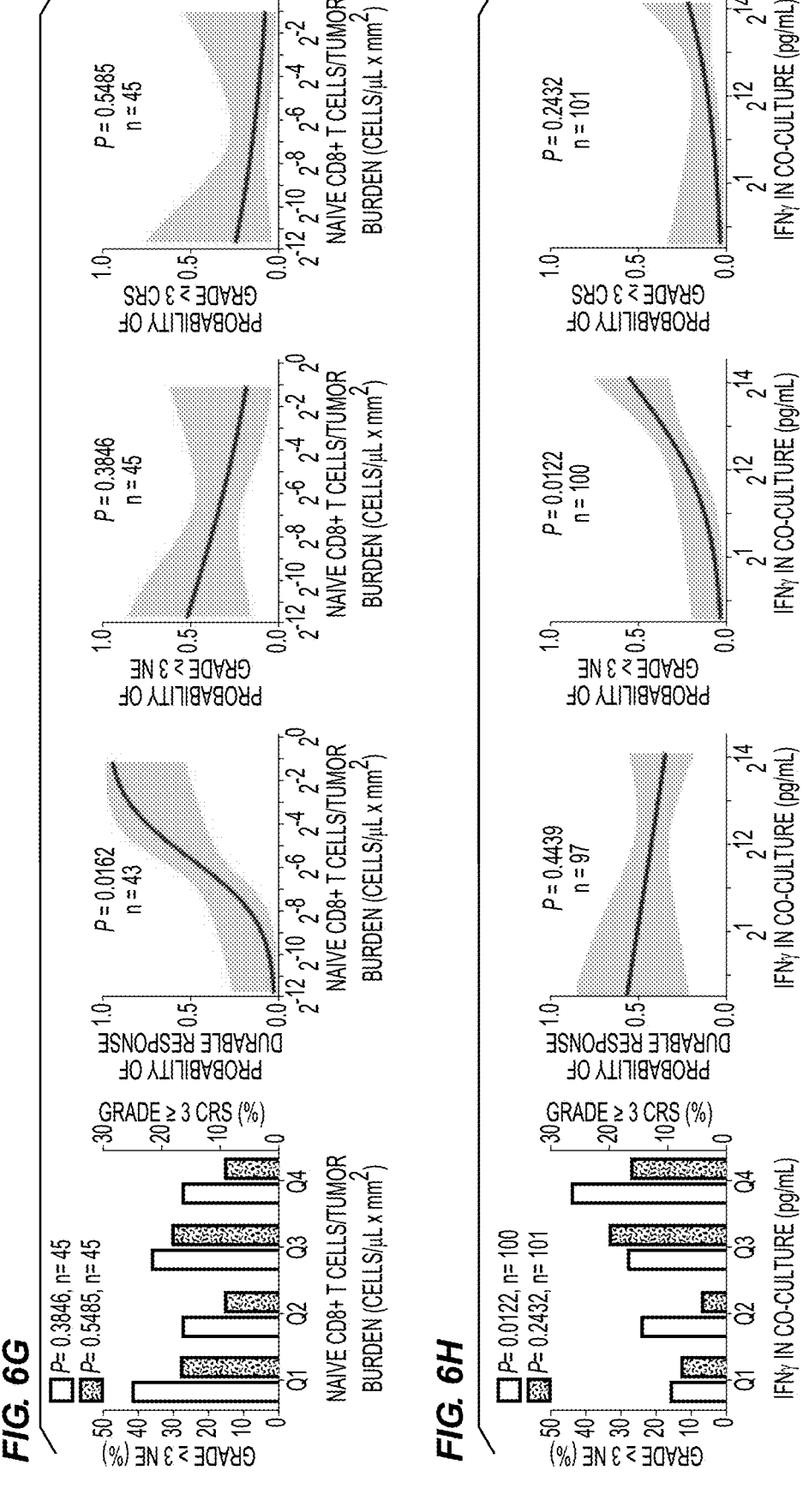
Figures 18A, 18B:
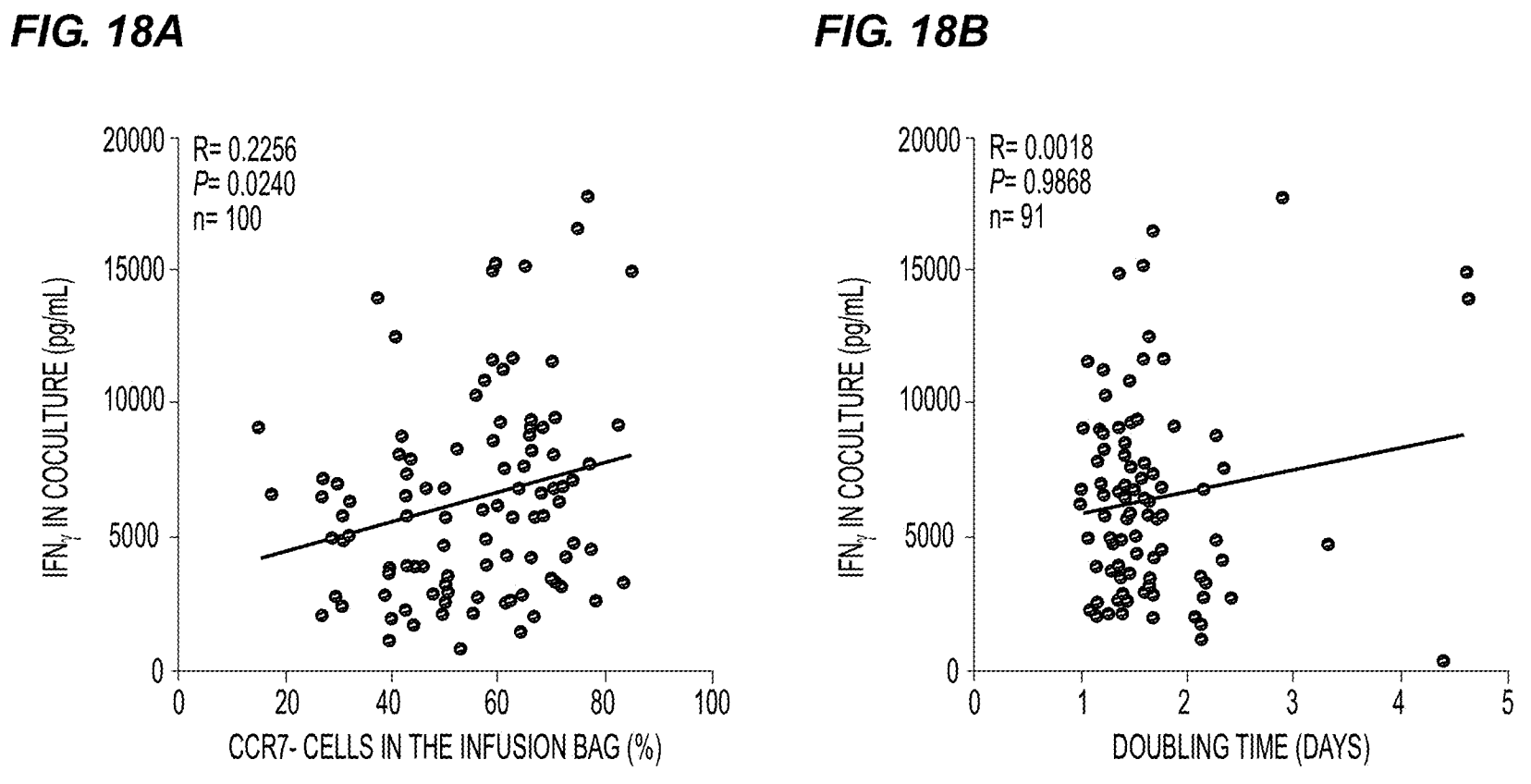
Figures 19A, 19B, 19C, 19D:
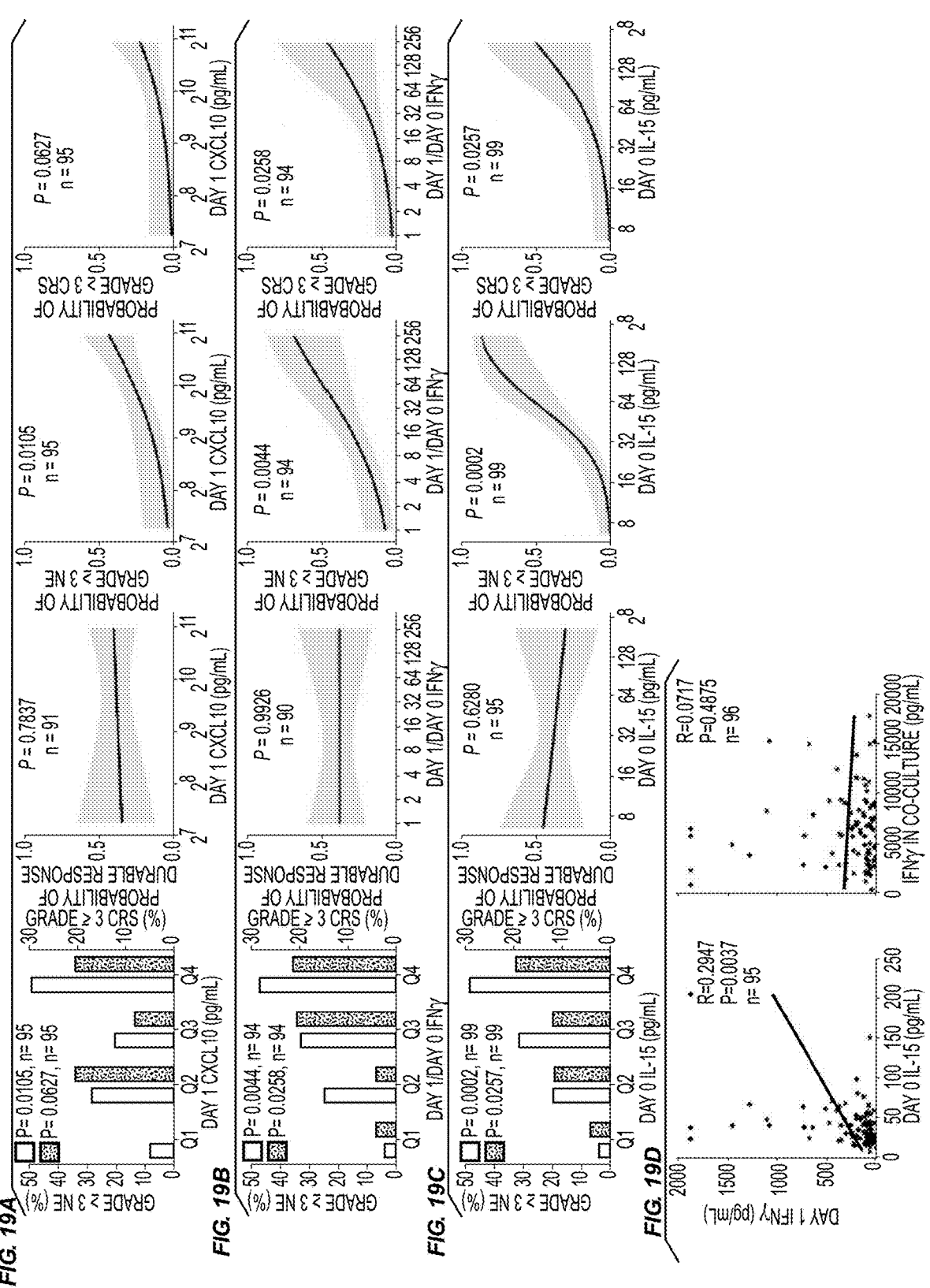
FIGS. 19A-19D. Association of toxicity and efficacy with post-infusion cytokines. P values were calculated using logistic regression for bar graphs and probability curves (FIG. 19A-FIG. 19C), and Spearman's correlation was used to calculate r and P values for scatter plots (FIG. 19D). CXCL, chemokine (C-X-C motif) ligand; IL, interleukin; IFN, interferon FIGS. 20A-20C. A) Cluster analysis summarizing the strength of association between covariates from the two major categories: product attributes and pre-treatment tumor/inflammatory markers.

In addition to covariates associated with clinical efficacy, it was also systematically analyzed other routinely-measured product attributes for their differential association with efficacy and toxicity. Notably, interferon-γ secretion of the final product after co-culture with CD19-expressing targets positively associated with grade 3-5 neurologic events but not efficacy or grade 3-5 CRS in ZUMA-1 (FIG. 6H). There was a direct association between product co-culture interferon-γ and the proportion of differentiated CCR7-negative T cells in the infusion bag and product DT (FIG. 18). Further, serum levels of interferon-γ, CXCL10, and IL-15, measured early post-treatment, also associated positively with neurotoxicity but were not associated with durable response rate (FIG. 19A-FIG. 19C). We also found that day 0 IL-15 serum levels significantly associated with day 1 interferon-γ serum levels, rather than product co-culture interferon-γ. (FIG. 19D). Altogether, these findings point to product attributes and pre- and post-treatment inflammatory biomarkers that associated differentially with efficacy and toxicities post axicabtagene ciloleucel.

Example 6

Figures 7A, 7B, 7C, 7D:
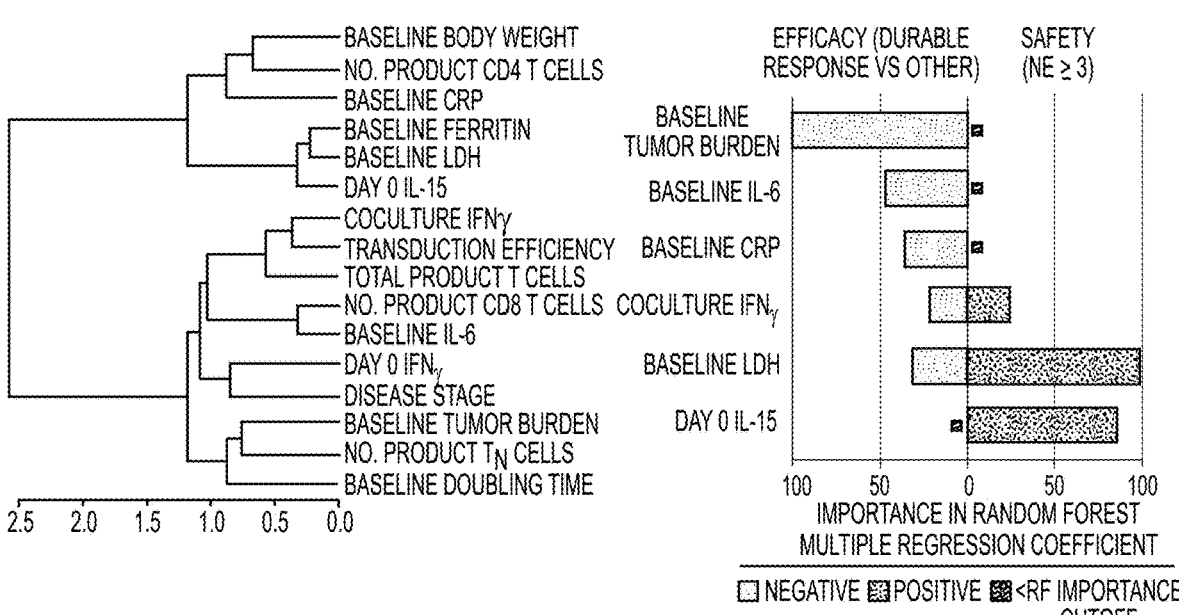
FIGS. 7A-7D. Tumor burden, LDH, and pro-inflammatory markers measured pre-CAR T-cell infusion associate differentially with clinical outcomes in multivariate analysis. A) Cluster analysis summarizing the strength of association between covariates from the two major categories: product attributes and pretreatment tumor/inflammatory markers.

Multivariate Analysis Further Elucidated Parameters Differentially Associated with Efficacy and Toxicity To further validate the results obtained by univariate analysis and understand the interdependence of individual variables, Multivariable analyses were conducted with a group of key covariates that associated with efficacy, grade ≥3 toxicities, and peak CAR T-cell levels after infusion. A set of biological control variables, which were not associated with these outcomes by univariate analysis, were included in the model as internal controls (ie, disease stage, CAR transduction efficiency, total number of infused T cells). Hierarchical clustering was employed to show the relationships between covariates by principal component analysis (FIG. 7A). As expected, variables aggregated into clusters comprising product characteristics, tumor burden in association with baseline pro-inflammatory state, and day zero cytokines.

Random forest analysis was applied to rank the major covariates impacting clinical outcome. In multivariate analysis, tumor burden and pretreatment inflammatory markers were most influential in regard to efficacy (negatively associated with durable response rate) and toxicities (positively associated with grade 3-5 neurotoxicity (FIG. 7B-FIG. 7D; FIG. 22). More specifically, in addition to pretreatment tumor burden, baseline serum LDH, and the baseline inflammatory markers IL-6 and CRP negatively associated with efficacy. Furthermore, baseline serum LDH and day 0 IL-15 measured post-conditioning but prior to CAR T-cell infusion, associated positively with grade ≥3 neurologic events. In turn, baseline serum IL-6 and LDH associated positively with grade ≥3 CRS. These findings were supported by multivariate analysis evaluating covariates differentially associated with CAR T-cell expansion (FIG. 22; FIGS. 20A-20C). Altogether, these findings support the outcome of the univariate analysis.

In sum, rapid in vivo CAR T-cell expansion commensurate with pretreatment tumor burden and influenced by the intrinsic product T-cell fitness, dose of specialized T-cell subsets, and host systemic inflammation, were significant determining factors for durable response. Suboptimal product T-cell fitness was a factor related to primary treatment resistance, and limited numbers of naïve-like or CD8+ T cells in proportion to tumor burden were associated with a failure to achieve durable response. High tumor burden, pronounced inflammatory status reflected by myeloid activation markers pre- and post-CAR T-cell infusion, and excess treatment-related type-1 cytokines associated negatively with durable efficacy and positively with severe toxicities.

A correlate of durable response was peak CAR T-cell levels in blood normalized to pretreatment tumor burden. This index was positively associated with durable response rate and separated subsets of patients with high (~60%) vs. low (~10%) probability of achieving a durable response. The data also point to the importance of enumerating CAR cells/unit of blood volume, as it was a more informative PK measurement compared with the number of CAR gene copies/μg of host DNA reported in other studies. The number of CAR T cells in peripheral blood early (within two weeks) after infusion associated with clinical efficacy. However, CAR levels at later points (1 and 3 months postinfusion) were not significantly associated with durable efficacy. It has been previously showed that most responders show profound tumor regression at the first assessment (28 days), that levels of the immune effector molecule granzyme B peak within 5 days postinfusion, and that normal B cells recover gradually in durable responders. In one aspect, the results here, taken together with prior findings, suggest that a window for anti-CD19 CAR T cell anti-tumor activity in LBCL may occur within the first weeks postinfusion. These findings may contradict the hypothesis that persisting CAR T cells are needed to achieve and maintain clinical efficacy, at least in the context of an anti-CD19 CAR T-cell therapy with a CD28 costimulation domain for LBCL.

Higher numbers of CAR T cells in the peripheral blood associated with DT, underscoring the importance of intrinsic T-cell fitness independent of the CAR construct. Diminished product T-cell fitness (e.g., high DT) associated with primary treatment resistance, as most nonresponding patients showed a product DT>1.6 days. In turn, this kinetic product attribute directly correlated with the frequency of TN cells in the product infusion bag, but not with the frequency of TCM cells, hypothesized by others to play a major role in T-cell therapy. T-cell fitness in the context of an autologous T-cell product like anti-CD19 CAR T cell therapy may be an intrinsic feature of a patient's T-cells. Indeed, product attributes such as a less-differentiated phenotype (CCR7+ CD45RA+), associated directly with the corresponding attributes of the starting peripheral blood cell population collected at apheresis. Within apheresis starting material, CD28+CD27+ TN cells associated best with product DT.

The results suggest that rather than the total number of product T cells or CAR T cells, it was the total number of specialized T cells normalized to pretreatment tumor burden that associated best with clinical efficacy. These findings indicate that a suboptimal number of such T cell subsets in the infusion bag may be a major cause for relapse post-anti-CD19 CAR T cell treatment, especially in context of high pretreatment disease burden. Together with the correlative results of CAR T-cell levels normalized to pretreatment tumor burden, these findings suggest that optimized dosing would integrate categories of parameters reminiscent of the effector-to-target ratio utilized in preclinical tumor immunology.

Besides product attributes linked to T-cell fitness and dose of specialized T cells, the results suggest that markers related to tumor burden and inflammation, both of which may be influenced by the underlying tumor biology, were highly associated with clinical outcomes. Pretreatment serum levels of LDH and pro-inflammatory markers such as IL6 and ferritin, were prominently and negatively associated with clinical efficacy, and were positively, but weakly, associated with tumor burden. Concordantly, patients with low tumor burden and diminished tissue hypoxia (e.g., LDH) and inflammation markers showed a high durable response rate (>60%) and limited rate of inflammation-driven serious adverse events, namely CRS and neurotoxicity (<10%). The data herein (generated by univariate and multivariate analyses of patient data) indicate that tumor hypoxia and an enhanced pro-inflammatory state reminiscent of myeloid cell hyperactivity might inhibit the activation, expansion, and/or survival of CAR T cells within the tumor microenvironment, while simultaneously contributing to toxicities possibly through facilitating excess cytokine production.

To optimize CAR T-cell therapy, it is useful to define factors that may associate differentially with efficacy and treatment-related toxicities. Univariate and multivariate analyses revealed several parameters that associated differentially with durable efficacy and severe NE or severe CRS. Pretreatment tumor burden and levels of circulating pro-inflammatory molecules associated negatively with efficacy and positively with toxicities. Specifically, pretreatment tumor burden, tissue hypoxia, LDH, serum ferritin, and postconditioning serum IL15 levels at day 0 associated directly with grade ≥3 NE, while pretreatment serum IL6 associated with grade ≥3 CRS. The total number of infused T cells of naïve-like phenotype (CCR7+ CD45RA+) associated positively with durable efficacy but did not significantly associate with severe toxicities. Pretreatment product T-cell IFNγ production linked to the more differentiated T cells in the infusion bag and associated positively with severe neurologic toxicities and to a lesser degree with decreased efficacy.

Based on these findings, this study suggests several actionable strategies to increase efficacy without exacerbating the toxicity profile of anti-CD19 CAR T cell therapy: 1] systematic evaluation of bridging therapy agents, to curb tumor burden and inflammation pre-CAR T-cell infusion; 2] testing of agents known to modulate effects on myeloid cells or low dose corticosteroids administered immediately pre- or post-CAR T-cell infusion; 3] optimization of CAR configuration to eliminate excess production of myeloid and type-1 molecules by the product cells; 4] dosing or process optimizations to increase both the percentage and number of product $T_N$ and CD8+ T cells especially in context of bulky disease; and 5] improving T-cell fitness through optimizing product T-cell metabolism or combining with immune checkpoint modulators.

Example 7

Methods Used for Examples 1 Through 6

Patient Samples

Available samples from patients in ZUMA-1 (NCT02348216) clinical trial were analyzed. Safety and efficacy results were previously reported ((Neelapu, S S et al. 2017, N Engl J Med 2017; 377(26):2531-44). Durable response refers to those patients who were in ongoing response at least one year post-CAR T cell infusion. Relapse refers to those patients who achieved a CR or PR and subsequently experienced disease progression. Patients who achieved stable disease as best response are included in no response category.

Quantification of CAR T Cells

CAR T cells were quantified using TaqMan quantitative PCR (qPCR; ThermoFisher Scientific) as described (Locke F L, at al. 2017. Mol Ther; 25:285-95) and confirmed by droplet digital PCR (Bio Rad) per manufacturer's instructions. Unless otherwise noted, results shown use the qPCR method. To report frequencies of CAR+ cells, cells per microliter were calculated by normalizing CAR gene expression to actin expression in peripheral blood mononuclear cells.

Analysis of Biomarkers and Clinical Covariates

Serum cytokines were analyzed by Luminex (EMD Millipore) or V-Plex Multiplex assay panels (Meso Scale Discovery) as previously described (Locke F L, at al. 2017. Mol Ther; 25:285-95)) at baseline (prior to conditioning), on day 0 (CAR T cell infusion day) or day 1 (1 day post-CAR T cell infusion) as specified. T-cell phenotype was assessed by multicolor flow cytometry using established protocols and antibodies (Locke F L, at al. 2017. Mol Ther; 25:285-95)). CD45RA and CCR7 were used to define effector memory T cells (TEM; CD45RA–CCR7–), naïve-like T cells (TN; CD45RA+CCR7+); central memory T cells (TCM; CD45RA–CCR7+), and effector T cells (TEFF, CD45RA+ CCR7–). Apheresis samples were presented as a percentage of live, CD45+ cells, and product samples were presented as a percentage of live cells.

LDH was quantified in the clinical lab at each study site. Tumor burden was estimated as the sum of product diameters (SPD) of up to six index lesions per Cheson 2007 criteria (Cheson B D, et al. 2007 *J Clin Oncol*; 25:579-86) by local study site radiologist assessment. Product T-cell fitness was estimated by product DT in culture per the following formula:

$$\text{Doubling Time} = \frac{\ln(2) \times \text{duration}}{\ln\left(\frac{\text{Total viable cells at harvest}}{\text{Total viable cells at Day 3}}\right)}$$

Statistical Analyses

Covariates and biomarkers from prespecified secondary endpoints were interrogated for associations with safety, efficacy, and CAR T-cell expansion.

Quartile Analysis. Specified covariates were assessed by quartile analysis, i.e., divided across 4 groupings of equal quantity, or as equal as possible with a given sample size, based on minimum to quartile 1 (Q1), Q1 to median, median to Q3, and Q3 to maximum. Where quartile analysis is presented visually, the P value for logistic regression analysis is provided.

Univariate Analysis. Spearman's rank-order correlation was used to evaluate association between any two analytes. Logistic regression was used to evaluate relationship between covariate and outcome. Kruskal-Wallis and Dunn's tests were used when 3 or more subgroups were involved in the comparison. P values of <0.05 (not adjusted for multiplicity) were considered significant associations.

Multivariate Analysis. Principal component analysis (Chavent M, et al. 2012 *Journal of Statistical Software*; 50:1-16) was used to generate hierarchical clustering and demonstrate the relationships between covariates. Random forest analysis (Hothorn T, et al. 2006. *Journal of Computational and Graphical Statistics*; 15:651-7450) was used to identify covariates most associated with durable response, grade ≥3 CRS, grade ≥3 NE, and peak CAR T-cell expansion.

Manufacturing of Chimeric Antigen Receptor (CAR) T Cell Therapy

Apheresis material was enriched for T cells at the start of the manufacturing process. T cells were activated by stimulation with anti-CD3 monoclonal antibody (OKT3) in the presence of IL-2 for 2 days. Activated T cells were transduced to introduce the CAR gene by retroviral transduction. To achieve the desired dose of CAR-positive cells, the transduced T cells were expanded in the presence of interleukin 2 (IL-2) for 4-6 days. T cell doubling time was measured from day 3 through the end of the manufacturing process, when transduced T cells were grown with medium containing recombinant IL-2.

Example 8

Evolution of TME Gene Signatures
Post-Axicabtagene Ciloleucel is a Hallmark of
Clinical Response And Relapse To uncover treatment-related TME patterns that separate responders from nonresponders early post-axicabtagene

Figure 23A:
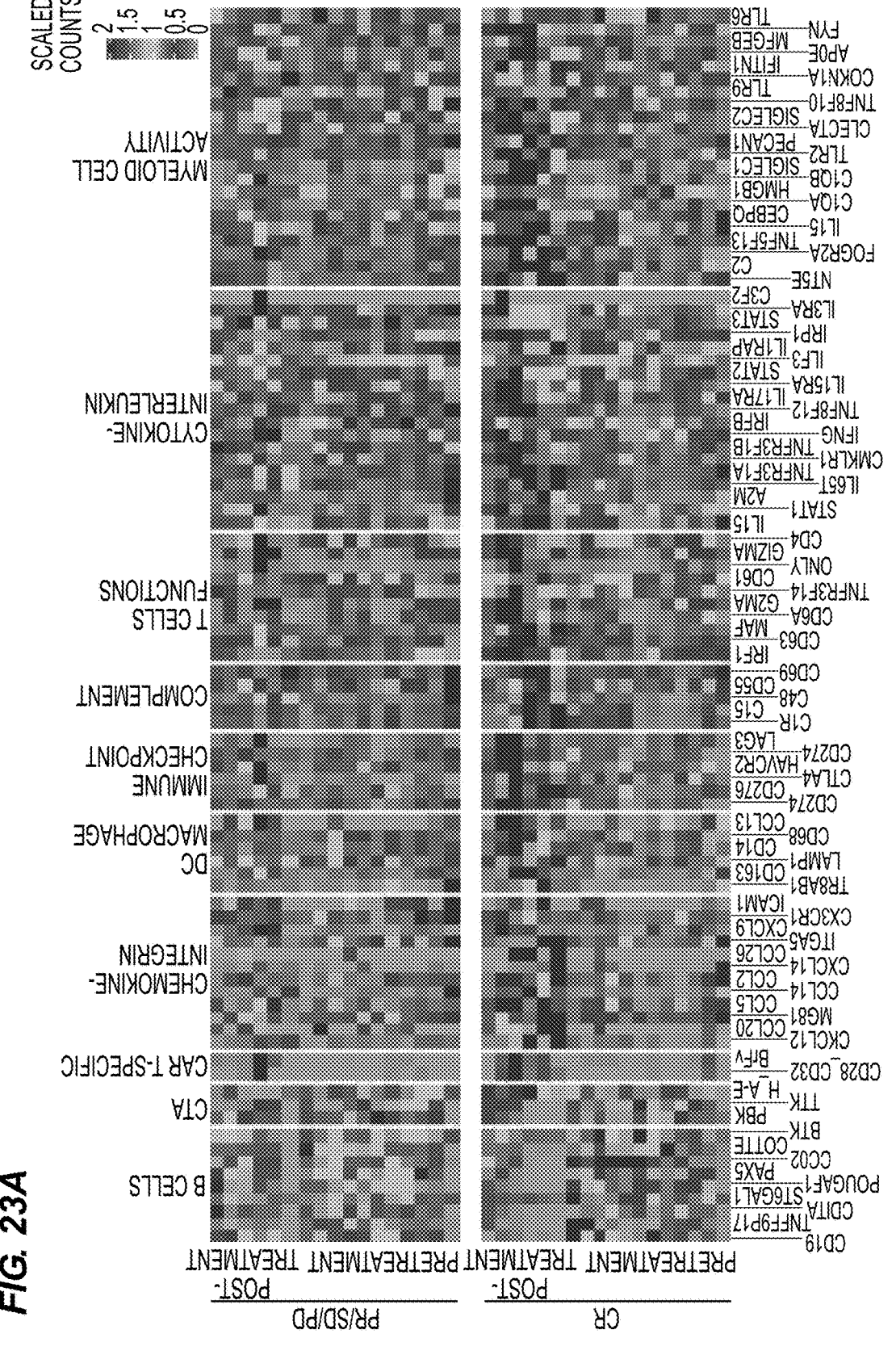
Figure 24A:
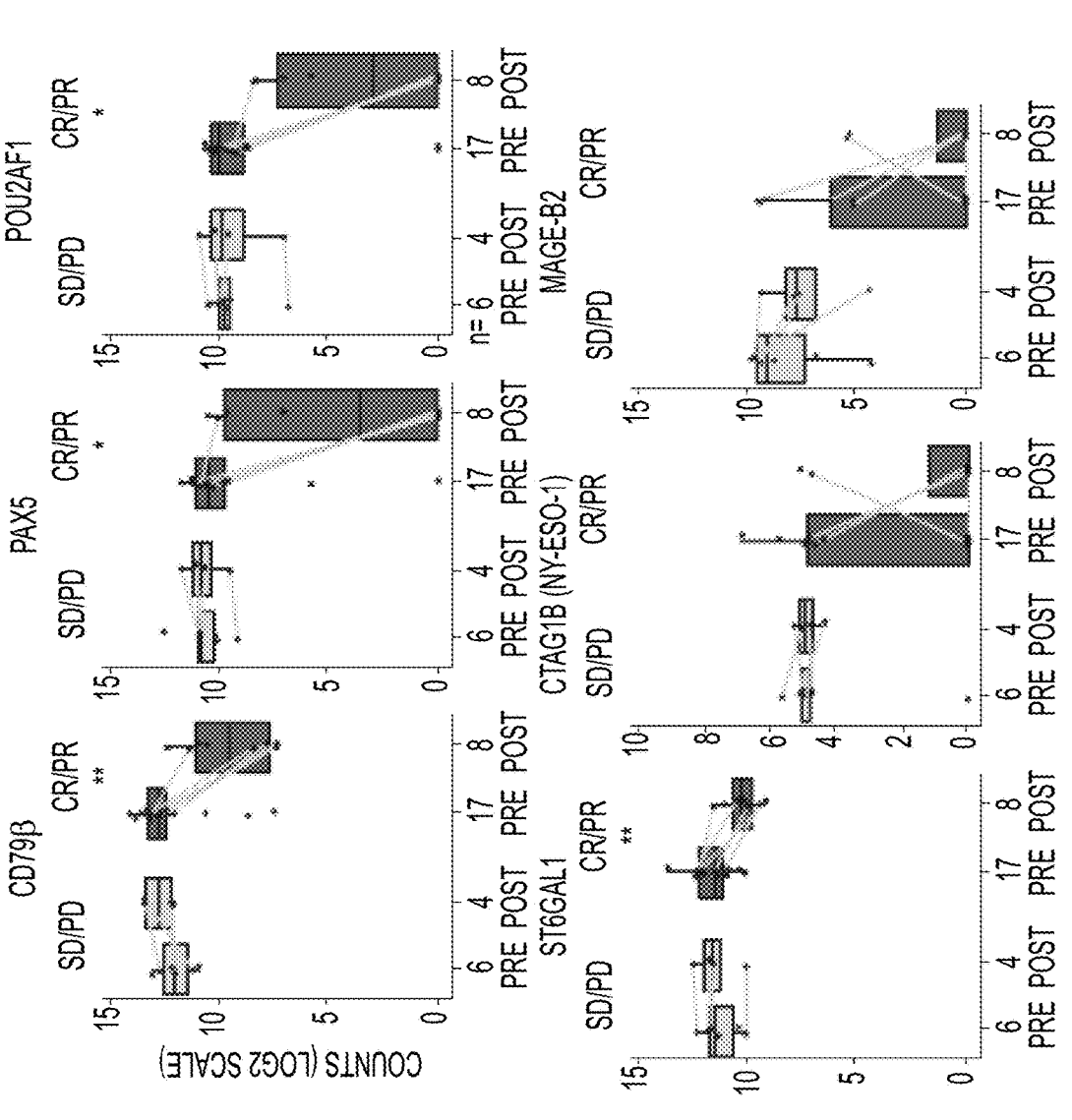
FIG. 24A, FIG. 24B, FIG. 24E, Gene expression from fresh frozen tumor biopsies was compared at baseline (before conditioning chemotherapy and axicabtagene ciloleucel) versus early after axicabtagene ciloleucel infusion using the PanCancer Immune Profiling+ CAR T gene panel in patients with CR/PR (n=25; [17 pretreatment; 8 within 2 weeks posttreatment]) versus SD/PD (n=10; 6 pretreatment; 3 within 2 weeks posttreatment; 1 within 4 weeks posttreatment]).
Figure 24B:
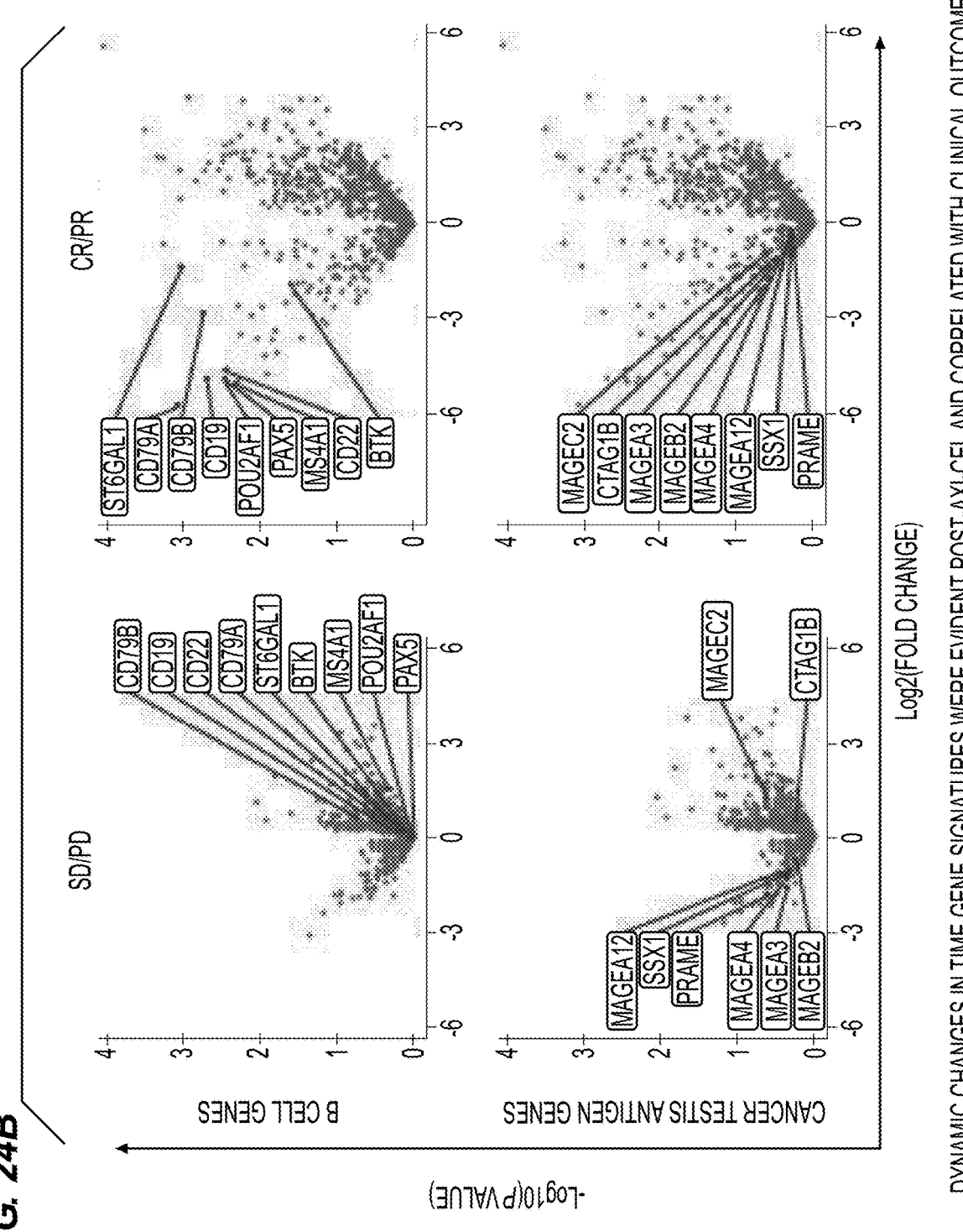
Figures 24D, 24E:
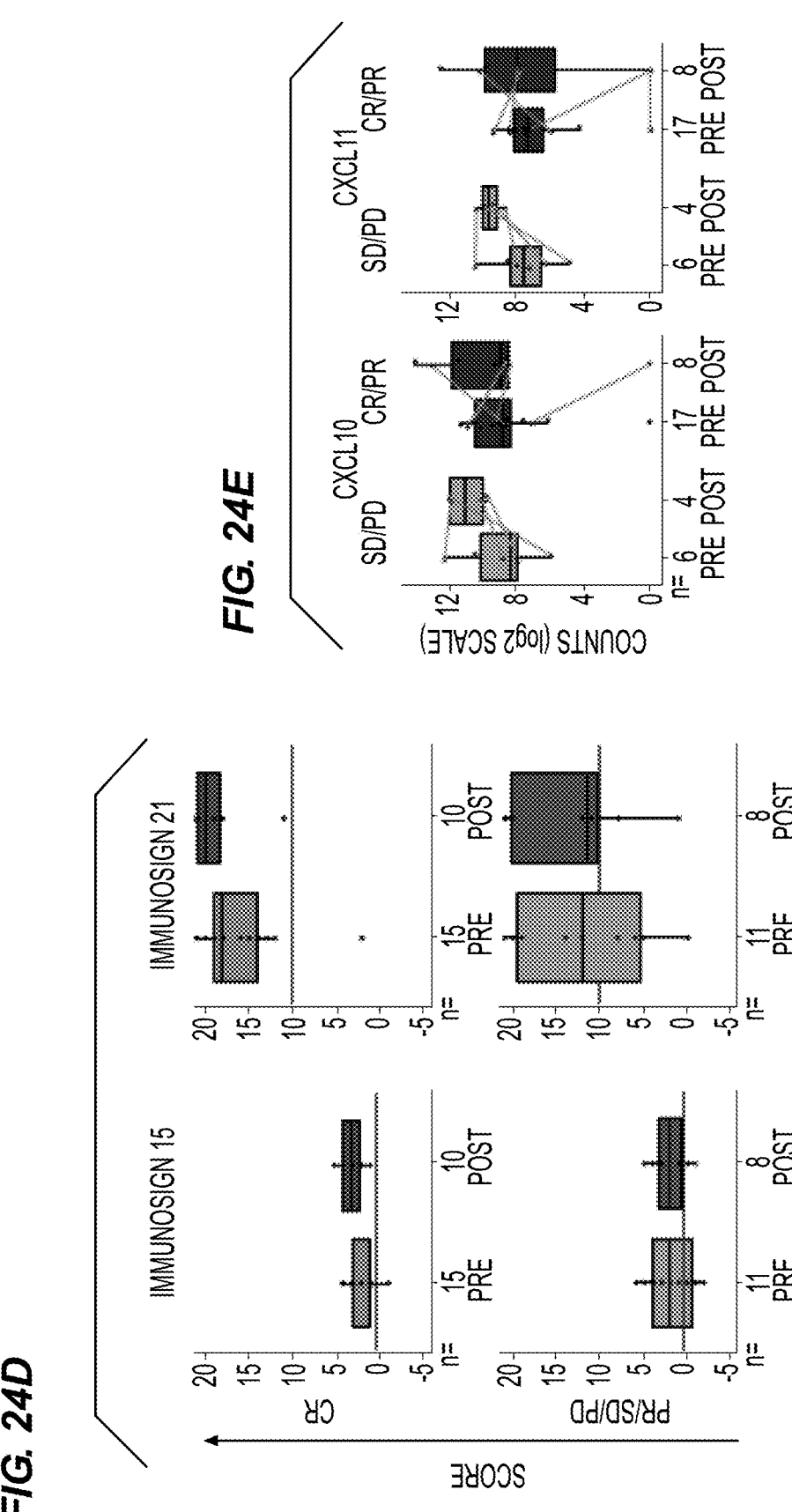
FIG. 24D, Immunoscore 21 and 15 were compared at baseline and early after axicabtagene ciloleucel infusion in fresh frozen tumor biopsies from patients with CR (n=25 [15 pretreatment; 10 within 2 weeks posttreatment]) versus PR/SD/PD (n=19; 11 pretreatment; 7 within 2 weeks posttreatment; 1 within 4 weeks posttreatment]). The red line designates the low/high score cutoff.

186 ciloleucel treatment (two weeks), before the first clinical assessment at one month, global gene expression changes in tumor tissues were evaluated. Changes in TME gene expression patterns of responders strikingly differed from those of nonresponders (FIG. 23A, FIG. 24, FIG. 25). Differences spanned all major categories of TME genes, including innate and adaptive immunity and tumor- and stroma-related genes with well-described immune activity or unknown functionality. Gene expression across all B cell lineage markers, including CD19, CD20, CD22, and CD75 (ST6GAL1), B cell transcriptional master switch PAX5, and transcriptional coactivator POU2AF1, markedly decreased in the TME of responders (FIG. 23B, FIG. 24A). Decreased expression of CTAG1B (NY-ESO-1) and MAGE-C2 were observed only in responders (FIG. 24A, FIG. 24B). Furthermore, responders, but not nonresponders, showed early and brisk elevation of cytotoxic T cell-related genes, including CD8α, immune effector molecules (granzyme A), key T cell growth factors and chemokines (IL-15), interferon (IFN)γ-regulated immune checkpoints (PD-L1, B7-H3, CTLA-4), and myeloid-related genes and corresponding chemokines (CD14, CCL2) (FIG. 23C-FIG. 23E). These early TME modifications in axicabtagene ciloleucel responders were paralleled by an increase of the prespecified Immunosign 21 index (Rossi, et al. (ZUMA-1). SITC 2017), which integrates T cell, IFN, chemokine, and immune checkpoint genes (FIG. 26, FIG. 24C, FIG. 24D). These patterns were vastly different in nonresponders, where increased expression of immune-related genes in the TME did not occur, except for 2 proinflammatory chemokine genes (CXCL10, CXCL11) known to be modulated by conditioning (Moschella, et al. *Clin Cancer Res.* 2013; 19:4249-61) (FIG. 24E). Thus, the TME gene expression profile of responders evolved rapidly, within 2 weeks post-axicabtagene ciloleucel treatment, towards an activated T cell-related signature paralleled by a declining tumor-related signature, markedly differing from the pattern seen in nonresponders despite comparable clinical outcomes across classical prognostic markers.

Figure 27A:
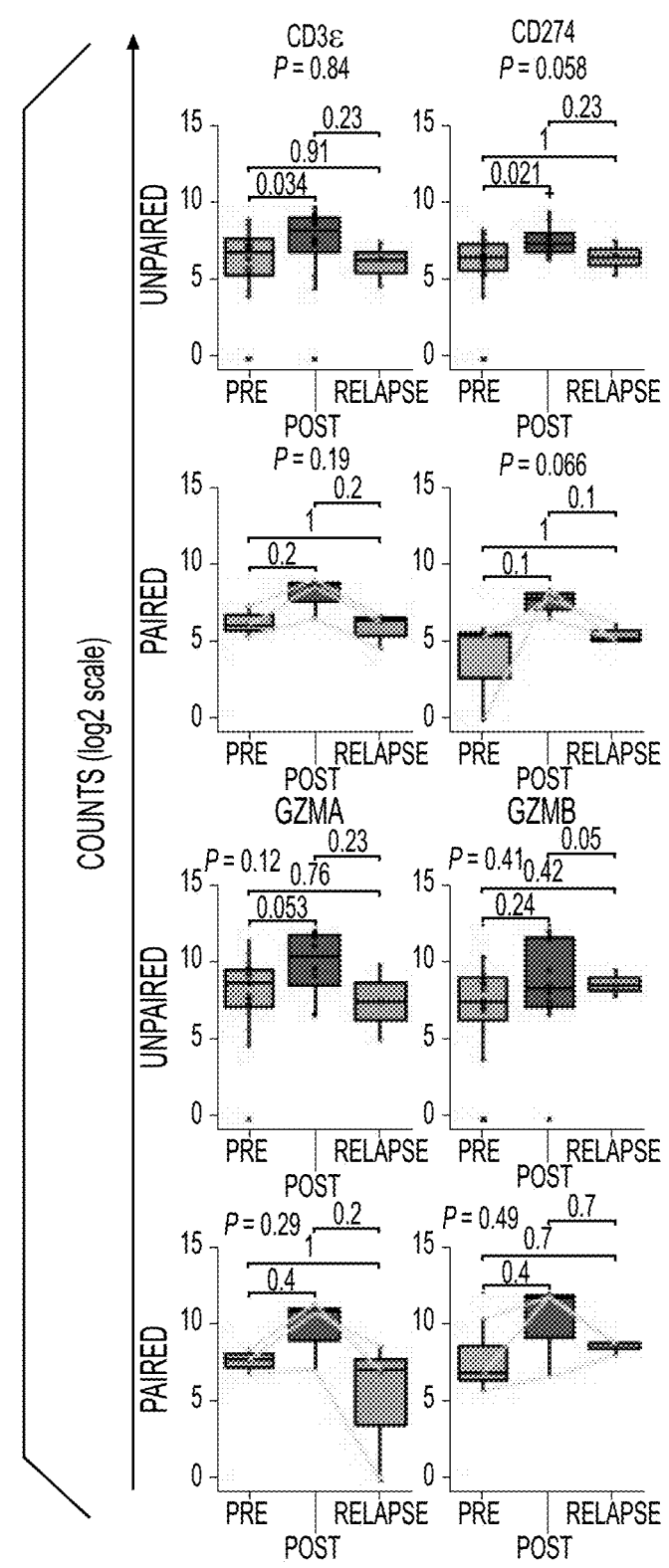
FIGS. 27A-27C At relapse, the TME evolved towards an immune-detrimental contexture with reduction of T cell, CAR T cell, and myeloid cell genes and Immunosign. Gene expression was compared at baseline (before lymphodepletion and axicabtagene ciloleucel infusion), within 4 weeks after axicabtagene ciloleucel infusion, and at relapse (as indicated) in fresh frozen biopsies analysed by PanCancer Immune Profiling+CAR T gene NanoString panel (unpaired samples, n=23 pretreatment; 12 posttreatment [11 within 2 weeks; 1 within 4 weeks]; 3 relapse) or Immunosign Clinical Research panel (paired samples, n=3).
Figure 27B:
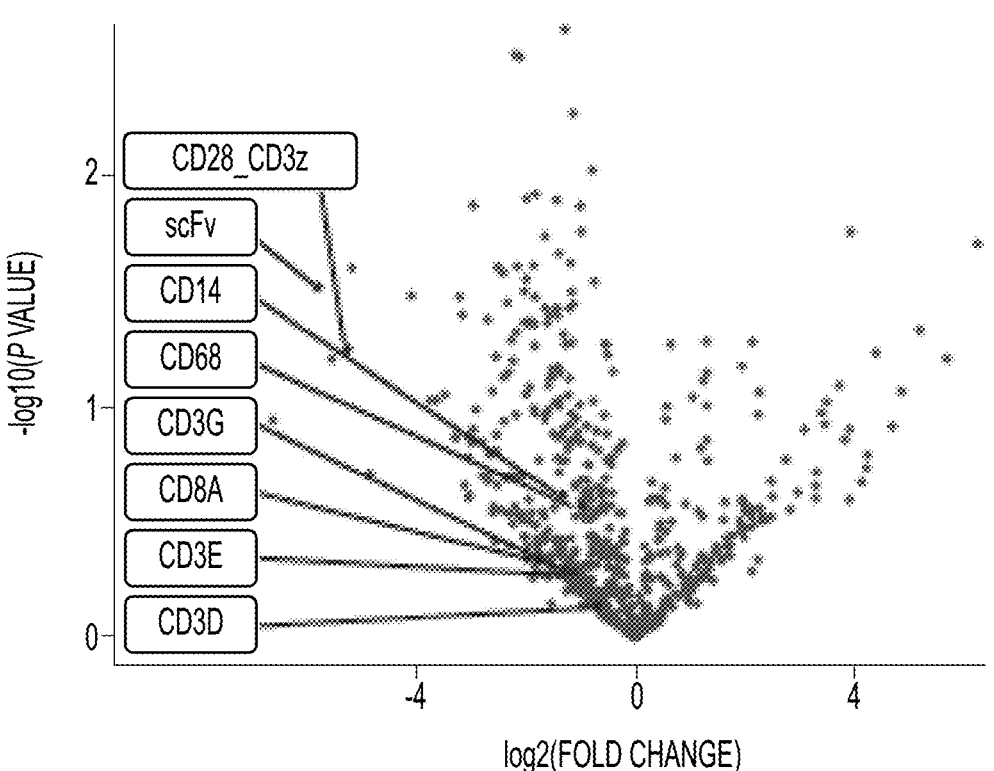
Figure 27C:
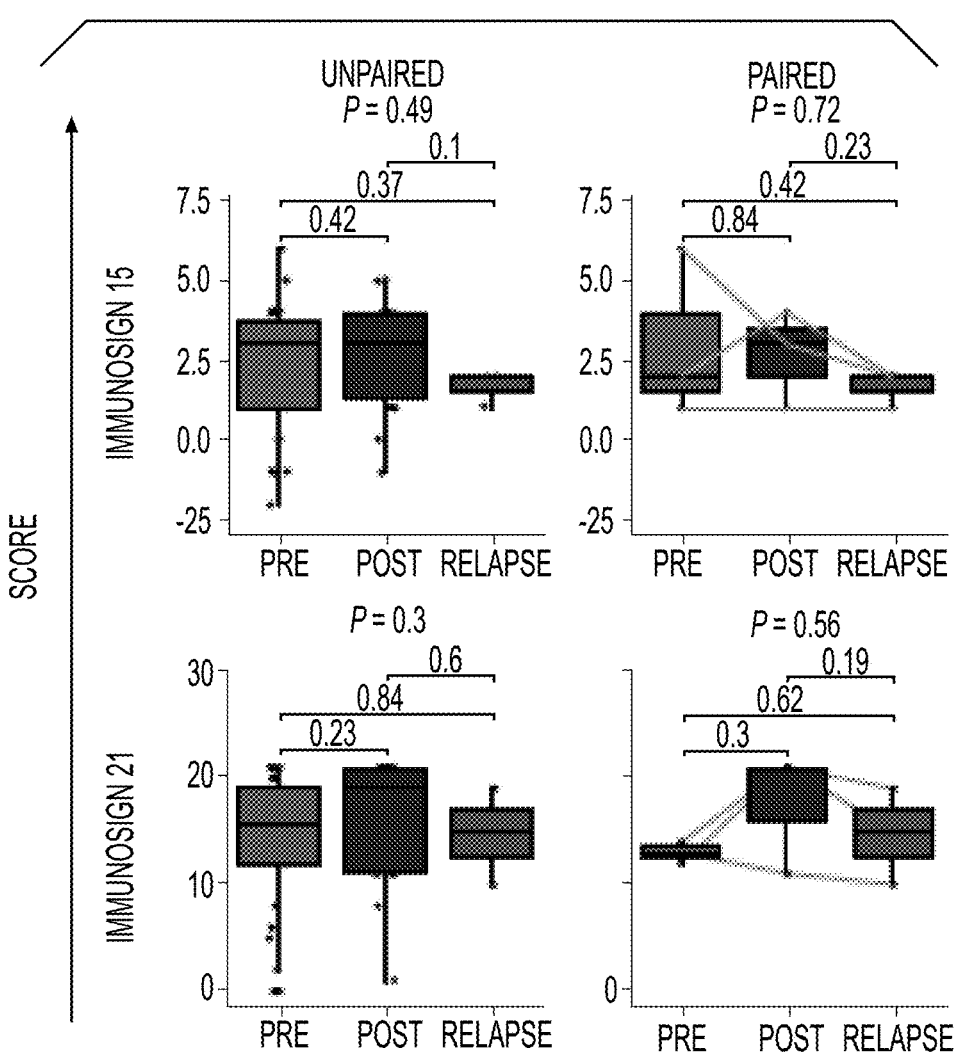
Figure 28A:
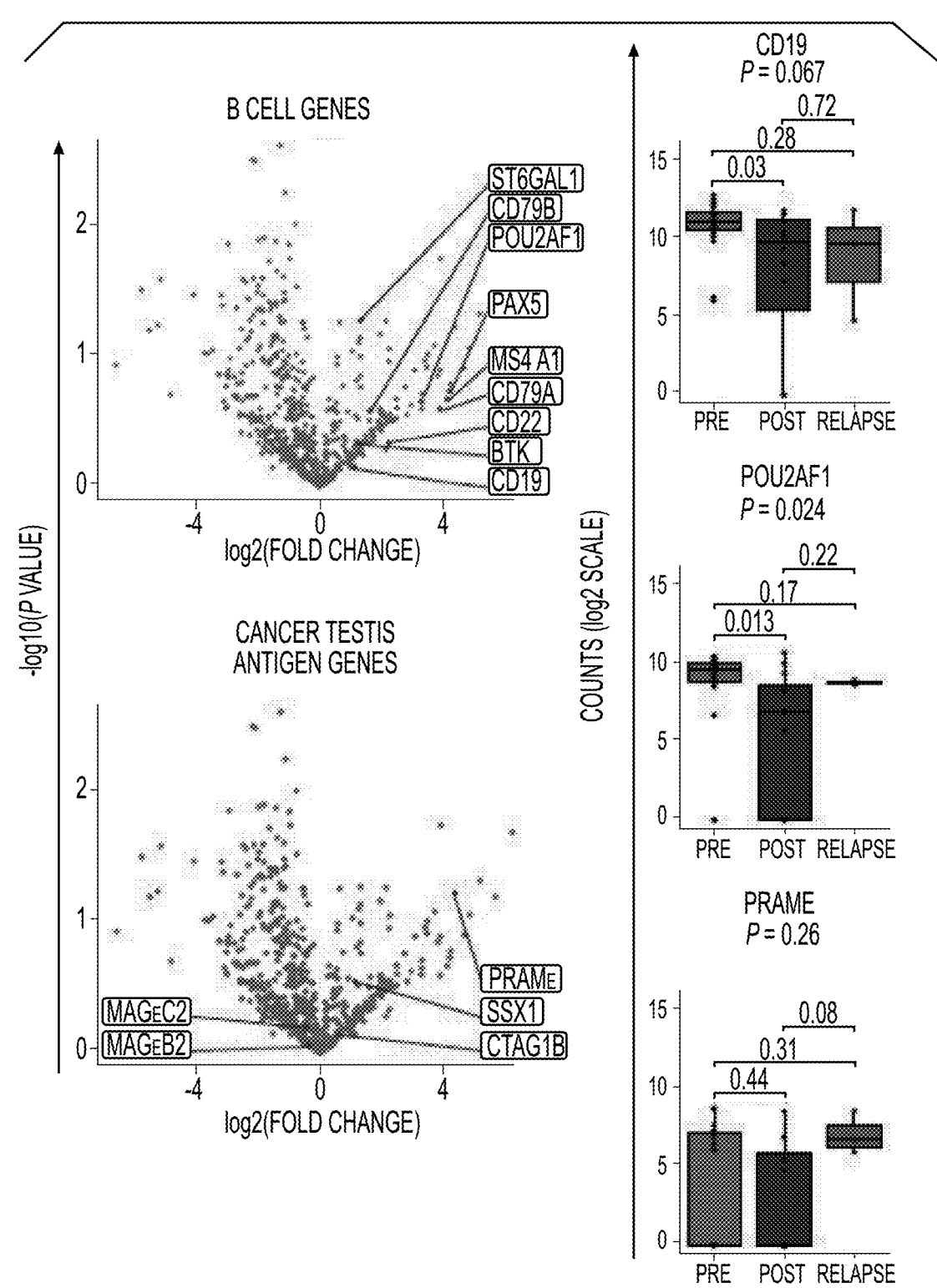
FIG. 28A, Volcano plots of B cell lineage and CTA gene expression within 4 weeks after axicabtagene ciloleucel infusion (left) versus at relapse (right). The plot was constructed using log 2(fold change) and −log 10(P value) for all genes analysed by PanCancer Immune Profiling+CAR T gene panel. Red dots represent the top differentially expressed genes with P<0.01. P values are from Kruskal-Wallis test.
Figure 28B:
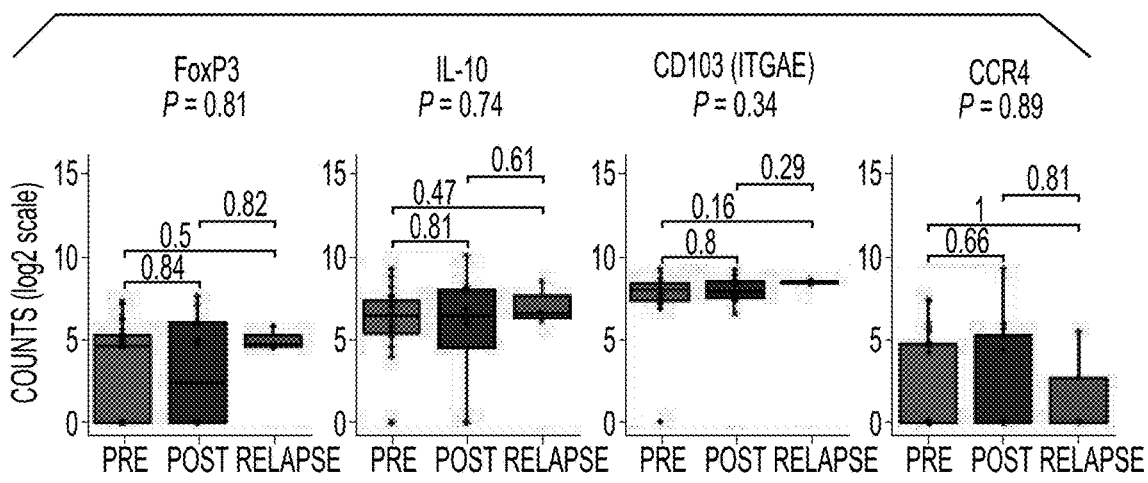
FIG. 28B, Treg-related genes.
Figure 28C:
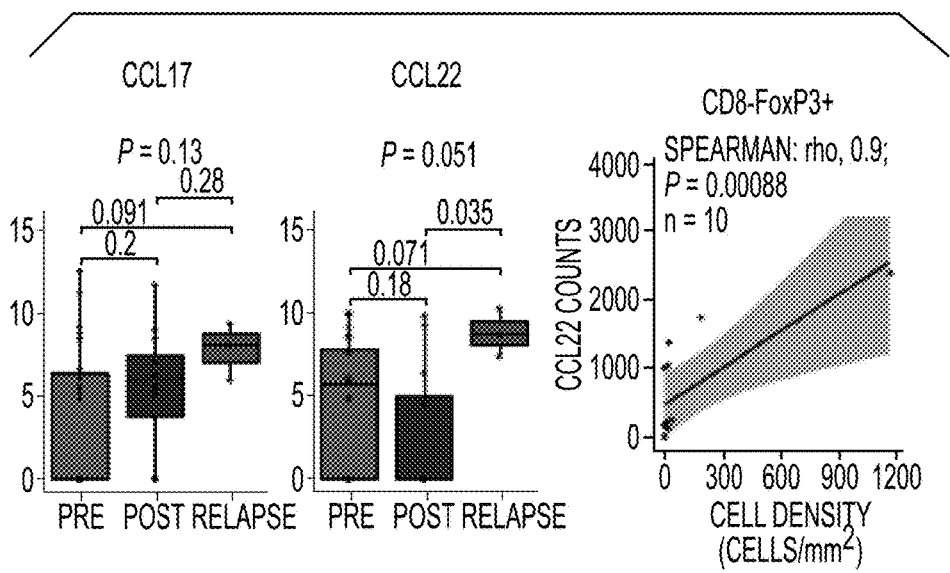
FIG. 28C, Correlation between CCL22 gene expression and CD3+CD8−FoxP3+ (Treg) cell density (cells/mm$^2$) at baseline. Abbreviations: axicabtagene ciloleucel, axicabtagene ciloleucel; CAR, chimeric antigen receptor; CTA, cancer testis antigen; TME, tumor microenvironment; Treg, regulatory T cell.

In a subset of patients who relapsed several months after achieving a clinical response to axicabtagene ciloleucel, the TME evolved towards an immune detrimental contexture (FIGS. 27A-FIG. 27C and FIGS. 28A-FIG. 28C). There was a global reduction of T cell and immune checkpoint gene expression, CAR T and myeloid cell signatures, and Immunosign versus levels measured within 4 weeks post-axicabtagene ciloleucel treatment (FIGS. 27A-FIG. 27C). Concurrently, an increase in tumor-associated and immune counterregulatory markers was observed at relapse, including a rebound of B cell lineage, cancer testis antigen (CTA), and regulatory T cell (Treg)-related gene expression (IL-10, CD103, CCR4, CCL17, CCL22; FIG. 28A-FIG. 28B). Among the latter, CCL22 gene expression correlated with Treg (CD3+CD8–FoxP3+) cell density (FIG. 28C). Altogether, these results uncovered dynamic gene expression patterns in the TME that associated with response or relapse post-axicabtagene ciloleucel treatment, linking TME immune features with clinical efficacy.

Example 9

Figures 29A, 29B:
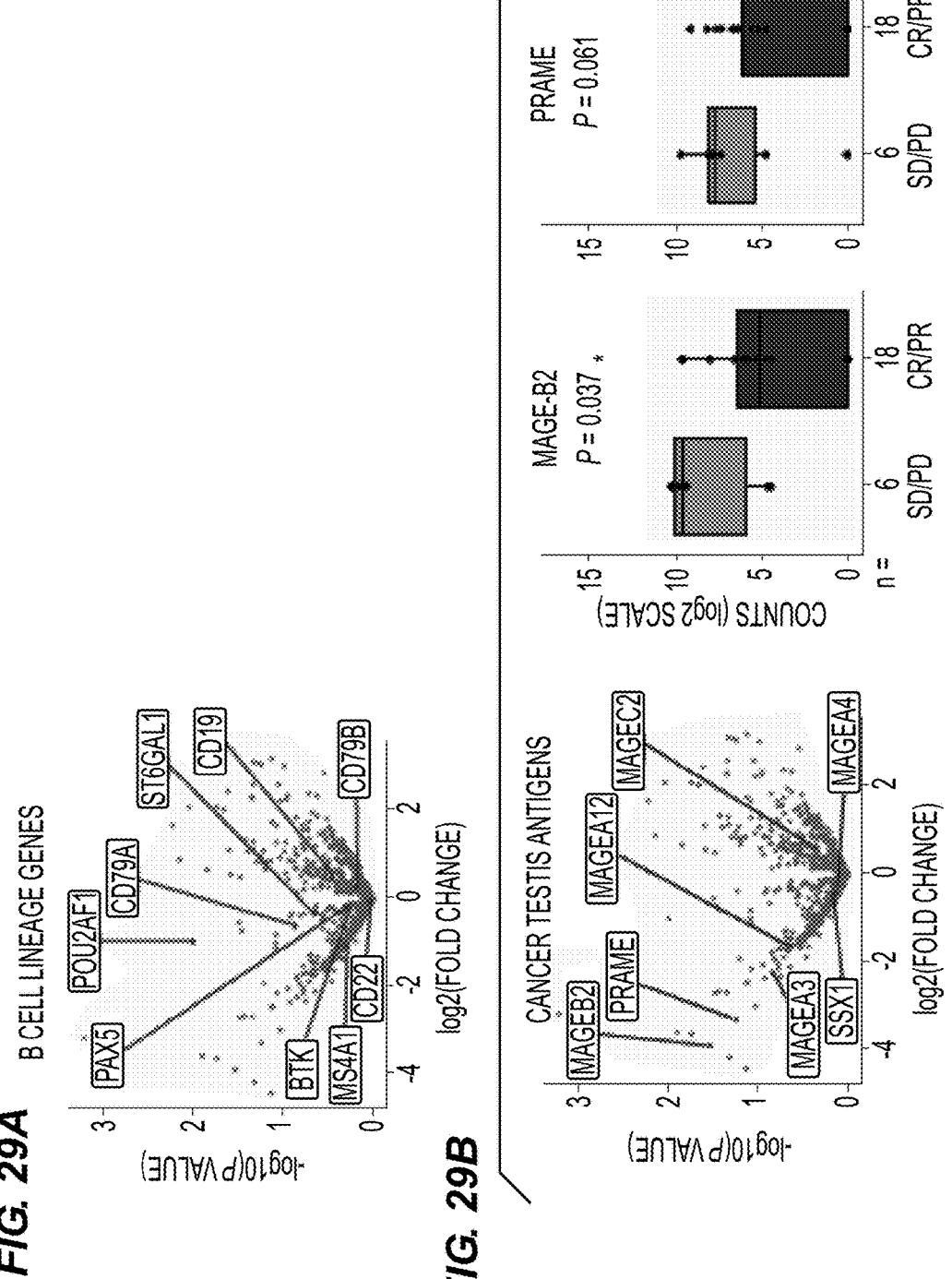
FIGS. 29A-29F An immunologically involved, pretreatment TME associated with axicabtagene ciloleucel clinical response.
Figure 29C:
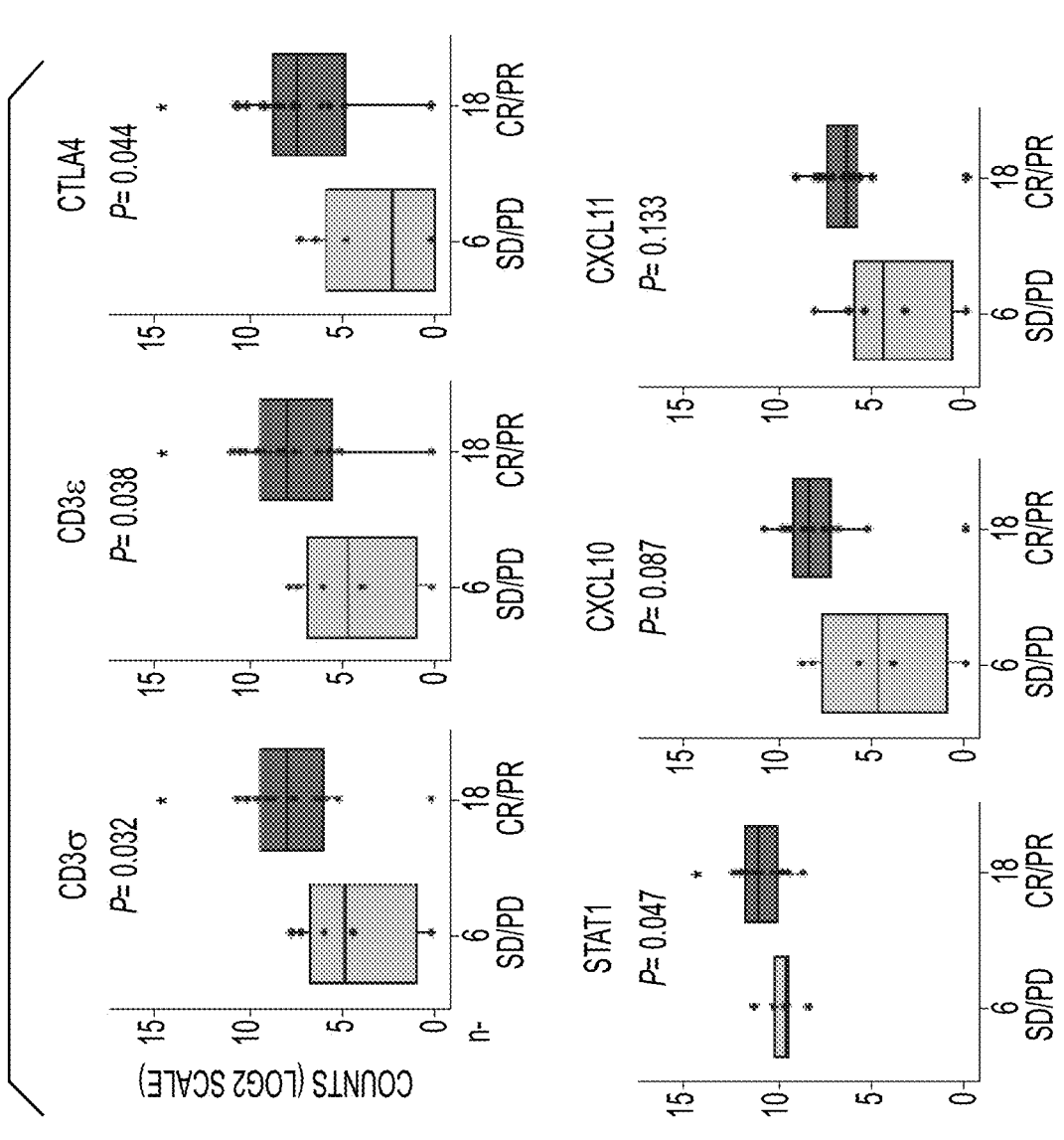

An Immunologically Involved TME Before
Lymphodepletion Associated with Axicabtagene
Ciloleucel Clinical Response While axicabtagene ciloleucel showed comparable efficacy across prognostic groups (Fu, et al. *J Clin Oncol*. 2008;

26:4587-94; Carbone, Gloghini, Kwong and Younes. *Ann Hematol.* 2014; 93:1263-77; Neelapu, et al. *N Engl J Med.* 2017; 377:2531-2544; Locke, et al. *ASCO* 2017. 2017), ~60% of patients exhibited primary treatment resistance (15%) or relapse (45%) within the first year (Locke, et al. Long-term safety and activity of axicabtagene ciloleucel in refractory large B-cell lymphoma (ZUMA-1): a single-arm, multicentre, phase 1-2 trial. *Lancet Oncol.* 2019; 20:31-42), suggesting that yet-to-be-determined tumor or immune features may influence clinical response to this treatment. Systematic analysis of pretreatment (before lymphodepletion (Kochenderfer, et al. *J Clin Oncol.* 2015; 33:540-9.) TME characteristics showed comparable expression of genes corresponding to B cell lineage antigens, including CAR target CD19 as well as CD79 and PAX5, in responders and nonresponders (FIG. 29A). This likely reflected the status of tumor cells of B cell-lineage origin, given that ZUMA-1 patients were largely B cell aplastic at enrollment due to prior rituximab treatment[6]. CTA gene expression (PRAME and MAGE family members) was elevated in the pretreatment TME of nonresponders versus responders (FIG. 29B). Conversely, increased gene expression of select immune-related genes, including T cells (CD3δ, CD3ε), immune checkpoints (CTLA-4), and STAT/IFN program (STAT-1), associated with the TME of patients who later responded to axicabtagene ciloleucel versus nonresponders (FIG. 29C)

Figure 29D:
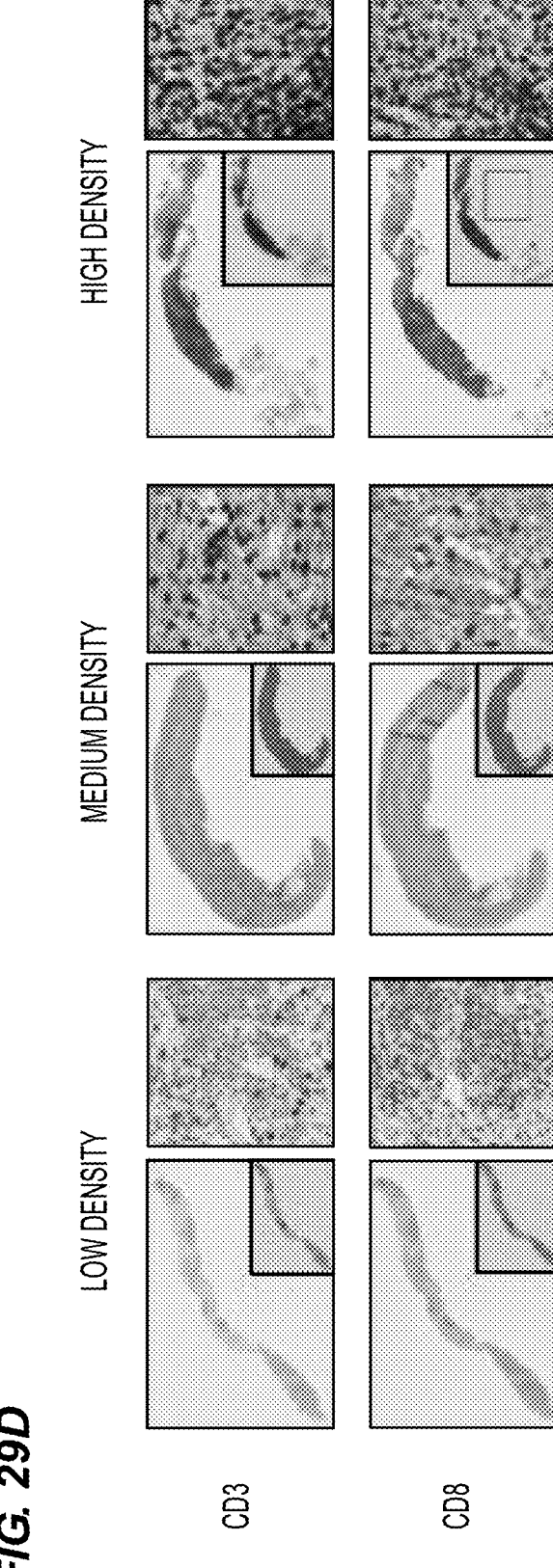
Figures 29E, 29F:
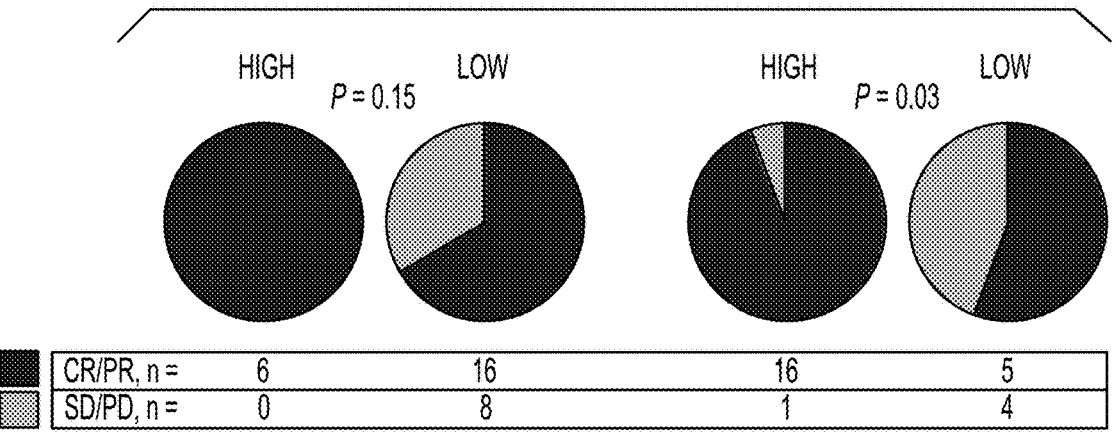
Figure 30A:
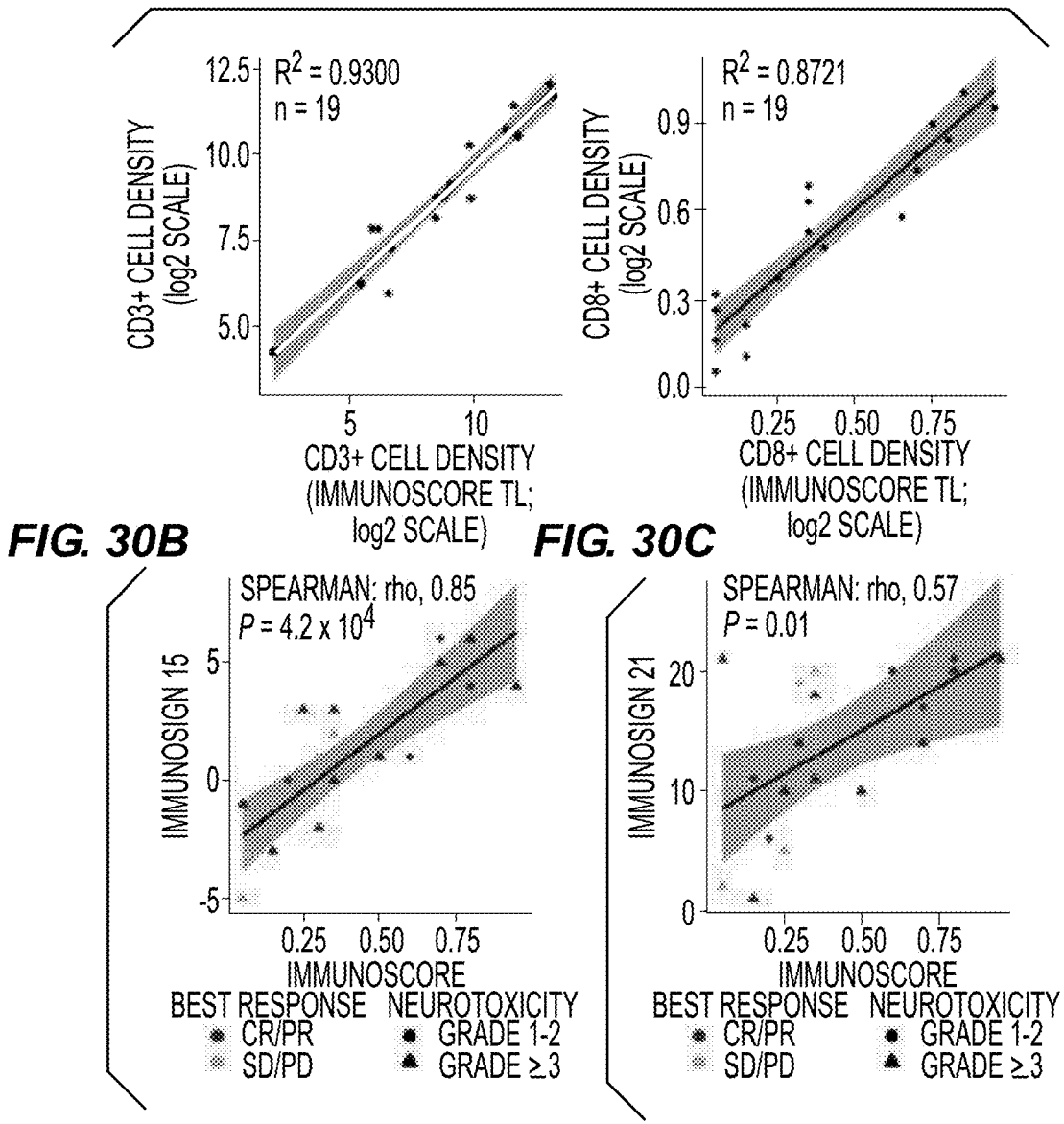
Figure 30D:
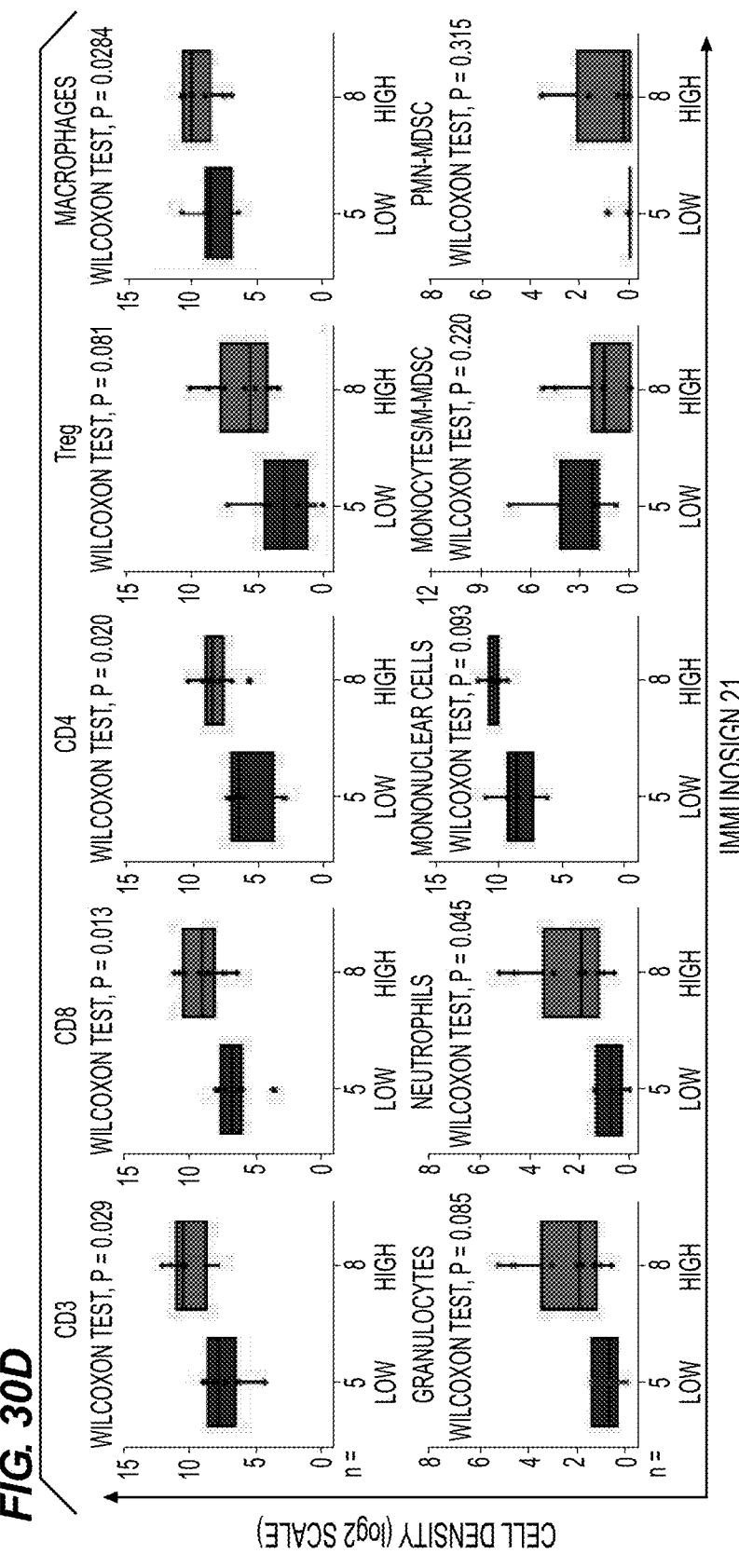
Figure 30E:
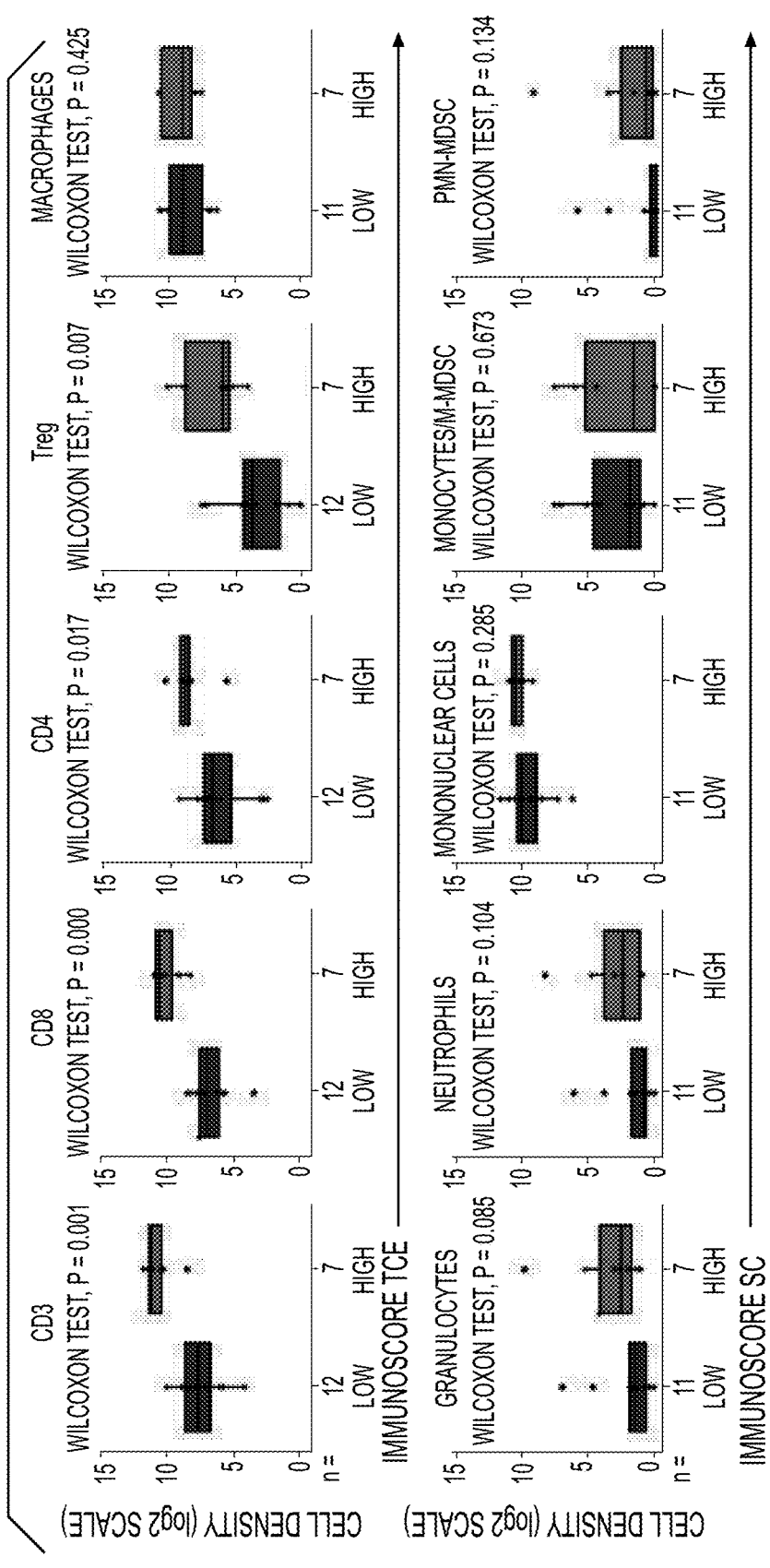
Figure 31A:
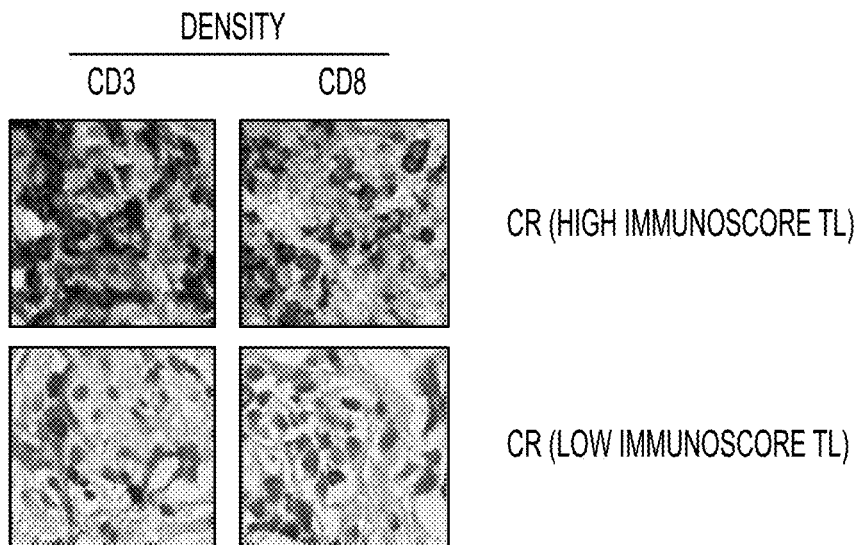
FIGS. 31A-31B Representative expression of tumor-infiltrating immune cells in patients with CR versus PR/SD/PD as assessed using Immunoscore TL, TCE, and SC.
Figure 31B:
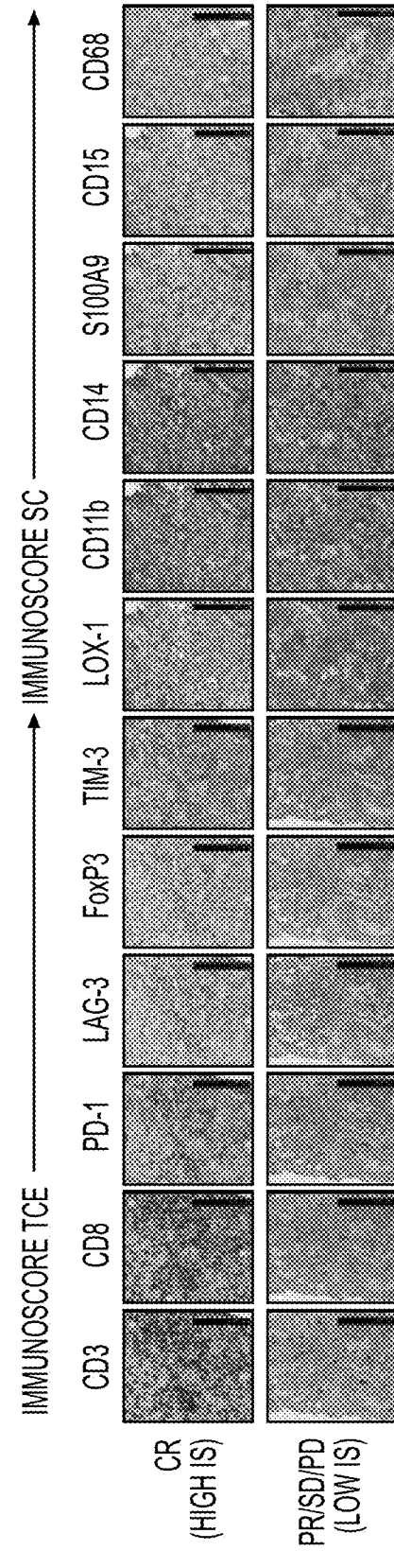
Figure 33A:
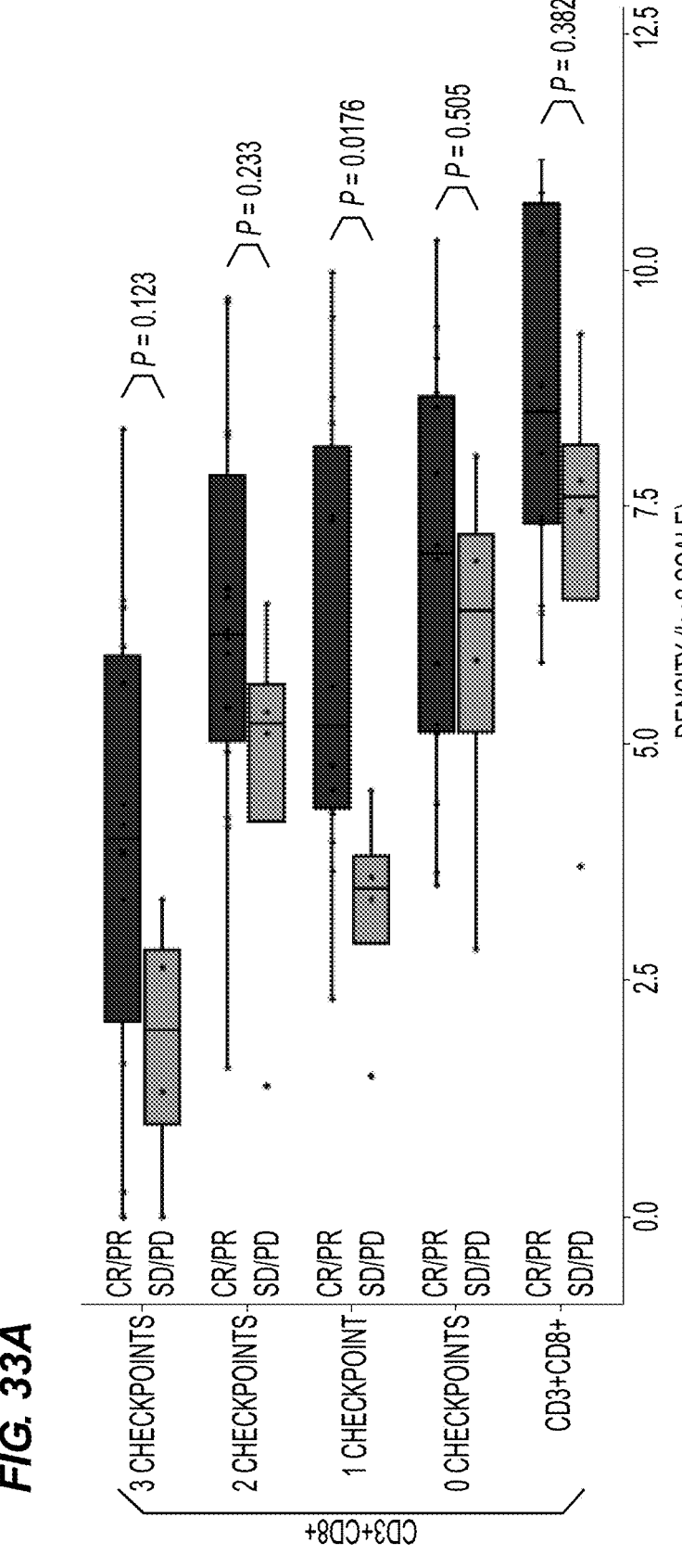
FIG. 33A, Relative densities of activated CD8+ tumor-infiltrating T cell subsets before lymphodepletion was determined by Immunoscore TCE in patients who achieved a response to axicabtagene ciloleucel (CR/PR) versus no response (SD/PD). From top to bottom, CD8+ T cells expressing: 3 checkpoints (PD-1+LAG-3+ TIM-3+), 2 checkpoints (PD-1+LAG-3+ TIM-3- or PD-1+LAG-3-TIM-3+), 1 checkpoint (PD-1+ or LAG-3+), or no checkpoints (PD-1-LAG-3-TIM-3-). Total CD3+CD8+ T cells are shown last.
Figure 33B:
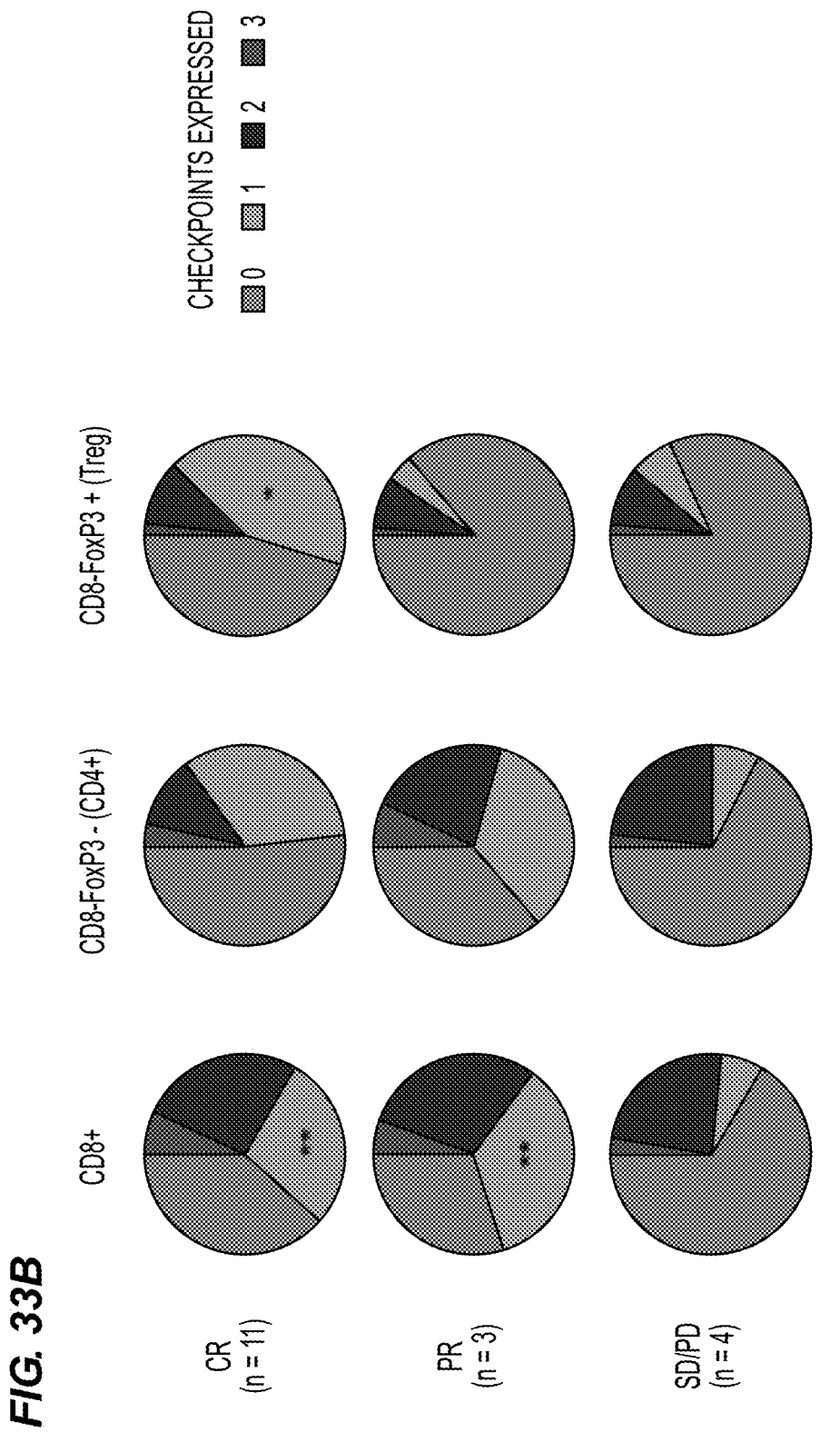
FIG. 33B, Distribution of checkpoints expressed (0, 1, 2, or 3) on tumor-infiltrating T cell subset according to clinical response (CR, PR, SD/PD).

There was marked pretreatment heterogeneity of tumor-infiltrating T cells (FIG. 29D). Notably, corroborating with gene expression analyses, pretreatment density of CD3+ and CD8+ T cells (Immunoscore TL T-Lymphocyte [Immunoscore TL]) positively associated with axicabtagene ciloleucel response (FIG. 29E, FIG. 29F). Similarly, Immunosign 21 (gene panel) measured in pretreatment TME was higher in patients who subsequently responded to axicabtagene ciloleucel versus nonresponders and had significant predictive value of objective response (CR/partial response [PR]; FIG. 29E, FIG. 29F). These findings were paralleled by a positive association between pretreatment Immunoscore TL, Immunosign 15 and 21, and T cell, but not myeloid cell, density (FIGS. 30A-FIG. 30E), underscoring that these indexes capture immune contexture-related features. Further, multiplex IHC (Immunoscore TCE T-Cell Exhaustion [Immunoscore TCE], Immunoscore SC Suppressive Cells [Immunoscore SC]; FIGS. 31A-FIG. 31B; FIGS. 34A-FIG. 34C) uncovered that the pretreatment density of CD8+ T cells with activated phenotype (expression of 1 checkpoint [PD-1+ or LAG-3+]) was most significantly associated with response versus other cell subsets, including nonactivated (expression of 0 checkpoints [PD-1-LAG-3-TIM-3-]) or exhausted (expression of 3 checkpoints [PD-1+LAG-3+TIM-3+]) CD8+ T cells (FIG. 33A, FIG. 33B).

Figure 32A:
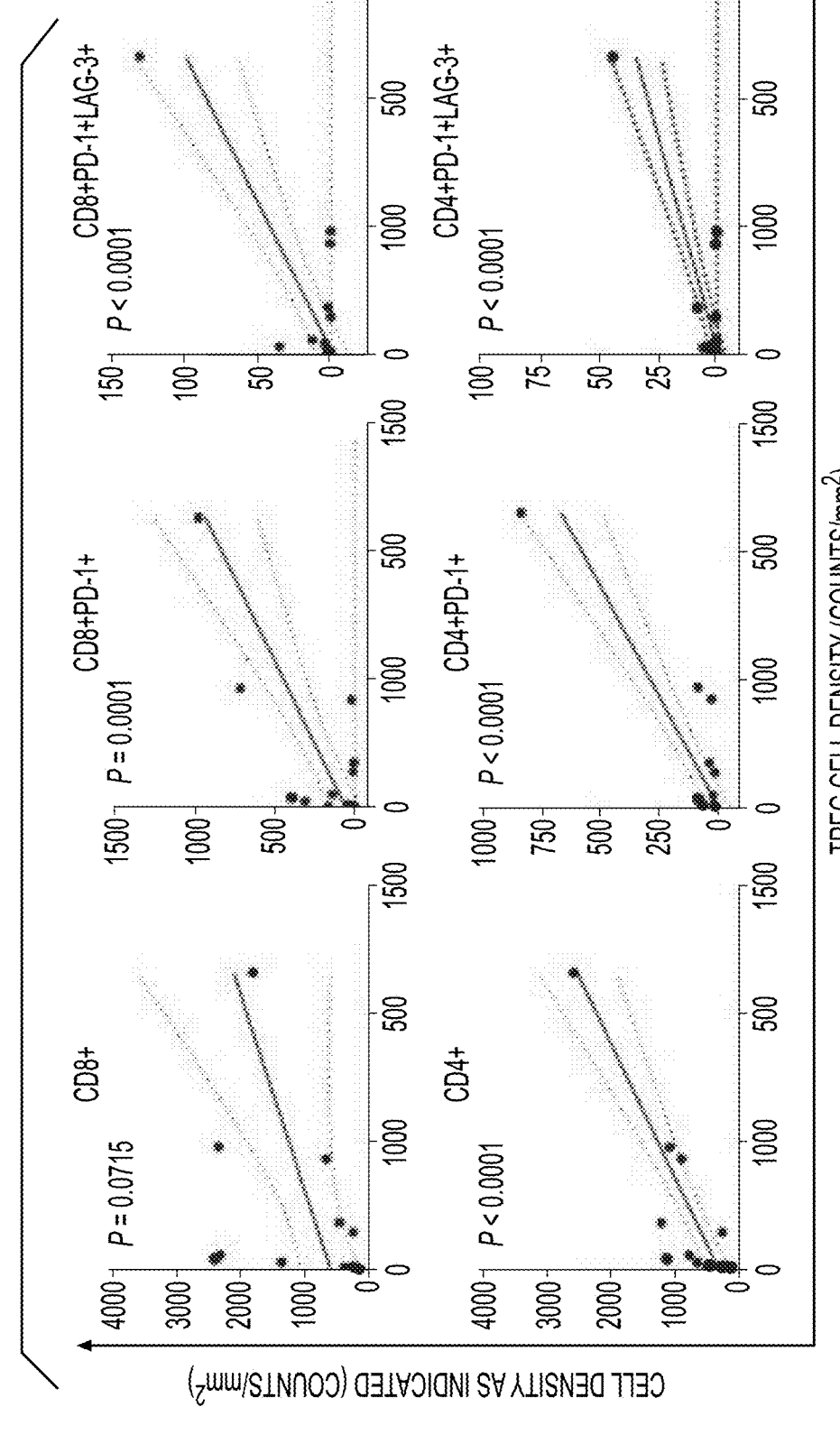
FIG. 32A, Regression analysis of CD3+CD8–FoxP3+ (Treg) cell density with cell density of other immune subsets in the pretreatment TME.
Figure 32B:
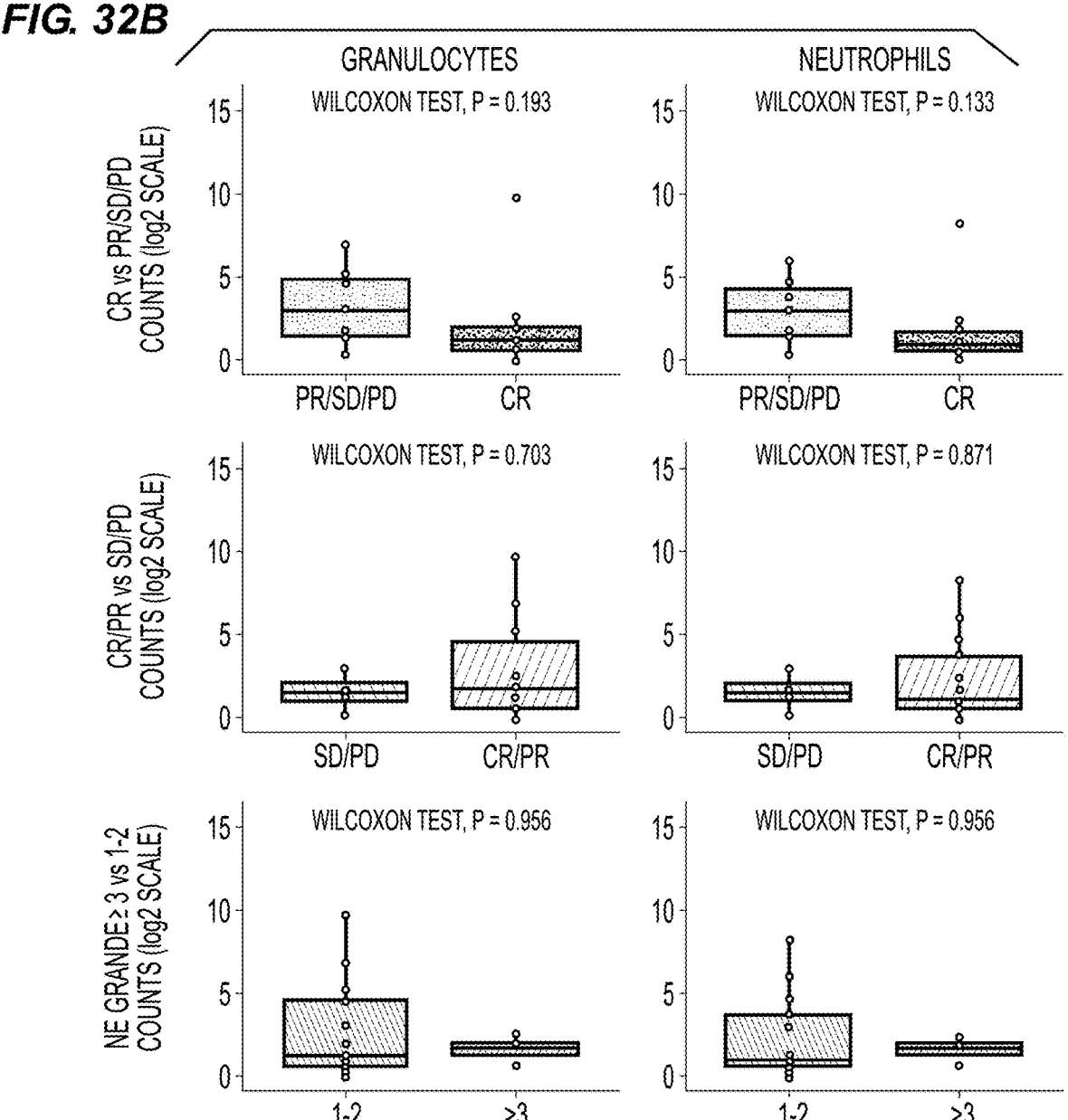
FIG. 32B, Comparison of pretreatment TME density of myeloid cell subsets in patients who achieved CR (n=10) versus PR/SD/PD (n=7; top panels), CR/PR (n=13) versus SD/PD (n=4; middle panels), and by neurotoxicity Grades 1-2 (n=13) versus ≥3 (n=4; bottom panels). Abbreviations: CR, complete response; M-MDSC, monocytic myeloid-derived suppressor cell; PD, progressive disease; PMN-MDSC, polymorphonuclear myeloid-derived suppressor cell; PR, partial response; TME, tumor microenvironment; Treg, regulatory T cell FIGS. 33A-33C Density of activated tumor-infiltrating T cells within the TME before lymphodepletion associated with axicabtagene ciloleucel clinical outcomes.
Figure 33C:
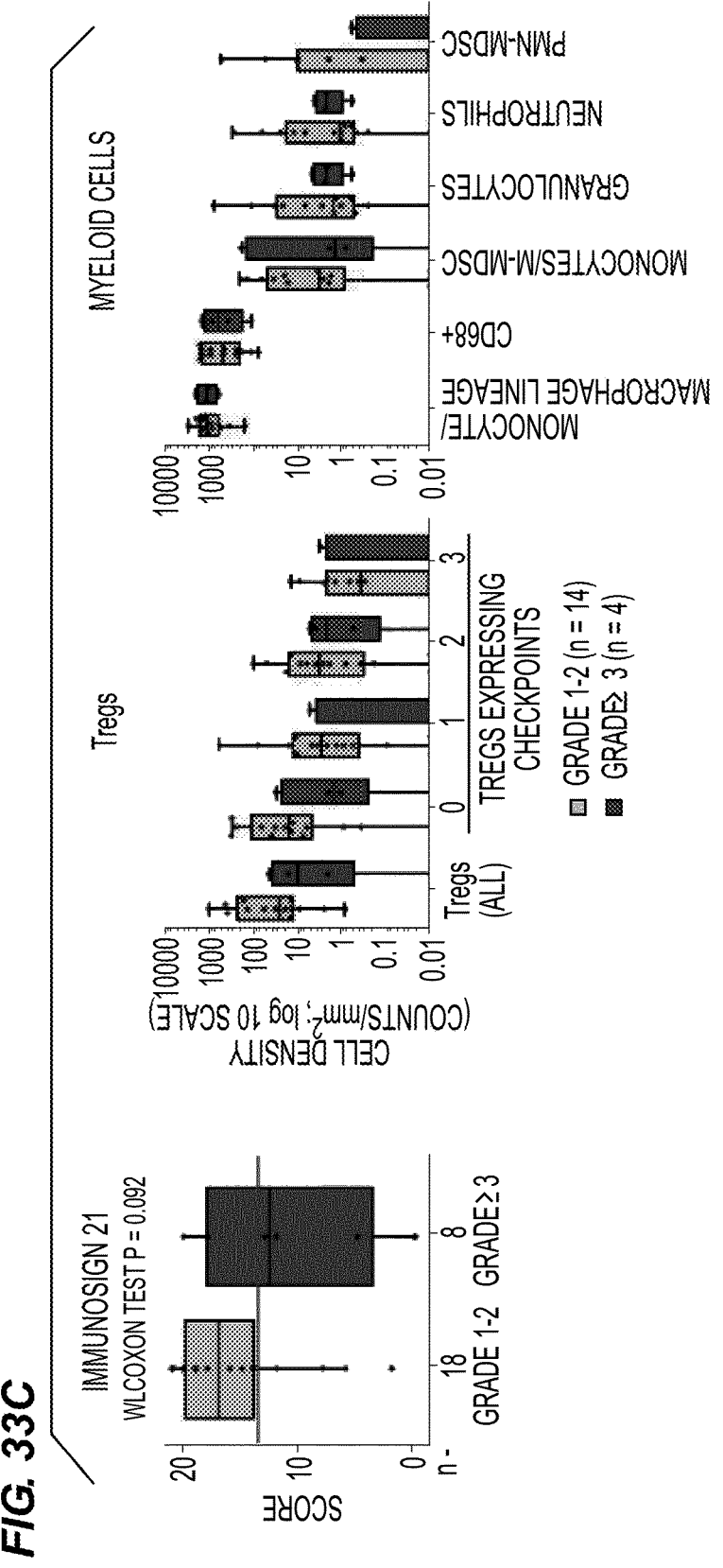
FIG. 33C, Correlation between Immunoscore TL and tumor-infiltrating CD8+ T cells. Immunosign 21 score according to neurotoxicity grade (Grades 1-2 [n=8] versus ≥3 [n=18]); the red line designates the low/high score cutoff. Relative densities of Treg cells and other immune subsets according to neurotoxicity grade (Grades 1-2 [n=14] versus ≥3 [n=4]). *P<0.1 and **P<0.05. Abbreviations: axicabtagene ciloleucel, axicabtagene ciloleucel; CR, complete response; NE, neurotoxicity; PD, progressive disease; PR, partial response; SD, stable disease; TME, tumor microenvironment; Treg, regulatory T cell.

Other features of the pretreatment TME immune contexture were characterized, including the density of Treg and myeloid cells in association with axicabtagene ciloleucel response. The pretreatment TME of patients who developed high-grade neurotoxicity (Grade ≥3) after axicabtagene ciloleucel infusion revealed decreased Immunosign 21 index and reduced infiltration of Treg and polymorphonuclear myeloid-derived suppressor cells (PMN-MDSCs) (Serafini, Mgebroff, Noonan and Borrello. *Cancer Res.* 2008; 68:5439-49; Lindau, Gielen, Kroesen, Wesseling and Adema. *Immunology.* 2013; 138:105-15) versus patients with Grade 1-2 neurotoxicity (FIG. 33C). Interestingly, pretreatment TME density of Treg (CD3+CD8−FoxP3+) cells positively associated with TME features that are desirable from an efficacy standpoint, including with CD8+PD- 1+ T cell density (FIG. 32A). Further, while the pretreatment TME density of CD11b+CD15-CD14+ monocytes and CD68+ macrophages was greater than that of T cell infiltrates (FIGS. 34A-34C), in contrast to T cell subsets, the density of myeloid cell subsets or in aggregate was not significantly associated with clinical outcomes (FIG. 32b).

Figure 35C:
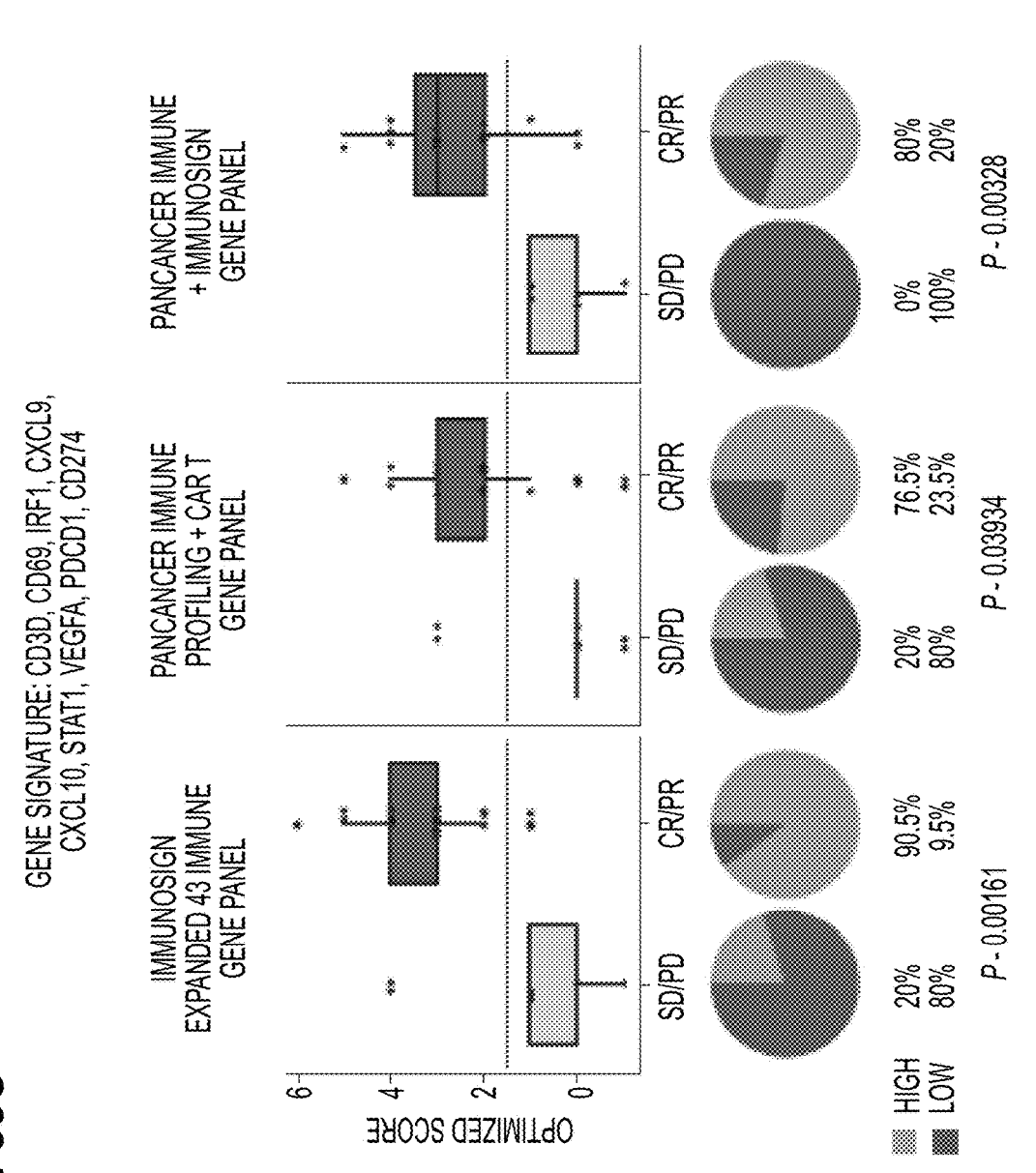
FIG. 35C, The optimized TME gene signature at baseline, comprised of 9 genes, predicted response (CR/PR versus SD/PD) to axicabtagene ciloleucel across 3 NanoString panels. The red line designates the low/high Immunosign score cutoff. P values from Fisher exact test. Abbreviations: CR, complete response; PD, progressive disease; PR, partial response; SD, stable disease; TME, tumor microenvironment FIG. 36 Unsupervised clustering by self-organized neural network map. Each node (neuron) is shown as a circle. Schemas inside each circle are the weight vectors of each node and summarize the cell type distribution representative of the samples mapped to that particular node. Clockwise from the right quadrant: CD3+ T cells; myeloid cells (CD68+, M-MDSC, mononuclear cells, PMN-MDSC, neutrophils, granulocytes); CD3+CD8–FoxP3-T cells expressing 0-3 checkpoints (PD-1-LAG-3-TIM-3–, LAG-3+ TIM-3+PD-1–, LAG-3+PD-1-TIM-3–, PD-1+LAG-3+ TIM-3+, PD-1+LAG-3+ TIM-3–, PD-1+ TIM-3+LAG-3–, PD-1+ LAG-3-TIM-3–); CD3+CD8–FoxP3+ T cells expressing 0-3 checkpoints (same order as previous); and CD3+CD8+ T cells expressing 0-3 checkpoints (same order as previous). Two clusters separated, representing 6 patients with CR (cluster A) and 11 patients with PD or PR (cluster B). Abbreviations: CR, complete response; M-MDSC, monocytic myeloid-derived suppressor cell; PD, progressive disease; PMN-MDSC, polymorphonuclear myeloid-derived suppressor cell; PR, partial response FIGS. 37A-37K Gene list by pathway for patients who subsequently responded to axicabtagene ciloleucel.

Since these indexes were initially developed as prognostic/predictive markers for solid tumors (Angell, Bruni, Barrett, Herbst and Galon. *Clin Cancer Res.* 2019; Yomoda, et al. *Ann Surg Oncol.* 2019; 26:415-424; Sun, Nie, Huang, Kim and Wei. *Lancet.* 2018; 392:1624), retrospective machine learning analysis was applied to 43 immune-related genes (FIG. 26) measured pretreatment using Immunosign to discover a TME index tailored to axicabtagene ciloleucel response and potentially applicable to CAR T cell treatment generally. The resultant signature, which highly associated with axicabtagene ciloleucel response, comprised 9 genes (FIGS. 35A-35C) and requires prospective validation in subsequent trials.

Finally, to determine whether the profile of pretreatment tumor immune infiltrates could stratify patients based on axicabtagene ciloleucel response, a neural network approach with unsupervised clustering was used. By this method, 2 clusters were separated, representing patients with CR (cluster A) and progressive disease or PR (cluster B; FIG. 36). Altogether, these results link pretreatment TME immune features, most notably the density of activated CD8+ T cells expressing 1 checkpoint and Tregs to axicabtagene ciloleucel efficacy and lower neurotoxicity, respectively.

Example 10

Figure 39A:
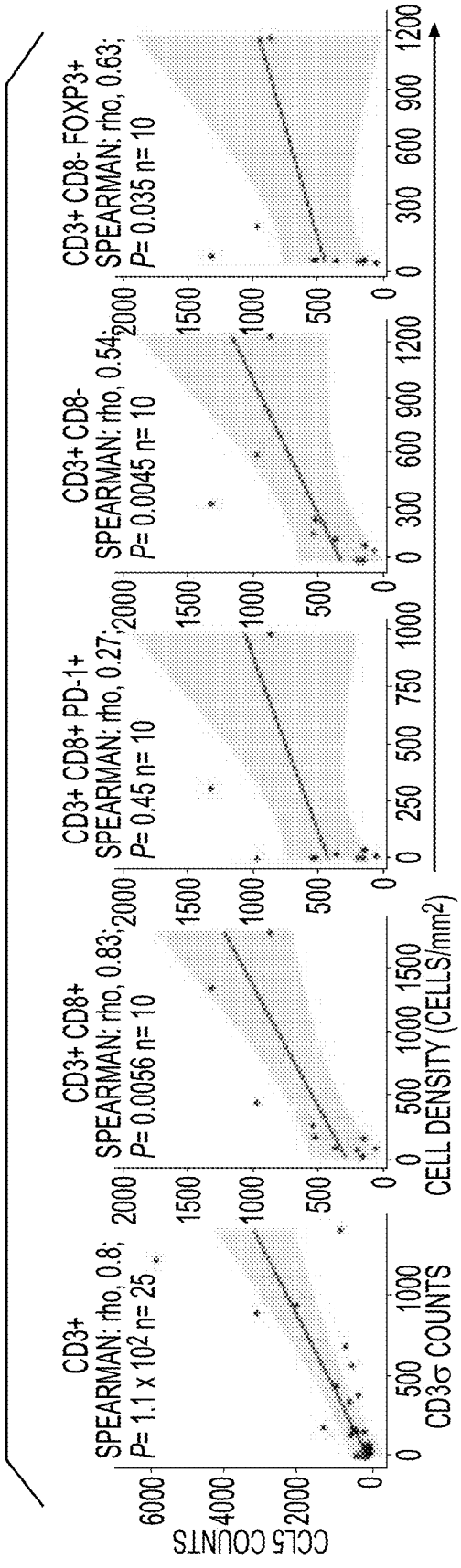
FIG. 39C-FIG. 39E, Correlation between gene expression of FIG. 39C, CCR5 and CCL4, FIG. 39D, IFN-related genes, and FIG. 39E, CXCL9 with the pretreatment density of mononuclear and myeloid cells. Abbreviations: IFN, interferon; TME, tumor microenvironment.
Figure 39B:
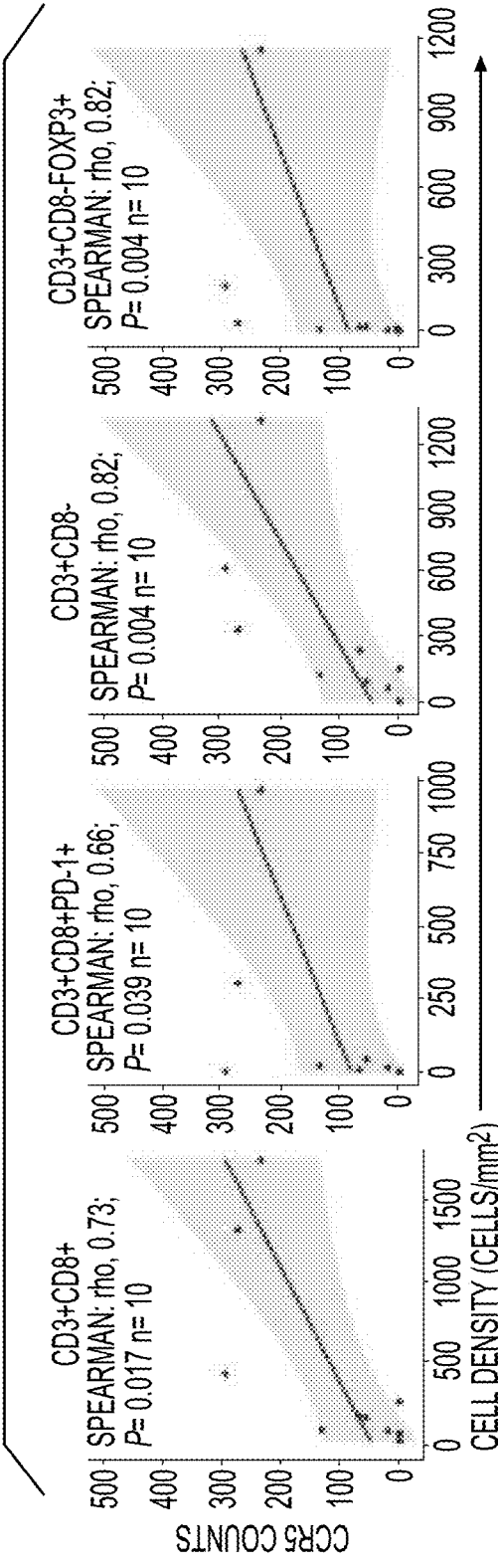
Figure 39C:
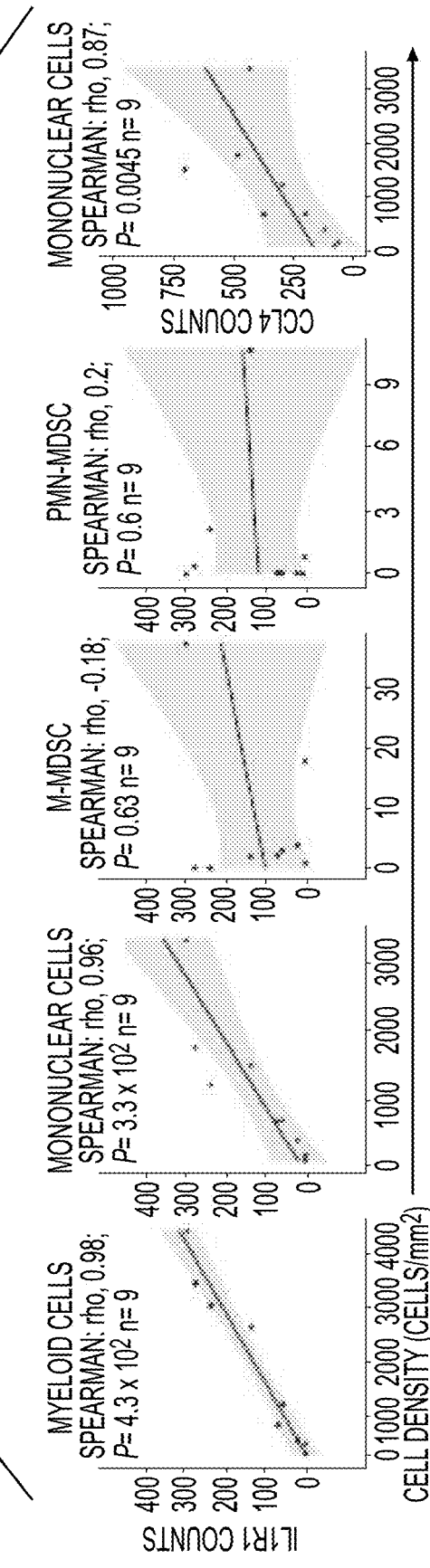
Figure 39D:
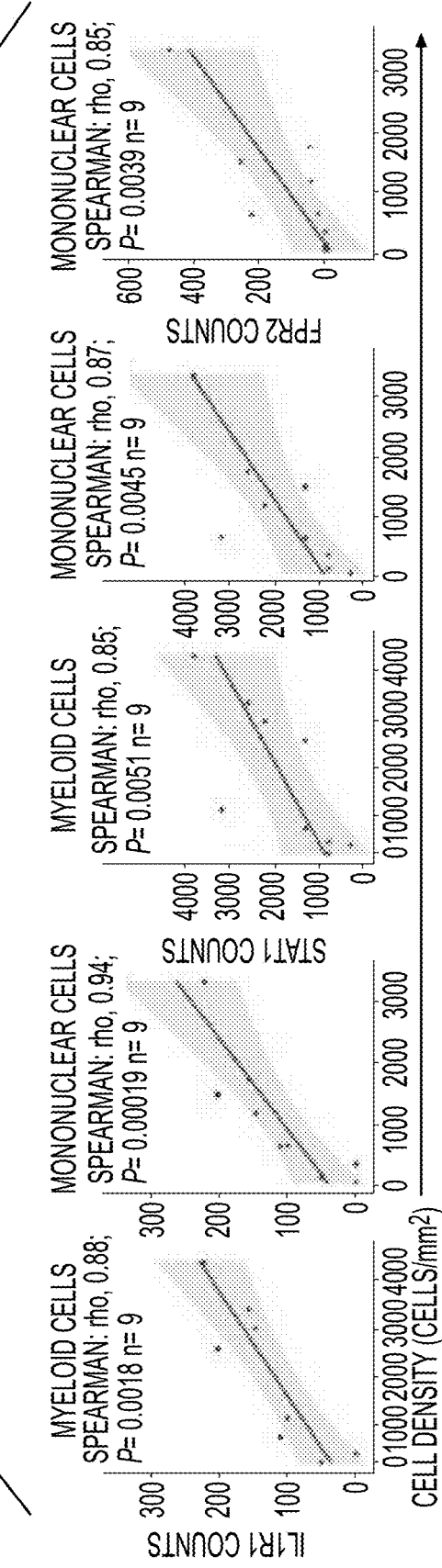
Figure 39E:
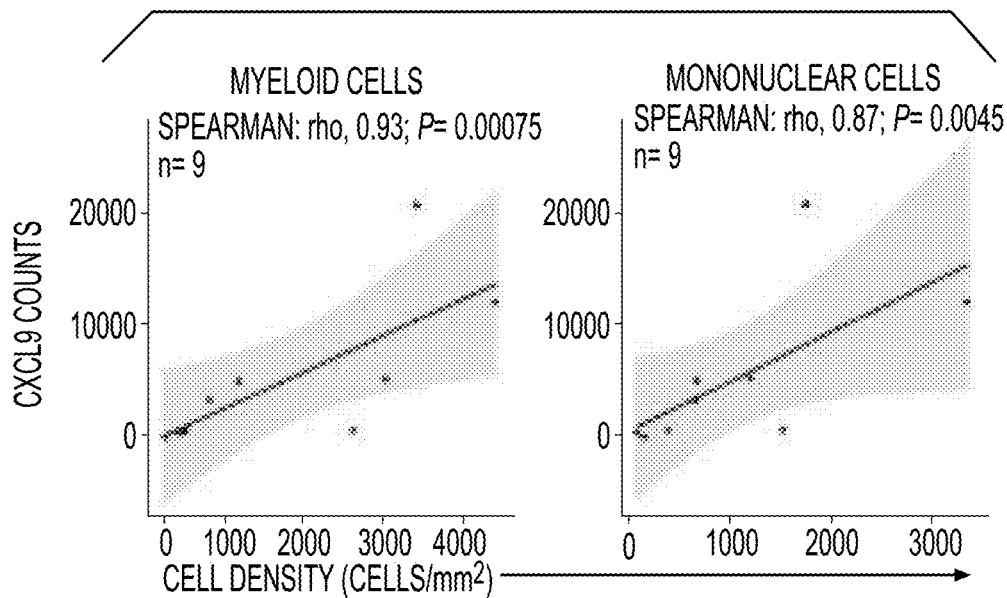

A T Cell-Involved Tme, Comprising Cytokines and Chemokines with Known Effect on T Cells, Associated with the Ratio of Car T Cell Expansion/Pretreatment Tumor Burden Since select features of tumor biology and TME may determine the degree of T cell involvement, which associated with axicabtagene ciloleucel clinical response, pretreatment TME cytokine and chemokine genes and their receptors were analysed for their association with T cell gene expression and density. Expression of key cytokines and chemokines directly correlated with T cell gene expression, including IL-7/IL-7R, IL-18, CCL5 (CD3δ, CD8α, CD4), CCR5, IL-15 (CD3δ, CD8α), and IL-21 (CD3δ) (FIGS. 37A-37K, FIGS. 38A-38C). Concordantly, a direct association was observed between pretreatment TME density of CD8+ and CD4+ T cells by IHC and gene expression of CCL5 and CCR5 (FIG. 39A, FIG. 39B). Pretreatment TME myeloid cell density (CD11b+ and CD14+) also directly associated with CCR5, IL-1R, STAT1, FPR2, and CXCL9 gene expression levels (FIG. 39C-FIG. 39E).

Figure 40A:
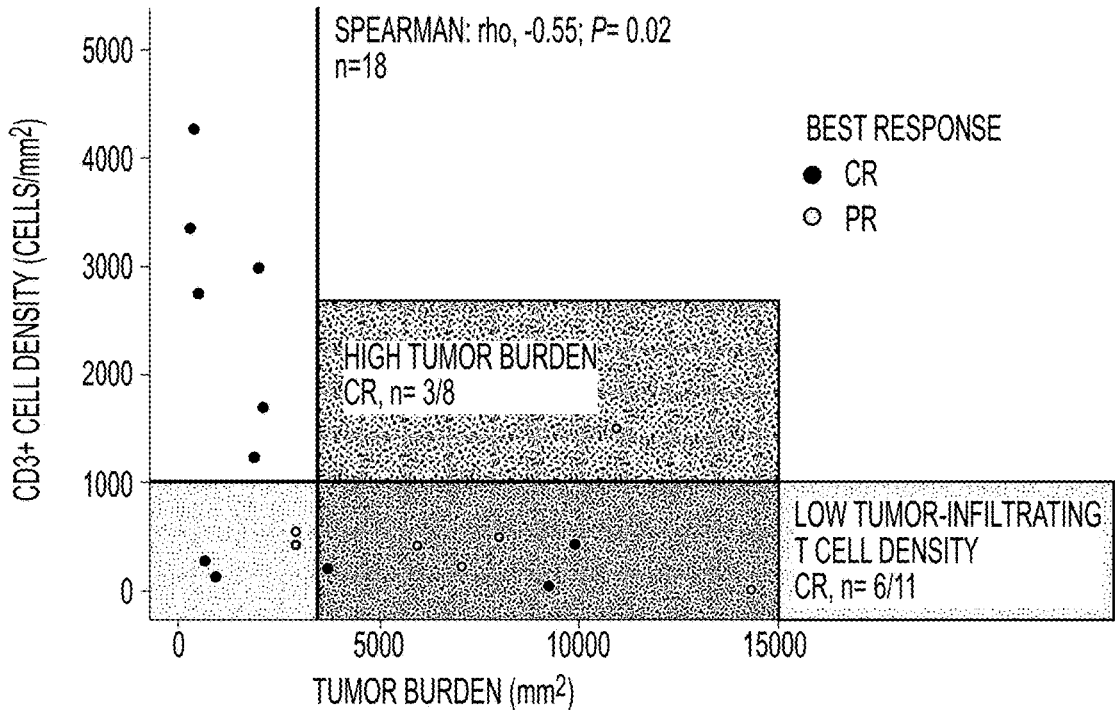
FIGS. 40A-40B Correlation between pretreatment TME T cell density and tumor burden in relation to axicabtagene ciloleucel clinical outcomes. TME infiltration of CD3+ cells was determined pretreatment (prelymphodepletion) via Immunoscore TL (cell count/mm$^2$). Tumor burden was measured using the sum of the products of the diameters for the selected lesions at baseline in absolute numbers (mm$^2$).
Figure 40B:
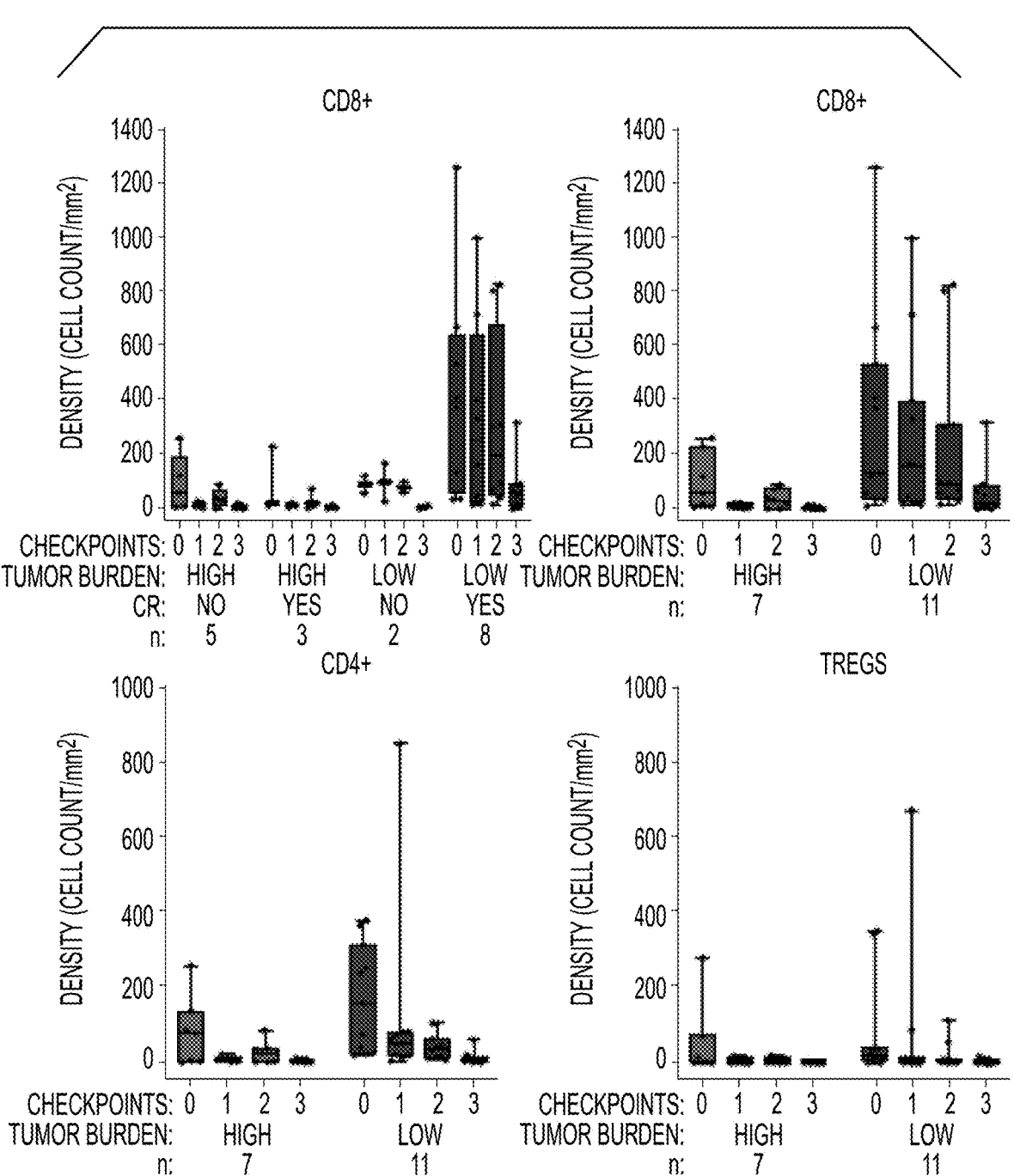
Figure 41A:
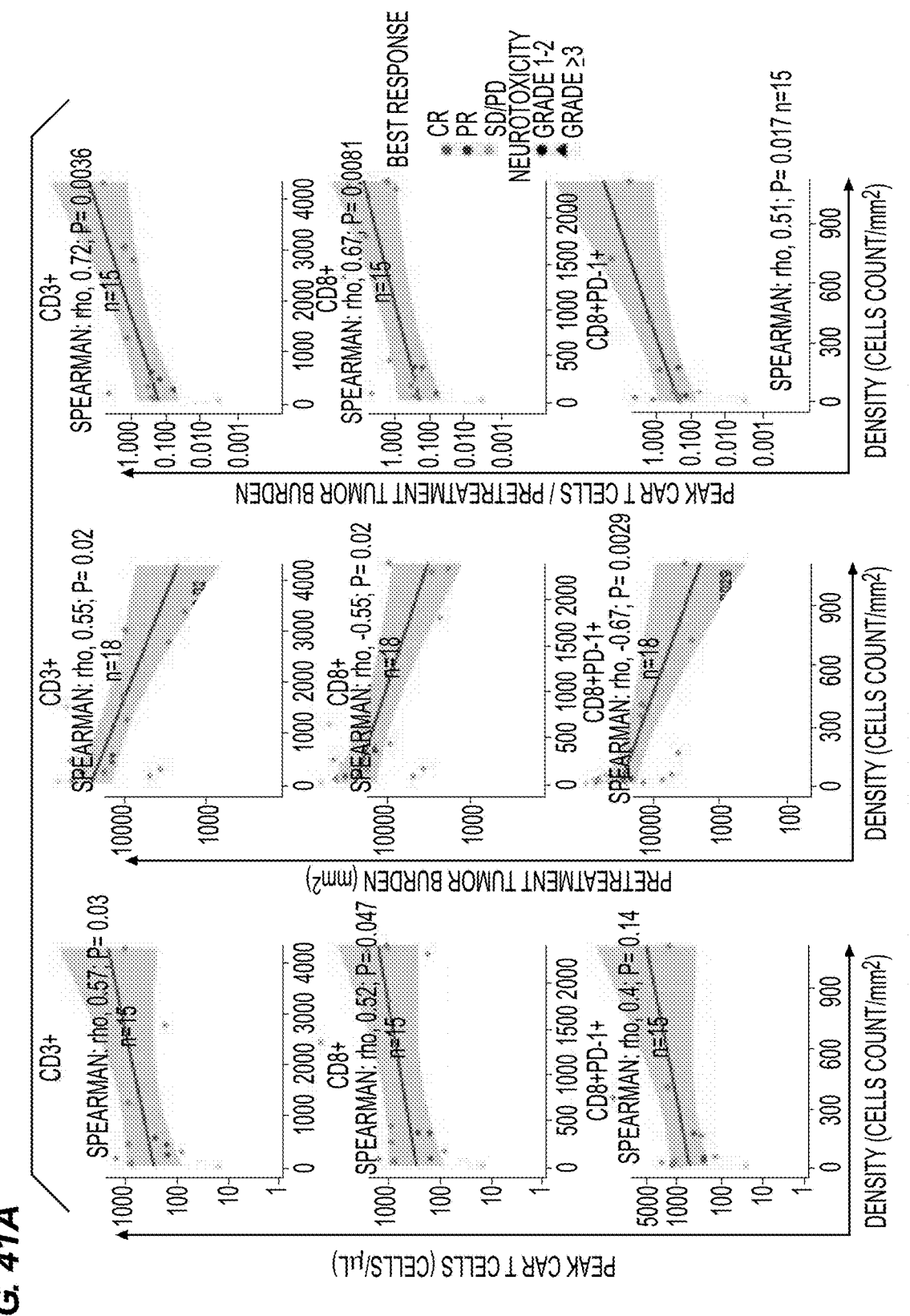
FIGS. 41A-41B Peak CAR T cell levels/tumor burden regression analyses.
Figure 41B:
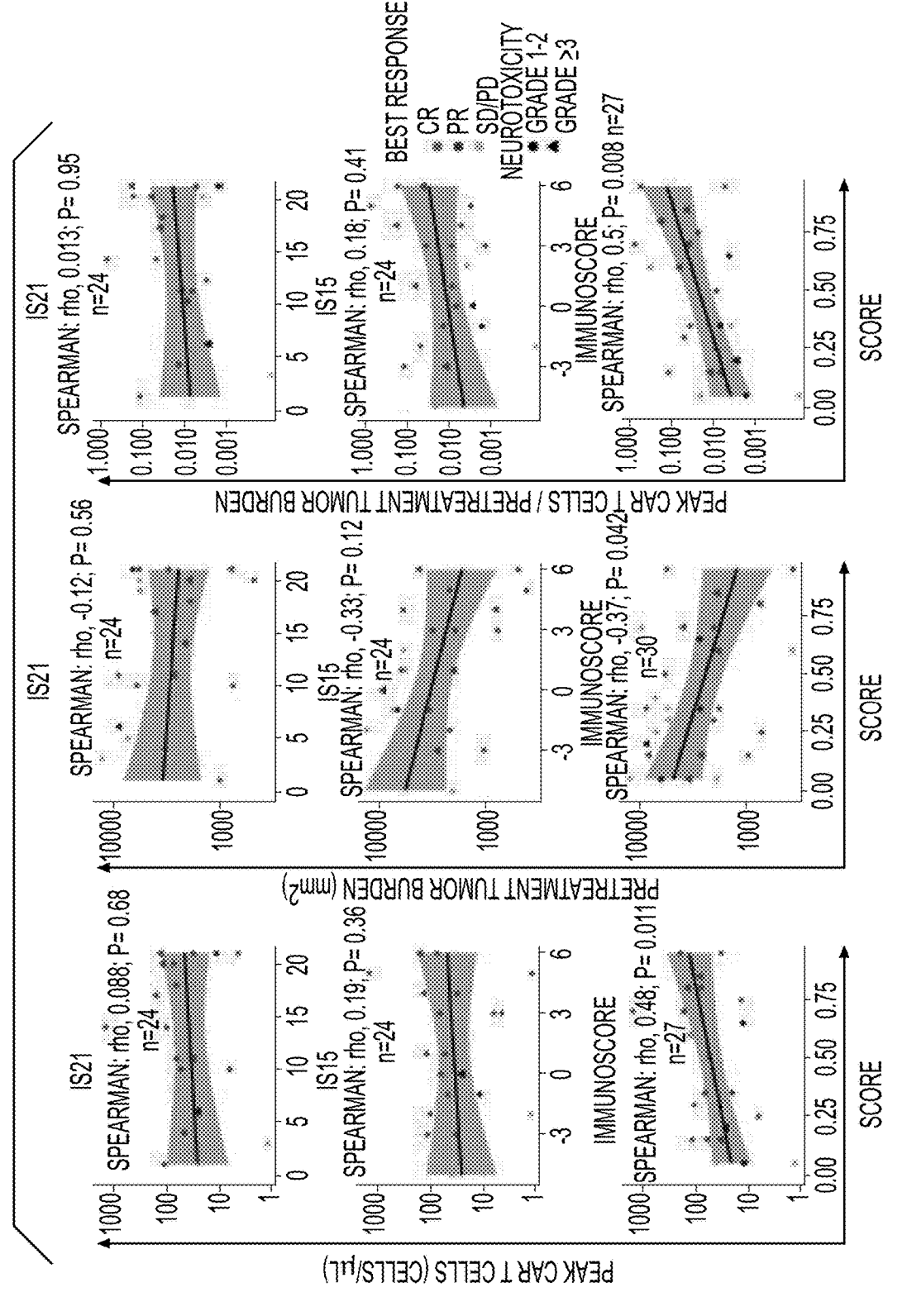

As higher pretreatment tumor burden may be a negative predictor for axicabtagene ciloleucel (Locke, et al. Long-term safety and activity of axicabtagene ciloleucel in refractory large B-cell lymphoma (ZUMA-1): a single-arm, multicentre, phase 1-2 trial. *Lancet Oncol.* 2017 20:31-42) efficacy, the relationship between T cell infiltration and tumor burden was examined. Indeed, higher pretreatment tumor burden negatively associated with density and activation of tumor-infiltrating T cells. All patients with low tumor burden and high tumor-infiltrating T cell density achieved CR, and pretreatment TME CD8+ T cell density and checkpoint expression were higher for CR patients with low tumor burden than in any other group. In contrast, fewer than half of the patients with high tumor burden achieved CR (FIGS. 40A-40B). These results support that 2 major tumor characteristics, immune contexture and tumor burden, jointly influence axicabtagene ciloleucel efficacy. Notably, about half of patients with low pretreatment tumor-infiltrating T cell density still achieved CR, suggesting that CAR T cell intervention may be capable of overcoming a less immunologically involved TME. Indeed, there was a significant, direct association between pretreatment TME CD8+PD-1+ T cell density, or Immunoscore, and peak CAR T cell levels in blood normalized to pretreatment tumor burden (FIGS. 41A-41B).

Overall, these data support the hypothesis that a T cell-involved TME may be driven by the local production of T cell-attractive chemokines and γ-chain receptor cytokines, which defines a favorable niche for axicabtagene ciloleucel activity with maximal efficacy in patients with both favorable immune contexture and low tumor burden.

Current adoptive CAR T cell strategies are based on synthetic biology to endow T cells with the capability of recognizing and eliminating tumor cells through CAR expression (June, O'Connor, Kawalekar, Ghassemi and Milone. *Science*. 2018; 359:1361-1365; June and Sadelain. *N Engl J Med*. 2018; 379:64-73; Boyiadzis, et al. *J Immunother Cancer*. 2018; 6:137). While a number of prognostic markers, like cell of origin (ABC, GCB) and cytogenetic abnormalities (translocation or overexpression of c-Myc, BCL-2, BCL-6, Ki-67), are widely utilized for high-grade LBCL designation, CAR T cell intervention has shown comparable efficacy across these prognostic subgoups (Sesques and Johnson. *Blood*. 2017; 129:280-288; Locke, et al. *ASCO* 2017. 2017). We present here the comprehensive gene expression analyses and multiplex IHC of 115 biopsies from LBCL patients treated with axicabtagene ciloleucel (n=55), with documented anatomic location in 56% of the cases (FIG. 42). We discovered that immune contexture plays a major role in therapeutic response. Foremost, this study showed that evolution of the TME gene signature occurs rapidly post-axicabtagene ciloleucel treatment and is a hallmark of, as well as a potential pharmacodynamic marker for, clinical response. Responders show rapid upregulation of T cell-related signature and downregulation of B cell tumor-related markers, defining a dynamic pattern that separated responders from nonresponders within 2 weeks posttreatment. While these changes were observed rapidly post-axicabtagene ciloleucel treatment, it would be valuable in future studies to assess TME changes that occur before Day 5 following CAR T cell infusion, given that patients with strong response tend not to have assessible tumor by Day 7, suggesting that even greater changes may have been observed with earlier assessment. Responders also had increased gene expression of immune checkpoints (predominantly PD-1) and IL-15, which have known involvement in CAR T cell expansion and activity. This suggests that the local provision of γ-chain receptor cytokines, like IL-15, may help overcome primary treatment failure. *J Clin Oncol*. 2015; 33:540-9). Upon patient relapse, the TME acquired an immune-detrimental contexture with decreased T cell signature and increased tumor-associated and immune counterregulatory markers (Okeke and Uzonna. *Front Immunol*. 2019; 10:680), including IL-10. *J Immunol*. 2008; 180:5771-7), FoxP3 and CCR4 (Sugiyama, et al. *Proc Natl Acad Sci USA*. 2013; 110:17945-50), CCL17 and CCL22 (Mizukami, et al. *Int J Cancer*. 2008; 122:2286-93), and ITGAE (CD103) (Anz, et al. Though our sample size was limited, these results, pending validation, suggest that immune-based therapies with curative potential, like axicabtagene ciloleucel, should be considered in earlier lines of treatment to potentially maximize clinical benefit.

Figure 43:
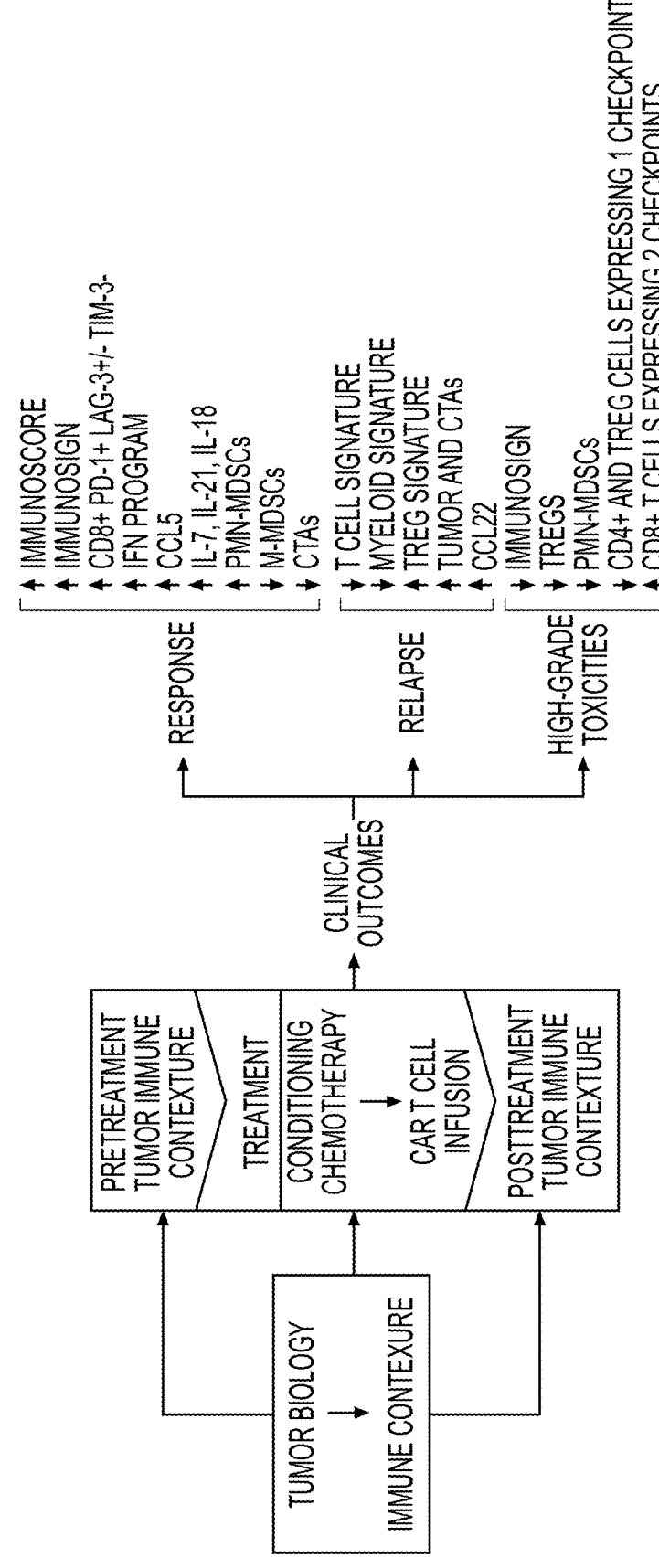
FIG. 43 Proposed model linking pretreatment tumor immune contexture and an immunologically involved TME with response to axicabtagene ciloleucel. Pretreatment tumor biology features supporting a TME rich in select chemokines (CCL5), γ-chain receptor cytokines (IL-15, IL-7), and IFN-regulated molecules help favor recruitment and activation of tumor-infiltrating T cells, thereby facilitating clinical response to axicabtagene ciloleucel following infusion. The TME gene expression profile of axicabtagene ciloleucel responders evolves rapidly towards an activated T cell-related signature paralleled by a declining tumor-related signature, markedly differing from the pattern observed in nonresponders. At relapse, the TME evolves once more, but towards an immune-detrimental contexture, with decreased T cell signature and increased counterregulatory molecules. Further, the pretreatment TME of patients who developed high-grade neurotoxicities differed compared to that of patients who did not. Patients with Grade ≥3 neurotoxicity had decreased expression of immune-related genes and reduced infiltration of Tregs within the pretreatment TME, suggesting a protective role for Tregs against toxicity without an apparent impact on response under the conditions evaluated. Abbreviations: CAR, chimeric antigen receptor; CTA, cancer testis antigen; IFN, interferon; M-MDSC, monocytic myeloid-derived suppressor cell; PMN-MDSC, polymorphonuclear myeloid-derived suppressor cell; TME, tumor microenvironment; Treg, regulatory T cell.
Figure 44A:
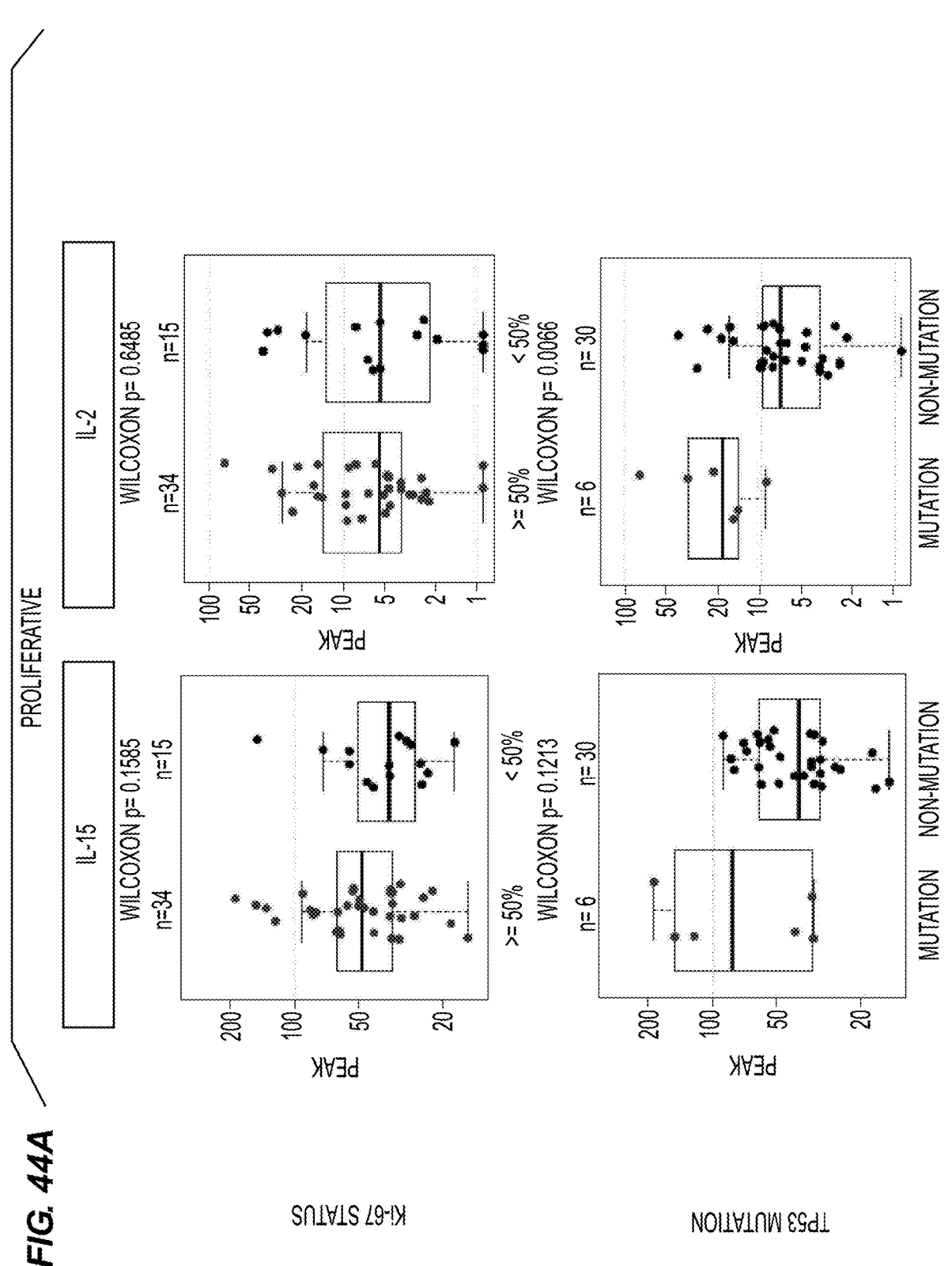
FIGS. 44A-44F: Comparable pharmacodynamic profile in prognostic groups defined by Ki-67 proliferation index, and trend for increased cytokine levels in patients with mutated TP53.
Figure 44B:
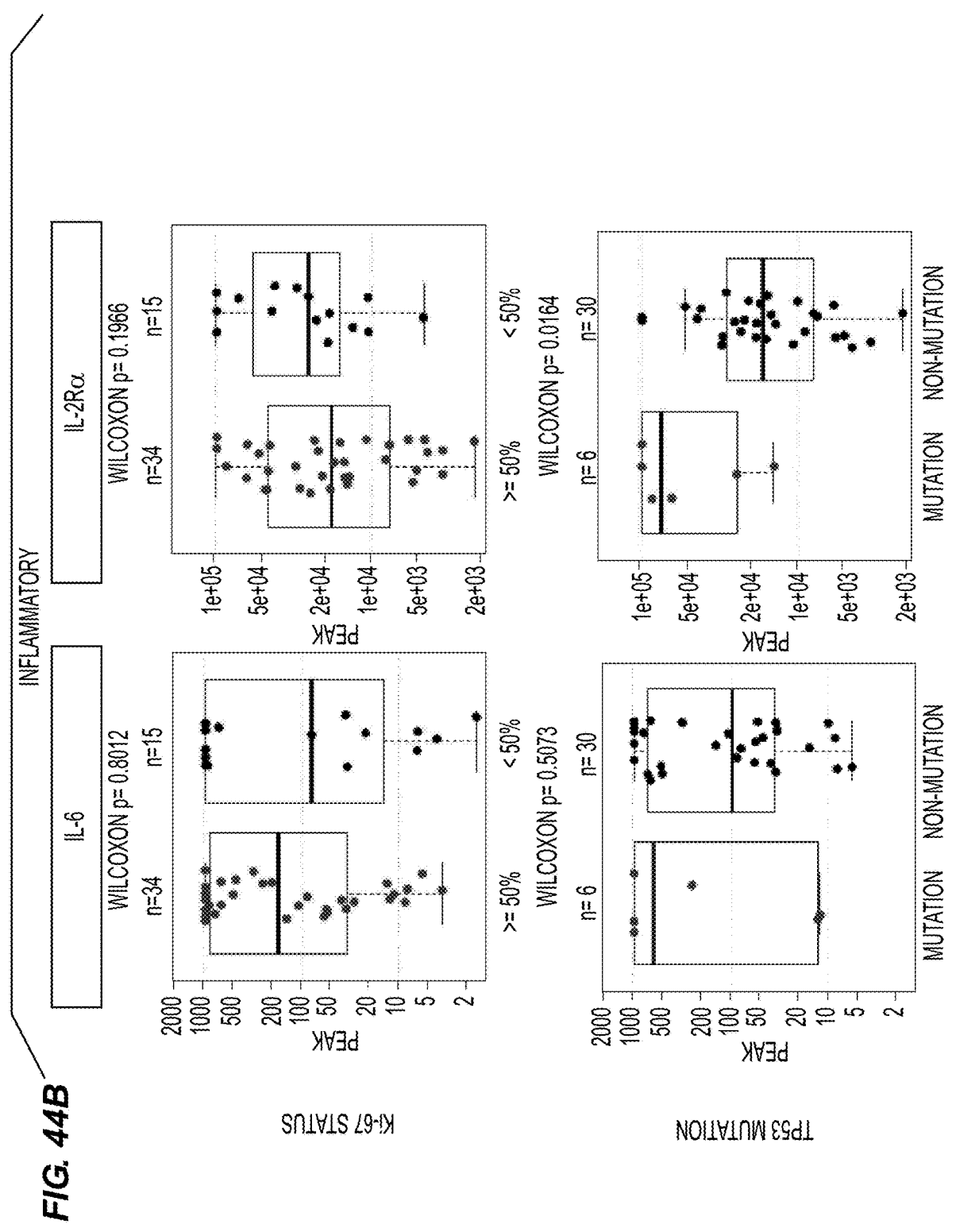
Figure 44C:
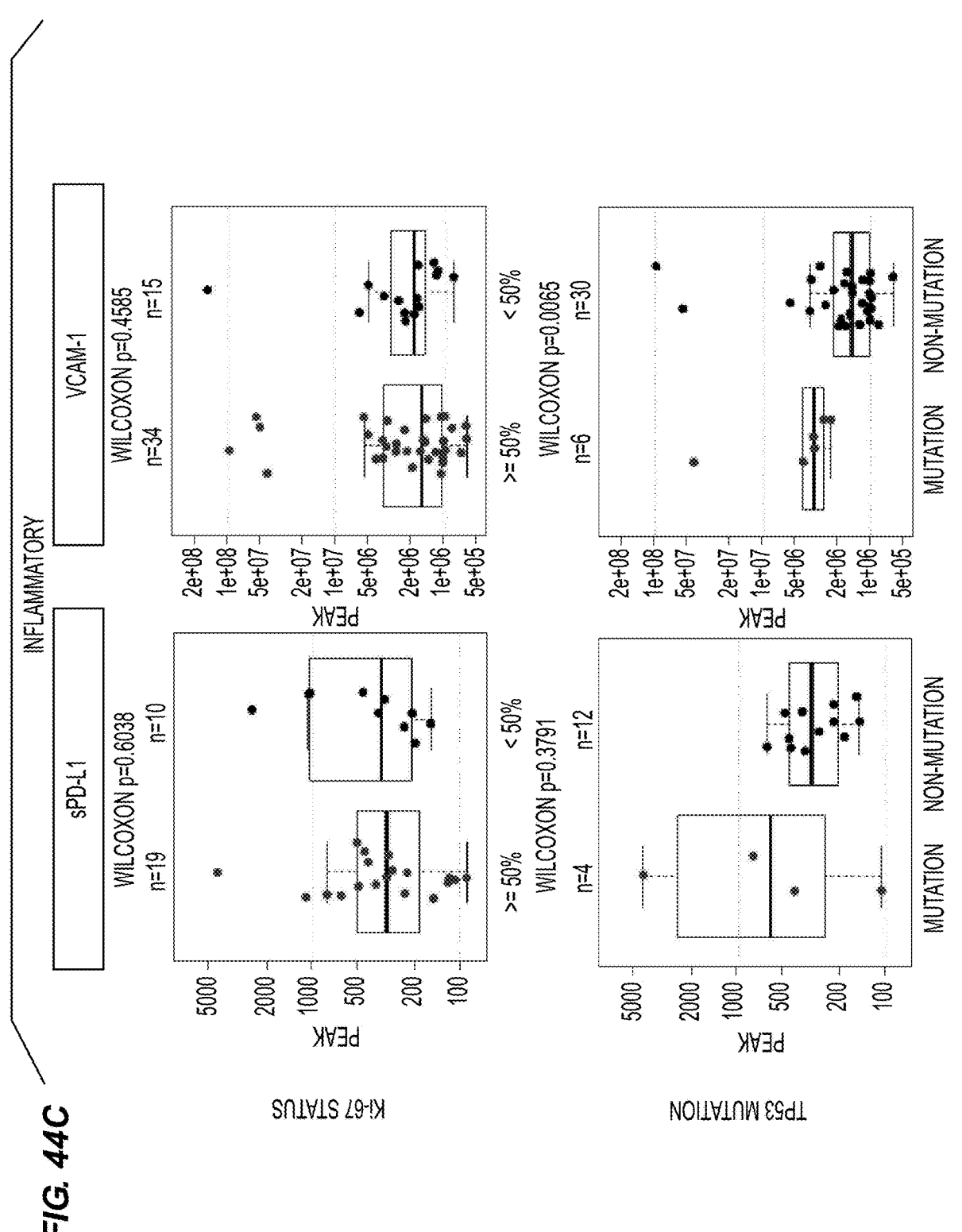
Figure 44D:
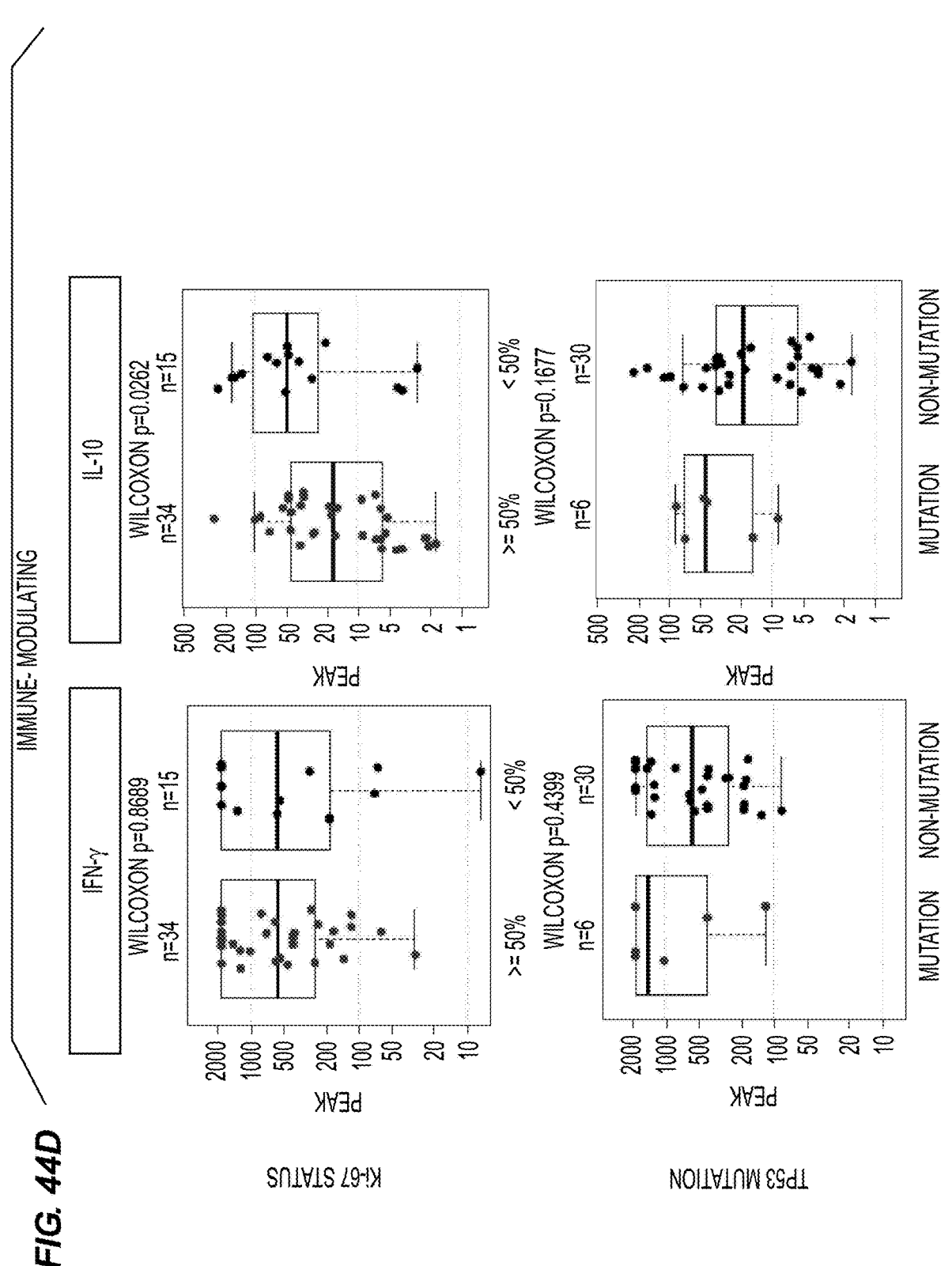
Figure 44E:
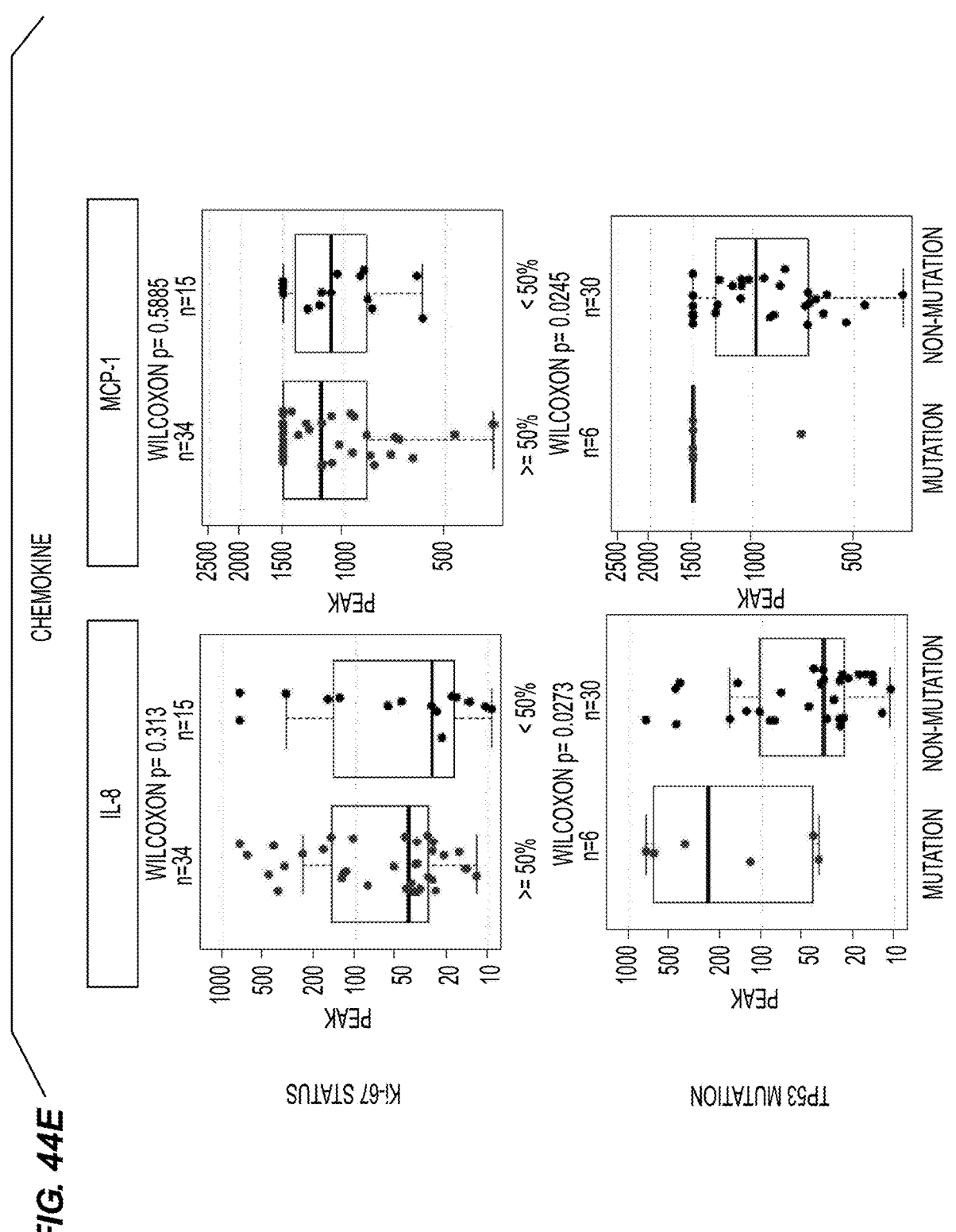
Figure 44F:
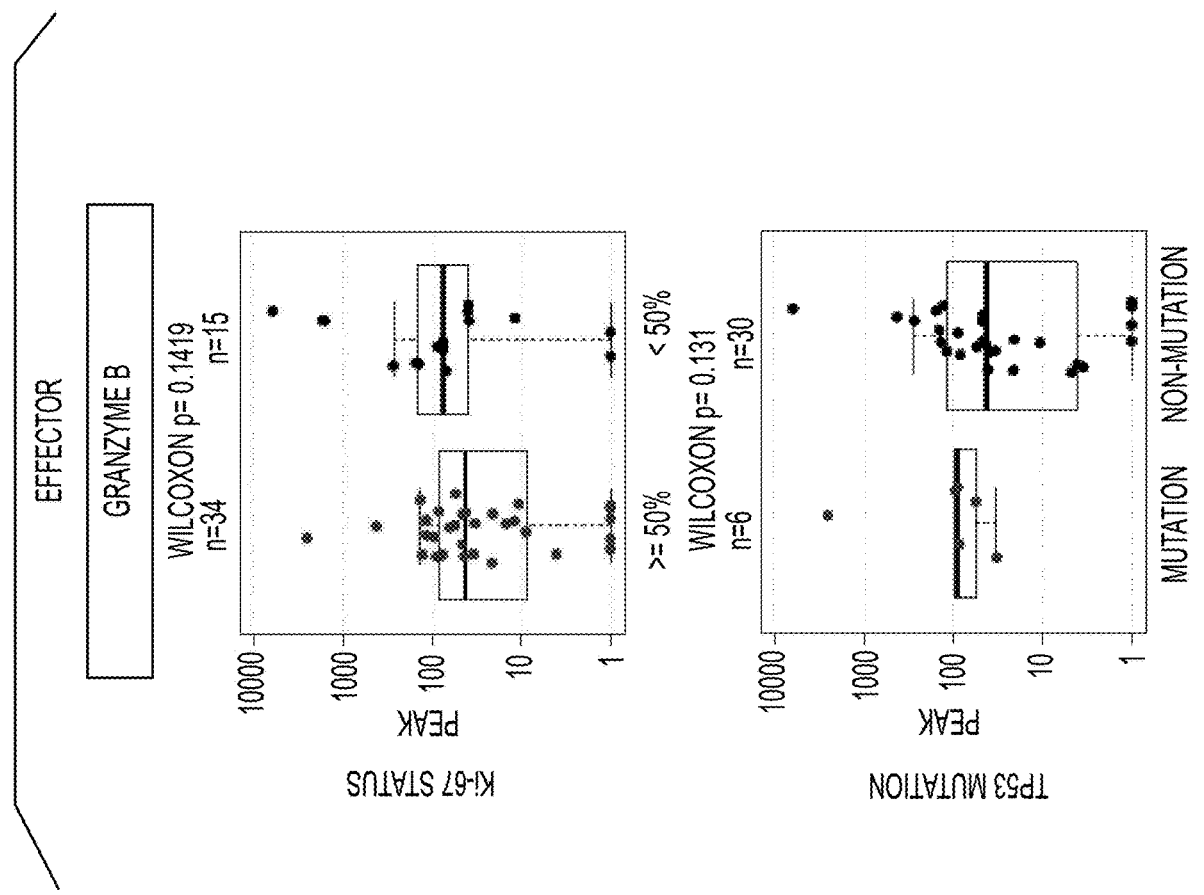
Figure 45A:
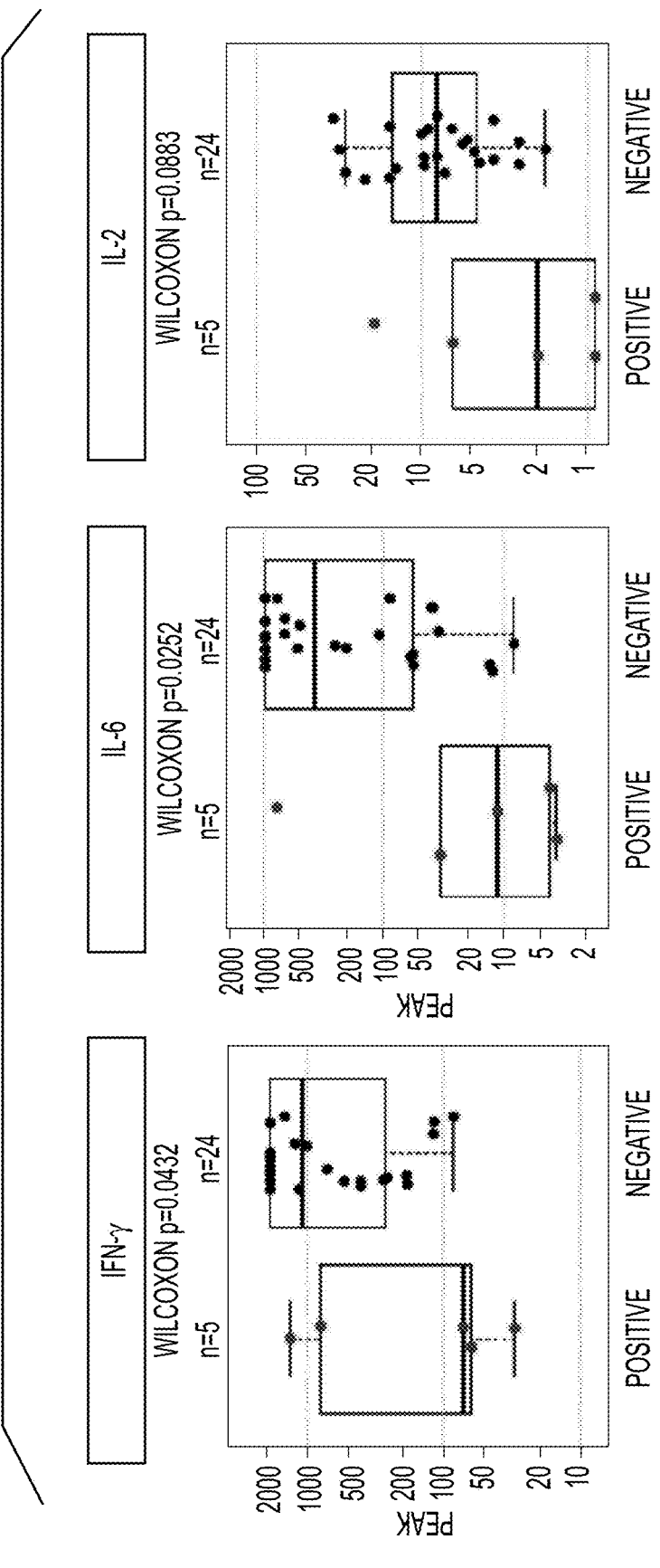
FIGS. 45A-45I: Increased peak levels of select cytokines in serum among patients who achieved MRD-negative status.
Figure 45B:
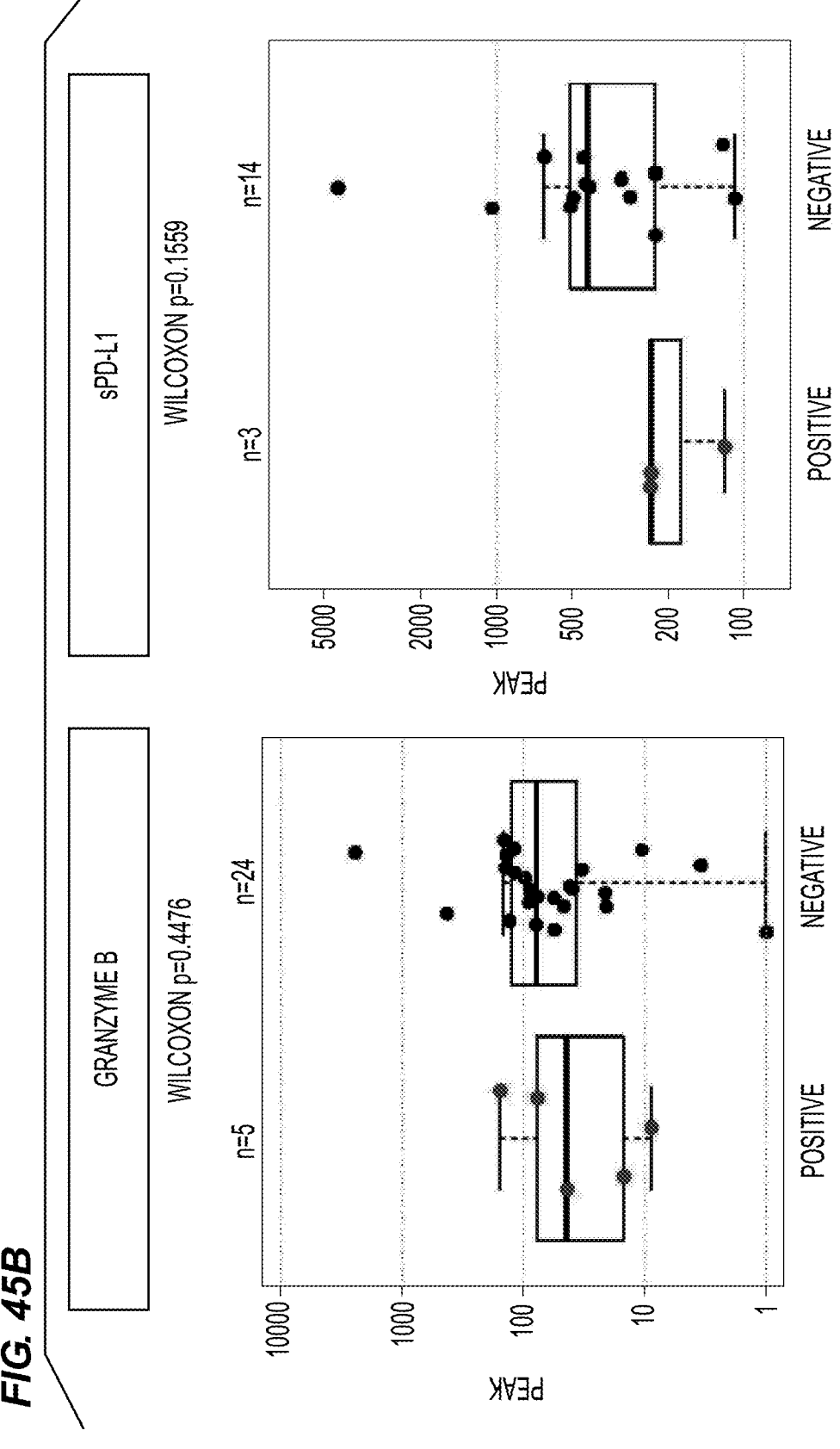
Figure 45C:
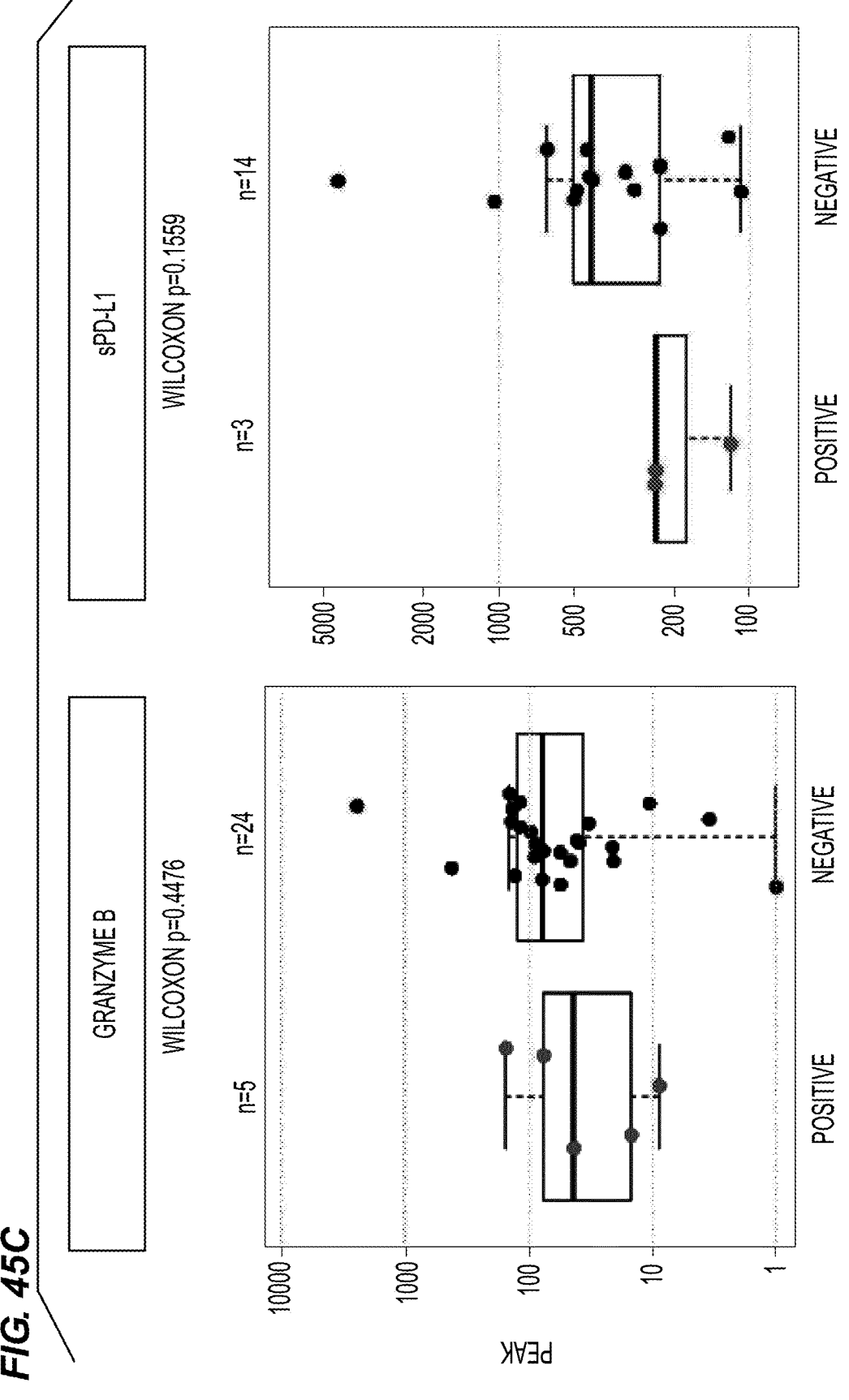
Figure 45D:
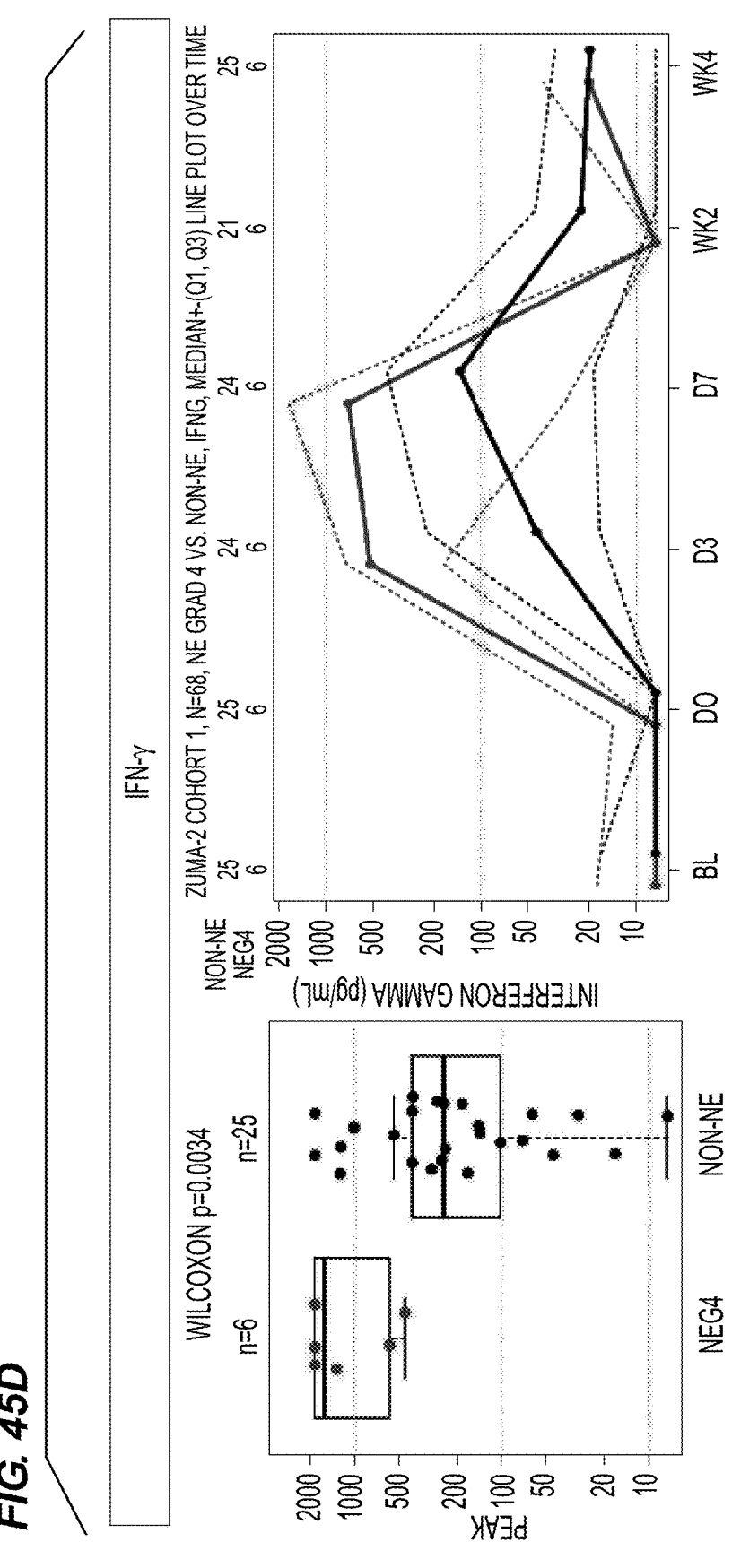
Figure 45E:
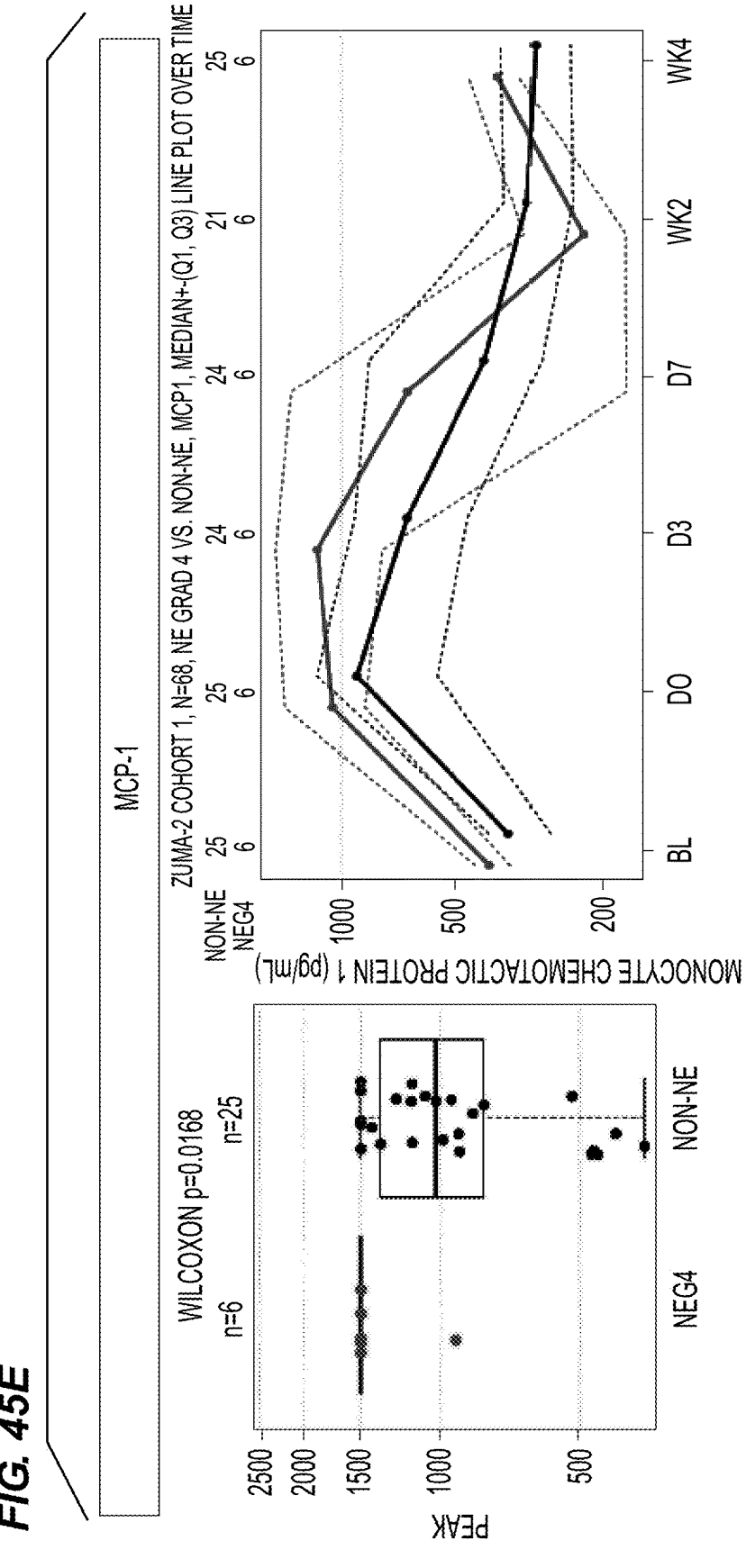
Figure 45F:
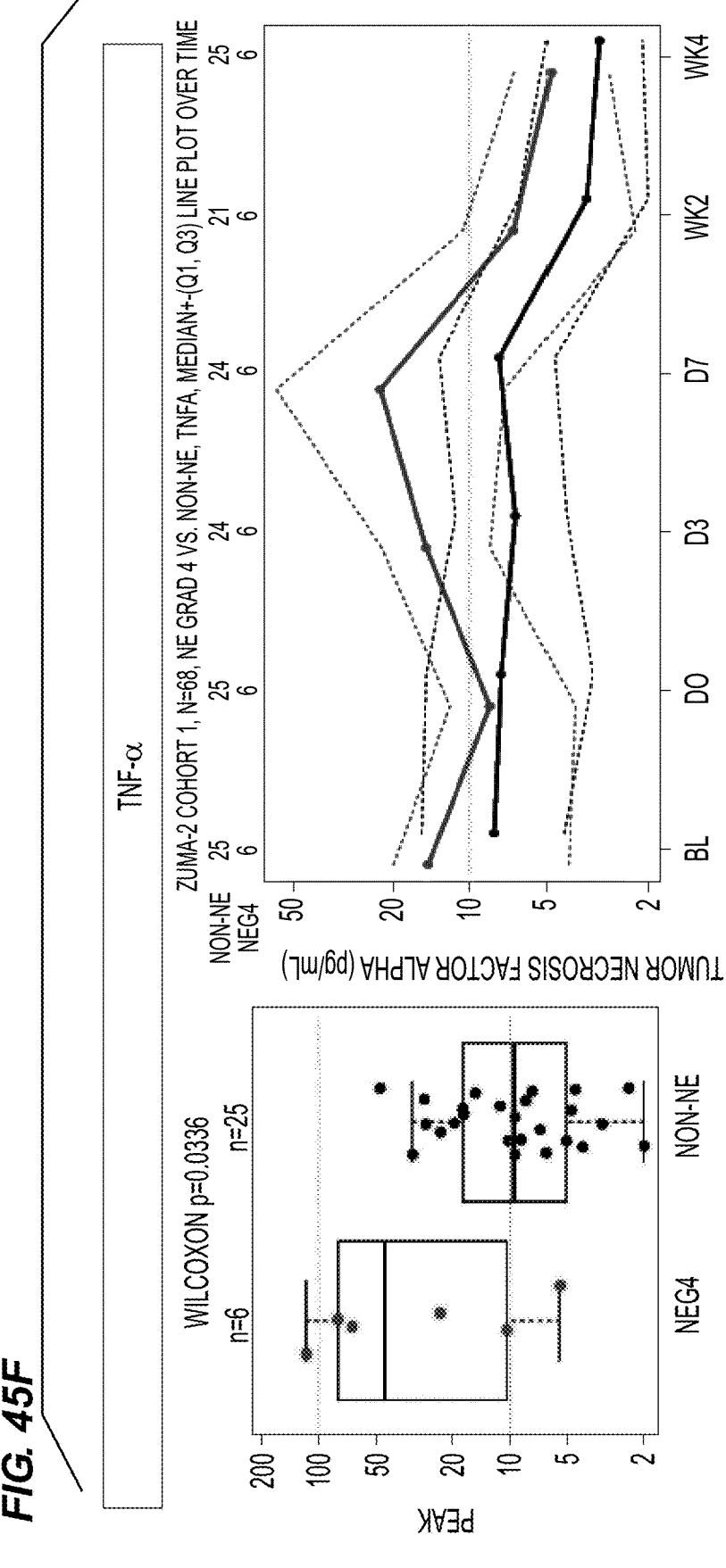
Figure 45G:
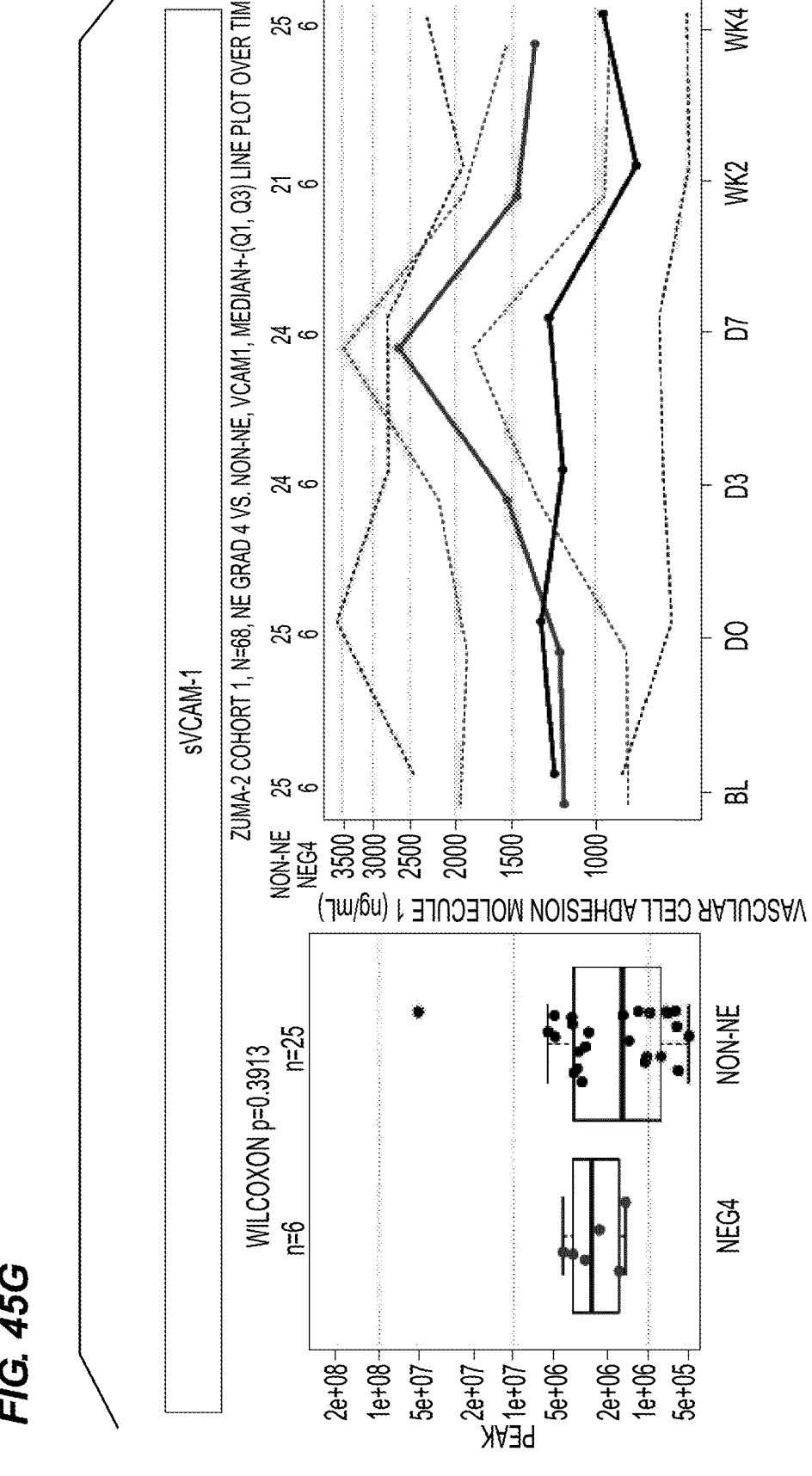
Figure 45H:
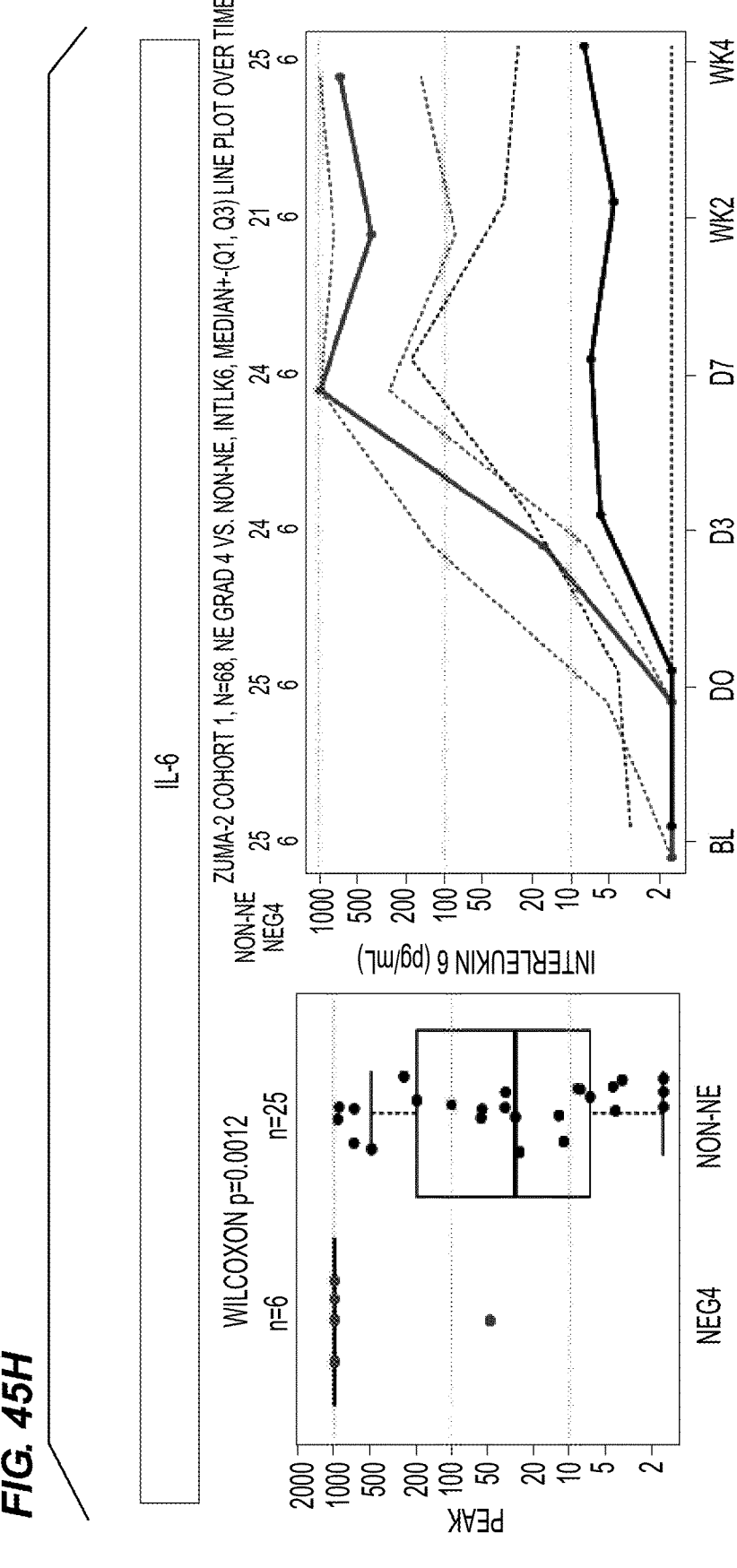
Figure 45I:
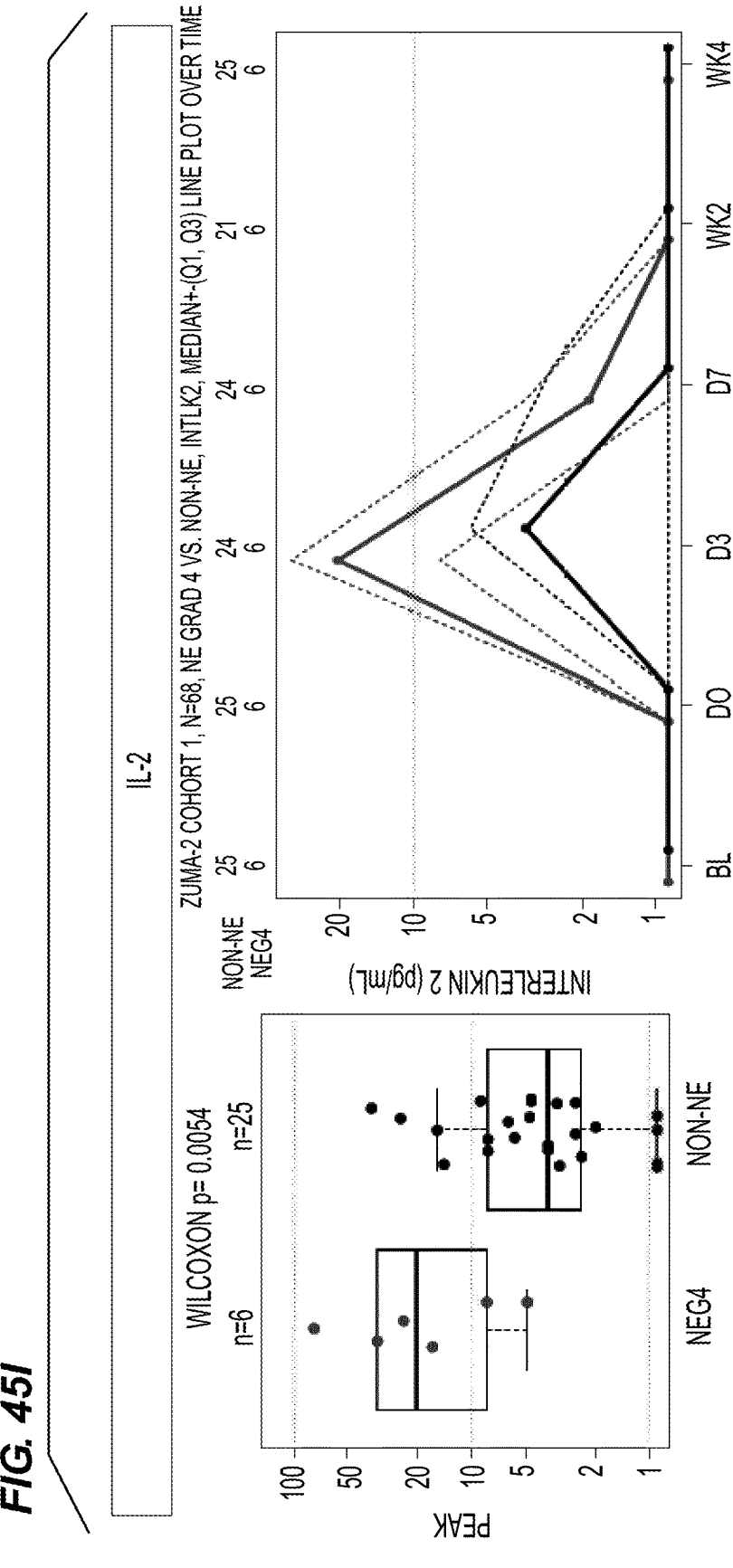

Moreover, an immunologically involved TME before lymphodepletion associated with axicabtagene ciloleucel response. The density of activated CD8+PD-1+LAG-3+/−TIM-3− T cells was most associated with clinical efficacy, paralleled by gene expression patterns reminiscent of a T cell-favorable tumor immune contexture. This major observation links fundamental features of tumor biology with the degree of T cell infiltration and optimal activation through chemokines (eg, CCL5; FIGS. 39A-39E) and cytokines (eg, IL-7, IL-15, IL-18, IL-21; FIGS. 37A-37K, FIGS. 38A-38C) that are produced in the TME and associated with T cell infiltration level (FIG. 43). These findings contrast with other recent reports pointing to B cell-driven tertiary lymphoid structures as key to immune-mediated tumor regression (Helmink, et al. B. *Nature*. 2020; 577:549-555; Cabrita, et al. *Nature*. 2020; 577:561-565; Petitprez, et al. *Nature*. 2020; 577:556-560), highlighting that CAR T cell intervention could drive tumor regression in patients who are profoundly B cell aplastic. Altogether, these results define an optimal TME rich in select T cell and T cell-modulating molecules and support rational immune intervention optimizations and novel predictive biomarker advancement.

Further, PD-1 upregulation on T cells reflects a unique epigenetic landscape associated with long-term survival of T cells in chronically inflamed environments (Blank, et al. *Nat Rev Immunol*. 2019; 19:665-674; Odorizzi, Pauken, Paley, Sharpe and Wherry. *J Exp Med*. 2015; 212:1125-37). The positive association between CD8+PD-1+ T cells and axicabtagene ciloleucel response parallels previous findings in solid tumors where checkpoint blockade improves survival (Galon, Angell, Bedognetti and Marincola. *Immunity*. 2013; 39:11-26; Hu-Lieskovan, et al. *Cancer. Clin Cancer Res*. 2019; 25:5061-5068). In addition, patients with low pretreatment tumor burden and high T cell involvement had the best chance of achieving CR, illustrating the interplay between these 2 major characteristics. Notably, a T cell-involved TME directly associated with axicabtagene ciloleucel expansion relative to tumor burden, providing a mechanistic link between the tumor immune contexture and axicabtagene ciloleucel engraftment in vivo. Finally, the pretreatment TME density of CD3+CD8−FoxP3+ (Treg) cells and CCL22 gene expression positively associated with low-grade neurotoxicity and high activated T cell density, suggesting a possible protective role for Tregs against toxicity without an apparent impact on response under evaluated conditions. Collectively, these results highlight that patients with low tumor burden and a higher degree of activated CD8+ T cells and Tregs infiltrating the TME pretreatment may have a more favorable efficacy and safety outlook.

highlight that mechanisms of action of CAR T cells are potentially dependent upon immune contexture. Clinically, these findings may yield new predictive/prognostic markers and new strategies to overcome primary treatment resistance in patients with immune detrimental TME pretreatment via local or systemic provision of T cell chemokines, γ-chain receptor cytokines, or IFN program-stimulating factors through T cell engineering or combinatorial approaches. In addition, the inverse associations between efficacy and tumor expression of CTAs (Hudolin, et al. *J Transl Med*. 2013; 11:123) and transcriptional factors (master switch PAX5, B cell-specific transcriptional coactivator POU2AF1 (Galiegue-Zouitina, et al. *C R Acad Sci III*. 1995; 318:1125-31), marker of epigenetic heterogeneity AICDA (Teater, et al. *Nat Commun*. 2018; 9:222), surface sialyltransferase B cell antigen CD75 [ST6GAL1 (Stamenkovic, et al. *J Exp Med.* 1990; 172:641-3; Johnston, et al. P. *Mol Cell Proteomics.* 2018; 17:776-791)]) suggest possible epigenetic dysregulation as a primary resistance mechanism to T cell intervention (Siebenkas, et al. *PLoS One.* 2017; 12:e0179501), similar to that observed in other cancer types (Spranger and Gajewski. *Nat Rev Cancer.* 2018; 18:139-147), that may be actionable via epigenetic modulators, checkpoint blocking agents, agonists, or CAR T cell design improvements (Feinberg, Koldobskiy and Gondor. *Nat Rev Genet.* 2016; 17:284-99). Collectively, the early, global TME gene expression changes shown in this study, including the ratio of T cell activity-related genes/tumor cell-related markers, may serve as a pharmacodynamic marker to monitor patients at risk for primary treatment failure[3,5]

This study advances mechanistic understanding of axicabtagene ciloleucel, linking its performance to tumor immune contexture pre- and posttreatment. Owing to the practical implications, further validation and analysis in large, prospective, randomized studies is warranted in LBCL, as well as other cancers where T cell therapies are being developed.

Axicabtagene ciloleucel (axicabtagene ciloleucel) is a first-in-class anti-CD19 chimeric antigen receptor (CAR) T cell therapy approved for treatment of relapsed/refractory large B cell lymphoma (LBCL). Axicabtagene ciloleucel has comparable efficacy across conventional histological, cytological, and molecular prognostic markers utilized for LBCL, suggesting that they poorly associate with axicabtagene ciloleucel response. Here, it was analysed whether pre- and posttreatment tumor microenvironment (TME) immune contexture determined clinical outcomes in axicabtagene ciloleucel-treated patients in the pivotal ZUMA-1 study (NCT02348216). Pretreatment TME features favoring localization of CD8+PD-1+LAG-3+/–TIM-3– T cells in higher numbers associated with axicabtagene ciloleucel clinical response. Data suggest that tumor biology features leading to a TME rich in select chemokines (CCL5), gamma (γ)-chain receptor cytokines (IL-15, IL-7, IL-21), and interferon-regulated molecules directly associate with T cell infiltration and activity. TME longitudinal evaluation uncovered dynamic patterns that occurred rapidly post-axicabtagene ciloleucel, including pronounced enhancement of T and myeloid cell signatures and diminution of tumor B cell signature, measurable within 2 weeks post-axicabtagene ciloleucel in responders versus nonresponders. At relapse post-axicabtagene ciloleucel, the TME evolved towards an immune-detrimental contexture with decreased T cell and increased counterregulatory signatures. These findings advance mechanistic understanding of CAR T cell therapy and pave the way for novel predictive biomarker development and therapy optimization.

Example 11

Tumor Immune Contexture is a Determinant of Anti-CD19 CAR T Cell Efficacy in Large B Cell Lymphoma During the last 3 decades, immunotherapies such as immune checkpoint blockade and genetically engineered T cell therapies have revolutionized cancer treatment (Couzin-Frankel. *Science.* 2013; 342:1432-3; Roberts, Better, Bot, Roberts and Ribas. *Leuk Lymphoma.* 2018; 59: 1785-1796; Yang and Rosenberg. *Adv Immunol.* 2016; 130:279-94; Dunbar, et al. *Gene therapy comes of age. Science.* 2018; 359; June, O'Connor, Kawalekar, Ghassemi and Milone.

*Science.* 2018; 359:1361-1365). Axicabtagene ciloleucel (axicabtagene ciloleucel) is a first-in-class anti-CD19 chimeric antigen receptor (CAR) T cell therapy approved in the United States, Canada, and Europe for treatment of relapsed/refractory large B cell lymphoma (LBCL), including diffuse LBCL (DLBCL; Canada), DLBCL not otherwise specified (US/Canada), primary mediastinal LBCL (US/Canada/Europe), high-grade B cell lymphoma (US/Canada), and transformed follicular lymphoma (US/Canada). In the pivotal ZUMA-1 study (NCT02348216), the objective response rate (ORR) was 83% (58% complete response [CR] rate), and 39% of patients had ongoing responses after a median of 27.1 months of follow-up (Locke, et al. *Lancet Oncol.* 2019; 20:31-42). In contrast with other therapies, such as rituximab (Fu, et al. *J Clin Oncol.* 2008; 26:4587-94; Carbone, Gloghini, Kwong and Younes. *Ann Hematol.* 2014; 93:1263-77), axicabtagene ciloleucel has comparable efficacy across various subsets of LBCL defined through conventional histological, cytogenetic, and molecular prognostic markers such as activated B cell (ABC), germinal center B cell (GCB), double-hit, double-expressor, and high-grade B cell lymphoma (HGBCL) (Roberts, Better, Bot, Roberts and Ribas. Axicabtagene ciloleucel, a first-in-class CAR T cell therapy for aggressive NHL. (*Leuk Lymphoma.* 2018; 59:1785-1796; Sesques and Johnson. *Blood.* 2017; 129:280-288; Neelapu, et al. *N Engl J Med.* 2017; 377:2531-2544; Locke, et al. *ASCO* 2017. 2017). However, about 60% of patients showed either primary treatment resistance (15%) or relapse (45%) within the first year (Locke, et al. *Lancet Oncol.* 2019; 20:31-42.)

While the role of the tumor microenvironment (TME) (Galon and Bruni. *Immunity.* 2020; 52:55-81; Galon and Bruni. *Nat Rev Drug Discov.* 2019; 18:197-218; Galon, Fridman and Pages. *Cancer Res.* 2007; 67:1883-6; Mascaux, et al. *Nature.* 2019; 571:570-575; Bedognetti, et al. *J Immunother Cancer.* 2019; 7:131; Spranger and Gajewski. *Nat Rev Cancer.* 2018; 18:139-147; Angelova, et al. *Cell.* 2018; 175:751-765 e16) in some solid tumors has been established (Angell, Bruni, Barrett, Herbst and Galon. *Clin Cancer Res.* 2019; Pages, et al. *Lancet.* 2018; 391:2128-2139; Yomoda, et al. *Ann Surg Oncol.* 2019; 26:415-424) in the context of checkpoint inhibitors, the importance of TME for CAR T cell therapy is poorly described. To test whether immune contexture influenced clinical outcomes in patients treated with axicabtagene ciloleucel in ZUMA-1, we utilized comprehensive gene expression and multiplex immunohistochemistry (IHC). Immune programs and cell types implicated in facilitating clinical response, safety, primary resistance, and relapse post-axicabtagene ciloleucel treatment were analysed. Here, we show that an immunologically involved TME associated with particular features associates with clinical response to axicabtagene ciloleucel in patients with LBCL, but not with conventional predictive or prognostic markers. These findings advance mechanistic understanding of CAR T cell therapy in relation to TME and will promote biomarker development and treatment optimizations.

Example 12

Methods for Examples 8 Through 10

Patient Sample Collection and Preparation

In ZUMA-1, patients received axicabtagene ciloleucel at a target dose of $2.0 \times 10^6$ CAR T cells/kg[1,2]. Tumor biopsies from patients (FIG. 42) were performed at baseline (before conditioning chemotherapy [prelymphodepletion] and axicabtagene ciloleucel infusion), early after CAR T cell infusion (Day 7-Day 14), or later at relapse. After controlling for sample quality, a total of 115 baseline and posttreatment biopsies from 55 patients with LBCL were analysed in this study. All posttreatment biopsies were acquired between Day 7 and Day 14, except for 1 patient with stable disease where the biopsy was collected at Week 4. Patient characteristics and clinical outcomes described in this study were consistent with those observed in the overall ZUMA-1 cohort. During the study, gene expression profiling was performed using 3 panels (FIG. 25) on 73 baseline biopsies (49 fresh frozen [FF] and 24 formalin-fixed, paraffin-embedded [FFPE] from 40 patients, with both FF and FFPE biopsies for 11 patients) and on 85 FF post-axicabtagene ciloleucel biopsies from 18 patients. Clinical research (CR) tests, including Immunoscore TL, Immunoscore TCE, Immunoscore SC, and Immunosign, were performed in a Clinical Laboratory Improvement Amendments (CLIA)-certified laboratory (HalioDx). For pre/post-axicabtagene ciloleucel comparisons, FF biopsies analysed with PanCancer Immune Profiling+CAR T gene panel are shown. For baseline analysis, FFPE biopsies with PanCancer Immune+Immunosign Gene Panel are shown. For relapse paired samples, FF biopsies with Immunosign expanded 43 immune gene panel are shown. Best response was evaluated within 2 years of axicabtagene ciloleucel infusion for patients enrolled in ZUMA-1 phases 1 and 2, cohorts 1 and 2, and within 6 months of axicabtagene ciloleucel infusion for patients enrolled in ZUMA-1 phase 2, cohort 3. Slide sets were prepared from each FFPE block by cutting 10 consecutive 4 μm sections which were further immobilized on Superfrost plus slides. One slide was used for hematoxylin and eosin (H&E) staining, 2 consecutive slides for Immunoscore TL (automatic staining CD3/CD8, BenchMark XT), and 4 or 5 consecutive slides for RNA extraction and NanoString profiling. Slides were deidentified and tracked using a unique number for each preanalytical step, and 2 workflows per patient were performed.

Gene Expression Analysis and Immunosign

RNA was extracted from frozen or fixed biopsies using QIAGEN RNeasy kit or QIAGEN RNeasy FFPE extraction kit, respectively. Annotations from the pathologist performing H&E staining were used to guide removal of normal tissue from the slides by macrodissection prior to RNA extraction, which occurred after tissue deparaffinization and lysis. Each RNA extraction was independently quantified (NanoDrop) and qualified (Agilent Bioanalyzer). Degradation assessment was quantified as the percentage of RNA fragments smaller than 300 base pairs (Agilent Bioanalyzer, RNA 6000 Nano Kit). The qualification assessments (RNA quantity or quality) were informative but not used as acceptance criteria. When needed, overdiluted RNA was concentrated using the clean-up approach from QIAGEN RNeasy kit protocols. Good sample quality was defined as less than 50% of RNA fragments of 50 to 300 base pairs in size. All the extracted RNA was tested independent of the concentration or the degradation rate. One RNA QC sample was included in each testing run as a positive control for extraction.

RNA expression profiling was performed using 3 NanoString datasets (FIG. 25). Immunosign custom-expanded 43 immune gene panel (nCounter technology, NanoString) was used to determine the gene expression level of multiple immune genes in a multiplex format. PanCancer Immune Profiling Panel (nCounter) was supplemented with 2 probes for CAR T cell detection, and the CD28zeta probe (coverage across engineered costimulatory domain junction of the CAR) was prioritized for analysis and interpretation based on signal-to-noise ratio. In one assay, the PanCancer Immune Profiling Panel and the Immunosign custom panels were combined, permitting the simultaneous profiling of 763 genes from immune cells. After data normalization and analysis, high/low Immunosign score cutoff was arbitrarily defined as the 25th percentile of the observed scores among samples, and gene expression levels for 21 or 15 predefined genes were compositely scored as Immunosign 21 or Immunosign 15, respectively (FIG. 26). High scores indicated expression of immune-related genes that were potentially associated with tumor response. Univariate analyses were performed to determine whether pretreatment tumor or immune feature influence clinical responses.

Immunohistochemistry, Immunoscore TL, Immunoscore TCE, and Immunoscore SC

H&E staining allowed preliminary tissue evaluation for FFPE-block quality controls. Slides were scanned with the NanoZoomer-XR to generate digital images (20×). A pathologist identified the tumor area and provided qualitative and semi-quantitative assessments. CD19 IHC staining (LE-CD19) was scored by composite H-score (0-5="No"; 6-300="Yes").

Results of the Immunoscore TL assay, which measures the density of CD8+ cytotoxic T cells and CD3+ T cells in resected or biopsied cancer samples, are expressed as a score determined by a percentile approach. 3 Immunostainings were performed using a qualified BenchMark XT on consecutive FFPE slices (4 μm) in accordance with the following workflow and reagents: antigen retrieval, staining with primary antibody (CD3, HD1, or CD8, HDX2), detection with a secondary antibody using ultraView Universal DAB Detection Kit (Roche, catalog #760-500), and counterstaining using the hematoxylin and bluing reagent Hematoxylin II (Roche, catalog #790-2208). Control slides were systematically included in each staining run to permit quality control of the obtained measurements. Following coverslipping, slides were scanned with the NanoZoomer-XR to generate digital images (20×) and were analysed in parallel by 2 independent, qualified operators. CD3 and CD8 IHC staining was scored and converted into Immunoscore using the HalioDx algorithm.

The Immunoscore TCE and SC sequential IHC panels were performed to measure 14 myeloid and T cell subsets using FFPE biopsies from 18 and 17 patients, respectively (15 samples overlapped between the 2 panels; FIGS. 34A-34C). Successive stainings were performed on the same slide using a Leica Bond RX. For both panels, signal detection was performed using MACH 2 rabbit universal HRP polymer or MACH 2 mouse universal HRP polymer as secondary antibody and ImmPACT™ AMEC Red substrate detection. Counterstaining of cellular nuclei using hematoxylin was performed at the end of each staining workflow. One control slide was systematically included in each run to permit quality control of the obtained measurements using qualitative acceptance criteria (specificity, staining location [nucleus/membrane], cell type, and lack of background or unspecific staining). After each individual staining, coverslipping was performed automatically by the workstation CTM6 with aqueous mounting. Slides were scanned with the NanoZoomer-XR (×20) and a visual quality control permitted qualification. Coverslips were carefully removed from slides using a warm water bath, slides were AMEC-destained by ethanol, and antibodies were stripped with denaturing solution. Each sample was analysed using HalioDx Digital Pathology Platform. Images were aligned with Brightplex-fuse (in-house software). Tumor areas were identified using annotation tools; subsequently, positively stained cells were detected and quantified in the selected regions of interest using HALO software (Indica Labs). Phenotypes of stained cells were visually verified according to expected staining and analysed with Brightplex Multi-plexR (in-house software).

CAR T Cell Detection

CAR T cell genes were detected with probes directed against scFv and CD28_CD3z domains. CAR T cell presence and expansion in blood was measured by quantitative polymerase chain reaction (qPCR) as previously described.

Example 13

This example provides results from an analysis of clinical trial ZUMA-2. Eligible patients were aged ≥18 years with pathologically confirmed Mantle Cell Lymphoma (MCL) with documentation of either cyclin D1 overexpression or presence of t(11;14), and were relapsed/refractory to 1-5 prior regimens for MCL. Prior therapy having included anthracycline or bendamustine-containing chemotherapy, an anti-CD20 monoclonal antibody, and ibrutinib or acalabru-tinib. All patients received prior BTKi. Although patients must have had prior BTKi therapy, it was not required as the last line of therapy before study entry, and patients were not required to be refractory to BTKi therapy. Eligible patients had an absolute lymphocyte count ≥100/µL Patients who underwent autologous SCT within 6 weeks of CD19 CAR-T infusion or had previous CD19-targeted therapy or alloge-neic SCT were excluded. All patients underwent leukaphere-sis to obtain cells for CD19 CAR-T cell treatment manu-facturing. Patients received optional bridging therapy, which included dexamethasone (20-40 mg or equivalent), ibrutinib (560 mg by mouth (PO) daily), or acalabrutinib (100 mg PO twice daily). The manufacturing process was modified rela-tive to that of axicabtagene ciloleucel to remove circulating lymphoma cells through positive enrichment for CD4$^+$/CD8$^+$ cells. This product is referred to herein as "the CAR T cells." Conditioning chemotherapy with fludarabine (30 mg/m$^2$/day) and cyclophosphamide (500 mg/m$^2$/day) was administered on days −5, −4, and −3 prior to a single intravenous infusion of 2×10$^6$ CAR T cells/kg of CD19 CAR-T cells on day 0.

The goals of this study were two-fold. First, to compare the pharmacological profile of the CAR T product in lower- and higher-risk patients in the clinical trial ZUMA-2, defined by TP53, (tumor protein p53) gene mutation status and Ki-67 tumor proliferation index. Patients with high-risk MCL characteristics, including tumor protein p53 gene (TP53) mutation and high Ki-67 proliferation index, typi-cally have a poor prognosis with current standard therapies. Cheah C Y, et al. *J Clin Oncol.* 2016; 34:1256-1269. Lower-risk patients in this analysis had a Ki-67 proliferation index <50% (by central evaluation) or wild-type TP53; higher-risk patients had Ki-67≥50% or TP53 mutation by next generation sequencing. In the primary efficacy analysis of ZUMA-2 (N=60), the ORR was 93% (67% CR) after a median follow-up of 12.3 months. 57% of all patients and 78% of patients in CR had ongoing responses. The ORR was generally comparable between lower- and higher-risk patients in ZUMA-2, including in patients with Ki-67 pro-liferation index < or ≥50% and unmutated vs mutated TP53. Wang M, et al. *New Engl J Med.* 2020; 382:1331-1342.

The second goal was to characterize the pharmacody-namic profile in patients who achieved early (Day 28) Minimal residual disease (MRD)-negative status and those with Grade 4 neurotoxicity. In a previous analysis of ZUMA-2 results, CAR T cell levels in blood by peak and area under the curve (AUC) on Days 0-28 were associated with ORR (including undetectable MRD) and Grade ≥3 CRS and neurologic events. Wang M, et al. *New Engl J Med.* 2020; 382:1331-1342. In that analysis, CRS and neurologic events were mostly reversible (N=68 treated patients): 15% had Grade ≥3 CRS; 31% had Grade ≥3 neurologic events; and two had Grade 5 AEs (one of which was CAR T product-related). MRD (10$^{-5}$ sensitivity) was assessed by next-generation sequencing, as previously reported. Wang M, et al. *New Engl J Med.* 2020; 382:1331-1342.

This update reports pharmacology data for all 68 patients in ZUMA-2 who were treated with the CAR T cells Product attributes, CAR T cell levels in blood, and cytokine levels in serum, and their associations with clinical outcomes, were analyzed by using previously described methods. Locke F L, et al. *Mol Ther.* 2017; 25:285-295. Wilcoxon rank-sum test was used to measure associations between subgroup out-comes and CAR T cell and cytokine levels. P values were not adjusted for multiple testing.

CAR T cell product attributes were generally comparable across prognostic groups defined by Ki-67 proliferation index and TP53 mutation status. There was a trend toward more differentiated phenotypes in the high-Ki-67 subgroup, and CD4-based phenotypes in patients with TP53 mutation. (Table 7).

TABLE 7

| | | Median (range) | | | |
|---|---|---|---|---|---|
| | Treated | Ki-67 Proliferation Index | | TP53 | |
| | Patients$^a$ (n = 65) | <50% (n = 14) | ≥50% (n = 34) | Mutation (n = 6) | Nonmutation (n = 30) |
| CD4/CD8 Ratio | 0.7 (0.04, 3.7) | 0.8 (0.4, 1.7) | 0.7 (0.04, 3.7) | 1.2 (0.7, 3.7) | 0.7 (0.04, 1.9) |
| Naive T cells, % | 24.5 (0.3, 80.7) | 30.4 (11.0, 57.0) | 20.1 (0.3, 68.8) | 23.0 (11.8, 46.5) | 25.2 (0.3, 78.1) |
| Central memory T cells, % | 12.8 (2.3, 51.6) | 10.1 (8.4, 45.0) | 12.0 (2.3, 51.6) | 13.2 (6.0, 51.6) | 10.2 (2.3, 45.0) |
| Effector memory T cells, % | 24.5 (0.8, 70.3) | 19.4 (6.3, 56.1) | 29.1 (5.8, 70.3) | 25.9 (7.0, 38.2) | 29.4 (2.2, 70.3 |
| Effector T cells, % | 28.7 (2.8, 65.2) | 23.7 (11.5, 49.30) | 32.4 (2.8, 65.2) | 29.1 (2.8, 44.7) | 29.1 (8.4, 54.5) |

$^a$Of all 68 treated patients, product characteristic data were available for 65 total patients. Product characteristic data were available for 48/49 total patients with Ki-67 data available and for all 36 patients with TP53 mutation data available. TP53, tumor protein p53 gene There was also comparable CAR T cell expansion in groups with different prognostic factors defined by Ki-67 proliferation index and TP53 mutation status. Both peak levels and AUC of CAR T cells in the blood after administration were comparable in patients with wild-type vs mutated TP53 or Ki-67 proliferation index <50% vs ≥50%, which was consistent with the comparable efficacy in these subgroups.

The ORR was 100% vs 94% in patients with Ki-67 proliferation index <50% vs ≥50% whereas the CR rate was 64% vs 78% in patients Ki-67 proliferation index <50% vs ≥50%. Table 8. The number of patients with available data for Ki-67 proliferation index was 49.

TABLE 8

|  | ORR (95% CI), % | CR Rate (95% CI), % |
|---|---|---|
| Ki-67 PI < 50% | 100 (77-100) | 64 (35-87) |
| Ki-67 PI ≥ 50% | 94 (79-99) | 78 (60-91) |

The ORR was 100% for both in patients with wild-type vs mutated TP53 whereas the CR rate was 67% vs 100% in wild-type vs mutated TP53. Table 9. The number of patients with available data for TP53 was 36. All six patients with TP53 mutation and all 30 patients with no mutation responded. Among the six patients with TP53 mutation, three had Grade ≥3 neurotoxicity and two had Grade ≥3 CRS

TABLE 9

|  | ORR (95% CI), % | CR Rate (95% CI), % |
|---|---|---|
| TP53 mutation | 100 (54-100) | 100 (54-100) |
| TP53 nonmutation | 100 (88-100) | 67 (47-83) |

(IL-8 and MCP-1)), and effector cytokines (Granzyme B). In addition, there was a trend for increased proliferative (IL-15, IL-2) and inflammatory (IL-6, IL-2Rα, sPD-L1 and VCAM-1) cytokine levels in patients with mutated TP53 vs wild-type TP53. FIGS. 44A-44F.

There was also an increase in the peak levels of select cytokines in serum among patients who achieved MRD-negative status. MRD was analyzed in 29 of 68 patients (43%); 24 of these patients (83% [19 patients with a complete response and 5 with a partial response]) were MRD negative at one month post CAR T cell administration. At one month post CAR T cell administration, MRD negative (n=24/29) vs -positive patients (n=5/29) had increased median peak levels of interferon (IFN)-γ and interleukin (IL)-6 and a trend towards increased IL-2. Cytokine levels peaked in serum within 7 days of treatment. Consistent trends were seen for PD-L1 and Granzyme B. Increased peak CAR T cell levels, measured within 14 days posttreatment, were also seen in patients who were MRD negative at 1 month. FIGS. 45A-45I.

Six patients developed Grade 4 neurologic events, including one with cerebral edema. Three patients had concurrent Grade 4 CRS. Patients with Grade 4 neurologic events showed increased peak levels of proinflammatory serum biomarkers (e.g., IFNγ, MCP-1, TNF-α, IL-2 and IL-6) compared to patients without neurologic events.

The cerebral edema was completely resolved following aggressive multimodality therapy. Wang M, et al. *New Engl J Med.* 2020; 382:1331-1342. Expansion of CART cells and peak serum levels of IL-2 were highest in this patient; the rise in multiple cytokines was several-fold higher in this patient compared with the median of other study/ZUMA-2 patients. Table 10.

TABLE 10

|  | Patient With Cerebral Edema | | Other ZUMA-2 Patients (n = 67), Median (IQR) | |
|---|---|---|---|---|
|  | Baseline (Day 0) | Peak (Post CAR T cell administration) | Baseline (Day 0) | Peak (Post CAR T cell administration) |
| CAR T cell levels, cells/μL | 0 | 431.3 | 0 | 83.1 (17.2-264.3)[a] |
| IFN-γ, pg/mL | 7.5 | 584.4 | 7.5 (7.5-17.7) | 411.2 (144.8-1876) |
| MCP-1, pg/mL | 462.6 | 1500 | 882.9 (557.2-1164.8) | 1084.3 (804.2-1500) |
| TNFα, pg/mL | 1.9 | 10.4 | 5.7 (3.2-10.6) | 9.5 (5.5-23.2) |
| sVCAM-1, ng/mL | 527.5 | 1659.7 | 1195.9 (791.7-2533.1) | 1900.7 (1032.4-3646.7) |
| IL-2, ng/mL | 0.9 | 16.7 | 0.9 (0.9-0.9) | 6.0 (3.0-14.4) |
| IL-6, pg/mL | 1.6 | 159.5 | 1.6 (1.6-6.4) | 87.9 (12.9-879.1) |
| CRP, mg/L | 6.8 | 18.2 | 30.5 (15.1-63.0) | 119.4 (54.6-173.8) |
| Ferritin, ng/mL | 606.3 | 824.2 | 502.4 (273.5-877.7) | 1265 (597.8-2970.1) |
| IL-15, ng/mL | 29.1 | 56.1 | 33.2 (25.4-48) | 38.4 (29.7-61.7) |

[a]Out of 66 patients with available data.

Up to 44 biomarkers in serum were measured pretreatment, at Day 0, and at various time points through Day 28 post CAR T cell infusion, including IL (interleukins); INF-γ (interferon gamma), MCP-1 (monocyte chemoattractant protein-1), IL-2Rα (IL-2 receptor alpha), sPD-L1 (soluble programmed death-ligand 1) and sVCAM (soluble vascular cell adhesion molecule). The pharmacodynamic profile for the two prognostic groups with Ki-67 proliferation index <50% vs ≥50% was comparable with regard to proliferative (IL-15, IL-2), inflammatory (IL-6, IL-2Rα, sPD-L1 and VCAM-1), immune-modulating (IFN-γ, IL-10), chemokine CAR T cell pharmacokinetic and pharmacodynamic profiles were comparable across MCL patient groups with different prognostic marker status associated with lower and higher risk (defined by Ki-67 and mutated TP53), consistent with comparable clinical response rates. There was a trend toward higher levels of proinflammatory markers in patients with mutated TP53.

The pharmacodynamic profile of CART cell administration was associated with efficacy (MRD status at 1 month) and Grade 4 treatment-emergent neurologic events. The patient who developed cerebral edema had the highest peak CAR T cell levels and serum IL-2, as well as elevated proinflammatory markers posttreatment.

Example 14

This Example reports on the effects of early steroid use for adverse event management in patients receiving axicabtagene ciloleucel for Relapsed/Refractory Large B-cell Lymphoma (R/R LBCL). Axicabtagene ciloleucel (axi-cel), an autologous anti-CD19 chimeric antigen receptor (CAR) T-cell therapy, is approved for the treatment of patients with relapsed or refractory large B-cell lymphoma (R/R LBCL) after failing two or more prior systemic therapies. Regulatory approvals were based on results of Cohorts 1+2 (N=101) of the phase 2 ZUMA-1 study, which evaluated the efficacy and safety of axicabtagene ciloleucel in patients with refractory LBCL. In a 2-year analysis (median follow-up, 27.1 months; N=101), axicabtagene ciloleucel treatment showed objective response, complete response, and ongoing response rates of 83%, 58%, and 39%, respectively. After a median of 39.1 months of follow-up, median overall survival (OS) was 25.8 months, with a 3-year OS rate of 47%. Cytokine release syndrome (CRS) and neurologic events are common in patients receiving anti-CD19 CAR T-cell therapies and may be severe or life-threatening. At the 2-year follow-up of the 108 patients in phases 1 and 2 of ZUMA-1 (data cutoff, Aug. 11, 2018), grade ≥3 CRS was reported in 11% of patients and grade ≥3 neurologic events were reported in 32%. The majority of CRS cases and neurologic events were manageable and reversible.

CRS and neurologic events are thought to be initiated by the activation of T cells upon CAR engagement of cognate antigen on target cells. This activation leads to CAR T-cell proliferation and cytokine release, subsequently activating and mobilizing a broad range of immune cells. Activation of "bystander" immune cells, including non-CAR T cells and myeloid cells is also common, and may contribute to the amplification of these adverse events. The IL-6/IL-6R axis has been directly implicated in the pathogenesis of severe CRS, and tocilizumab, a monoclonal antibody against the interleukin (IL)-6 receptor (IL-6R), is indicated for the treatment of severe or life-threatening CAR T-cell-induced CRS.

The etiology of neurologic events is not identical to that of CRS, and while incompletely elucidated, appears to be mediated by excess activation and mobilization of both T and myeloid cells, triggered by strong CAR triggered signaling in T cells. Proposed mechanisms include peripheral cytokine release followed by cytokine diffusion across a breached blood brain barrier (BBB) and/or translocation of activated anti-CD19 CAR T and other immune cells, most notably myeloid cells, across the BBB, aided by vascular inflammatory injury and leading to a local inflammatory effect. In Cohorts 1+2 of ZUMA-1, CAR T-cell expansion together with higher levels of proinflammatory markers (IL-15, IL-2, GM-CSF, CXCL10, CCL2), were significantly associated with the incidence of severe neurologic events. Low tumor burden seems to be associated with lower rates of both CRS and neurologic events and higher rates of ongoing response at one year.

Safety expansion cohorts were added to phase 2 of ZUMA-1 for the purpose of evaluating new strategies for management of CRS and neurologic events in patients treated with axicabtagene ciloleucel. Cohort 3 evaluated the use of prophylactic tocilizumab on day 2, which appeared to decrease rates of grade ≥3 CRS but not grade ≥3 neurologic events. In addition to pointing to differences in the pathogenesis of these two categories of AEs, these data suggested that down-modulation of a broader range of immune programs may be required to reduce the rates of both categories of serious adverse events. Thus, Cohort 4 was studied to evaluate the impact of earlier intervention with corticosteroids on the incidence and severity of CRS and neurologic events.

Figure 46:
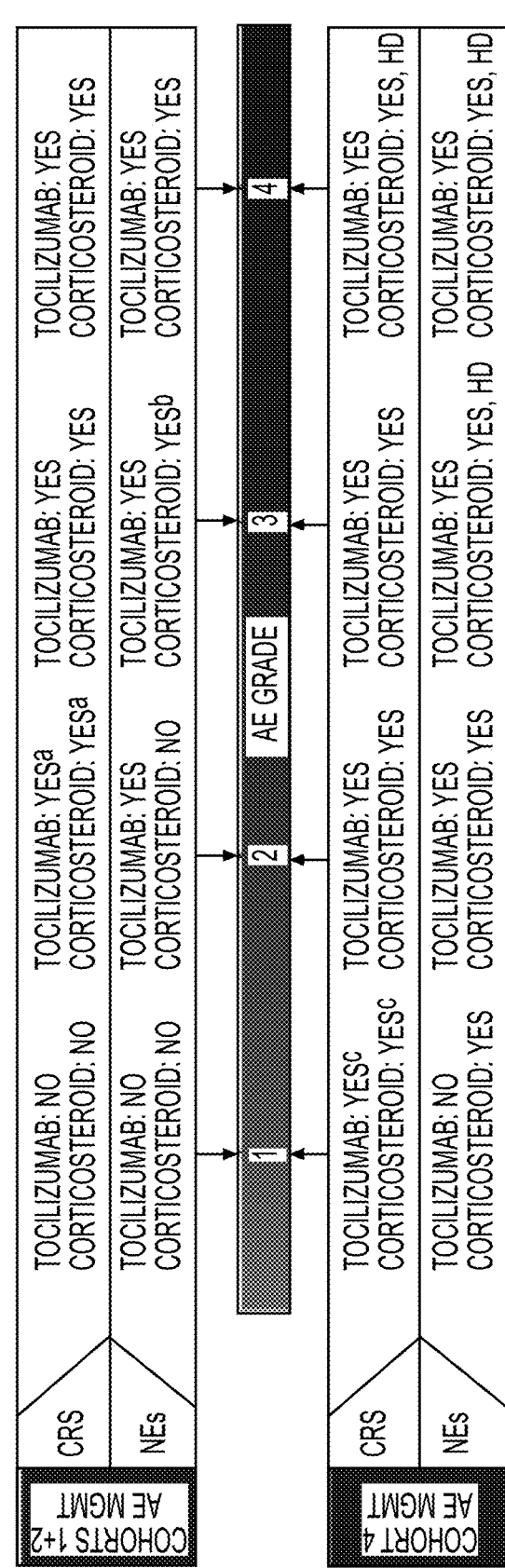
FIG. 46: Toxicity Management in Cohorts 1+2 Versus Cohort 4. The figure summarizes toxicity management of ZUMA-1 for Cohorts 1+2 (upper panel) and Cohort 4 (lower panel). Yes or No indicates if tocilizumab or corticosteroid was or was not administered, respectively. [a] Only in case of comorbidities or older age. [b] Only if no improvement to tocilizumab, use standard dose. If no improvement after 3 days. AE, adverse event; CRS, cytokine release syndrome; HD, high dose; NEs, neurologic events; mgmt, management.

This study reports 12-month results of Cohort 4 alongside 12-month data from Cohorts 1+2 to contextualize the findings. In this study, two adverse even management protocols were compared: Cohorts (1+2) and Cohort 4. Details of the protocols can be found in FIG. 46. In Cohort 4, eligible patients with R/R LBCL received $2 \times 10^6$ anti-CD19 CART cells/kg after conditioning therapy. Cohort 4 procedures were nearly identical to those described for Cohorts 1+2. Neelapu S S, Locke F L, Bartlett N L, et al: Axicabtagene ciloleucel CAR T-cell therapy in refractory large B-cell lymphoma. N Engl J Med 377:2531-2544, 2017. The primary exception was the Cohort 4 implementation of levetiracetam prophylaxis and earlier corticosteroid intervention for CRS and neurologic events. Additional exceptions are described below. Patients received steroid intervention starting at grade 1 CRS (if no improvement after 3 days) and at grade 1 neurologic events. This intervention was earlier than that in Cohorts 1+2. FIG. 46.

The primary endpoint in Cohort 4 was the incidence and severity of CRS and neurologic events. Key secondary endpoints related to safety included the incidence of other adverse events and clinically significant changes in safety laboratory values. Key secondary endpoints related to efficacy included objective response rate (ORR) per investigator assessment, duration of response (DOR), progression-free survival (PFS), and overall survival (OS), levels of anti-CD19 CAR T cells in the blood, and levels of cytokines in the serum. The modified intent-to-treat (mITT) population included all patients enrolled and treated with axicabtagene ciloleucel at a dose of at least $1 \times 10^6$ anti-CD19 CART cells/kg. This analysis set was used for all analyses of objective response and endpoints based on objective response. The safety analysis set included all patients treated with any dose of axicabtagene ciloleucel. Analyses of CAR T-cell levels, safety, and efficacy outcomes by tumor burden were based on the median tumor burden values of Cohorts 1+2. Cohort 4 tumor burdens were measured after bridging therapy and before conditioning chemotherapy. Cumulative steroid dose was calculated by conversion to systemic cortisone-equivalent dose during the initial hospitalization period. Findings were compared to pivotal Cohorts 1+2, where tocilizumab was first introduced at grade 2 CRS and grade 2 NE, whereas corticosteroids were introduced at grade 2 CRS and grade 3 NE. While the incidence of any-grade CRS (both 93%) and neurologic events (64% vs 61%) were comparable in Cohorts 1+2 and Cohort 4, respectively, incidence of grade ≥3 CRS (12% vs 2%) and grade ≥3 neurologic events (29% vs 17%) were lower in Cohort 4. There was no grade 4 or 5 CRS in Cohort 4. Cumulative steroid dose in patients requiring steroid therapy in Cohort 4 was lower in Cohorts 1+2. Durable response rates were comparable in Cohort 4 (51%) and Cohorts 1+2 (42%) with median follow-ups of 14.8 and 15.4 months, respectively. These findings were corroborated by comparable CAR T cell levels, yet lower inflammatory cytokine levels in Cohort 4.

Patients eligible for Cohort 4 had R/R LBCL after ≥2 systemic lines of therapy or refractory disease to first-line therapy, defined as a best response of progressive disease or stable disease to at least four cycles of first line therapy with stable disease duration no longer than 6 months. Unlike Cohorts 1+2 in which patients had to be refractory after second-line or later therapy, patients in Cohort 4 could be relapsed or refractory. Prior therapy having included an anti-CD20 monoclonal antibody (unless the tumor was CD20-negative) and an anthracycline-containing chemotherapy regimen. Patients were required to have an Eastern Cooperative Oncology Group (ECOG) performance status of 0 or 1. Additional inclusion criteria were absolute neutrophil count >1,000 cells per microliter, an absolute lymphocyte count >100 cells per microliter, a platelet count >75,000 cells per microliter, adequate organ function, no central nervous system involvement, and no active infection.

Patients received a conditioning regimen of cyclophosphamide (500 mg/m$^2$/day) and fludarabine (30 mg/m$^2$/day) on days −5 to −3, and one dose of axicabtagene ciloleucel (target dose of 2×10$^6$ CAR T cells/kg) on day 0. Bridging therapy prior to initiation of conditioning chemotherapy (Table 11) was allowed in Cohort 4 at the discretion of the investigator (eg, bulky disease or rapidly progressing disease at screening or baseline). Bridging therapy was not allowed in Cohorts 1+2.

TABLE 11

| Type | Therapy Regimens | Timing and Washout Requirements |
|---|---|---|
| Corticosteroid | Dexamethasone at a dose of 20 mg to 40 mg or equivalent, either PO or IV daily for 1 to 4 days. Choice of corticosteroid and dose can be adjusted for age/comorbidities or per local or institutional guidelines | May be administered after apheresis/enrollment and must be completed prior to the start of conditioning chemotherapy |
| HDMP + Rituximab | 1 gram/m$^2$ of HDMP for 3 days in combination with rituximab at 375 mg/m$^2$ weekly for 3 weeks | May be administered after enrollment and completed at least 7 days prior to the start of conditioning chemotherapy |
| Combination Chemotherapy | B-R: Bendamustine (90 mg/m$^2$, Day 1 + 2); Rituximab (375 mg/m2, Day 1) | May be administered after enrollment and completed at least 14 days prior to the start of conditioning chemotherapy, |

CBC, complete blood count;
HDMP, high-dose methylprednisolone;
IV, intravenous;
[a]A new baseline PET-CT was performed post bridging therapy.

In Cohort 4, patients received levetiracetam (750 mg orally or intravenous twice daily) starting on day 0 and also at the onset of grade ≥2 neurologic toxicities if neurologic events occurred after the discontinuation of prophylactic levetiracetam. If a patient did not experience any grade ≥2 neurologic toxicities, levetiracetam was tapered and discontinued as clinically indicated. Corticosteroid therapy was initiated earlier for toxicity management in Cohort 4 than in Cohorts 1+2 per protocol (FIG. 46). In Cohort 4, corticosteroid therapy was initiated for management of all cases of grade 1 CRS if there was no improvement after 3 days and for all grade ≥1 neurologic events. Tocilizumab was initiated for all cases of grade 1 CRS if there was no improvement after 3 days and for all grade ≥2 neurologic events (Table 12).

TABLE 12

| CRS Grade | Tocilizumab Dose[a] | Corticosteroid Dose[a] |
|---|---|---|
| 1 | 8 mg/kg over 1 hr,[b] repeat every 4-6 hr as needed if no improvement after 3 days | Dexamethasone 10 mg × 1 if no improvement after 3 days |

TABLE 12-continued

| | | |
|---|---|---|
| 2 | 8 mg/kg over 1 hr,[b] repeat every 4-6 hr as needed | Dexamethasone 10 mg × 1 |
| 3 | Per grade 2 | Methylprednisolone 1 mg/kg IV twice daily or equivalent dexamethasone dose |
| 4 | Per grade 2 | Methylprednisolone 1000 mg/day IV × 3 days |

| NE Grade | Tocilizumab Dose | Corticosteroid Dose |
|---|---|---|
| 1 | N/A | Dexamethasone 10 mg × 1 |
| 2 | 8 mg/kg over 1 hr, repeat every 4-6 hr as needed | Dexamethasone 10 mg 4 times/day |
| 3 | As per grade 2 | Methylprednisolone 1 g once daily |
| 4 | As per grade 2 | Methylprednisolone 1 g twice daily |

[a]Therapy to be tapered upon improvement of symptoms at investigator's discretion;
[b]Not to exceed 800 mg;
IV, intravenous; N/A, not applicable.

Forty-six patients were enrolled and leukapheresed in Cohort 4, and 41 received the minimum target dose of axicabtagene ciloleucel. The latter group comprised both the mITT and safety analysis sets. Five patients did not receive conditioning chemotherapy due to disease progression (n=4) or suicide in the setting of disease progression (n=1). Sixty-eight percent of Cohort 4 patients (n=28/41) received bridging therapy prior to receiving axicabtagene ciloleucel. As of the Nov. 6, 2019 data cutoff, the median follow-up for Cohort 4 was 14.8 months (range, 8.9-19.9 months). The data cutoff presented here for Cohorts 1+2 was Aug. 11, 2017, with a median follow-up of 15.1 months (range, 10.9-20.4 months).

Baseline characteristics for Cohort 4 were generally comparable to those of Cohorts 1+2, with the exceptions of lower pre-treatment tumor burden, lower levels of inflammatory markers (eg, ferritin, lactate dehydrogenase [LDH]), and a lower proportion of patients with progressive disease in response to the most recent line of therapy in Cohort 4 (Table 13). Unlike Cohorts 1+2 in which patients had to be refractory after second-line or later therapy, patients in Cohort 4 could be relapsed or refractory. Consequently, there were 12% who were relapsed after second-line or later therapy (0 in Cohorts 1+2).

TABLE 13

| Characteristic | Cohorts 1 + 2 (N = 101) | Cohort 4 (N = 41) |
|---|---|---|
| Disease type, n (%) | | |
| DLBCL | 77 (76) | 26 (63) |
| PMBCL | 8 (8) | 2 (5) |
| TFL | 16 (16) | 10 (24) |
| HGBCL | NA[a] | 3 (7) |
| Age | | |
| Median (range), years-old | 58 (23-76) | 61.0 (19-77) |
| ≥65 years-old, n (%) | 24 (24) | 13 (32) |
| Male sex, n (%) | 68 (67) | 28 (68) |
| ECOG performance status score of 1, n (%) | 59 (58) | 20 (49) |
| Disease stage, n (%) | | |
| I or II | 15 (15) | 11 (27) |
| III or IV | 86 (85) | 29 (71) |
| IPI score, n (%) | | |
| 0-2 | 55 (54) | 21 (51) |
| 3-4 | 46 (46) | 20 (49) |
| CD19 positivity, n/N (%) | | |
| Yes | 74/82 (90) | 22/24 (92) |
| No | 8/82 (10) | 2/24 (8) |
| Number of prior lines of chemotherapy, % | | |
| 1 | 3 (3) | 0 |
| 2 | 28 (28) | 15 (37) |

TABLE 13-continued

| Characteristic | Cohorts 1 + 2 (N = 101) | Cohort 4 (N = 41) |
|---|---|---|
| 3 | 29 (29) | 15 (37) |
| 4 | 29 (29) | 8 (20) |
| ≥5 | 12 (12) | 3 (7) |
| Prior SCT, n (%) | 25 (25) | 14 (34) |
| PD as best response to most recent chemotherapy[b], n (%) | 67 (66) | 15 (37) |
| Median tumor burden by SPD[c] (range), mm$^2$ | 3721 (171-23,297) | 2100 (204-24,758) |
| Median LDH, U/L (range) | 344 (116-7802) | 262 (145-4735) |
| Median ferritin, ng/mL (range) | 777 (1-10,576) | 393 (23-3457) |
| Refractory subgroup, n (%) | | |
| Primary refractory | 3 (3) | 0 (0) |
| Refractory ≥ 2$^{nd}$-line therapy | 77 (76) | 28 (68) |
| Relapsed ≥ 2$^{nd}$-line therapy | NA | 5 (12) |
| Relapsed post-ASCT | 21 (21) | 8 (20) |

[a]HGBCL was captured as DLBCL in Cohorts 1 + 2. Pretreatment tumor samples were assessed in 47 patients; 7 (15%) had HGBCL.20
[b]For patients who had not relapsed post-ASCT.
[c]Measured after bridging.
ASCT, autologous stem cell transplant; DLBCL, diffuse large B-cell lymphoma; ECOG, Eastern Cooperative Oncology Group; HGBCL, high grade B-cell lymphoma; IPI, International Prognostic Index; LDH, lactate dehydrogenase; NA, not applicable; PMBCL, primary mediastinal B-cell lymphoma; SPD, sum of the products of diameters; TFL, transformed follicular lymphoma.

Total T-cell numbers infused, transduction rate, and phenotypic characterization of T cells in Cohort 4 were generally consistent with those of Cohorts 1+2 (Table 14, summary of product characteristics).

TABLE 14

| Parameter | Median (Min-Max) | |
| | Cohorts 1 + 2 (N = 101) | Cohort 4 (N = 41) |
|---|---|---|
| Total number of CAR T-cells per µL | 298.51 (149.07-760.46) | 275.36 (176.39-487.80) |
| Total Number of T-cells per µL | 165.00 (75.00-200.00) | 160.00 (100.00-200.00) |
| Transduction Rate, % | 52.60 (21.60-85.10) | 55.00 (33.00-73.00) |
| IFN-γ level, pg/mL | 1.03E+04 (1355.45-3.64E+04) | 1.51E+04 (2262.50-3.40E+04) |
| Viability, % | 94.40 (83.50-97.40) | 92.00 (72.00-96.00) |
| CD4/CD8 ratio | 0.87 (0.03-5.81) | 1.39 (0.30-17.60) |
| Naïve T cells, % | 13.75 (1.00-76.00) | 13.40 (2.48-53.50) |
| Central memory T cells, % | 25.70 (9.00-50.10) | 29.00 (4.50-44.90) |

Although the overall incidence of CRS in Cohort 4 was comparable to that of Cohorts 1+2 (both 93%), the incidence of grade ≥3 CRS was 2% in Cohort 4 and 12% in Cohorts 1+2 (Table 15); incidence, severity, onset, and duration of CRS and neurologic Events). In Cohort 4, no grade 4 CRS events occurred while in Cohorts 1+2, grade 4 CRS occurred in 3% of patients. CRS resolved by the data cutoff date in all patients in Cohort 4 and 93 of 94 patients in Cohorts 1+2. There were no deaths in the setting of CRS in Cohort 4. In Cohorts 1+2, one patient died from hemophagocytic lymphohistiocytosis and one grade 5 cardiac arrest occurred in a patient with CRS. Time to onset and duration of CRS were similar across cohorts.

A similar pattern was observed with neurologic events: the overall incidence was comparable in Cohort 4 and Cohorts 1+2 (61% vs 64%, respectively), with incidences of grade ≥3 neurologic events of 17% and 29% (Table 15). In Cohort 4, no grade 4 neurologic events were observed while 2% of patients in Cohorts 1+2 experienced grade 4 neurologic events. There were no grade 5 neurologic events in either cohort. Neurologic events resolved in 20 of 25 patients in Cohort 4 and 60 of 64 patients in Cohorts 1+2. Time to onset and duration of neurologic events were both similar across cohorts. All grade ≥3 neurologic events in Cohort 4 occurred in patients who received bridging therapy, possibly due to selection of patients with more aggressive disease in this group.

TABLE 15

| TEAE | Cohorts 1 + 2 (N = 101) | Cohort 4 (N = 41) |
|---|---|---|
| | CRS | |
| Any, n (%) | 94 (93) | 38 (93) |
| Worst grade 1, n (%) | 37 (37) | 13 (32) |
| Worst grade 2, n (%) | 45 (45) | 24 (59) |
| Worst grade 3, n (%) | 8 (8) | 1 (2) |
| Worst grade 4, n (%) | 3 (3) | 0 |

TABLE 15-continued

| TEAE | Cohorts 1 + 2 (N = 101) | Cohort 4 (N = 41) |
|---|---|---|
| Worst grade 5, n (%) | 1 (1) | 0 |
| Median (range) time to onset, days | 2.0 (1.0-12.0) | 2.0 (1.0-8.0) |
| Median (range) duration, days | 7.0 (2.0-58.0) | 6.5 (2.0-16.0) |
| | Neurologic events | |
| Any, n (%) | 65 (64) | 25 (61) |
| Worst grade 1, n (%) | 21 (21) | 14 (34) |
| Worst grade 2, n (%) | 15 (15) | 4 (10) |
| Worst grade 3, n (%) | 27 (27) | 7 (17) |
| Worst grade 4, n (%) | 2 (2) | 0 |
| Worst grade 5, n (%) | 0 | 0 |
| Median (range) time to onset, days | 5.0 (1.0-17.0) | 6.0 (1.0-93.0) |
| Median (range) duration, days | 12.0 (1.0-450.0) | 8.0 (1.0-144.0) |

CRS, cytokine release syndrome;
TEAE, treatment-emergent adverse event

Figure 47:
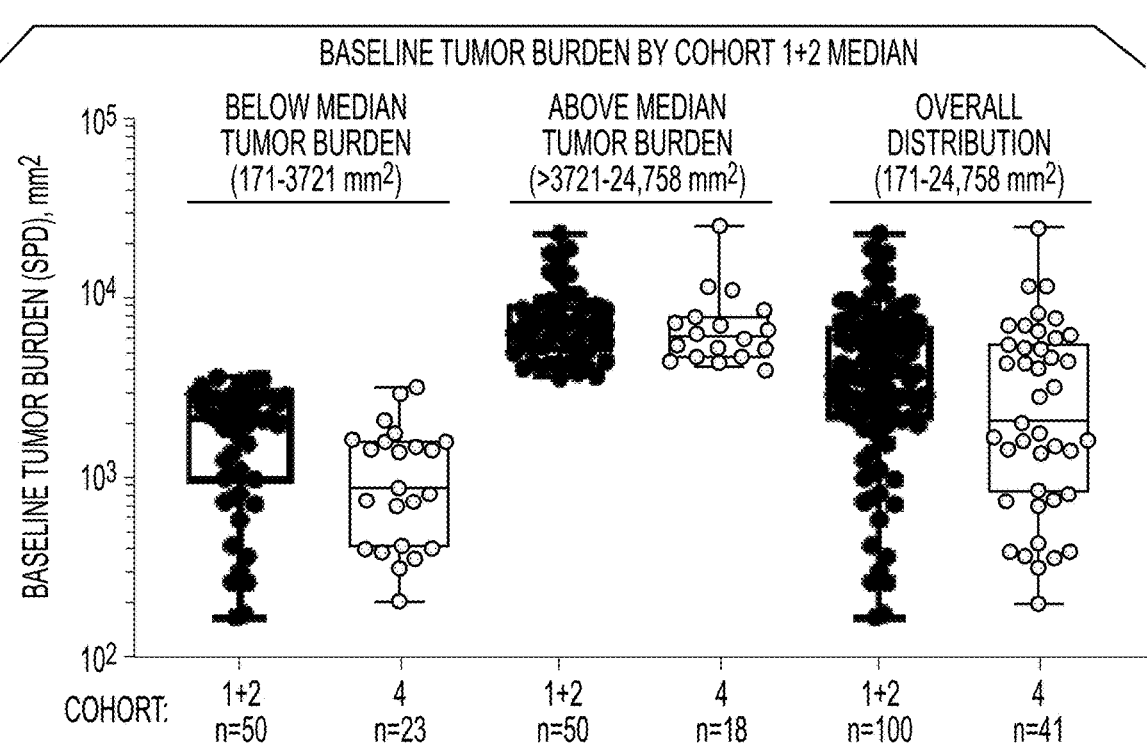
FIG. 47: Distribution of baseline tumor burden. The figure shows baseline tumor burden of patients in Cohorts 1+2 and 4 divided into high and low tumor burden groups based on the median tumor burden of Cohorts 1+2. Tumor burden in Cohort 4 was measured after bridging therapy and before conditioning chemotherapy.
Figure 48:
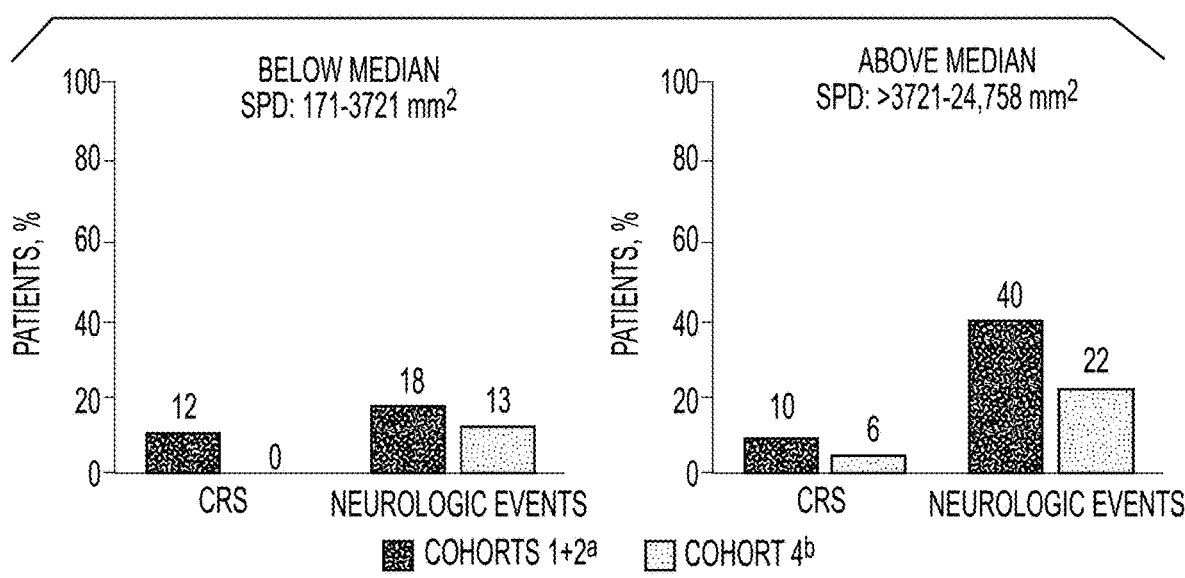
FIG. 48: Grade ≥3 CRS and neurologic events by Tumor Burden. The figure shows percentages of patients with tumor burden below (left panel) or above (right panel) the median who experienced CRS (left bars) or an NE (right bars). Median tumor burden was defined based on Cohorts 1+2. Tumor burden in Cohort 4 was measured after bridging therapy and before conditioning chemotherapy. Blue bars: Cohorts 1+2. Purple bars: Cohort 4. [a]N=50 in the below median group and 50 in the above median group. Tumor burden was not available for one patient. [b]N=23 in the below median group and 18 in the above median group. CRS, cytokine release syndrome; SPD, sum of the products of diameters.

To determine the potential impact of baseline tumor burden, incidences of grade ≥3 CRS and neurologic events among patients with tumor burdens above or below the median of Cohorts 1+2 (FIG. 47) were compared. Although limited by small sample size, the analysis showed that the incidence of both grade ≥3 CRS and grade ≥3 neurologic events was numerically lower in Cohort 4 than in Cohorts 1+2, with the greatest difference observed being in grade ≥3 neurologic events in patients with tumor burden above the median (FIG. 48). Additionally, bridging therapy did not appear to contribute to a reduction in the incidence of grade ≥3 CRS (bridging, ⅟₂₈ [4%]; no bridging, ⁰⁄₁₃ [0%]) or neurologic events (bridging, ⁷⁄₂₈ [25%]; no bridging, ⁰⁄₁₃ [0%]) in Cohort 4.

The incidence of grade ≥3 infection in Cohort 4 (24%) was comparable to that of Cohorts 1+2 (25%; Table 16; incidence and severity of TEAE5). The incidences of prolonged grade ≥3 anemia and thrombocytopenia were numerically lower in Cohort 4, but prolonged grade ≥3 neutropenia was comparable between cohorts.

TABLE 16

| TEAE, n (%) | Cohorts 1 + 2 (N = 101) | | | Cohort 4 (N = 41) | | |
|---|---|---|---|---|---|---|
| | Any Grade | Worst Grade 3 | Worst Grade 4 | Any Grade | Worst Grade 3 | Worst Grade 4 |
| Pyrexia | 87 (86) | 13 (13) | 0 | 39 (95) | 10 (24) | 0 |
| Anemia | 68 (67) | 42 (42) | 3 (3) | 19 (46) | 10 (24) | 0 |
| Hypotension | 60 (59) | 13 (13) | 1 (1) | 25 (61) | 4 (10) | 0 |
| Neutropenia | 46 (46) | 10 (10) | 30 (30) | 16 (39) | 4 (10) | 12 (29) |
| Infection | 40 (40) | 23 (23) | 2 (2) | 25 (61) | 8 (20) | 1 (2) |
| Thrombocytopenia | 36 (36) | 11 (11) | 13 (13) | 7 (17) | 4 (10) | 1 (2) |
| Encephalopathy | 35 (35) | 20 (20) | 1 (1) | 7 (17) | 2 (5) | 0 |
| Febrile neutropenia | 34 (34) | 29 (29) | 1 (1) | 3 (7) | 3 (7) | 0 |
| Neutrophil count decreased | 33 (33) | 6 (6) | 26 (26) | 12 (29) | 1 (2) | 11 (27) |
| White blood cell count decreased | 31 (31) | 3 (3) | 26 (26) | 6 (15) | 1 (2) | 5 (12) |
| Hypophosphatemia | 28 (28) | 16 (16) | 2 (2) | 6 (15) | 4 (10) | 0 |
| Platelet count decreased | 28 (28) | 8 (8) | 7 (7) | 10 (24) | 2 (5) | 2 (5) |
| Leukopenia | 21 (21) | 5 (5) | 13 (13) | 7 (17) | 1 (2) | 5 (12) |
| Lymphocyte count decreased | 21 (21) | 2 (2) | 19 (19) | 4 (10) | 2 (5) | 1 (2) |

[a]Listed are TEAEs that occurred as grade ≥3 in >10% of patients in either Cohorts 1 + 2 or Cohort 4.

A total of 73% of Cohort 4 patients received steroids compared with 26% in Cohorts 1+2. Earlier use of steroids for management of CRS and neurologic events in Cohort 4 resulted in a cumulative steroid dose less than one-fifth of that in Cohorts 1+2 for patients requiring steroid therapy. Overall, 85% of patients requiring steroids in Cohorts 1+2 received ≥5 doses versus only 43% in Cohort 4 (Table 17; cumulative dose and frequency of steroid use). Most Cohort 4 patients (76%) received tocilizumab compared with 43% in Cohorts 1+2.

TABLE 17

| | Cohorts 1 + 2 (N = 26[a]) | Cohort 4 (N = 30) |
|---|---|---|
| Patients receiving steroids, n (%)[b] | | |
| 1 dose | 3 (12) | 7 (23) |
| 2 doses | 1 (4) | 7 (23) |
| 3 doses | 0 (0) | 3 (10) |
| ≥5 doses | 22 (85) | 13 (43) |
| Cumulative steroid dose, mg[c] | | |
| Median (Min-Max) | 6388 (6.3-42,412) | 939 (313-33,463) |
| Mean (SD) | 10,756 (12,063) | 5152 (7654) |

[a]N of patients with evaluable steroid dosing data until initial hospitalization; dosing information was not available for two patients with Cohorts 1 + 2. Percentages may not equal 100% due to rounding;
[b]Steroid use includes those doses that started on or after the start date of the first dose of axicabtagene ciloleucel but prior to or on hospital discharge date;
[c]Cumulative systemic cortisone equivalent dose.
max, maximum; min, minimum; SD, standard deviation.

Figure 49:
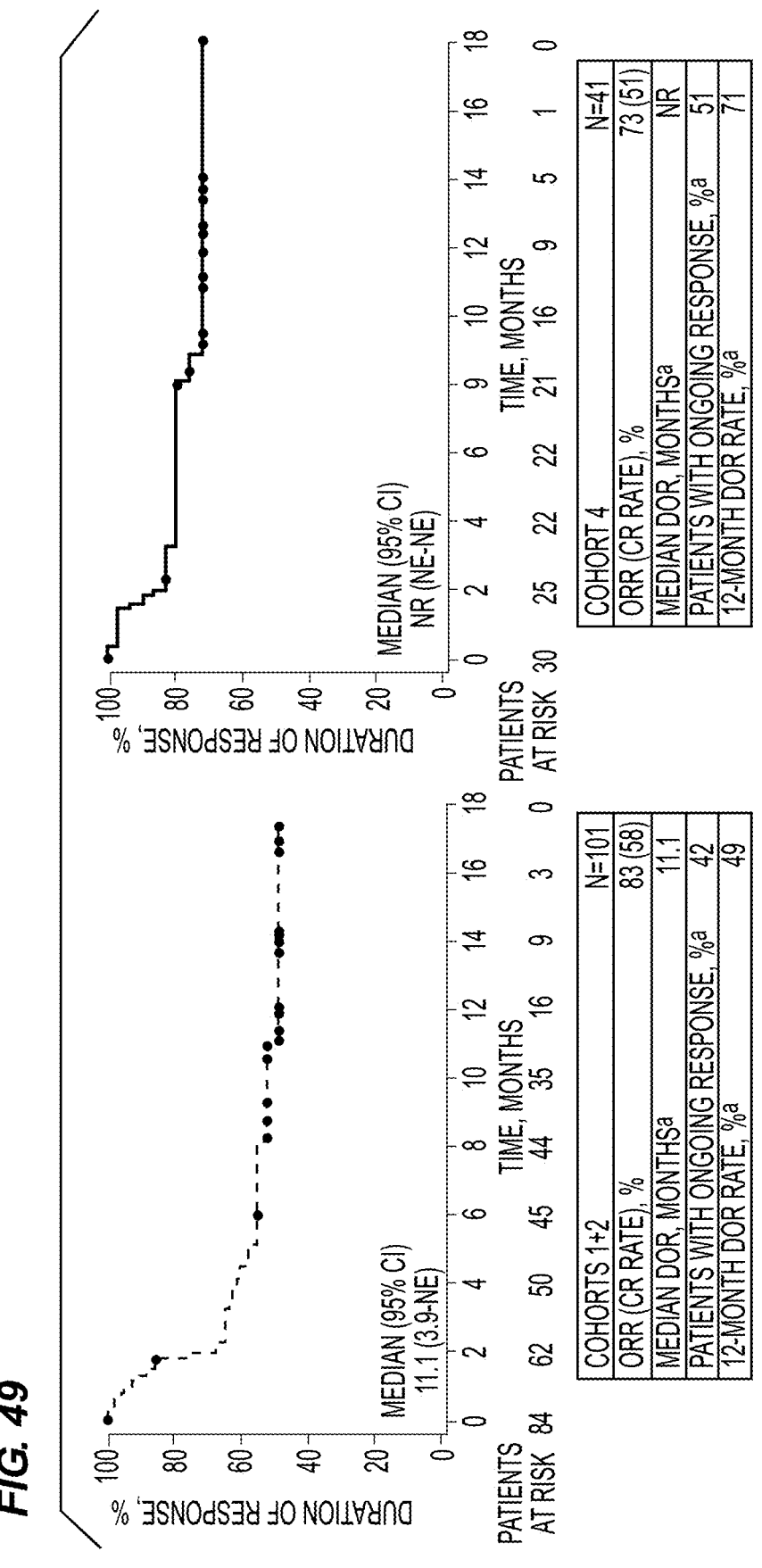
FIG. 49: Overall Response and Duration of Response in Cohort 4 Versus Cohorts 1+2.

Earlier steroid intervention for toxicity management did not appear to negatively impact the efficacy of axicabtagene ciloleucel. Objective response rates for Cohort 4 and Cohorts 1+2 were 73% and 83%, respectively. While the study was not designed to evaluate the bridging therapy, comparable ORRs were observed in patients who did and did not receive bridging therapy (bridging, 71%; no bridging, 77%). Complete response rate was numerically lower in patients who received bridging therapy (46% vs 62%). While 12-month DOR rates were 71% for Cohort 4 and 49% for Cohort 1+2 (FIG. 49), 51% and 42% of patients, respectively, were in response as of their respective data cut-offs.

Figure 50:
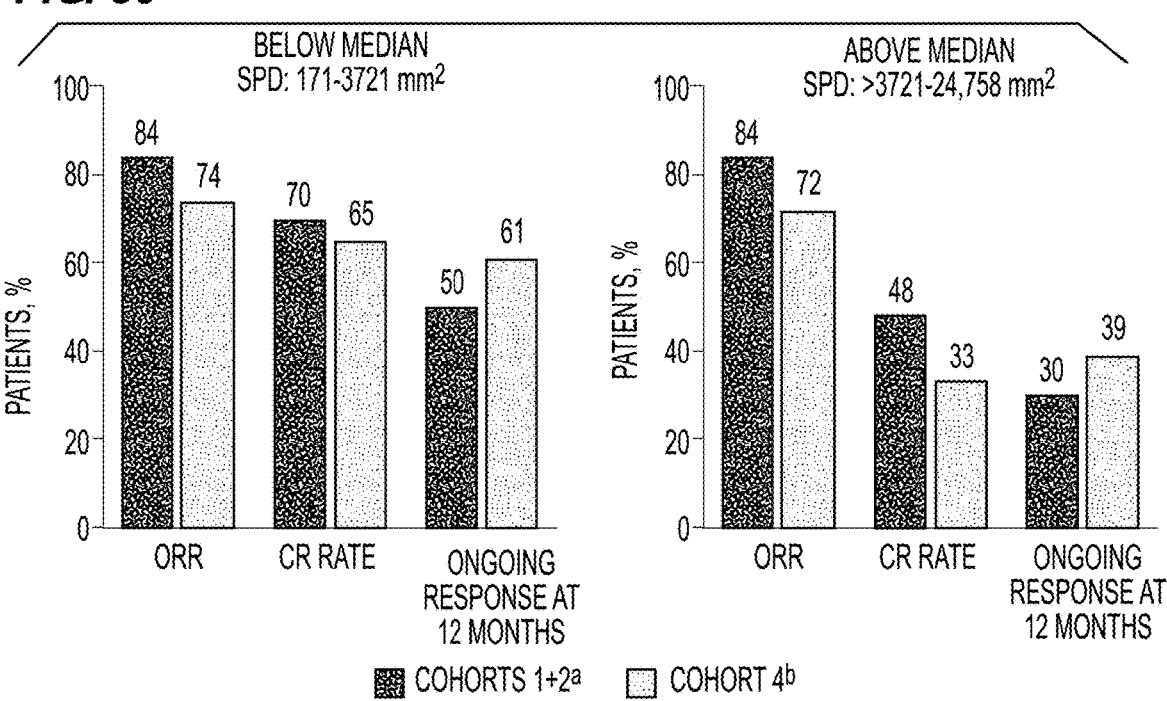
FIG. 50: Best Response by Tumor Burden. The figure shows percentages of patients with tumor burden below (left panel) or above (right panel) the median with corresponding ORR (left bars), CR (middle bars), and ongoing response at 12 months (right bars). Median tumor burden was defined based on Cohorts 1+2. Tumor burden in Cohort 4 was measured after bridging therapy and before conditioning chemotherapy. Blue bars: Cohorts 1+2. Purple bars: Cohort 4. N=50 in the below median group and 50 in the above median group. Tumor burden was not available for one patient. [b]N=23 in the below median group and 18 in the above median group. CR, complete response; ORR, objective response rate; SPD, sum of the products of diameters.
Figure 51:
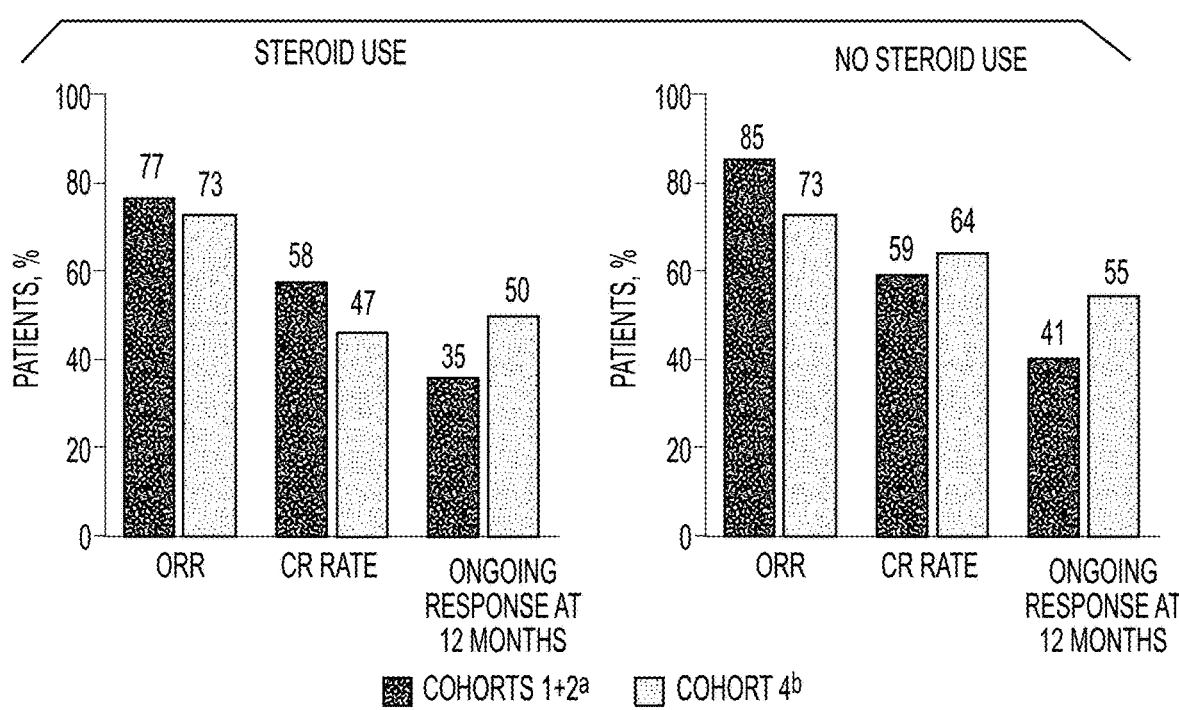
FIG. 51: Best Response by Steroid Use. The figure shows percentages of patients who did (left panel) or did not (right panel) receive steroids with corresponding ORR (left bars), CR (middle bars), and ongoing response at 12 months (right bars). Blue bars: Cohorts 1+2. Purple bars: Cohort 4. [a]N=26 in the steroid use group and 75 in the no steroid use group. [b]N=30 in the steroid use group and 11 in the no steroid use group. CR, complete response; ORR, objective response rate.

Objective and ongoing response rates were similar across Cohort 4 and Cohorts 1+2 in patients with tumor burden above and below the tumor burden median (FIG. 50), as were those in patients who did or did not receive steroids (FIG. 51). In patients with tumor burden above the median, complete response rates were 33% and 48%, respectively, in Cohort 4 and Cohort 1+2 (FIG. 50)

Figure 52:
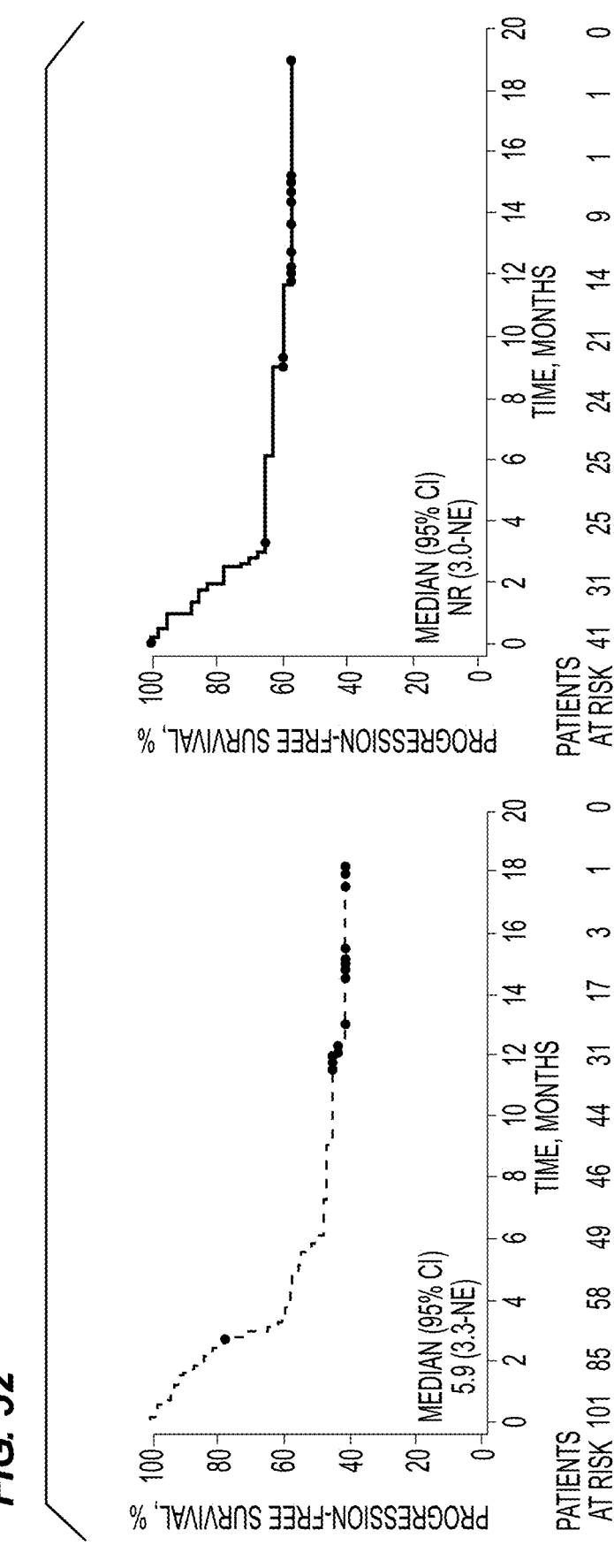
FIG. 52: Progression-free Survival in Cohort 4 Versus Cohorts 1+2.

Neither median PFS nor median OS were reached with a minimum of 1 year of follow-up in Cohort 4 (PFS: 95% CI, 3.0 months to not estimable; OS: 95% CI, 15.8 months to not estimable). In Cohorts 1+2, median PFS was 5.9 months (95% CI, 3.3 months to not estimable; FIG. 52) but median OS was not reached (95% CI, 12.8 months to not estimable).

Serum was obtained at multiple timepoints for quantification of soluble markers, including cytokines. Cerebrospinal fluid (CSF) was collected after confirmation of eligibility, prior to conditioning chemotherapy, on Day 5 (±3 days) after axicabtagene ciloleucel infusion, and at the Week 4 visit (±3 days). Up to 46 soluble markers were measured in serum and CSF by multiplex MSD®, Luminex®, Protein-Simple® Simple Plex, or Quantikine® enzyme-linked immunosorbent assay (ELISA). Product cells were characterized by flow cytometry and coculture with CD19-expressing target cells followed by ELISA or Meso Scale Discovery (MSD).

Pretreatment serum levels of LDH were lower in Cohort 4 than in Cohorts 1+2, consistent with lower pretreatment tumor burden. Additionally, baseline ferritin in Cohort 4 was lower than in Cohorts 1+2, potentially suggesting a lower baseline inflammatory state (Table 13).

Figure 53:
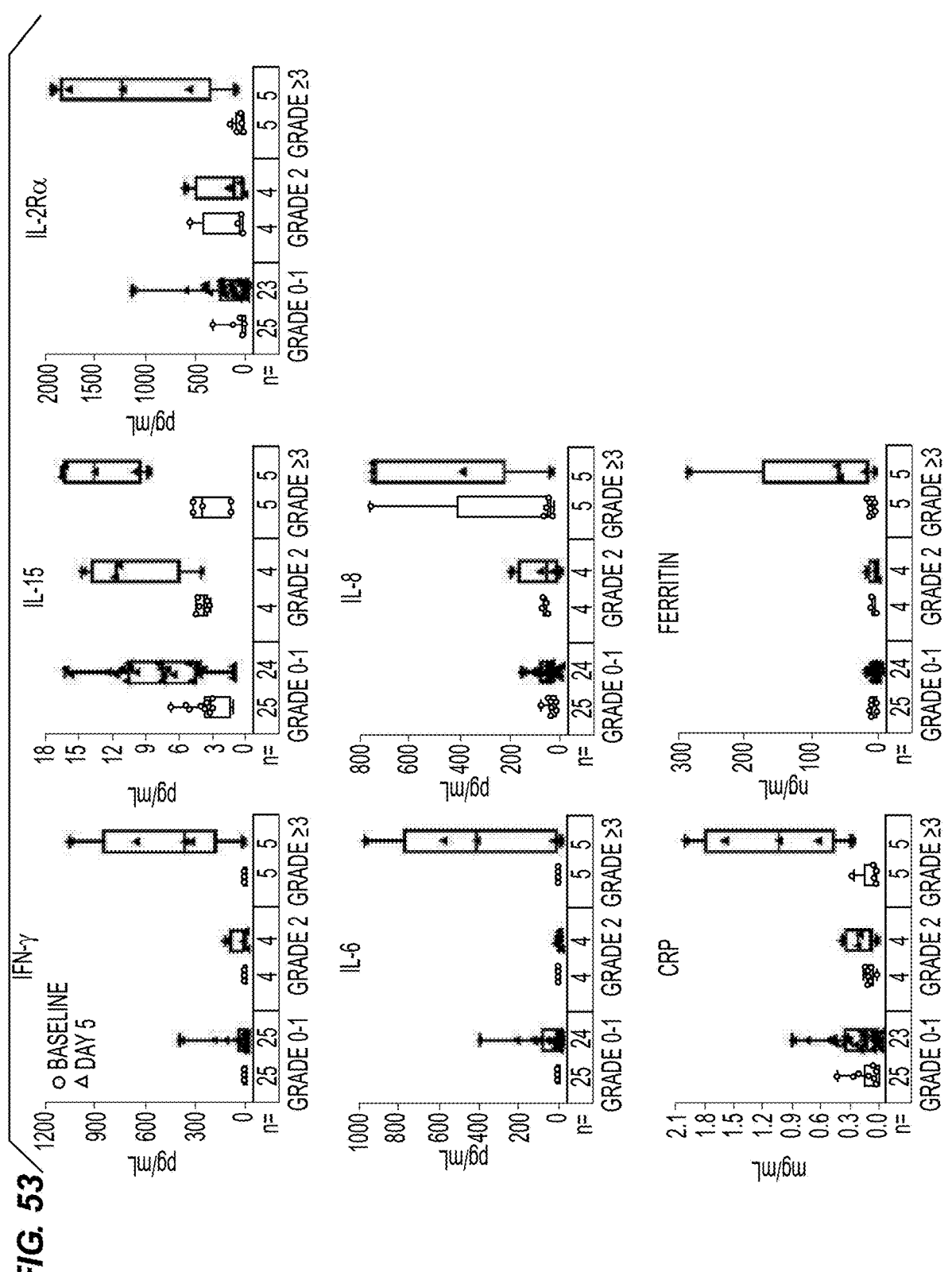
FIG. 53: Selected CSF Analysis at Baseline and Day 5 and Association with Neurologic Events.
Figure 54:
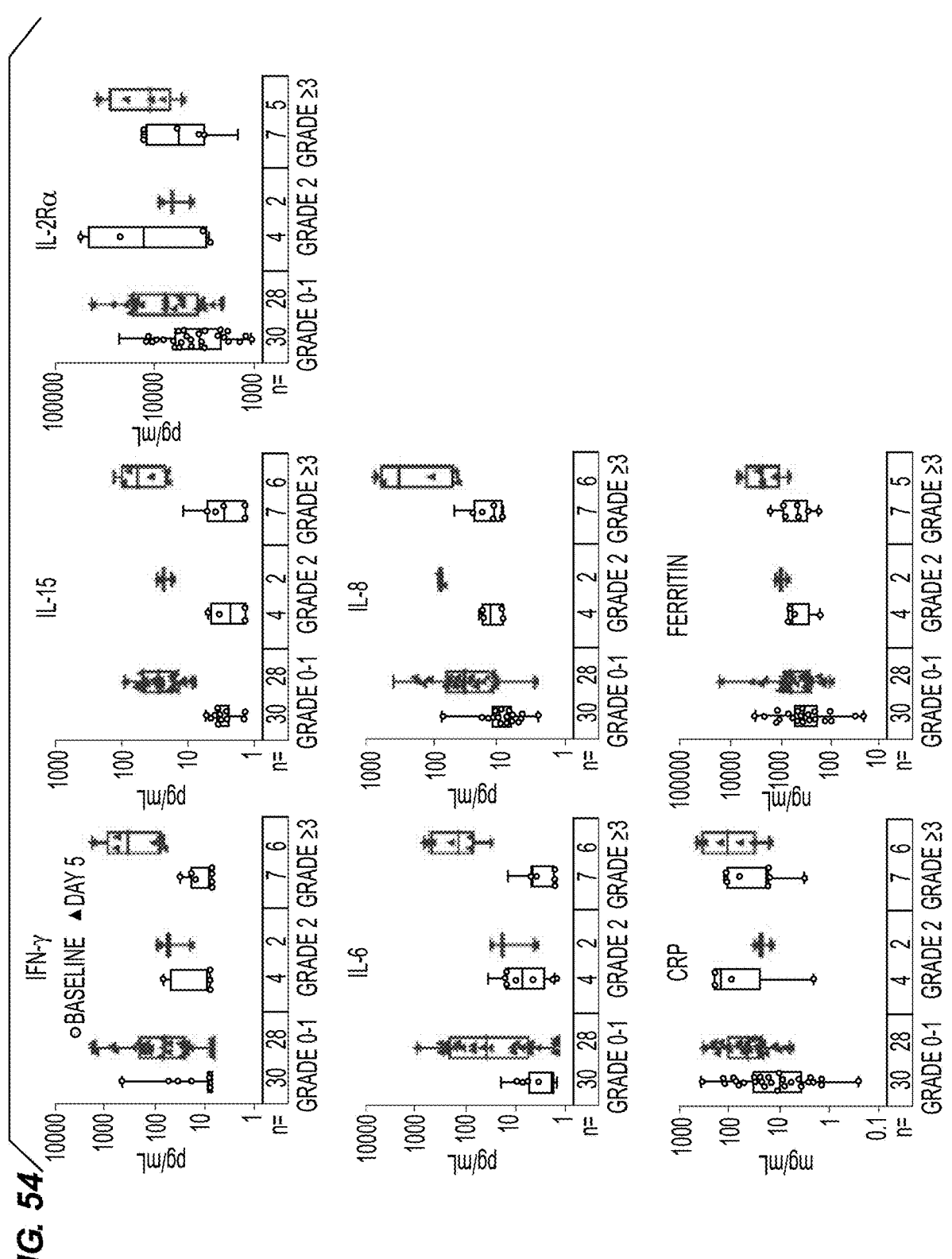
FIG. 54: Selected Serum Analysis at Baseline and Day 5 and Association with Neurologic Events.

Patients with evaluable samples and grade ≥3 neurologic events had numerically greater post-infusion (Day 5) CSF levels of IFNγ, IL-15, IL-2Rα, IL-6, and IL-8 than did those with grade 0 to 1 neurologic events, despite low and comparable baseline levels across Cohort 4 (FIG. 53). A similar pattern was observed for serum cytokines (FIG. 54).

Figure 55A:
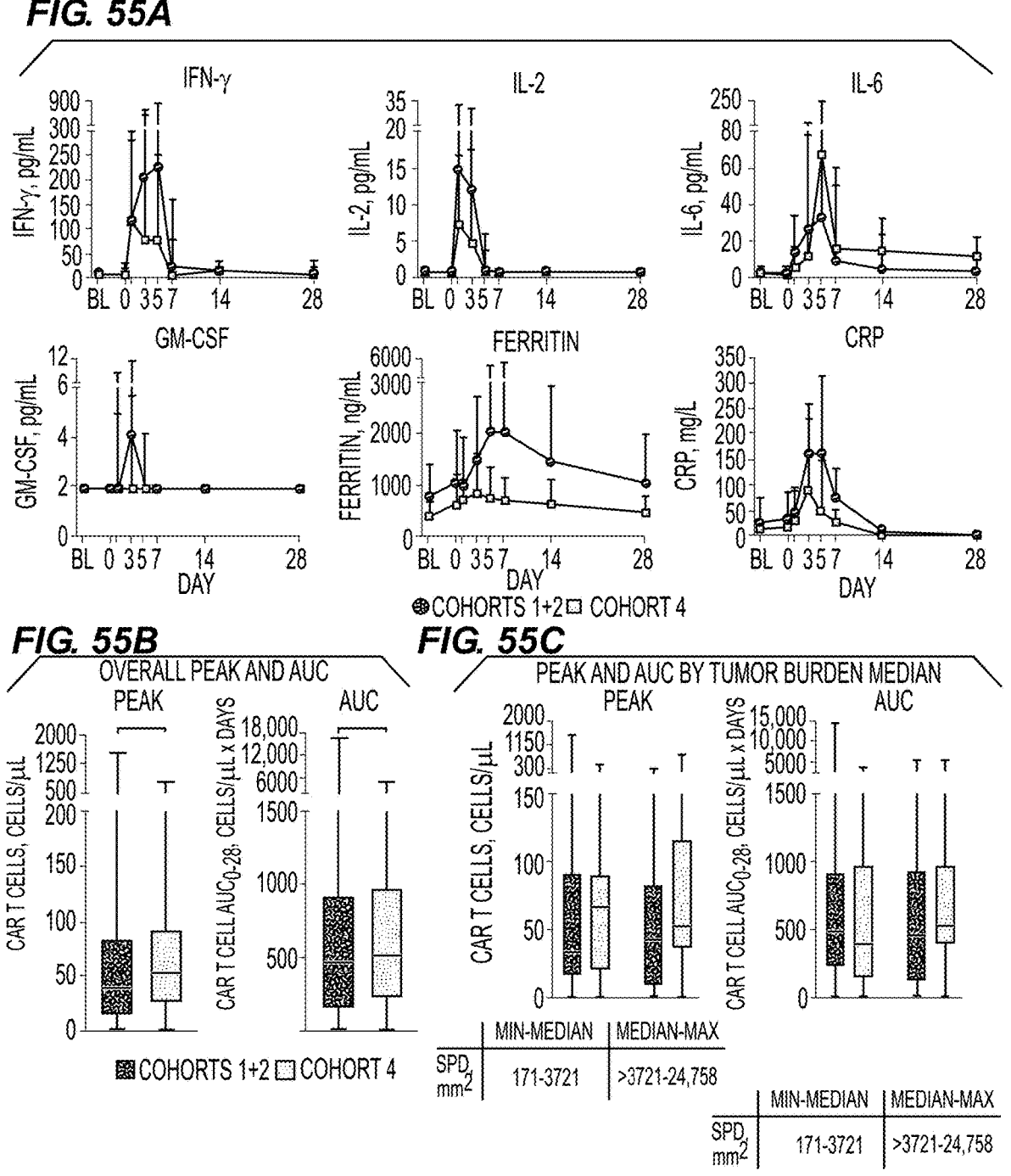

Nevertheless, post-treatment median peak levels of key inflammatory serum cytokines including interferon (IFN-)γ, IL-2, and granulocyte monocyte colony-stimulating factor (GM-CSF), previously shown to be associated with adverse events, were numerically lower in Cohort 4 than in Cohorts 1+2 (Table 18; summary of serum biomarkers). This was paralleled by lower levels of C-reactive protein (CRP) and ferritin (FIG. 55A) in Cohort 4 versus Cohorts 1+2.

TABLE 18

| | Peak Median (range), pg/mL | | AUC$_{0-28}$ Median (range), pg/ml × day | |
|---|---|---|---|---|
| Biomarker | Cohorts 1 + 2 (N = 101) | Cohort 4 (N = 41) | Cohorts 1 + 2 (N = 101) | Cohort 4 (N = 41) |
| CRP | 214.2 (18.5-496.0) mg/L | 126.5 (18.2-496.0) mg/L | 1555.2 (150.8-7934.0) mg/L × day | 852.8 (209.5-5698.2) mg/L × day |
| Eotaxin-1 | 141.1 (12.3-768.7) | 206.7 (93.4-638.1) | 2793.3 (405.9-14815.2) | 4822.2 (1047.9-15619.8) |
| Eotaxin-3 | 10.2 (10.2-915.8) | 10.2 (10.2-318.7) | 336.6 (122.4-1520.6) | 336.6 (81.6-3884.4) |
| FGFBF | 22.7 (2.6-1481.0) | NA | 212.9 (41.6-1168.1) | NA |
| FLT-1 | 293.0 (73.7-12820.0) | NA | 4828.3 (1409.1-86156.0) | NA |
| Ferritin | 3001.4 (0.8-25,000.0) | 1086.4 (95.5-23869.6) | 49334.1 (21.8-537182.1) | 22655.3 (1323.0-336530.8) |
| GM-CSF | 7.3 (1.9-513.0) | 4.4 (1.9-47.0) | 77.3 (29.8-590.1) | 62.7 (39.9-177.2) |
| Granzyme A | 20.0 (20.0-8362.4) | 20.0 (20.0-3396.4) | 660.0 (240.0-140362.1) | 660.0 (160.0-46773.3) |
| Granzyme B | 22.7 (1.0-3306.0) | NA | 153.3 (19.0-3672.8) | NA |
| ICAM-1 | 1257.0 (544.6-7495.1) × 10³ | 938.7 (359.5-5141.6) × 10³ | 1257.0 (544.6-7495.1) × 10³ | 20147.4 (10002.8-64670.3) × 10³ |
| IFN-gamma | 477.4 (7.5-1876.0) | 334.5 (24.9-1876.0) | 2251.9 (247.5-21598.0) | 1758.7 (429.6-16408.0) |
| IL-1 RA | 2314.2 (510.8-4000.0) | 1093.7 (193.3-4493.1) (n = 31) | 25259.3 (9526.5-49402.6) | 16397.4 (3278.4-41090.6) (n = 27) |
| IL-1 alpha | 2.9 (2.9-118.2) | 2.9 (2.9-2.9) | 95.7 (34.8-3022.2) | 95.7 (23.2-95.7) |
| IL-1 beta | 2.1 (2.1-23.6) | 2.1 (2.1-6.4) | 69.3 (25.2-112.3) | 69.3 (16.8-69.3) |

TABLE 18-continued

| | Peak Median (range), pg/mL | | $AUC_{0-28}$ Median (range), pg/ml × day | |
|---|---|---|---|---|
| Biomarker | Cohorts 1 + 2 (N = 101) | Cohort 4 (N = 41) | Cohorts 1 + 2 (N = 101) | Cohort 4 (N = 41) |
| IL-10 | 41.0 (0.7-466.0) | 19.6 (1.4-466.0) | 219.9 (19.6-2090.9) | 142.5 (25.2-6032.4) |
| IL-12 P40 | 266.2 (25.3-4500.0) | 160.5 (5.7-756.1) | 4246.7 (333.9-24040.6) | 3425.6 (218.3-13023.2) |
| IL-12 P70 | 1.2 (1.2-206.1) | 1.2 (1.2-6.4) | 39.6 (19.1-274.9) | 39.6 (9.6-48.7) |
| IL-13 | 4.2 (4.2-86.5) | 4.2 (4.2-8.5) | 138.6 (50.4-303.1) | 138.6 (33.6-138.6) |
| IL-15 | 52.9 (11.3-226.6) | 45.8 (22.3-272.7) | 567.3 (127.6-3930.1) | 463.3 (223.6-2783.9) |
| IL-16 | 256.6 (51.8-3740.0) | 216.8 (98.9-3740.0) | 5114.2 (681.9-16720.8) | 5309.4 (2003.9-61679.4) |
| IL-17 | 27.1 (9.3-664.2) | 9.3 (9.3-314.1) | 360.5 (111.6-2815.7) | 306.9 (126.5-1193.1) |
| IL-2 | 21.7 (0.9-123.1) | 11.2 (0.9-79.4) | 90.8 (17.1-409.2) | 56.9 (29.7-244.3) |
| IL-2R alpha | 12.1 (0.1-100.0) × $10^3$ | 10.8 (2.8-94.6) × $10^3$ | 160.3 (2.2-1285.9) × $10^3$ | 184.5 (70.8-1063.9) × $10^3$ |
| IL-4 | 0.5 (0.5-23.9) | 0.5 (0.5-4.1) | 16.5 (6.0-33.1) | 16.5 (4.0-40.3) |
| IL-5 | 56.6 (6.3-1124.0) | 34.4 (6.3-853.7) | 378.4 (119.7-5287.4) | 274.4 (178.9-8978.1) |
| IL-6 | 83.3 (3.5-976.0) | 136.7 (1.6-976.0) | 406.3 (47.8-17567.6) | 952.8 (56.6-9322.4) |
| IL-7 | 40.8 (13.8-153.5) | 33.1 (18.0-67.5) | 791.6 (228.4-3238.1) | 689.8 (353.6-1307.8) |
| IL-8 | 93.6 (9.8-750.0) | 67.4 (8.5-750.0) | 772.4 (126.2-18517.7) | 687.5 (214.2-9972.8) |
| CXCL10 | 2000.0 (434.2-2000.0) | 1571.7 (469.2-2000.0) | 27083.4 (4550.8-65313.7) | 21961.7 (4013.2-51730.6) |
| MCP-1 | 1500.0 (428.8-1500.0) | 1221.8 (510.2-1500.0) | 15097.5 (5194.1-46383.5) | 14412.0 (8259.1-37739.2) |
| MCP-4 | 277.3 (77.0-1493.2) | 129.7 (47.3-741.6) | 4634.1 (625.6-18111.7) | 2709.1 (558.6-14063.6) |
| MDC | 929.2 (88.3-30,000.0) | 852.3 (88.3-18936.9) | 20611.2 (2472.4-362776.2) | 19171.7 (1833.7-338618.7) |
| MIP-1 alpha | 13.8 (13.8-444.1) | 13.8 (13.8-434.3) | 455.4 (262.2-4763.5) | 455.4 (262.2-2146.6) |
| MIP-1 beta | 270.4 (73.3-3000.0) | 235.4 (67.3-1689.2) | 3728.0 (1524.5-23122.2) | 3827.8 (1600.2-7533.5) |
| PDL1 | | 163.2 (45.1-1136.6) (n = 27) | | 4248.6 (422.3-8979.7) (n = 22) |
| PLGF | 161.6 (57.7-413.7) | NA | 2830.3 (1180.9-5634.6) | NA |
| Perforin | 10.5 (2.3-39.8) × $10^3$ | 17.2 (3.9-44.4) × $10^3$ | 177.5 (42.1-675.8) × $10^3$ | 348.5 (66.5-744.5) × $10^3$ |
| SAA | 560.1 (18.5-1380.0) × $10^6$ | 408.8 (4.1-1380.0) × $10^6$ | 3358.3 (105.6-21408.6) × $10^6$ | 1459.4 (363.5-13278.9) |
| SFASL | 10.0 (10.0-499.3) | 10.0 (10.0-543.2) | 330.0 (120.0-8122.3) | 330.0 (190.0-1547.4) × $10^6$ |
| CCL 17 (TARC) | 1456.4 (88.8-4480.0) | 871.8 (82.7-4480.0) | 17317.6 (1986.3-115566.2) | 18808.2 (834.6-127561.0) |
| TIE-2 | 4583.0 (2301.3-10,773.7) | NA | 120027.6 (47431.4-217515.2) | NA |
| TNF alpha | 7.9 (2.2-166.9) | 5.7 (2.0-54.6) | 129.1 (41.1-1501.9) | 92.6 (35.1-286.1) |
| TNF beta | 1.2 (1.2-81.1) | 1.2 (1.2-19.5) | 39.6 (17.4-568.5) | 39.6 (9.6-76.2) |
| VCAM-1 | 1391.3 (634.8-3859.4) × $10^3$ | 1255.9 (594.5-3932.6) × $10^3$ | 29062.3 (12266.2-102187.1) × $10^3$ | 27501.1 (7089.9-62349.7) × $10^3$ |
| VEGF | 488.0 (82.7-3020.0) | NA | 9468.1 (1390.4-50353.9) | NA |
| VEGFC | 146.0 (146.0-499.0) | NA | 4818.0 (1752.0-11782.3) | NA |
| VEGFD | 1593.6 (744.2-4057.2) | NA | 37326.7 (15832.1-114306.8) | NA |

$AUC_{0-28}$, area under the curve from day 0 to 28;
CCL, chemokine (C-C motif) ligand;
CXCL, chemokine (C-X-C motif) ligand;
FGFBF, fibroblast growth factor basic form;
FLT, vascular endothelial growth factor receptor;
GM-CSF, granulocyte macrophage colony stimulating factor;
ICAM, intercellular adhesion molecule;
IFN, interferon;
IL, interleukin;
MCP, monocyte chemotactic protein;
MDC, macrophage-derived chemokine;
MIP, macrophage inflammatory protein;
PLGF, placental growth factor;
R, receptor;
RA, receptor antagonist;
SAA, serum amyloid A;
SFASL, serum soluble Fas ligand;
TIE, TEK tyrosine kinase;
TNF, tumor necrosis factor;
VCAM, vascular cell adhesion molecule;
VEGF, vascular endothelial growth factor In contrast, post-infusion CAR T-cell expansion, a correlate of clinical efficacy and neurotoxicity, was comparable between Cohort 4 and Cohorts 1+2, even after adjustment for tumor burden level (FIG. 55B and FIG. 55C). Altogether, these findings corroborate with clinical outcomes.

ZUMA-1 Cohort 4 showed that earlier intervention with steroids has the potential to improve the benefit:risk profile of axicabtagene ciloleucel in patients with R/R LBCL. Earlier steroid intervention was associated with lower rates of severe CRS and neurologic events in Cohort 4 than what was observed in Cohorts 1+2. Earlier use of steroids in Cohort 4 was associated with a median cumulative cortisone-equivalent dose approximately 15% of that in Cohorts 1+2, suggesting that earlier steroid use may allow reduction of overall steroid exposure. Earlier steroid use was not associated with increased risk for severe infection. The percent of patients in ongoing response at 1 year was similar across cohorts, regardless of tumor burden. Furthermore, this study supports the safety of levetiracetam prophylaxis in R/R LBCL patients receiving axicabtagene ciloleucel.

Although there may be a theoretical concern that the use of immunosuppressive agents to manage CRS or neurologic events may abrogate CAR T-cell expansion and tumor response, earlier and measured introduction of steroid use did not appear to significantly affect either. More specifically, cohort 4 showed CAR T-cell levels comparable to those of Cohorts 1+2 regardless of tumor burden, but numerically lower levels of key inflammatory cytokines associated with CAR-related inflammatory events (eg, IFNγ, IL-2 and GM-CSF). These findings corroborated with the clinical outcomes, suggested that early utilization of steroids may have a greater impact on cytokine production by immune cells, than on CAR T-cell expansion capability While the study was not designed to statistically evaluate the impact of steroid use on efficacy compared with earlier findings, the results presented here are consistent with the primary analysis of ZUMA-1 (Cohorts 1+2), which suggested no substantial effect of glucocorticoid use on ORR (glucocorticoid, 78% [58-91%]; no glucocorticoid, 84% [73-91%]). Although a retrospective study of 100 patients with R/R LBCL showed diminished survival outcomes in those receiving corticosteroids ≤7 days versus >7 days (or no steroid) after axicabtagene ciloleucel infusion, the clinical applicability of these findings is unclear given the possible poorer efficacy in subjects at higher risk for adverse events owing to independent factors such as tumor burden median time to onset of CRS in axicabtagene ciloleucel-treated patients is 2 days. A detrimental impact of higher versus lower (or no) cumulative steroid doses on PFS and OS was reported in the same study, but the higher dose threshold was similar to the median cumulative dose observed in Cohorts 1+2 and thus, substantially greater than that in Cohort 4. Studies of other CAR T-cell products have reported no substantial effect of corticosteroid use on CAR T-cell expansion or tumor response in B-cell acute lymphoblastic leukemia. In safety expansion Cohort 4, earlier use of steroids reduced rates of grade ≥3 CRS and neurologic events with no decrement in efficacy compared with ZUMA-1 pivotal cohorts Example 15

This Example reports on the effects of early or prophylactic use of tocilizumab for adverse event management in patients receiving axicabtagene ciloleucel for Relapsed/Refractory Large B-cell Lymphoma (R/R LBCL). Axicabtagene ciloleucel (axi-cel), an autologous anti-CD19 chimeric antigen receptor (CAR) T-cell therapy, is approved for the treatment of patients with relapsed or refractory large B-cell lymphoma (R/R LBCL) after failing two or more prior systemic therapies. Regulatory approvals were based on results of Cohorts 1+2 (N=101) of the phase 2 ZUMA-1 study, which evaluated the efficacy and safety of axicabtagene ciloleucel in patients with refractory LBCL. In a 2-year analysis (median follow-up, 27.1 months; N=101), axicabtagene ciloleucel treatment showed objective response, complete response, and ongoing response rates of 83%, 58%, and 39%, respectively. After a median of 39.1 months of follow-up, median overall survival (OS) was 25.8 months, with a 3-year OS rate of 47%.

Cytokine release syndrome (CRS) and neurologic events were common in patients receiving anti-CD19 CAR T-cell therapies and may be severe or life-threatening. At the 2-year follow-up of the 108 patients in phases 1 and 2 of ZUMA-1, grade ≥3 CRS was reported in 11% of patients and grade ≥3 neurologic events were reported in 32%. The majority of CRS cases and neurologic events were manageable and reversible. The results presented below showed that early or prophylactic tocilizumab following axicabtagene ciloleucel for adverse event management decreased grade ≥3 cytokine release syndrome but increased grade ≥3 neurologic events. Increased grade ≥3 neurologic events was associated with higher levels of select cytokines (e.g., interferon-γ and granzyme B). Post-CAR T-cell infusion levels of serum interleukin (IL)-6, a pro-inflammatory cytokine, have been associated with both severe CRS and neurologic events, and IL-6 receptor (IL-6R) blockade with tocilizumab, a monoclonal antibody against IL-6R, is indicated for the treatment of CAR T-cell-induced CRS. However, it is unclear whether IL-6R signaling plays a key role in pathogenesis of neurologic events, and whether early or prophylactic IL-6R blockade may prevent both categories of high-grade adverse events. Below are reported the primary analysis of ZUMA-1 Cohort 3, which evaluated the use of early or prophylactic tocilizumab in patients with R/R LBCL receiving axicabtagene ciloleucel. It was hypothesized that early or prophylactic tocilizumab may attenuate bystander immune cell activation in both product-derived and endogenous cells and lower levels of proinflammatory cytokines, thus reducing the incidence and severity of both CRS and neurologic events without interfering with CAR T-cell expansion and anti-tumor efficacy post-axicabtagene ciloleucel.

Safety expansion Cohort 3 was added to ZUMA-1, the pivotal phase ½ study of axicabtagene ciloleucel in R/R LBCL, to evaluate how early or prophylactic tocilizumab use affects rates of CRS and neurologic events. Cohort 3 patients received tocilizumab on day 2. The primary endpoint was incidence and severity of CRS and neurologic events. Findings were contextualized with the 1-year analysis of the ZUMA-1 pivotal Cohorts 1+2 (N=101) owing to similar follow-up. Thirty-eight Cohort 3 patients received axicabtagene ciloleucel. Overall incidence of CRS in Cohort 3 was comparable to Cohorts 1+2 (92% vs 93%), but rates of grade ≥3 CRS were reduced (3% vs 12%). There were no CRS-related deaths in Cohort 3. Any-grade (87% vs 64%) and grade ≥3 (39% vs 29%) neurologic events were more common in Cohort 3, and one grade 5 neurologic event (cerebral edema) occurred. Objective response rates were 63% versus 83% in Cohort 3 vs 1+2, respectively; 39% and 42% of patients had ongoing responses at data cutoff. CAR T-cell levels were comparable but increased levels of select inflammatory cytokines in Cohort 3 may have contributed to increased grade ≥3 neurologic events. Early or prophylactic tocilizumab may decrease the rate of grade ≥3 CRS but not grade ≥3 neurologic events in patients receiving axicabtagene ciloleucel.

Most Cohort 3 procedures were identical to those described for Cohorts 1+2 (described in EXAMPLE 14), with key exceptions being the use of levetiracetam and tocilizumab prophylaxis in Cohort 3. See FIG. 56 for comparison between cohorts. Additional exceptions are described below. Patients eligible for Cohort 3 were adults with R/R LBCL after ≥2 systemic lines of therapy or refractory disease to first-line therapy. Refractory disease was defined as progressive disease as best response or stable disease as best response to at least 4 cycles of first-line therapy with stable disease duration no longer than 6 months. Prior therapy having included an anti-CD20 monoclonal antibody (unless the tumor was CD20-negative) and an anthracycline-containing chemotherapy regimen. Patients were required to have an Eastern Cooperative Oncology Group performance status of 0 or 1. Additional inclusion criteria were absolute neutrophil count >1,000 cells per microliter, absolute lymphocyte count >100 cells per microliter, platelet count >75,000 cells per microliter, adequate organ function, no central nervous system (CNS) involvement, and no active infection.

Figure 56:
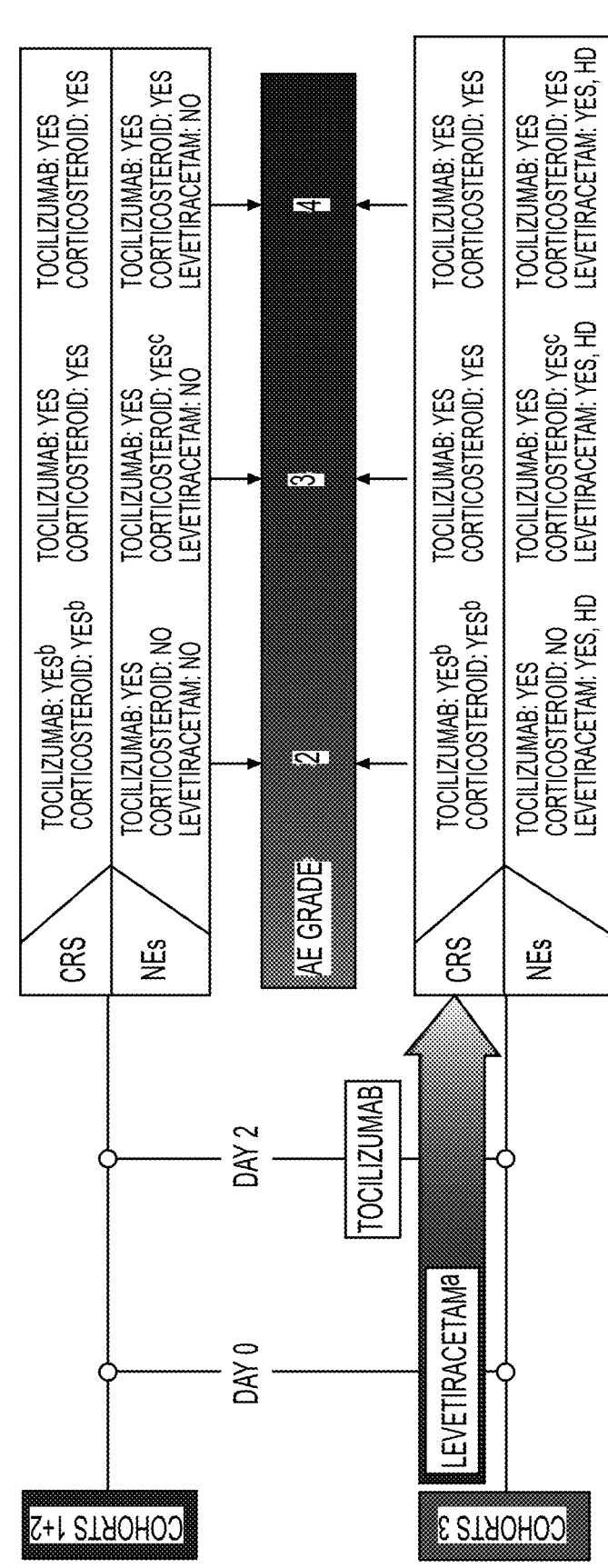
FIG. 56: Adverse Event Management in ZUMA-1 Cohort 3 vs Cohorts. The figure summarizes the study design of ZUMA-1 for Cohorts 1+2 (upper box) and Cohort 3 (lower box). Yes or No indicates if tocilizumab, corticosteroid, or levetiracetam was or was not administered, respectively. Grade 2, 3, or 4 refers to the grade of severity of CRS or NE. [a] Started and continued at 750 mg PO or IV twice daily; if patient did not experience any neurologic event ≥grade 2, levetiracetam was tapered and discontinued as clinically indicated. [b] Only in case of comordbidities or older age. Only if no improvement to tocilizumab, use standard dose. CRS, cytokine release syndrome; HD, high dose (1000 mg PO or IV twice daily); IV, intravenous; NE, neurologic events; PO, by mouth.

Patients received a conditioning regimen of cyclophosphamide (500 mg/m$^2$/day) and fludarabine (30 mg/m$^2$/day) on days –5, –4, and –3, and one dose of axicabtagene ciloleucel (target dose of 2×10$^6$ CAR T– cells/kg with a maximum of 2×10$^8$ CAR T-cells) on day 0. Bridging therapy was not allowed in Cohorts 1, 2, or 3. All Cohort 3 patients received levetiracetam (750 mg oral or intravenous twice daily) starting on day 0. At the onset of grade ≥2 neurologic events, levetiracetam dose was increased to 1000 mg twice daily. If a patient did not experience any grade ≥2 neurologic event, levetiracetam was tapered and discontinued as clinically indicated. Cohort 3 patients received tocilizumab (8 mg/kg IV over 1 hour [not to exceed 800 mg]) on day 2. Further tocilizumab (±corticosteroids) was recommended at the onset of grade 2 CRS in patients with comorbidities or older age, or otherwise in case of grade ≥3 CRS. For patients experiencing grade ≥2 neurologic events, tocilizumab was initiated, and corticosteroids were added for patients with comorbidities or older age, or if there was any occurrence of a grade ≥3 neurologic event with worsening symptoms despite tocilizumab use. (FIG. 56.)

Figure 61:
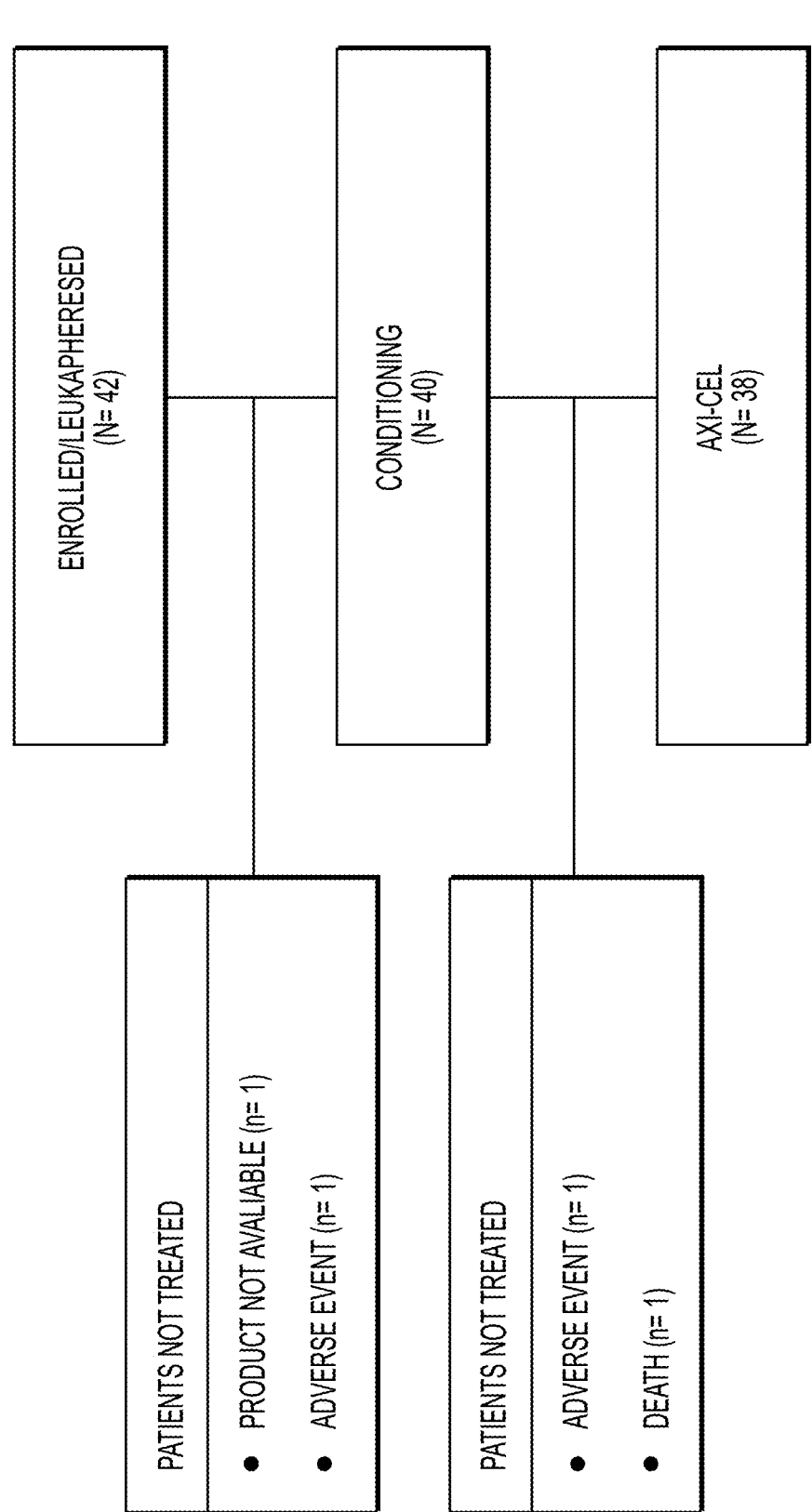
FIG. 61: Disposition diagram. The figure summarizes the disposition of patients enrolled in ZUMA-1 Cohort 3.

Forty-two patients were enrolled and leukapheresed in Cohort 3, 40 received conditioning chemotherapy, and 38 received the minimum target dose of axicabtagene ciloleucel (FIG. 61). The latter group made up both the modified intent-to-treat (mITT) and safety sets. Four patients were not treated because of death due to sepsis (n=1), adverse events that precluded treatment (n=2), and dose not successfully manufactured (n=1). The latter 3 patients died due to disease progression. As of the Apr. 26, 2018 data cutoff, median Cohort 3 follow-up was 13.9 months (range, 6.0-18.0 months). The data cutoff for Cohorts 1+2 was Aug. 11, 2017, with a median follow-up of 15.1 months (range, 10.9-20.4 months). Baseline characteristics in Cohort 3 were generally similar to those in Cohorts 1+2 (Table 19).

TABLE 19

| | Baseline Characteristics | |
|---|---|---|
| Characteristic | Cohorts 1 + 2 (N = 101) | Cohort 3 (N = 38) |
| Disease type, n (%) | | |
| DLBCL | 77 (76) | 23 (61) |
| PMBCL | 8 (8) | 7 (18) |
| TFL | 16 (16) | 8 (21) |
| Age | | 51 (21-74) |
| Median (range), years-old | 58 (23-76) | 51 (21-74) |
| ≥65 years-old, n (%) | 24 (24) | 8 (21) |
| Male sex, n (%) | 68 (67) | 21 (55) |
| ECOG performance status score of 1, n (%) | 59 (58) | 19 (50) |

TABLE 19-continued

| | Baseline Characteristics | |
|---|---|---|
| Characteristic | Cohorts 1 + 2 (N = 101) | Cohort 3 (N = 38) |
| Disease stage, n (%) | | |
| I or II | 15 (15) | 15 (39) |
| III or IV | 86 (85) | 23 (61) |
| IPI score, n (%) | | |
| 0-2 | 55 (54) | 25 (66) |
| 3 or 4 | 46 (46) | 13 (34) |
| CD19 positivity, n/N (%) | | |
| Yes | 74/82 (90) | 18/19 (95) |
| No | 8/82 (10) | 1/19 (5)[b] |
| Number of prior lines of chemotherapy, % | | |
| 1 | 3 (3) | 1 (3)[a] |
| 2 | 28 (28) | 7 (18) |
| 3 | 29 (29) | 17 (45) |
| 4 | 29 (29) | 6 (16) |
| ≥5 | 12 (12) | 7 (18) |
| Prior SCT, n (%) | 25 (25) | 10 (26) |
| PD as best response to most recent chemotherapy[c], n (%) | 67 (66) | 20 (53) |
| Median tumor burden by SPD (range), mm$^2$ | 3721 (171-23,297) | 3632.5 (355-39,658) |
| Median LDH, U/L (range) | 344 (116-7802) | 326 (105-1810) |
| Median ferritin, ng/mL (range) | 786 (1-10,576) | 598 (1-2219) |
| Refractory subgroup, n (%) | | |
| Primary refractory | 3 (3) | 1 (3) |
| Refractory ≥2$^{nd}$-line therapy | 77 (76) | 26 (68) |
| Relapsed ≥2$^{nd}$-line therapy | NA | 2 (5) |
| Relapsed post-ASCT | 21 (21) | 9 (24) |

[a]Patient had primary refractory disease.
[b]Patient sample was obtained after conditioning chemotherapy.
[c]For patients who had not relapsed post-ASCT.
ASCT, autologous stem cell transplant;
DLBCL, diffuse large B-cell lymphoma;
ECOG, Eastern Cooperative Oncology Group;
IPI, International Prognostic Index;
LDH, lactate dehydrogenase;
NA, not applicable;
PMBCL, primary mediastinal B-cell lymphoma;
SPD, sum of the products of diameters;
TFL, transformed follicular lymphoma.

The primary endpoint for Cohort 3 was the incidence and severity of CRS and neurologic events. Key secondary endpoints included the incidence of adverse events, clinically significant changes in safety laboratory safety values, objective response rate (ORR) per investigator assessment, duration of response (DOR), progression-free survival (PFS), overall survival (OS), and levels of anti-CD19 CAR T cells, cytokines, and chemokines in the blood and cerebrospinal fluid (CSF). No formal hypothesis testing was conducted, and comparisons to Cohorts 1+2 (combined) were descriptive. The modified intent-to-treat (mITT) population included patients enrolled and treated with axicabtagene ciloleucel at a dose of at least 1×10$^6$ anti-CD19 CAR T cells/kg. This analysis set was used for analyses of objective response and study endpoints based on objective response. The safety analysis set included patients treated with any dose of axicabtagene ciloleucel.

The overall incidence of CRS in Cohort 3 was comparable to that of Cohorts 1+2 (92% vs 93%; Table 20), but early or prophylactic use of tocilizumab on day 2 in Cohort 3 was associated with decreased rates of grade ≥3 CRS compared with Cohorts 1+2 (3% vs 12%). Grade 4 CRS occurred in 3% of patients in both Cohorts 3 and 1+2. There was no grade 5 CRS in Cohort 3. In Cohorts 1+2, 1 patient died from hemophagocytic lymphohistiocytosis and one event of grade 5 cardiac arrest occurred in a patient with CRS.

TABLE 20

Incidence, Severity, Onset, and Duration
of CRS and Neurologic Events.

| TEAE | Cohorts 1 + 2 (N = 101) | Cohort 3 (N = 38) |
|---|---|---|
| CRS | | |
| Any, n (%) | 94 (93) | 35 (92) |
| Worst grade 1, n (%) | 37 (37) | 13 (34) |
| Worst grade 2, n (%) | 45 (45) | 21 (55) |
| Worst grade 3, n (%) | 8 (8) | 0 |
| Worst grade 4, n (%) | 3 (3) | 1 (3) |
| Worst grade 5, n (%) | 1 (1) | 0 |
| Median (range) time to onset, days | 2.0 (1.0-12.0) | 2 (1.0-9.0) |
| Median (range) duration, days | 7.0 (2.0-58.0) | 6.5 (2.0-21.0) |
| Neurologic Events | | |
| Any, n (%) | 65 (64) | 33 (87) |
| Worst grade 1, n (%) | 21 (21) | 9 (24) |
| Worst grade 2, n (%) | 15 (15) | 9 (24) |
| Worst grade 3, n (%) | 27 (27) | 13 (34) |
| Worst grade 4, n (%) | 2 (2) | 1 (3) |
| Worst grade 5, n (%) | 0 | 1 (3) |

216

TABLE 20-continued

Incidence, Severity, Onset, and Duration
of CRS and Neurologic Events.

| TEAE | Cohorts 1 + 2 (N = 101) | Cohort 3 (N = 38) |
|---|---|---|
| Median (range) time to onset, days | 5.0 (1.0-17.0) | 7.0 (1.0-32.0) |
| Median (range) duration, days | 12.0 (1.0-450.0) | 14.0 (1.0-234.0) |

CRS, cytokine release syndrome;
TEAE, treatment-emergent adverse event.

The incidence of any-grade neurologic events was numerically greater in Cohort 3 compared with Cohorts 1+2 (87% vs 64%; Table 20), as was the incidence of grade ≥3 neurologic events (39% vs 29%). In Cohort 3, grade 4 neurologic events were reported in 3% of patients while 2% of patients in Cohorts 1+2 experienced grade 4 neurologic events. There was one grade 5 neurologic event in Cohort 3 (cerebral edema) and no grade 5 neurologic event in Cohorts 1+2. Median time to onset and duration of both CRS and neurologic events were similar in Cohort 3 vs Cohorts 1+2 (Table 20).

The incidence of grade ≥3 infection was 8% in Cohort 3 and was 25% in Cohorts 1+2 (Table 21). The difference may be explained by the fact that treatment-emergent adverse events included those during or after axicabtagene ciloleucel infusion in Cohort 3 and during or after conditioning chemotherapy in Cohorts 1+2.

TABLE 21

Incidence and Severity of TEAEs.[a]

| TEAE, n (%) | Cohorts 1 + 2 (N = 101) | | | | Cohort 3 (N = 38) | | | |
|---|---|---|---|---|---|---|---|---|
| | Any Grade | Worst Grade 3 | Worst Grade 4 | Worst Grade 5 | Any Grade | Worst Grade 3 | Worst Grade 4 | Worst Grade 5 |
| Pyrexia | 87 (86) | 13 (13) | 0 | 0 | 35 (92) | 3 (8) | 0 | 0 |
| Anemia | 68 (67) | 42 (42) | 3 (3) | 0 | 21 (55) | 13 (34) | 2 (5) | 0 |
| Hypotension | 60 (59) | 13 (13) | 1 (1) | 0 | 23 (61) | 8 (21) | 1 (3) | 0 |
| Fatigue | 52 (51) | 2 (2) | 0 | 0 | 18 (47) | 5 (13) | 0 | 0 |
| Neutropenia | 46 (46) | 10 (10) | 30 (30) | 0 | 19 (50) | 4 (11) | 13 (34) | 0 |
| Infection | 40 (40) | 23 (23) | 2 (2) | 0 | 19 (50) | 0 | 1 (3) | 2 (5) |
| Thrombocytopenia | 36 (36) | 11 (11) | 13 (13) | 0 | 12 (32) | 4 (11) | 6 (16) | 0 |
| Encephalopathy | 35 (35) | 20 (20) | 1 (1) | 0 | 13 (34) | 8 (21) | 1 (3) | 0 |
| Febrile neutropenia | 34 (34) | 29 (29) | 1 (1) | 0 | 11 (29) | 10 (26) | 0 | 0 |
| Neutrophil count decreased | 33 (33) | 6 (6) | 26 (26) | 0 | 10 (26) | 2 (5) | 6 (16) | 0 |
| White blood cell count decreased | 31 (31) | 3 (3) | 26 (26) | 0 | 10 (26) | 4 (11) | 6 (16) | 0 |
| Hypoxia | 30 (30) | 8 (8) | 1 (1) | 0 | 11 (29) | 4 (11) | 1 (3) | 0 |
| Hypophosphatemia | 28 (28) | 16 (16) | 2 (2) | 0 | 5 (13) | 0 | 0 | 0 |
| Confusional state | 28 (28) | 10 (10) | 0 | 0 | 17 (45) | 5 (13) | 0 | 0 |
| Platelet count decreased | 28 (28) | 8 (8) | 7 (7) | 0 | 9 (24) | 2 (5) | 6 (16) | 0 |
| Leukopenia | 21 (21) | 5 (5) | 13 (13) | 0 | 0 | 0 | 0 | 0 |
| Lymphocyte count decreased | 21 (21) | 2 (2) | 19 (19) | 0 | 4 (11) | 3 (8) | 1 (3) | 0 |
| Dysphagia | 8 (5) | 0 | 0 | 0 | 6 (16) | 4 (11) | 0 | 0 |

[a]Listed are TEAEs that occurred as grade ≥3 in >10% of patients in either Cohorts 1 + 2 or Cohort 3.
TEAE, treatment-emergent adverse event.

The incidence of prolonged grade ≥3 thrombocytopenia was numerically greater in Cohort 3, but prolonged grade ≥3 neutropenia and anemia were comparable between cohorts (Table 22).

TABLE 22

Incidence of Prolonged Grade ≥3 Cytopenias[a]

| TEAE, n (%) | Cohorts 1 + 2 (N = 101) | Cohort 3 (N = 38) |
|---|---|---|
| Anemia | 16 (16) | 6 (16) |
| Neutropenia | 31 (31) | 11 (29) |
| Thrombocytopenia | 26 (26) | 13 (34) |

[a]Present on or after day 30 following infusion.
TEAE, treatment-emergent adverse event.

Tocilizumab was used in 37 (97%) of patients in Cohort 3 and 43% of patients in Cohorts 1+2, with 29% of the patients in Cohort 3 receiving tocilizumab prophylactically before any CRS and 32% receiving it early compared with contemporary guidelines. Increased steroid use in Cohort 3 (63%) compared with Cohorts 1+2 (26%) paralleled the overall increase in neurologic events in Cohort 3.

Efficacy was also evaluated. The ORR was numerically lower in Cohort 3 compared with Cohorts 1+2; ongoing response rates at data cutoff were similar. ORRs for Cohort 3 and Cohorts 1+2 were 63% (CR, 47%) and 83% (CR, 58%), respectively, with 39% and 42% of patients in ongoing response as of the respective data cutoffs. All ongoing responders in Cohort 3 and 40/42 in Cohorts 1+2 were in ongoing complete response. Median DOR was not reached in Cohort 3 (95% CI, 5.0 months to not estimable [NE]) and was 11.1 months (95% CI, 3.9 months to NE) in Cohorts 1+2. Twelve-month DOR rates were 71% and 49%, respectively. Median PFS was comparable between Cohort 3 (6.2 months [95% CI, 2.4 months to NE) and Cohorts 1+2 (5.9 months [95% CI, 3.3 months to NE). Median OS was 15.4 months (95% CI, 5.4 months to NE) in Cohort 3 and was not reached in the 12-month analysis of Cohorts 1+2 (95% CI, 12.8 months to NE).

Figure 62:
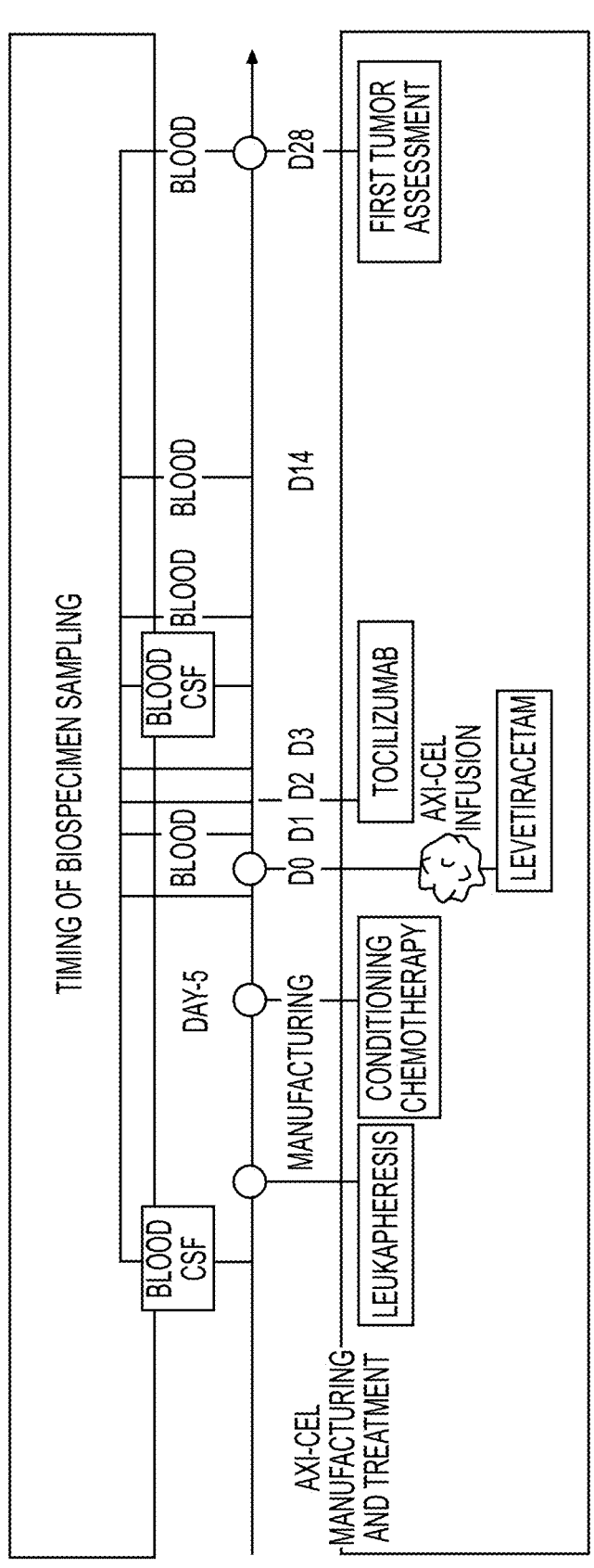
FIG. 62: Timing of Biospecimen Sampling and Treatment. The figure summarizes the timeline of axicabtagene ciloleucel manufacturing and infusion in relation to collection of patients' samples. CSF, cerebrospinal fluid.

Pharmacokinetic analysis was performed by using a validated polymerase chain reaction (PCR) assay enumerating the levels of gene-marked cells in blood. (Neelapu S S, Locke F L, Bartlett N L, et al. *N Engl J Med.* 2017; 377(26):2531-2544; Kochenderfer J N, Dudley M E, Kassim S H, et al. *J Clin Oncol.* 2015; 33(6):540-549). Pharmacodynamic analysis was conducted on longitudinal serum samples. CSF was collected at baseline prior to conditioning chemotherapy and on day 5 (±3 days) after axicabtagene ciloleucel infusion (FIG. 62). Up to 46 soluble markers were measured in serum and CSF by multiplex MSD®, Luminex®, or Quantikine® enzyme-linked immunosorbent assay (ELISA).

Figure 57:
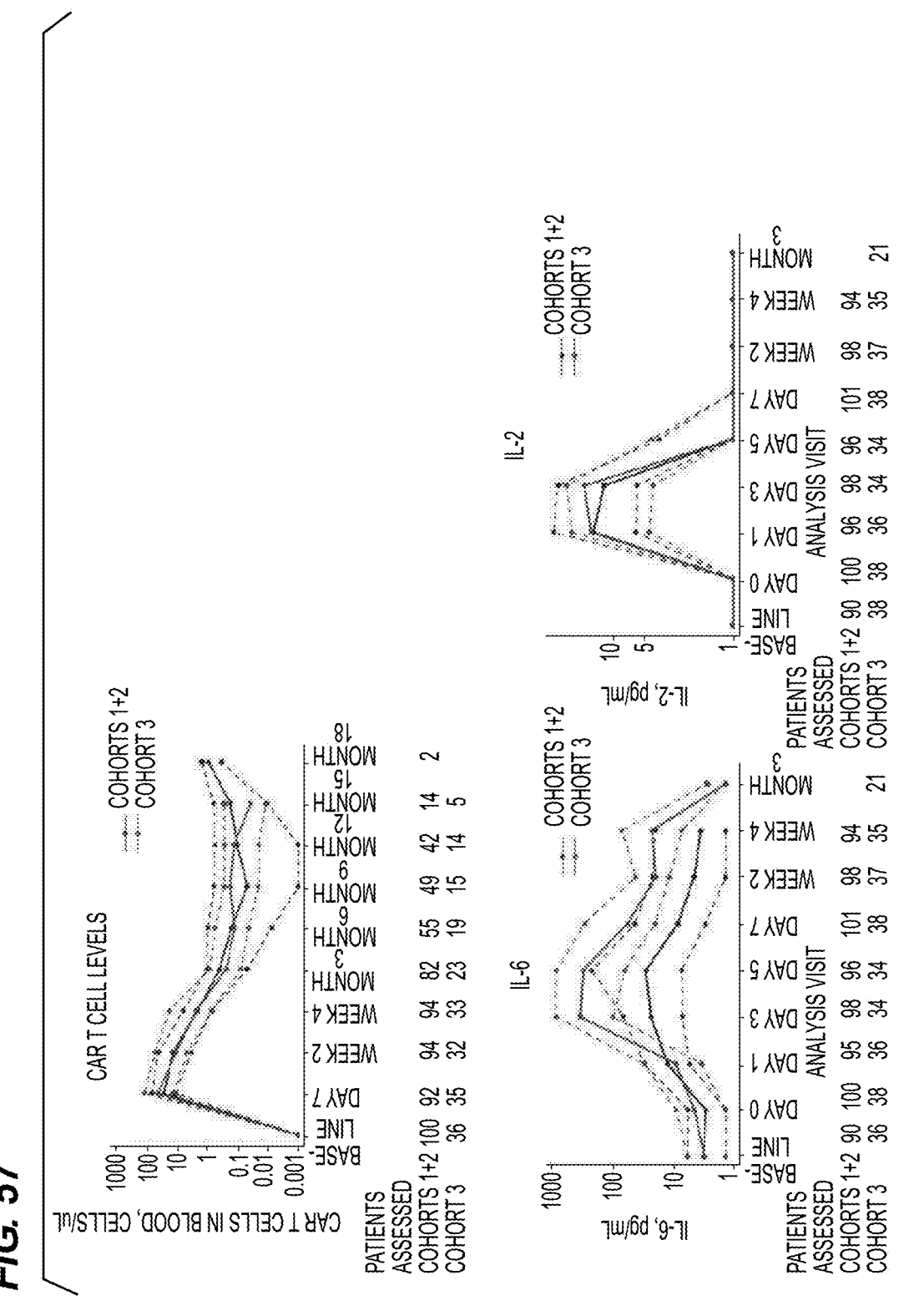
FIG. 57: Changes in Blood CAR T-Cell Levels and Serum Cytokines Over Time. Panels show levels of CART cells or serum cytokines in blood by visit. Counter-clockwise from upper left: CAR T cells (per mL), IL-6, granzyme B, IFN-γ (all pg/mL), Ferritin (g/mL), CRP (mg/L), IL-2 (pg/mL). Green tracings: ZUMA-1 Cohort 1+2; Red tracings: ZUMA-1 Cohort 3. Solid lines: median; dashed lines: quartiles. CAR, chimeric antigen receptor; CRP, C-reactive protein; IFN, interferon; IL, interleukin.
Figures 58A, 58B:
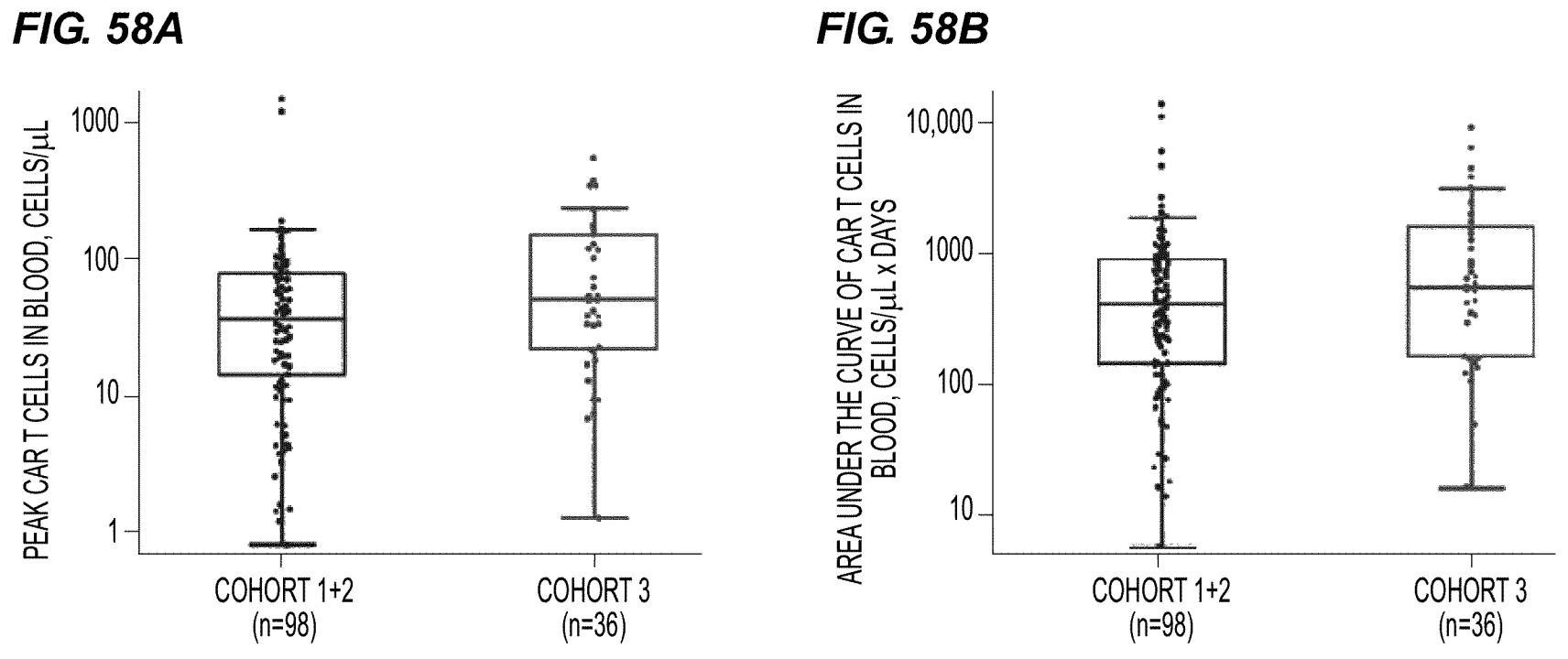

Post-infusion CAR T-cell expansion is a correlate of clinical efficacy. Early or prophylactic use of tocilizumab did not appear to significantly modify CAR T-cell expansion over time in Cohort 3, as compared to Cohorts 1+2 (FIG. 57). Post-infusion CAR T-cell levels in blood (based on peak and $AUC_{day0-28}$) were comparable between patients Cohort 3 and those in Cohorts 1+2 who did not receive early or prophylactic tocilizumab (FIGS. 58A-58B).

Use of early or prophylactic tocilizumab (a humanized monoclonal antibody against the interleukin-6 receptor (IL-6R)) in Cohort 3 resulted in a measurable increase in peak serum IL-6 relative to Cohorts 1+2, consistent with IL-6R blockade. Reduced serum levels of the acute phase response (APR) protein C-reactive protein (CRP) were accompanied by a negative trend in serum amyloid A (SAA) protein. Surprisingly, increased serum levels of IFN-γ and granzyme B were observed in Cohort 3 compared with Cohorts 1+2, suggestive of a type 1 (T1) lateralization of T-cell function. Finally, serum levels of other treatment-related cytokines and chemokines, including IL-2, granulocyte-macrophage colony stimulating factor (GM-CSF), and ferritin, in Cohort 3 were comparable to those of Cohorts 1+2 (FIG. 57).

Figure 59:
FIG. 59: Selected Serum and CSF Analytes at Baseline and Day 5 and Association with Neurologic Events. Panels show serum (upper panel) and CSF (lower panel) analyte levels plotted against cases of neurologic events. Left to right: IFN-γ, IL-15, IL-2Ra, IL-6 and IL-8. All values in pg/mL. Middle line represents the median and the box represents the maximum and minimum values. The number of patients is shown below each box. Other analytes showing similar profile: C-reactive protein, ICAM-1, and VCAM-1. CSF, cerebrospinal fluid; G, grade; ICAM, intracellular adhesion molecule; IFN, interferon; IL, interleukin; R, receptor; VCAM, vascular cell adhesion molecule.

Consistent with serum cytokine findings, Cohort 3 patients with evaluable samples and grade ≥2 neurologic events had numerically greater post-infusion (day 5) CSF levels of IFN-γ, IL-15, IL-2Rα, IL-6, IL-8, CRP, intercellular adhesion molecule (ICAM)-1, and vascular cell adhesion molecule (VCAM)-1 compared with those with grade 0 to 1 neurologic events, despite low and comparable baseline levels across Cohort 3 (FIG. 59).

Figure 60:
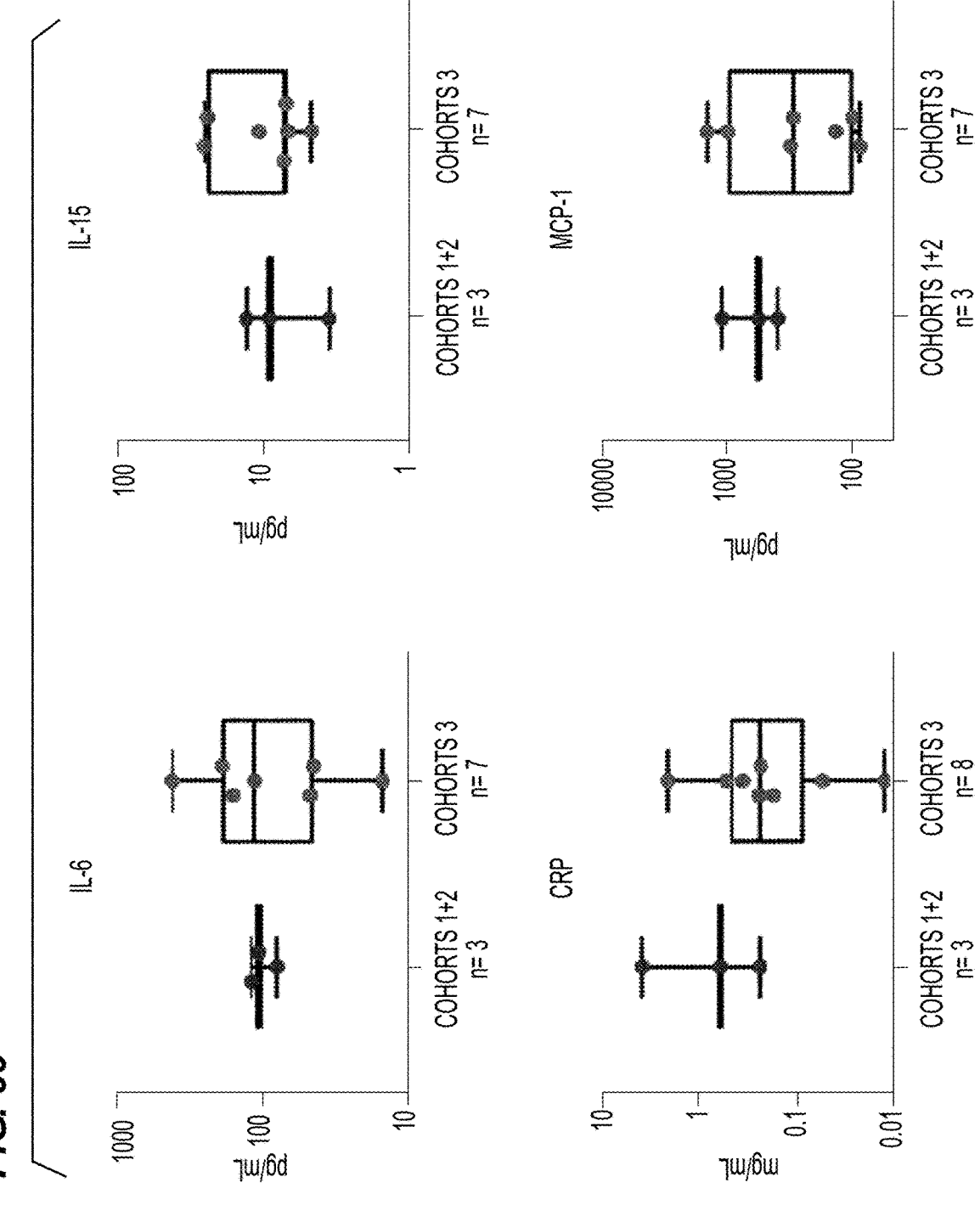
FIG. 60: Cytokine Levels in CSF of Patients with Grade ≥3 Neurologic Events. The figure shows day 5 CSF cytokine levels in Cohorts 1+2 and Cohort 3 in patients with grade ≥3 neurologic events. Closed symbols show individual patients. Open symbols show mean values. The middle line of the box plots represents the median, box represents the bounds of the first and third quartiles, whiskers show range. CRP, C-reactive protein; CSF, cerebrospinal fluid; IL, interleukin; MCP-1, monocyte chemoattractant protein-1 (CCL2).

Phenotypic analysis of immune cell subsets in product, in peripheral blood mononuclear cells (PBMCs) post infusion in blood, and in CSF was performed by flow cytometry. Analyses for product cells and peripheral blood mononuclear cells post infusion in blood included CD3, CD4, CD8, CD19, CCR7, CD45RA, PD-1, 4-1BB, CAR and viability marker. Flow cytometric analyses of CSF included surface markers for both T cells and myeloid cells (CD3, CD4, CD8, CD14, CD45, CD45RA, CCR7, CD56, CD19, and CD66b0, in addition to a reagent for CAR detection. (Sievers S A, Kelley K A, Astrow S H, Bot A, Wiltzius J J. *Cancer Research.* 2019; 79(13 Supplement):1204-1204). Dead or apoptotic cells were excluded and cell numbers/volume unit of CSF were computed. Product cells were also co-cultured with CD19-expressing target cells, with soluble markers measured in supernatant by Luminex®. (Locke F L, Neelapu S S, Bartlett N L, et al. *Mol Ther.* 2017; 25(1):285-295). Interestingly, patients with grade ≥3 neurologic events also had greatly elevated CSF levels of CD14+ myeloid cells at day 5. There was also a preferential trafficking of CAR+CD4 T cells as shown by a greater CD4:CD8 ratio of CAR+ T cells in CSF versus blood (Table 23), suggesting active migration (vs passive diffusion) of CAR+CD4 T cells into the CNS space in Cohort 3 patients. Notably, CSF cytokine levels in patients with grade ≥3 neurologic events, including IL-6, measured at day 5 post infusion, did not appear to be elevated in Cohort 3 as compared with Cohorts 1+2 (FIG. 60).

TABLE 23

| | | CSF Cell Populations Post-CAR T Cell Infusion by Grade of Neurologic Event (Cohort 3) | | | |
|---|---|---|---|---|---|
| | | Neurologic Event Grade 0-2 (N = 23) | | Neurologic Event Grade ≥3 (N = 15) | Neurologic Event Grade ≥3/ |
| Cell Populations[a] | n | Median cells/mL (Q1, Q3) | n | Median cells/mL (Q1,Q3) | Grade 0-2 Ratio |
| CD45+ (leukocytes), cells/mL | 15 | 23.9 (2.0, 268.3) | 9 | 10.20 (27.4, 324.0) | 4.3 |
| CD 14+ (myeloid cells), cells/mL | 15 | 2.8 (1.3, 126.0) | 9 | 78.4 (21.6, 174.7) | 28.5 |
| CAR+ T cells, cells/mL | | | | | |
| CD3+ | 15 | 3.8 (0.1, 10.3) | 9 | 3.8 (1.4, 10.2) | 1.0 |
| CD4+ | 15 | 3.2 (0.1, 8.4) | 9 | 3.8 (0.8, 9.8) | 1.2 |
| CD8+ | 14 | 0.0 (0.0, 1.5) | 9 | 3.0 (0.0, 0.3) | — |
| CD4/CD8 T cell ratio[b] | 14 | 2.1 (1.1, 2.6) | 9 | 3.8 (2.0, 5.3) | 1.8 |
| CAR+ CD4/ CAR+ CD8 T-cell ratio[c] | 8 | 8.7 (6.9, 80.7) | 6 | 19.3 (16.7, 23.0) | 2.2 |

[a] CSF values were from day 5.
[b] Median (range) blood CD4/CD8 T-cell ratio at day 7 = 0.4 (0.0-8.0)
[c]Median (range) blood CAR+ CD4/CAR CD8 T-cell ratio at day 7 = 0.9 (0.1-33.2);
CAR, chimeric antigen receptor Product characteristics for Cohort 3 showed general comparability to Cohort 1+2 except minor differences in percentage transduction rate, product co-culture interferon (IFN)-γ, and percentages of central memory T cells and effector memory T cells (Table 24).

TABLE 24

| | Summary of Product Characteristics. | |
|---|---|---|
| Parameter Median (Min-Max) | Cohorts 1 + 2 (N = 101) | Cohort 3 (N = 38) |
| Total number of CAR T cells, per μL | 298.5 (149.1-760.5) | 150.0 (76.0, 200.0) |
| Total Number of T cells, per μL | 165.00 (75.0-200.0) | 336.3 (157.7, 898.8) |
| Transduction Rate, % | 52.60 (21.6-85.1) | 45.0 (15.1, 71.0) |
| IFN-γ level, pg/mL | $1.03 \times 10^4$ (1355.5-$3.6 \times 10^4$) | 2950.5 (459.0, 24170.0) |
| Viability, % | 94.4 (83.5-97.4) | 95.0 (88.3-97.0) |
| CD4/CD8 Ratio | 0.9 (0.03-5.8) | 1.2 (0.2-6.2) |
| Naive T cells, % | 13.8 (1.0-76.0) | 15.9 (0.4-75.3) |
| Central memory T cells, % | 25.7 (9.0-15.1) | 20.0 (2.0-51.4) |
| Effector memory T cells, % | 38.0 (5.1-70.4) | 39.0 (2.5-83.2) |
| Effector T cells, % | 15.5 (4.7-39.1) | 20.0 (4.3-64.6) |

A patient in Cohort 3 developed grade 5 cerebral edema. The patient was a 21-year old man with refractory, stage IVB PMBCL, two prior therapies, and evidence of rapid disease progression at baseline (FIG. 63). Post hoc analysis revealed that, prior to conditioning chemotherapy and/or axicabtagene ciloleucel infusion, the patient had elevated serum levels of IL-15, IL-8, tumor necrosis factor (TNF)-β, VCAM-1, IFN-γ, IL-1RA, monocyte chemoattractant protein (MCP)-1, chemokine (C-C motif) ligand 17 (CCL17; TARC), and C-X-C motif chemokine 10 (CXCL-10; Tables 25 and 26). This baseline cytokine and chemokine profile was consistent with the presence of activated myeloid and lymphoid cells and a pre-existing inflammatory or infectious process. Baseline levels of VCAM-1 and ICAM-1 in CSF were above the medians of the overall population (Table 25), suggesting a favorable environment for immune cell trafficking. Low levels of CD3+ T cells were detectable, but no CD19+ cells were detected in the CSF. On day 0 (prior to axicabtagene ciloleucel infusion), continued workup for B symptoms revealed cytomegalovirus (CMV) reactivation.

TABLE 25

| | | | | | | |
|---|---|---|---|---|---|---|
| Baseline Serum and CSF Biomarkers in Cohort 3 and the Patient with Cerebral Edema | | | | | | |
| | Serum | | | CSF | | |
| Analyte (units) | Cohort 3, n | Cohort 3, median (range) | Cerebral Edema | Cohort 3, n | Cohort 3, median (range) | Cerebral Edema |
| CRP (mg/L) | 37 | 29.76 (0.89-415.57) | 43.00 | 27 | 0.13 (0.00-1.39) | 0.03 |
| CXCL10 (pg/mL) | 37 | 393.60 (122.10-2000.00) | 2000.00 | 27 | 168.00 (1.40-1086.00) | 328.30 |
| Eotaxin-1 (pg/mL) | 37 | 126.90 (12.30-412.20) | 51.20 | 27 | 12.30 (12.30-61.60) | 12.30 |
| Eotaxin-3 (pg/mL) | 37 | 10.20 (10.20-170.10) | 10.20 | 27 | 10.20 (10.20-10.20) | 10.20 |
| FGFBF (pg/mL) | 9 | 14.30 (2.60-57.50) | NA | 14 | 1.30 (1.30-1.30) | NA |
| FLT-1 (pg/mL) | 9 | 83.30 (45.70-767.30) | NA | 14 | 32.60 (5.00-55.80) | NA |
| Ferritin (ng/mL) | 37 | 617.40 (0.80-2219.20) | 0.80 | NA | NA | NA |
| GM-CSF (pg/mL) | 37 | 1.90 (1.90-1.90) | 1.90 | 27 | 1.90 (1.90-1.90) | 1.90 |
| Granzyme A (pg/mL) | 37 | 20.00 (20.00-7887.80) | 20.00 | 27 | 10.00 (10.00-10.00) | 10.00 |
| Granzyme B (pg/mL) | 37 | 1.00 (1.00-138.10) | 1.00 | 27 | 0.50 (0.50-6.30) | 0.50 |
| ICAM-1 (pg/mL) | 37 | 613576.50 (197057.30-1655585.30) | 979104.80 | 27 | 2624.30 (6.40-18503.10) | 3649.10 |
| IFN-γ (pg/mL) | 37 | 7.50 (7.50-197.30) | 54.50 | 28 | 7.50 (7.50-47.50) | 7.50 |
| IL-1 RA (pg/mL) | 37 | 501.40 (236.20-3968.50) | 3779.30 | 26 | 15.60 (15.60-151.20) | 15.60 |
| IL-1 alpha (pg/mL) | 37 | 2.90 (2.90-2.90) | 2.90 | 27 | 2.90 (2.90-2.90) | 2.90 |
| IL-1 beta (pg/mL) | 37 | 2.10 (2.10-2.10) | 2.10 | 28 | 2.10 (2.10-2.10) | 2.10 |
| IL-10 (pg/mL) | 37 | 0.70 (0.70-47.30) | 1.50 | 28 | 0.70 (0.70-6.40) | 0.70 |
| IL-12 P40 (pg/mL) | 37 | 189.90 (24.70-3658.10) | 147.20 | 27 | 5.70 (5.70-50.90) | 5.70 |
| IL-12 P70 (pg/mL) | 37 | 1.20 (1.20-2.60) | 1.20 | 28 | 1.20 (1.20-1.20) | 1.20 |
| IL-13 (pg/mL) | 37 | 4.20 (4.20-4.20) | 4.20 | 28 | 4.20 (4.20-4.20) | 4.20 |
| IL-15 (pg/mL) | 37 | 3.20 (1.40-7.80) | 4.30 | 27 | 2.90 (1.40-7.20) | 2.90 |
| IL-16 (pg/mL) | 37 | 224.70 (83.90-1988.20) | 541.00 | 27 | 19.10 (19.10-40.90) | 19.10 |
| IL-17 (pg/mL) | 37 | 9.30 (9.30-27.80) | 9.30 | 27 | 9.30 (9.30-9.30) | 9.30 |
| IL-2 (pg/mL) | 37 | 0.90 (0.90-0.90) | 0.90 | 28 | 0.90 (0.90-0.90) | 0.90 |
| IL-2 R alpha (pg/mL) | 37 | 2517.10 (78.00-46069.70) | 17835.80 | 27 | 39.00 (39.00-195.90) | 271.40 |
| IL-4 (pg/mL) | 37 | 0.50 (0.50-0.50) | 0.50 | 28 | 0.50 (0.50-0.50) | 0.50 |
| IL-5 (pg/mL) | 37 | 6.30 (6.30-6.30) | 6.30 | 27 | 6.30 (6.30-6.30) | 6.30 |
| IL-6 (pg/mL) | 37 | 3.70 (1.60-47.90) | 3.40 | 28 | 1.60 (1.60-17.50) | 1.60 |
| IL-7 (pg/mL) | 37 | 20.40 (6.70-58.30) | 23.50 | 27 | 1.40 (1.40-4.60) | 1.40 |
| IL-8 (pg/mL) | 37 | 10.00 (1.10-65.50) | 46.80 | 28 | 29.15 (1.10-101.50) | 41.10 |

TABLE 25-continued

Baseline Serum and CSF Biomarkers in Cohort 3 and the Patient with Cerebral Edema

| | | Serum | | | CSF | |
|---|---|---|---|---|---|---|
| Analyte (units) | Cohort 3, n | Cohort 3, median (range) | Cerebral Edema | Cohort 3, n | Cohort 3, median (range) | Cerebral Edema |
| MCP-1 (pg/mL) | 37 | 305.80 (142.50-1390.80) | 686.30 | 27 | 291.70 (1.10-508.50) | 299.70 |
| MCP-4 (pg/mL) | 37 | 91.60 (5.10-918.30) | 31.40 | 27 | 5.10 (5.10-5.10) | 5.10 |
| MDC (pg/mL) | 37 | 967.70 (387.60-30000.00) | 16206.50 | 27 | 88.30 (88.30-88.30) | 88.30 |
| MIP-1 alpha (pg/mL) | 37 | 13.80 (13.80-92.60) | 13.80 | 27 | 13.80 (13.80-13.80) | 13.80 |
| MIP-1 beta (pg/mL) | 37 | 90.70 (44.20-634.60) | 150.80 | 27 | 2.30 (2.30-23.20) | 14.10 |
| PLGF (pg/mL) | 9 | 56.30 (33.90-75.10) | NA | 14 | 46.30 (5.40-89.70) | NA |
| Perforin (pg/mL) | 37 | 8575.00 (1228.00-24205.30) | 7308.20 | 27 | 5.00 (5.00-267.00) | 5.00 |
| SAA (pg/mL) | 37 | 39158.17 (870.82-1380000.00) × $10^3$ | 14187.64 × $10^3$ | 27 | 19309.70 (5.40-13800000.00) | 9022.80 |
| SFASL (pg/mL) | 37 | 10.00 (10.00-2739.10) | 10.00 | 27 | 5.00 (5.00-13.70) | 5.00 |
| CCL-17 (TARC) (pg/mL) | 37 | 777.90 (37.30-4480.00) | 4480.00 | 27 | 3.30 (3.30-160.40) | 89.00 |
| TIE-2 (pg/mL) | 9 | 2748.90 (2408.30-3251.10) | NA | 14 | 198.00 (198.00-198.00) | NA |
| TNF alpha (pg/mL) | 37 | 3.20 (1.50-101.90) | 9.90 | 28 | 0.70 (0.70-0.70) | 0.70 |
| TNF beta (pg/mL) | 37 | 1.20 (1.20-5.90) | 1.20 | 27 | 1.20 (1.20-1.20) | 1.20 |
| VCAM-1 (pg/mL) | 37 | 841249.70 (37.60-1785709.80) | 1235210.50 | 27 | 7460.90 (37.60-31046.30) | 7567.90 |
| VEGF (pg/mL) | 9 | 513.10 (247.80-1299.10) | NA | 14 | 2.50 (2.50-6.50) | NA |
| VEGFC (pg/mL) | 9 | 146.00 (146.00-435.70) | NA | 14 | 73.00 (73.00-73.00) | NA |
| VEGFD (pg/mL) | 9 | 785.70 (583.30-1746.20) | NA | 14 | 33.60 (33.60) | NA |

Baseline was before initiation of conditioning chemotherapy. Baseline values for Cohort 3 show the median of the baseline value measured for all patients with available samples, excluding the patient with cerebral edema. Bolded text indicates markers whose values for the cerebral edema patient exceed the maximum for the remainder of Cohort 3. CCL, chemokine (C-C motif) ligand; CXCL, chemokine (C-X-C motif) ligand; CRP, C-reactive protein; FGFBF, fibroblast growth factor basic form; FLT, vascular endothelial growth factor receptor; GM-CSF, granulocyte macrophage colony stimulating factor; ICAM, intercellular adhesion molecule; IFN, interferon; IL, interleukin; MCP, monocyte chemotactic protein; MDC, macrophage-derived chemokine; MIP, macrophage inflammatory protein; NA, not assayed; PLGF, placental growth factor; R, receptor; RA, receptor antagonist; SAA, serum amyloid A; SFASL, serum soluble Fas ligand; TIE, TEK tyrosine kinase; TNF, tumor necrosis factor; VCAM, vascular cell adhesion molecule; VEGF, vascular endothelial growth factor

TABLE 26

Day 0 Serum Biomarkers in Cohort 3 and the Patient with Cerebral Edema.

| | Serum | | |
|---|---|---|---|
| Analyte (units) | Cohort 3, n | Cohort 3, median (range) | Cerebral Edema |
| CRP (mg/L) | 37 | 60.63 (0.92-496.00) | 225.27 |
| CXCL10 (pg/mL) | 37 | 404.50 (68.00-2000.00) | 2000.00 |
| Eotaxin-1 (pg/mL) | 37 | 98.40 (12.30-496.70) | 100.60 |
| Eotaxin-3 (pg/mL) | 37 | 10.20 (10.20-10.20) | 10.20 |
| FGFBF (pg/mL) | 9 | 10.20 (2.60-41.50) | NA |
| FLT-1 (pg/mL) | 9 | 60.80 (27.90-789.60) | NA |
| Ferritin (ng/mL) | 37 | 1053.40 (0.80-6563.80) | 2844.10 |
| GM-CSF (pg/mL) | 37 | 1.90 (1.90-1.90) | 1.90 |
| Granzyme A (pg/mL) | 37 | 20.00 (20.00-7376.50) | 20.00 |
| Granzyme B (pg/mL) | 37 | 1.00 (1.00-53.70) | 1.00 |
| ICAM-1 (pg/mL) | 37 | 581.89 (124.12-1881.19)× $10^3$ | 3168.36 × $10^3$ |

TABLE 26-continued

Day 0 Serum Biomarkers in Cohort 3 and the Patient with Cerebral Edema.

| | | Serum | |
| Analyte (units) | Cohort 3, n | Cohort 3, median (range) | Cerebral Edema |
| --- | --- | --- | --- |
| IFN-γ (pg/mL) | 37 | 7.50 (7.50-485.30) | 1876.00 |
| IL-1 RA (pg/mL) | 37 | 503.10 (31.20-3236.30) | 4000.00 |
| IL-1 alpha (pg/mL) | 37 | 2.90 (2.90-2.90) | 2.90 |
| IL-1 beta (pg/mL) | 37 | 2.10 (2.10-2.10) | 2.10 |
| IL-10 (pg/mL) | 37 | 0.070 (0.70-9.00) | 29.40 |
| IL-12 P40 (pg/mL) | 37 | 77.10 (5.70-926.30) | 36.80 |
| IL-12 P70 (pg/mL) | 37 | 1.20 (1.20-4.70) | 1.20 |
| IL-13 (pg/mL) | 37 | 4.20 (4.20-4.20) | 4.20 |
| IL-15 (pg/mL) | 37 | 36.90 (13.20-103.80) | 248.00 |
| IL-16 (pg/mL) | 37 | 183.90 (58.00-1256.70) | 386.80 |
| IL-17 (pg/mL) | 37 | 9.30 (9.30-9.30) | 9.30 |
| IL-2 (pg/mL) | 37 | 0.90 (0.90-4.40) | 0.90 |
| IL-2 R alpha (pg/mL) | 37 | 3103.20 (78.00-32903.60) | 37930.80 |
| IL-4 (pg/mL) | 37 | 0.50 (0.50-0.50) | 0.50 |
| IL-5 (pg/mL) | 37 | 6.30 (6.30-18.50) | 6.30 |
| IL-6 (pg/mL) | 37 | 4.60 (1.60-25.40) | 57.10 |
| IL-7 (pg/mL) | 37 | 34.80 (16.90-83.80) | 38.10 |
| IL-8 (pg/mL) | 37 | 11.40 (2.60-34.30) | 646.00 |
| MCP-1 (pg/mL) | 37 | 629.50 (263.70-1500.00) | 1500.00 |
| MCP-4 (pg/mL) | 37 | 83.70 (21.40-982.60) | 70.20 |
| MDC (pg/mL) | 37 | 700.40 (88.30-13034.90) | 8382.50 |
| MIP-1 alpha (pg/mL) | 37 | 13.80 (13.80-97.10) | 13.80 |
| MIP-1 beta (pg/mL) | 37 | 107.70 (53.00-636.60) | 99.50 |
| PLGF (pg/mL) | 9 | 89.20 (65.10-164.40) | NA |
| Perforin (pg/mL) | 37 | 1668.20 (10.00-14735.60) | 10.00 |
| SAA (pg/mL) | 37 | 61067.14 (1456.66-1380000.00) $\times 10^3$ | $69609.56 \times 10^3$ |
| SFASL (pg/mL) | 37 | 10.00 (10.00-2458.30) | 10.00 |
| CCL-17 (TARC) (pg/mL) | 37 | 568.20 (20.20-4480.00) | 4480.00 |
| TIE-2 (pg/mL) | 9 | 2337.20 (1705.00-2754.90) | NA |
| TNF alpha (pg/mL) | 37 | 3.10 (0.70-23.50) | 26.20 |
| TNF beta (pg/mL) | 37 | 1.20 (1.20-4.80) | 130.20 |
| VCAM-1 (pg/mL) | 37 | 734486.30 (37.60-1749722.10) | 3060406.10 |
| VEGF (pg/mL) | 9 | 362.80 (98.70-1135.80) | NA |
| VEGFC (pg/mL) | 9 | 146.00 (146.00-385.00) | NA |
| VEGFD (pg/mL) | 9 | 1301.60 (729.60-2272.30) | NA |

Day 0 was the day of axicabtagene ciloleucel infusion. Day 0 values for Cohort 3 show the median of the day 0 value measured for all patients with available samples, excluding the patient with cerebral edema. Bolded text indicates markers whose values for the cerebral edema patient exceed the maximum for the remainder of Cohort 3. CCL, chemokine (C-C motif) ligand; CXCL, chemokine (C-X-C motif) ligand; CRP, C-reactive protein; FGFBF, fibroblast growth factor basic form; FLT, vascular endothelial growth factor receptor; GM-CSF, granulocyte macrophage colony stimulating factor; ICAM, intercellular adhesion molecule; IFN, interferon; IL, interleukin; MCP, monocyte chemotactic protein; MDC, macrophage-derived chemokine; MIP, macrophage inflammatory protein; NA, not assayed; PLGF, placental growth factor; R, receptor; RA, receptor antagonist; SAA, serum amyloid A; SFASL, serum soluble Fas ligand; TIE, TEK tyrosine kinase; TNF, tumor necrosis factor; VCAM, vascular cell adhesion molecule; VEGF, vascular endothelial growth factor Post-treatment samples (obtained after brain death at day 9) showed extremely elevated levels of serum and CSF cytokines (Table 27), accompanied by massive recruitment of CD14 myeloid cells, CAR-negative and CAR-positive CD4 T cells, and CAR-positive CD8 T cells to the CSF (Table 28). Interestingly, highly elevated serum and CSF cytokines were not accompanied by substantially increased levels of CAR T cells in blood, a pattern that contrasted with that observed in other Cohort 3 patients. Blood CAR T-cell levels measured on day 7 post-infusion were comparable between the patient with cerebral edema (35 CAR+ cells/μL) and Cohorts 1+2 (n=98; median, 38 CAR+ cells/μL.

TABLE 27

Post-Treatment Serum and CSF Biomarkers in Cohort 3 and the Patient with Cerebral Edema.

| | | Serum (Peak) | | | CSF (Peak) | |
| Analyte (units) | Cohort 3, n | Cohort 3, median (range) | Cerebral Edema | Cohort 3, n | Cohort 3, median (range) | Cerebral Edema |
| --- | --- | --- | --- | --- | --- | --- |
| CRP (mg/L) | 37 | 136.83 (2.12-496.00) | 225.27 | 22 | 0.11 (0.01-2.15) | 4.96 |
| CXCL10 (pg/mL) | 37 | 2000.00 (541.00-2000.00) | 2000.00 | 20 | 2000.00 (152.90-2000.00) | 2000.00 |

TABLE 27-continued

Post-Treatment Serum and CSF Biomarkers in Cohort 3 and the Patient with Cerebral Edema.

| Analyte (units) | Serum (Peak) | | | CSF (Peak) | | |
|---|---|---|---|---|---|---|
| | Cohort 3, n | Cohort 3, median (range) | Cerebral Edema | Cohort 3, n | Cohort 3, median (range) | Cerebral Edema |
| Eotaxin-1 (pg/mL) | 37 | 178.90 (89.50-496.70) | 375.30 | 20 | 164.75 (12.30-290.60) | 72.60 |
| Eotaxin-3 (pg/mL) | 37 | 10.20 (10.20-240.70) | 10.20 | 20 | 10.20 (10.20-426.70) | 104.90 |
| FGFBF (pg/mL) | 9 | 23.20 (2.60-46.60) | NA | 10 | 1.30 (1.30-1.30) | NA |
| FLT-1 (pg/mL) | 9 | 789.60 (75.60-1639.50) | NA | 10 | 37.70 (30.10-87.50) | NA |
| Ferritin (ng/mL) | 37 | 2216.60 (0.80-25000.00) | 7243.00 | NA | NA | NA |
| GM-CSF (pg/mL) | 37 | 5.40 (1.90-167.60) | 28.00 | 20 | 1.90 (1.90-6.60) | 1.90 |
| Granzyme A (pg/mL) | 37 | 20.00 (20.00-7636.60) | 20.00 | 22 | 10.00 (10.00-359.50) | 10.00 |
| Granzyme B (pg/mL) | 37 | 43.80 (1.00-534.60) | 66.30 | 22 | 1.90 (0.50-53.20) | 6.80 |
| ICAM-1 (pg/mL) | 37 | 1005.85 (256.77-3546.63) × 10$^3$ | 4879.75 × 10$^3$ | 22 | 7.91 (2.37-50.61) × 10$^3$ | 1084.72 × 10$^3$ |
| IFN-γ (pg/mL) | 37 | 1839.30 (65.00-1876.00) | 1876.00 | 20 | 37.00 (7.50-1036.90) | 285.90 |
| IL-1 RA (pg/mL) | 37 | 2096.70 (653.70-4000.00) | 4000.00 | 22 | 351.45 (15.60-1480.50) | 458.70 |
| IL-1 alpha (pg/mL) | 37 | 2.90 (2.90-34.60) | 2.90 | 20 | 2.90 (2.90-2.90) | 2.90 |
| IL-1 beta (pg/mL) | 37 | 2.10 (2.10-2.10) | 2.10 | 20 | 2.10 (2.10-2.10) | 2.10 |
| IL-10 (pg/mL) | 37 | 48.70 (1.80-466.00) | 43.60 | 20 | 3.60 (0.70-37.70) | 3.40 |
| IL-12 P40 (pg/mL) | 37 | 212.70 (68.40-1252.50) | 142.00 | 20 | 5.70 (5.70-12.80) | 22.00 |
| IL-12 P70 (pg/mL) | 37 | 2.60 (1.20-27.70) | 13.60 | 20 | 1.20 (1.20-3.70) | 7.40 |
| IL-13 (pg/mL) | 37 | 4.20 (4.20-18.80) | 4.20 | 20 | 4.20 (4.20-15.30) | 13.20 |
| IL-15 (pg/mL) | 37 | 50.20 (21.90-194.10) | 537.30 | 20 | 7.20 (1.40-26.30) | 47.40 |
| IL-16 (pg/mL) | 37 | 357.50 (86.80-3740.00) | 480.90 | 20 | 19.10 (19.10-45.60) | 324.60 |
| IL-17 (pg/mL) | 37 | 9.30 (9.30-282.50) | 9.30 | 20 | 9.30 (9.30-23.60) | 9.30 |
| IL-2 (pg/mL) | 37 | 19.90 (0.90-189.40) | 24.90 | 20 | 0.90 (0.90-3.60) | 4.90 |
| IL-2 R alpha (pg/mL) | 37 | 11238.30 (3002.60-100000.00) | 65093.40 | 22 | 201.05 (39.00-5000.00) | 3114.40 |
| IL-4 (pg/mL) | 37 | 0.50 (0.50-4.60) | 1.90 | 20 | 0.50 (0.50-0.50) | 0.50 |
| IL-5 (pg/mL) | 37 | 44.20 (6.30-1124.00) | 35.20 | 20 | 6.30 (6.30-42.60) | 6.30 |
| IL-6 (pg/mL) | 37 | 867.60 (13.30-976.00) | 976.00 | 20 | 40.70 (1.60-582.70) | 949.80 |
| IL-7 (pg/mL) | 37 | 38.10 (19.10-83.80) | 41.90 | 20 | 1.40 (1.40-1.40) | 3.10 |
| IL-8 (pg/mL) | 37 | 119.90 (10.30-750.00) | 750.00 | 20 | 85.50 (8.50-750.00) | 750.00 |
| MCP-1 (pg/mL) | 37 | 1500.00 (543.60-1500.00) | 1500.00 | 20 | 433.15 (94.60-1500.00) | 1500.00 |
| MCP-4 (pg/mL) | 37 | 252.50 (107.10-1439.50) | 279.30 | 20 | 5.10 (5.10-32.50) | 5.10 |
| MDC (pg/mL) | 37 | 1274.10 (88.30-30000.00) | 15081.80 | 20 | 88.30 (88.30-88.30) | 552.90 |
| MIP-1 alpha (pg/mL) | 37 | 13.80 (13.80-445.00) | 116.20 | 20 | 13.80 (13.80-66.50) | 13.80 |
| MIP-1 beta (pg/mL) | 37 | 317.20 (92.30-1152.80) | 500.50 | 20 | 13.45 (2.30-43.50) | 33.10 |
| PLGF (pg/mL) | 9 | 108.40 (83.00-276.40) | NA | 10 | 50.50 (41.20-89.90) | NA |
| Perforin (pg/mL) | 37 | 15368.10 (4327.40-30575.90) | 29721.00 | 22 | 5.00 (5.00-128.70) | NA |

TABLE 27-continued

Post-Treatment Serum and CSF Biomarkers in Cohort 3 and the Patient with Cerebral Edema.

| Analyte (units) | Serum (Peak) | | | CSF (Peak) | | |
|---|---|---|---|---|---|---|
| | Cohort 3, n | Cohort 3, median (range) | Cerebral Edema | Cohort 3, n | Cohort 3, median (range) | Cerebral Edema |
| SAA (pg/mL) | 37 | 276722.66 (2417.95-1380000.00) × $10^3$ | 104618.20 × $10^3$ | 22 | 13954.50 (5.40-369701.60) | 6695.00 |
| SFASL (pg/mL) | 37 | 10.00 (10.00-2516.20) | 10.00 | 22 | 5.00 (5.00-61.80) | 223664.10 |
| CCL-17 (TARC) (pg/mL) | 37 | 2856.90 (159.70-4480.00) | 4480.00 | 20 | 83.50 (3.30-365.90) | 87.30 |
| TIE-2 (pg/mL) | 9 | 2945.40 (1968.00-3846.90) | NA | 10 | 198.00 (198.00-198.00) | 849.10 |
| TNF alpha (pg/mL) | 37 | 10.80 (3.30-52.10) | 48.50 | 20 | 0.70 (0.70-6.80) | NA |
| TNF beta (pg/mL) | 37 | 2.80 (1.20-30.30) | 388.50 | 20 | 1.20 (1.20-1.20) | 9.30 |
| VCAM-1 (pg/mL) | 37 | 1344.74 (721.05-3364.80) × $10^3$ | 5184.24 × $10^3$ | 22 | 16744.20 (4774.30-39133.40) | 1.20 |
| VEGF (pg/mL) | 9 | 362.80 (98.70-1230.90) | NA | 10 | 2.50 (2.50-2.50) | 733212.60 |
| VEGFC (pg/mL) | 9 | 146.00 (146.00-416.90) | NA | 10 | 73.00 (73.00-73.00) | NA |
| VEGFD (pg/mL) | 9 | 1731.00 (751.80-4211.50) | NA | 10 | 33.60 (33.60-33.60) | NA |

Peak values for Cohort 3 show the median of the maximum value measured for all patients with available samples, excluding the patient with cerebral edema. For the patient with cerebral edema, the peak serum was the highest value measured. Peak CSF value for the patient with cerebral edema was measured on day 9. Bolded text indicates markers whose values for the cerebral edema patient exceed the maximum for the remainder of Cohort 3.

TABLE 28

Post-Treatment CSF Cell Populations in Cohort 3 and the Patient with Cerebral Edema.

| Cell Population | Visit | Cohort 3 | | | Cerebral edema |
|---|---|---|---|---|---|
| | | n | Median (range) | | |
| CD14, cells/mL | Baseline[a] | 32 | 12.1 | (0.0-172.2) | 15.2 |
| | Post-treatment[b] | 24 | 16.4 | (0.0-559.1) | 226.0 |
| CD4, cells/mL | Baseline[a] | 32 | 6.0 | (0.0-131.8) | 4.2 |
| | Post-treatment[b] | 24 | 9.1 | (0.0-1407.4) | 864.7 |
| CD4 CAR+, cells/mL | Baseline[a] | 32 | 0.0 | (0.0-2.0) | 0.0 |
| | Post-treatment[b] | 24 | 3.5 | (0.0-1286.6) | 441.3 |
| CD8 CAR+, cells/mL | Baseline[a] | 32 | 0 | (0.0-0.6) | 0.0 |
| | Post-treatment[b] | 24 | 0.0 | (0.0-9.4) | 754.4 |

[a]Prior to initiation of conditioning chemotherapy.
[b]Day 9 for cerebral edema case and day 5 for the remainder of Cohort 3.

The contribution of tocilizumab to the case of grade 5 cerebral edema in Cohort 3 is not known. The patient had rapidly progressing disease, CMV reactivation, and notably, high levels of proinflammatory biomarkers prior to axicabtagene ciloleucel infusion, and high levels of such biomarkers post infusion. These findings were suggestive of a pre-existing inflammatory or infectious process that may have predisposed the patient to both systemic and local inflammation leading to cerebral edema.

Although the study was not designed to statistically compare the impact of early or prophylactic tocilizumab with the earlier findings in ZUMA-1 Cohorts 1+2, Cohort 3 patients experienced a numerical decrease in the rate of grade ≥3 CRS and a numerical increase in rates of grade ≥3 neurologic events. The Cohort 3 protocol resulted in CR rates near 50%, robust durability of response, and did not appear to affect levels of CAR T cells in blood. This suggested that IL-6R signaling may be dispensable in vivo for sustaining CAR T-cell expansion. Consistent with effective blockade of the IL-6R, which removes a major sink for IL-6, Cohort 3 showed increased levels of free serum IL-6 and reduced rates of grade ≥3 CRS. Decreased levels of the acute phase response (APR) proteins CRP and SAA relative to Cohorts 1+2 were also consistent with a pivotal role of the IL-6/IL-6R axis in the regulation of APR proteins.

Comparable blood levels of CART cells and most serum cytokines and chemokines in Cohort 3 versus Cohorts 1+2 suggested a limited impact of IL-6R on the PK/PD profile of axicabtagene ciloleucel. However, the elevated serum levels of IFN-γ and granzyme B observed in Cohort 3 implicated the IL-6/IL-6R axis in regulation of T-cell functionality. Specifically, elevated levels of IFN-γ and granzyme B were suggestive of an enhanced T1 functionality, a finding that is consistent with a previously characterized effect of IL-6 activity on differentiation of T2 vs T1 cells. Furthermore, IFN-γ and granzyme B were previously associated with grade ≥3 neurologic events ipatients receiving CAR T-cell therapy. Thus, a polarization to a T1 T-cell immunity may have contributed to the elevated rate of neurologic events in Cohort 3. An alternate hypothesis is that IL-6R blockade led to increased IL-6 exposure in the CNS in Cohort 3. Although that is not supported by the comparable CSF levels of IL-6 in patients with grade ≥3 neurologic events in Cohort 3 and Cohorts 1+2 at day 5 (FIG. 61), it cannot be ruled out that CSF levels of IL-6 may have differed more substantially at later timepoints. In addition, it cannot be ruled out that higher levels of serum IL-6 may have acted both systemically and locally in the CNS through the non-canonical gp130 receptor (on endothelial cells, pericytes and other categories of cells), thus contributing to the increased rate of high-grade neurologic events in Cohort 3 patients.

There was no notable impact of IL-6R blockade on serum levels of other cytokines and chemokines spanning a broad range of immune programs, underscoring a relatively limited mechanistic impact of the IL-6/IL-6R axis in the CAR T-cell related inflammatory cascade and paralleling the clinical outcomes observed. At day 5, levels of CSF cytokines, myeloid cells, and CAR+ CD4 T cells, were higher in patients with grade ≥2 neurologic events, indicating active cellular trafficking and a local inflammatory component in the pathogenesis of neurologic events. Although median peak levels of serum IL-6 (day 3-5) were approximately 10-fold higher in Cohort 3 than Cohorts 1+2 due to receptor blockade and availability of free IL-6 for measurement, median CSF levels of IL-6 at day 5 were comparable.

Example 16

Patients with high-risk LBCL have poor outcomes with R-CHOP chemoimmunotherapy and approximately 50% of patients will not achieve long-term disease remission, highlighting unmet need for new therapies. Axicabtagene ciloleucel was approved for treatment of adults with relapsed/refractory LBCL after ≥2 lines of systemic therapies based on the pivotal ZUMA-1 study. This Example reports on interim efficacy, safety, and pharmacokinetics results from a phase 2 study (ZUMA-12) of axicabtagene ciloleucel as first-line therapy in patients with high-risk Large B Cell Lymphoma (LBCL). ZUMA-12 was the first study evaluating CAR T cell therapy as first-line therapy in high-risk LBCL, which notably was defined by both histology and/or IPI and dynamic risk assessment with PET scans. First line therapy may include combination with another anti-cancer treatment. Axicabtagene ciloleucel treatment showed significant clinical benefit, with high ORR and CR rates and a manageable safety profile in patients for whom there is an unmet medical need. The study also provided new insights into the pharmacology of CAR T cell therapy for patients exposed to fewer therapies.

Eligible adults (≥18 years old) met two criteria for high-risk LBCL: i) double- or triple-hit lymphoma by fluorescent in situ hybridization per investigator or LBCL with International Prognostic Index (IPI) score ≥3; and ii) positive interim positron emission tomography (PET) per Lugano Classification (Cheson, et al. *J Clin Oncol.* 2014; Deauville criteria [DC] 4 or 5) after 2 cycles of an anti-CD20 monoclonal antibody and anthracycline containing regimen, which served as a dynamic risk assessment. In this setting, axicabtagene ciloleucel is first line therapy in combination with the anti-CD20 monoclonal antibody and anthracycline containing regimen. Patients underwent leukapheresis (≥2 weeks after prior systemic therapy) and optional non-chemotherapy bridging at investigator discretion, followed by conditioning chemotherapy (cyclophosphamide 500 mg/m²/day and fludarabine 30 mg/m²/day for 3 days) and a single axicabtagene ciloleucel infusion (target dose, $2\times10^6$ CAR T cells/kg). The primary endpoint was investigator-assessed complete response (CR) rate per Lugano Classification. Key secondary endpoints included objective response rate (ORR), frequency of adverse events (AEs), and levels of CAR T cells and cytokines in blood and serum.

As of Jul. 15, 2020, 31 patients have been enrolled and treated, and as of Jan. 24, 2020, 15 patients were treated with axicabtagene ciloleucel and had ≥3 months of follow-up. Median age was 60 years old (range, 39-86), 67% of patients were male, 73% had ECOG of 1, 40%/60% had DC4/DC5; 60% had double- or triple-hit status per investigator, and 67% had International Prognostic Index (IPI) score ≥3.

Baseline characteristics were largely comparable to ZUMA-1 Cohort 1 (see previous Examples) except for lower tumor burden in ZUMA-12 (ZUMA-1: 3897 mm² vs ZUMA-12: 1610 mm²). Of 12 response evaluable patients (patients with centrally confirmed high-risk LBCL who received axicabtagene ciloleucel), the investigator-assessed ORR was 92% (95% CI, 62%-100%) with a CR rate of 75% (95% CI, 43%-95%); 75% of patients had ongoing responses at data cutoff. Of 15 safety evaluable patients, 80% experienced Grade ≥3 AEs. The most common Grade ≥3 AEs (≥25% of patients) were white blood cell count decreased (40%), anemia (27%), and encephalopathy (27%). Grade ≥3 cytokine release syndrome (CRS) and neurologic events (NEs) occurred in 20% and 27% of patients, respectively. All CRS and 10/11 NE events of any grade resolved (causally unrelated Grade 1 tremor was ongoing in 1 patient at data cutoff). Median time to onset of CRS was 4 days (range, 1-8), with median duration of 5 days (range, 2-12). Median time to onset of NEs was 9 days (range, 2-44), with median duration of 10 days (range, 1-40). Grade ≥3 infection was reported in 27% and Grade 3 neutrophil count decreased was reported in 20%. No Grade 5 AEs occurred. Despite similar assessment schedule and methodology, median peak CAR T cell levels were greater in ZUMA-12 vs ZUMA-1 (ZUMA-12: 131 cells/μL [range, 10-555]; ZUMA-1 Phase 2 Cohort 1: 32 cells/μL [range, 1-1514]). Median CART cell expansion, ie, area under the curve in the first 28 days, was also greater in ZUMA-12 (1124 cells/μL×day [range, 147-4261]; ZUMA-1: 357 cells/μL×day [range, 5-11,507]). Median time to peak levels of CART cells in blood was 7 days after infusion. Pharmacokinetics were similar in patients with double- or triple-hit lymphoma and IPI score ≥3.

Example 17

Patients with advanced-stage indolent non-Hodgkin lymphoma (iNHL), including follicular lymphoma (FL) and marginal zone lymphoma (MZL), frequently relapse with standard treatment, underscoring a need for novel therapies. Axicabtagene ciloleucel autologous anti-CD19 chimeric antigen receptor (CAR) T cell therapy is approved for the treatment of relapsed/refractory (R/R) large B cell lymphoma after ≥2 lines of systemic therapy. This Example presents the primary analysis of ZUMA-5, a Phase 2, multicenter, single-arm study of axicabtagene ciloleucel in patients with R/R iNHL. Axicabtagene ciloleucel had significant and durable clinical benefit in patients with iNHL, with high ORR and CR rates. Axicabtagene ciloleucel had a manageable safety profile, with lower rates of Grade ≥3 NEs observed in patients with FL, versus those in patients with MZL and those previously reported in aggressive NHL (Locke, et al. *Lancet Oncol.* 2019; 20(1):31-42).

Adults with FL (Grades 1-3a) or MZL (nodal or extranodal) had R/R disease after ≥2 lines of therapy (including an anti-CD20 mAb plus an alkylating agent), and ECOG 0-1. Patients underwent leukapheresis followed by conditioning therapy (intravenous fludarabine (30 mg/m² body-surface area) and cyclophosphamide (500 mg/m² body-surface area) on days −5, −4, and −3) and a single infusion of axicabtagene ciloleucel at $2\times10^6$ CAR T cells/kg on day 0. The primary endpoint was objective response rate (ORR) (Complete response (CR)+partial response (PR)) by central review (per Lugano classification; Cheson B D, Fisher R I, Barrington S F, et al. Recommendations for initial evaluation, staging, and response assessment of Hodgkin and non-Hodgkin lymphoma: the Lugano classification. J Clin Oncol. 2014; 32(27):3059-3068. doi:10.1200/JCO.2013.54.8800). Secondary endpoints included complete response (CR) rate (per Lugano classification; Cheson, et al. *J Clin Oncol.* 2014), duration of response (DOR)(DOR is defined only for subjects who experience an objective response and is the time from the first objective response to disease progression per (Cheson et al, 2014) or disease-related death, whichever comes first), progression-free survival (PFS)(PFS is defined as the time from the axicabtagene ciloleucel infusion date to the date of disease progression per (Cheson et al, 2014) or death from any cause)), overall survival (OS)(OS is defined as the time from axicabtagene ciloleucel infusion to the date of death), incidence of adverse events (AEs), and levels of CAR T cells in blood and cytokines in serum. The primary efficacy analysis occurred when ≥80 treated patients with FL had ≥12-months follow-up.

146 patients with iNHL (124 FL; 22 MZL) received axicabtagene ciloleucel; 84 patients with FL had ≥12-months follow-up. The median age was 61 years (range, 34-79); 57% of patients were male. Thirty-eight percent of patients had ECOG 1, 86% had stage III/IV disease, 47% had ≥3 Follicular Lymphoma International Prognostic Index (FLIPI), and 49% had high tumor bulk (GELF). Patients had a median 3 prior lines of therapy (range, 1-10); 64% had ≥3 prior lines. Progression <2 years after initial anti-CD20 mAb-containing therapy (POD24) occurred in 55% of patients, and 68% were refractory to last prior treatment. With a median follow-up of 17.5 months (range, 1.4-31.6), the ORR was 92% among efficacy-evaluable patients with iNHL (n=104), with a 76% CR rate. In patients with FL (n=84), the ORR was 94% (80% CR rate); in those with MZL (n=20), the ORR was 85% (60% CR rate). ORR was comparable across key risk groups analyzed by FLIPI, Progression of disease within 24 months of first treatment (POD24), Groupe d'Etude des Lymphomes Folliculaires (GELF), refractory status, and prior lines of therapy. As of the data cutoff, 62% of all treated patients had ongoing responses (64% for FL). The medians for DOR, PFS, and OS were not reached; 12-month estimated rates were 72% (95% CI, 61-80), 74% (95% CI, 63-82), and 93% (95% CI, 86-97), respectively.

AEs of any grade occurred in 99% of all treated patients. Grade ≥3 AEs occurred in 86% of patients with iNHL (85% in FL; 95% in MZL), most commonly neutropenia (33%), decreased neutrophil count (27%), and anemia (23%). Grade ≥3 cytokine release syndrome (CRS; per Lee, et al, *Blood.* 2014) occurred in 7% of patients with iNHL (6% in FL; 9% in MZL). Grade ≥3 neurologic events (NEs; per CTCAE v4.03) occurred in 19% of patients with iNHL (15% in FL; 41% in MZL). Most CRS (118/119) and NEs (81/87) of any grade resolved by data cutoff. Grade 5 AEs occurred in 3 patients: multisystem organ failure in the context of CRS (related to axicabtagene ciloleucel; n=1 FL), aortic dissection (unrelated to axicabtagene ciloleucel; n=1 FL), and coccidioidomycosis infection (unrelated to axicabtagene ciloleucel; n=1 MZL).

The median peak CAR T cell level was 38 cells/µL (range, 0-1415) in all treated patients with iNHL, with 36 cells/µL (range, 0-1415) in those with FL and 53 cells/µL (range, 2-453) in those with MZL. The area under the curve Day 0-28 was 448 cells/µL×days (range, 6-19,900) in all treated patients with iNHL, with 422 cells/µL×days (range, 6-19,900) and 552×days (range, 13-6468) in those with FL and MZL, respectively. The median time to peak was 9 days (range, 8-371) in all patients, 8 days (range, 8-371) in patients with FL, and 15 days (range, 8-29) in patients with MZL. In efficacy-evaluable patients with FL, median peak CAR T cell levels were numerically greater in those with ongoing response at 12 months than in those who relapsed (P=0.057); in all treated patients with FL, CAR T cell peak was associated with Grade ≥3 CRS (P=0.031) and NEs (P=0.005).

Example 18

Axicabtagene ciloleucel is approved for treatment of adult patients with R/R LBCL after ≥2 lines of systemic therapy. In the pivotal ZUMA-1 study, axicabtagene ciloleucel treatment showed durable responses and a largely manageable safety profile (Locke F L, et al. *Lancet Oncol.* 2019 and previous Examples). ZUMA-9, a multicenter open-label study of Axicabtagene Ciloleucel in R/R LBCL (Diffuse Large B Cell Lymphoma; Primary Mediastinal B Cell Lymphoma; Transformed Follicular Lymphoma; and High-Grade B-Cell Lymphoma) for expanded access and commercial Out-of-Specification (OOS) product, provided patients with R/R LBCL with expanded access to axicabtagene ciloleucel until commercial availability (Cohort 1 [C1]) and later, if commercially manufactured product did not meet commercial release specification(s) (Cohort 2 [C2]). This Example describes the outcomes of patients in ZUMA-9 and the safety and efficacy of axicabtagene ciloleucel (C1 and C2) and translational analyses (C2) are presented. Axicabtagene ciloleucel treatment showed a manageable safety profile and meaningful clinical benefit. While CAR T cell treatment showed clinical benefit in C2 (OOS product), the lower CR rate was corroborated by lower CAR T cell expansion and a more differentiated product versus ZUMA-1 C1+2.

Inclusion Criteria included:

Histologically confirmed large B-cell lymphoma, including the following types defined by WHO 2008 (Campo et al., *Blood.* 2011; 117(19):5019-32):

a. DLBCL, not otherwise specified;

b. Primary mediastinal large B-cell lymphoma;

c. High-grade B-cell lymphoma; and d. DLBCL arising from follicular lymphoma (transformed follicular lymphoma, or TFL);

Relapsed or refractory disease, defined as one or more of the following:

a. No response to first-line therapy (primary refractory disease); subjects who were intolerant to first-line therapy chemotherapy were excluded; or b. No response or relapse to second or greater lines of therapy; or c. Relapsed after ASCT;

Subjects received adequate prior therapy including at a minimum:

a. anti-CD20 monoclonal antibody unless investigator determined that tumor was CD20 negative; and b. an anthracycline containing chemotherapy regimen;

No evidence, suspicion, and/or history of central nervous system (CNS) involvement of lymphoma; Age 18 or older; Eastern cooperative oncology group (ECOG) performance status of 0 or 1; Absolute neutrophil count ANC ≥1000/µL; Platelet count ≥75,000/µL; Absolute lymphocyte count ≥100/µL; and Adequate renal, hepatic, pulmonary and cardiac function defined as:

a. Creatinine clearance (as estimated by Cockcroft Gault) ≥60 mL/min;

b. Serum alanine aminotransferase/aspartate aminotransferase (ALT/AST) ≤2.5 upper limit of normal (ULN);

c. Total bilirubin ≤1.5 mg/dL, except in subjects with Gilbert's syndrome;

d. Cardiac ejection fraction ≥50% and no evidence of pericardial effusion within 180 days provided the subject did not receive an anthracycline based treatment or experience a cardiac event or change in performance status;

e. No clinically significant pleural effusion; and f. Baseline oxygen saturation >92% on room air.

Cohort 2 inclusion criteria: Subjects whose commercial manufacture of axicabtagene ciloleucel did not meet commercial release specification(s).

Exclusion Criteria included: history of malignancy other than nonmelanoma skin cancer or carcinoma in situ (e.g. cervix, bladder, breast) or follicular lymphoma unless disease free for at least 3 years; History of allogeneic stem cell transplantation (SCT); Prior CD19 targeted therapy; Prior chimeric antigen receptor therapy or other genetically modified T-cell therapy; History of severe, immediate hypersensitivity reaction attributed to aminoglycosides; Presence or suspicion of fungal, bacterial, viral, or other infection that is uncontrolled or requiring intravenous (IV) antimicrobials for management. Simple urinary tract infection (UTI) and uncomplicated bacterial pharyngitis are permitted if responding to active treatment and after consultation with the Kite Pharma Medical Monitor; History of human immunodeficiency virus (HIV) infection or acute or chronic active hepatitis B or hepatitis C infection. Subjects with a history of hepatitis infection having cleared their infection as determined by standard serological and genetic testing per current Infectious Diseases Society of America (IDSA) guidelines; History or presence of primary CNS lymphoma and/or CNS disorder such as seizure disorder, cerebrovascular ischemia/hemorrhage, dementia, cerebellar disease, or any autoimmune disease with CNS involvement.

Cohort 2 exclusion criteria: Any medical condition that, deemed by the investigator, may have interfered with assessment of safety or efficacy of study treatment.

Eligible adults had histologically confirmed R/R LBCL, ECOG ≤1, and had received prior CD20-targeting and an anthracycline-containing regimen. Cohort 2 patients have had a commercial OOS product. Patients underwent leukapheresis and conditioning chemotherapy (cyclophosphamide 500 mg/m$^2$/day and fludarabine 30 mg/m$^2$/day) on days −5, −4, and −3, followed by a single axicabtagene ciloleucel infusion (target dose, 2×10$^6$ CAR T cells/kg) on day 0. Cohort 1 and Cohort 2 patients with high disease burden could have received bridging therapy before conditioning at investigator's discretion. Endpoints included frequency of adverse events (AEs), objective response rate (ORR) per standard-of-care imaging assessment, overall survival (OS) for Cohort 1 and Cohort 2, and blood CAR T cells levels and serum cytokines for Cohort 2 only. Outcomes were contextualized with the primary analysis of ZUMA-1 C1+2 (n=101; ≥6 months of follow-up; Neelapu S S, et al. *NEJM* 2017). See previous Examples.

As of Nov. 29, 2019 (Cohort 1) and 3/15/2020 (Cohort 2), 25 C1 patients and 36 C2 patients had received axicabtagene ciloleucel with a median follow-up of 27.1 months (range, 23.6-29.6) and 13.2 months (range, 0.4-25.7), respectively. In C1, median age was 56 years-old (range, 28-76), 60% were male, 80% had DLBCL, 48%/0% had ECOG1/≥2, 44% had IPI ≥3, and 64% had ≥3 prior lines of therapy. In C2, median age was 61 years-old (range, 24-81), 75% were male, 78% had DLBCL, 58%/17% had ECOG 1/≥2, 56% had IPI ≥3, and 69% had ≥3 prior lines of therapy. In C2, 50% of patients had OOS product with low viability (≤80%), 28% had high IFN-γ (≥19,000 pg/mL), 14% had low IFN-γ (≤520 pg/mL), 14% received a low dose (≤1×10$^6$ CAR T cells/kg), and 6% had high transduction ratio (≥84%). The ORR was 76% (64% complete response [CR]) for C1, 53% (36% CR) for C2, and 82% (54% CR) for ZUMA-1 C1+2. Median OS was 23.8 months (95% CI, 13.5-NE) for C1 and not reached (95% CI, 3.4-NE) for C2, respectively. ORR and OS were consistent in C2 OOS subgroups (Table 29).

TABLE 29

Clinical and translational outcomes by cohort and within OOS subgroups.

| | Efficacy | | | | |
| --- | --- | --- | --- | --- | --- |
| | ZUMA-1[1] | ZUMA-9 | | | |
| | | | | C2 OOS Subgroups | |
| | C1 + 2 (N = 101) | C1 (N = 25) | C2 (N = 36) | Low Viability (n = 18) | High IFN-γ (n = 10) |
| ORR, % | 82 | 76 | 53 | 61 | 50 |
| CR, % | 54 | 64 | 36 | 39 | 50 |
| Median OS (95% CI), months | NR (12.0-NE) | 23.8 (13.5-NE) | NR (3.4-NE) | NR (3.4-NE) | NR (0.2-NE) |
| 12-month OS (95% CI), months | | 76 (54-88) | 62 (43-77) | 65 (35-84) | 70 (33-89) |

| | Safety | | |
| --- | --- | --- | --- |
| | C1 + 2 (N = 101) | C1 (N = 25) | C2 (N = 36) |
| Grade ≥3 AEs | | 88 | 89 |
| Grade ≥3 CRS | 13 | 0 | 3 |
| Grade ≥3 NEs | 28 | 36 | 19 |

TABLE 29-continued

Clinical and translational outcomes by cohort and within OOS subgroups.

| | Biomarkers | |
| | C1 + 2 (N = 101) | C2 (N = 36) |
| --- | --- | --- |
| Median Peak CAR T cell level (range), cells/µL | 42 (1-1514) | 12 (0-442) |
| Median $AUC_{0-28}$ (range), cells/µL × days) | 462 (5-14,329) | 112 (0-3413) |
| Median serum IFN-γ (range), pg/mL | 477 (8-8209) | 170 (8-1876) |

[1]Neelapu S S, et al. *N. Engl J Med.* 2017; 377: 2531-2544.
AEs, adverse events;
AUC, area under the curve;
C1, cohort 1;
C2, cohort 2;
CAR, chimeric antigen receptor;
CRS, cytokine release syndrome;
CR, complete response;
IFN, interferon;
NE, not evaluable;
NEs, neurologic events;
NR, not reached;
ORR, objective response rate;
OOS, out-of-specification;
OS, overall survival.

Grade ≥3 AEs were reported in 88% and 89% of C1 and C2 patients, respectively. Grade ≥3 CRS (Lee et al, *Blood.* 2014, 124(2): 188-195) was not observed in C1 but was reported in 3% of C2 patients (13% in ZUMA-1 C1+2). Grade ≥3 neurologic events (NEs) occurred in 36% and 19% of patients in C1 and C2, respectively, and 28% of patients in ZUMA-1 C1+2. No Grade 5 CRS or NEs occurred in C1 or C2. All CRS and NEs resolved in C1, and most CRS (29/30) and NEs (19/24) resolved in C2 as of the data cutoff. Of 3 Grade 5 AEs in C1, 2 were unrelated to axicabtagene ciloleucel (clostridial sepsis [on Day (D) 6] and respiratory failure [on D212]) and 1 was related to conditioning (myelodysplastic syndrome [on D563]). Of 3 Grade 5 AEs in C2, 2 were unrelated to axicabtagene ciloleucel (multiple organ dysfunction syndrome [on D6] and cardiac arrest [on D482]) and 1 was related to axicabtagene ciloleucel (systemic mycosis [on D30]).

Median peak CAR T cell levels and median CAR T cell expansion (area under the curve in the first 28 days) were lower in ZUMA-9 C2 (n=32/36; 12 cells/µL [range, 0-442] and 112 cells/µL×days [range, 0-3413]) vs ZUMA-1 C1+2 (n=96/101; 42 cells/µL [range, 1-1514] and 462 cells/µL× days [range, 5-14,329]). Serum IFN-γ levels peaked within 8 days after axicabtagene ciloleucel infusion (median, 170 pg/mL [range, 8-1876]) and were lower vs ZUMA-1 C1+2 (median, 477 pg/mL [range, 8-8209]). Axicabtagene ciloleucel in ZUMA-9 C2 contained fewer, less differentiated CCR7+ naïve and central memory T cells, and a greater proportion of more differentiated CCR7-effector memory and effector T cells vs ZUMA-1 C1+2. No cases of replication-competent retroviruses were reported in C1 or C2.

Example 19

In Cohorts 1+2 (C1+2; N=101) of ZUMA-1, the multicenter, single-arm, registrational Phase ½ study of axicabtagene ciloleucel in patients with refractory LBCL, rates of Grade ≥3 cytokine release syndrome (CRS) and neurologic events (NEs) were 13% and 28% at the 6-months primary analysis (Neelapu et al, *New Engl J Med* 2017). In C1+2 (N=101), the objective response rate (ORR) was 82%, and complete response (CR) rate was 54%. In the non-randomized safety management Cohort 4 (C4; N=41) earlier steroid use appeared to reduce the rate of Grade ≥3 CRS (2%) and NEs (17%), with similar efficacy (73% ORR; 51% CR; Topp et al, ASH 2019, #243). See EXAMPLE 14 for a Cohort 4 report. This EXAMPLE now presents the interim analysis of ZUMA-1 Cohort 6 (C6), along with 6-months analyses of C4 and C1+2 for context. Safety management Cohort 6 evaluated the effect of prophylactic steroid use on the incidence and severity of CRS and NEs. Although conclusions are limited by short follow-up in C6 and differences in population sizes and baseline characteristics between cohorts, prophylactic steroid use appears to reduce the rate of severe CRS and NEs to a similar extent as early steroid use.

Eligible patients were leukapheresed and preconditioned, could receive optional bridging chemotherapy (allowed in C4 and C6 but not C1+2), and received conditioning chemotherapy prior to axicabtagene ciloleucel (target dose, $2×10^6$ anti-CD19 CAR T cells/kg). Patients in C6 received dexamethasone 10 mg PO on Days 0 (prior to axicabtagene ciloleucel infusion), 1, and 2. Steroids were also administered starting at Grade 1 NE, and for Grade 1 CRS when no improvement was observed after 3 days of supportive care. Tocilizumab was also administered for Grade ≥1 CRS if no improvement was observed after 24 hours of supportive care. Primary endpoints were incidence and severity of CRS and NE. Additional endpoints were efficacy outcomes and biomarker measures. ORR and CAR T cell levels were compared across quartiles of tumor burden, the values of which were determined by C1+2.

As of Oct. 18, 2019, 21 (of 40 planned) C6 patients had received axicabtagene ciloleucel, with median follow-up of 2.4 mos. All patients had ≥1 months of follow-up. The median age was 63 years-old (range, 37-85 years-old; 43%≥65 years-old); 62% were female. Disease types included DLBCL (57%), TFL (19%) and HGBCL (24%). More than half (57%) had ECOG 1, 43% had disease stage III/IV, 62% were refractory to ≥$2^{nd}$-line therapy, 5% were relapsed after ≥$2^{nd}$-line therapy, 29% had ≥3 prior lines of therapy, and 29% had relapsed after ASCT. Patients enrolled in C6 at the interim data cutoff had a median tumor burden (by sum of product diameters [SPD] before the start of conditioning chemotherapy) lower than C1+2 and similar to C4 (C6: 2044 mm$^2$; C1+2: 3723 mm$^2$; C4: 2100 mm$^2$) with similar trends observed for baseline LDH (C6: 244 U/L; C1+2: 356 U/L; C4: 262 U/L).

Tocilizumab was used in 62%, 76%, and 43% of patients in C6, C4, and C1+2, respectively. Among patients who received steroids, median cumulative steroid use (cortisone equivalents) in C6 (1252 mg [n=21]) was greater than C4 (939 mg [n=30]) but less than that observed in C1+2 (5451 mg [n=25]). Prophylactic steroid use in C6 was associated with rates of Grade ≥3 CRS and NE of 5% and 14%, respectively, with no Grade 5 CRS or NE. Onset of CRS appeared to be delayed in C6 (median, 5 days vs 2 days in C4 and C1+2). Infection rate was 38% (Grade ≥3, 5%) in C6, 51% (20%) in C4, and 38% (23%) in C1+2. ORR was 86%, with a CR rate of 38% that is likely to improve with longer follow-up. At the data cutoff, 81% of patients had ongoing responses, and median duration of response was not reached.

CART cell expansion in C6 was greater than C1+2 and C4 based on median CAR peak levels (C6: 73 cells/μL; C1+2: 42 cells/μL; C4: 53 cells/μL) and median CAR AUC (C6: 611 cells/μL×days; C1+2: 462 cells/μL×days; C4: 512 cells/μL×days) in blood. Across tumor burden quartiles, C6 CAR T cell expansion was greater than C1+2. Median CAR T cell levels in blood at 4 weeks and 3 months were 2 and <1 cells/μL, respectively, across cohorts. Compared with early steroid intervention in C4, prophylactic steroid use in C6 further reduced peak serum levels of biomarkers associated with CAR T cell treatment-related adverse events (eg, C-reactive protein, interferon-γ, granulocyte monocyte colony-stimulating factor, interleukin-2).

Example 20

As reported above, Grade ≥3 cytokine release syndrome (CRS) and neurologic events (NEs) occurred in 11% and 32% of patients in ZUMA-1, respectively (see previous EXAMPLES). Although CRS can be ameliorated with use of the anti-IL-6 receptor antibody tocilizumab (see, e.g., EXAMPLE 15), NEs may be unaffected or worsened by tocilizumab in some situations. Identification of mitigation strategies for NEs is complicated by a significant association between CAR T-cell expansion and both ORR and Grade ≥3 NEs, suggesting a correlation between efficacy and adverse events (AEs). ZUMA-1 Cohort 4 suggested that earlier utilization of systemic corticosteroids for broad immune system suppression in patients with mild NEs and low-grade CRS may reduce the incidence of Grade ≥2 NEs without significant impact on efficacy (see, e.g., EXAMPLE 14). Further proactive strategies to further improve safety management with CAR T-cell therapy without negatively impacting efficacy are needed. This EXAMPLE describes the Phase ½ ZUMA-19 study, which has been designed to evaluate sequenced therapy with lenzilumab and axicabtagene ciloleucel to prevent axicabtagene ciloleucel-related CRS and NEs in patients with R/R LBCL. Lenzilumab is a humanized monoclonal antibody that neutralizes and depletes GM-CSF.

Eligible patients are adults (≥18 y) with LBCL who relapsed after ≥2 systemic lines of therapy or are chemorefractory—defined as i) a best response of progressive disease (PD) or stable disease (SD) to ≥4 cycles of first-line systemic therapy (SD duration ≤6 months); or ii) a best response of PD or SD after ≥2 cycles of the most recent second-or-later line of systemic therapy. Prior therapy included an anti-CD20 monoclonal antibody and an anthracycline-containing regimen. Patients undergo leukapheresis and may receive optional corticosteroid bridging therapy. Patients then receive lymphodepleting chemotherapy on Days -3 to -5 followed by Day 0 administration of lenzilumab and, 6 hours later, a single infusion of axicabtagene ciloleucel (target dose, 2×$10^6$ CAR T cells/kg). Phase 1 initially enrolls patients in 2 dose-escalation cohorts. Patients receive a single infusion of 600 mg (over 1 h) or 1800 mg (over 2 h) lenzilumab. Safety data is reviewed after 3 and 6 (if needed) patients in each cohort have been followed for 28 days. The recommended Phase 2 dose (RP2D) of lenzilumab is based on the dose-limiting toxicity rate (phase 1 primary endpoint), and, if necessary, translational assessment of GM-CSF axis suppression.

Phase 2 assumes a Simon 2-stage design. The primary endpoint for phase 2 is the incidence of Grade ≥2 NEs within 28 days of axicabtagene ciloleucel administration. Efficacy, safety (including CRS and NEs), and blood levels of CAR T cells and cytokines (including GM-CSF) are evaluated as secondary endpoints. An interim analysis is performed when 14 subjects have received the recommended phase 2 dose (RP2D) in Phase 1 or 2 and are followed for 28 days after axicabtagene ciloleucel infusion. If futility criteria are not met, enrollment continues. Primary analysis is performed after 30 patients are treated with RP2D of lenzilumab and have ≥6 months of follow up.

Example 21

Despite high clinical efficacy, approximately 60% of patients do not respond to or relapse within two years of treatment with axicabtagene ciloleucel or other anti-CD19 CAR T-cell therapies. Mechanisms associated with durable responses remain incompletely elucidated, and previous correlative analyses have largely focused on toxicity and immune programs associated with CAR T-cell therapy. Limited data exist on mechanisms of treatment resistance, including target antigen loss seen in a subset of responding patients. To date, most published correlative data have been generated in leukemia patients, and limited information has been obtained in large multicenter trials irrespective of the tumor type. Previous analyses of prespecified clinical covariates, including performance status, age, disease subtype, disease stage, International Prognostic Index, and cytogenetic status were not clearly predictive of clinical efficacy in ZUMA-1. This EXAMPLE reports on a study that analyzed biomarker data from ZUMA-1 patients according to an expanded statistical analysis plan for correlates of durable response and parameters differentially associated with efficacy and toxicities. Several strong correlations were revealed.

High TB Associated with Lower Probability of Durable Response, which could be Overcome by Commensurate In Vivo CAR T-cell Expansion Consistent with previous reports, higher peak expansion of CAR T cells in the peripheral blood, specifically estimated as CAR cells per unit of blood volume, associated with both objective and durable response (FIG. 1A; FIG. 64; Table 30).

TABLE 30

| PK measurements in association with clinical efficacy. | | | | | | | |
|---|---|---|---|---|---|---|---|
| Measurement, | | Response Category | | | P Values from Dunn's Test | | P Value |
| n | median (Q1 – Q3) | Method | Durable Response | Relapsed | No Response | Durable vs Relapsed | Durable vs No Response | Relapsed vs No Response | from KW Test |
| Peak number of CAR cells/µL blood | TaqMan | 39 | 58.63 (20.9454-92.115) | 40 | 33.3881 (16.7621-79.79) | 16 | 15.6318 (3.0162-35.3708) | 0.088 | 0.0036 | 0.0437 | 0.0098 |
| Peak % CAR cells | | 40 | 7.52 (2.92-14.305) | 40 | 6.445 (4.355-14.46) | 16 | 3.975 (1.56-8) | 0.4275 | 0.0621 | 0.0572 | 0.1021 |
| Peak CAR gene copies/µg DNA | ddPCR | 39 | 50382 (17577-84078) | 37 | 50463 (15633-77679) | 15 | 25920 (11178-52974) | 0.4324 | 0.1985 | 0.1719 | 0.296 |

| Measurement, | | Response Category | | | P Values from Dunn's Test | | P Value |
|---|---|---|---|---|---|---|---|
| n | median (Q1 – Q3) | Method | Complete Response | Partial Response | No Response | CR vs PR | CR vs No Response | PR vs No Response | from KW Test |
| Peak number of CAR cells/µL blood | TaqMan | 57 | 47.1073 (21.6104-87.9564) | 25 | 26.1504 (12.2698-84.916) | 16 | 15.6318 (3.0162-35.3708) | 0.0664 | 0.0041 | 0.1278 | 0.0084 |
| Peak % CAR cells | | 59 | 8.2312 (3.38-15.1) | 25 | 6.06 (4.33-11.8) | 16 | 3.975 (1.56-8) | 0.2395 | 0.0419 | 0.1592 | 0.0881 |
| Peak CAR gene copies/µg DNA | ddPCR | 57 | 50382 (18873-81972) | 23 | 49734 (14499-77679) | 15 | 25920 (11178-52974) | 0.2329 | 0.1632 | 0.3902 | 0.2603 |

Abbreviations: CAR, chimeric antigen receptor; CR, complete response; ddPCR, droplet digital polymerase chain reaction; KW, Kruskal-Wallis test; PK, pharmacokinetics; PR, partial response; Q, quartile.

Cumulative CAR T-cell levels over the first 28 days, measured in blood by area under the curve (AUC), were also associated with objective and durable responses (FIGS. 64E-64H). Levels of CAR T cells at 3 months and beyond were very low or nonmeasurable and did not correlate with durable response (FIG. 1E).

Figures 64I, 64J, 64K:
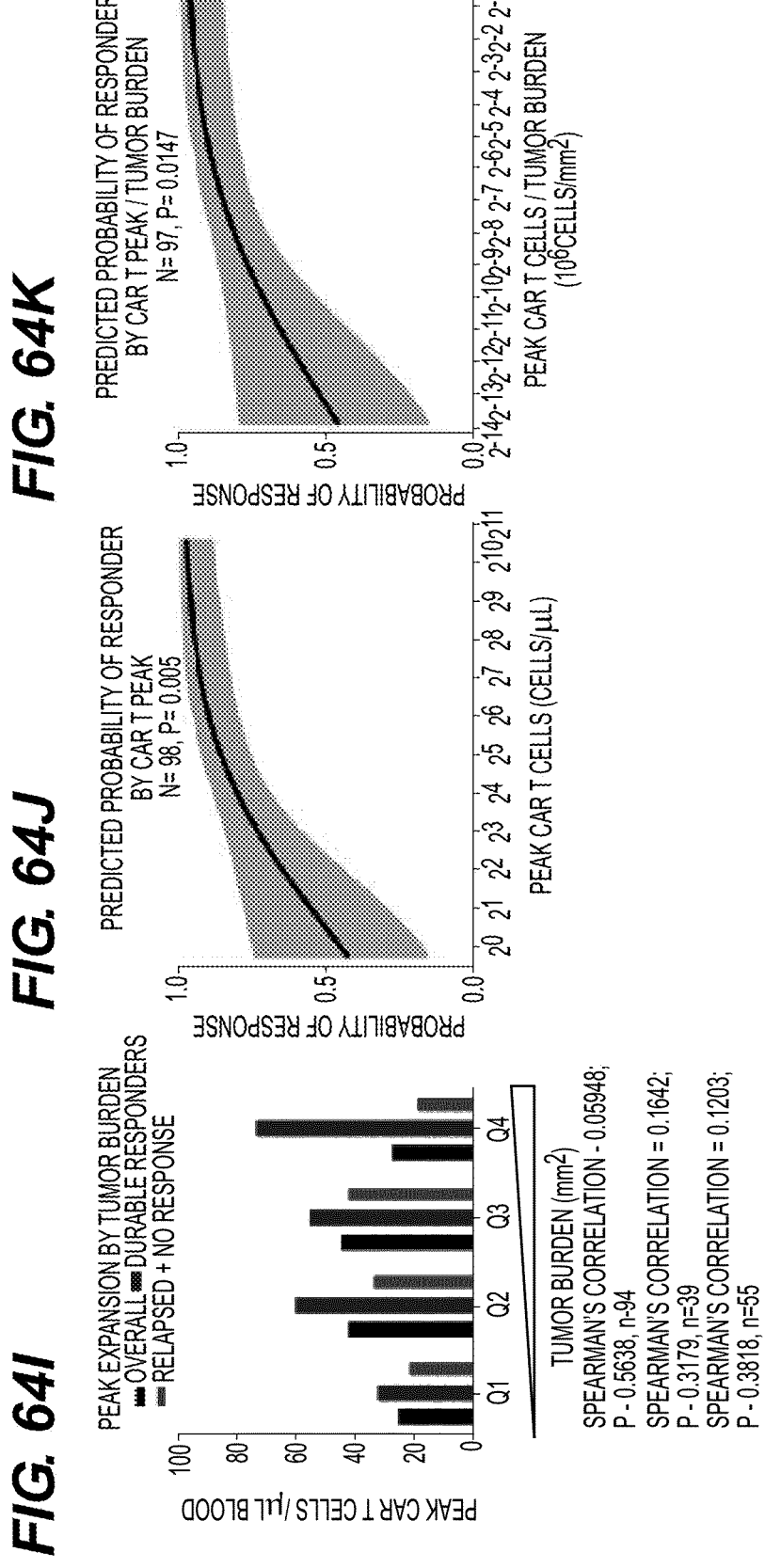

Baseline tumor burden (TB) and CAR T-cell numbers in the peripheral blood after axicabtagene ciloleucel infusion were measured in association with the clinical outcome to provide a mathematical derivation that would allow for the assessment of effector-to-target ratio following CAR T-cell therapy in lymphoma. In ZUMA-1 patients, low TB pre-CAR T-cell therapy was a strong positive predictor of durable response (FIG. 1O). It was hypothesized that higher TB, due to increased CD19 antigen, would associate with increased CAR T-cell numbers in the peripheral blood. While TB was not significantly associated with CAR T-cell expansion, CAR T-cell levels trended positively with TB in patients with durable response (FIG. 64I). Additionally, there was a lower durable response rate at comparable peak CAR T-cell levels in patients with higher TB compared with patients who had lower TB (FIG. 1I). Notably, durable responders had a higher peak CAR T-cell/TB ratio compared with nonresponders (P=0.005) or responders who subsequently relapsed within one year posttreatment (P=0.01; FIG. 1I). Similar differences were observed between peak CAR T-cell levels and TB ratio in complete responders compared with partial responders (P=0.001) or nonresponders (P=0.004; FIG. 1K). Finally, there was a significant association between overall peak CAR T cells and those normalized to TB with both durable response rate and objective response rate (FIGS. 1O and P); FIGS. 64J-64K). These findings indicate that early expansion, commensurate with TB, rather than persistence of functional circulating CAR T cells, is necessary for achievement of durable responses in refractory LBCL with an anti-CD19 CAR T-cell therapy containing a CD28 costimulatory domain.

Figure 65A:
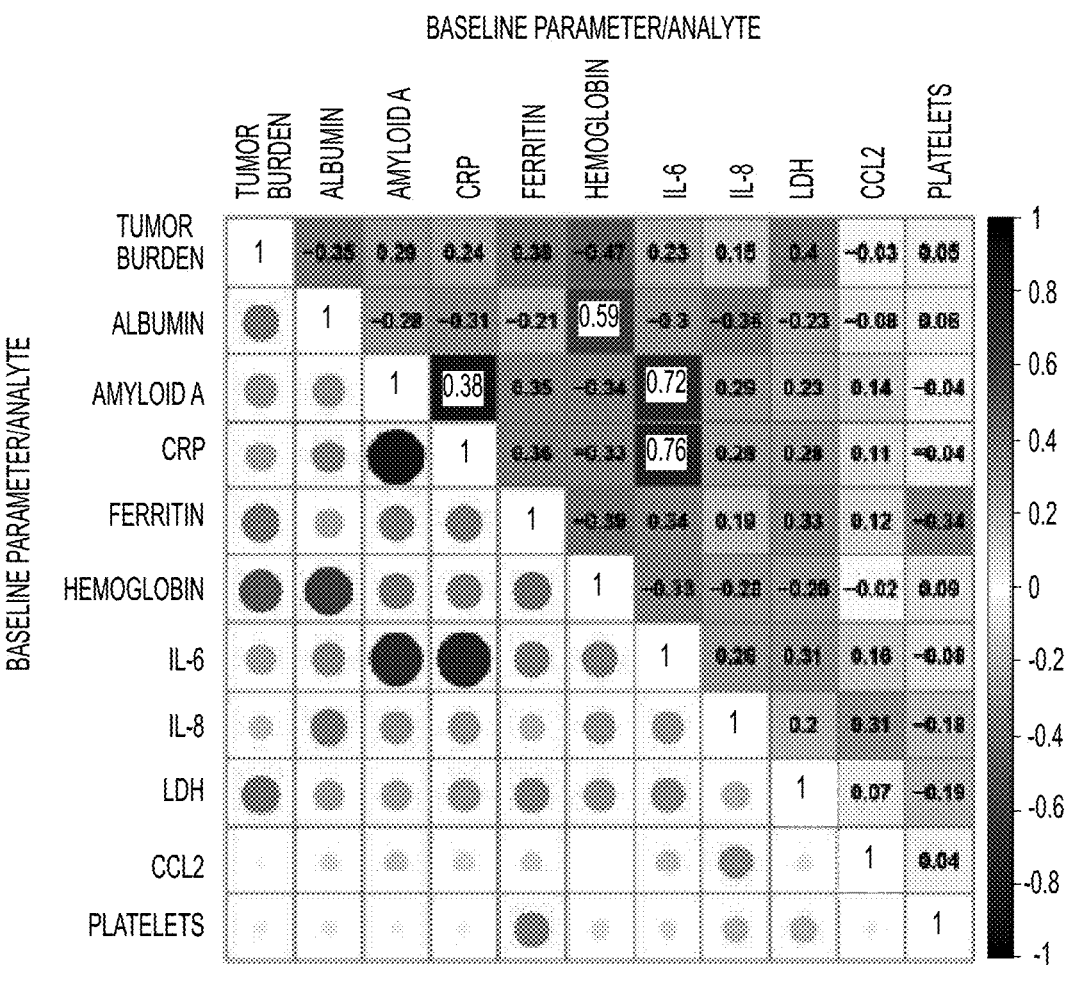

Pro-inflammatory and Myeloid Activation Markers Correlated with Impaired In Vivo CAR T-Cell Expansion and Decreased Rate of Durable Response It was hypothesized that inflammatory factors associated with high TB may impact CAR T-cell expansion and efficacy. Pre-treatment TB was generally associated with an enhanced inflammatory state reflected by IL-6, ferritin, and IL-8, reminiscent of myeloid cell activation, as well as with LDH, indicative of a tumor hypoxic microenvironment (FIG. 65A). However, tumor expression of myeloid- and inflammation-associated biomarkers did not correlate to TB: IL-1A (R=0.036; P=0.84), CD68 (R=0.13; P=0.45), IL-6 (R=-0.02; P=0.91), and CD14 (R=0.04; P=0.81).

Figures 66A, 66B, 66C, 66D, 66E, 66F:
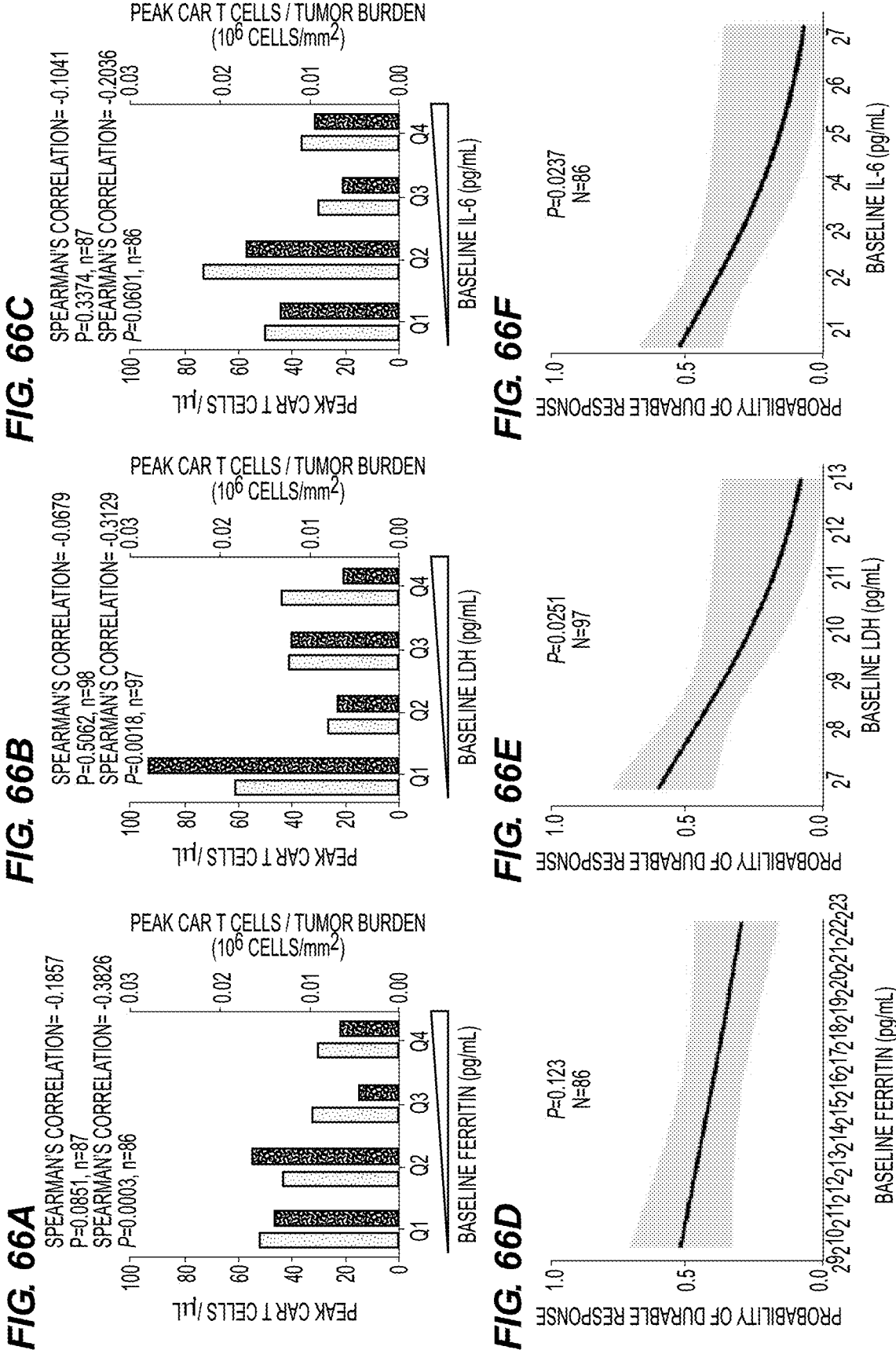
FIGS. 66A-66F: Baseline systemic inflammation is negatively associated with both CAR T-cell expansion relative to pretreatment tumor burden and the rate of durable responses.
Figures 67A, 67B, 67C:
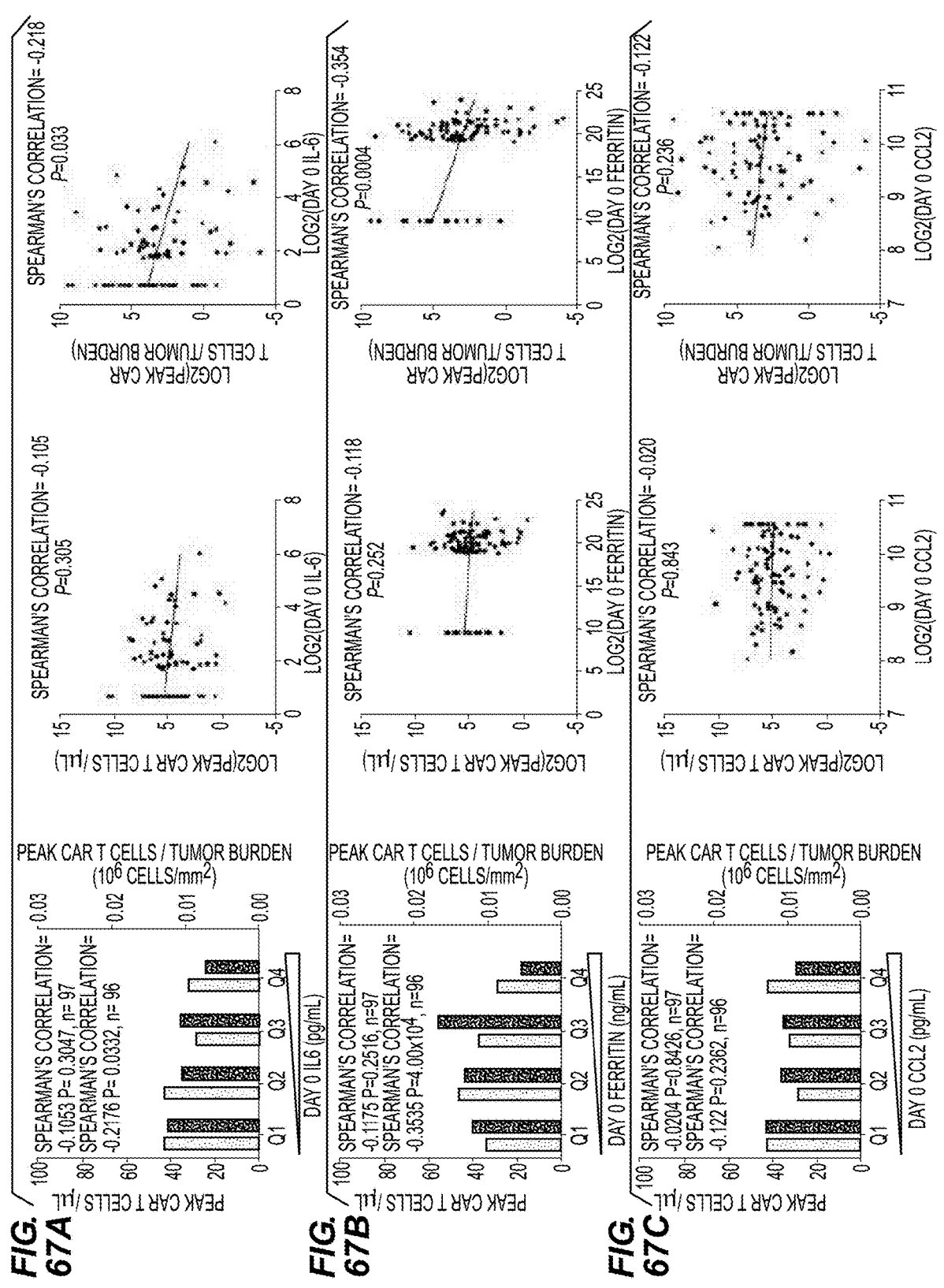
FIGS. 67A-67F: Association of Day 0 and Day 1 IL-6, ferritin, and CCL2 with in vivo CAR T-cell expansion. Bar charts show medians per quartile. Spearman's correlation was used to calculate r and P values. CAR, chimeric antigen receptor; CCL2, chemokine (C-C motif) ligand 2; IL, interleukin.
Figures 67D, 67E, 67F:
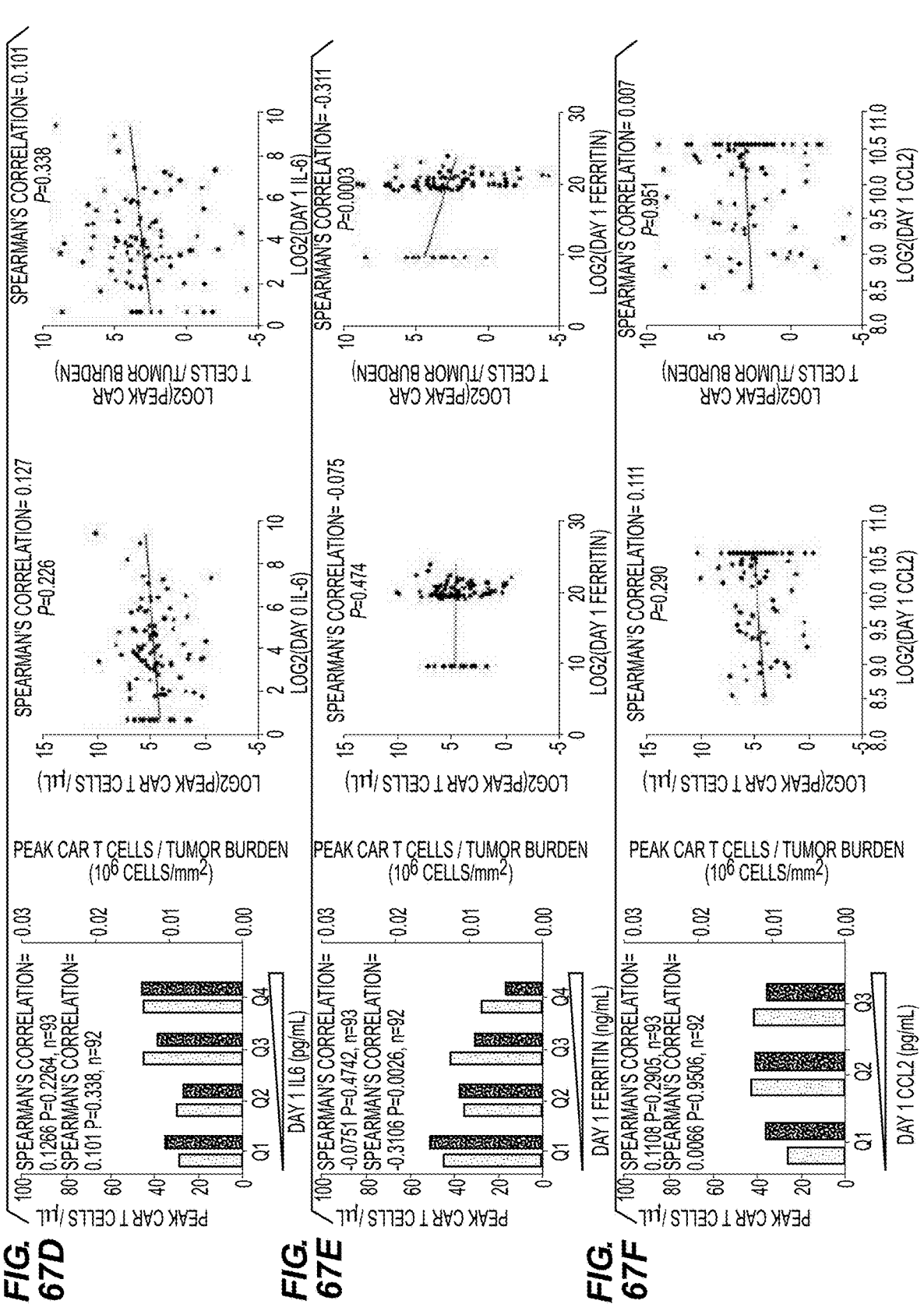
Figures 68A, 68B, 68C:
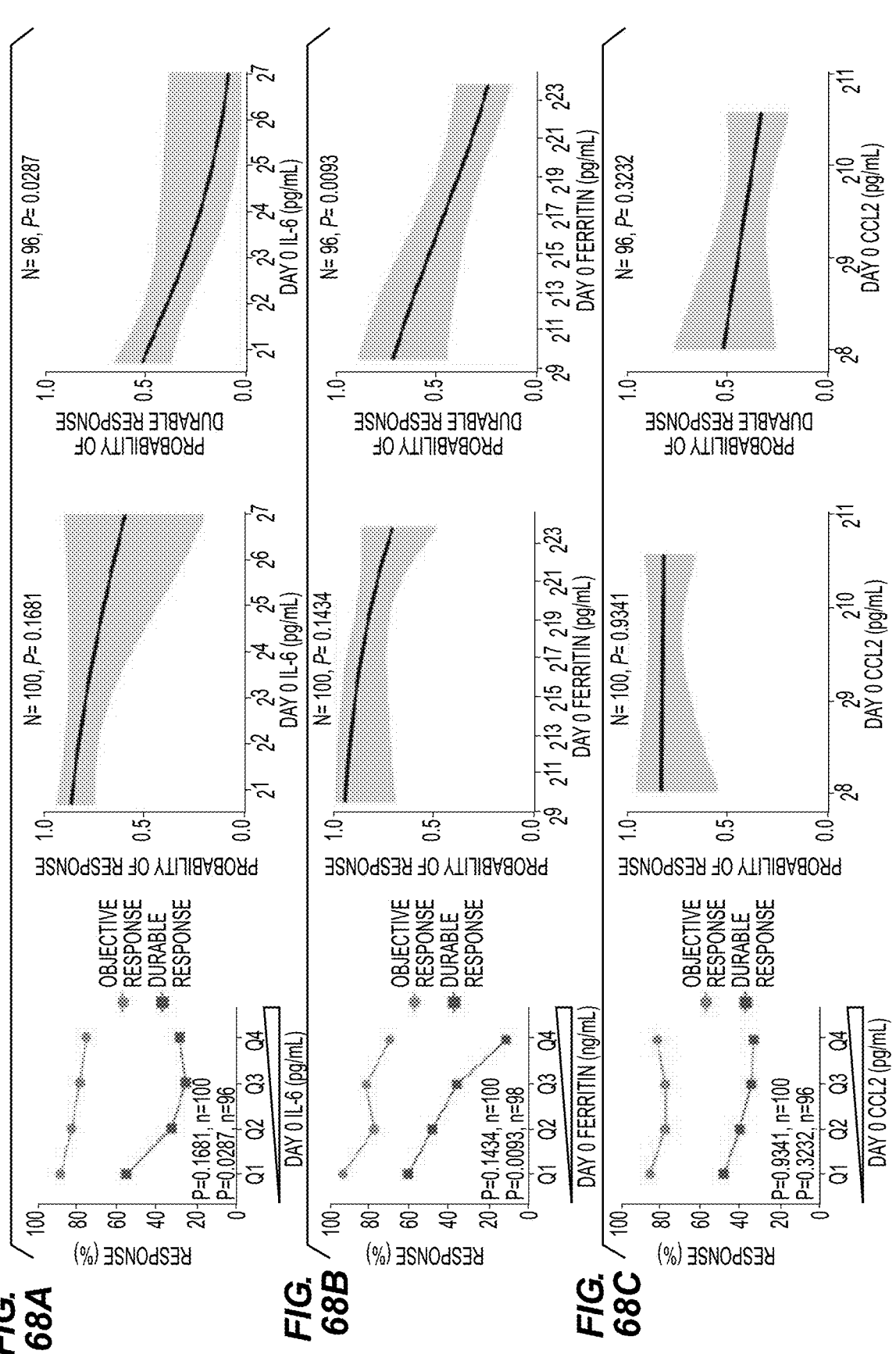
FIGS. 68A-68F: Quartile and logistic regression analyses show associations of Day 0 and Day 1 IL-6, ferritin, and CCL2 with objective and durable response. Line graphs show medians per quartile. All P values were calculated using logistic regression. CAR, chimeric antigen receptor; CCL2, chemokine (C-C motif) ligand 2; IL, interleukin; Q, quartile.
Figures 68D, 68E, 68F:
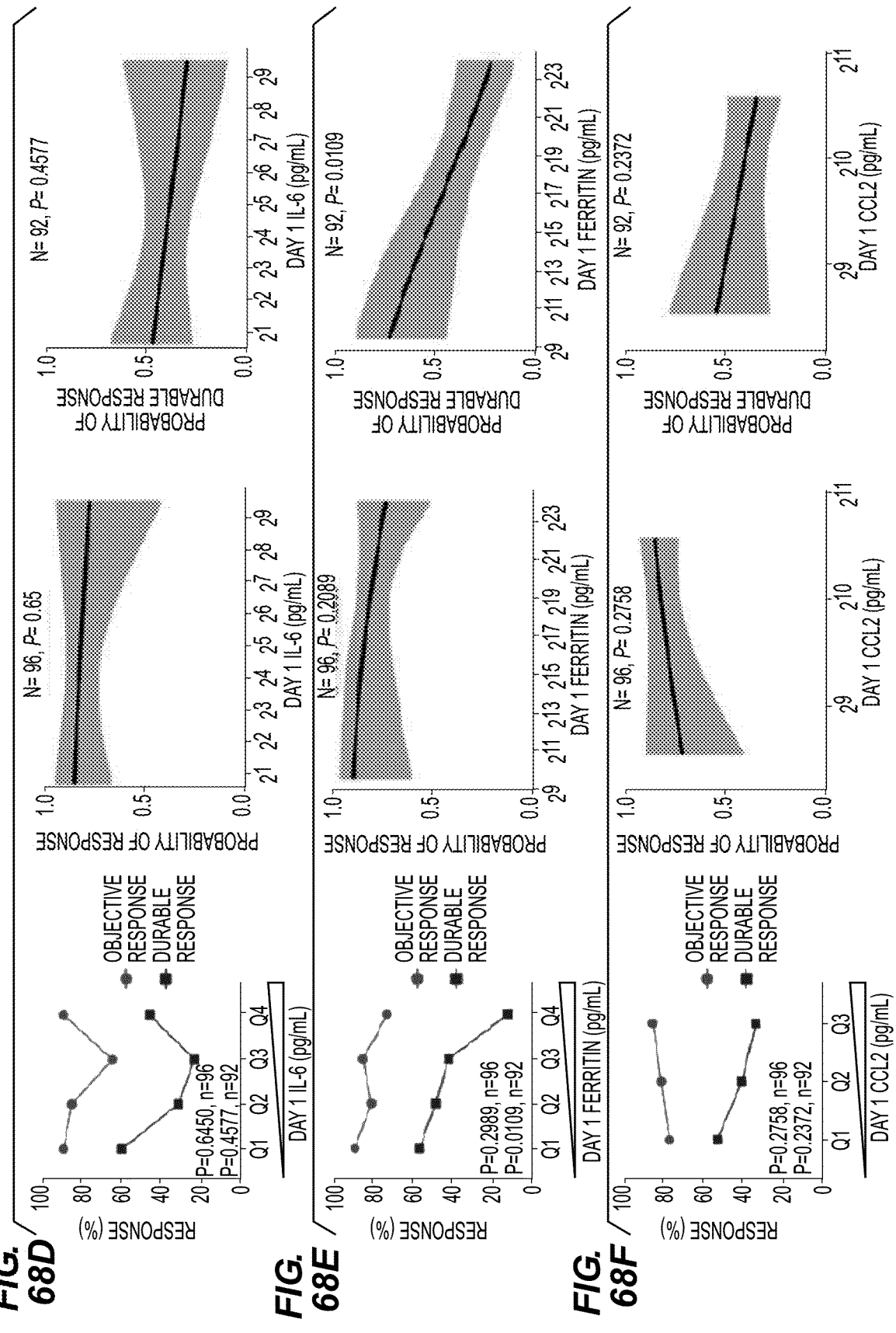

Pretreatment ferritin, LDH, and IL-6 were not associated directly with in vivo CAR T-cell expansion; however, ferritin and LDH, but not IL-6, were significantly (P<0.01) but modestly (R<-0.3) associated with lower CAR T-cell expansion normalized to pretreatment TB (peak CAR T-cell expansion/TB; FIG. 2A-2C). Pretreatment elevation of LDH and IL-6, but not ferritin, were associated with decreased durable response rates while only baseline IL-6 was associated with decreased objective response (FIGS. 66D-66F; FIGS. 65B-65G). Similar associations were seen when day 0 or day 1 levels of ferritin and IL-6 were evaluated (FIGS. 67A-67F and FIGS. 68A-68F; Table 31).

TABLE 31

Response rates, pairwise comparisons, and overall significance
of specified analytes at baseline, on Day 0, and on Day 1.

| Analyte,<br><br>n \| median<br>(Q1 – Q3) | Response Category | | | P Values from Dunn's Test | | | P Value<br><br>from<br>KW Test |
|---|---|---|---|---|---|---|---|
| | Durable<br>Response | Relapsed | No Response | Durable vs<br>Relapsed | Durable vs<br>No Response | Relapsed vs<br>No Response | |
| Baseline<br>IL-6, pg/mL | 35 \| 1.6<br>(1.6-4.53) | 35 \| 4.1<br>(1.6-6.7) | 16 \| 7.48<br>(4.7-16.7) | 0.0242 | 5.00E-04 | 0.0421 | 0.0013 |
| Day 0<br>IL-6, pg/mL | 39 \| 1.6<br>(1.6-4.6) | 40 \| 3.65<br>(1.6-6.765) | 17 \| 3.8<br>(1.6-15.14) | 0.0505 | 0.0378 | 0.2337 | 0.0411 |
| Day 1<br>IL-6, pg/mL | 38 \| 13.235<br>(4.4-42.8) | 39 \| 14.85<br>(9.39-46.69) | 15 \| 18.17<br>(11-31.01) | 0.5421 | 0.3663 | 0.4122 | 0.5498 |
| Baseline<br>ferritin, mg/L | 35 \| 567.2<br>(LLOQ-1174.8) | 35 \| 0.9<br>(LLOQ-1464.1) | 16 \| 1000.3<br>(611.2-2348.6) | 0.1359 | 0.0461 | 0.1971 | 0.0936 |
| Day 0<br>ferritin, mg/L | 39 \| 737.9<br>(LLOQ-1185.1) | 40 \| 1439.0<br>(658.3-2514.3) | 17 \| 1116.6<br>(760.5-2854.8) | 0.0043 | 0.0052 | 0.3132 | 0.0024 |
| Day 1<br>ferritin, mg/L | 38 \| 773.2<br>(542.1-1040.4) | 39 \| 1412.0<br>(798.2-2430.5) | 15 \| 1169.6<br>(773.1-3240.9) | 0.0044 | 0.015 | 0.4166 | 0.0045 |
| Baseline<br>CCL2, pg/mL | 35 \| 314.6<br>(277.3-426.0) | 35 \| 356.5<br>(293.7-445.6) | 16 \| 331.52<br>(265.1-370.5) | 0.3334 | 0.4941 | 0.341 | 0.4168 |
| Day 0<br>CCL2, pg/mL | 39 \| 766.5<br>(534.5-1274.8) | 40 \| 929.65<br>(622.1-1346.9) | 17 \| 904<br>(644.8-1282.2) | 0.4975 | 0.617 | 0.4003 | 0.619 |
| Day 1<br>CCL2, pg/mL | 38 \| 1292.85<br>(691.85-1500) | 39 \| 1500<br>(1086.6-1500) | 15 \| 1132.27<br>(599.2-1500) | 0.1014 | 0.4137 | 0.1118 | 0.116 |
| Baseline LDH,<br>pg/mL | 40 \| 239.5<br>(184-578) | 40 \| 367<br>(254-607.5) | 17 \| 537<br>(454-977) | 0.0239 | 0.0053 | 0.1207 | 0.0067 |
| Day 0<br>LDH, pg/mL | 35 \| 226<br>(178-609) | 36 \| 288.5<br>(204.5-465.5) | 17 \| 372<br>(205-617) | 0.5141 | 0.3822 | 0.4552 | 0.5529 |
| Day 1<br>LDH, pg/mL | 35 \| 202<br>(154-518) | 39 \| 272<br>(198-403) | 17 \| 340<br>(254-520) | 0.2154 | 0.1811 | 0.2789 | 0.2423 |

Figure 69:
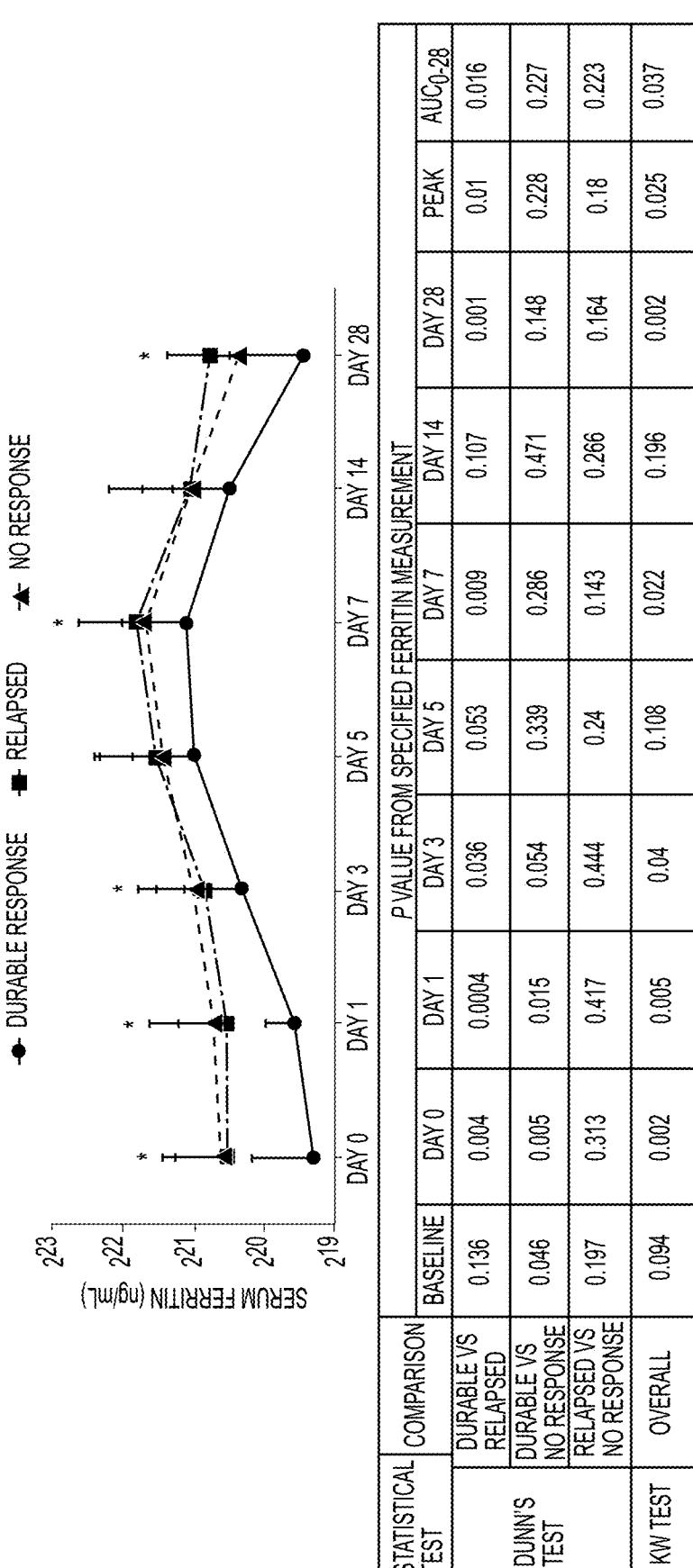
FIG. 69: Association between response group and ferritin over time. Symbols represent median serum ferritin levels for the specified population and bars represent interquartile range. Samples were available for 35-40 (each durable responders or relapsed) or 12-17 (no response) patients at each timepoint. AUC, area under the curve from Day 0 to 28; KW, Kruskal-Wallis. *, P<0.05.

Additionally, there was a weak but significant association between ferritin levels over the first 28 days, and peak CAR T-cell levels normalized to TB (R=−0.2236; P=0.0277). Significantly higher levels of serum ferritin were observed at most time points after CAR T-cell infusion in patients who relapsed or had no response compared with those who had durable responses (FIG. 69). These data show that pretreatment TB and systemic inflammation were both negatively associated with the rate of durable responses and that this effect was largely mediated by decreased CAR T-cell expansion relative to the pretreatment TB.

Product T-Cell Fitness and Dose of CD8 and CCR7+CD45RA+ T Cells Associated with Response Key CAR T-cell product characteristics associated with improved in vivo expansion and tumor responses were determined. The intrinsic ability of the entire product T-cell population, including CAR T-cells, to expand during non-specific stimulation in vitro (ie, anti-CD3 antibodies in the presence of IL-2 during manufacturing) was characterized by the culture DT. Product characteristics were evaluated for association with responses and it was found that low DT was the product characteristic most significantly associated with objective response as compared to nonresponse (FIG. 70).

The median DT in responders versus nonresponders was 1.6 vs 2.1 day (P=0.0067), and high DT was associated with a lower response rate (FIG. 71A; FIG. 72A). DT itself was not associated with durable response, however there was a correlation between product DT and expansion of CART cells in vivo after infusion (FIGS. 71B-71C; FIGS. 72A72-B). This was mirrored by a similar negative association between DT and peak CAR T cells normalized to TB, as well as between DT and CAR T-cell AUC (FIGS. 71C-71D; FIG. 72C).

Relative to other product characteristics, DT most strongly associated with the frequency of T-cell differentiation subsets in the final infusion bag. Specifically, DT positively associated with the frequency of CCR7− CD45RA− T cells (T_{EM}-like) (R=0.4341, P<0.0001) and negatively associated with the frequency of CCR7+ CD45RA+ T cells (T_{naive-like}) (R=−0.3837, P=0.0004; FIG. 71E-3H). DT was not associated with CD4:CD8 ratio (FIG. 71I). Together these results suggest that intrinsic product T-cell fitness, as measured by the product DT, is positively associated with a more differentiated product and influences the ability of CAR T cells to expand in vivo to a sufficient effector-to-target ratio that supports tumor eradication.

Figures 73A, 73B, 73C, 73D, 73E, 73F:
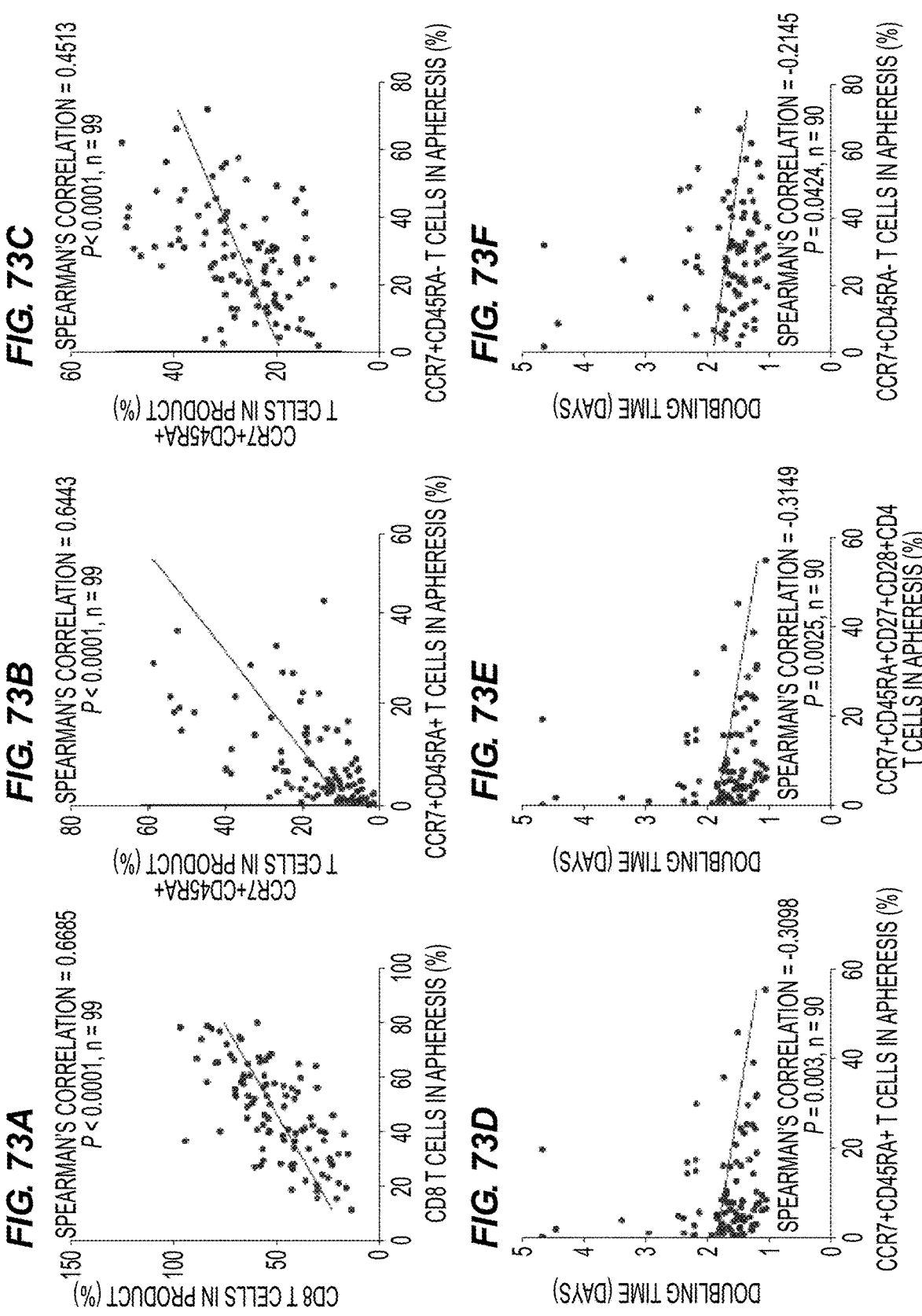
Figure 73H:
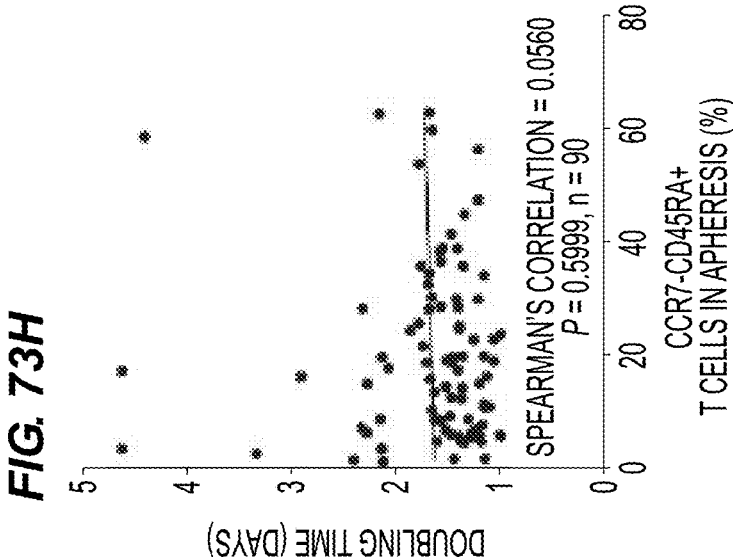
Figure 73G:
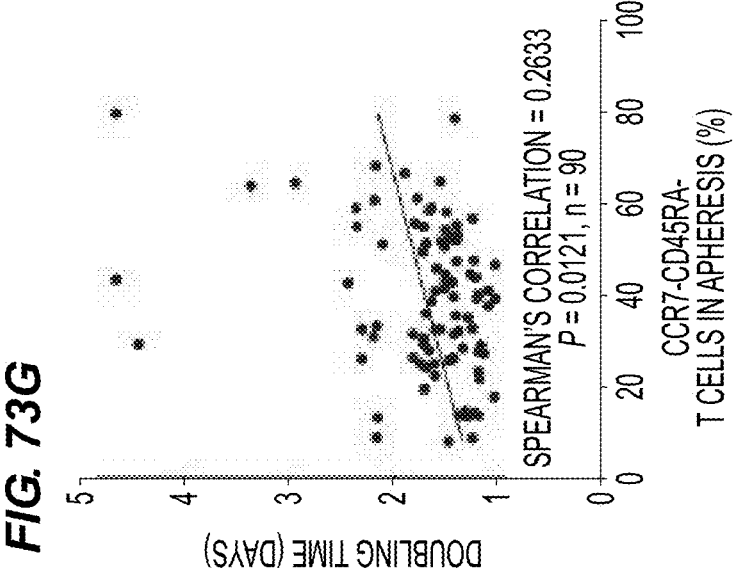
Figures 75A, 75B, 75C, 75D, 75E:
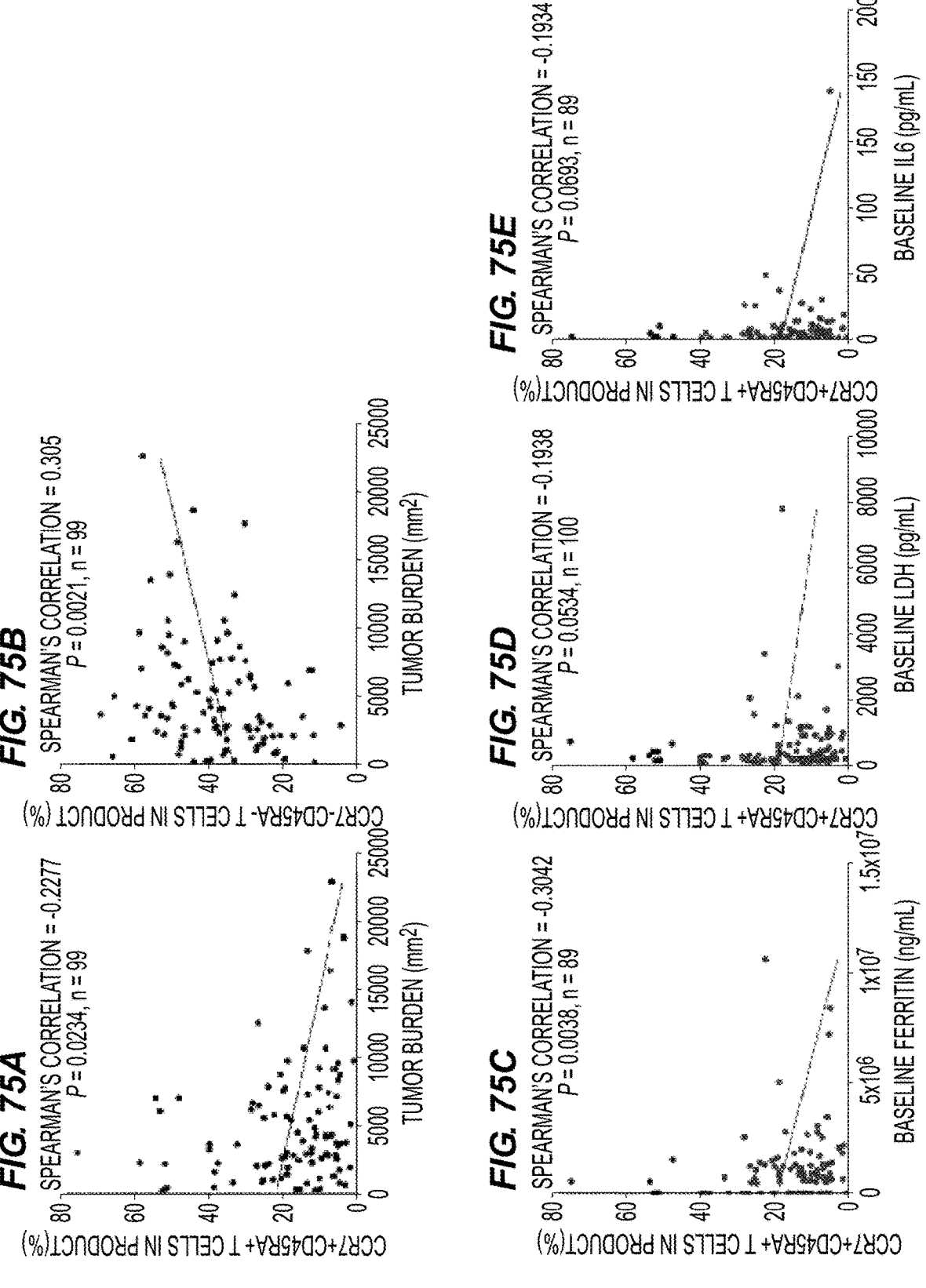
Figures 78A, 78B, 78C:
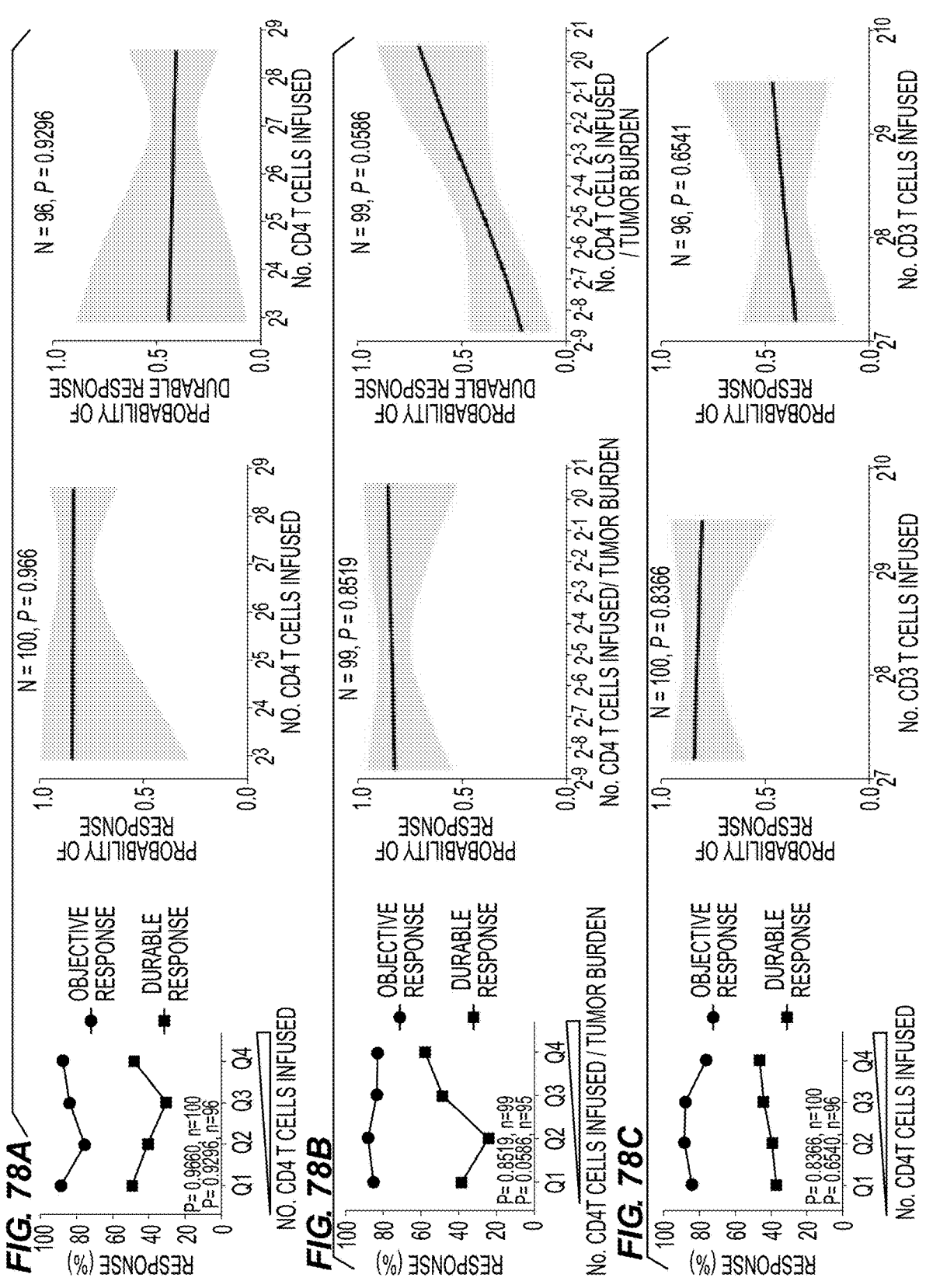
Figures 78D, 78E:
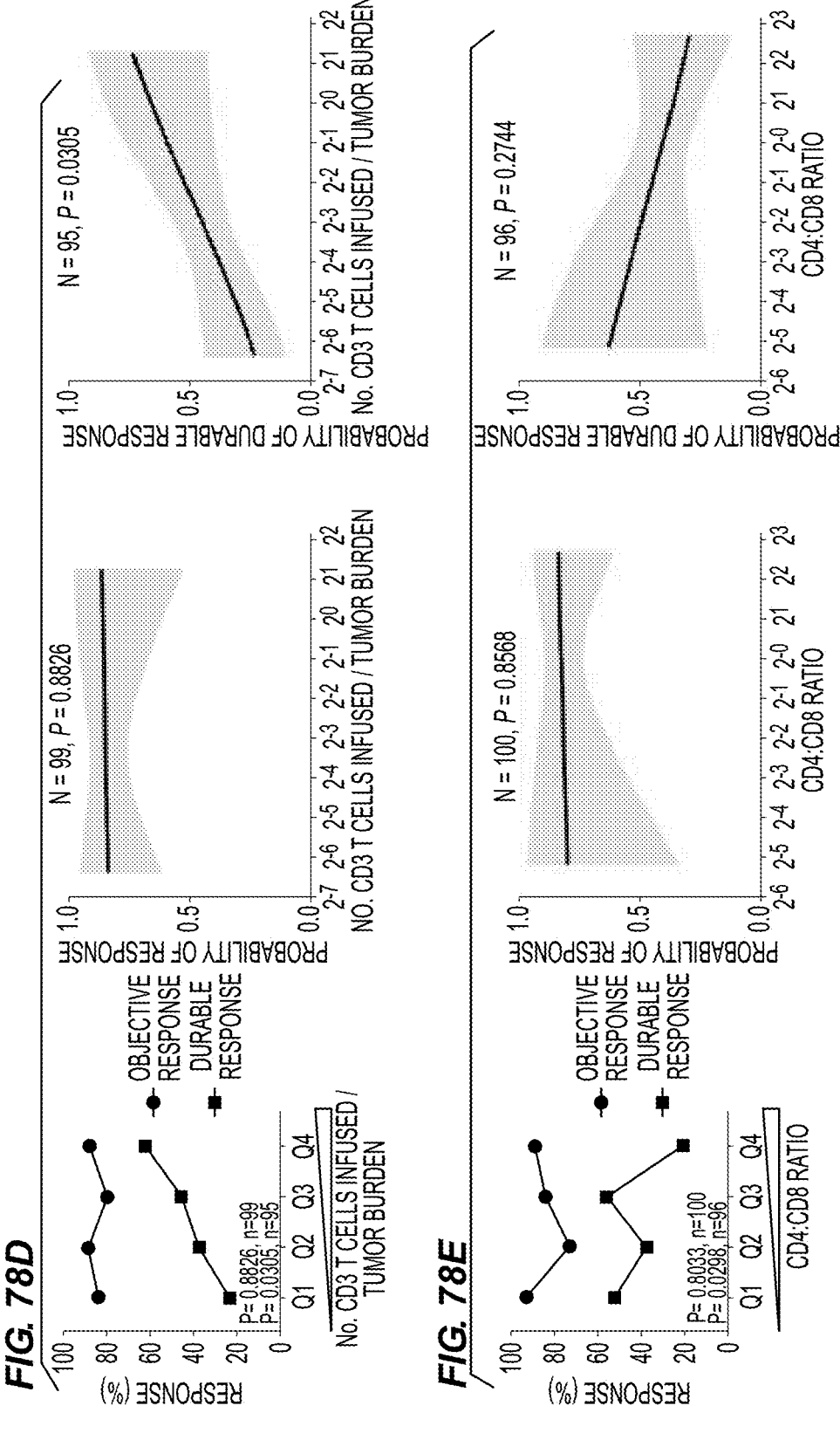
Figures 79A, 79B, 79C:
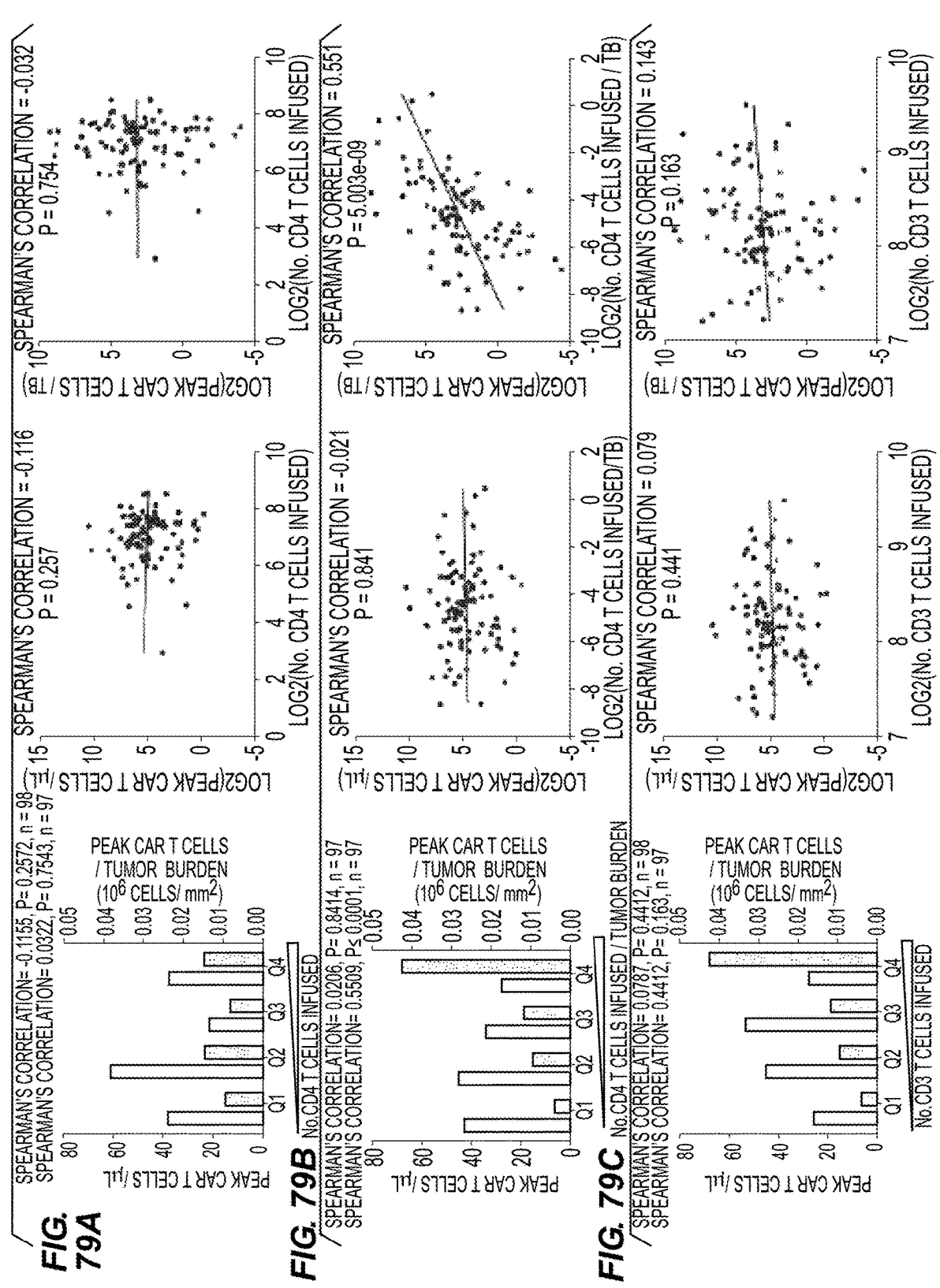
Figures 79D, 79E:
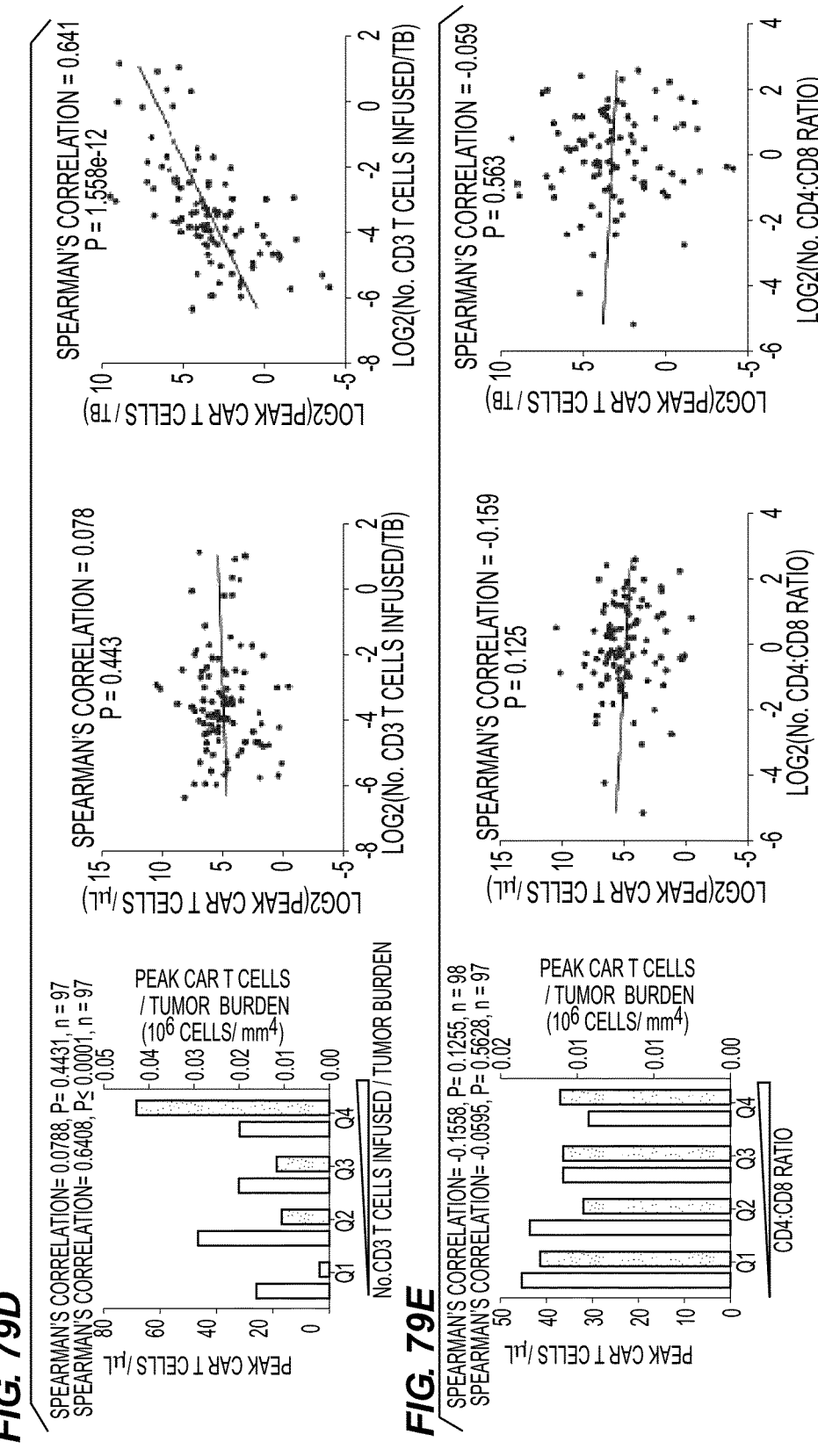
Figures 81A, 81B, 81C, 81D:
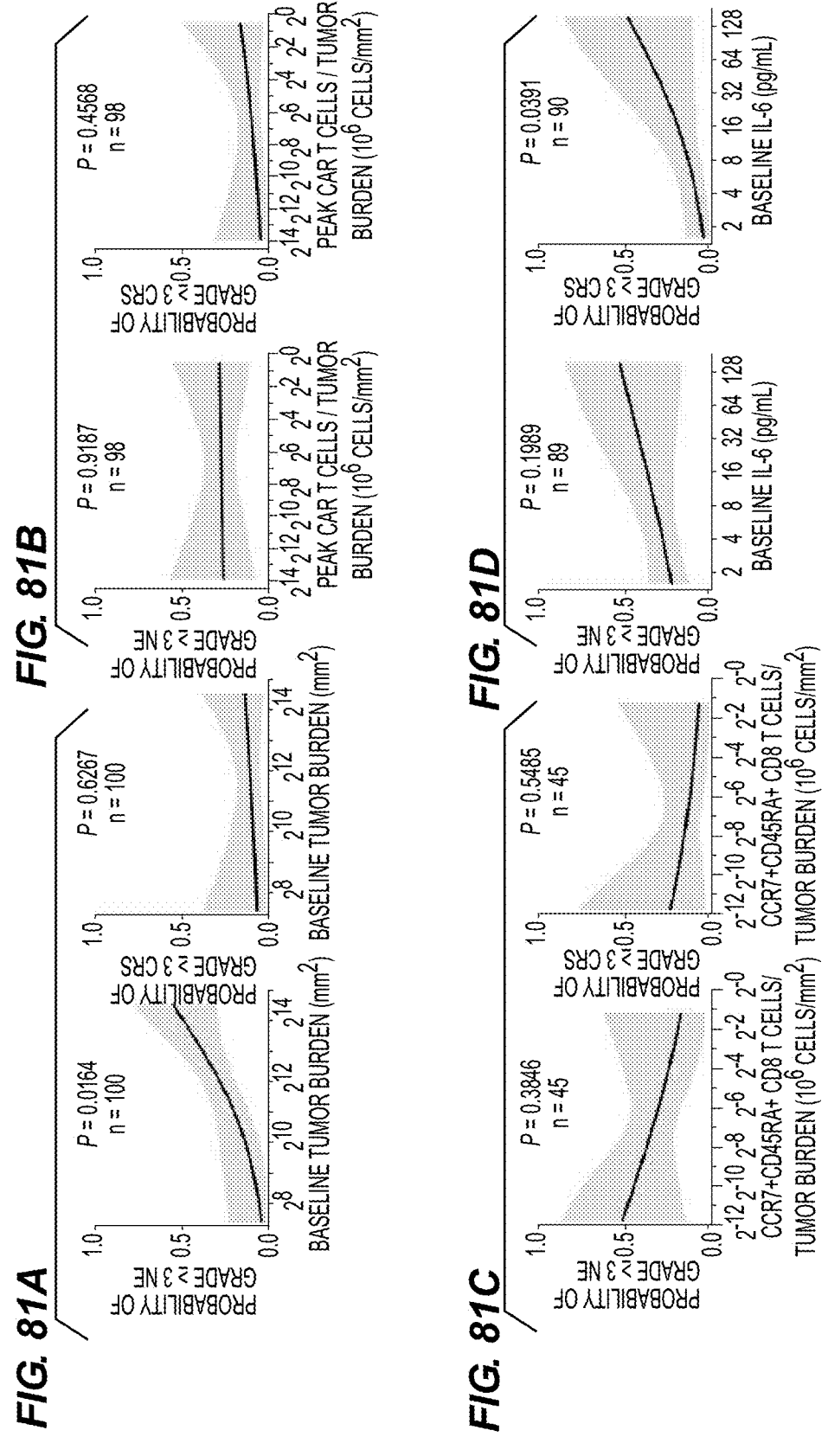
Figures 81E, 81F, 81G, 81H:
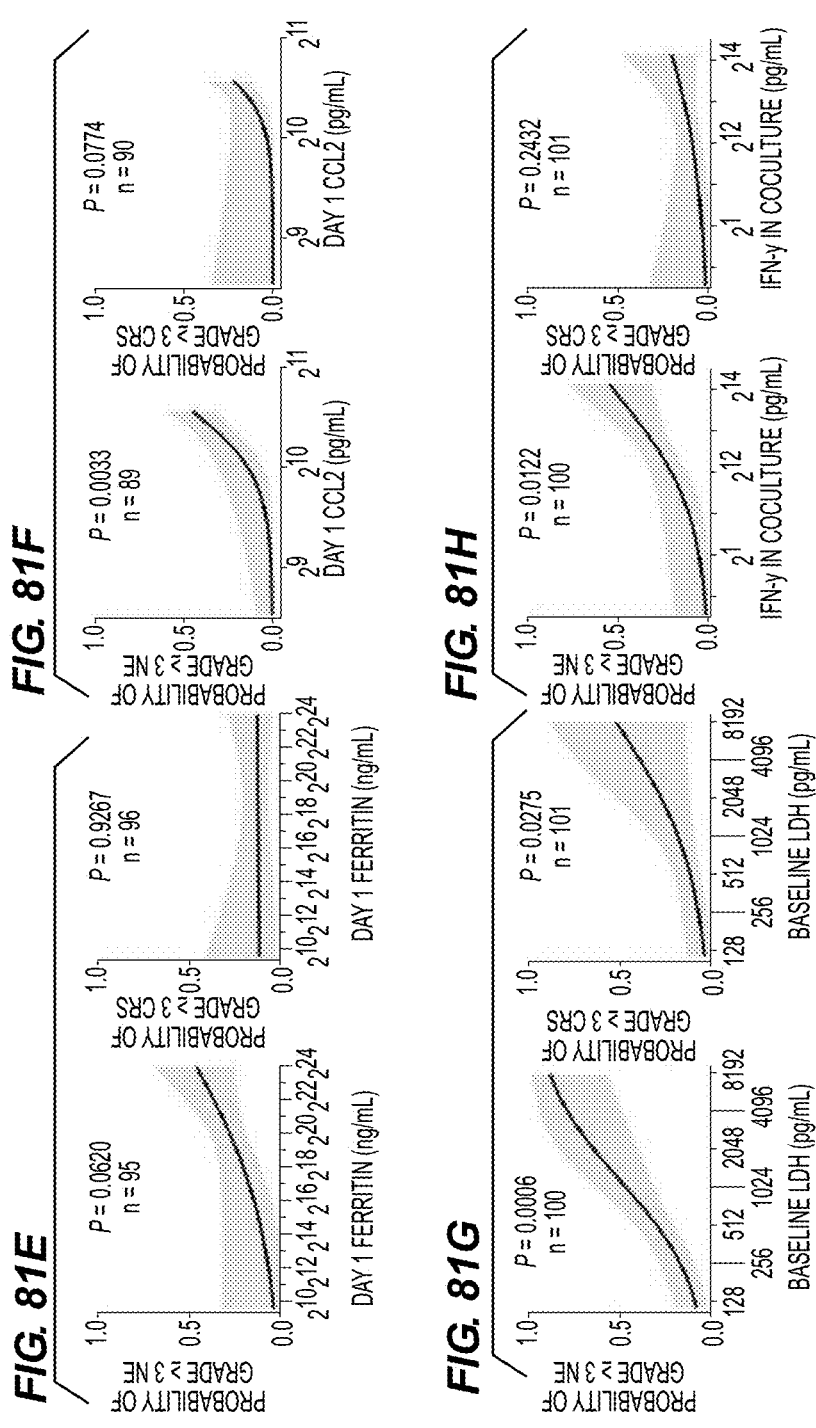

It was hypothesized that manufacturing DT, and product T-cell fitness in general, may be a direct result of the differentiation state of patients' T cells prior to enrollment. Apheresis T-cell phenotypes were directly associated with the final product phenotype (FIGS. 73A-73C). The phenotype of T cells in the apheresis product associated with DT: greater proportions of CCR7+CD45RA+ T cells consistently associated negatively with product DT (FIGS. 73D-73H; FIGS. 74A-74J). It was additionally found that TB and baseline ferritin were significantly associated with the differentiation phenotype of the final product (FIG. 75). Altogether, these findings connect product composition and clinical performance to the pretreatment immune status of the patient.

To look at the association of product characteristics beyond DT with durable response, the number of infused specialized T-cell subsets was assessed. The total number of infused CD8 T cells was not statistically associated with response or peak CAR T-cell levels (FIGS. 76A-76C; FIGS. 77A-77C). Incorporating effector-to-target ratio, the number of infused CD8 T cells normalized to TB was strongly associated with durable response and expansion of CAR T cells (FIGS. 76D-76F; FIGS. 77D-77F), and patients in the lowest quartile showed a durable response rate of 16% versus 58% in the top (FIG. 77D). This suggests that higher numbers of product CD8 T cells are needed to establish durable responses in patients with higher TB. Indeed, in patients with high TB, but not low TB, those who achieved durable responses showed a significantly higher number of infused CD8 T cells compared with patients who responded and then relapsed (FIG. 76G).

In addition, the number of infused CCR7+CD45RA+ T cells associated with objective responses and peak CAR T-cell levels (FIGS. 76H-76J; FIGS. 77G-77I), and a significant association with durable response emerged when normalized to TB, (FIGS. 76K-76M; FIGS. 77J-77L). In contrast, the number of infused cells of other subsets were not associated with peak CAR T-cell levels (FIGS. 78A-78D; FIGS. 79A-79D; Table 32). Notably the CD4:CD8 ratio did not associate with peak CAR T-cell levels but was associated with durable response (FIGS. 76N-76P).

TABLE 32

Association between product phenotypes and ongoing response or peak CAR T-cell levels.

| Parameter | Association With Durable Response | | Association With Peak CAR T-cell Levels | |
|---|---|---|---|---|
| | P value | Direction of association | P value | Direction of association |
| CD3 infused (%) | 0.2018 | NS | 0.762 | NS |
| Number of CD3 infused | 0.654 | NS | 0.441 | NS |
| Number of CD3 infused/tumor burden | 0.030 | Positive | 0.443 | NS |
| CCR7+CD45RA+ T cells infused (%) | 0.2161 | NS | 0.099 | NS |
| Number of CCR7+ CD45RA+ T cells infused | 0.182 | NS | 0.091 | NS |
| Number of CCR7+ CD45RA+ T cells infused/tumor burden | 0.025 | Positive | 0.114 | NS |
| % CD8 infused | 0.0709 | NS | 0.126 | NS |
| Number of CD8 | 0.116 | NS | 0.154 | NS |
| Number of CD8 infused/tumor burden | 0.009 | Positive | 0.273 | NS |
| CD4 infused (%) | 0.6792 | NS | 0.124 | NS |
| Number of CD4 infused | 0.930 | NS | 0.257 | NS |
| Number of CD4 infused/tumor burden | 0.059 | NS | 0.841 | NS |

P values are from LOG2 transformation of analyte; P values were calculated using logistic regression for durable response and by Spearman correlation for CAR T-cell levels. Abbreviations: NS, not significant.

Based on these findings, it was hypothesized that the CCR7+CD45RA+subset of CD8 product T cells were most responsible for achieving durable response. A detailed subset analysis was done in all patients with evaluable product samples (n=45 patients) and it was found that among CD8 T cells, the number of CCR7+CD45RA+ T cells were most significantly associated with durable response (Table 33; FIGS. 80A-80P).

TABLE 33

Association between product phenotypes and durable response. P values were calculated using logistic regression.

| Product CD8 T-cell phenotypes | P value | Direction of association |
|---|---|---|
| CCR7+CD45RA+, n | 0.048 | Positive |
| CCR7+CD45RA-, n | 0.22 | NS |

TABLE 33-continued

Association between product phenotypes and durable response. P values were calculated using logistic regression.

| Product CD8 T-cell phenotypes | P value | Direction of association |
|---|---|---|
| CCR7-CD45RA-, n | 0.82 | NS |
| CCR7-CD45RA+, n | 0.28 | NS |
| CCR7+CD45RA+ (%) | 0.06 | NS |
| CCR7+CD45RA- (%) | 0.32 | NS |
| CCR7-CD45RA- (%) | 0.49 | NS |
| CCR7-CD45RA+ (%) | 0.95 | NS |
| Product CD4 T-cell phenotypes | | |
| CCR7+CD45RA+, n | 0.77 | NS |
| CCR7+CD45RA-, n | 0.85 | NS |
| CCR7-CD45RA-, n | 0.043 | Negative |
| CCR7-CD45RA+, n | 0.07 | NS |
| CCR7+CD45RA+ (%) | 0.4833 | NS |
| CCR7+CD45RA- (%) | 0.7254 | NS |
| CCR7-CD45RA- (%) | 0.0114 | Negative |
| CCR7-CD45RA+ (%) | 0.0198 | Negative |

P values are from LOG2 transformation of analyte. P values were calculated using logistic regression.
Abbreviations: NS, not significant.

Figures 83A, 83B, 83C, 83D, 83E, 83F, 83G:
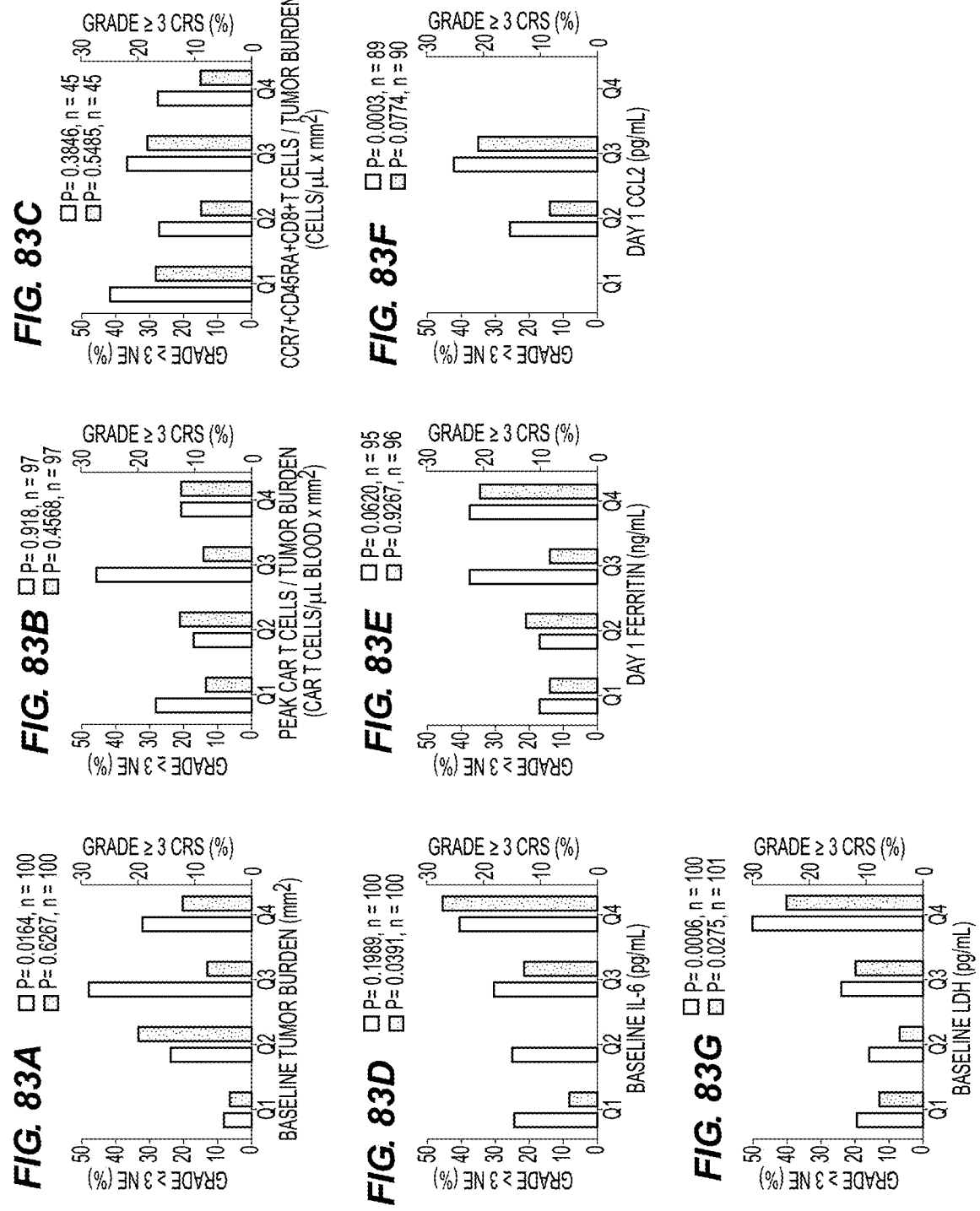

Product T-Cell Attributes, TB, Host Inflammatory Markers, and Treatment-Related Type-1 T-Cell Activity Differentially Associated with Efficacy and Toxicities Patient- and product-related markers were examined for their associations with severe toxicities to define actionable targets and approaches to improve the risk:benefit profile of axicabtagene ciloleucel. Higher peak CAR T-cell expansion and baseline TB were associated with grade ≥3 neurologic events but not grade ≥3 CRS (FIGS. 81A-81H; FIG. 82A; FIG. 83A). However, there was no significant association between peak CAR T-cell expansion and B-cell aplasia, a known on-target toxicity of anti-CD19 CAR T-cell intervention (FIG. 84). Several parameters, including CAR T-cell levels normalized to either pretreatment TB or body weight associated, DT, CD8 T cells or CCR7+CD45RA+ CD8 T cells normalized to TB, while associated with efficacy, they were not associated with severe toxicities (FIGS. 81B-81C; FIGS. 82B-82D, FIGS. 83B-83C). Elevated pretreatment or posttreatment pro-inflammatory, myeloid-related cytokines, including IL-6, ferritin, CCL2, as well as LDH, were positively associated with grade ≥3 NE or CRS (FIGS. 81D-81G; FIGS. 85A-85D).

Key features were evaluated by the number of prior lines of therapy. TB, markers of baseline inflammation, and DT increased with increasing lines of therapy, while the proportion and absolute numbers of CCR7+CD45RA+ cells decreased (Table 34). These findings support the observation that efficacy decreases and toxicity increases with increasing lines of prior therapy.

TABLE 34

Product and baseline characteristics by prior line of therapy.

| | Prior Lines of Therapy Before Enrollment on ZUMA-1 | | | |
|---|---|---|---|---|
| n Median (range) | 1-2 (n = 31) | 3 (n = 29) | 4 (n = 29) | ≥5 (n = 12) |
| Tumor Burden at Baseline, SPD | 31 3014 | 29 3355 | 28 4310 | 12 4448 |

TABLE 34-continued

Product and baseline characteristics by prior line of therapy.

| | Prior Lines of Therapy Before Enrollment on ZUMA-1 | | | |
|---|---|---|---|---|
| n Median (range) | 1-2 (n = 31) | 3 (n = 29) | 4 (n = 29) | ≥5 (n = 12) |
| | (180-12,795) | (171-19,201) | (268-23,297) | (310-14,354) |
| Ferritin at Baseline (mg/L) | 27 | 25 | 27 | 11 |
| | 567.2 | 776.8 | 1038 | 1174.8 |
| | (LLOQ-2752.2) | (LLOQ-5016) | (LLOQ-10576.1) | (LLOQ-8795.1) |
| LDH at Baseline (U/L) | 31 | 29 | 29 | 12 |
| | 329 | 331 | 320 | 866 |
| | (148-2105) | (153-2165) | (150-7802) | (116-3062) |
| Doubling time (days) | 28 | 26 | 25 | 12 |
| | 1.42 | 1.51 | 1.7 | 1.68 |
| | (1.04-3.37) | (1.11-2.37) | (1.11-4.67) | (1.26-4.67) |
| Transduction rate (%) | 31 | 29 | 29 | 12 |
| | 59.5 | 52 | 50.4 | 53.7 |
| | (22.4-85.1) | (25.5-72.4) | (34.2-76.4) | (21.6-67) |
| CCR7+ T cells (%) | 31 | 29 | 29 | 11 |
| | 48 | 42.4 | 42.1 | 37.4 |
| | (25.7-85) | (16.7-82.7) | (17.6-71.6) | (14.9-60.6) |
| CCR7+CD45RA+ T Cells in product (%) | 31 | 29 | 29 | 11 |
| | 19.3 | 12.6 | 11.4 | 9.1 |
| | (4.9-76) | (3.4-52.8) | (1-52.2) | (1.6-38.9) |
| CCR7+CD45RA+ Cells in product bag (×10$^6$ cells) | 31 | 29 | 29 | 11 |
| | 54.8 | 36.0 | 31.5 | 22.1 |
| | (10.6-215.0) | (11.3-158.0) | (2.1-200.6) | (5.5-110.1) |

Abbreviations: LDH, lactate dehydrogenase; LLOQ, lower limit of quantification; SPD, sum of product diameters.

Other routinely measured product attributes were systematically analyzed for their differential association with efficacy and toxicity. Notably, IFN-γ secretion of the final product after co-culture with CD19-expressing targets positively associated with grade ≥3 NE but not efficacy or grade ≥3 CRS in ZUMA-1 (FIG. 81H; FIG. 82F). There was a weak, direct association between product co-culture IFN-γ and the proportion of differentiated CCR7-negative T cells in the infusion bag and product DT (FIG. 86). Further, serum levels of IFN-γ, CXCL10, and IL-15, measured early post-treatment, also associated positively with grade ≥3 neurologic events but were not associated with durable response (FIGS. 87A-87C). We also found that day 0 IL-15 serum levels significantly associated release criteria were not associated with efficacy or toxicity (Table 35). Altogether, these findings point to product attributes and inflammatory biomarkers that associated differentially with efficacy and toxicities post-axicabtagene ciloleucel treatment.

TABLE 35

Product release criteria and association with outcomes.

| Variable | Subgroup | N | Median | Range | Wilcoxon/ KW test P-value |
|---|---|---|---|---|---|
| Viability, (%) | Grade 1-2 CRS | 89 | 94.3 | 83.5-97.4 | 0.7688 |
| | Grade ≥3 CRS | 12 | 94.8 | 87.8-97.1 | |
| | Grade 1-2 NEs | 72 | 94.25 | 83.5-97.4 | 0.4245 |
| | Grade ≥3 NEs | 28 | 94.75 | 83.7-97.1 | |
| | Ongoing Response | 40 | 94.6 | 85.2-97.1 | 0.5752 |

TABLE 35-continued

Product release criteria and association with outcomes.

| Variable | Subgroup | N | Median | Range | Wilcoxon/ KW test P-value |
|---|---|---|---|---|---|
| | Relapsed | 40 | 94.45 | 87.8-97.4 | |
| | Other | 17 | 93.6 | 83.5-97.3 | |
| | Responder | 84 | 94.5 | 84.7-97.4 | 0.3381 |
| | Nonresponder | 17 | 93.6 | 83.5-97.3 | |
| Transduction Rate (%) | Grade 1-2 CRS | 89 | 52.5 | 21.6-85.1 | 0.6746 |
| | Grade ≥3 CRS | 12 | 56.55 | 34.2-78.6 | |
| | Grade 1-2 NEs | 72 | 53.15 | 21.6-85.1 | 0.9053 |
| | Grade ≥3 NEs | 28 | 52.95 | 25.5-78.6 | |
| | Ongoing Response | 40 | 51.9 | 22.4-76.4 | 0.341 |
| | Relapsed | 40 | 60.1 | 25.5-85.1 | |
| | Other | 17 | 52.1 | 21.6-73.5 | |
| | Responder | 84 | 53.75 | 22.4-85.1 | 0.8631 |
| | Nonresponder | 17 | 52.1 | 21.6-73.5 | |
| Vector Copy Number | Grade 1-2 CRS | 85 | 2.08 | 0.72-4.59 | 0.2976 |
| | Grade ≥3 CRS | 12 | 1.67 | 0.46-4.33 | |
| | Grade 1-2 NEs | 68 | 1.99 | 0.64-4.59 | 0.7693 |
| | Grade ≥3 NEs | 28 | 1.79 | 0.46-4.33 | |
| | Ongoing Response | 39 | 1.79 | 0.46-4.59 | 0.4204 |
| | Relapsed | 39 | 1.92 | 0.48-4.33 | |
| | Other | 15 | 1.72 | 0.51-3.27 | |
| | Responder | 82 | 1.92 | 0.48-4.33 | 0.4586 |
| | Nonresponder | 15 | 2.04 | 0.46-4.59 | |

CRS, cytokine release syndrome; NEs, neurologic events.

Hierarchical clustering and random forest multivariable analysis were done to further evaluate the univariate analysis findings. Overall, random forest analysis confirmed the main findings by univariate analysis and pointed to several parameters that associate differentially with response and toxicities, namely baseline TB, IL-6, CRP, and LDH; day 0 IL-15; and coculture interferon-γ (FIGS. 88A-88E; FIGS. 90A-90B)]. These findings were supported by multivariate analysis evaluating covariates differentially associated with CAR T-cell expansion (FIGS. 90A-90B; FIGS. 89A-89C).

The above findings are consistent with the hypothesis that axicabtagene ciloleucel may act rapidly against LBCL tumors, through early activation and expansion of CAR T cells within 2 weeks post-treatment and driven by CCR7+ CD45RA+ T cells in the product infusion bag, with persisting CAR T cells not needed to achieve and maintain durable clinical response.

Higher numbers of CAR T cells in the peripheral blood associated with DT, underscoring the importance of intrinsic T-cell fitness independent of the CAR construct. Diminished product T-cell fitness (ie, high DT) associated with primary treatment resistance, as most nonresponding patients showed a product DT >1.6 days. The higher the frequency of CCR7+CD45RA+ T cells in the product infusion bag, the higher the product T-cell fitness, as frequency of CCR7+ CD45RA+ T cells negatively associated with DT. The majority of CCR7+CD45RA+ T cells in the axicabtagene ciloleucel product infusion bag are stem-like memory cells, not canonical naïve T cells. This aligns with the observation that the subpopulation that best associated with DT was CCR7+CD45RA+CD27+CD28+ T cells, as such specialized T-cell subsets have been previously described and linked with product T-cell performance. The findings additionally corroborate with preclinical data pointing to CCR7+ CD45RA+ cells as drivers of anti-tumor activity in context of T-cell intervention. That CCR7+CD45RA+ T cells from peripheral blood can differentiate in vitro into stem-like memory cells, both of which express CCR7 and CD45RA, provides a biological link for the observations here that CCR7+CD45RA+ T cells in both the apheresis material as well as in the product associate with DT and outcomes. Furthermore, rather than the total number of product T cells or CAR T cells, it was the total number of specialized T cells normalized to pretreatment TB that associated best with clinical efficacy. Additionally, the frequency of CCR7+ CD45RA− T cells in the product infusion bag associated inversely with DT, a result that is concordant with the view that this subset may drive T-cell product performance.

Besides product attributes linked to T-cell fitness and dose of specialized T cells, markers related to TB and inflammation, both of which may be influenced by the underlying tumor biology, were highly associated with clinical outcomes. Pretreatment serum levels of LDH and pro-inflammatory markers, including IL-6 and ferritin, were prominently and negatively associated with clinical efficacy, and were positively, but weakly, associated with TB. Concordantly, patients with low TB and diminished tissue hypoxia and inflammation markers showed a high durable response rate (>60%) and limited rate of inflammation-driven serious adverse events, namely CRS and neurotoxicity (<10%). Evidence of excessive activation and mobilization of myeloid cells in context of CAR T-cell therapy has been also generated in preclinical models. The univariate and multivariate analyses of patient data presented here indicate that tumor hypoxia and an enhanced pro-inflammatory state reminiscent of myeloid cell hyperactivity might inhibit the activation, expansion, and/or survival of CAR T cells within the tumor microenvironment, while simultaneously contributing to toxicities possibly through facilitating excess cytokine production.

Based on these findings, several strategies may increase efficacy without exacerbating the toxicity profile of axicabtagene ciloleucel: 1] systematic evaluation of bridging therapy agents, which were not allowed in ZUMA-1, to curb TB and inflammation pre-CAR T-cell infusion; 2] testing of agents that modulate effects on myeloid cells or low dose corticosteroids administered immediately pre- or post-CAR T-cell infusion; 3] optimization of CAR configuration to eliminate excess production of myeloid and type-1 molecules by the product cells; 4] dosing or process optimizations to increase both the percentage and number of product CCR7+CD45RA+ and CD8 T cells especially in context of bulky disease; and 5] improving T-cell fitness through optimizing product T-cell metabolism or combining with immune checkpoint modulators.

Achieving durable response may require CAR T-cell expansion within each patient that is commensurate with that patient's tumor burden, which may be attributable to the frequency of CCR7+CD45RA+CD8+ CAR T cells in the product infusion bag. Insufficient expansion in proportion to tumor burden may allow for minimal residual malignancy, above or below levels of detection, and lead to a PR or an apparent CR before relapse due to tumor outgrowth. Another mechanism of transient remission is ascribable to CD19-related evasion through selection of tumor cells that lack axicabtagene ciloleucel target, and ongoing studies indicate that this may occur in about 25-33% of the treated patients who have an objective response. This hypothesis also aligns with the observation that patient-related characteristics, as well as product characteristics, associate differentially with response and toxicities.

Methods for Example 21

Quantification of CART Cells:

CAR T cells were quantified using TaqMan quantitative PCR (qPCR; ThermoFisher Scientific) and confirmed by droplet digital PCR (Bio Rad) per manufacturer's instructions. Plaks V, Mojadid M, Salunkhe S, et al. *Molecular Therapy*. 2020; 28(4):abstr 54. This method has been previously utilized and reported extensively. Kochenderfer J N, Dudley M E, Feldman S A, et al. *Blood*. 2012; 119(12): 2709-2720; Kochenderfer J N, Dudley M E, Kassim S H, et al. J Clin Oncol. 2015; 33(6):540-54; Kochenderfer J N, Somerville R P, Lu T, et al. *Lancet Oncol*. 2019; 20(1):31-42; Neelapu S S, Locke F L, Bartlett N L, et al. *N Engl J Med*. 2017; 377(26):2531-2544.

For each patient, DNA was extracted from PBMC collected before treatment and at multiple time-points after treatment. DNA was extracted by using a DNeasy blood and tissue kit (Qiagen). DNA from each timepoint was amplified in duplicate with a primer and probe set that was specific for the anti-CD19 CAR. Similar to an approach used previously by other investigators (Kochenderfer J N, Dudley M E, Feldman S A, et al. Blood. 2012; 119(12):2709-2720), serial 1:5 dilutions of DNA from the infused T cells of each patient were prepared into pretreatment DNA prepared from leukocytes from the same patient, and standard curves were made by performing qPCR on this DNA. The percentage of the infused T cells that expressed the anti-CD19 CAR was determined by flow cytometry utilizing an antibody for the CAR construct. Arihara Y, Jacobsen C A A, P, Rossi J M, et al. Therapy of Cancer. 2019; 7(Suppl 1):P210; Sievers S A, Kelley K A, Astrow S H, Bot A, Wiltzius J J. Abstract 1204: Cancer Research. 2019; 79(13 Supplement):1204-1204. It was assumed that only infused T cells with surface CAR expression detected by flow cytometry contained the CAR gene. This assumption may underestimate the actual number of cells containing the CAR gene because all cells containing the CAR gene might not express the CAR protein on the cell surface. To estimate frequencies of CAR+ cells, cells per microliter were calculated by normalizing CAR gene expression to actin expression in peripheral blood mononuclear cells. The percentage of PBMC that contained the CAR gene at each time-point was estimated by comparing the qPCR results obtained with DNA of PBMC to the qPCR results obtained from each patient's infused T-cell standard curve. To estimate the number of CAR+ cell/μL of blood, the proportion of CAR+ cells in mononuclear cells was multiplied with the number of peripheral blood mononuclear cells/μL of blood.

Product Doubling Time

Product doubling time was calculated for the entire pre infusion product from day 3 of manufacturing through the end of manufacturing process. As previously described (Better M, et all. *Cell & Gene Therapy Insights*. 2018; 4(4):173-186) manufacturing was initiated by culturing in serum-free media with activating anti-CD3 antibody and recombinant human interleukin-2. Cells were transduced on day 2, and calculation of doubling time began at day 3. Cells were expanded in presence of IL-2, assessed for growth on day 6, and if insufficient, were given up to an additional 48 hours. Doubling time, which is related to the expansion rate, was calculated per the following formula:

$$\text{Doubling Time} = \frac{\ln(2) \times \text{duration}}{\ln\left(\frac{\text{Total viable cells at harvest}}{\text{Total viable cells at Day 3}}\right)}$$

The global product expansion rate measured through DT may reflect the result of two opposing processes—proliferation and apoptosis.

Study day 0: is defined as the day the patient received the first KTE-C19 infusion. The day prior to study day 0 will be study day –1. Any days after enrollment and prior to study day –1 will be sequential and negative integer-valued.

Durable response: refers to the patients who were in ongoing response at least by one year follow up post KTE-C19 infusion.

Relapse: refers to the patients who achieved a complete response (CR) or partial response (PR) and subsequently experienced disease progression.

Non-response: refers to the patients who had never experienced CR or PR post KTE-C19 infusion.

The expansion and persistence of anti-CD19 CAR T cells in peripheral blood will be monitored by qPCR analysis, using KTE C19-specific primers for the scFv portion of the CAR (heavy chain of FMC63) and its hinge/CD28 transmembrane domain. This qPCR assay has been qualified and validated at an external CRO in a regulated GLP environment.

Scheduled blood draw for anti-CD19 CAR T cell: before KTE-C19 infusion, Day 7, Week 2 (Day 14), Week 4 (Day 28), Month 3 (Day 90), Month 6 (Day 180), Month 12 (Day 360), and Month 24 (Day 720).

Peak of CART cell: is defined as the maximum absolute number of CAR+ PBMC/µL in serum attained after Day 0.

Time to Peak of CART cell: is defined as the number of days from Day 0 to the day when the peak of CAR T cell was attained.

Area Under Curve (AUC) of level of CART cell from Day 0 to Day 28: is defined as the area under the curve in a plot of levels of CART cells against scheduled visits from Day 0 to Day 28. This AUC measures the total levels of CART cells overtime Key Measurements of Cytokines:

Scheduled blood draw for cytokines: before or on the day of conditioning chemotherapy (Day –5), Day 0, Day 1, Day 3, Day 5, Day 7, every other day if any through hospitalization, Week 2 (Day 14), and Week 4 (Day 28).

Baseline of cytokines: is defined as the last value measured prior to conditioning chemotherapy.

Fold change from baseline at Day X: is defined as $$\frac{\text{Cytokine level at Day } X - \text{Baseline}}{\text{Baseline}}$$

Peak of cytokine post baseline: is defined as the maximum level of cytokine in serum attained after baseline (Day –5) up to Day 28.

Time to peak of cytokine post KTE-C19 infusion: is defined as the number of days from Day 0 to the day when the peak of cytokine was attained.

Area Under Curve (AUC) of cytokine levels from Day –5 to Day 28: is defined as the area under the curve in a plot of levels of cytokine against scheduled visits from Day –5 to Day 28. This AUC measures the total levels of cytokine overtime. Given the cytokine and CAR+ T cell are measured at certain discrete time points, the trapezoidal rule will be used to estimate the AUCs.

Statistical Methods of Analysis
Univariate Analysis:

The covariates were categorized mechanistically to examine the relationships between each covariate and clinical outcomes of interest. The following univariate analyses are performed:

Logistic regression
Wilcoxon rank sum test
Summary by quartiles of covariates
Pairwise correlation (ie, Spearman correlation)

A covariate is selected for further evaluations when any of the methods above demonstrate its significance or interest.
Logistic Regression Logistic regression, a parametric model, will be used to explore the relationship between the covariate and outcomes. It explains the question like "how does the probability of getting NE grade 3+ change for every unit increase in the covariate?", where the estimated odds ratio and p-value can assist the screening of covariate, for example, the ones with p-value <=0.05 can be considered as having meaningful relationship with outcome in positive or negative (depending on the estimated odds ratio >1 or <1) trend. The predictive curve based on the univariate logistic regression calculation provides the visualization of such trend.
Wilcoxon Rank Sum Test It is also called Mann-Whitney U test, which is to determine whether the covariates from outcome subgroups have the same distribution. It is non-parametric and can provide additional information about the relationship between covariate and outcomes.

Similarly, nominal p-values (i.e. without multiplicity control) of the Wilcoxon test are provided for screening, where the covariate with p-value <=0.05 is deemed as significant for further evaluation.

Kruskal-Wallis (KW) test is used if 3 or more subgroups are involved in the comparison. Following a KW test, Dunn's test will be applied on multiple pairwise comparisons.
Multivariate Analysis Several statistical and machine learning methods are used to build a more complicated multivariate model for the purpose of prediction on new data, examination of joint effect of different covariates on the outcomes, as well as relationships among covariates.
Random Forest Random forest has been a popular and efficient machine learning algorithm recently. It was first introduced by Breiman taking the advantages of aggregation, ensemble modeling ideas, designed for both classification and regression problems. Hothorn et al. further introduced conditional inference trees, which helped eliminate the selection bias existed in the traditional classification or regression tree.

In this analysis, the conditional inference tree based random forest, cforest, is applied to get variable importance and rank all the covariates. Due to the randomness existed in the resampling procedure such as cross validation, the variable importance from cforest vary from different random seeds. In order to eliminate this effect of randomness, Genuer et al. is followed to retrieve the variable importance from 50 different random seeds, i.e. 100, 200, 300, until 5000, and take the average as the final variable importance. The variables are then ranked from most important to least important based on the average importance. Conditional importance is used here as the measurement of variable importance from random forest. The idea is to calculate the mean decrease of accuracy in out-of-bag (OOB) sample with permutation within conditional covariate grid.

Genuer et al. also observed that the more important a variable is, the higher importance standard deviation it will have across different seeds. Noise variable is assumed to have zero average importance with a small standard deviation. A regression tree is built to predict the importance standard deviation across 50 random seeds. A further variable pre-elimination method is followed by removing variables with average importance lower than the lowest fitted value of the regression tree method.

Hierarchical Clustering

Principal component analysis (PCA) is a statistical procedure that uses an orthogonal transformation to convert a set of observations of possibly correlated variables into a set of values of linearly uncorrelated, orthogonal variables, i.e. principal components.

A PCA based hierarchical clustering method, proposed by Chavent et al., is applied to cluster all the variables. Starting with p clusters (p is the number of variables), each consist of a single variable, gradually combine two clusters at each step. The two clusters resulting in the lowest dissimilarity is combined at each step, until there is only one cluster left. Dissimilarity is defined as the difference between the sum of first eigenvalues of descendant clusters and the first eigenvalue of combined cluster. That is, each of the two variables clustered together should carry similar information as combined. Particularly, R package "ClustOfVar" is used to implement this method. With clustering the covariates, the relationships among covariates are explored. This can further help variable selection and redundancy elimination.

Example 22

As set forth in the previous Examples, axicabtagene ciloleucel is an autologous anti-CD19 CAR T cell therapy approved for the treatment of patients with relapsed/refractory large B cell lymphoma (LBCL) with ≥2 prior systemic therapies. ZUMA-1 is the multicenter, single-arm, registrational Phase ½ study of axicabtagene ciloleucel in patients with refractory LBCL. In a 2-year analysis of ZUMA-1 (median follow-up, 27.1 months; N=101), axicabtagene ciloleucel showed objective response, complete response (CR), and ongoing response rates of 83%, 58%, and 39%, respectively. This Example presents additional survival follow up and recovery of normal, polyclonal B cells from ongoing responders in ZUMA-1. Axicabtagene ciloleucel produced rapid responses and long-term disease control in patients with refractory LBCL. Most responses occurred by the first assessment, and the brief time elapsed between enrollment and response supports both the speed and success of manufacturing. Furthermore, axicabtagene ciloleucel-treated patients with ongoing responses at ≥3 years showed evidence of restoration of a normal B cell compartment and clearance of functional CAR T cells, a critical component of the long-term safety of CD19-directed CAR T cell therapies.

Eligible patients with refractory large B cell lymphoma (diffuse large B cell lymphoma, primary mediastinal B cell lymphoma, transformed follicular lymphoma) underwent leukapheresis at enrollment and subsequently received low-dose conditioning chemotherapy (fludarabine and cyclophosphamide) followed by a target dose of 2×10⁶ anti-CD19 CAR T cells/kg (Neelapu, S S et al. 2017, *N Engl J Med* 2017; 377(26):2531-44; clinical trial NCT02348216). The primary endpoint was objective response rate (ORR), and the first response assessment was 4 weeks post infusion. Response assessments were performed per protocol up to 24 months or disease progression, whichever occurred first. For patients in ongoing response beyond Month 24, response assessments continued per institutional standard-of-care (SOC). Blood levels of CAR T cells were quantified using polymerase chain reaction and B cells were characterized using flow cytometry in patients with ongoing responses and evaluable samples.

A total of 111 patients were enrolled, and axicabtagene ciloleucel was administered to 101 patients. As previously reported in the ZUMA-1 2-year analysis, among patients who received axicabtagene ciloleucel, the median time from axicabtagene ciloleucel infusion to both objective response and CR was 1.0 month (range, 1-12 months). When the entire enrolled population (N=111) was included on an intent-to-treat basis, the median manufacturing time was 17 days (range, 14-51; n=110 as manufacturing was not feasible for 1 pt). Additionally, among the 111 patients, the median time from enrollment/leukapheresis to objective response and CR was 1.7 months (range, 0.7-12.9) and 1.9 months (range, 0.7-13.3), respectively. Responses were durable, and with a minimum of 3 years of follow-up (median, 39.1 months), the median overall survival (OS) was 25.8 months, and the 3-year OS rate was 47%. Importantly, no axicabtagene ciloleucel-related secondary malignancies have been reported.

Patients in ongoing response after 2 years had significantly greater peak CAR T cell expansion in blood 7-14 days after axicabtagene ciloleucel infusion than did those with relapse (P=0.014) or no response (P=0.0003). Blood samples from 22 patients in ongoing response (per institutional SOC) at ≥3 years were available for analysis of CAR T cells and evaluation of B cell recovery. All evaluable patients had detectable B cells in blood at 3 years post axicabtagene ciloleucel. Notably, 91% of patients in ongoing response at 3-year follow-up showed recovery of polyclonal B cells measured by presence of both kappa and lambda light chains on non-malignant CD19+CD20+ B cells. The median kappa-lambda ratio of 1.6 and relative levels of key B cell subsets, including memory and naïve B cell immunophenotypes, suggested reconstitution of B cell repertoire, consistent with published data from healthy individuals (Deneys et al. *J Immunol Methods* 2001 Jul. 1; 253 21:23-36. doi: 10.1016/s0022-1759(01)00338-6; Scott et al. *J Clin Pathol* 2018 February; 71(2):174-179 doi: 10.1136/jclinpath-2017-204687. Epub 2017 Sep. 15). Additionally, 15/22 (68%) had both minimal levels of detectable CAR gene-marked cells and detectable polyclonal B cells in blood. Altogether, these findings support the hypothesis that persistence of functional CAR T cells is not necessary for durable remissions of LBCL.

Example 23

Axicabtagene Ciloleucel CAR T-Cell Therapy in Relapsed or Refractory Indolent Non-Hodgkin Lymphoma Most patients with advanced-stage indolent non-Hodgkin lymphoma (iNHL), including indolent follicular lymphoma (FL) and marginal zone lymphoma (MZL), experience multiple relapses. In this phase 2 ZUMA-5 study, axicabtagene ciloleucel (axi-cel), an autologous anti-CD19 chimeric antigen receptor (CAR) T-cell therapy, was evaluated in relapsed/refractory iNHL. Patients with ≥2 lines of therapy, including an anti-CD20 monoclonal antibody with an alkylating agent, underwent leukapheresis and received conditioning chemotherapy followed by a single axicabtagene ciloleucel infusion (2×10⁶ CAR T cells/kg). The primary endpoint was overall response rate assessed by an independent radiology review committee after ≥80 treated patients with FL were followed for ≥12 months. Axicabtagene ciloleucel was successfully manufactured for all 151 enrolled patients and administered to 146 (124 FL; 22 MZL). The overall response rate in the primary analysis (N=104) was 92% (95% CI, 85-97); 76% had complete responses. Among patients with FL (n=84), 94% responded. After a median 17.5-months follow-up, 62% of patients had ongoing responses. Twelve-month estimated progression-free and overall survival were 74% and 93%, respectively. Grade ≥3 cytokine release syndrome and neurologic events occurred in 7% (6% FL; 9% MZL) and 19% (15% FL; 41% MZL) of patients, respectively. Three grade 5 adverse events occurred (1 related to axicabtagene ciloleucel). Pharmacokinetic and pharmacodynamic profiles were associated with safety outcomes in patients with FL.

Eligible adults had histologically confirmed iNHL, including grade 1-3a FL, or nodal or extranodal MZL, per the World Health Organization 2016 classification criteria. Swerdlow S H, et al. *Blood* 2016; 127:2375-90. Patients had relapsed/refractory disease after ≥2 prior lines of therapy that included an anti-CD20 monoclonal antibody combined with an alkylating agent. The full eligibility criteria were as follows:

Additional Inclusion Criteria:

Relapsed or refractory disease after 2 or more prior lines of therapy. Prior therapy having included an anti-CD20 monoclonal antibody combined with an alkylating agent (single-agent anti-CD20 antibody did not count as line of therapy for eligibility). Stable disease (without relapse) >1 year from completion of last therapy was not eligible Eastern Cooperative Oncology Group performance status of 0 to 1

At least 1 measurable lesion according to the Lugano Response Criteria for Malignant Lymphoma. Cheson B D et al. *Journal of clinical oncology* 2014; 32:3059-68. Lesions that had been previously irradiated were considered measurable only if progression had been documented following completion of radiation therapy No known history or suspicion of central nervous system (CNS) involvement by lymphoma At least 2 weeks or 5 half-lives, whichever was shorter, having elapsed since any prior systemic therapy and enrollment, except for systemic inhibitory/stimulatory immune checkpoint therapy. At least 3 half-lives having elapsed from any prior systemic inhibitory/stimulatory immune checkpoint molecule therapy and enrollment (eg, ipilimumab, nivolumab, pembrolizumab, atezolizumab, OX40 agonists, and 4-1BB agonists)

Toxicities due to prior therapy having been stable and recovered to grade 1 or lower (except for clinically non-significant toxicities, such as alopecia)

Platelet count ≥75,000/µL,

Absolute neutrophil count ≥1000/µL,

Absolute lymphocyte count ≥100/µL,

Adequate renal, hepatic, pulmonary, and cardiac function defined as the following Creatinine clearance (as estimated by Cockcroft-Gault formula) ≥60 mL/min Serum alanine aminotransferase/aspartate aminotransferase ≤2.5 upper limit of normal Total bilirubin ≤1.5 mg/dL, except in patients with Gilbert's syndrome Left ventricular ejection fraction ≥50%, no evidence of pericardial effusion as determined by an echocardiogram, and no clinically significant arrhythmias No clinically significant pleural effusion Baseline resting oxygen saturation >92% on room air

Females of childbearing potential having had a negative serum or urine pregnancy test (females who had undergone surgical sterilization or who had been postmenopausal for ≥2 years were not considered to be of childbearing potential)

Additional Exclusion Criteria:

Transformed follicular lymphoma (FL) or marginal zone lymphoma (MZL)

Small lymphocytic lymphoma

FL histological grade 3b

Lymphoplasmacytic lymphoma

History of malignancy other than nonmelanoma skin cancer or carcinoma in situ (eg, cervix, bladder, breast) unless disease-free and without anticancer therapy for ≥3 years Autologous stem cell transplant (SCT) within 6 weeks of planned axicabtagene ciloleucel infusion History of allogenic SCT Prior CD19 targeted therapy with the exception of patients who received axicabtagene ciloleucel (axi-cel) in this study and were eligible for retreatment Prior chimeric antigen receptor (CAR) therapy or other genetically modified T-cell therapy History of severe, immediate hypersensitivity reaction attributed to aminoglycosides Presence or suspicion of fungal, bacterial, viral, or other infection that was uncontrolled or requiring intravenous antimicrobials for management History of human immunodeficiency virus infection or active acute or chronic hepatitis B or hepatitis C infection. Patients with a history of hepatitis infection having cleared their infection as determined by standard serological and genetic testing per current Infectious Diseases Society of America guidelines or applicable country guidelines Presence of lymphoma that was known to involve the full thickness of the gastric wall Presence of any indwelling line or drain (eg, percutaneous nephrostomy tube, indwelling Foley catheter, biliary drain, or pleural/peritoneal/pericardial catheter). Dedicated central venous access catheters, such as a Port-a-Cath or Hickman catheter, were permitted Detectable cerebrospinal fluid malignant cells or known brain metastases or with a history of cerebrospinal fluid malignant cells or brain metastases History or presence of nonmalignant central nervous system (CNS) disorder, such as seizure disorder, cerebrovascular ischemia/hemorrhage, dementia, cerebellar disease, cerebral edema, posterior reversible encephalopathy syndrome, or any autoimmune disease with CNS involvement Cardiac atrial or cardiac ventricular lymphoma involvement History of myocardial infarction, cardiac angioplasty or stenting, unstable angina, New York Heart Association Class II or greater congestive heart failure, or other clinically significant cardiac disease within 12 months of enrollment Possible requirement for urgent therapy within 6 weeks after leukapheresis due to ongoing or impending oncologic emergency (eg, tumor mass effect, tumor lysis syndrome)

History of autoimmune disease (eg, Crohn's disease, rheumatoid arthritis, systemic lupus erythematosus) resulting in end organ injury or requiring systemic immunosuppression or systemic disease modifying agents within the last 2 years. Patients with a history of autoimmune-related hypothyroidism on a stable dose of thyroid replacement hormone and patients with controlled type 1 diabetes mellitus on a stable insulin regimen were eligible for this study History of symptomatic deep vein thrombosis (DVT) or pulmonary embolism within 6 months of enrollment. History of upper extremity line-related DVT within 3 months of conditioning chemotherapy Any medical condition likely to interfere with assessment of safety or efficacy of study treatment History of severe immediate hypersensitivity reaction to any of the agents used in this study Treatment with a live, attenuated vaccine within 6 weeks prior to the planned start of conditioning chemotherapy or anticipation of need for such a vaccine during the course of the study Women of childbearing potential who were pregnant or breastfeeding because of the potentially dangerous effects of the preparative chemotherapy on the fetus or infant. Females who had undergone surgical sterilization or who had been postmenopausal for ≥2 years were not considered to be of childbearing potential Patients of either sex who were not willing to practice birth control from the time of consent through 6 months following conditioning chemotherapy administration or 6 months following axicabtagene ciloleucel infusion, whichever was longer In the investigator's judgment, the patient was unlikely to complete all protocol-required study visits or procedures, including follow-up visits, or comply with the study requirements for participation Patients underwent leukapheresis to obtain T cells for axicabtagene ciloleucel manufacturing, followed by conditioning chemotherapy with cyclophosphamide at 500 mg/m²/day and fludarabine at 30 mg/m²/day administered on days −5, −4, and −3. On day 0, patients received a single intravenous infusion of axicabtagene ciloleucel at a target dose of $2 \times 10^6$ CAR T cells/kg. Bridging therapy was administered to patients strictly at the discretion of the treating investigator. Axicabtagene ciloleucel dosing was based on aggregate safety and efficacy data in patients with relapsed LBCL. Neelapu S S et al. *N Engl J Med* 2017; 377:2531-44. Hospitalization after axicabtagene ciloleucel infusion was required through day 7. Patients who progressed after responding at the month 3 assessment could receive retreatment with axicabtagene ciloleucel.

A total of 151 patients with iNHL (127 FL; 23 MZL; 1 diffuse LBCL) were enrolled and leukapheresed. Axicabtagene ciloleucel was successfully manufactured for all enrolled patients (100%); the median time from leukapheresis to axicabtagene ciloleucel delivery to the trial site was 17 days. Prior to conditioning chemotherapy, 1 patient was discontinued after pretreatment biopsy revealed diffuse LBCL, 3 were deemed ineligible for treatment due to low platelet levels (n=1) or a CR (n=2), and 1 died from cardiac arrest. Axicabtagene ciloleucel was administered to 146 patients with iNHL (97%), including 124 with FL (98%) and 22 with MZL (96%). As of Mar. 12, 2020, the median follow-up was 17.5 months (range, 1.4-31.6) for the primary efficacy analysis and 15.1 months (range, 0.5-31.6) for the safety analyses.

Patients were heavily pretreated, with the majority receiving ≥3 prior lines of therapy; 29% received a phosphoinositide 3-kinase (PI3K) inhibitor and 23% underwent autologous stem cell transplantation (SCT; Table 36). Over half of patients (55%) progressed <24 months after initiating their first chemoimmunotherapy regimen (POD24). Casulo C et al., *J Clin Oncol* 2015; 33:2516-22 Other common high-risk features included stage III/IV disease (86%), refractory disease (68%), and high tumor burden (49%). A greater percentage of patients with MZL than with FL were ≥65 years (59% vs. 31%) and had stage IV disease (77% vs. 49%).

TABLE 36

Baseline Patient Characteristics in all Treated Patients

| Characteristic | Patients with FL n = 124 | Patients with MZL n = 22 | All Patients N = 146 |
|---|---|---|---|
| Age, median (range), years | 60 (34-79) | 66 (48-77) | 61 (34-79) |
| ≥65 years, n (%) | 38 (31) | 13 (59) | 51 (35) |
| Male sex, n (%) | 73 (59) | 10 (45) | 83 (57) |
| ECOG PS of 1, n (%) | 46 (37) | 9 (41) | 55 (38) |
| Stage III-IV disease | 106 (85) | 20 (91) | 126 (86) |
| High-risk FLIPI (≥3), n (%) | 54 (44) | 14 (64) | 68 (47) |
| High tumor burden (GELF criteria)* | 64 (52) | 8 (36) | 72 (49) |
| Number of prior therapies, median (range)† | 3 (1-10) | 3 (2-8) | 3 (1-10) |
| ≥3 prior lines of therapy, n (%) | 78 (63) | 15 (68) | 93 (64) |
| Prior PI3K inhibitor | 34 (27) | 9 (41) | 43 (29) |
| Prior autologous SCT | 30 (24) | 3 (14) | 33 (23) |
| Prior anti-CD20 + alkylating agent | 123 (99) | 21 (95) | 144 (99) |
| Prior anti-CD20 single agent | 39 (31) | 10 (45) | 49 (34) |
| Prior alkylating single agent | 16 (13) | 6 (27) | 22 (15) |
| Prior lenalidomide | 38 (31) | 7 (32) | 45 (31) |
| Relapsed/refractory subgroup, n (%)‡ | | | |
| Refractory to last prior therapy | 84 (68) | 16 (73) | 100 (68) |
| POD24 from initiating first anti-CD20 mAb-containing therapy, n (%)§ | 68 (55) | 11 (52) | 79 (55) |
| Positive CD19 status, n/n (%)¶ | 93/104 (89) | 14/16 (88) | 107/120 (89) |
| Lymphoma present in bone marrow** | 32 (36) | 10 (45) | 42 (29) |

*Tumor burden, as defined by any of GELF criteria: Involvement of ≥3 nodal sites, each with a diameter of ≥3 cm, any nodal or extranodal tumor mass with a diameter of ≥7 cm, B symptoms, splenomegaly, pleural effusions or peritoneal ascites, cytopenias, or leukemia.
†One patient received prior therapy for diffuse large B-cell lymphoma, not for the primary disease of follicular lymphoma.
‡Patients who progressed within 6 months of completion of the most recent prior therapy are defined as refractory.
§POD24 defined as 24 months from initiation of the first line of anti-CD20-containing immunochemotherapy to progression. Percentages are based on the number of patients who ever received anti-CD20-chemotherapy combination therapy.
¶CD19 status of the tumor was assessed by immunohistochemistry, with a positive score defined as the H-score of staining ≥5. Of those with CD19-negative status at baseline, 11 patients had FL and 2 had MZL.
** Bone marrow was assessed by the investigator at baseline for lymphoma presence per Lugano bone marrow assessment/bone marrow assessment using aspirate or core biopsy at screening. If these were not available, lymphoma presence was based on diagnosis history of bone marrow involvement.
ECOG PS, Eastern Cooperative Oncology Group performance status; FLIPI, Follicular Lymphoma International Prognostic Index; GELF, Groupe d Etude des Lymphomes Folliculaires; SCT, stem-cell transplantation.

Bridging therapy was administered before conditioning chemotherapy to 6 patients (4 FL; 2 MZL; Table 37). All 6 had measurable disease after bridging.

TABLE 37

| | | Bridging Therapies |
|---|---|---|
| Patient | Disease Subtype | Bridging Therapies |
| 1 | FL | Dexamethasone |
| 2 | FL | Rituximab, Etoposide, Carboplatin, Ifosfamide |
| 3 | FL | Dexamethasone |
| 4 | FL | Bendamustine-rituximab, Methylprednisolone, Ifosfamide, Etoposide, Mitoxantrone |
| 5 | MZL | Rituximab, Bendamustine |
| 6 | MZL | Dexamethasone, Rituximab, Etoposide, Carboplatin, Ifosfamide, Cyclophosphamide, Fludarabine, Ibrutinib |

The primary endpoint was overall response rate (ORR; CR and partial response) assessed by an independent radiology review committee per the Lugano classification. Cheson B D et al., *Journal of clinical oncology* 2014; 32:3059-68. Secondary endpoints included CR rate, investigator-assessed ORR, DOR, progression-free survival (PFS), OS, incidence of adverse events, and levels of CART cells in blood and cytokines in serum.

As specified by the protocol, 104 patients with iNHL were efficacy-evaluable at data cutoff; 84 with FL had ≥12 months follow-up and 20 with MZL had ≥4 weeks follow-up. The ORR assessed by the independent radiology review committee in patients with iNHL was 92% (95% CI, 85-97), with 76% achieving a CR (FIG. 91A). The ORR was 94% in patients with FL (80% CR rate) and 85% in those with MZL (60% CR rate). Concordance between investigator- and independent radiology review committee-assessed ORR was 91% (Table 38).

TABLE 38

Efficacy Endpoints in the Primary Analysis Based on
Investigator Assessment per the Lugano Classification

| | Follicular Lymphoma (n = 84) | Marginal Zone Lymphoma (n = 20) | All Patients (N = 104) |
|---|---|---|---|
| Overall response rate, n (%) | 80 (95) | 19 (95) | 99 (95) |
| Complete response | 67 (80) | 13 (65) | 80 (77) |
| Partial response | 13 (15) | 6 (30) | 19 (18) |
| Stable disease, n (%) | 2 (2) | 1 (5) | 3 (3) |
| Disease Progression, n (%) | 1 (1) | 0 (0) | 1 (1) |

TABLE 38-continued

Efficacy Endpoints in the Primary Analysis Based on
Investigator Assessment per the Lugano Classification

| | Follicular Lymphoma (n = 84) | Marginal Zone Lymphoma (n = 20) | All Patients (N = 104) |
|---|---|---|---|
| Not Done*, n (%) | 1 (1) | 0 (0) | 1 (1) |
| Concordance with IRRC-assessed ORR, %† | 94.0 | 80.0 | 91.3 |
| Kappa coefficient (95% CI) | 0.25 (−0.19, 0.70) | −0.08 (−0.21, 0.04) | 0.14 (−0.18, 0.45) |

The median time to initial response was 1 month (range, 0.8-3.1), consistent across disease types. Among patients with FL, 13 (15%) had an initial partial response at Week 4 and later converted to a CR; 12/13 (92%) remained in response at data cutoff. Responses were consistent among patients with high-risk characteristics, including POD24, ≥3 prior lines of therapy, refractory disease, and high tumor burden (FIG. 91B; FIG. 92).

At data cutoff, 62% of efficacy-evaluable patients had ongoing responses (64% FL; 50% MZL). Of those who achieved a CR, 73% remained in remission (78% FL; 50% MZL). Eleven patients (9 FL; 2 MZL) who relapsed after initial response to axicabtagene ciloleucel were subsequently retreated; all responded to retreatment, with 91% achieving a CR.

Estimated 12-month rates of DOR and PFS for all patients with iNHL were 72% and 74%, respectively (FIGS. 93A-93C). Among patients with FL, these rates were 77% and 78%, respectively. Among patients with MZL, median DOR and PFS were 10.6 months and 11.8 months, respectively. Estimated 12-month DOR and PFS were largely consistent among patients with high-risk characteristics (FIG. 94 and FIG. 95). Estimated 12-month OS rate was 93%, consistent across disease types (FIG. 93D; FIG. 96).

Disease progression occurred in 21/96 responding patients with iNHL (22%), including 11/79 CRs (14%) and 10/17 partial responses (59%). Of all 146 treated patients, 132 (90%) were alive as of the data cutoff date (111/124 with FL and 21/22 with MZL). All but 2 deaths occurred >3 months post-infusion. Four patients with FL underwent subsequent SCT (1 autologous and 3 allogeneic) due to progressive disease.

Adverse events of any grade occurred in 99% of treated patients with iNHL (Table 39). Grade ≥3 adverse events occurred in 86% of patients (85% FL; 95% MZL), commonly cytopenias (70%) and infections (16%). Grade ≥3 cytopenias were present ≥30 days post-infusion in 32% each of patients with FL and MZL, mostly consisting of neutropenias (27% and 32%, respectively).

TABLE 39

Adverse Events, Cytokine Release Syndrome, and Neurologic Events

| n (%)* | Follicular Lymphoma (n = 124) | | Marginal Zone Lymphoma (n = 22) | | All Patients (N = 146) | |
|---|---|---|---|---|---|---|
| | Any Grade | Grade ≥3 | Any Grade | Grade ≥3 | Any Grade | Grade ≥3 |
| Any adverse event | 123 (99) | 105 (85) | 22 (100) | 21 (95) | 145 (99) | 126 (86) |
| Pyrexia | 103 (83) | 9 (7) | 20 (91) | 2 (9) | 123 (84) | 11 (8) |
| Neutropenia | 79 (64) | 75 (60) | 15 (68) | 14 (64) | 94 (64) | 89 (61) |
| Hypotension | 59 (48) | 3 (2) | 13 (59) | 3 (14) | 72 (49) | 6 (4) |
| Headache | 54 (44) | 2 (2) | 11 (50) | 0 (0) | 65 (45) | 2 (1) |
| Fatigue | 51 (41) | 1 (1) | 13 (59) | 0 (0) | 64 (44) | 1 (1) |
| Nausea | 45 (36) | 0 (0) | 13 (59) | 0 (0) | 58 (40) | 0 (0) |

TABLE 39-continued

| Adverse Events, Cytokine Release Syndrome, and Neurologic Events | | | | | | |
|---|---|---|---|---|---|---|
| | Follicular Lymphoma (n = 124) | | Marginal Zone Lymphoma (n = 22) | | All Patients (N = 146) | |
| n (%)* | Any Grade | Grade ≥3 | Any Grade | Grade ≥3 | Any Grade | Grade ≥3 |
| Anemia | 44 (35) | 28 (23) | 11 (50) | 6 (27) | 55 (38) | 34 (23) |
| Sinus tachycardia | 41 (33) | 2 (2) | 7 (32) | 0 (0) | 48 (33) | 2 (1) |
| Tremor | 36 (29) | 1 (1) | 9 (41) | 0 (0) | 45 (31) | 1 (1) |
| Chills | 33 (27) | 0 (0) | 9 (41) | 0 (0) | 42 (29) | 0 (0) |
| Constipation | 35 (28) | 0 (0) | 6 (27) | 0 (0) | 41 (28) | 0 (0) |
| Diarrhea | 33 (27) | 0 (0) | 8 (36) | 0 (0) | 41 (28) | 0 (0) |
| Decreased appetite | 28 (23) | 2 (2) | 8 (36) | 0 (0) | 36 (25) | 2 (1) |
| Confusional state | 28 (23) | 6 (5) | 7 (32) | 2 (9) | 35 (24) | 8 (5) |
| Vomiting | 29 (23) | 1 (1) | 6 (27) | 0 (0) | 35 (24) | 1 (1) |
| Hypoxia | 27 (22) | 8 (6) | 7 (32) | 4 (18) | 34 (23) | 12 (8) |
| Cough | 28 (23) | 0 (0) | 5 (23) | 0 (0) | 33 (23) | 0 (0) |
| Encephalopathy | 24 (19) | 10 (8) | 6 (27) | 3 (14) | 30 (21) | 13 (9) |
| Thrombocytopenia | 26 (21) | 20 (16) | 3 (14) | 2 (9) | 29 (20) | 22 (15) |
| Symptoms of cytokine release syndrome | | | | | | |
| Any | 97 (78) | 8 (6) | 22 (100) | 2 (9) | 119 (82) | 10 (7) |
| Pyrexia | 94 (97) | 6 (6) | 20 (91) | 2 (9) | 114 (96) | 8 (7) |
| Hypotension | 39 (40) | 3 (3) | 10 (45) | 2 (9) | 49 (41) | 5 (4) |
| Chills | 25 (26) | 0 (0) | 7 (32) | 0 (0) | 32 (27) | 0 (0) |
| Sinus tachycardia | 25 (26) | 2 (2) | 6 (27) | 0 (0) | 31 (26) | 2 (2) |
| Hypoxia | 23 (24) | 6 (6) | 7 (32) | 4 (18) | 30 (25) | 10 (8) |
| Headache | 19 (20) | 0 (0) | 1 (5) | 0 (0) | 20 (17) | 0 (0) |
| Neurologic events | | | | | | |
| Any | 70 (56) | 19 (15) | 17 (77) | 9 (41) | 87 (60) | 28 (19) |
| Tremor | 36 (29) | 1 (1) | 9 (41) | 0 (0) | 45 (31) | 1 (1) |
| Confusional state | 28 (23) | 6 (5) | 7 (32) | 2 (9) | 35 (24) | 8 (5) |
| Encephalopathy | 24 (19) | 10 (8) | 6 (27) | 3 (14) | 30 (21) | 13 (9) |
| Aphasia | 16 (13) | 3 (2) | 4 (18) | 3 (14) | 20 (14) | 6 (4) |

Cytokine release syndrome (CRS) occurred in 82% of patients with iNHL (78% FL; 100% MZL; Table 39). Most cases were grade ½ (75% overall; 72% FL; 91% MZL). Grade ≥3 CRS occurred in 7% of patients (6% FL; 9% MZL). Tocilizumab, corticosteroids, and vasopressors were administered to 49%, 17%, and 5% of patients, respectively, for CRS management. The median time to onset of CRS was 4 days post-infusion (range, 1-15) and the median duration was 6 days, consistent across disease types. All events occurring in the context of CRS resolved except one grade 5 event of multisystem organ failure in a patient with FL (day 7).

Neurologic events occurred in 60% of patients with iNHL (56% FL; 77% MZL) and grade ½ events occurred in 40% (FL 41%; MZL 36%; Table 39). Grade ≥3 neurologic events occurred in 19% of patients. A lower incidence of grade ¾ neurologic events occurred in patients with FL (15%) than in those with MZL (41%). No grade 5 neurologic events occurred. For the management of neurologic events, corticosteroids were used in 36% of patients and tocilizumab was used in 6%. The median time to onset was 7 days (range, 1-177), consistent across disease types. Median duration was 14 days and 10 days for patients with FL and MZL, respectively. As of data cutoff, 3 patients with FL had ongoing grade 1 neurologic events: attention disturbance, memory impairment, or intermittent paresthesia. Three patients with MZL had ongoing events: grade 1 tremor, grade 1 memory impairment, or grade 2 facial paresthesia.

Serious adverse events of any grade occurred in 48% of patients with iNHL (44% FL; 73% MZL; Table 40).

TABLE 40

| Serious Adverse Events Occurring in at Least 3 Patients | | | | | | |
|---|---|---|---|---|---|---|
| | Follicular Lymphoma (n = 124) | | Marginal Zone Lymphoma (n = 22) | | All Patients (N = 146) | |
| n (%) | Any Grade | Grade ≥3 | Any Grade | Grade ≥3 | Any Grade | Grade ≥3 |
| Any serious event | 54 (44) | 40 (32) | 16 (73) | 14 (64) | 70 (48) | 54 (37) |
| Pyrexia | 16 (13) | 2 (2) | 5 (23) | 1 (5) | 21 (14) | 3 (2) |
| Encephalopathy | 8 (6) | 8 (6) | 3 (14) | 2 (9) | 11 (8) | 10 (7) |
| Pneumonia | 8 (6) | 7 (6) | 2 (9) | 2 (9) | 10 (7) | 9 (6) |
| Confusional State | 7 (6) | 4 (3) | 1 (5) | 0 (0) | 8 (5) | 4 (3) |
| Hypotension | 2 (2) | 1 (1) | 3 (14) | 2 (9) | 5 (3) | 3 (2) |
| Hypoxia | 3 (2) | 2 (2) | 2 (9) | 2 (9) | 5 (3) | 4 (3) |
| Somnolence | 2 (2) | 2 (2) | 3 (14) | 2 (9) | 5 (3) | 4 (3) |
| Febrile Neutropenia | 2 (2) | 2 (2) | 2 (9) | 2 (9) | 4 (3) | 4 (3) |
| Aphasia | 2 (2) | 0 (0) | 1 (5) | 1 (5) | 3 (2) | 1 (1) |

TABLE 40-continued

| | Serious Adverse Events Occurring in at Least 3 Patients | | | | | |
|---|---|---|---|---|---|---|
| | Follicular Lymphoma (n = 124) | | Marginal Zone Lymphoma (n = 22) | | All Patients (N = 146) | |
| n (%) | Any Grade | Grade ≥3 | Any Grade | Grade ≥3 | Any Grade | Grade ≥3 |
| Embolism | 3 (2) | 2 (2) | 0 (0) | 0 (0) | 3 (2) | 2 (1) |
| Headache | 3 (2) | 0 (0) | 0 (0) | 0 (0) | 3 (2) | 0 (0) |
| Neutropenia | 2 (2) | 2 (2) | 1 (5) | 1 (5) | 3 (2) | 3 (2) |
| Urinary Tract Infection | 3 (2) | 3 (2) | 0 (0) | 0 (0) | 3 (2) | 3 (2) |

Severity of adverse events was graded using the National Cancer Institute Common Terminology Criteria for Adverse Events, version 4.03

Grade ≥3 infections occurred in 23 patients (16%), including pneumonia in 11 (8%), opportunistic infections in 3 (2%), and upper respiratory tract infection in 1 (Table 41).

TABLE 41

| | Infections Occurring in ≥3 Patients With iNHL | | | | | |
|---|---|---|---|---|---|---|
| | Follicular Lymphoma (n = 124) | | Marginal Zone Lymphoma (n = 22) | | All Patients (N = 146) | |
| n (%) | Any Grade | Grade ≥3 | Any Grade | Grade ≥3 | Any Grade | Grade ≥3 |
| Any infection* | 65 (52) | 18 (15) | 13 (59) | 5 (23) | 78 (53) | 23 (16) |
| Upper respiratory tract infection | 14 (11) | 0 (0) | 7 (32) | 1 (5) | 21 (14) | 1 (1) |
| Pneumonia | 14 (11) | 8 (6) | 3 (14) | 3 (14) | 17 (12) | 11 (8) |
| Oral candidiasis | 9 (7) | 0 (0) | 4 (18) | 0 (0) | 13 (9) | 0 (0) |
| Sinusitis | 8 (6) | 1 (1) | 3 (14) | 0 (0) | 11 (8) | 1 (1) |
| Urinary tract infection | 8 (6) | 3 (2) | 2 (9) | 0 (0) | 10 (7) | 3 (2) |
| Influenza | 4 (3) | 0 (0) | 2 (9) | 0 (0) | 6 (4) | 0 (0) |
| Bronchitis | 4 (3) | 0 (0) | 0 (0) | 0 (0) | 4 (3) | 0 (0) |
| Rhinovirus infection | 3 (2) | 0 (0) | 1 (5) | 0 (0) | 4 (3) | 0 (0) |
| Herpes zoster | 2 (2) | 1 (1) | 1 (5) | 0 (0) | 3 (2) | 1 (1) |
| Nasopharyngitis | 1 (1) | 0 (0) | 2 (9) | 0 (0) | 3 (2) | 0 (0) |
| Staphylococcal infection | 3 (2) | 1 (1) | 0 (0) | 0 (0) | 3 (2) | 1 (1) |

*3 patients had grade ≥3 opportunistic infections, including grade 5 coccidioidomycosis (n = 1, MZL), grade 3 cryptococcosis (n = 1, MZL), and grade 3 systemic Candida (n = 1, FL). These infections are not included in the table since each was present in only 1 patient.

Immunoglobulin therapy was administered to 44 patients (30% [27% FL; 50% MZL]). One patient with FL experienced grade 3 hypogammaglobulinemia. No tumor lysis syndrome, replication-competent retrovirus, or immunogenicity were reported. Eight patients had secondary malignancies considered not axicabtagene ciloleucel-related (Table 42).

TABLE 42

| | Secondary Malignancies | | |
|---|---|---|---|
| | Follicular Lymphoma (n = 124) | Marginal Zone Lymphoma (n = 22) | All Patients (N = 146) |
| Myelodysplastic syndrome | 0 | 2 (9) | 2 (1) |
| Squamous cell carcinoma | 2 (2) | 0 | 2 (1) |
| Basal cell carcinoma | 1 (1) | 0 | 1 (1) |
| Prostate cancer | 1 (1) | 0 | 1 (1) |
| Breast cancer | 0 | 1 (5) | 1 (1) |
| Acute myeloid leukemia | 1 (1) | 0 | 1 (1) |

Of all treated patients with iNHL, 13 with FL (10%) and 1 with MZL (5%) died. Of those, 7 patients with FL (6%)

died from progressive disease. Grade 5 adverse events occurred in 3 patients with iNHL, including 1 with multisystem organ failure described above (related to axicabtagene ciloleucel). Grade 5 aortic dissection occurred 399 days post-infusion in a patient with FL and grade 5 coccidioidomycosis infection 327 days post-infusion in a patient with MZL, both considered unrelated to treatment.

The presence, expansion, and persistence of axicabtagene ciloleucel anti-CD19 CAR T cells were measured in peripheral blood mononuclear cells as previously reported. Locke F L et al, Mol Ther 2017; 25:285-95 Briefly, a quantitative polymerase chain reaction assay observed concentration peak anti-CD19 CAR T cells/μL, the AUC) from day 0 to day 28 ($AUC_{0-28}$), and the persistence of anti-CD19 CAR T cells over time in patients with evaluable samples. Levels of key analytes (proinflammatory and immune-modulating cytokines, chemokines, and effector molecules) were evaluated in serum samples as described previously. Neelapu S S et al., N Engl J Med 2017; 377:2531-44; Locke F L et al., Proc of the 107th Annu Meet Am Assoc Cancer Res 2017: CT019; Kochenderfer J N et al., Journal of clinical oncology, 2017; 35:1803-13. H-scores to determine CD19 tumor status were calculated as previously reported. Neelapu S S et al., N Engl J Med 2017; 377:2531-44. Briefly, a product of IHC intensity (grade 1-3) multiplied by the percentage of tumor cells at a given intensity (0-100%) by central pathology review.

To monitor the on-target/off-tumor effect of axicabtagene ciloleucel (ie, cytotoxic effects on normal CD19-expressing B cells), the presence and frequency of B cells in blood were evaluated by a flow cytometry assay specifically designed to detect B cells. CD19 expression on archival tumor was determined using the validated Ventana CD19 immunohistochemistry assay (NeoGenomics, Fort Myers, FL). Serum cytokines were analyzed by Luminex (EMD Millipore) or V-Plex Multiplex assay panels (Meso Scale Discovery) as previously described at baseline (prior to conditioning), on day 0 (axicabtagene ciloleucel infusion day) or day 1 (1 day post-axicabtagene ciloleucel infusion) as specified. T-cell phenotype was assessed by multicolor flow cytometry using established protocols and antibodies. Locke F L et al., *Mol Ther* 2017; 25:285-95.

The median time to peak of anti-CD19 CAR T-cell levels post-infusion was 9 days (range, 8-371; FIG. 97A) in all patients with iNHL, 8 days (range, 8-371) in patients with FL, and 15 days (range, 8-29) in patients with MZL. One patient with FL had a second peak of CAR T cells on day 371 in the context of florid relapse. CAR T-cell expansion by peak and area under the curve was slightly higher in patients with MZL than with FL. Most patients with evaluable samples (52/67; 78%) had low levels of detectable CAR gene-marked cells 12 months post-infusion; by 24 months, $7/13$ patients with evaluable samples (54%) still had detectable cells (FIGS. 98A-98B). Of evaluable patients in ongoing response at 12 months, B cells were detectable in 20/39 (51%), most of whom (14/20) had detectable CAR gene-marked cells. The 3 nonresponding patients with FL had detectable B cells at baseline; all had detectable CAR T-cell expansion and none experienced B-cell aplasia.

In efficacy-evaluable patients with FL, peak CAR T-cell expansion was numerically greater in those with ongoing response at 12 months than in those who relapsed (FIG. 97B). In all treated patients with FL, peak CAR T-cell expansion was associated with grade ≥3 CRS and neurologic events (FIG. 97B).

Associations between outcomes and levels of CART cells and cytokine were measured using the Wilcoxon rank-sum test for two independent samples and Kruskal-Wallis test for comparing >2 independent samples. Logistic regression was also used to evaluate relationship between covariates and clinical outcomes. The P values and confidence intervals shown in the tables and figures have not been adjusted for multiplicity and therefore should be inferred as indicative of possible trend in associations between serum cytokines, CAR T-cell levels and clinical outcomes.

Levels of most cytokines peaked at 8 days, with many resolving by week 4 (FIGS. 99A-99B; FIGS. 100A-100B). In patients with FL, baseline levels of CCL17 (TARC), CCL22 (MDC), Ferritin, IL-16, IL-10, TNFα, IL-2Rα, and CRP in serum were negatively associated with response (FIG. 101; FIG. 102). Median peak levels of multiple serum analytes were positively associated with grade ≥3 CRS (IL-1RA), neurologic events (IL-15, CRP, Granzyme B, CCL26 [Eotaxin-3], and IL-17), or both (IL-2, IL-6, IL-2Rα, GM-CSF, IFN-γ, IL-8, CXCL10 [IP-10], CCL2 [MCP-1], IL-10, CCL4 [MIP-10], and TNF-α; FIG. 103; FIG. 97C; FIGS. 100A-100B). The pharmacodynamic profile in patients with FL was associated with the well-tolerated safety profile. High numbers of naïve and central memory T cells (CCR7+ cells) in axicabtagene ciloleucel products were positively associated with ongoing response in patients with FL (FIG. 104). Evaluation of biomarker associations with outcomes in patients with MZL was limited by sample size, though similar trends were observed (FIGS. 105A-105B).

Patients with relapsed/refractory iNHL have progressively shorter responses to subsequent lines of treatment, highlighting the need for durable treatment options. Wang T P et al., *Ther Adv Hematol* 2017; 8:329-44. The results showed that axicabtagene ciloleucel induced a high ORR (92%) and CR rate (76%) after a single infusion in heavily pretreated patients with iNHL. Responses were consistent among patients with high-risk disease features. Importantly, with 17.5-months median follow-up, responses were durable, with 62% of all patients in ongoing response and 73% of those achieving a CR remaining in remission.

The ORR (94%) and CR rate (80%) were substantially higher with axicabtagene ciloleucel in patients with FL than with approved therapies after ≥2 prior lines of treatment, including PI3K inhibitors and tazemetostat (ORR 34%-77%; CR rates 6-14%). Responses in ZUMA-5 also compared favorably with lenalidomide-rituximab, approved in in less heavily pretreated patients with FL (78% ORR; 34% CR rate). Though medians for DOR and PFS were not reached for patients with FL in ZUMA-5, CR rates with axicabtagene ciloleucel likely associate with a durability, as observed in previous studies. Mangal N et al., Hematol Oncol 2018; 36:37; Shi Q et al., *J Clin Oncol* 2017; 35:552-60. In comparison, PI3K inhibitors and tazemetostat have limited median DOR (8.3-13.0 months) and PFS (5.7-11.2 months). CR rates were consistently high among patients with iNHL who had prior autologous SCT in ZUMA-5, suggesting axicabtagene ciloleucel may be a viable option for patients with FL who relapse post-SCT, a population with a median PFS of 1 year. Of the 11 patients in ZUMA-5 who were retreated with axicabtagene ciloleucel, 91% achieved a CR, showing the clinical potential of retreatment.

Patients with relapsed/refractory MZL have a high unmet need as no therapies are approved for third-line treatment in the United States or European Union. The ORR for patients with MZL in ZUMA-5 (85%), 68% of whom had ≥3 prior lines of treatment, was superior to ibrutinib or lenalidomide-rituximab in the second-line setting (48%-65%). With 12.1 months median follow-up, median DOR and PFS for patients with MZL in ZUMA-5 were 10.6 months and 11.8 months, respectively.

The safety profile of axicabtagene ciloleucel was manageable, generally reversable, and appeared favorable in patients with FL compared with that previously reported in LBCL. Among patients with FL, 22% did not experience CRS; those who did had later onset than that in LBCL (4 versus 2 days). Of note, grade ≥3 neurologic events were numerically lower among patients with FL (15%) compared with those with MZL (41%) and LBCL (32%). Locke F L et al., *Lancet Oncol* 2019; 20:31-42.

The expansion and subsequent decline of CAR T-cell levels was largely similar to that previously reported, slightly higher in patients with MZL than those with FL. Locke F L et al., *Lancet Oncol* 2019; 20:31-42; Neelapu S S et al., *N Engl J Med* 2017; 377:2531-44. All patients in ongoing response at 12 months had robust T-cell expansion and B-cell aplasia at the first assessment, and ongoing responses appeared to be correlated with peak CAR T-cell levels. B-cells recovered in about half of patients with ongoing response, although most also had low levels of CAR gene-marked cells. Collectively, baseline and peak levels of serum biomarkers in patients with FL associated with well-tolerated toxicity, compared with LBCL. Lastly, high numbers of naïve and central memory T cells in axicabtagene ciloleucel product associated with ongoing responses.

The results showed that axicabtagene ciloleucel induced durable clinical benefit in a substantial proportion of patients with relapsed/refractory iNHL after ≥2 lines of therapy. Manageable safety was observed with axicabtagene ciloleucel, with less CAR T-cell-associated toxicities in patients with FL vs. those with MZL and those previously reported in LBCL. Locke F L et al., *Lancet Oncol* 2019; 20:31-42; Neelapu S S et al., *N Engl J Med* 2017; 377:2531-44.

Example 24

Previous results of the ZUMA-5 clinical trial (NCT03105336) have been described above in EXAMPLES 17 and 23. In the primary analysis of efficacy-evaluable patients in ZUMA-5 (N=104; median follow-up 17.5 months), the ORR was 92%, with a 76% CR rate. Jacobson C A, et al. ASH 2020. #700. Retreatment of CART cell therapy resulted in limited responses for LBCL. Locke F L, et al. *J Clin Oncol.* 2020; 38(suppl, abstr):8012. However, the clinical efficacy of retreatment in iNHL was unknown. This Example describes additional results associated with the ZUMA-5 clinical trial, particularly the retreatment of patients with relapsed/refractory indolent Non-Hodgkin Lymphoma with axicabtagene ciloleucel.

Patients were screened based on key eligibility criteria, including R/R FL (Grade 1-3a) or MZL (nodal or extranodal) and two or more prior lines of therapy, which included an anti-CD20 monoclonal antibody combined with an alkylating agent. After leukapheresis, patients received a conditioning regimen of cyclophosphamide 500 mg/m²/day and fludarabine 30 mg/m²/day for 3 days prior to the first treatment and then again prior to retreatment. Patients with stable disease (without relapse) >1 year from completion of last therapy were not eligible. At day zero, and then again at retreatment, patients received 2×10⁶ CAR T cells/kg. Patients were first evaluated at day 28. After progression, patients received conditioning chemotherapy and axicabtagene ciloleucel retreatment. Key eligibility criteria for retreatment included response of a CR or PR at the month 3 disease assessment with subsequent progression; no evidence of CD19 loss in progression biopsy by local review; and no Grade 4 CRS or neurologic events, or life-threatening toxicities with the first treatment. A total of 11 patients received retreatment, 9 of which had FL and 2 of which had MZL. The median retreatment follow-up was 2.3 months.

The patients' baseline characteristics are summarized in Table 43. Prior to first treatment, most retreated patients had high-risk disease characteristics. Out of the 13 patients with available data at relapse, 100% had detectable CD19. All patients who received retreatment were CD19-positive at relapse.

TABLE 43

Baseline Characteristics

| Characteristic | Nonretreated (n = 135) | Retreated (n = 11) | All Patients (N = 146) |
|---|---|---|---|
| Disease type, n (%) | | | |
| FL | 115 (85) | 9 (82) | 124 (85) |
| MZL | 20 (15) | 2 (18) | 22 (15) |
| Median age (range), y | 60 (34-79) | 62 (49-70) | 61 (34-79) |

TABLE 43-continued

Baseline Characteristics

| Characteristic | Nonretreated (n = 135) | Retreated (n = 11) | All Patients (N = 146) |
|---|---|---|---|
| ≥65, n (%) | 47 (35) | 4 (36) | 51 (35) |
| Male, n (%) | 76 (56) | 7 (64) | 83 (57) |
| Disease stage III-IV, n (%) | 117 (87) | 9 (82) | 126 (86) |
| ≥3 FLIPI score, n (%) | 58 (43) | 10 (91) | 68 (47) |
| High tumor bulk (GELF criteria), n (%)[a] | 62 (46) | 10 (91) | 72 (49) |
| Median no. of prior therapies (range) | 3 (1-10) | 4 (2-7) | 3 (1-10) |
| POD24 from first anti-CD20 mAb-containing therapy, n/n (%)[b] | 73/133 (55) | 6/11 (55) | 79/144 (55) |
| Refractory disease, n (%)[c] | 91 (67) | 9 (82) | 100 (68) |

[a]Disease burden, per GELF criteria: involvement of ≥3 nodal sites (≥3 cm diameter each); any nodal or extranodal tumor mass with ≥7 cm diameter; B symptoms; splenomegaly; pleural effusions or peritoneal ascites; cytopenias; or leukemia.
[b]24 months from initiation of first line of anti-CD20-containing immunochemotherapy to progression. Percentages are based on the number of patients who ever received anti-CD20-chemotherapy combination therapy.
[c]Patients with iNHL who progressed within 6 months of completion of the most recent prior treatment. FL, follicular lymphoma; FLIPI, Follicular Lymphoma International Prognostic Index; GELF, Groupe d'Etude des Lymphomes Folliculaires; iNHL, indolent non-Hodgkin lymphoma; mAb, monoclonal antibody; MZL, marginal zone lymphoma; POD24, progression of disease <24 months; SCT, stem cell transplantation.

In patients who were retreated, the ORR following the first treatment was 100% (91% CR rate). Table 44. The median first treatment DOR was 8.3 months. The ORR following retreatment was 100% (91% CR rate). The median DOR to retreatment was not reached. Responses were ongoing for 9 patients (82%) at data cutoff.

TABLE 44

Response to First Treatment and to Retreatment

| Pt No. | Tumor Type | 1st Treatment | | Retreatment Source | Retreatment | |
|---|---|---|---|---|---|---|
| 1 | FL | PR | 8.3 | 2nd bag | CR | 4.86[a] |
| 2 | FL | CR | 11.8 | Re-Aph | CR | 0.03[a] |
| 3 | FL | CR | 5.3 | PBMCs | PR | 2.27[a] |
| 4 | FL | CR | 11.5 | Re-Aph | CR | 5.22[a] |
| 5 | FL | CR | 5 | Re-Aph | CR | 0.03[a] |
| 6 | FL | CR | 1.9 | 2nd bag | CR | 4.90 |
| 7 | FL | CR | 10.9 | 2nd bag | CR | 8.41[a] |
| 8 | FL | CR | 4.8 | PBMCs | CR | 1.97[a] |
| 9 | FL | CR | 5 | Re-Aph | CR | 1.84[a] |
| 10 | MZL | CR | 10.6 | 2nd bag | CR | 8.31[a] |
| 11 | MZL | CR | 8.2 | 2nd bag | CR | 0.03 |

Duration of response was calculated as the time from initial overall response after retreatment to disease progression per the Lugano Classification1 or death from any cause. Patients not meeting criteria by data cutoff were censored at their last disease assessment before data cutoff or new anticancer therapy start date (including SCT), whichever was earlier. PBMCs refers to axicabtagene ciloleucel manufactured from frozen PBMCs collected during initial apheresis and were used in a 2nd round of manufacturing prior to retreatment. 2nd bag refers to a second bag of axicabtagene ciloleucel that was generated during the initial manufacturing. Re-Aph refers to axicabtagene ciloleucel that was manufactured from a 2nd round of apheresis and manufacturing prior to retreatment. [a]Response ongoing as of the data cutoff date. 1. Cheson BD, et al. J Clin Oncol. 2014; 32: 3059-68. 2nd bag, second bag produced from original manufacturing; axi-cel, axicabtagene-ciloleucel; CR complete response; DOR duration of response; FL, follicular lymphoma; MZL, marginal zone lymphoma; ORR, overall response rate; PBMC, peripheral blood mononuclear cells; PR partial response; Re-Aph, re-apheresis; SCT, stem cell transplantation.

Incidences of CRS and neurologic events were comparable at first treatment and at retreatment. Table 45. No Grade ≥3 CRS or neurologic events occurred with retreatment.

TABLE 45

| Adverse Event, n (%) | 1st Treatment (n = 11) | Retreatment (n = 11) |
|---|---|---|
| CRS | 7 (64) | 8 (73) |
| Grade 1 | 4 (36) | 6 (55) |
| Grade 2 | 3 (27) | 2 (18) |
| Grade 3 | 0 | 0 |
| Grade 4 | 0 | 0 |
| Neurologic events | 4 (36) | 4 (36) |
| Grade 1 | 3 (27) | 1 (9) |
| Grade 2 | 0 | 3 (27) |
| Grade 3 | 1 (9) | 0 |
| Grade 4 | 0 | 0 |

Adverse Events

Median peak levels of cytokines typically associated with severe CRS and neurologic events were numerically similar at first treatment and retreatment. Table 46.

TABLE 46

Cytokine Levels

| Peak Cytokine Levels (Range) | 1st Treatment (n = 11) | Retreatment (n = 11) |
|---|---|---|
| IL-6, pg/mL | 5.5 (1.6[a]-533.5) | 5.4 (1.6[a]-976.0[b]) |
| IL-2, pg/mL | 0.9[a] (0.9[a]-15.8) | 1.8 (0.9[a]-5.2) |
| IFN-γ, pg/mL | 64.2 (7.5[a]-1876.0[b]) | 62.9 (7.5[a]-1876.0[b]) |
| TNF-α, pg/mL | 5.8 (1.8-20.8) | 3.7 (2.2-21.4) |
| IL-IRA, pg/mL | 708.1 (377.1-9000.0[b]) | 757.0 (403.0-9000.0[b]) |
| GM-CSF, pg/mL | 1.9[a] (1.9[a]-11.6) | 1.9[a] (1.9[a]-10.1) |
| CCL2 (MCP-1), pg/mL | 949.7 (402.7-1500.0[b]) | 644.7 (355.9-1500.0[b]) |
| IL-15, pg/mL | 35.5 (26.3-64.3) | 37.0 (15.2-49.2) |
| CXCL10, pg/mL | 1085.8 (402.6-2000.0[b]) | 1179.4 (168.4-2000.0[b]) |
| Ferritin, ng/mL | 746.4 (245.2-9799.5) | 490.9 (178.9-12015.0) |

[a]Lower limit of quantification in assay used.
[b]Upper limit of quantification in assay used.
CCL, chemokine (C-C motif) ligand; CRS, cytokine release syndrome; CXCL, C-X-C motif chemokine ligand; GM-CSF, Granulocyte-macrophage colony-stimulating factor; IFN, interferon; IL, interleukin; MCP-1, monocyte chemoattractant protein 1; TNF, tumor necrosis factor.

Axicabtagene ciloleucel product characteristics were generally similar at first treatment and retreatment. The frequency of naïve+central memory T cells (CCR7+ cells) appeared higher in 3 of 4 samples from re-apheresis at retreatment, compared to first treatment. No differences in CD4/CD8 ratio, transduction efficiency, or IFN-γ in co-culture were observed between first treatment and retreatment. FIG. 106. Peak expansion was similar for patients with FL at retreatment as at first treatment (9.0 vs 13.2 cells/μL). CAR T cell expansion by $AUC_{0-28}$ appeared lower after retreatment than after 1st treatment in patients with FL and MZL, though this difference was not significant. Patients with FL who were retreated had significantly higher tumor burden (by SPD) before first treatment than non-retreated patients (3981 vs 2342 mm²). FIG. 107. Among patients with FL, those who received retreatment had lower median peak CAR T cell levels at 1st treatment than non-retreated patients (13.2 vs 41.9 cells/μL). Median peak expansion was also lower when normalized by SPD (0.003 vs 0.023 cells/μL×mm²). Patients with FL had lower tumor burden at retreatment than before first treatment (847 vs 3981 mm²). FIG. 108. Median peak CART cell levels were similar for patients with FL at retreatment as at first treatment (9.0 vs 13.2 cells/μL blood), remaining so when normalized to tumor burden. Median levels of cytokines typically associated with SPD appeared lower before retreatment than before first treatment in patients with FL (TNF-α, 1.4 vs 5.3 pg/mL; IL-2Rα, 1.6 vs 19.4 ng/mL).

Based on a limited sample, axicabtagene ciloleucel retreatment showed a 100% ORR in patients with iNHL, most of whom had high-risk disease characteristics. Responses were ongoing in 82% of patients at data cutoff. Responses with axicabtagene ciloleucel retreatment appeared favorable in patients with iNHL compared to those previously reported in aggressive lymphomas. Locke F L, et al. *J Clin Oncol.* 2020; 38(suppl, abstr):8012; Abramson J S, et al. *Lancet.* 2020; 396:839-852. Safety profiles, product characteristics, and CAR T cell expansion were largely similar at first treatment and retreatment. Tumor burden in patients with FL was significantly lower at retreatment compared to first treatment, supported by pretreatment cytokine levels. Patients with FL who were retreated had lower median peak CAR T cell levels and higher tumor burden before first treatment than non-retreated patients.

Example 25

As previously described in Example 18, ZUMA-9 (NCT03153462) is a multicenter, open-label expanded-access study to provide patients with relapsed/refractory LBCL with access to axicabtagene ciloleucel until commercial availability (Cohort 1) and out-of-specification (OOS) product (Cohort 2). Axicabtagene ciloleucel has been approved for treatment of adult patients with R/R LBCL after ≥2 prior lines of systemic therapy. In the ZUMA-1 study, the ORR was 82%, with a CR rate of 58%. Locke F L, et al. *Lancet Oncol.* 2019; 2019; 20:31-42. With 51 months of follow-up in the ZUMA-1 study of axicabtagene ciloleucel, the median OS was 25.8 months and the 4-year OS rate was 44%. Jacobson C A, et al. ASH 2020. #1187. Commercial specifications for axicabtagene ciloleucel were established based on statistical analysis of data from previous studies. This Example reports additional safety profile and efficacy of axicabtagene ciloleucel in Cohorts 1 and 2 and translational analyses in Cohort 2 of ZUMA-9. The outcomes were contextualized with the primary analysis of ZUMA-1 Cohorts 1+2. (n=101; ≥6 months of follow-up). Neelapu S S, et al. *N Engl J Med.* 2017; 377:2531-2544. ZUMA-1 has been described in more detail in earlier Examples (e.g., Examples 19-22). Briefly, in ZUMA-1, all the patients had histologically confirmed large B-cell lymphoma, including diffuse large B-cell lymphoma (cohort 1) and primary mediastinal B-cell lymphoma or transformed follicular lymphoma (cohort 2), on the basis of the 2008 World Health Organization guidelines. WHO classification of tumours of haematopoietic and lymphoid tissue. 4th ed. Geneva: World Health Organization, 2008. Table 47 describes the patients' baseline disease characteristics. In addition, in ZUMA-9 Cohort 2, 50% of patients had OOS product with low viability; 28% had high IFN-γ; 14% had low IFN-γ; 14% received low-dose CAR T cell infusion; and 6% of patients had high transduction ratio.

TABLE 47

| Characteristic | ZUMA-9 | | | | ZUMA-1 |
|---|---|---|---|---|---|
| Median age (range), years | 56 (28-76) | 61 (24-81) | 57.5 (30-81) | 55 (39-74) | 58 (23-76) |
| ≥65 years, n (%) | 10 (40) | 10 (28) | 5 (28) | 2 (20) | 24 (24) |
| DLBCL, n (%) | 20 (80) | 28 (78) | 13 (72) | 10 (100) | 77 (76) |
| Disease stage III/IV, n (%) | 18 (72) | 29 (81) | 12 (67) | 9 (90) | 86 (85) |
| ECOG 1/≥2, %/% | 48/0 | 58/17 | 72/11 | 30/10 | 58/0 |
| ≥3 prior lines of chemotherapy | 16 (64) | 25 (69) | 14 (78) | 6 (60) | 64 (64) |
| Prior ASCT, n (%) | 4 (16) | 15 (42) | 10 (56) | 5 (50) | 25 (25) |
| International prognostic index ≥3, n (%) | 11 (44) | 20 (56) | 7 (39) | 6 (60) | 48 (48) |
| Relapsed/Refractory subgroup, n (%) | | | | | |
| Primary refractory | 2 (8) | 6 (17) | 3 (17) | 3 (30) | 2 (2) |
| Relapsed or refractory ≥2$^{nd}$-line therapy | 21 (84) | 18 (50) | 7 (39) | 3 (30) | 78 (77) |
| Relapsed post-ASCT | 2 (8) | 12 (33) | 8 (44) | 4 (40) | 21 (21) |
| Received bridging therapy, n (%) | 5 (20) | 8 (22) | 4 (22) | 2 (20) | — |

ASCT, autologous stem cell transplantation; DLBCL, diffuse large B cell lymphoma; ECOG, Eastern Cooperative Oncology Group; IFN-y, interferon gamma; OOS, out-of-specification.

The ORR in ZUMA-9 by IRRC assessment was 76% (95% CI, 55-91) for Cohort 1, 53% (95% CI, 35-70) for Cohort 2, and 82% (95% CI 73-89) for ZUMA-1 Cohorts 1+2. FIG. 109. The median OS was 23.8 months (95% CI, 13.5-NE) for Cohort 1 and was not reached (95% CI, 3.4-NE) for Cohort 2, respectively. FIG. 110. The median OS for patients with low viability or high IFN-$\gamma$ in Cohort 2 was not reached (95% CI, 3.4-NE and 0.2-NE, respectively). FIG. 110.

Of the three Grade 5 AEs in Cohort 1, two were unrelated to axicabtagene ciloleucel (clostridial sepsis on Day 6 and respiratory failure on Day 212), and one was related to conditioning (myelodysplastic syndrome on Day 563). Of the three Grade 5 AEs in Cohort 2, two were unrelated to axicabtagene ciloleucel (multiple organ dysfunction syndrome on Day 60 and cardiac arrest on Day 482), and one was related to axicabtagene ciloleucel (systemic mycosis on Day 30). Table 48.

TABLE 48

Treatment-Emergent Adverse Events

| | ZUMA-9 | | | | ZUMA-1 |
|---|---|---|---|---|---|
| | | | Cohort 2 | | |
| TEAE | Cohort 1 (N = 25) | Overall (N = 36) | Low Viability (N = 18) | High IFN-γ (N = 10) | Cohorts 1 + 2 (N = 101) |
| Pyrexia | 20 (80) | 33 (92) | 17 (94) | 9 (90) | 86 (85) |
| Hypotension | 19 (76) | 22 (61) | 12 (67) | 5 (50) | 60 (59) |
| Fatigue | 13 (52) | 20 (56) | 9 (50) | 7 (70) | 52 (51) |
| Headache | 13 (52) | 20 (56) | 13 (72) | 3 (30) | 47 (47) |
| Anemia | 11 (44) | 18 (50) | 11 (61) | 5 (50) | 67 (66) |

TABLE 48-continued

Treatment-Emergent Adverse Events

| | ZUMA-9 | | | | ZUMA-1 |
|---|---|---|---|---|---|
| | | | Cohort 2 | | |
| TEAE | Cohort 1 (N = 25) | Overall (N = 36) | Low Viability (N = 18) | High IFN-γ (N = 10) | Cohorts 1 + 2 (N = 101) |
| Sinus tachycardia | 12 (48) | 15 (42) | 10 (56) | 3 (30) | 22 (22) |
| White blood cell count decreased | 7 (28) | 15 (42) | 8 (44) | 3 (30) | 31 (31) |
| Neutrophil count decreased | 6 (24) | 14 (39) | 8 (44) | 3 (30) | 32 (32) |
| Diarrhea | 7 (28) | 13 (36) | 6 (33) | 4 (40) | 43 (43) |
| Neutropenia | 6 (24) | 13 (36) | 9 (50) | 3 (30) | 44 (44) | aTEAEs shown in the table were those that occurred in ≥35% of patients in ZUMA-9 Cohort 2. AE, adverse event; CRS, cytokine release syndrome; TEAE, treatment-emergent adverse event As of data cutoff, all CRS events resolved in ZUMA-9 Cohort 1, and most CRS (29/30) resolved in ZUMA-9 Cohort 2. There were no Grade 5 CRS events in ZUMA-9 Cohort 1 or Cohort 2. Table 49.

TABLE 49

| | | ZUMA-9 | | | ZUMA-1 |
| | | | Cohort 2 | | |
| Parameter | Cohort 1 (N = 25) | Overall (N = 36) | Low Viability (N = 18) | High IFN-γ (N = 10) | Cohorts 1 + 2[b] (N = 101) |
|---|---|---|---|---|---|
| Cytokine Release Syndrome | | | | | |
| CRS, n (%)[a] | | | | | |
| Any grade | 21 (84) | 30 (83) | 15 (83) | 9 (90) | 94 (93) |
| Grade ≥3 | 0 | 1 (3) | 0 | 1 (10) | 13 (13) |
| Most common symptoms of any grade, n (%) | | | | | |
| Pyrexia | 20 (95) | 29 (97) | 14 (93) | 9 (100) | 77 (76) |
| Hypotension | 10 (48) | 15 (50) | 10 (67) | 4 (44) | 41 (41) |
| AE management, n (%) | | | | | |
| Tocilizumab | 10 (40) | 12 (33) | 6 (33) | 4 (40) | 17 (17) |
| Corticosteroids | 1 (4) | 5 (14) | 3 (17) | 2 (20) | 6 (6) |
| Median time to onset (range), days | 3 (1-16) | 6 (1-13) | 6 (1-13) | 5 (1-10) | 2 (1-12) |
| Median duration of events (range), days | 6 | 7 | 8 | 6.5 | 8 |
| Patients with resolved events, n/n (%)[c] | 21/21 (100) | 29/30 (97) | 15/15 (100) | 8/9 (89) | 93/94 (99) |

[a]Overall CRS is graded according to a modification of the criteria of Lee DW, et al. *Blood.* 2014; 124: 188-195.
[b]Between the ZUMA-1 Cohorts 1 + 2 primary analysis shown here and subsequent published updates, the definition of treatment-emergent AEs changed from time since conditioning to time since axicabtagene ciloleucel infusion. Later data updates report one fewer patient with CRS than shown here.
[c]Percentages are calculated as the number of patients with resolved events out of the number of patients with events. AE, adverse event; CRS, cytokine release syndrome; IFN-γ, interferon gamma All NEs resolved in ZUMA-9 Cohort 1, and most NEs (19/24) resolved in ZUMA-9 Cohort 2 as of the data cutoff date. There were no Grade 5 NEs in ZUMA-9 Cohort 1 or Cohort 2. Table 50.

TABLE 50

| | | ZUMA-9 | | | ZUMA-1 |
| | | | Cohort 2 | | |
| Parameter | Cohort 1 (N = 25) | Overall (N = 36) | Low Viability (N = 18) | High IFN-γ (N = 10) | Cohorts 1 + 2[b] (N = 101) |
|---|---|---|---|---|---|
| Neurologic Events | | | | | |
| NE, n (%)[a] | | | | | |
| Any grade | 19 (76) | 24 (67) | 16 (89) | 6 (60) | 65 (64) |
| Grade ≥3 | 9 (36) | 7 (19) | 7 (39) | 0 | 28 (28) |
| Most common symptoms of any grade, n (%) | | | | | |
| Encephalopathy | 7 (28) | 5 (14) | 4 (22) | 1 (10) | 34 (34) |
| Confusional state | 10 (40) | 10 (28) | 9 (50) | 1 (10) | 29 (29) |
| AE management, n (%) | | | | | |
| Tocilizumab | 5 (20) | 3 (8) | 1 (6) | 2 (20) | 33 (33) |
| Corticosteroids | 9 (36) | 8 (22) | 4 (22) | 3 (30) | 15 (15) |
| Median time to onset (range), days | 7 (2-23) | 9 (1-84) | 9 (1-38) | 9 (6-84) | 5 (1-17) |
| Median duration of events (range), days | 11 | 12 | 14.5 | 9 | 12 |
| Patients with resolved events, n/n (%)[c] | 19/19 (100) | 19/24 (79) | 12/16 (75) | 6/6 (100) | 60/65 (92) |

[a]NEs are identified based on Topp MS, et al. Lancet. 2015; 16: 57-66.
[b]Between the ZUMA-1 Cohorts 1 + 2 primary analysis shown here and subsequent published updates, the definition of treatment-emergent AEs changed from time since conditioning to time since axicabtagene ciloleucel infusion. Later data updates report one fewer patient with NEs than shown here.
[c]Percentages are calculated as the number of patients with resolved events out of the number of patients with events. AE, adverse event; IFN-γ, interferon gamma; NE, neurological events.

Axicabtagene ciloleucel in ZUMA-9 Cohort 2 contained fewer, less differentiated CCR7+ $T_N$ and $T_{CM}$ and a greater proportion of more differentiated CCR7– $T_{EM}$+ $T_{EFF}$ cells than ZUMA-1 Cohorts 1+2, possibly contributing to the observed differences in expansion. Table 51.

TABLE 51

Peak CAR T Cell Levels and Median CAR T Cell Expansion

| Biomarkers | ZUMA-9 Cohort 2 | | | ZUMA-1 |
| | Overall (N = 36) | Low Viability (N = 18) | High IFN-γ (N = 10) | Cohorts 1 + 2 (N = 101) |
|---|---|---|---|---|
| Median peak CAR T cell level (range), cells/μL | 12 (0-442) | 15 (6.51 × 10⁻³–264) | 13 (0-182) | 42 (1-1514) |
| Responders[a] | 16 (1-72) | — | — | 46 (1.5-1514) |
| Nonresponders[b] | 3 (0-182) | — | — | 11 (0.8-322.5) |
| Median $AUC_{0-28}$ (range), cells/μL × days | 112 (0-3413) | 169 (<1-942) | 161 (0-1662) | 462 (5-14,329) |
| Median peak serum IFN-γ (range), pg/mL | 170 (n = 33) (8-1876) | 287 (n = 16) (7.5-1876) | 155 (n = 10) (7.5-1876) | 477 (n = 101) (8-8209) |
| CCR7+ [$T_N$ + $T_{CM}$]/ CCR7– [$T_{EM}$ + $T_{EFF}$], ratio (range) | 0.3 (0.05-2.6) | 0.5 (0.06-2.6) | 0.2 (0.07-0.9) | 0.7 (0.2-5.7) |

[a]Responders are defined as subjects experiencing best response of partial or complete response.
[b]Nonresponders are defined as subjects experiencing best response of stable or progressive disease. AE, adverse event; AUC, area under the curve; CAR, chimeric antigen receptor; CCR7, chemokine receptor 7; CRP, C-reactive protein; IFN-γ, interferon gamma; TCM, central memory T cell phenotype; $T_{EFF}$, effector T cell phenotype; $T_{EM}$, effector memory T cell phenotype; $T_N$, naïve T cell phenotype.
Axicabtagene ciloleucel treatment showed a manageable safety profile and meaningful clinical benefit in this expanded-access and OOS product study, although the numbers of patients in the OOS cohort were limited due to the high manufacturing success of axicabtagene ciloleucel. CAR T cell therapy showed clinical benefit and lower CR rate in Cohort 2 (OOS product), and there appeared to be lower CAR T cell expansion and a more differentiated product than in ZUMA-1 Cohorts 1 + 2.

Example 26

ZUMA-12 (NCT03761056) is a Phase 2, multicenter, open-label, single-arm study of axicabtagene ciloleucel as part of first-line therapy in patients with high-risk LBCL. It has been previously described in Example 12. Patients with high-risk LBCL have poor outcomes, including lower response rates and poorer OS. Patients with high-risk LBCL have poor outcomes, including lower response rates and poorer OS. Patients with early disease resistance (assessed by dynamic PET) after first-line rituximab-based chemoimmunotherapy have an increased risk of death. Mamot C, et al. *J Clin Oncol.* 2015; 33(23):2523-2529; Casasnovas R O, et al. *Blood.* 2017; 130(11):1315-1326. Presented here are updated efficacy, safety, and PK results following from a planned interim analysis of the ZUMA-12 study. The results are compared to those of the ZUMA-1 study, described in various examples of this application (e.g., Examples 20-22). Axicabtagene ciloleucel has been approved for treatment of adults with R/R LBCL after ≥2 lines of systemic therapies based on ZUMA-1. With a median of 51.1 months of follow-up in ZUMA-1, the median OS was 25.8 months; 4-year OS rate was 44%. Jacobson C A, et al. ASH 2020. #1187.

For ZUMA-12, eligible adults (≥18 years old, ECOG PS 0-1) met two criteria for high-risk LBCL: i) High-grade B cell lymphoma, with MYC and BCL2 and/or BCL6 translocations or DLBCL with International Prognostic Index (IPI) score ≥3; before enrollment and ii) positive interim positron emission tomography (PET) per Lugano Classification (Cheson, et al. *J Clin Oncol.* 2014; Deauville criteria [DC] 4 or 5) after 2 cycles of an anti-CD20 monoclonal antibody and anthracycline containing regimen, which served as a dynamic risk assessment. 32 patients underwent leukapheresis (≥2 weeks after prior systemic therapy) and some had optional non-chemotherapy bridging therapy (administered after leukapheresis and completed prior to initiating conditioning chemotherapy) at investigator discretion (PET-CT was required after bridging), all of which were followed by conditioning chemotherapy (cyclophosphamide 500 mg/m²/day and fludarabine 30 mg/m²/day for 3 days at days –5, –4, and –3) and a single axicabtagene ciloleucel infusion (target dose, 2×10⁶ CAR T cells/kg) on day 0. 5 patients were not treated, of which 3 were awaiting axicabtagene ciloleucel infusion as of data cutoff (Aug. 25, 2020), 1 requested no treatment, an one withdrew from the study due to additional biopsy which revealed a second primary tumor. The primary endpoint was investigator-assessed complete response (CR) rate per Lugano Classification (Cheson B D, et al. *J Clin Oncol.* 2014; 32:3059-3068). 32 patients were safety-evaluable (includes all treated patients who received any dose of axicabtagene ciloleucel who have ≥1 month of follow-up) and the median follow-up was 9.5 months (range 0.9-18). 27 patients were efficacy evaluable (includes all treated patients with centrally confirmed disease type (double-/triple-hit lymphomas) or IPI score ≥3 who received ≥1×10⁶ CART cells/kg and have ≥1 month of follow-up) and the median follow-up was 9.3 months (range 0.9-18). Key secondary endpoints included objective response rate (ORR), duration of response (DOR), event-free survival (EFS), progression-free survival (PFS), overall survival (OS), frequency of adverse events (AEs), and levels of CAR T cells and cytokines in blood and serum. The baseline patient characteristics are summarized in Table 52.

TABLE 52

Baseline Patient Characteristics

| Characteristic | N = 32 | |
|---|---|---|
| Median age (range), years | 61 | (23-86) |
| ≥65 years, n (%) | 13 | (41) |
| Male, n (%) | 23 | (72) |
| Stage IV disease, n (%) | 18 | (56) |
| ECOG PS ≥1, n (%) | 21 | (66) |
| One prior line of systemic therapy, n (%) | 32 | (100) |
| Translocations per investigator, n (%) | | |
| c-MYC | 19 | (59) |
| BCL-2 | 26 | (81) |
| BCL-6 | 20 | (63) |
| DH/TH as determined by FISH per investigator, n (%) | 17 | (53) |
| IPI score ≥3 | 23 | (72) |
| Deauville five-point scale, n (%) | | |
| 4 | 16 | (50) |
| 5 | 16 | (50) |

BCL, B cell lymphoma; DH, double-hit; ECOG PS, Eastern Cooperative Oncology Group performance status; FISH, fluorescent in situ hybridization; IPI, International Prognostic Index; TH, triple-hit.

In the safety analysis set (n=32), the ORR was 88%, the CR (n=20) rate was 78% and the PR (n=3) rate was 11%.

15% (n=4) of the patients had SD and 0% (n=0) had PD. 27 patients were response evaluable. Table 53. Median PFS, median OS, and median DOR were not reached after a median follow-up of 9.3 months. FIG. 111.

TABLE 53

Response Evaluation

| | Response Evaluable N = 27[b] |
|---|---|
| Median follow-up (range), mo | 9.3 (0.9-18.0) |
| Patients with ≥6 mo follow-up, n (%) | 19 (70) |
| Patients with ongoing response | 19 (70) |
| Median time to response (range), mo | |
| Initial objective response | 1.0 (0.9-3.1) |
| CR | 1.0 (0.9-6.4) |
| Patients converted from PR/SD to CR, n (%) | 5 (19) |
| PR to CR | 4 (15) |
| SD to CR | 1 (4) |

CAR chimeric antigen receptor; CR complete response; ORR, objective response rate; PD, progressive disease; PR partial response; SD, stable disease.

The most common axicabtagene ciloleucel-related Grade ≥3 AEs were encephalopathy (16%), alanine aminotransferase increased (9%), and neutrophil count decreased (9%). One Grade 5 AE occurred on the study due to COVID-19. Table 54.

TABLE 54

Treatment-Emergent Adverse Events

| AE, n (%)[a] | N = 32 | | | | | |
|---|---|---|---|---|---|---|
| | Any | Grade 1 | Grade 2 | Grade 3 | Grade 4 | Grade 5 |
| Any TEAE | 32 (100) | 1 (3) | 5 (16) | 7 (22) | 18 (56) | 1 (3) |
| Pyrexia | 32 (100) | 8 (25) | 24 (75) | 0 (0) | 0 (0) | 0 (0) |
| Headache | 24 (75) | 16 (50) | 8 (25) | 0 (0) | 0 (0) | 0 (0) |
| Fatigue | 18 (56) | 7 (22) | 11 (34) | 0 (0) | 0 (0) | 0 (0) |
| Diarrhea | 15 (47) | 9 (28) | 6 (19) | 0 (0) | 0 (0) | 0 (0) |
| Nausea | 15 (47) | 7 (22) | 8 (25) | 0 (0) | 0 (0) | 0 (0) |
| Neutrophil count decreased | 15 (47) | 0 (0) | 1 (3) | 1 (3) | 13 (41) | 0 (0) |
| White blood cell count decreased | 15 (47) | 0 (0) | 1 (3) | 2 (6) | 12 (38) | 0 (0) |
| Encephalopathy | 10 (31) | 2 (6) | 2 (6) | 4 (13) | 2 (6) | 0 (0) |
| Hypotension | 10 (31) | 6 (19) | 3 (9) | 1 (3) | 0 (0) | 0 (0) |
| Sinus tachycardia | 10 (31) | 9 (28) | 1 (3) | 0 (0) | 0 (0) | 0 (0) |

[a]Table displays any-grade TEAEs that occurred in >30% of patients. AEs were coded using MedDRA v23.0 and graded per National Cancer Institute's CTCAE v5.0.

AE, adverse event; axi-cel, axicabtagene ciloleucel; CTCAE, Common Terminology Criteria for Adverse Events; MedDRA, Medical Dictionary for Regulatory Activities; TEAE, treatment-emergent adverse event.

No Grade 4 and 5 CRS occurred. Table 55. Grade 4 NEs occurred in 2 (6%) patients (both encephalopathy and both resolved[a]) and no Grade 5 NEs occurred. Table 56. The 2 unresolved NE events at data cutoff were Grade 1 tremor and Grade 1 memory impairment.

TABLE 55

Cytokine Release Syndrome

| Parameter | N = 32 |
|---|---|
| CRS, n (%)[a] | |
| Any grade | 32 (100) |
| Grade ≥3 | 3 (9) |
| Most common symptoms of any grade CRS, n (%) | |
| Pyrexia | 32 (100) |
| Chills | 8 (25) |
| Hypotension | 8 (25) |
| AE management for CRS, n (%) | |
| Tocilizumab | 17 (53) |
| Steroids | 8 (25) |
| Median time to onset (range), days | 4.0 (1-10) |
| Median duration of events, days | 6.0 (1-13) |
| Patients with resolved events, n/N (%) | 32/32 (100) |

[a]CRS was graded per Lee D W, et al. *Blood.* 2014; 124: 188-195. Individual symptoms of CRS were graded per National Cancer Institute's CTCAE v5.0.
AE, adverse event; CRS, cytokine release syndrome; CTCAE, Common Terminology Criteria for Adverse Events.

TABLE 56

Neurologic Events

| Parameter | N = 32 |
|---|---|
| NE, n (%) | |
| Any grade | 22 (69) |
| Grade ≥3 | 8 (25) |
| Most common any grade symptoms of NE, n (%) | |
| Encephalopathy | 10 (31) |
| Confusional state | 9 (28) |
| AE management for NE, n (%) | |
| Tocilizumab | 0 (0) |
| Steroids | 11 (34) |
| Median time to onset (range), days | 9.0 (2-44) |
| Median duration of events, days | 6.0 (1-54) |
| Patients with resolved events, n/N (%) | 20/22 (91) |

[a] No patients needed mechanical ventilation.
AE, adverse event; NE, neurological event.

There was a higher frequency of naïve T cells in the ZUMA-12 product compared with the product in ZUMA-1. Table 57. In addition, CAR T cell expansion was greater in ZUMA-12 patients compared with ZUMA-1 patients. Table 57.

TABLE 57

Product Characteristics

| Parameter<br>Median (Range) | ZUMA-12[a]<br>(N = 32) | ZUMA-1 Cohort 1[b]<br>(N = 77) |
|---|---|---|
| Total no. of T cells infused × $10^6$, n | 306.11 (169.01-603.03) | 295.28 (149.07-760.46) |
| Total no. of $T_N$ cells[c] infused × $10^6$, n | 105.02 (35.12-254.29) | 40.47 (2.09-214.95) |
| Total no. of CAR T cells infused × $10^6$, n | 170.00 (95.0-200.0) | 160.00 (96.00-200.00) |
| Transduction rate, % | 56.50 (30.00-76.00) | 55.30 (22.40-85.10) |
| IFN-γ level, pg/mL | 3932 (529.00-14,700) | 5826 (858.00-17,800) |
| Viability, % | 93.00 (85.00-97.00) | 94.20 (83.50-97.40) |
| CD4/CD8 ratio | 1.25 (0.21-8.42) | 1.06 (0.03-5.81) |
| Naïve T cells[c], % | 34.45 (6.50-76.30) | 14.20 (1.00-76.00) |
| $(T_N + T_{CM})/(T_{EM} + T_{EFF})$[c] ratio | 1.79 (0.23-15.39) | 0.78 (0.18-5.67) |

[a]ZUMA-12 includes all treated patients who received any dose of axicabtagene ciloleucel who have ≥1 month of follow-up.

[b]ZUMA-1 Cohort 1 data are presented, as this cohort enrolled patients with DLBCL, including some with HGBCL (though not an inclusion criterion). Data include all treated patients who received any dose of axicabtagene ciloleucel and have ≥24 months of follow-up.

[c]Data are reported based on the total number of T cells infused and the CAR + T cell population.

Axi-cel, axicabtagene ciloleucel; CAR, chimeric antigen receptor; DLBCL, diffuse large b cell lymphoma; HGBCL, high grade B cell lymphoma; IFN, interferon; $T_{CM}$, central memory T cell; $T_{EFF}$, effector T cell; $T_{EM}$, effector memory T cell; $T_N$, naïve T cell.

The median time to peak levels of CAR T cells in blood was 8 days for ZUMA-12. FIG. 112. PK were similar in patients with double- or triple-hit lymphoma and DLBCL with IPI score ≥3. Median tumor burden was lower in ZUMA-12 versus ZUMA-1 Cohort 1 (2091 mm$^2$ versus 3684 mm$^2$, respectively. FIG. 113. The blood levels of various cytokines were associated with severe NEs (e.g., IL-6, IL-5, IFN-γ, IL-8) and CRS (e.g., IL-6, IL-8, VCAM-1, GM-CSF). Cytokines associated with NEs and CRS were selected for having median ratio >2 after taking the ratio of median peak levels in Grade ≥3 events to Grade <3 events. FIG. 114.

ZUMA-12 is the first study evaluating CART cell therapy as first-line therapy in high-risk LBCL, defined by both histology and/or IPI and dynamic risk assessment with PET scan. Axicabtagene ciloleucel shows substantial clinical benefit in patients with an unmet medical need. In this analysis, patients experienced high ORR (85%) and CR (74%) rates. 83% of patients have ongoing response after median follow-up of 9.5 months. The study also provides new insights into the pharmacology of CAR T cell therapy for patients exposed to fewer prior therapies.

Example 27

This Example provides an update to Examples 17 and 25. ZUMA-5 is a registrational Phase 2 study of the anti-CD19 CAR T-cell therapy Axicabtagene ciloleucel in patients with R/R iNHL (follicular lymphoma [FL] and marginal zone lymphoma [MZL]). With a 17.5-month median follow-up in the primary analysis (Jacobson et al. ASH 2020. #700), 92% of patients responded (76% complete response [CR] rate). Patients with FL had lower rates of Grade ≥3 neurologic events (NEs; 15%) than patients with MZL (41%). This Example describes axicabtagene ciloleucel product attributes and pharmacologic characteristics associated with clinical outcomes in ZUMA-5. Associations with axicabtagene ciloleucel product attributes, levels of CAR T cells and biomarkers in blood, and CD19 expression in tumor biopsies at progression were analyzed with previously described methods (Neelapu et al. *New Engl J Med.* 2017; Locke et al. *Blood Adv.* 2020). Patients with FL (n=124) and MZL (n=22) treated with axicabtagene ciloleucel were included (median follow-up 17.5 months).

In patients with FL, the numbers of total infused CCR7+ CD45RA+ T cells in axicabtagene ciloleucel and peak CAR T-cell levels positively associated with ongoing response (P=0.0044; P=0.0212). When normalized to tumor burden (sum of product diameters [SPD]), the numbers of CCR7+ CD45RA+ T cells and peak CAR T-cell levels associated with both CR (P=0.0217; P=0.0383) and ongoing response (P=0.0065; P=0.0184). Similar trends were shown in patients with MZL. In patients with FL, the numbers of CCR7+CD45RA+ T cells and peak CAR T-cell levels positively associated with Grade ≥2 cytokine release syndrome (P=0.0398; P<0.0001) and Grade ≥3 NEs (P=0.0356; P=0.0032). Pretreatment levels of regulatory T (Treg) cell-related chemoattractants CCL22/MDC and CCL17; immune-modulating factors IL-10, IL-16, and IL-2Rα; and inflammatory marker TNF-α were higher in patients with FL who relapsed post-axicabtagene ciloleucel. Patients with FL had higher pretreatment levels of CCL17 than those with MZL. Peak levels of immune-modulating factors IL-6 and IFN-γ; inflammatory markers SAA and CRP; homeostatic marker IL-2; and chemokine CXCL10 positively associated with ongoing response in patients with FL. While peak CAR T-cell levels were comparable in patients with FL and MZL, patients with FL had lower CAR T peak normalized to SPD, as well as posttreatment levels of inflammatory GM-CSF; immune-modulating IL-6, IL-10, IFN-γ; homeostatic IL-2; chemokines CCL2/MCP-1 and CXCL10; and effector granzyme B than patients with MZL. All evaluable tumor samples from patients with iNHL at progression (12 FL; 1 MZL) retained CD19 expression.

In patients with FL, the numbers of CCR7+CD45RA+ T cells in axicabtagene ciloleucel associated positively with efficacy and toxicity, while Treg cell chemotaxis associated negatively with ongoing response. Differences in pre- and post-treatment levels of select disease-related biomarkers corroborated the favorable safety profile of axicabtagene ciloleucel in patients with FL compared with MZL.

Example 28

This Example is related to Examples 17, 25, and 27. ZUMA-5 is a registrational Phase 2 study of the anti-CD19 CAR T-cell therapy axicabtagene ciloleucel in patients with R/R iNHL (follicular lymphoma [FL] and marginal zone lymphoma [MZL]). In 11 patients retreated with axicabtagene ciloleucel in the primary analysis, the overall response rate (ORR) at a median 2.3 months post-retreatment was 100% (91% complete response [CR] rate), with no Grade ≥3 cytokine release syndrome (CRS) or neurologic events (NEs). This Example reports updated clinical and translational outcomes in patients retreated with axicabtagene ciloleucel. Eligible adults with FL or MZL had R/R disease after ≥2 lines of therapy. Patients were considered for retreatment if they progressed after a response at month 3, had no evidence of CD19 loss in progression biopsy per investigator, and had no Grade 4 CRS or NEs with first treatment. At both treatments, patients received axicabtagene ciloleucel (2×10$^6$ CAR T cells/kg) after conditioning chemotherapy.

As of Sep. 14, 2020, 13 patients with iNHL (11 FL; 2 MZL) received axicabtagene ciloleucel retreatment. Before the first treatment, patients had a median of 4 prior lines of therapy; 85% had stage 3-4 disease; 77% had ≥3 FLIPI; 46% had POD24; 77% had refractory disease. At first treatment, the ORR was 92% (85% CR rate). Median duration of response (DOR) was 8.2 months. Following retreatment, the ORR was 100% (77% CR rate). The median DOR after 11.4 months median follow-up post-retreatment was not reached; 46% of retreated patients had ongoing responses at data cutoff. At first treatment, CRS occurred in 9 patients (5 Grade 1, 4 Grade 2) and NEs occurred in 5 (3 Grade 1, 1 Grade 2, 1 Grade 3). At retreatment, CRS occurred in 8 patients (6 Grade 1, 2 Grade 2); NEs occurred in 4 (3 Grade 1, 1 Grade 2). The median peak levels of biomarkers typically associated with severe CRS and NEs were similar at retreatment and first treatment (IL-6, 7.7 vs 5.7 pg/mL; IL-2, 1.8 vs 0.9 pg/mL; IFN-γ, 62.9 vs 64.2 pg/mL). Among patients with FL before first treatment, 11 retreatment patients had higher tumor burden (median sum of product diameters [SPD]) than 113 nonretreatment patients (4770 vs 2303 mm$^2$). The median peak CAR T-cell level at first treatment appeared lower in retreatment vs nonretreatment patients (14.3 vs 38.3 cells/μL), remaining lower relative to SPD (0.005 vs 0.02 cells/μL×mm$^2$). Retreatment patients had lower total infused CCR7+CD45RA+ T cells in the axicabtagene ciloleucel product (8.9×10$^6$ vs 19.1×10$^6$ cells) and peak IL-2 levels (0.9 vs 3.3 μg/mL) vs nonretreatment patients. Of 13/26 patients with available data at relapse, 100% had detectable CD19. In the 11 retreatment patients with FL, the median SPD was lower before retreatment than first treatment (1416 vs 4770 mm²). The median peak CAR T-cell level appeared lower at retreatment vs first treatment (5.2 vs 14.3 CAR+ cells/μL blood), though similar relative to SPD (0.003 vs 0.005 cellsμL×mm²). The median frequency of CCR7+ T cells appeared higher in product from retreatment vs first treatment (45% vs 28%).

Axicabtagene ciloleucel retreatment exhibited 100% ORR in patients with iNHL (77% CR rate); responses were durable in nearly half of patients. At first treatment, CAR T-cell expansion and infused CCR7+CD45RA+ T cells appeared lower in retreatment patients vs nonretreatment patients. Maintained CD19 expression at relapse, along with durable responses and manageable safety, support axicabtagene ciloleucel retreatment in iNHL.

Example 29

This Example is an update to Example 19. ZUMA-1 is the pivotal, multicenter, single-arm Phase ½ study in which axicabtagene ciloleucel, an autologous anti-CD19 CAR T-cell therapy, was evaluated in patients with refractory LBCL. In the 6-month ZUMA-1 primary analysis (median follow-up, 8.7 months). Investigator-assessed ORR was 82%, and the CR rate was 54%. Grade ≥3 CRS and NEs were reported in 13% and 28% of patients, respectively. With median of 51.1 months of follow-up, median OS was 25.8 months, and the KM estimate of the 4-year OS rate was 44%. With increased safety experience, the management of CRS and NEs has been under evaluation. In safety management Cohort 4, levetiracetam prophylaxis and earlier corticosteroid and/or tocilizumab use appeared to reduce Grade ≥3 CRS and NE rates, without affecting CAR T-cell expansion or ongoing response rates. To build on the rationale of Cohort 4, Cohort 6 was added to determine if addition of prophylactic corticosteroids to the Cohort 4 toxicity management regimen could further reduce the incidence and severity of CRS and NE. Presented here is the 6-month primary analysis of Cohort 6 supported by propensity score-based comparison of outcomes in Cohort 6 and Cohorts 1+2 to enable an accurate comparison of patients with highly similar characteristics across the 2 studies. FIG. 115.

The primary analyses were done with data cutoff dates of Jan. 27, 2017 for Cohorts 1+2 (Neelapu S S, et al. N Engl J Med. 2017; 377:2531-2544) and Jun. 16, 2020 for Cohort 6. The median follow-up times were 8.7 months for Cohorts 1+2 and 8.9 months for Cohort 6. An exploratory propensity score analysis was performed. Propensity score-matched comparisons (Rosenbaum P R, Rubin D B. Biometriks. 1983; 70:41-55) were performed to compare clinical safety, efficacy, and PK profiles of patients in Cohort 6 and Cohorts 1+2 after balancing for known baseline disease characteristics: tumor burden, IPI score, number of prior lines of chemotherapy, disease stage and LDH level. Propensity score matching was used to select matching patient subgroups from Cohorts 1+2 and Cohort 6.

The different cohorts were subjected to different protocols of adverse event management. FIG. 116. The guidelines for adverse event management in Cohort 6 with tocilizumab and corticosteroids are summarized in Table 58.

TABLE 58

Tocilizumab and Corticosteroid Guidelines for AE Management in Cohort 6.

| CRS Grade | Tocilizumab Dose[a] | Corticosteroid Dose[a] |
|---|---|---|
| 1 | 8 mg/kg over 1 hour[b] if no improvement after 24 hours of supportive care; repeat every 4-6 hours as needed | Dexamethasone 10 mg ×1 if no improvement after 3 days |
| 2 | 8 mg/kg over 1 hour[b]; repeat every 4-6 hours as needed | Dexamethasone 10 mg ×1 |
| 3 | Per Grade 2 | Methylprednisolone 1 mg/kg IV twice daily or equivalent dexamethasone dose |
| 4 | Per Grade 2 | Methylprednisolone 1000 mg/d IV for 3 days |

| NE Grade | Tocilizumab Dose | Corticosteroid Dose |
|---|---|---|
| 1 | N/A | Dexamethasone 10 mg ×1 |
| 2 | Only in the case of concurrent CRS; 8 mg/kg over 1 hour; repeat every 4-6 hours as needed | Dexamethasone 10 mg 4×/day |
| 3 | Per Grade 2 | Methylprednisolone 1 g once daily |
| 4 | Per Grade 2 | Methylprednisolone 1 g twice daily |

[a]Therapy to be tapered on improvement of symptoms at investigator's discretion;
[b]Not to exceed 800 mg;
AE, adverse event;
CRS, cytokine release syndrome;
IV, intravenous;
N/A, not applicable;
NE, neurologic event The baseline patient characteristics are summarized in Table 59. Twenty-one patients (53%) received bridging therapy prior to axicabtagene ciloleucel.

TABLE 59

Baseline patient characteristics

| Characteristic | Cohort 6 (N = 40) |
|---|---|
| Disease stage IV, n (%) | 16 (40) |
| No. of prior lines of chemotherapy, % 1 \| 2 \| 3 \| 4 \| 5 | 5 \| 58 \| 30 \| 5 \| 3 |
| Prior SCT, n (%) | 10 (25) |
| PD as best response to most recent chemotherapy[a], n (%) | 17 (43) |
| Median tumor burden by SPD (range), mm$^2$ | 1184 (116-17,057) |
| Median LDH (range), U/L | 236 (155-2042) |
| Refractory subgroup, n (%) | |
| Primary refractory | 2 (5) |
| Refractory to ≥2L therapy | 23 (58) |
| Relapsed after ≥2L therapy | 7 (18) |
| Relapsed post-ASCT | 8 (20) |

[a]For patients who had not relapsed post-ASCT;
2L, second line;
ASCT, autologous stem cell transplantation;
LDH, lactate dehydrogenase;
PD, progressive disease
SCT, stem cell transplantation;
SPD, sum of product diameters Key CAR T-cell product characteristics were examined. Table 60.

TABLE 60

Axicabtagene ciloleucel product characteristics

| Parameter Median (Range) | Cohort 6 (N = 40) |
|---|---|
| Total no. of T cells infused × 10$^6$ | 261 (132-632) |
| Total no. of CAR T cells infused × 10$^6$ | 160 (95-200) |
| Percent transduction, % | 62 (19-91) |
| IFN-γ level in coculture, pg/mL | 5767 (588-14,000) |
| Viability, % | 93 (68-97) |
| CD4/CD8 ratio | 0.8 (0.1-13.9) |
| Naive (CCR7 + CD45RA+) T cells, % | 27.8 (7.1-70.6) |
| Central memory (CCR7 + CD45RA−) T cells, % | 15.2 (2.1-38.2) |

CAR, chimeric antigen receptor;
CCR7, C-C chemokine receptor type 7;
IFN, interferon The primary end points were incidence and severity of adverse events. Table 61. The severity of CRS and NEs were graded per Lee et al criteria (*Blood.* 2014; 124:188-195) and Common Terminology Criteria for Adverse Events version 4.03, respectively. There were no Grade ≥3 CRS in Cohort 6. There were also no Grade 5 NEs occurred in Cohort 6 as of the data cutoff date. 27/40 patients (68%) did not experience either CRS or NEs within 72 hours (Days 0-3) of axicabtagene ciloleucel infusion.

TABLE 61

Incidence and severity of CRS and NEs.

| | Cohort 6 (N = 40) |
|---|---|
| CRS, n (%) | 32 (80) |
| Worst Grade 1 | 14 (35) |

TABLE 61-continued

Incidence and severity of CRS and NEs.

| | Cohort 6 (N = 40) |
|---|---|
| Worst Grade 2 | 18 (45) |
| Worst Grade ≥3 | 0 (0) |
| Median time to onset (range), days | 5 (1-15) |
| Median duration (range), days | 4 (1-11) |
| NE, n (%) | 23 (58) |
| Worst Grade 1 | 10 (25) |
| Worst Grade 2 | 8 (20) |
| Worst Grade ≥3 | 5 (13) |
| Median time to onset (range), days | 6 (2-162) |
| Median duration (range), days | 19 (1-103) |

Axi-cel, axicabtagene ciloleucel;
CRS, cytokine release syndrome;
NE, neurologic event The median time to onset of corticosteroid therapy to treat CRS or NEs (post-infusion; excluding prophylaxis) was 5 days (range, 3-9 days). All 40 patients in Cohort 6 received ≥1 dose of corticosteroids. Table 62.

TABLE 62

Cumulative Dose and Frequency of Corticosteroid Use (Including Prophylaxis).

| | Cohort 6 (N = 40) |
|---|---|
| Patients receiving corticosteroids, n (%)[a] | |
| 1 Dose | 1 (3) |
| 2 Doses | 0 |
| 3 Doses | 14 (35) |
| 4 Doses | 10 (25) |
| ≥5 Doses | 15 (38) |
| Cumulative corticosteroid dose, mg[b] | |
| Mean (SD) | 110,080 (670,033) |
| Median (min-max) | 1252 (313-4,241,649) |

[a]Corticosteroid doses starting on or after the start date of the first axicabtagene ciloleucel dose but before or on the hospital discharge date are included.
[b]Cumulative systemic cortisone equivalent dose between infusion and hospital discharge date.

Responses were investigator-assessed per Cheson et al (*J Clin Oncol.* 2007; 25:579-586). Table 63. Duration of Response can be seen in FIG. 117.

TABLE 63

Overall Response

| | Cohort 6 (N = 40) |
|---|---|
| ORR, n (%) | 38 (95) |
| CR rate, n (%) | 32 (80) |
| Median DOR, months | NR |
| Median DOR follow-up (range), months | 5.8 (5.1-8.0) |
| Ongoing response at data cutoff date, % | 63 |
| KM estimate of 6-month DOR rate, % | 62 |

After propensity score-based matching, baseline disease characteristics were comparable between matched patients in Cohort 6 and Cohorts 1+2. Table 64.

TABLE 64

| | Cohorts 1 + 2 Overall (N = 101) | Cohort 6 Overall (N = 40) | Cohorts 1 + 2 After Matching (N = 32) | Cohort 6 After Matching (N = 32[a]) |
|---|---|---|---|---|
| Propensity Score Comparison of Baseline Patient and Product Characteristics | | | | |
| Patient Characteristics | | | | |
| Disease stage III or IV, n (%) | 86 (85.1) | 26 (65.0) | 23 (71.9) | 21 (65.6) |
| IPI score 3-4, n (%) | 48 (47.5) | 18 (45.0) | 12 (37.5) | 15 (46.9) |
| No. of prior lines of chemotherapy, % ≤2 \| 3 \| ≥4 | 31 \| 30 \| 40 | 63 \| 30 \| 8 | 63 \| 31 \| 6 | 53 \| 38 \| 9 |
| Median tumor burden by SPD[b] (Q1, Q3), mm$^2$ | 3723 (2200, 7138) | 1184 (498, 3391) | 2212 (816, 4245) | 1973 (632, 4641) |
| Median LDH (Q1, Q3), U/L | 356 (219, 743) | 236 (209, 329) | 240 (192, 369) | 247 (215, 504) |
| Product Characteristics, median (Q1, Q3) | | | | |
| CD8 + T cells, % | 53.6 (34.9, 65.1) | 56 (37.3, 69.2) | 54.4 (40.6, 64.5) | 57.0 (37.3, 71.5) |
| Naive (CCR7 + CD45RA+) T cells, % | 13.9 (8.1, 24.4) | 27.8 (19.9, 39.1) | 20.0 (12.2, 26.7) | 29.4 (19.8, 38.4) |
| Percent transduction, % | 52.6 (44.3, 63.6) | 62.0 (54.0, 69.0) | 55.0 (38.6, 64.6) | 62.0 (53.5, 68.5) |

[a]Eight patients were excluded due to low tumor burden and no match in the pivotal cohorts.
[b]Measured before conditioning therapy. For patients in Cohort 6, baseline tumor burden was measured after bridging therapy, for patients who received bridging therapy, but before conditioning therapy.
IPI, International Prognostic Index; LDH, lactate dehydrogenase; Q, quartile; SPD, sum of the products of diameters.

Differences in incidence of Grade ≥3 CRS and time to onset of CRS observed between patients in Cohorts 1+2 and Cohort 6 before propensity score-based matching were maintained after matching, and clinical efficacy remained comparable. Table 65.

TABLE 65

Propensity Score Comparison of Outcomes.

| | Cohorts 1 + 2 Overall (N = 101) | Cohort 6 Overall (N = 40) | Cohorts 1 + 2 After Matching (N = 32) | Cohort 6 After Matching (N = 32[a]) |
|---|---|---|---|---|
| Efficacy | | | | |
| Objective response, n (%) | 83 (82) | 38 (95) | 30 (94) | 30 (94) |
| Complete response, n (%) | 55 (54) | 32 (80) | 23 (72) | 24 (75) |
| Ongoing response at data cutoff date[b], n (%) | 44 (44) | 25 (63) | 20 (63) | 19 (59) |
| Safety | | | | |
| CRS | | | | |
| Worst Grade ≥2, n (%) | 57 (56) | 18 (45) | 19 (59) | 15 (47) |
| Worst Grade ≥3, n (%) | 13 (13) | 0 | 4 (13) | 0 |
| Median time to onset of any grade CRS (Q1, Q3), days | 2 (2, 4) | 5 (4, 6) | 2 (2, 4) | 5 (4, 6) |
| NEs | | | | |
| Worst Grade ≥2, n(%) | 42 (42) | 13 (33) | 11 (34) | 13 (41) |
| Worst Grade ≥3, n(%) | 28 (28) | 5 (13) | 6 (19) | 5 (16) |
| Median time to onset of any grade NE (Q1, Q3), days | 5 (3, 7) | 6 (5, 9) | 6 (3, 7) | 6 (5, 8) |
| Median time to onset of Grade ≥3 NE (Q1, Q3), days | 7 (5, 7) | 9 (6,15) | 7 (6, 8) | 9 (6, 15) |
| No CRS or NE within 72 hours (Days 0-3) of axicabtagene ciloleucel, n (%) | 20 (20) | 27 (68) | 8 (25) | 21 (66) |

[a]Eight patients were excluded due to low tumor burden and no match in the pivotal cohorts.

[b]Represents the number of patients in response at the data cutoff date among all treated patients.

Clinical outcomes were corroborated by lower levels of peak inflammatory cytokines and comparable peak CAR T cell levels in Cohort 6 versus those in Cohorts 1+2 before and after propensity score matching. Prophylactic corticosteroid use may affect the production of cytokines by various immune cells to a greater extent relative to CAR T-cell proliferative capability. Table 66.

TABLE 66

| | Propensity Score Comparison of CAR T-Cell and Cytokine Levels. | | | |
|---|---|---|---|---|
| Median (Q1, Q3) | Cohorts 1 + 2 Overall (N = 101) | Cohort 6 Overall (N = 40) | Cohorts 1 + 2 After Matching (N = 32) | Cohort 6 After Matching (N = 32$^a$) |
| Peak CAR T-cell levels | | | | |
| CAR T-cell expansion, cells/µL | 42  (16, 84) | 64  (6, 131) | 43  (15, 114) | 65  (18, 146) |
| Peak cytokine levels | | | | |
| IFN-γ, pg/mL | 477  (196, 1097) | 208  (87, 446) | 481  (120, 1096) | 227  (103, 424) |
| IL-2, pg/mL | 22  (10, 38) | 8  (3, 23) | 23  (10, 58) | 8  (3, 16) |
| GM-CSF, pg/mL | 7  (2, 16) | 2  (2, 5) | 9  (2, 21) | 2  (2, 4) |
| Ferritin, ng/mL | 3001  (1326, 6648) | 904  (489, 1529) | 2312  (1225, 4777) | 809  (489, 1529) |
| CRP, mg/L | 214  (141, 353) | 76  (39, 136) | 175  (124, 345) | 78  (44, 131) |

$^a$Eight patients were excluded due to low tumor burden and no match in the pivotal cohorts.

Prophylactic corticosteroids and early corticosteroid and/or tocilizumab intervention have the potential to improve the benefit/risk profile of CAR T-cell therapy: the incidence of Grade ≥3 CRS was lower in Cohort 6 (0%) than in Cohorts 1+2 (13%); the median CRS duration was shorter and time to CRS onset was delayed in Cohort 6 versus Cohorts 1+2; and 27/40 patients (68%) in Cohort 6 did not experience CRS or NEs within 72 hours of axicabtagene ciloleucel infusion. There was no negative impact on axicabtagene ciloleucel efficacy or CAR T-cell expansion. No impact on ORRs, CR rates, and ongoing response rates at a median follow-up of 8.9 months was observed. The levels of inflammatory cytokines that are correlates of toxicities (Neelapu S S, et al. *N Engl J Med.* 2017; 377:2531-2544) were lower in Cohort 6 versus Cohorts 1+2. Prophylactic corticosteroid use may affect the production of cytokines by various immune cells to a greater extent relative to CAR T-cell proliferative capability. The differences in rate of Grade ≥3 CRS and time to onset of CRS observed between patients in Cohort 6 and Cohorts 1+2 were maintained after propensity score-based matching, and response rates remained comparable and were corroborated by CAR T-cell level. Following propensity score-based matching, the incidence, severity, and onset of NEs were generally similar between Cohort 6 and Cohorts 1+2.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments/aspects have been illustrated and described, it will be appreciated that various changes can be made without departing from the spirit and scope of the disclosure.

We claim:

1. A method of manufacturing an anti-CD19 immunotherapy infusion T cell product with improved durable clinical efficacy and increased likelihood of a rapid response within approximately two weeks in the treatment of Non-Hodgkin's Lymphoma (NHL) in a human subject in need thereof, with decreased toxicity, comprising:

(i) Preparing a baseline T cell product from an expanded population of lymphocytes comprising anti-CD19 chimeric antigen receptor (CAR)-T cells with various baseline T cell phenotypes; and (ii) Preparing an immunotherapy infusion T cell product from the baseline T cell product by increasing or maximizing a percentage of CD4+ T cells and CD8+ T cells with a CD45RA+ CCR7+ naïve phenotype in the immunotherapy infusion T cell product and normalizing the number of said cells to the subject's tumor burden;

wherein the immunotherapy infusion T cell product comprises anti-CD19 CAR-T cells;

wherein the various baseline T cell phenotypes comprise CD45RA-CCR7+ $T_{CM}$, central memory T cells; CD45RA+CCR7- $T_{EFF}$, effector T cells; CD45RA-CCR7- $T_{EM}$, effector memory T cells; and/or $T_N$, CD45RA+CCR7+ naïve T cells, and wherein the step of increasing or maximizing a percentage of CD4+ T cells and CD8+ T cells with a CD45RA+ CCR7+ naïve phenotype in the T cell product comprises ensuring that the immunotherapy infusion T cell product includes at least a total of $20 \times 10^6$ CD4+ T cells and CD8+ T cells with the CD45RA+ CCR7+ naïve phenotype in the immunotherapy infusion T cell product for administration to the human subject, thereby manufacturing an immunotherapy infusion T cell product with improved durable clinical efficacy, as measured by durable clinical response, wherein durable clinical response is defined as ongoing response at a median follow up time of 1 year after administration of the immunotherapy infusion T cell product, and increased likelihood of a rapid response within approximately two weeks, with decreased toxicity in terms of Grade >3 neurologic events (NE) and Grade >3 cytokine release syndrome (CRS) after infusion, said improvement in durable clinical efficacy and said increased likelihood of rapid response within approximately two weeks being relative to that of the baseline T cell product without said increase or maximization of the percentage of CD4+ T cells and CD8+ T cells with a CD45RA+ CCR7+ naïve phenotype, and wherein treatment comprises reversing, alleviating, ameliorating, or slowing lymphoma progression, wherein decreased toxicity means that the higher the number of CD45RA+ CCR7+ in the infusion product normalized to the subject's tumor burden, the lower the probability of the subject experiencing post-infusion Grade >3 NE and Grade >3 CRS.

2. The method of claim 1, wherein the immunotherapy infusion T cell product is administered as a first line therapy, as a second line therapy, or as a third line therapy to a patient in need thereof, and wherein the patient has been diagnosed with lymphoma.

3. The method of claim 2, wherein the cancer is a non-Hodgkin's Lymphoma (NHL); advanced-stage indolent NHL (iNHL), including grades 1-3a follicular lymphoma (FL) and marginal zone lymphoma (MZL) that is R/R after ≥2 lines of therapy, including an anti-CD20 monoclonal antibody plus an alkylating agent, and Eastern Cooperative Oncology Group (ECOG) 0-1; large B-cell lymphoma (LBCL) that has relapsed after ≥2 systemic lines of therapy or is chemorefractory—defined as i) a best response of progressive disease (PD) or stable disease (SD) to ≥4 cycles of first-line systemic therapy with SD duration ≤6 months; or ii) a best response of PD or SD after ≥2 cycles of the most recent second-or-later line of systemic therapy; high-risk LBCL: i) double- or triple-hit lymphoma by fluorescent in situ hybridization per investigator or LBCL with International Prognostic Index (IPI) score ≥3; and ii) positive interim positron emission tomography (PET) per Lugano Classification and Deauville criteria [DC] 4 or 5 after 2 cycles of an anti-CD20 monoclonal antibody and anthracycline containing regimen; or Mantle Cell Lymphoma (MCL) with documentation of either cyclin D1 overexpression or presence of t(11;14).

4. The method of claim 3, wherein the MCL with documentation of either cyclin D1 overexpression or presence of t(11;14) is relapsed/refractory to 1-5 prior regimens for MCL.

5. The method of claim 4, wherein prior therapy having included anthracycline or bendamustine-containing chemotherapy, an anti-CD20 monoclonal antibody, and ibrutinib or acalabrutinib.

6. The method of claim 1, wherein the immunotherapy infusion T cell product comprises anti-CD19 CAR-T cells comprising axicabtagene ciloleucel or brexucabtagene autoleucel.

7. The method of claim 1, wherein the immunotherapy infusion T cell product comprises axicabtagene ciloleucel, brexucabtagene autoleucel, tisagenlecleucel, or lisocabtagene maraleucel.

8. The method of claim 1, further comprising increasing or maximizing a percentage of CD8+ T cells with a CD45RA+ CCR7+ naïve phenotype in the immunotherapy infusion T cell product, relative to all other T cell populations.

9. The method of claim 1, wherein the step of increasing or maximizing a percentage of CD4+ T cells and CD8+ T cells with a CD45RA+ CCR7+ naïve phenotype in the immunotherapy infusion T cell product comprises positively selecting for T cells comprising a naïve phenotype.

10. The method of claim 1, wherein the step of increasing or maximizing a percentage of CD4+ T cells and CD8+ T cells with a CD45RA+ CCR7+ naïve phenotype in the immunotherapy infusion T cell product comprises decreasing or minimizing a percentage or a number of CCR7− T cells with a differentiated phenotype in the T cell product.

11. The method of claim 1, wherein the increase or maximization of the percentage of CD4+ T cells and CD8+ T cells with a CD45RA+ CCR7+ naïve phenotype is partially achieved through optimization of CAR-T cell expansion capability during step (i) of the process for producing the immunotherapy infusion T cell product.

12. A T cell immunotherapy infusion T cell product produced according to the method of claim 1.

13. A method for administering T cells to a subject comprising injecting to the subject a pharmaceutical composition comprising the immunotherapy infusion T cell product of claim 1.

14. The method of claim 13, further comprising administering an anti-inflammatory treatment to the subject prior to administering the immunotherapy infusion T cell product.

\* \* \* \* \*